US009321832B2

(12) United States Patent
Tomlinson et al.

(10) Patent No.: US 9,321,832 B2
(45) Date of Patent: *Apr. 26, 2016

(54) LIGAND

(75) Inventors: Ian Tomlinson, Cambridge (GB);
Laurent Jespers, Cambridge (GB);
Jasper Clube, Cambridge (GB); Lucy J. Holt, Cambridge (GB); Oliver Schon, Cambridge (GB)

(73) Assignee: Domantis Limited (GB)

( * ) Notice: Subject to any disclaimer, the term of this patent is extended or adjusted under 35 U.S.C. 154(b) by 1051 days.

This patent is subject to a terminal disclaimer.

(21) Appl. No.: 11/704,832

(22) Filed: Feb. 8, 2007

(65) Prior Publication Data

US 2009/0259026 A1  Oct. 15, 2009

Related U.S. Application Data

(63) Continuation-in-part of application No. 11/023,959, filed on Dec. 28, 2004, now abandoned, which is a continuation of application No. PCT/GB03/02804, filed on Jun. 30, 2003.

(30) Foreign Application Priority Data

Jun. 28, 2002 (WO) .................. PCT/GB02/03014
Dec. 27, 2002 (GB) .................... 0230202.4

(51) Int. Cl.
*C12P 21/08* (2006.01)
*C07K 16/00* (2006.01)
*C07K 17/00* (2006.01)
*C07K 17/14* (2006.01)
*C07K 16/18* (2006.01)
*C07K 16/24* (2006.01)
*C07K 16/28* (2006.01)

(52) U.S. Cl.
CPC ............ *C07K 16/18* (2013.01); *C07K 16/241* (2013.01); *C07K 16/2878* (2013.01); *C07K 2317/31* (2013.01); *C07K 2317/34* (2013.01); *C07K 2317/35* (2013.01); *C07K 2317/53* (2013.01); *C07K 2317/55* (2013.01); *C07K 2317/569* (2013.01); *C07K 2317/624* (2013.01); *C07K 2317/76* (2013.01); *C07K 2317/94* (2013.01); *C07K 2318/20* (2013.01); *C07K 2319/00* (2013.01); *C07K 2319/01* (2013.01); *C07K 2319/31* (2013.01)

(58) Field of Classification Search
None
See application file for complete search history.

(56) References Cited

U.S. PATENT DOCUMENTS

| 5,120,712 | A | 6/1992 | Habener |
| 5,459,061 | A | 10/1995 | Sato et al. |
| 5,558,864 | A | 9/1996 | Bendig et al. |
| 5,664,034 | A | 9/1997 | Mock |
| 5,726,152 | A | 3/1998 | Bayne et al. |
| 5,770,195 | A | 6/1998 | Hudziak et al. |
| 5,824,782 | A | 10/1998 | Holzer et al. |
| 5,837,243 | A | 11/1998 | Deo et al. |
| 5,840,693 | A | 11/1998 | Eriksson et al. |
| 5,891,996 | A | 4/1999 | Mateo de Acosta del Rio et al. |
| 5,906,820 | A | 5/1999 | Bacha |
| 5,922,845 | A | 7/1999 | Deo et al. |
| 5,928,939 | A | 7/1999 | Eriksson et al. |
| 5,989,830 | A | 11/1999 | Davis et al. |
| 6,013,780 | A | 1/2000 | Neufeld et al. |
| 6,020,473 | A | 2/2000 | Keyt et al. |
| 6,057,428 | A | 5/2000 | Keyt et al. |
| 6,121,230 | A | 9/2000 | Charnock-Jones et al. |
| 6,193,966 | B1 | 2/2001 | Deo et al. |
| 6,214,974 | B1 | 4/2001 | Rosenblum et al. |
| 6,217,866 | B1 | 4/2001 | Schlessinger et al. |
| 6,270,765 | B1 | 8/2001 | Deo et al. |
| 6,303,755 | B1 | 10/2001 | Deo et al. |
| 6,331,301 | B1 | 12/2001 | Eriksson et al. |
| 6,342,219 | B1 | 1/2002 | Thorpe et al. |
| 6,342,221 | B1 | 1/2002 | Thorpe et al. |
| 6,395,272 | B1 | 5/2002 | Deo et al. |
| 6,416,758 | B1 | 7/2002 | Thorpe et al. |
| 6,475,796 | B1 | 11/2002 | Pollitt et al. |
| 6,485,942 | B1 | 11/2002 | Zioncheck et al. |
| 6,583,276 | B1 | 6/2003 | Neufeld et al. |
| 6,676,941 | B2 | 1/2004 | Thorpe et al. |
| 6,699,473 | B2 | 3/2004 | Raisch et al. |
| 6,703,020 | B1 | 3/2004 | Thorpe et al. |
| 6,750,044 | B1 | 6/2004 | Keyt et al. |
| 6,777,534 | B1 | 8/2004 | Klagsbrun et al. |
| 6,965,010 | B2 | 11/2005 | Alitalo et al. |
| 7,696,320 | B2 * | 4/2010 | Ignatovich et al. ........ 530/387.1 |
| 2001/0014328 | A1 | 8/2001 | Deo et al. |

(Continued)

FOREIGN PATENT DOCUMENTS

EA   EP 0339505   11/1989
EP   0298654   1/1989

(Continued)

OTHER PUBLICATIONS

Paul, Fundamental Immunology, 3rd Edition, 1993, pp. 292-295.*
Rudikoff et al., Proc. Natl. Acad. Sci. USA, 79(6):1979-1983, Mar. 1982.*
Colman, Research in Immunology, 145:33-36, 1994.*
Bendig, Methods: A Companion to Methods in Enzymology, 1995; 8:83-93.*
Zabetakis et al., PLOS One, 2013, 8(10), 1-7.*

(Continued)

*Primary Examiner* — Hong Sang
(74) *Attorney, Agent, or Firm* — Jason C. Fedon; William T. Han

(57) ABSTRACT

The invention provides a dual-specific ligand comprising a first immunoglobulin variable domain having a first binding specificity and a complementary or non-complementary immunoglobulin variable domain having a second binding specificity.

7 Claims, 23 Drawing Sheets

(56) References Cited

U.S. PATENT DOCUMENTS

| | | | |
|---|---|---|---|
| 2001/0018507 A1 | 8/2001 | Rathjen et al. | |
| 2002/0004587 A1 | 1/2002 | Miller et al. | |
| 2002/0009454 A1 | 1/2002 | Boone et al. | |
| 2002/0012663 A1 | 1/2002 | Waksal | |
| 2002/0014328 A1 | 2/2002 | Mitrovic et al. | |
| 2002/0032315 A1 | 3/2002 | Baca et al. | |
| 2002/0103345 A1 | 8/2002 | Zhu | |
| 2002/0173629 A1 | 11/2002 | Jakobovits et al. | |
| 2002/0192211 A1 | 12/2002 | Hudziak et al. | |
| 2002/0192634 A1 | 12/2002 | Ferrara et al. | |
| 2003/0023046 A1 | 1/2003 | Ferrara et al. | |
| 2003/0032145 A1 | 2/2003 | Zioncheck et al. | |
| 2003/0091561 A1 | 5/2003 | van de Winkel et al. | |
| 2003/0096373 A1 | 5/2003 | Majumdar et al. | |
| 2003/0148409 A1 | 8/2003 | Rossi et al. | |
| 2003/0157104 A1 | 8/2003 | Waksal | |
| 2003/0165467 A1 | 9/2003 | Neufeld et al. | |
| 2003/0166524 A1 | 9/2003 | Ford et al. | |
| 2003/0170253 A1 | 9/2003 | Eriksson et al. | |
| 2003/0175271 A1 | 9/2003 | Shitara et al. | |
| 2003/0175276 A1 | 9/2003 | Thorpe et al. | |
| 2003/0185832 A1 | 10/2003 | Thorpe et al. | |
| 2003/0190317 A1 | 10/2003 | Baca et al. | |
| 2003/0203409 A1 | 10/2003 | Kim | |
| 2003/0224001 A1 | 12/2003 | Goldstein et al. | |
| 2004/0006212 A1 | 1/2004 | Goldstein et al. | |
| 2004/0018557 A1 | 1/2004 | Qu et al. | |
| 2004/0057950 A1 | 3/2004 | Waksal et al. | |
| 2004/0077022 A1 | 4/2004 | Feige et al. | |
| 2004/0097712 A1 | 5/2004 | Varnum et al. | |
| 2004/0106605 A1 | 6/2004 | Carboni et al. | |
| 2004/0131611 A1 | 7/2004 | Oliver et al. | |
| 2004/0133357 A1 | 7/2004 | Zhong et al. | |
| 2004/0152636 A1 | 8/2004 | Keyt et al. | |
| 2004/0219643 A1* | 11/2004 | Winter et al. | 435/70.21 |
| 2004/0248196 A1 | 12/2004 | Adams et al. | |
| 2004/0265309 A1 | 12/2004 | Kandel et al. | |
| 2005/0019826 A1 | 1/2005 | Tournaire et al. | |
| 2005/0032699 A1 | 2/2005 | Holash et al. | |
| 2005/0043233 A1 | 2/2005 | Stefanic et al. | |
| 2005/0053599 A1 | 3/2005 | Van Bruggen et al. | |
| 2005/0053608 A1 | 3/2005 | Weber et al. | |
| 2005/0059087 A1 | 3/2005 | Weber et al. | |
| 2005/0064522 A1 | 3/2005 | Ferrara et al. | |
| 2005/0079184 A1 | 4/2005 | Hsing-Chang et al. | |
| 2005/0100546 A1 | 5/2005 | Jakobovits et al. | |
| 2005/0123537 A1 | 6/2005 | Thorpe et al. | |
| 2005/0158829 A1 | 7/2005 | Fandl et al. | |
| 2005/0186208 A1 | 8/2005 | Fyfe et al. | |
| 2005/0196340 A1 | 9/2005 | Holash et al. | |
| 2005/0202028 A1 | 9/2005 | Ledbetter et al. | |
| 2005/0202534 A1 | 9/2005 | Ledbetter et al. | |
| 2005/0220786 A1 | 10/2005 | Mahler et al. | |
| 2005/0244405 A1 | 11/2005 | Van Bruggen et al. | |
| 2005/0255555 A1 | 11/2005 | Johns et al. | |
| 2005/0271663 A1 | 12/2005 | Ignatovich et al. | |
| 2010/0056439 A1* | 3/2010 | Beckmann et al. | 514/12 |

FOREIGN PATENT DOCUMENTS

| | | |
|---|---|---|
| EP | 89311731.7 | 5/1990 |
| EP | 0467416 | 1/1992 |
| EP | 0619322 | 10/1994 |
| EP | 0739981 | 10/1996 |
| EP | 1026239 | 8/2000 |
| EP | 1160255 | 12/2001 |
| EP | 1378520 | 1/2004 |
| WO | WO-90/05144 | 5/1990 |
| WO | WO-90/14430 | 11/1990 |
| WO | WO 91/01743 | 2/1991 |
| WO | WO-91/02078 | 2/1991 |
| WO | WO 92/01787 | 2/1992 |
| WO | WO-9201787 | 2/1992 |
| WO | WO-92/20791 | 11/1992 |
| WO | WO-93/11236 | 6/1993 |
| WO | WO 95/19374 | 7/1995 |
| WO | WO-97/30084 | 8/1997 |
| WO | WO-98/40469 | 9/1998 |
| WO | WO 98/48837 | 11/1998 |
| WO | WO-99/23221 | 5/1999 |
| WO | WO-99/37791 | 7/1999 |
| WO | WO-00/17369 | 3/2000 |
| WO | WO-00/29004 | 5/2000 |
| WO | WO-00/63243 | 10/2000 |
| WO | WO-01/45746 | 6/2001 |
| WO | WO-01/58953 | 8/2001 |
| WO | WO-01/94585 | 12/2001 |
| WO | WO 02/46227 | 6/2002 |
| WO | WO-02/051870 | 7/2002 |
| WO | WO-02/072141 | 9/2002 |
| WO | WO-03/002609 | 1/2003 |
| WO | WO-03/026591 | 4/2003 |
| WO | WO-03/035694 | 5/2003 |
| WO | WO-03/046560 | 6/2003 |
| WO | WO-03/057235 | 7/2003 |
| WO | WO-04/001064 | 12/2003 |
| WO | WO-2004/003019 | 1/2004 |
| WO | WO-2004/032961 | 4/2004 |
| WO | WO-2004/041863 | 5/2004 |
| WO | WO 2004/041863 | 5/2004 |
| WO | WO-2004/058821 | 7/2004 |
| WO | WO 2004/062551 | 7/2004 |
| WO | WO-2004081026 | 9/2004 |
| WO | WO-2004101790 | 11/2004 |
| WO | WO-2005035572 | 4/2005 |
| WO | WO 2005/044858 | 5/2005 |
| WO | WO-2005044853 | 5/2005 |
| WO | WO 2005/052002 | 6/2005 |
| WO | WO 2005/118642 A2 | 12/2005 |
| WO | WO-2006003388 | 1/2006 |
| WO | WO-2006/051288 | 5/2006 |
| WO | WO 2006/059110 A2 | 6/2006 |
| WO | WO 2006059108 A2 * | 6/2006 |
| WO | WO 2006/122787 A1 | 11/2006 |
| WO | WO-2007/066106 | 6/2007 |
| WO | WO 2008/052933 A2 | 5/2008 |

OTHER PUBLICATIONS

Conrath, et al., "Camel Single-domain Antibodies as Modular Building Units in Bispecific and Bivalent Antibody Constructs," J. Biol. Chem. (2001) 276: 7346-7350.

Casali, et al., "Probing the human B-Cell Reertoire with EBV: Polyreactive Antibodies and CD5+B Lymphocytes", Annual Review Immunology (1989), V. 7, pp. 513-535.

Reiter, et al.; "An Antibody Single-domain Phage Display Library of a Native Heavy Chain Variable Region: Isolation of Functional Single-domain VH Molecules with a Unique Interface"; (1999); J. Mol. Biol.; 290: 685-698.

Smith, et al.; "Prolonged in Vivo Residence Times of Antibody Fragments Associated with Albumin"; (2001); Bioconjugate Chem. ; 12: 750-756.

Van den Beucken, et al.; "Building Novel Binding Ligands to B7.1 and B7.2 Based on Human Antibody Single Variable Light Chain Domains" (2001); J. Mol. Biol.; 310: 591-601.

Muyldermans and Lauwereys; "Unique single-domain antigen binding fragments derived from naturally occurring camel heavy-chain antibodies"; (1999) J. Mol. Recognit. ; 12: 131-140.

Holliger, et al.; "Retargeting serum immunoglobulin with bispecific diabodies"; (1997); *Nature Biotechnology* ; 15: 632-636.

Tanha, et al.; "Optimal Design Features of Camelized Human Single-domain Antibody Libraries"; (2001); *The Journal of Biological Chemistry*; 276(27): 24774-24780.

Hussain, I. etal. "Identification of novel aspartic protease . . . ", Mol. Cell. Neurosci., vol. 14, 1999, pp. 419-427.

Haniu, M. et al. "Characterization of Alzheimer's . . . ", J. Biol Chem., vol. 275, 2000, pp. 735-741.

Rozner et al. "A dual altered peptide ligand down-regulates myastheogenic T cell responses by up-regulating CD25 and CTLA-

(56) References Cited

OTHER PUBLICATIONS 4-expressing CD4+T cells". Proc. Natl Acad Sci USA, May 27, 2003; 100(11); 6676-81, Epub May 12, 2003.
Yan, R. et al. "Membrane-anchored aspartly . . . ", Nature, vol. 402, 1999 p. 553-537.
Vassar, R. et. "Beta-secretase cleavage of Alzheimer's." vol. 286, 1999, pp. 735-741.
Bendele et al., "Combination benefit of treatment with the cytokine inhibitors interleukin-1 receptor antagonist and PEGylated souble tumor necrosis factor receptor type I in animal models of rheumatoid arthritis", Arthritis and Rheumatism. Dec. 12, 2000; 43 (12) 2648-2659.
Cai et al., "Comparison of fusion phage libraries displaying vh or single-chain fv antibody repertoire of a vaccinated melanoma patient as a source of melanoma-specific targeting molecules", Proceedings of the National Academy of Sciences of USA. Aug. 1997; 94, 9261-9266.
Chan et al., "A Domain in TFN receptors that mediates ligand-independent receptor assembly and signaling", Science. Jun. 30, 2000; 288 (5475) 2351-2354.
Chapman, "Pegylated antibodies and antibody fragments for improved therapy: a review", Advanced Drug Delivery Reviews. Jun. 17, 2002; 54 (4) 531-545.
Cortez-Retamozo et al., "Efficient cancer therapy with a nanobody-based conjugate", Cancer Research. Apr. 15, 2004; 64 (8) 2853-2857.
Davies et al., "Affinity improvement of single antibody VH domains: residues in all three hypervariable regions affect antigen binding", Immunotechnology. Sep. 3, 1996; 2 (3) 169-179.
Deng, et al., "A Potential therapeutic molecule for inflammatory arthritis targeting pre ligand assembly domain (PLAD) of TFN receptors", FASEB Journal. Mar. 2005; 19 (4) A915.
Deng et al., "Amelioration of inflammatory arthritis by targeting the pre-ligand assembly domain of tumor necrosis factor receptors", Nature Medicine. Oct. 2005; 11 (10) 1066-1072.
Dennis et al., "Albumin binding as a general strategy for improving the pharmacokinetics of proteins", Journal of Biological Chemistry. Sep. 20, 2002;277(38) 35035-35043.
Desmyter et al., "Antigen specificity and high affinity binding provided by one single loop of a camel single-domain antibody", Journal of Biological Chemistry. Jul. 13, 2001; 276 (28) 26285-26290.
Els Conrath et al., "Camel single-domain antibodies as modular building units in bispecific and bivalent antibody constructs", Journal of Biological Chemistry. Mar. 9, 2001; 276 (10) 7346-7350.
Fredericks et al., "Identification of potent human anti-IL-IRI antagonist antibodies", Protein Engineering Design & Selection. Jan. 1, 2004; 17 (1) 95-106.
Golstein "Signal transduction: FasL binds preassembled Fas", Science. Jun. 30, 2000; 288 (5475) 2328-2329.
Gouze-Jn, "A Comparative study of the inhibitory effects of interleukin-1 receptor antagonist following administration as a recombinant protein or by gene transfer", Arthritis Res Ther. 2003; 5 (5) 301-309.
Green et al., "Lys9 for Glu9 substitution in glucagon-like peptide-1 (7-36) amide confers dipeptidylpeptidase IV resistance with cellular and metabolic actions similar to those of established antagonists glucagon-like peptide-1 (9-36) amide and exedin (9-36)", Metabolism Clinical and Experimental. Feb. 2, 2004; 53 (2) 252-259.
Green et al., "Metabolic stability, receptor binding, cAMP generation, insulin secretion and antihyperglycaemic activity of novel N-terminal Glu9-substituted analogues of glucagon-like peptide-1", Biological Chemistry. Dec. 2003; 384 (12) 1543-1551.
Green et al., "Novel dipeptidyl peptidase IV resistant analogues of glucagon-like peptide-1 (7-36) amide have preserved biological activities in vitro conferring improved glucose-lowering action in vivo", Journal of Molecular Endocrinology. Dec. 3, 2003; 31 (3) 529-540.
Green et al., "N-terminal His7-modification of glucagon-like peptide-1 (7-36) amide generates dipeptidyl peptidase IV-stable analogues with potent antihyperglycaemic activity", Journal of Endocrinology. Mar. 3, 2004; 180 (3) 379-388.

Hansson et al., "An in vitro selected binding protein (affibody) shows conformation-dependent recognition of the respiratory syncytial virus (RSV) G protein", Immunotechnology. Mar. 1999; 4 (3-4) 237-252.
Harmsen et al., "Prolonged in vivo residence times of llama single-domain antibody fragments in pigs by binding to porcine immunoglobulins", Vaccine. Jun. 13, 2005; 23 (41) 4926-4934.
Hinton et al., "Engineered human IgG antibodies with longer serum half-lives in primates", Journal of Biological Chemistry. Feb. 20, 2004; 279 (8) 6213-6216.
Hoang et al., PD-144 Tumor response augmentation with combination cetuximab (erbitux(R) and bevacizumab (Avastin(R)), Lung Cancer. Jul. 2005; 49 S108-S109.
Holt et al., "Domain antibodies: proteins for therapy", Trends in Biotechnology. Nov. 2003; 21 (11) 484-490.
Hoogenboom, "Mix and match: Building manifold binding sites", Nature Biotechnology. Feb. 1, 1997; 15 (2) 125-126.
Jespers et al., "Crystal structure of HEL4, a soluble, refoldable human VH single domain with a germ-line scaffold", Journal of Molecular Biology. Apr. 2, 2004; 337 (4) 893-903.
Koumenis et al., "Modulating pharmacokinetics of an an anti-interleukin-8 F(AB')2 by amine-specific pegylation with preserved bioactivity", International Journal of Pharmaceutics. 2000; 198 (1) 83-95.
Lee Sang-Neon et al., "Synthesis, characterization, and pharmacokinetic studies of PEGylated glucagon-like peptide-1", Bioconjugate Chemistry. Feb. 23, 2005; 16 (2) 377-382.
Makrides Savvas et al., "Extended in vivo half-life of human soluble complement receptor type 1 fused to a serum albumin-binding receptor", Journal of Pharmacology and Experimental. 1996; 277(1) 534-542.
Martsev et al., "Antiferritin single-chain antibody: a functional protein with incomplete folding?", Febs Letters, Dec. 28, 1998; 441 (3) 458-462.
McFarlane et al., "Stimulation of stress-activated but not mitogen-activated protein kinases by tumour necrosis factor receptor subtypes in airway smooth muscle", Biochemical Pharmacology. Mar. 15, 2001; 61 (6) 749-759.
Meier et al., "Glucagon-like peptide 1 as a regulator of food intake and body weight: therapeutic perspectives", European Journal of Pharmacology. Apr. 12, 2002; 440 (2/3) 269-279.
Muyldermans et al., "Recognition of antigens by single-domain antibody fragments: the superfluous luxury of paired domains", Tibs Trends in Biochemical Sciences. Apr. 1, 2001; 26 (4) 230-235.
Nord et al., "Binding proteins selected from combinatorial libraries of an alpha-helical bacterial receptor domain", Nature Biotechnology. Aug. 1997; 15 (8) 772-777.
Riechmann et al., "Single domain antibodies comparison of camel VH and camelised human VH domains", Journal of Immunological Methods. Dec. 10, 1999; 231 (1-2) 25-38.
Servin et al., "Peptide YY and neuropeptide-Y inhibit vasoactive intestinal peptide-stimulated amp production in rat small intestine structural requirements of peptides for interacting with peptide YY-preferring receptors", Endocrinology. 1989; 124 (2) 692-700.
Shechter et al., "Reversible PEGylation of peptide YY3-36 prolongs its inhibition of food intake in mice", FEBS Letters. Apr. 25, 2005; 579 (11) 2439-2444.
Siegel et al., "Fas preassociation required for apoptosis signaling and dominant inhibition by pathogenic mutations", Science. Jun. 30, 2000; 288 (5475) 2354-2357.
Silva et al., "Camelized Rabbit-derived VH single-domain intrabodies against vif strongly neutralize HIV-1 infectivity", Journal of Molecular Biology. Jul. 9, 2004; 340(3) 525-542.
US Natl Inst Health, "Bevacizumab and Cetuximab with or without Irinotecan in treating patients with Irinotecan-refractory metastatic colon cancer", Internet Citation. Feb. 10, 2004; XP002424711.
Painter, et al., "Contributions of Heavy and Light Chains of Rabbit Immunoglobulin G to antibody Activity. I. Binding Studies on Isolated Heavy and Light Chains" Biochemistry, vol. 11, No. 8, (1972) pp. 1327-1337.

(56) References Cited

OTHER PUBLICATIONS

Rubenhagen, et al., Osmosensor and Osmoregulator Properties of the Betaine Carrier BetP from Corynebacterium *glutamicum* in Proteoliposomes, The Journal of Biological Chemistry, vol. 275, No. 2, Issue of Jan. 14, pp. 735-741-2000.

Roopenian et al., "FcRn: the neonatal Fc receptor comes of age" *Nature Reviews Immunology*, vol. 7, Sep. 2007, pp. 715-725.
Dick, BMJ. Apr. 14, 1990; 300(6730): 659-660.
Holt et al., TRENDS in Biotechnology (2003), 21(11):484-490.
Holt. et al., Prot. Eng., Des. & Select., vol. 21, No. 5, pp. 283-288, 2008.

\* cited by examiner

FIG. 1

```
H1                                                                                                                    H30
E    V    Q    L    L    E    S    G    G    G    L    V    Q    P    G    G    S    L    R    L    S    C    A    A    S    G    F    T    F    S
GAG  GTG  CAG  CTG  TTG  GAG  TCT  GGG  GGA  GGC  TTG  GTA  CAG  CCT  GGG  GGG  TCC  CTG  AGA  CTC  TCC  TGT  GCA  GCC  TCT  GGA  TTC  ACC  TTT  AGC

H40                                              H50              H52 a
S    Y    A    M    S    W    V    R    Q    A    P    G    K    G    L    E    W    V    S    A    I    S    G    S    G    G    S    T    Y    Y
AGC  TAT  GCC  ATG  AGC  TGG  GTC  CGC  CAG  GCT  CCA  GGG  AAG  GGG  CTG  GAG  TGG  GTC  TCA  GCT  ATT  AGT  GGT  AGT  GGT  GGT  AGC  ACA  TAC  TAC
     HCDR1                                                                                     HCDR2

H60                           H70                                                       H82 a b c
A    D    S    V    K    G    R    F    T    I    S    R    D    N    S    K    N    T    L    Y    L    Q    M    N    S    L    R    A    E    D
GCA  GAC  TCC  GTG  AAG  GGC  CGG  TTC  ACC  ATC  TCC  AGA  GAC  AAT  TCC  AAG  AAC  ACG  CTG  TAT  CTG  CAA  ATG  AAC  AGC  CTG  AGA  GCC  GAG  GAC

H90                      H98 H100                                                  H110      H113
T    A    V    Y    Y    C    A    K    A    F    D    Y    W    G    Q    G    T    L    V    T    V    S    S    G    G    G    G    S    G    G
ACG  GCC  GTA  TAT  TAC  TGT  GCG  AAA  GCT  TTT  GAC  TAC  TGG  GGC  CAG  GGA  ACC  CTG  GTC  ACC  GTC  TCG  AGC  GGT  GGA  GGC  GGT  TCA  GGC  GGA
                              HCDR3                                                          XhoI

L1                                              L10
G    G    S    G    G    G    G    S    T    D    I    Q    M    T    Q    S    P    S    S    L    S    A    S    V    G    D    R
GGC  GGA  TCA  GGT  GGC  GGC  GGT  TCG  ACG  GAC  ATC  CAG  ATG  ACC  CAG  TCT  CCA  TCC  TCC  CTG  TCT  GCA  TCT  GTA  GGA  GAC  AGA

L20                                              L30
V    T    I    T    C    R    A    S    Q    S    I    S    S    Y    L    N    W    Y    Q    Q    K    P    G    K    A    P    K    L    L    I
GTC  ACC  ATC  ACT  TGC  CGG  GCA  AGT  CAG  AGC  ATT  AGC  AGC  TAT  TTA  AAT  TGG  TAT  CAG  CAG  AAA  CCA  GGG  AAA  GCC  CCT  AAG  CTC  CTG  ATC
                              LCDR1

L50                                              L60                                              L70
Y    A    A    S    S    L    Q    S    G    V    P    S    R    F    S    G    S    G    S    G    T    D    F    T    L    T    I    S    S    L
TAT  GCT  GCA  TCC  AGT  TTG  CAA  AGT  GGG  GTC  CCA  TCA  AGG  TTC  AGT  GGC  AGT  GGA  TCT  GGG  ACA  GAT  TTC  ACT  CTC  ACC  ATC  AGC  AGT  CTG
        LCDR2

L80                                              L90                                              L100                                L107
Q    P    E    D    F    A    T    Y    Y    C    Q    Q    S    Y    S    T    P    N    T    F    G    Q    G    T    K    V    E    I    K    R
CAA  CCT  GAA  GAT  TTT  GCA  ACT  TAC  TAC  TGT  CAA  CAG  AGT  TAC  AGT  ACG  CCT  AAT  ACG  TTC  GGC  CAA  GGG  ACC  AAG  GTG  GAA  ATC  AAA  CGG
                                                                  LCDR3
```

FIG. 3

V_H chains

| | FR1 | CDR1 | FR2 | CDR2 | FR3 | CDR3 | FR4 |
|---|---|---|---|---|---|---|---|
| | 1234567890123456789 0123 | 12345 | 6789012345 6789 | 012a3456789012345 | 6789012345678901 2abc345678901234 | 567801 | 234567890123 |
| V_H dummy | EVQLLESGGGLVQPGGSLRLSCAASGFTFS | SYAMS | WVRQAPGKGLEWVS | AISGSGGSTYYADSVKG | RFTISRDNSKNTLYLQMNSLRAEDTAVYYCAK | SYGAFDY | WGQGTLVTVSS |
| K8 | ------------------------------ | ----- | -------------- | H-SPY-AN-R------ | -------------------------------- | GLRA--- | ----------- |
| VH2 | ------------------------------ | ----- | -------------- | D-GAT-SK-G----P- | -------------------------------- | KVLT--- | ----------- |
| VH4 | ------------------------------ | ----- | -------------- | R-NGP-*A-G------ | -----------------I-------------- | HGAP--- | ----------- |
| VHC11 | -------------------------N | ----- | -------------- | S-PAS-LH-R------ | -------------------------------- | PGLG--- | ----------- |
| VHA10sd | ------------------------------ | ----- | -------------- | D-ERT-Y*-R------ | -------------------------------- | KVLV--- | ----------- |
| VHA1sd | ------------------------------ | ----- | -------------- | E-SAN-SK-Q------ | -------------------------------- | KVLQ--- | ----------- |
| VHA5sd | ------------------------------ | ----- | -------------- | T-PAN-*V-R------ | ----------------L--------------- | SLLQ--- | ----------- |
| VHC5sd | ------------------------------ | ----- | -------------- | D-AAT-SA-S------ | -------------------------------- | KLLK--- | ----------- |
| VHC11sd | ----------S------------------- | ----- | -------------- | T-SSV-QS-R------ | -------------------------------- | NLMS--- | ----------- |

V_k chains

| | FR1 | CDR1 | FR2 | CDR2 | FR3 | CDR3 | FR4 |
|---|---|---|---|---|---|---|---|
| | 12345678901234567890123 | 45678901234 | 5678901234567 89 | 0123456 | 7890123456789012345678 | 901234567 | 89012345678 |
| V_k dummy | DIQMTQSPSSLSASVGDRVTITC | RASQSISSYLN | WYQQKPGKAPKLLIY | AASSLQS | GVPSRFSGSGSGTDFTLTISSLQPEDFATYYC | QQSYSTPNT | FGQGTKVEIKR |
| K8 | ----------------------- | ----------- | --------------- | R--H--- | -------------------------------- | --PWRS-G- | ----------- |
| E5sd | ----------V------------ | ----------- | --------------- | L--R--- | -------------------------------- | --NWWL-P- | ----------- |
| C3 | ----------------------- | ----------- | --------------- | *--L--- | -------------------------------- | --RVYD-L- | ----------- |

Phage ELISA of a dual specific ScFv antibody K8

1-HSA
2-APS
3-b-gal
4-Peanut
5-BSA
6-lysosyme
7-cytochrome c

Soluble ELISA of the Dual Specific ScFv Antibody K8

FIG. 6

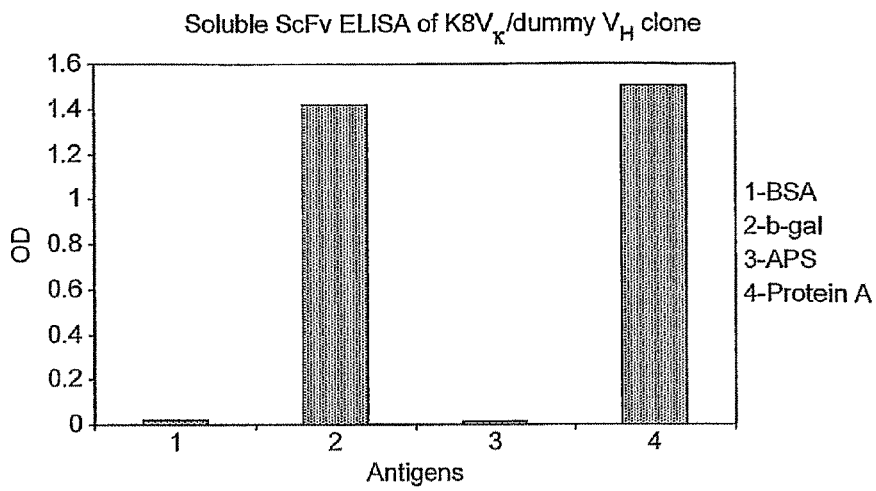

Soluble ScFv ELISA of K8V$_\kappa$/dummy V$_H$ clone

1-BSA
2-b-gal
3-APS
4-Protein A

FIG. 7

```
                                                    RBS
CAGGAAACAGCTATGACCATGATTACGCCAAGCTTGCATGCAAATTCTATTTCAAGGAGACAGTCATA ATG AAA TAC CTA
------------------>                                                   M   K   Y   L
       LMB3

SfiI       NcoI
TTG CCT ACG GCA GCC GCT GGA TTG TTA TTA CTC GCG GCC CAG CCG GCC ATG GCC GAG GTG TTT
 L   P   T   A   A   A   G   L   L   L   L   A   A   Q   P   A   M   A   E   V   F

XhoI                            linker
GAC TAC TGG GGC CAG GGA ACC CTG GTC ACC GTC TCG AGC GGT GGA GGC GGT TCA GGC GGA GGT
 D   Y   W   G   Q   G   T   L   V   T   V   S   S   G   G   G   G   S   G   G   G SalI                         NotI
GGC AGC GGC GGT GGC GGG TCG ACG GAC ATC CAG ATG ACC CAG GCG GCC GCA GAA CAA AAA CTC
 G   S   G   G   G   S   T   D   I   Q   M   T   Q   A   A   A   E   Q   K   L
 <------------------------
       link seq new HIS-tag
                                           CAT CAT CAT CAC CAT CAC GGG GCC GCA
                                            H   H   H   H   H   H   G   A   A
                                           (insertion in V domain vector 2 only myc-tag                                              Gene III
ATC TCA GAA GAG GAT CTG AAT GGG GCC GCA TAG ACT GTT GAA AGT TGT TTA GCA AAA CCT CAT
 I   S   E   E   D   L   N   G   A   A   *   T   V   E   S   C   L   A   K   P   H
                    <------------------------
                           pHEN seq
```

FIG. 13

Dummy V$_H$ sequence for library 1

```
      E   V   Q   L   L   E   S   G   G   G   L   V   Q   P   G   G
  1   GAG GTG CAG CTG TTG GAG TCT GGG GGA GGC TTG GTA CAG CCT GGG GGG
      CTC CAC GTC GAC AAC CTC AGA CCC CCT CCG AAC CAT GTC GGA CCC CCC

S   L   R   L   S   C   A   A   S   G   F   T   F   S   S   Y
 49   TCC CTG CGT CTC TCC TGT GCA GCC TCC GGA TTC ACC TTT AGC AGC TAT
      AGG GAC GCA GAG AGG ACA CGT CGG AGG CCT AAG TGG AAA TCG TCG ATA

A   M   S   W   V   R   Q   A   P   G   K   G   L   E   W   V
 97   GCC ATG AGC TGG GTC CGC CAG GCT CCA GGG AAG GGT CTA GAG TGG GTC
      CGG TAC TCG ACC CAG GCG GTC CGA GGT CCC TTC CCA GAT CTC ACC CAG

S   A   I   S   G   S   G   S   T   Y   Y   A   D   S   V
145   TCA GCT ATT AGT GGT AGT GGT GGT AGC ACA TAC TAC GCA GAC TCC GTG
      AGT CGA TAA TCA CCA TCA CCA CCA TCG TGT ATG ATG CGT CTG AGG CAC

K   G   R   F   T   I   S   R   D   N   S   K   N   T   L   Y
193   AAG GGC CGG TTC ACC ATC TCC CGT GAC AAT TCC AAG AAC ACG CTG TAT
      TTC CCG GCC AAG TGG TAG AGG GCA CTG TTA AGG TTC TTG TGC GAC ATA

L   Q   M   N   S   L   R   A   E   D   T   A   V   Y   Y   C
241   CTG CAA ATG AAC AGC CTG CGT GCC GAG GAC ACC GCG GTA TAT TAC TGT
      GAC GTT TAC TTG TCG GAC GCA CGG CTC CTG TGG CGC CAT ATA ATG ACA

A   K   S   Y   G   A   F   D   Y   W   G   Q   G   T   L   V
289   GCG AAA AGT TAT GGT GCT TTT GAC TAC TGG GGC CAG GGA ACC CTG GTC
      CGC TTT TCA ATA CCA CGA AAA CTG ATG ACC CCG GTC CCT TGG GAC CAG

T   V   S   S
337   ACC GTC TCG AGC
      TGG CAG AGC TCG
```

FIG. 14

Dummy V$_H$ sequence for library 2

```
      E   V   Q   L   L   E   S   G   G   G   L   V   Q   P   G   G
  1   GAG GTG CAG CTG TTG GAG TCT GGG GGA GGC TTG GTA CAG CCT GGG GGG
      CTC CAC GTC GAC AAC CTC AGA CCC CCT CCG AAC CAT GTC GGA CCC CCC

S   L   R   L   S   C   A   A   S   G   F   T   F   S   S   Y
 49   TCC CTG CGT CTC TCC TGT GCA GCC TCC GGA TTC ACC TTT AGC AGC TAT
      AGG GAC GCA GAG AGG ACA CGT CGG AGG CCT AAG TGG AAA TCG TCG ATA

A   M   S   W   V   R   Q   A   P   G   K   G   L   E   W   V
 97   GCC ATG AGC TGG GTC CGC CAG GCT CCA GGG AAG GGT CTA GAG TGG GTC
      CGG TAC TCG ACC CAG GCG GTC CGA GGT CCC TTC CCA GAT CTC ACC CAG

S   A   I   S   G   S   G   S   T   Y   Y   A   D   S   V
145   TCA GCT ATT AGT GGT AGT GGT GGT AGC ACA TAC TAC GCA GAC TCC GTG
      AGT CGA TAA TCA CCA TCA CCA CCA TCG TGT ATG ATG CGT CTG AGG CAC

K   G   R   F   T   I   S   R   D   N   S   K   N   T   L   Y
193   AAG GGC CGG TTC ACC ATC TCC CGT GAC AAT TCC AAG AAC ACG CTG TAT
      TTC CCG GCC AAG TGG TAG AGG GCA CTG TTA AGG TTC TTG TGC GAC ATA

L   Q   M   N   S   L   R   A   E   D   T   A   V   Y   Y   C
241   CTG CAA ATG AAC AGC CTG CGT GCC GAG GAC ACC GCG GTA TAT TAC TGT
      GAC GTT TAC TTG TCG GAC GCA CGG CTC CTG TGG CGC CAT ATA ATG ACA

A   K   S   Y   G   A   X   X   X   X   F   D   Y   W   G   Q
289   GCG AAA AGT TAT GGT GCT NNK NNK NNK NNK TTT GAC TAC TGG GGC CAG
      CGC TTT TCA ATA CCA CGA NNK NNK NNK NNK AAA CTG ATG ACC CCG GTC

G   T   L   V   T   V   S   S
337   GGA ACC CTG GTC ACC GTC TCG AGC
      CCT TGG GAC CAG TGG CAG AGC TCG
```

FIG. 15

Dummy V$_K$ sequence for library 3

```
      D   I   Q   M   T   Q   S   P   S   S   L   S   A   S   V   G
  1   GAC ATC CAG ATG ACC CAG TCT CCA TCC TCC CTG TCT GCA TCT GTA GGA
      CTG TAG GTC TAC TGG GTC AGA GGT AGG AGG GAC AGA CGT AGA CAT CCT

D   R   V   T   I   T   C   R   A   S   Q   S   I   S   S   Y
 49   GAC CGT GTC ACC ATC ACT TGC CGG GCA AGT CAG AGC ATT AGC AGC TAT
      CTG GCA CAG TGG TAG TGA ACG GCC CGT TCA GTC TCG TAA TCG TCG ATA

L   N   W   Y   Q   Q   K   P   G   K   A   P   K   L   L   I
 97   TTA AAT TGG TAC CAG CAG AAA CCA GGG AAA GCC CCT AAG CTC CTG ATC
      AAT TTA ACC ATG GTC GTC TTT GGT CCC TTT CGG GGA TTC GAG GAC TAG

Y   A   A   S   L   Q   S   G   V   P   S   R   F   S   G
145   TAT GCT GCA TCC AGT TTG CAA AGT GGG GTC CCA TCA CGT TTC AGT GGC
      ATA CGA CGT AGG TCA AAC GTT TCA CCC CAG GGT AGT GCA AAG TCA CCG

S   G   S   G   T   D   F   T   L   T   I   S   S   L   Q   P
193   AGT GGA TCT GGG ACA GAT TTC ACT CTC ACC ATC AGC AGT CTG CAA CCT
      TCA CCT AGA CCC TGT CTA AAG TGA GAG TGG TAG TCG TCA GAC GTT GGA

E   D   F   A   T   Y   Y   C   Q   Q   S   Y   S   T   P   N
241   GAA GAT TTT GCT ACG TAC TAC TGT CAA CAG AGT TAC AGT ACC CCT AAT
      CTT CTA AAA CGA TGC ATG ATG ACA GTT GTC TCA ATG TCA TGG GGA TTA

T   F   G   Q   G   T   K   V   E   I   K   R
289   ACG TTC GGC CAA GGG ACC AAG GTG GAA ATC AAA CGG
      TGC AAG CCG GTT CCC TGG TTC CAC CTT TAG TTT GCC
```

FIG. 16

Nucleotide and amino acid sequence of anti MSA dAbs MSA 16 and MSA 26

A: MSA 16

```
GAC ATC CAG ATG ACC CAG TCT CCA TCC TCC CTG TCT GCA TCT
 D   I   Q   M   T   Q   S   P   S   S   L   S   A   S

GTA GGA GAC CGT GTC ACC ATC ACT TGC CGG GCA AGT CAG AGC
 V   G   D   R   V   T   I   T   C   R   A   S   Q   S

ATT ATT AAG CAT TTA AAG TGG TAC CAG CAG AAA CCA GGG AAA
 I   I   K   H   L   K   W   Y   Q   Q   K   P   G   K

GCC CCT AAG CTC CTG ATC TAT GGT GCA TCC CGG TTG CAA AGT
 A   P   K   L   L   I   Y   G   A   S   R   L   Q   S

GGG GTC CCA TCA CGT TTC AGT GGC AGT GGA TCT GGG ACA GAT
 G   V   P   S   R   F   S   G   S   G   S   G   T   D

TTC ACT CTC ACC ATC AGC AGT CTG CAA CCT GAA GAT TTT GCT
 F   T   L   T   I   S   S   L   Q   P   E   D   F   A

ACG TAC TAC TGT CAA CAG GGG GCT CGG TGG CCT CAG ACG TTC
 T   Y   Y   C   Q   Q   G   A   R   W   P   Q   T   F

GGC CAA GGG ACC AAG GTG GAA ATC AAA CGG
 G   Q   G   T   K   V   E   I   K   R
```

B: MSA 26

```
GAC ATC CAG ATG ACC CAG TCT CCA TCC TCC CTG TCT GCA TCT
 D   I   Q   M   T   Q   S   P   S   S   L   S   A   S

GTA GGA GAC CGT GTC ACC ATC ACT TGC CGG GCA AGT CAG AGC
 V   G   D   R   V   T   I   T   C   R   A   S   Q   S

ATT TAT TAT CAT TTA AAG TGG TAC CAG CAG AAA CCA GGG AAA
 I   Y   Y   H   L   K   W   Y   Q   Q   K   P   G   K

GCC CCT AAG CTC CTG ATC TAT AAG GCA TCC ACG TTG CAA AGT
 A   P   K   L   L   I   Y   K   A   S   T   L   Q   S

GGG GTC CCA TCA CGT TTC AGT GGC AGT GGA TCT GGG ACA GAT
 G   V   P   S   R   F   S   G   S   G   S   G   T   D

TTC ACT CTC ACC ATC AGC AGT CTG CAA CCT GAA GAT TTT GCT
 F   T   L   T   I   S   S   L   Q   P   E   D   F   A

ACG TAC TAC TGT CAA CAG GTT CGG AAG GTG CCT CGG ACG TTC
 T   Y   Y   C   Q   Q   V   R   K   V   P   R   T   F

GGC CAA GGG ACC AAG GTG GAA ATC AAA CGG
 G   Q   G   T   K   V   E   I   K   R
```

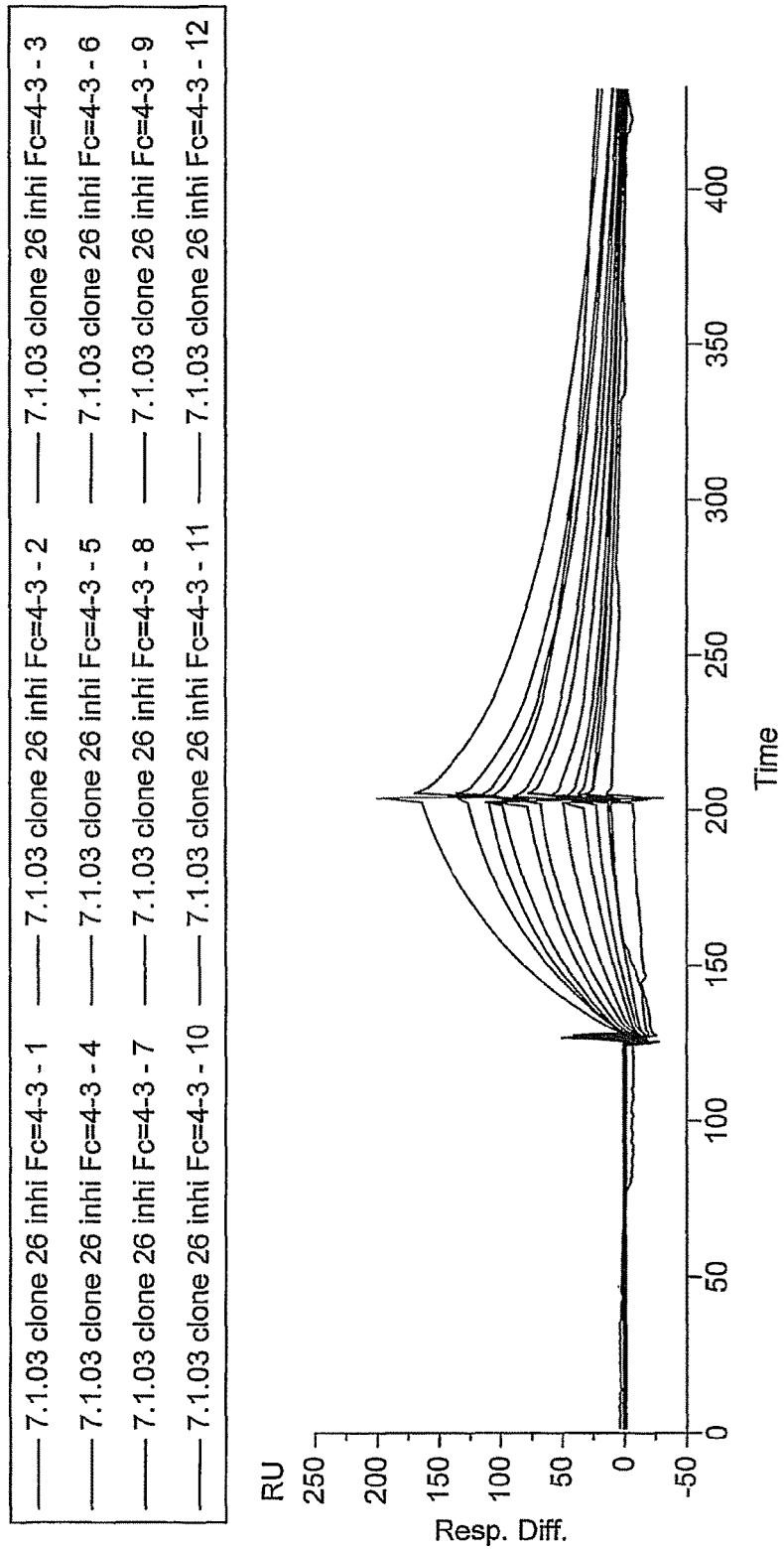

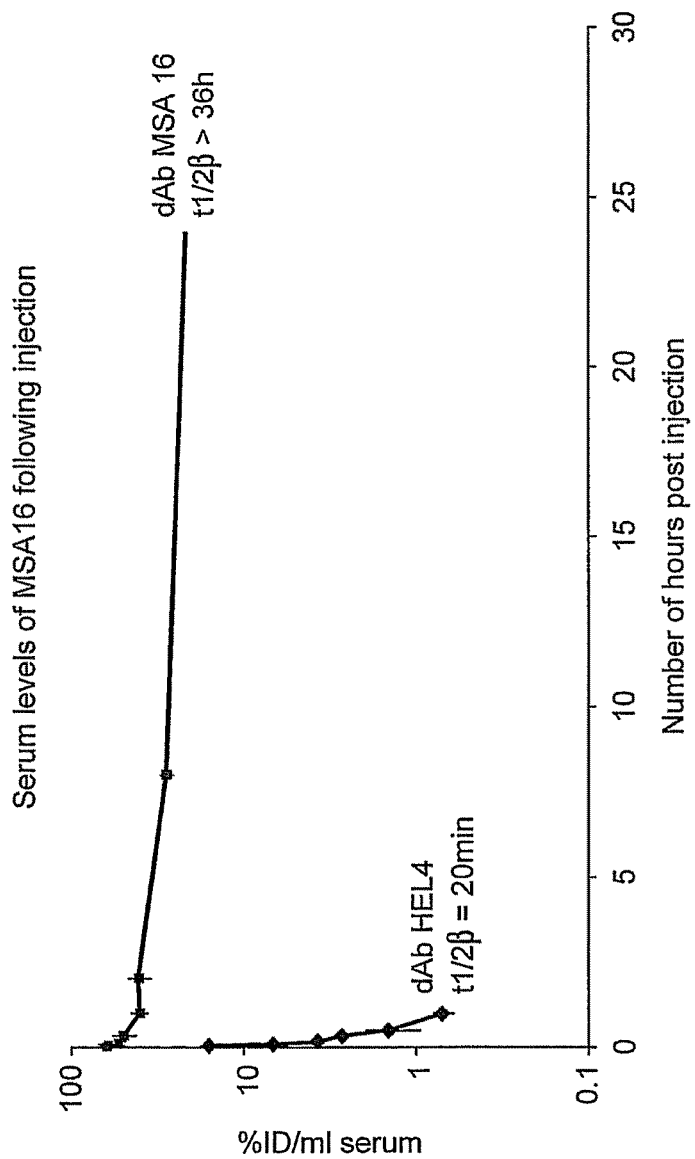

FIG. 19
(a)
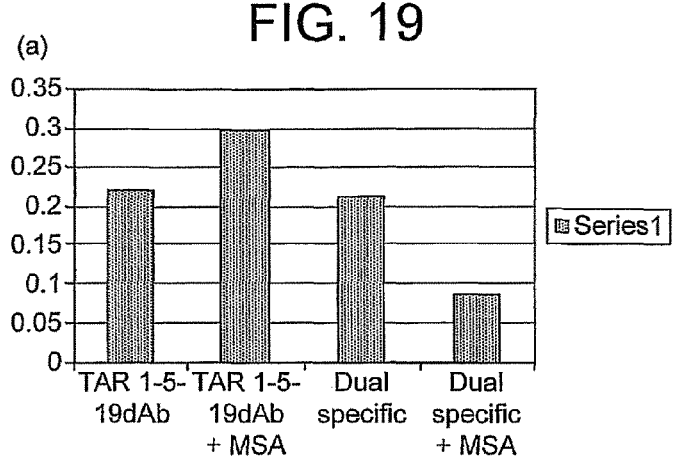
(b)
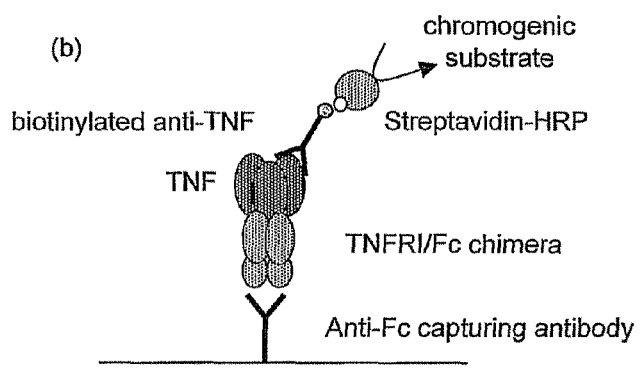
(c)
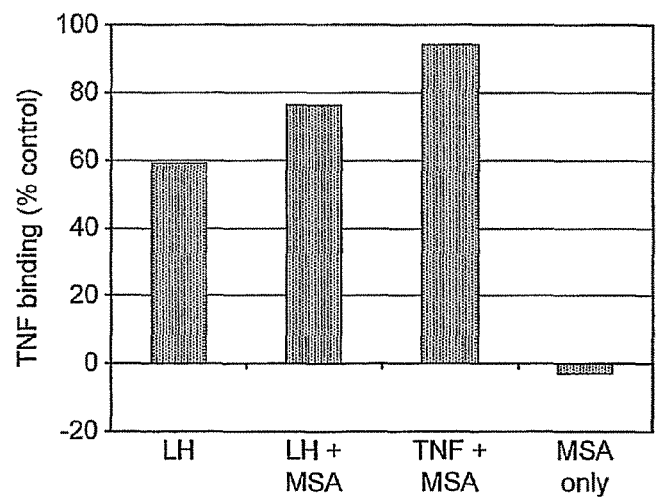

```
                  7                                                        56
HSAD1      (7)    DAHKS-----SVAHRFKDLGEENFKALVLIAFAQYLQQCPFEDHVKLVNEV
HSAD2      (7)    GKASSAKQRLKCASLQKFGERAFKAWAVARLSQRFPKAEFAEVSKLVTDL
HSAD3      (7)    VEEPQNLIKQNCELFEQLGEYKFQNALLVRYTKKVPQVSTPTLVEVSRNL
Consensus  (7)         S   K   C   F   LGE  FKA LLIRFSQKLPQ   F DLVKLV DL 57                                                       106
HSAD1      (53)   TEFAKICVAD--ESAENCDKSLHTLFGDKLCFVATLRETYGEMADCCAKQ
HSAD2      (57)   TKVHIECCHG---DLLECADDRADLAK--Y-ICEMQDSISSKLHECCEKP
HSAD3      (57)   GKVGSKCCKHPEAKRMPCAEDYLSVVLNQLCVLHEKIPVSDRVTKCCTES
Consensus  (57)   TKVAS CC     L CADD SL    LCIL     IS KL DCC K 107                                                      156
HSAD1      (101)  RPERNECFLQHKDDNPNLPRLVRPEVDVM----CTAFHDNEETFLKKYLY
HSAD2      (101)  LLEKSHCIAEVENDEMPADLPSLAADFVESKDVCKNYAEAKDVFLGMFLY
HSAD3      (107)  LVNRRPCFSALEVDEIYVPKEFNAETFTFHADICTLSEKERQIKKQTALV
Consensus  (107)  LLER CFA LE DE  LPK    AE FV    DICT F D KDIFL FLY 157                                                      206
HSAD1      (147)  EIARRHPYFYAPELLFFAKRYKAAFTECCQAADKAACLLPKLDELRDEGK
HSAD2      (151)  SYAPRHPDYSVVLLLRLAKTYETTLEKCCAAADPHECTAKVFDEFKPLVE
HSAD3      (157)  ELVKHKFKATKEQLAKAVNDDFAAFVEKCCKADDKETCFAEEGKKLVAASQ
Consensus  (157)  EIARRHP FS   LL LAK Y A LEKCC AADK   CFA    DELK 207
HSAD1      (197)  ASSAKQR
HSAD2      (202)  EP-----
HSAD3      (207)  AALG---
Consensus  (207)  AA A
```

LIGAND

RELATED APPLICATIONS

This application is a continuation in part of U.S. application Ser. No. 11/023,959, filed Dec. 28, 2004, which is a continuation of International Application PCT/GB2003/002804, filed 30 Jun. 2003, which claims the priority of PCT/GB02/03014, filed 28 Jun. 2002 and Great Britain Application GB 0230202.4, filed 27 Dec. 2002, the contents of which are incorporated herein by reference. This application is also a continuation in part of WO2005118642, filed May 31, 2005, which claims the benefit of U.S. 60/576,271 filed Jun. 1, 2004, and U.S. 60/632,361 filed Dec. 2, 2004, the contents of which are incorporated herein by reference.

The present invention relates to dual specific ligands. In particular, the invention provides a method for the preparation of dual-specific ligands comprising a first immunoglobulin single variable domain binding to a first antigen or epitope, and a second immunoglobulin single variable domain binding to a second antigen or epitope. More particularly, the invention relates to dual-specific ligands wherein binding to at least one of the first and second antigens or epitopes acts to increase the half-life of the ligand in vivo. Open and closed conformation ligands comprising more than one binding specificity are described.

INTRODUCTION

The antigen binding domain of an antibody comprises two separate regions: a heavy chain variable domain ($V_H$) and a light chain variable domain ($V_L$: which can be either $V_\kappa$ or $V_\lambda$). The antigen binding site itself is formed by six polypeptide loops: three from $V_H$ domain (H1, H2 and H3) and three from $V_L$ domain (L1, L2 and L3). A diverse primary repertoire of V genes that encode the $V_H$ and $V_L$ domains is produced by the combinatorial rearrangement of gene segments. The $V_H$ gene is produced by the recombination of three gene segments, $V_H$, D and $J_H$. In humans, there are approximately 51 functional $V_H$ segments (Cook and Tomlinson (1995) *Immunol Today*, 16: 237), 25 functional D segments (Corbett et al. (1997) *J. Mol. Biol.*, 268: 69) and 6 functional $J_H$ segments (Ravetch et al. (1981) *Cell*, 27: 583), depending on the haplotype. The $V_H$ segment encodes the region of the polypeptide chain which forms the first and second antigen binding loops of the $V_H$ domain (H1 and H2), whilst the $V_H$, D and $J_H$ segments combine to form the third antigen binding loop of the $V_H$ domain (H3). The $V_L$ gene is produced by the recombination of only two gene segments, $V_L$ and $J_L$. In humans, there are approximately 40 functional $V_\kappa$ segments (Schable and Zachau (1993) *Biol. Chem. Hoppe-Seyler*, 374: 1001), 31 functional $V_\lambda$ segments (Williams et al. (1996) *J. Mol. Biol.*, 264: 220; Kawasaki et al. (1997) *Genome Res.*, 7: 250), 5 functional $J_\kappa$ segments (Hieter et al. (1982) *J. Biol. Chem.*, 257: 1516) and 4 functional $J_\lambda$ segments (Vasicek and Leder (1990) *J. Exp. Med.*, 172: 609), depending on the haplotype. The $V_L$ segment encodes the region of the polypeptide chain which forms the first and second antigen binding loops of the $V_L$ domain (L1 and L2), whilst the $V_L$ and $J_L$ segments combine to form the third antigen binding loop of the $V_L$ domain (L3). Antibodies selected from this primary repertoire are believed to be sufficiently diverse to bind almost all antigens with at least moderate affinity. High affinity antibodies are produced by "affinity maturation" of the rearranged genes, in which point mutations are generated and selected by the immune system on the basis of improved binding.

Analysis of the structures and sequences of antibodies has shown that five of the six antigen binding loops (H1, H2, L1, L2, L3) possess a limited number of main-chain conformations or canonical structures (Chothia and Lesk (1987) *J. Mol. Biol.*, 196: 901; Chothia et al. (1989) *Nature*, 342: 877). The main-chain conformations are determined by (i) the length of the antigen binding loop, and (ii) particular residues, or types of residue, at certain key position in the antigen binding loop and the antibody framework. Analysis of the loop lengths and key residues has enabled us to the predict the main-chain conformations of H1, H2, L1, L2 and L3 encoded by the majority of human antibody sequences (Chothia et al. (1992) *J. Mol. Biol.*, 227: 799; Tomlinson et al. (1995) *EMBO J.*, 14: 4628; Williams et al. (1996) *J. Mol. Biol.*, 264: 220). Although the H3 region is much more diverse in terms of sequence, length and structure (due to the use of D segments), it also forms a limited number of main-chain conformations for short loop lengths which depend on the length and the presence of particular residues, or types of residue, at key positions in the loop and the antibody framework (Martin et al. (1996) *J. Mol. Biol.*, 263: 800; Shirai et al. (1996) *FEBS Letters*, 399: 1.

Bispecific antibodies comprising complementary pairs of $V_H$ and $V_L$ regions are known in the art. These bispecific antibodies must comprise two pairs of $V_H$ and $V_L$s, each $V_H/V_L$ pair binding to a single antigen or epitope. Methods described involve hybrid hybridomas (Milstein & Cuello A C, Nature 305:537-40), minibodies (Hu et al., (1996) Cancer Res 56:3055-3061), diabodies (Holliger et al., (1993) Proc. Natl. Acad. Sci. USA 90, 6444-6448; WO 94/13804), chelating recombinant antibodies (CRAbs; (Neri et al., (1995) J. Mol. Biol. 246, 367-373), biscFv (e.g. Atwell et al., (1996) Mol. Immunol. 33, 1301-1312), "knobs in holes" stabilised antibodies (Carter et al., (1997) Protein Sci. 6, 781-788). In each case each antibody species comprises two antigen-binding sites, each fashioned by a complementary pair of $V_H$ and $V_L$ domains. Each antibody is thereby able to bind to two different antigens or epitopes at the same time, with the binding to EACH antigen or epitope mediated by a $V_H$ and its complementary $V_L$ domain. Each of these techniques presents its particular disadvantages; for instance in the case of hybrid hybridomas, inactive $V_H/V_L$ pairs can greatly reduce the fraction of bispecific IgG. Furthermore, most bispecific approaches rely on the association of the different $V_H/V_L$ pairs or the association of $V_H$ and $V_L$ chains to recreate the two different $V_H/V_L$ binding sites. It is therefore impossible to control the ratio of binding sites to each antigen or epitope in the assembled molecule and thus many of the assembled molecules will bind to one antigen or epitope but not the other. In some cases it has been possible to engineer the heavy or light chains at the sub-unit interfaces (Carter et al., 1997) in order to improve the number of molecules which have binding sites to both antigens or epitopes but this never results in all molecules having binding to both antigens or epitopes.

There is some evidence that two different antibody binding specificities might be incorporated into the same binding site, but these generally represent two or more specificities that correspond to structurally related antigens or epitopes or to antibodies that are broadly cross-reactive. For example, cross-reactive antibodies have been described, usually where the two antigens are related in sequence and structure, such as hen egg white lysozyme and turkey lysozyme (McCafferty et al., WO 92/01047) or to free hapten and to hapten conjugated to carrier (Griffiths A D et al. *EMBO J* 1994 13:14 3245-60). In a further example, WO 02/02773 (Abbott Laboratories) describes antibody molecules with "dual specificity". The antibody molecules referred to are antibodies raised or selected against multiple antigens, such that their specificity spans more than a single antigen. Each complementary $V_H/V_L$ pair in the antibodies of WO 02/02773 specifies a single binding specificity for two or more structurally related antigens; the $V_H$ and $V_L$ domains in such complementary pairs do not each possess a separate specificity. The antibodies thus have a broad single specificity which encompasses two antigens, which are structurally related. Furthermore natural autoantibodies have been described that are polyreactive (Casali & Notkins, Ann. Rev. Immunol. 7, 515-531), reacting with at least two (usually more) different antigens or epitopes that are not structurally related. It has also been shown that selections of random peptide repertoires using phage display technology on a monoclonal antibody will identify a range of peptide sequences that fit the antigen binding site. Some of the sequences are highly related, fitting a consensus sequence, whereas others are very different and have been termed mimotopes (Lane & Stephen, Current Opinion in Immunology, 1993, 5, 268-271). It is therefore clear that a natural four-chain antibody, comprising associated and complementary $V_H$ and $V_L$ domains, has the potential to bind to many different antigens from a large universe of known antigens. It is less clear how to create a binding site to two given antigens in the same antibody, particularly those which are not necessarily structurally related.

Protein engineering methods have been suggested that may have a bearing on this. For example it has also been proposed that a catalytic antibody could be created with a binding activity to a metal ion through one variable domain, and to a hapten (substrate) through contacts with the metal ion and a complementary variable domain (Barbas et al., 1993 Proc. Natl. Acad. Sci. USA 90, 6385-6389). However in this case, the binding and catalysis of the substrate (first antigen) is proposed to require the binding of the metal ion (second antigen). Thus the binding to the $V_H/V_L$ pairing relates to a single but multi-component antigen.

Methods have been described for the creation of bispecific antibodies from camel antibody heavy chain single domains in which binding contacts for one antigen are created in one variable domain, and for a second antigen in a second variable domain. However, the variable domains were not complementary. Thus a first heavy chain variable domain is selected against a first antigen, and a second heavy chain variable domain against a second antigen, and then both domains are linked together on the same chain to give a bispecific antibody fragment (Conrath et al., J. Biol. Chem. 270, 27589-27594). However, the camel heavy chain single domains are unusual in that they are derived from natural camel antibodies which have no light chains, and indeed the heavy chain single domains are unable to associate with camel light chains to form complementary $V_H$ and $V_L$ pairs.

Single heavy chain variable domains have also been described, derived from natural antibodies which are normally associated with light chains (from monoclonal antibodies or from repertoires of domains; see EP-A-0368684). These heavy chain variable domains have been shown to interact specifically with one or more related antigens, but have not been combined with other heavy or light chain variable domains to create a ligand with a specificity for two or more different antigens. Furthermore, these single domains have been shown to have a very short in vivo half-life. Therefore such domains are of limited therapeutic value.

It has been suggested to make bispecific antibody fragments by linking heavy chain variable domains of different specificity together (as described above). The disadvantage with this approach is that isolated antibody variable domains may have a hydrophobic interface that normally makes interactions with the light chain and is exposed to solvent and may be "sticky" allowing the single domain to bind to hydrophobic surfaces. Furthermore, in the absence of a partner light chain the combination of two or more different heavy chain variable domains and their association, possibly via their hydrophobic interfaces, may prevent them from binding to one if not both of the ligands they are able to bind in isolation. Moreover, in this case the heavy chain variable domains would not be associated with complementary light chain variable domains and thus may be less stable and readily unfold (Worn & Pluckthun, 1998 Biochemistry 37, 13120-7).

SUMMARY OF THE INVENTION

The inventors have described, in their copending international patent application WO 03/002609 as well as copending unpublished UK patent application 0230203.2, dual specific immunoglobulin ligands which comprise immunoglobulin single variable domains which each have different specificities. The domains may act in competition with each other or independently to bind antigens or epitopes on target molecules.

In a first configuration, the present invention provides a further improvement in dual specific ligands as developed by the present inventors, in which one specificity of the ligand is directed towards a protein or polypeptide present in vivo in an organism which can act to increase the half-life of the ligand by binding to it.

Accordingly, in a first aspect, there is provided a dual-specific ligand comprising a first immunoglobulin single variable domain having a binding specificity to a first antigen or epitope and a second complementary immunoglobulin single variable domain having a binding activity to a second antigen or epitope, wherein one or both of said antigens or epitopes acts to increase the half-life of the ligand in vivo and wherein said first and second domains lack mutually complementary domains which share the same specificity, provided that said dual specific ligand does not consist of an anti-HSA $V_H$ domain and an anti-$\beta$ galactosidase $V_\kappa$ domain. Preferably, neither of the first or second variable domains binds to human serum albumin (HSA).

Antigens or epitopes which increase the half-life of a ligand as described herein are advantageously present on proteins or polypeptides found in an organism in vivo. Examples include extracellular matrix proteins, blood proteins, and proteins present in various tissues in the organism. The proteins act to reduce the rate of ligand clearance from the blood, for example by acting as bulking agents, or by anchoring the ligand to a desired site of action. Examples of antigens/epitopes which increase half-life in vivo are given in Annex 1 below.

Increased half-life is useful in in vivo applications of immunoglobulins, especially antibodies and most especially antibody fragments of small size. Such fragments (Fvs, disulphide bonded Fvs, Fabs, scFvs, dAbs) suffer from rapid clearance from the body; thus, whilst they are able to reach most parts of the body rapidly, and are quick to produce and easier to handle, their in vivo applications have been limited by their only brief persistence in vivo. The invention solves this problem by providing increased half-life of the ligands in vivo and consequently longer persistence times in the body of the functional activity of the ligand.

Methods for pharmacokinetic analysis and determination of ligand half-life will be familiar to those skilled in the art. Details may be found in Kenneth, A et al: Chemical Stability of Pharmaceuticals: A Handbook for Pharmacists and in Peters et al, Pharmacokinetc analysis: A Practical Approach (1996). Reference is also made to "Pharmacokinetics", M Gibaldi & D Perron, published by Marcel Dekker, $2^{nd}$ Rev. ex edition (1982), which describes pharmacokinetic parameters such as t alpha and t beta half lives and area under the curve (AUC).

Half lives (t½ alpha and t½ beta) and AUC can be determined from a curve of serum concentration of ligand against time. The WinNonlin analysis package (available from Pharsight Corp., Mountain View, Calif. 94040, USA) can be used, for example, to model the curve. In a first phase (the alpha phase) the ligand is undergoing mainly distribution in the patient, with some elimination. A second phase (beta phase) is the terminal phase when the ligand has been distributed and the serum concentration is decreasing as the ligand is cleared from the patient. The t alpha half life is the half life of the first phase and the t beta half life is the half life of the second phase. Thus, advantageously, the present invention provides a ligand or a composition comprising a ligand according to the invention having a tα half-life in the range of 15 minutes or more. In one embodiment, the lower end of the range is 30 minutes, 45 minutes, 1 hour, 2 hours, 3 hours, 4 hours, 5 hours, 6 hours, 7 hours, 10 hours, 11 hours or 12 hours. In addition, or alternatively, a ligand or composition according to the invention will have a tα half life in the range of up to and including 12 hours. In one embodiment, the upper end of the range is 11, 10, 9, 8, 7, 6 or 5 hours. An example of a suitable range is 1 to 6 hours, 2 to 5 hours or 3 to 4 hours.

Advantageously, the present invention provides a ligand or a composition comprising a ligand according to the invention having a tβ half-life in the range of 2.5 hours or more. In one embodiment, the lower end of the range is 3 hours, 4 hours, 5 hours, 6 hours, 7 hours, 10 hours, 11 hours, or 12 hours. In addition, or alternatively, a ligand or composition according to the invention has a tβ half-life in the range of up to and including 21 days. In one embodiment, the upper end of the range is 12 hours, 24 hours, 2 days, 3 days, 5 days, 10 days, 15 days or 20 days. Advantageously a ligand or composition according to the invention will have a tβ half life in the range 12 to 60 hours. In a further embodiment, it will be in the range 12 to 48 hours. In a further embodiment still, it will be in the range 12 to 26 hours.

In addition, or alternatively to the above criteria, the present invention provides a ligand or a composition comprising a ligand according to the invention having an AUC value (area under the curve) in the range of 1 mg/min/ml or more. In one embodiment, the lower end of the range is 5, 10, 15, 20, 30, 100, 200 or 300 mg/min/ml. In addition, or alternatively, a ligand or composition according to the invention has an AUC in the range of up to 600 mg/min/ml. In one embodiment, the upper end of the range is 500, 400, 300, 200, 150, 100, 75 or 50 mg/min/ml. Advantageously, a ligand according to the invention will have a AUC in the range selected from, but preferably not limited to, the group consisting of the following: 15 to 150 mg/min/ml, 15 to 100 mg/min/ml, 15 to 75 mg/min/ml, and 15 to 50 mg/min/ml.

In a first embodiment, the dual specific ligand comprises two complementary variable domains, i.e. two variable domains that, in their natural environment, are capable of operating together as a cognate pair or group, even if in the context of the present invention they bind separately to their cognate epitopes. For example, the complementary variable domains may be immunoglobulin heavy chain and light chain variable domains ($V_H$ and $V_L$). $V_H$ and $V_L$ domains are advantageously provided by scFv or Fab antibody fragments. Variable domains may be linked together to form multivalent ligands by, for example: provision of a hinge region at the C-terminus of each V domain and disulphide bonding between cysteines in the hinge regions; or provision of dAbs each with a cysteine at the C-terminus of the domain, the cysteines being disulphide bonded together; or production of V-CH & V-CL to produce a Fab format; or use of peptide linkers (for example, Gly$_4$Ser linkers (SEQ ID NO: 1) discussed herein below) to produce dimers, trimers and further multimers.

The inventors have found that the use of complementary variable domains allows the two domain surfaces to pack together and be sequestered from the solvent. Furthermore, the complementary domains are able to stabilise each other. In addition, it allows the creation of dual-specific IgG antibodies without the disadvantages of hybrid hybridomas as used in the prior art, or the need to engineer heavy or light chains at the sub-unit interfaces. The dual-specific ligands of the first aspect of the present invention have at least one $V_H/V_L$ pair. A bispecific IgG according to this invention will therefore comprise two such pairs, one pair on each arm of the Y-shaped molecule. Unlike conventional bispecific antibodies or diabodies, therefore, where the ratio of chains used is determinative in the success of the preparation thereof and leads to practical difficulties, the dual specific ligands of the invention are free from issues of chain balance. Chain imbalance in conventional bi-specific antibodies results from the association of two different $V_L$ chains with two different $V_H$ chains, where $V_L$ chain 1 together with $V_H$ chain 1 is able to bind to antigen or epitope 1 and $V_L$ chain 2 together with $V_H$ chain 2 is able to bind to antigen or epitope 2 and the two correct pairings are in some way linked to one another. Thus, only when $V_L$ chain 1 is paired with $V_H$ chain 1 and $V_L$ chain 2 is paired with $V_H$ chain 2 in a single molecule is bi-specificity created. Such bi-specific molecules can be created in two different ways. Firstly, they can be created by association of two existing $V_H/V_L$ pairings that each bind to a different antigen or epitope (for example, in a bi-specific IgG). In this case the $V_H/V_L$ pairings must come all together in a 1:1 ratio in order to create a population of molecules all of which are bi-specific. This never occurs (even when complementary CH domain is enhanced by "knobs into holes" engineering) leading to a mixture of bi-specific molecules and molecules that are only able to bind to one antigen or epitope but not the other. The second way of creating a bi-specific antibody is by the simultaneous association of two different $V_H$ chain with two different $V_L$ chains (for example in a bi-specific diabody). In this case, although there tends to be a preference for $V_L$ chain 1 to pair with $V_H$ chain 1 and $V_L$ chain 2 to pair with $V_H$ chain 2 (which can be enhanced by "knobs into holes" engineering of the $V_L$ and $V_H$ domains), this paring is never achieved in all molecules, leading to a mixed formulation whereby incorrect pairings occur that are unable to bind to either antigen or epitope.

Bi-specific antibodies constructed according to the dual-specific ligand approach according to the first aspect of the present invention overcome all of these problems because the binding to antigen or epitope 1 resides within the $V_H$ or $V_L$ domain and the binding to antigen or epitope 2 resides with the complementary $V_L$ or $V_H$ domain, respectively. Since $V_H$ and $V_L$ domains pair on a 1:1 basis all $V_H/V_L$ pairings will be bi-specific and thus all formats constructed using these $V_H/V_L$ pairings (Fv, scFvs, Fabs, minibodies, IgGs, etc.) will have 100% bi-specific activity.

In the context of the present invention, first and second "epitopes" are understood to be epitopes which are not the same and are not bound by a single monospecific ligand. In the first configuration of the invention, they are advantageously on different antigens, one of which acts to increase the half-life of the ligand in vivo. Likewise, the first and second antigens are advantageously not the same.

The dual specific ligands of the invention do not include ligands as described in WO 02/02773. Thus, the ligands of the present invention do not comprise complementary $V_H/V_L$ pairs which bind any one or more antigens or epitopes cooperatively. Instead, the ligands according to the first aspect of the invention comprise a $V_H/V_L$ complementary pair, wherein the V domains have different specificities.

Moreover, the ligands according to the first aspect of the invention comprise $V_H/V_L$ complementary pairs having different specificities for non-structurally related epitopes or antigens. Structurally related epitopes or antigens are epitopes or antigens which possess sufficient structural similarity to be bound by a conventional $V_H/V_L$ complementary pair which acts in a co-operative manner to bind an antigen or epitope; in the case of structurally related epitopes, the epitopes are sufficiently similar in structure that they "fit" into the same binding pocket formed at the antigen binding site of the $V_H/V_L$ dimer.

In a second aspect, the present invention provides a ligand comprising a first immunoglobulin variable domain having a first antigen or epitope binding specificity and a second immunoglobulin variable domain having a second antigen or epitope binding specificity, wherein one or both of said first and second variable domains bind to an antigen which increases the half-life of the ligand in vivo, and the variable domains are not complementary to one another.

In one embodiment, binding to one variable domain modulates the binding of the ligand to the second variable domain.

In this embodiment, the variable domains may be, for example, pairs of $V_H$ domains or pairs of $V_L$ domains. Binding of antigen at the first site may modulate, such as enhance or inhibit, binding of an antigen at the second site. For example, binding at the first site at least partially inhibits binding of an antigen at a second site. In such an embodiment, the ligand may for example be maintained in the body of a subject organism in vivo through binding to a protein which increases the half-life of the ligand until such a time as it becomes bound to the second target antigen and dissociates from the half-life increasing protein.

Modulation of binding in the above context is achieved as a consequence of the structural proximity of the antigen binding sites relative to one another. Such structural proximity can be achieved by the nature of the structural components linking the two or more antigen binding sites, e.g., by the provision of a ligand with a relatively rigid structure that holds the antigen binding sites in close proximity. Advantageously, the two or more antigen binding sites are in physically close proximity to one another such that one site modulates the binding of antigen at another site by a process which involves steric hindrance and/or conformational changes within the immunoglobulin molecule.

The first and the second antigen binding domains may be associated either covalently or non-covalently. In the case that the domains are covalently associated, then the association may be mediated for example by disulphide bonds or by a polypeptide linker such as $(Gly_4Ser)_n$ (SEQ ID NO: 2), where n=from 1 to 8, e.g., 2, 3, 4, 5 or 7.

Ligands according to the invention may be combined into non-immunoglobulin multi-ligand structures to form multivalent complexes, which bind target molecules with the same antigen, thereby providing superior avidity, while at least one variable domain binds an antigen to increase the half life of the multimer. For example, natural bacterial receptors such as SpA have been used as scaffolds for the grafting of CDRs to generate ligands which bind specifically to one or more epitopes. Details of this procedure are described in U.S. Pat. No. 5,831,012. Other suitable scaffolds include those based on fibronectin and Affibodies™. Details of suitable procedures are described in WO 98/58965. Other suitable scaffolds include lipocallin and CTLA4, as described in van den Beuken et al., J. Mol. Biol. (2001) 310, 591-601, and scaffolds such as those described in WO0069907 (Medical Research Council), which are based for example on the ring structure of bacterial GroEL or other chaperone polypeptides.

Protein scaffolds may be combined; for example, CDRs may be grafted on to a CTLA4 scaffold and used together with immunoglobulin $V_H$ or $V_L$ domains to form a ligand. Likewise, fibronectin, lipocallin and other scaffolds may be combined.

In the case that the variable domains are selected from V-gene repertoires selected for instance using phage display technology as herein described, then these variable domains can comprise a universal framework region, such that is they may be recognised by a specific generic ligand as herein defined. The use of universal frameworks, generic ligands and the like is described in WO99/20749. In the present invention, reference to phage display includes the use of both phage and/or phagemids.

Where V-gene repertoires are used, variation in polypeptide sequence is preferably located within the structural loops of the variable domains. The polypeptide sequences of either variable domain may be altered by DNA shuffling or by mutation in order to enhance the interaction of each variable domain with its complementary pair.

In a preferred embodiment of the invention the 'dual-specific ligand' is a single chain Fv fragment. In an alternative embodiment of the invention, the 'dual-specific ligand' consists of a Fab region of an antibody. The term "Fab region" includes a Fab-like region where two $V_H$ or two $V_L$ domains are used.

The variable domains may be derived from antibodies directed against target antigens or epitopes. Alternatively they may be derived from a repertoire of single antibody domains such as those expressed on the surface of filamentous bacteriophage. Selection may be performed as described below.

In a third aspect, the invention provides a method for producing a ligand comprising a first immunoglobulin single variable domain having a first binding specificity and a second single immunoglobulin single variable domain having a second (different) binding specificity, one or both of the binding specificities being specific for an antigen which increases the half-life of the ligand in vivo, the method comprising the steps of:

(a) selecting a first variable domain by its ability to bind to a first epitope,
(b) selecting a second variable domain by its ability to bind to a second epitope,
(c) combining the variable domains; and
(d) selecting the ligand by its ability to bind to said first epitope and to said second epitope.

The ligand can bind to the first and second epitopes either simultaneously or, where there is competition between the binding domains for epitope binding, the binding of one domain may preclude the binding of another domain to its cognate epitope. In one embodiment, therefore, step (d) above requires simultaneous binding to both first and second (and possibly further) epitopes; in another embodiment, the binding to the first and second epitopes is not simultaneous.

The epitopes are preferably on separate antigens.

Ligands advantageously comprise $V_H/V_L$ combinations, or $V_H/V_H$ or $V_L/V_L$ combinations of immunoglobulin variable domains, as described above. The ligands may moreover comprise camelid $V_{HH}$ domains, provided that the $V_{HH}$ domain which is specific for an antigen which increases the half-life of the ligand in vivo does not bind Hen egg white lysozyme (HEL), porcine pancreatic alpha-amylase or NmC-A; hcg, BSA-linked RR6 azo dye or *S. mutans* HG982 cells, as described in Conrath et al., (2001) JBC 276:7346-7350 and WO99/23221, neither of which describe the use of a specificity for an antigen which increases half-life to increase the half life of the ligand in vivo.

In one embodiment, said first variable domain is selected for binding to said first epitope in absence of a complementary variable domain. In a further embodiment, said first variable domain is selected for binding to said first epitope/antigen in the presence of a third variable domain in which said third variable domain is different from said second variable domain and is complementary to the first domain. Similarly, the second domain may be selected in the absence or presence of a complementary variable domain.

Antigens or epitopes targeted by the ligands of the invention which increase the half-life of a ligand, are not limited to serum albumin targets. Other embodiments of antigens or epitopes targeted by the ligands of the invention which increase the half-life of a ligand in vivo include, but are preferably not limited to, those antigens and epitopes listed in Annex 1 below The antigens or epitopes targeted by the ligands of the invention, in addition to the half-life enhancing protein, may be any antigen or epitope, but advantageously is an antigen or epitope that is targeted with therapeutic benefit. The invention provides ligands, including open conformation, closed conformation and isolated dAb monomer ligands, specific for any such target, particularly those targets further identified herein. Such targets may be, or be part of, polypeptides, proteins or nucleic acids, which may be naturally occurring or synthetic. In this respect, the ligand of the invention may bind the epitope or antigen and act as an antagonist or agonist (e.g., EPO receptor agonist). One skilled in the art will appreciate that the choice is large and varied. They may be for instance, human or animal proteins, cytokines, cytokine receptors, where cytokine receptors include receptors for cytokines, enzymes, co-factors for enzymes or DNA binding proteins. Suitable cytokines and growth factors include, but are preferably not limited to: ApoE, Apo-SAA, BDNF, Cardiotrophin-1, EGF, EGF receptor, ENA-78, Eotaxin, Eotaxin-2, Exodus-2, EpoR, FGF-acidic, FGF-basic, fibroblast growth factor-10, FLT3 ligand, Fractalkine (CX3C), GDNF, G-CSF, GM-CSF, GF-β1, insulin, IFN-γ, IGF-I, IGF-II, IL-1α, IL-1β, IL-2, IL-3, IL-4, IL-5, IL-6, IL-7, IL-8 (72 a.a.), IL-8 (77 a.a.), IL-9, IL-10, IL-11, IL-12, IL-13, IL-15, IL-16, IL-17, IL-18 (IGIF), Inhibin α, Inhibin β, IP-10, keratinocyte growth factor-2 (KGF-2), KGF, Leptin, LIF, Lymphotactin, Mullerian inhibitory substance, monocyte colony inhibitory factor, monocyte attractant protein, M-CSF, MDC (67 a.a.), MDC (69 a.a.), MCP-1 (MCAF), MCP-2, MCP-3, MCP-4, MDC (67 a.a.), MDC (69 a.a.), MIG, MIP-1α, MIP-1β, MIP-3α, MIP-3β, MIP-4, myeloid progenitor inhibitor factor-1 (MPIF-1), NAP-2, Neurturin, Nerve growth factor, β-NGF, NT-3, NT-4, Oncostatin M, PDGF-AA, PDGF-AB, PDGF-BB, PF-4, RANTES, SDF1α, SDF10, SCF, SCGF, stem cell factor (SCF), TARC, TGF-α, TGF-β, TGF-β2, TGF-β3, tumour necrosis factor (TNF), TNF-α, TNF-β, TNF receptor I, TNF receptor II, TNIL-1, TPO, VEGF, VEGF receptor 1, VEGF receptor 2, VEGF receptor 3, GCP-2, GRO/MGSA, GRO-β, GRO-γ, HCC1, 1-309, HER 1, HER 2, HER 3 and HER 4, CD4, human chemokine receptors CXCR4 or CCR5, non-structural protein type 3 (NS3) from the hepatitis C virus, TNF-alpha, IgE, IFN-gamma, MMP-12, CEA, *H. pylori*, TB, influenza, Hepatitis E, MMP-12, internalizing receptors that are over-expressed on certain cells, such as the epidermal growth factor receptor (EGFR), ErBb2 receptor on tumor cells, an internalising cellular receptor, LDL receptor, FGF2 receptor, ErbB2 receptor, transferrin receptor, PDGF receptor, VEGF receptor, PsmAr, an extracellular matrix protein, elastin, fibronectin, laminin, a 1-antitrypsin, tissue factor protease inhibitor, PDK1, GSK1, Bad, caspase-9, Forkhead, an antigen of *Helicobacter pylori*, an antigen of *Mycobacterium tuberculosis*, and an antigen of influenza virus. It will be appreciated that this list is by no means exhaustive.

In one embodiment of the invention, the variable domains are derived from a respective antibody directed against the antigen or epitope. In a preferred embodiment the variable domains are derived from a repertoire of single variable antibody domains.

In a further aspect, the present invention provides one or more nucleic acid molecules encoding at least a dual-specific ligand as herein defined. The dual specific ligand may be encoded on a single nucleic acid molecule; alternatively, each domain may be encoded by a separate nucleic acid molecule. Where the ligand is encoded by a single nucleic acid molecule, the domains may be expressed as a fusion polypeptide, in the manner of a scFv molecule, or may be separately expressed and subsequently linked together, for example using chemical linking agents. Ligands expressed from separate nucleic acids will be linked together by appropriate means.

The nucleic acid may further encode a signal sequence for export of the polypeptides from a host cell upon expression and may be fused with a surface component of a filamentous bacteriophage particle (or other component of a selection display system) upon expression.

In a further aspect the present invention provides a vector comprising nucleic acid encoding a dual specific ligand according to the present invention.

In a yet further aspect, the present invention provides a host cell transfected with a vector encoding a dual specific ligand according to the present invention.

Expression from such a vector may be configured to produce, for example on the surface of a bacteriophage particle, variable domains for selection. This allows selection of displayed variable domains and thus selection of 'dual-specific ligands' using the method of the present invention.

The present invention further provides a kit comprising at least a dual-specific ligand according to the present invention.

Dual-Specific ligands according to the present invention preferably comprise combinations of heavy and light chain domains. For example, the dual specific ligand may comprise a $V_H$ domain and a $V_L$ domain, which may be linked together in the form of an scFv. In addition, the ligands may comprise one or more CH or CL domains. For example, the ligands may comprise a $C_H1$ domain, $C_H2$ or $C_H3$ domain, and/or a CL domain, Cμ1, Cμ2, Cμ3 or Cμ4 domains, or any combination thereof. A hinge region domain may also be included. Such combinations of domains may, for example, mimic natural antibodies, such as IgG or IgM, or fragments thereof, such as Fv, scFv, Fab or F(ab')$_2$ molecules. Other structures, such as a single arm of an IgG molecule comprising $V_H$, $V_L$, $C_H1$ and $C_L$ domains, are envisaged.

In a preferred embodiment of the invention, the variable regions are selected from single domain V gene repertoires. Generally the repertoire of single antibody domains is displayed on the surface of filamentous bacteriophage. In a preferred embodiment each single antibody domain is selected by binding of a phage repertoire to antigen.

In a preferred embodiment of the invention each single variable domain may be selected for binding to its target antigen or epitope in the absence of a complementary variable region. In an alternative embodiment, the single variable domains may be selected for binding to its target antigen or epitope in the presence of a complementary variable region. Thus, the first single variable domain may be selected in the presence of a third complementary variable domain, and the second variable domain may be selected in the presence of a fourth complementary variable domain. The complementary third or fourth variable domain may be the natural cognate variable domain having the same specificity as the single domain being tested, or a non-cognate complementary domain—such as a "dummy" variable domain.

Preferably, the dual specific ligand of the invention comprises only two variable domains although several such ligands may be incorporated together into the same protein, for example two such ligands can be incorporated into an IgG or a multimeric immunoglobulin, such as IgM. Alternatively, in another embodiment a plurality of dual specific ligands are combined to form a multimer. For example, two different dual specific ligands are combined to create a tetra-specific molecule.

It will be appreciated by one skilled in the art that the light and heavy variable domains of a dual-specific ligand produced according to the method of the present invention may be on the same polypeptide chain, or alternatively, on different polypeptide chains. In the case that the variable domains are on different polypeptide chains, then they may be linked via a linker, generally a flexible linker (such as a polypeptide chain), a chemical linking group, or any other method known in the art.

In a further aspect, the present invention provides a composition comprising a dual-specific ligand, obtainable by a method of the present invention, and a pharmaceutically acceptable carrier, diluent or excipient.

Moreover, the present invention provides a method for the treatment and/or prevention of disease using a 'dual-specific ligand' or a composition according to the present invention.

In a second configuration, the present invention provides multispecific ligands which comprise at least two non-complementary variable domains. For example, the ligands may comprise a pair of $V_H$ domains or a pair of $V_L$ domains. Advantageously, the domains are of non-camelid origin; preferably they are human domains or comprise human framework regions (FWs) and one or more heterologous CDRs. CDRs and framework regions are those regions of an immunoglobulin variable domain as defined in the Kabat database of Sequences of Proteins of Immunological Interest.

Preferred human framework regions are those encoded by germ line gene segments DP47 and DPK9. Advantageously, FW1, FW2 and FW3 of a $V_H$ or $V_L$ domain have the sequence of FW1, FW2 or FW3 from DP47 or DPK9. The human frameworks may optionally contain mutations, for example up to about 5 amino acid changes or up to about 10 amino acid changes collectively in the human frameworks used in the ligands of the invention.

The variable domains in the multispecific ligands according to the second configuration of the invention may be arranged in an open or a closed conformation; that is, they may be arranged such that the variable domains can bind their cognate ligands independently and simultaneously, or such that only one of the variable domains may bind its cognate ligand at any one time.

The inventors have realised that under certain structural conditions, non-complementary variable domains (for example two light chain variable domains or two heavy chain variable domains) may be present in a ligand such that binding of a first epitope to a first variable domain inhibits the binding of a second epitope to a second variable domain, even though such non-complementary domains do not operate together as a cognate pair.

Advantageously, the ligand comprises two or more pairs of variable domains; that is, it comprises at least four variable domains. Advantageously, the four variable domains comprise frameworks of human origin.

In a preferred embodiment, the human frameworks are identical to those of human germ line sequences.

The present inventors consider that such antibodies will be of particular use in ligand binding assays for therapeutic and other uses.

Thus, in a first aspect of the second configuration, the present invention provides a method for producing a multi-specific ligand comprising the steps of:
a) selecting a first epitope binding domain by its ability to bind to a first epitope,
b) selecting a second epitope binding domain by its ability to bind to a second epitope,
c) combining the epitope binding domains; and
d) selecting the closed conformation multispecific ligand by its ability to bind to said first second epitope and said second epitope.

In a further aspect of the second configuration, the invention provides method for preparing a closed conformation multi-specific ligand comprising a first epitope binding domain having a first epitope binding specificity and a non-complementary second epitope binding domain having a second epitope binding specificity, wherein the first and second binding specificities compete for epitope binding such that the closed conformation multi-specific ligand may not bind both epitopes simultaneously, said method comprising the steps of:
a) selecting a first epitope binding domain by its ability to bind to a first epitope,
b) selecting a second epitope binding domain by its ability to bind to a second epitope,
c) combining the epitope binding domains such that the domains are in a closed conformation; and
d) selecting the closed conformation multispecific ligand by its ability to bind to said first second epitope and said second epitope, but not to both said first and second epitopes simultaneously.

Moreover, the invention provides a closed conformation multi-specific ligand comprising a first epitope binding domain having a first epitope binding specificity and a non-complementary second epitope binding domain having a second epitope binding specificity, wherein the first and second binding specificities compete for epitope binding such that the closed conformation multi-specific ligand may not bind both epitopes simultaneously.

An alternative embodiment of the above aspect of the of the second configuration of the invention optionally comprises a further step (b1) comprising selecting a third or further epitope binding domain. In this way the multi-specific ligand produced, whether of open or closed conformation, comprises more than two epitope binding specificities. In a preferred aspect of the second configuration of the invention, where the multi-specific ligand comprises more than two epitope binding domains, at least two of said domains are in a closed conformation and compete for binding; other domains may compete for binding or may be free to associate independently with their cognate epitope(s).

According to the present invention the term 'multi-specific ligand' refers to a ligand which possesses more than one epitope binding specificity as herein defined.

As herein defined the term 'closed conformation' (multi-specific ligand) means that the epitope binding domains of the ligand are attached to or associated with each other, optionally by means of a protein skeleton, such that epitope binding by one epitope binding domain competes with epitope binding by another epitope binding domain. That is, cognate epitopes may be bound by each epitope binding domain individually, but not simultaneously. The closed conformation of the ligand can be achieved using methods herein described.

"Open conformation" means that the epitope binding domains of the ligand are attached to or associated with each other, optionally by means of a protein skeleton, such that epitope binding by one epitope binding domain does not compete with epitope binding by another epitope binding domain.

As referred to herein, the term 'competes' means that the binding of a first epitope to its cognate epitope binding domain is inhibited when a second epitope is bound to its cognate epitope binding domain. For example, binding may be inhibited sterically, for example by physical blocking of a binding domain or by alteration of the structure or environment of a binding domain such that its affinity or avidity for an epitope is reduced.

In a further embodiment of the second configuration of the invention, the epitopes may displace each other on binding. For example, a first epitope may be present on an antigen which, on binding to its cognate first binding domain, causes steric hindrance of a second binding domain, or a conformational change therein, which displaces the epitope bound to the second binding domain.

Advantageously, binding is reduced by 25% or more, advantageously 40%, 50%, 60%, 70%, 80%, 90% or more, and preferably up to 100% or nearly so, such that binding is completely inhibited. Binding of epitopes can be measured by conventional antigen binding assays, such as ELISA, by fluorescence based techniques, including FRET, or by techniques such as surface plasmon resonance which measure the mass of molecules. Specific binding of an antigen-binding protein to an antigen or epitope can be determined by a suitable assay, including, for example, Scatchard analysis and/or competitive binding assays, such as radioimmunoassays (RIA), enzyme immunoassays such as ELISA and sandwich competition assays, and the different variants thereof.

Binding affinity is preferably determined using surface plasmon resonance (SPR) and the Biacore (Karlsson et al., 1991), using a Biacore system (Uppsala, Sweden). The Biacore system uses surface plasmon resonance (SPR, Welford K. 1991, Opt. Quant. Elect. 23:1; Morton and Myszka, 1998, Methods in Enzymology 295: 268) to monitor biomolecular interactions in real time, and uses surface plasmon resonance which can detect changes in the resonance angle of light at the surface of a thin gold film on a glass support as a result of changes in the refractive index of the surface up to 300 nm away. Biacore analysis conveniently generates association rate constants, dissociation rate constants, equilibrium dissociation constants, and affinity constants. Binding affinity is obtained by assessing the association and dissociation rate constants using a Biacore surface plasmon resonance system (Biacore, Inc.). A biosensor chip is activated for covalent coupling of the target according to the manufacturer's (Biacore) instructions. The target is then diluted and injected over the chip to obtain a signal in response units of immobilized material. Since the signal in resonance units (RU) is proportional to the mass of immobilized material, this represents a range of immobilized target densities on the matrix. Dissociation data are fit to a one-site model to obtain $k_{off}$+/−s.d. (standard deviation of measurements). Pseudo-first order rate constant (Kd's) are calculated for each association curve, and plotted as a function of protein concentration to obtain $k_{on}$+/− s.e. (standard error of fit). Equilibrium dissociation constants for binding, Kd's, are calculated from SPR measurements as $k_{off}/k_{on}$.

As described by Phizicky and Field in Microb. Rev. (1995) 59:114-115, a suitable antigen, such as HSA, is immobilized on a dextran polymer, and a solution containing a ligand for HSA, such as a single variable domain, flows through a cell, contacting the immobilized HSA. The single variable domain retained by immobilized HSA alters the resonance angle of impinging light, resulting in a change in refractive index brought about by increased amounts of protein, i.e. the single variable domain, near the dextran polymer. Since all proteins have the same refractive index and since there is a linear correlation between resonance angle shift and protein concentration near the surface, changes in the protein concentration at the surface due to protein/protein binding can be measured, see Phizicky and Field, supra. To determine a binding constant, the increase in resonance units (RU) is measured as a function of time by passing a solution of single variable domain protein past the immobilized ligand (HSA) until the RU values stabilize, then the decrease in RU is measured as a function of time with buffer lacking the single variable domain. This procedure is repeated at several different concentrations of single variable domain protein. Detailed theoretical background and procedures are described by R. Karlsson, et. al. (991) J. Immunol. Methods, 145, 229.

The instrument software produces an equilibrium dissociation constant (Kd) as described above. An equilibrium dissociation constant determined through the use of Surface plasmon resonance is described in U.S. Pat. No. 5,573,957, as being based on a table of $dR_A/dt$ and $R_A$ values, where R in this example is the HSA/single variable domain complex as measured by the Biacore in resonance units and where dR/dt is the rate of formation of HSA/single variable domain complexes, i.e. the derivative of the binding curve; plotting the graph $dR_A/dt$ vs $R_A$ for several different concentrations of single variable domain, and subsequently plotting the slopes of these lines vs. the concentration of single variable domain, the slope of this second graph being the association rate constant ($M^{-1}$, $s^{-1}$). The Dissociation Rate Constant or the rate at which the HSA and the single variable domain release from each other, can be determined utilizing the dissociation curve generated on the Biacore. By plotting and determining the slope of the log of the drop in the response vs time curve, the dissociation rate constant can be measured. The Equilibrium dissociation constant Kd=Dissociation Rate Constant/Association Rate Constant.

According to the method of the present invention, advantageously, each epitope binding single variable domain is of a different epitope binding specificity.

In the context of the present invention, first and second "epitopes" are understood to be epitopes which are not the same and are not bound by a single monospecific ligand. They may be on different antigens or on the same antigen, but separated by a sufficient distance that they do not form a single entity that could be bound by a single mono-specific $V_H/V_L$ binding pair of a conventional antibody. Experimentally, if both of the individual variable domains in single chain antibody form (domain antibodies or dAbs) are separately competed by a monospecific $V_H/V_L$ ligand against two epitopes then those two epitopes are not sufficiently far apart to be considered separate epitopes according to the present invention.

The closed conformation multispecific ligands of the invention do not include ligands as described in WO 02/02773. Thus, the ligands of the present invention do not comprise complementary $V_H/V_L$ pairs which bind any one or more antigens or epitopes co-operatively. Instead, the ligands according to the invention preferably comprise non-complementary $V_H$-$V_H$ or $V_L$-$V_L$ pairs. Advantageously, each $V_H$ or $V_L$ domain in each $V_H$-$V_H$ or $V_L$-$V_L$ pair has a different epitope binding specificity, and the epitope binding sites are so arranged that the binding of an epitope at one site competes with the binding of an epitope at another site.

According to the present invention, advantageously, each epitope binding domain comprises an immunoglobulin variable domain. More advantageously, each epitope binding domain will be either a variable light chain domain ($V_L$) or a variable heavy chain domain ($V_H$) of an antibody. In the second configuration of the present invention, the immunoglobulin domains when present on a ligand according to the present invention are non-complementary, that is they do not associate to form a $V_H/V_L$ antigen binding site. Thus, multispecific ligands as defined in the second configuration of the invention comprise immunoglobulin domains of the same sub-type, that is either variable light chain domains ($V_L$) or variable heavy chain domains ($V_H$). Moreover, where the ligand according to the invention is in the closed conformation, the immunoglobulin domains may be of the camelid $V_{HH}$ type.

In an alternative embodiment, the ligand(s) according to the invention do not comprise a camelid $V_{HH}$ domain. More particularly, the ligand(s) of the invention do not comprise one or more amino acid residues that are specific to camelid $V_{HH}$ domains as compared to human $V_H$ domains.

Advantageously, the single variable domains are derived from antibodies selected for binding activity against different antigens or epitopes. For example, the variable domains may be isolated at least in part by human immunisation. Alternative methods are known in the art, including isolation from human antibody libraries and synthesis of artificial antibody genes.

In selected embodiments a single variable domain is a naturally occurring single variable domain. In other selected embodiments the single variable domain is non-naturally occurring. The term "naturally occurring" is used herein to indicate that an object, e.g., a protein domain, e.g., a single variable domain, or antibody single variable domain, can be found in nature. Thus, a naturally occurring protein domain, such as a V region of an antibody, exists in a protein, e.g. in an antibody chain protein, expressed in nature, for example, in a non-recombinant species, e.g., mammals, primates, rodents, fish, birds, reptiles, etc. For the avoidance of doubt, a single variable domain isolated from a repertoire of polypeptides expressed from nucleic acids to which diversity was introduced in vitro is a non-naturally occurring single variable domain. For the further avoidance of doubt, an antibody single variable domain originating from an antibody resulting from immunization of an animal is a naturally-occurring single variable domain.

The variable domains advantageously bind superantigens, such as protein A or protein L. Binding to superantigens is a property of correctly folded antibody variable domains, and allows such domains to be isolated from, for example, libraries of recombinant or mutant domains.

Epitope binding domains according to the present invention comprise a protein scaffold and epitope interaction sites (which are advantageously on the surface of the protein scaffold).

Epitope binding domains may also be based on protein scaffolds or skeletons other than immunoglobulin domains. For example, natural bacterial receptors such as SpA have been used as scaffolds for the grafting of CDRs to generate ligands which bind specifically to one or more epitopes. Details of this procedure are described in U.S. Pat. No. 5,831, 012. Other suitable scaffolds include those based on fibronectin and affibodies. Details of suitable procedures are described in WO 98/58965. Other suitable scaffolds include lipocallin and CTLA4, as described in van den Beuken et al., J. Mol. Biol. (2001) 310, 591-601, and scaffolds such as those described in WO0069907 (Medical Research Council), which are based for example on the ring structure of bacterial GroEL or other chaperone polypeptides.

Protein scaffolds may be combined; for example, CDRs may be grafted on to a CTLA4 scaffold and used together with immunoglobulin $V_H$ or $V_L$ domains to form a multivalent ligand. Likewise, fibronectin, lipocallin and other scaffolds may be combined.

It will be appreciated by one skilled in the art that the epitope binding domains of a closed conformation multispecific ligand produced according to the method of the present invention may be on the same polypeptide chain, or alternatively, on different polypeptide chains. In the case that the variable domains are on different polypeptide chains, then they may be linked via a linker, advantageously a flexible linker (such as a polypeptide chain), a chemical linking group, or any other method known in the art.

The first and the second epitope binding domains may be associated either covalently or non-covalently. In the case that the domains are covalently associated, then the association may be mediated for example by disulphide bonds.

In the second configuration of the invention, the first and the second epitopes are preferably different. They may be, or be part of, polypeptides, proteins or nucleic acids, which may be naturally occurring or synthetic. In this respect, the ligand of the invention may bind an epitope or antigen and act as an antagonist or agonist (e.g., EPO receptor agonist). The epitope binding domains of the ligand in one embodiment have the same epitope specificity, and may for example simultaneously bind their epitope when multiple copies of the epitope are present on the same antigen. In another embodiment, these epitopes are provided on different antigens such that the ligand can bind the epitopes and bridge the antigens. One skilled in the art will appreciate that the choice of epitopes and antigens is large and varied. They may be for instance human or animal proteins, cytokines, cytokine receptors, enzymes co-factors for enzymes or DNA binding proteins. Suitable cytokines and growth factors include but are preferably not limited to: ApoE, Apo-SAA, BDNF, Cardiotrophin-1, EGF, EGF receptor, ENA-78, Eotaxin, Eotaxin-2, Exodus-2, EpoR, FGF-acidic, FGF-basic, fibroblast growth factor-10, FLT3 ligand, Fractalkine (CX3C), GDNF, G-CSF, GM-CSF, GF-β1, insulin, IFN-γ, IGF-I, IGF-II, IL-1α, IL-1β, IL-2, IL-3, IL-4, IL-5, IL-6, IL-7, IL-8 (72 a.a.), IL-8 (77 a.a.), IL-9, IL-10, IL-11, IL-12, IL-13, IL-15, IL-16, IL-17, IL-18 (IGIF), Inhibin α, Inhibin β, IP-10, keratinocyte growth factor-2 (KGF-2), KGF, Leptin, LIF, Lymphotactin, Mullerian inhibitory substance, monocyte colony inhibitory factor, monocyte attractant protein, M-CSF, MDC (67 a.a.), MDC (69 a.a.), MCP-1 (MCAF), MCP-2, MCP-3, MCP-4, MDC (67 a.a.), MDC (69 a.a.), MIG, MIP-1α, MIP-1β, MIP-3α, MIP-3β, MIP-4, myeloid progenitor inhibitor factor-1

(MPIF-1), NAP-2, Neurturin, Nerve growth factor, β-NGF, NT-3, NT-4, Oncostatin M, PDGF-AA, PDGF-AB, PDGF-BB, PF-4, RANTES, SDF1α, SDF1β, SCF, SCGF, stem cell factor (SCF), TARC, TGF-α, TGF-β, TGF-β2, TGF-β3, tumour necrosis factor (TNF), TNF-α, TNF-β, TNF receptor I, TNF receptor II, TNIL-1, TPO, VEGF, VEGF receptor 1, VEGF receptor 2, VEGF receptor 3, GCP-2, GRO/MGSA, GRO-β, GRO-γ, HCC1, 1-309, HER 1, HER 2, HER 3, HER 4, TACE recognition site, TNF BP-I and TNF BP-II, CD4, human chemokine receptors CXCR4 or CCR5, non-structural protein type 3 (NS3) from the hepatitis C virus, TNF-alpha, IgE, IFN-gamma, MMP-12, CEA, *H. pylori*, TB, influenza, Hepatitis E, MMP-12, internalising receptors are overexpressed on certain cells, such as the epidermal growth factor receptor (EGFR), ErBb2 receptor on tumor cells, an internalising cellular receptor, LDL receptor, FGF2 receptor, ErbB2 receptor, transferrin receptor, PDGF receptor, VEGF receptor, PsmAr, an extracellular matrix protein, elastin, fibronectin, laminin, α1-antitrypsin, tissue factor protease inhibitor, PDK1, GSK1, Bad, caspase-9, Forkhead, an of an antigen of *Helicobacter pylori*, an antigen of *Mycobacterium tuberculosis*, and an antigen of influenza virus, as well as any target disclosed in Annex 2 or Annex 3 hereto, whether in combination as set forth in the Annexes, in a different combination or individually. Cytokine receptors include receptors for the above cytokines, e.g. IL-1 R1; IL-6R; IL-10R; IL-18R, as well as receptors for cytokines set forth in Annex 2 or Annex 3 and also receptors disclosed in Annex 2 and 3. It will be appreciated that this list is by no means exhaustive. Where the multispecific ligand binds to two epitopes (on the same or different antigens), the antigen(s) may be selected from this list.

Advantageously, dual specific ligands may be used to target cytokines and other molecules which cooperate synergistically in therapeutic situations in the body of an organism. The invention therefore provides a method for synergising the activity of two or more cytokines, comprising administering a dual specific ligand capable of binding to said two or more cytokines. In this aspect of the invention, the dual specific ligand may be any dual specific ligand, including a ligand composed of complementary and/or non-complementary domains, a ligand in an open conformation, and a ligand in a closed conformation. For example, this aspect of the invention relates to combinations of $V_H$ domains and $V_L$ domains, $V_H$ domains only and $V_L$ domains only.

Synergy in a therapeutic context may be achieved in a number of ways. For example, target combinations may be therapeutically active only if both targets are targeted by the ligand, whereas targeting one target alone is not therapeutically effective. In another embodiment, one target alone may provide some low or minimal therapeutic effect, but together with a second target the combination provides a synergistic increase in therapeutic effect.

Preferably, the cytokines bound by the dual specific ligands of this aspect of the invention are selected from the list shown in Annex 2.

Moreover, dual specific ligands may be used in oncology applications, where one specificity targets CD89, which is expressed by cytotoxic cells, and the other is tumour specific. Examples of tumour antigens which may be targeted are given in Annex 3.

In one embodiment of the second configuration of the invention, the variable domains are derived from an antibody directed against the first and/or second antigen or epitope. In a preferred embodiment the variable domains are derived from a repertoire of single variable antibody domains. In one example, the repertoire is a repertoire that is not created in an animal or a synthetic repertoire. In another example, the single variable domains are not isolated (at least in part) by animal immunisation. Thus, the single domains can be isolated from a naïve library.

The second configuration of the invention, in another aspect, provides a multi-specific ligand comprising a first epitope binding domain having a first epitope binding specificity and a non-complementary second epitope binding domain having a second epitope binding specificity. The first and second binding specificities may be the same or different.

In a further aspect, the present invention provides a closed conformation multi-specific ligand comprising a first epitope binding domain having a first epitope binding specificity and a non-complementary second epitope binding domain having a second epitope binding specificity wherein the first and second binding specificities are capable of competing for epitope binding such that the closed conformation multi-specific ligand cannot bind both epitopes simultaneously.

In a still further aspect, the invention provides open conformation ligands comprising non-complementary binding domains, wherein the domains are specific for a different epitope on the same target. Such ligands bind to targets with increased avidity. Similarly, the invention provides multivalent ligands comprising non-complementary binding domains specific for the same epitope and directed to targets which comprise multiple copies of said epitope, such as IL-5, PDGF-AA, PDGF-BB, TGF-β, TGF-β2, TGF-β3 and TNFα, for example, as well as human TNF Receptor 1 and human TNFα.

In a similar aspect, ligands according to the invention can be configured to bind individual epitopes with low affinity, such that binding to individual epitopes is not therapeutically significant; but the increased avidity resulting from binding to two epitopes provides a therapeutic benefit. In a particular example, epitopes may be targeted which are present individually on normal cell types, but present together only on abnormal or diseased cells, such as tumour cells. In such a situation, only the abnormal or diseased cells are effectively targeted by the bispecific ligands according to the invention.

Ligand specific for multiple copies of the same epitope, or adjacent epitopes, on the same target (known as chelating dAbs) may also be trimeric or polymeric (tertrameric or more) ligands comprising three, four or more non-complementary binding domains. For example, ligands may be constructed comprising three or four $V_H$ domains or $V_L$ domains.

Moreover, ligands are provided which bind to multisubunit targets, wherein each binding domain is specific for a subunit of said target. The ligand may be dimeric, trimeric or polymeric.

Preferably, the multi-specific ligands according to the above aspects of the invention are obtainable by the method of the first aspect of the invention.

According to the above aspect of the second configuration of the invention, advantageously the first epitope binding domain and the second epitope binding domains are non-complementary immunoglobulin variable domains, as herein defined. That is either $V_H$-$V_H$ or $V_L$-$V_L$ variable domains.

Chelating dAbs in particular may be prepared according to a preferred aspect of the invention, namely the use of anchor dAbs, in which a library of dimeric, trimeric or multimeric dAbs is constructed using a vector which comprises a constant dAb upstream or downstream of a linker sequence, with a repertoire of second, third and further dAbs being inserted on the other side of the linker. For example, the anchor or guiding dAb may be TAR1-5 (Vκ), TAR1-27(Vκ), TAR2h-5 (VH) or TAR2h-6(Vκ).

In alternative methodologies, the use of linkers may be avoided, for example by the use of non-covalent bonding or natural affinity between binding domains such as $V_H$ and $V_\kappa$. The invention accordingly provides a method for preparing a chelating multimeric ligand comprising the steps of:

(a) providing a vector comprising a nucleic acid sequence encoding a single binding domain specific for a first epitope on a target;

(b) providing a vector encoding a repertoire comprising second binding domains specific for a second epitope on said target, which epitope can be the same or different to the first epitope, said second epitope being adjacent to said first epitope; and (c) expressing said first and second binding domains; and (d) isolating those combinations of first and second binding domains which combine together to produce a target-binding dimer.

The first and second epitopes are adjacent such that a multimeric ligand is capable of binding to both epitopes simultaneously. This provides the ligand with the advantages of increased avidity if binding. Where the epitopes are the same, the increased avidity is obtained by the presence of multiple copies of the epitope on the target, allowing at least two copies to be simultaneously bound in order to obtain the increased avidity effect.

The binding domains may be associated by several methods, as well as the use of linkers. For example, the binding domains may comprise cys residues, avidin and streptavidin groups or other means for non-covalent attachment post-synthesis; those combinations which bind to the target efficiently will be isolated. Alternatively, a linker may be present between the first and second binding domains, which are expressed as a single polypeptide from a single vector, which comprises the first binding domain, the linker and a repertoire of second binding domains, for instance as described above.

In a preferred aspect, the first and second binding domains associate naturally when bound to antigen; for example, $V_H$ and $V_L$ (e.g. $V\kappa$) domains, when bound to adjacent epitopes, will naturally associate in a three-way interaction to form a stable dimer. Such associated proteins can be isolated in a target binding assay. An advantage of this procedure is that only binding domains which bind to closely adjacent epitopes, in the correct conformation, will associate and thus be isolated as a result of their increased avidity for the target.

In an alternative embodiment of the above aspect of the second configuration of the invention, at least one epitope binding domain comprises a non-immunoglobulin 'protein scaffold' or 'protein skeleton' as herein defined. Suitable non-immunoglobulin protein scaffolds include but are preferably not limited to any of those selected from the group consisting of: SpA, fibronectin, GroEL and other chaperones, lipocallin, CCTLA4 and affibodies, as set forth above.

According to the above aspect of the second configuration of the invention, advantageously, the epitope binding domains are attached to a 'protein skeleton'. Advantageously, a protein skeleton according to the invention is an immunoglobulin skeleton.

According to the present invention, the term 'immunoglobulin skeleton' refers to a protein which comprises at least one immunoglobulin fold and which acts as a nucleus for one or more epitope binding domains, as defined herein.

Preferred immunoglobulin skeletons as herein defined includes any one or more of those selected from the following: an immunoglobulin molecule comprising at least (i) the CL (kappa or lambda subclass) domain of an antibody; or (ii) the CH1 domain of an antibody heavy chain; an immunoglobulin molecule comprising the $CH_1$ and CH2 domains of an antibody heavy chain; an immunoglobulin molecule comprising the CH1, CH2 and CH3 domains of an antibody heavy chain; or any of the subset (ii) in conjunction with the CL (kappa or lambda subclass) domain of an antibody. A hinge region domain may also be included. Such combinations of domains may, for example, mimic natural antibodies, such as IgG or IgM, or fragments thereof, such as Fv, scFv, Fab or F(ab')$_2$ molecules. Those skilled in the art will be aware that this list is not intended to be exhaustive.

Linking of the skeleton to the epitope binding domains, as herein defined may be achieved at the polypeptide level, that is after expression of the nucleic acid encoding the skeleton and/or the epitope binding domains. Alternatively, the linking step may be performed at the nucleic acid level. Methods of linking a protein skeleton according to the present invention, to the one or more epitope binding domains include the use of protein chemistry and/or molecular biology techniques which will be familiar to those skilled in the art and are described herein.

Advantageously, the closed conformation multispecific ligand may comprise a first domain capable of binding a target molecule, and a second domain capable of binding a molecule or group which extends the half-life of the ligand. For example, the molecule or group may be a bulky agent, such as HSA or a cell matrix protein. As used herein, the phrase "molecule or group which extends the half-life of a ligand" refers to a molecule or chemical group which, when bound by a dual-specific ligand as described herein increases the in vivo half-life of such dual specific ligand when administered to an animal, relative to a ligand that does not bind that molecule or group. Examples of molecules or groups that extend the half-life of a ligand are described herein below. In a preferred embodiment, the closed conformation multispecific ligand may be capable of binding the target molecule only on displacement of the half-life enhancing molecule or group. Thus, for example, a closed conformation multispecific ligand is maintained in circulation in the bloodstream of a subject by a bulky molecule such as HSA. When a target molecule is encountered, competition between the binding domains of the closed conformation multispecific ligand results in displacement of the HSA and binding of the target.

A ligand according to any aspect of the present invention, incudes a ligand having or consisting of at least one single variable domain, in the form of a monomer single variable domain or in the form of multiple single variable domains, i.e. a multimer. The ligand can be modified to contain additional moities, such as a fusion protein, or a conjugate. Such a multimeric ligand, e.g., in the form of a dual specific ligand, and/or such a ligand comprising or consisting of a single variable domain, i.e. a dAb monomer useful in constructing such a multimeric ligand, may advantageously dissociate from their cognate target(s) with a Kd of 300 nM or less, 300 nM to 5 μM (i.e., $3\times10^{-7}$ to $5\times10^{-12}$M), preferably 50 nM to 20 pM, or 5 nM to 200 pM or 1 nM to 100 pM, $1\times10^{-7}$ M or less, $1\times10^{-8}$ M or less, $1\times10^{-9}$ M or less, $1\times10^{-10}$ M or less, $1\times10^{-11}$ M or less; and/or a $K_{off}$ rate constant of $5\times10^{-1}$ to $1\times10^{-7}$ $S^{-1}$, preferably $1\times10^{-2}$ to $1\times10^{-6}$ $S^{-1}$, or $5\times10^{-3}$ to $1\times10^{-5}$ $S^{-1}$, or $5\times10$ $S^{-1}$ or less, or $1\times10^{-2}$ $S^{-1}$ or less, or $1\times10^{-3}$ $S^{-1}$ or less, or $1\times10^{-4}$ $S^{-1}$ or less, or $1\times10^{-5}$ $S^{-1}$ or less, or $1\times10^{-6}$ $S^{-1}$ or less as determined, for example, by surface plasmon resonance. The Kd rate constant is defined as $K_{off}/K_{on}$. A Kd value greater than 1 Molar is generally considered to indicate non-specific binding. Preferably, a single variable domain will specifically bind a target antigen or epitope with an affinity of less than 500 nM, preferably less than 200 nM, and more preferably less than 10 nM, such as less than 500 pM In particular the invention provides an anti-TNFα dAb monomer (or dual specific ligand comprising such a dAb), homodimer, heterodimer or homotrimer ligand, wherein each dAb binds TNFα. The ligand binds to TNFα with a Kd of 300 nM to 5 pM (i.e., $3\times10^{-7}$ to $5\times10^{-12}$M), preferably 50 nM to 20 pM, more preferably 5 nM to 200 pM and most preferably 1 nM to 100 pM; expressed in an alternative manner, the Kd is $1\times10^{-7}$ M or less, preferably $1\times10^{-8}$ M or less, more preferably $1\times10^{-9}$ M or less, advantageously $1\times10^{-10}$ M or less and most preferably $1\times10^{-11}$ M or less; and/or a $K_{off}$ rate constant of $5\times10^{-1}$ to $1\times10^{-7}$ S$^{-1}$, preferably $1\times10^{-2}$ to $1\times10^{-6}$ S$^{-1}$, more preferably $5\times10^{-3}$ to $1\times10^{-5}$ S$^{-1}$, for example $5\times10^{-1}$ S$^{-1}$ or less, preferably $1\times10^{-2}$ S$^{-1}$ or less, more preferably $1\times10^{-3}$ S$^{-1}$ or less, advantageously $1\times10^{-4}$ S$^{-1}$ or less, further advantageously $1\times10^{-5}$ S$^{-1}$ or less, and most preferably $1\times10^{-6}$ S$^{-1}$ or less, as determined by surface plasmon resonance.

Preferably, the ligand neutralises TNFα in a standard L929 assay with an ND50 of 500 nM to 50 pM, preferably or 100 nM to 50 pM, advantageously 10 nM to 100 pM, more preferably 1 nM to 100 pM; for example 50 nM or less, preferably 5 nM or less, advantageously 500 pM or less, more preferably 200 pM or less and most preferably 100 pM or less.

Preferably, the ligand inhibits binding of TNF alpha to TNF alpha Receptor I (p55 receptor) with an IC50 of 500 nM to 50 pM, preferably 100 nM to 50 pM, more preferably 10 nM to 100 pM, advantageously 1 nM to 100 pM; for example 50 nM or less, preferably 5 nM or less, more preferably 500 pM or less, advantageously 200 pM or less, and most preferably 100 pM or less. Preferably, the TNFα is Human TNFα.

Furthermore, the invention provides an anti-TNF Receptor I dAb monomer, or dual specific ligand comprising such a dAb, that binds to TNF Receptor I with a Kd of 300 nM to 5 pM (i.e., $3\times10^{-7}$ to $5\times10^{-12}$M), preferably 50 nM to 20 pM, more preferably 5 nM to 200 pM and most preferably 1 nM to 100 pM, for example $1\times10^{-7}$ M or less, preferably $1\times10^{-8}$ M or less, more preferably $1\times10^{-9}$ M or less, advantageously $1\times10^{-10}$ M or less and most preferably $1\times10^{-11}$ M or less; and/or a $K_{off}$ rate constant of $5\times10^{-1}$ to $1\times10^{-7}$ S$^{-1}$, preferably $1\times10^{-2}$ to $1\times10^{-6}$ S$^{-1}$, more preferably $5\times10^{-3}$ to $1\times10^{-5}$ S$^{-1}$, for example $5\times10^{-1}$ S$^{-1}$ or less, preferably $1\times10^{-2}$ S$^{-1}$ or less, advantageously $1\times10^{-3}$ S$^{-1}$ or less, more preferably $1\times10^{-4}$ S$^{-1}$ or less, still more preferably $1\times10^{-5}$ S$^{-1}$ or less, and most preferably $1\times10^{-6}$ S$^{-1}$ or less, preferably as determined by surface plasmon resonance.

Preferably, the dAb monomer ligand neutralises TNFα in a standard assay (e.g., the L929 or HeLa assays described herein) with an ND50 of 500 nM to 50 pM, preferably 100 nM to 50 nM, more preferably 10 nM to 100 pM, advantageously 1 nM to 100 pM; for example 50 nM or less, preferably 5 nM or less, more preferably 500 pM or less, advantageously 200 pM or less, and most preferably 100 pM or less.

Preferably, the dAb monomer or ligand inhibits binding of TNF alpha to TNF alpha Receptor I (p55 receptor) with an IC50 of 500 nM to 50 pM, preferably 100 nM to 50 pM, more preferably 10 nM to 100 pM, advantageously 1 nM to 100 pM; for example 50 nM or less, preferably 5 nM or less, more preferably 500 pM or less, advantageously 200 pM or less, and most preferably 100 pM or less. Preferably, the TNF Receptor I target is Human TNFα.

Furthermore, the invention provides a dAb monomer (or dual specific ligand comprising such a dAb) that binds to serum albumin (SA) with a Kd of 1 nM to 500 μM (i.e., $1\times10^{-9}$ to $5\times10^{-4}$), preferably 100 nM to 10 μM. Preferably, for a dual specific ligand comprising a first anti-SA dAb and a second dAb to another target, the affinity (e.g. Kd and/or $K_{off}$ as measured by surface plasmon resonance, e.g. using Biacore) of the second dAb for its target is from 1 to 100000 times (preferably 100 to 100000, more preferably 1000 to 100000, or 10000 to 100000 times) the affinity of the first dAb for SA. For example, the first dAb binds SA with an affinity of approximately 10 μM, while the second dAb binds its target with an affinity of 100 pM. Preferably, the serum albumin is human serum albumin (HSA).

In one embodiment, the first dAb (or a dAb monomer) binds SA (e.g., HSA) with a Kd of approximately 50, preferably 70, and more preferably 100, 150 or 200 nM.

The invention moreover provides dimers, trimers and polymers of the aforementioned dAb monomers, in accordance with the above aspect of the present invention.

Ligands according to the invention, including dAb monomers, dimers and trimers, can be linked to an antibody Fc region, comprising one or both of $C_H2$ and $C_H3$ domains, and optionally a hinge region. For example, vectors encoding ligands linked as a single nucleotide sequence to an Fc region may be used to prepare such polypeptides.

In a further aspect of the second configuration of the invention, the present invention provides one or more nucleic acid molecules encoding at least a multispecific ligand as herein defined. In one embodiment, the multispecific ligand is a closed conformation ligand. In another embodiment, it is an open conformation ligand. The multispecific ligand may be encoded on a single nucleic acid molecule; alternatively, each epitope binding domain may be encoded by a separate nucleic acid molecule. Where the multispecific ligand is encoded by a single nucleic acid molecule, the domains may be expressed as a fusion polypeptide, or may be separately expressed and subsequently linked together, for example using chemical linking agents. Ligands expressed from separate nucleic acids will be linked together by appropriate means.

The nucleic acid may further encode a signal sequence for export of the polypeptides from a host cell upon expression and may be fused with a surface component of a filamentous bacteriophage particle (or other component of a selection display system) upon expression. Leader sequences, which may be used in bacterial expression and/or phage or phagemid display, include pelB, stII, ompA, phoA, bla and pelA.

In a further aspect of the second configuration of the invention the present invention provides a vector comprising nucleic acid according to the present invention.

In a yet further aspect, the present invention provides a host cell transfected with a vector according to the present invention.

Expression from such a vector may be configured to produce, for example on the surface of a bacteriophage particle, epitope binding domains for selection. This allows selection of displayed domains and thus selection of 'multispecific ligands' using the method of the present invention.

In a preferred embodiment of the second configuration of the invention, the epitope binding domains are immunoglobulin variable domains and are selected from single domain V gene repertoires. Generally the repertoire of single antibody domains is displayed on the surface of filamentous bacteriophage. In a preferred embodiment each single antibody domain is selected by binding of a phage repertoire to antigen.

The present invention further provides a kit comprising at least a multispecific ligand according to the present invention, which may be an open conformation or closed conformation ligand. Kits according to the invention may be, for example, diagnostic kits, therapeutic kits, kits for the detection of chemical or biological species, and the like.

In a further aspect still of the second configuration of the invention, the present invention provides a homogenous immunoassay using a ligand according to the present invention.

In a further aspect still of the second configuration of the invention, the present invention provides a composition comprising a closed conformation multispecific ligand, obtainable by a method of the present invention, and a pharmaceutically acceptable carrier, diluent or excipient.

Moreover, the present invention provides a method for the treatment of disease using a 'closed conformation multispecific ligand' or a composition according to the present invention.

In a preferred embodiment of the invention the disease is cancer or an inflammatory disease, e.g. rheumatoid arthritis, asthma or Crohn's disease.

In a further aspect of the second configuration of the invention, the present invention provides a method for the diagnosis, including diagnosis of disease using a closed conformation multispecific ligand, or a composition according to the present invention. Thus in general the binding of an analyte to a closed conformation multispecific ligand may be exploited to displace an agent, which leads to the generation of a signal on displacement. For example, binding of analyte (second antigen) could displace an enzyme (first antigen) bound to the antibody providing the basis for an immunoassay, especially if the enzyme were held to the antibody through its active site.

Thus in a final aspect of the second configuration, the present invention provides a method for detecting the presence of a target molecule, comprising:
(a) providing a closed conformation multispecific ligand bound to an agent, said ligand being specific for the target molecule and the agent, wherein the agent which is bound by the ligand leads to the generation of a detectable signal on displacement from the ligand;
(b) exposing the closed conformation multispecific ligand to the target molecule; and
(c) detecting the signal generated as a result of the displacement of the agent.

According to the above aspect of the second configuration of the invention, advantageously, the agent is an enzyme, which is inactive when bound by the closed conformation multi-specific ligand. Alternatively, the agent may be any one or more selected from the group consisting of the following: the substrate for an enzyme, and a fluorescent, luminescent or chromogenic molecule which is inactive or quenched when bound by the ligand.

Sequences similar or homologous (e.g., at least about 70% sequence identity) to the sequences disclosed herein are also part of the invention. In some embodiments, the sequence identity at the amino acid level can be about 80%, 85%, 90%, 91%, 92%, 93%, 94%, 95%, 96%, 97%, 98%, 99% or higher. At the nucleic acid level, the sequence identity can be about 70%, 75%, 80%, 85%, 90%, 91%, 92%, 93%, 94%, 95%, 96%, 97%, 98%, 99% or higher. Alternatively, substantial identity exists when the nucleic acid segments will hybridize under selective hybridization conditions (e.g., very high stringency hybridization conditions), to the complement of the strand. The nucleic acids may be present in whole cells, in a cell lysate, or in a partially purified or substantially pure form.

The percent identity can refer to the percent identity along the entire stretch of the length of the amino acid or nucleotide sequence. When specified, the percent identity of the amino acid or nucleic acid sequence refers to the percent identity to sequence(s) from one or more discrete regions of the referenced amino acid or nucleic acid sequence, for instance, along one or more antibody CDR regions, and/or along one or more antibody variable framework regions. For example, the sequence identity at the amino acid level across one or more CDRs of an antibody heavy or light chain single variable domain can have about 80%, 85%, 90%, 91%, 92%, 93%, 94%, 95%, 96%, 97%, 98%, 99% or higher identity to the amino acid sequence of corresponding CDRs of an antibody heavy or light chain single variable domain, respectively. At the nucleic acid level, the nucleic acid sequence encoding one or more CDRs of an antibody heavy or light chain single variable domain can have at least 70%, 75%, 80%, 85%, 90%, 91%, 92%, 93%, 94%, 95%, 96%, 97%, 98%, 99% or higher, identity to the nucleic acid sequence encoding the corresponding CDRs of an antibody heavy or light chain single variable domain. At the nucleic acid level, the nucleic acid sequence encoding one CDR of an antibody heavy or light chain single variable domain can have a percent identity of at least 80%, 85%, 90%, 91%, 92%, 93%, 94%, 95%, 96%, 97%, 98%, 99% or higher, than the nucleic acid sequence encoding the corresponding CDR of an antibody heavy or light chain single variable domain, respectively. In some embodiments, the structural characteristic of percent identity is coupled to a functional aspect. For instance, in some embodiments, a nucleic acid sequence or amino acid sequence with less than 100% identity to a referenced nucleic acid or amino acid sequence is also required to display at least one functional aspect of the reference amino acid sequence or of the amino acid sequence encoded by the referenced nucleic acid. In other embodiments, a nucleic acid sequence or amino acid sequence with less than 100% identity to a referenced nucleic acid or amino acid sequence, respectively, is also required to display at least one functional aspect of the reference amino acid sequence or of the amino acid sequence encoded by the referenced nucleic acid, but that functional characteristic can be slightly altered, e.g., confer an increased affinity to a specified antigen relative to that of the reference.

Calculations of "homology" or "sequence identity" or "similarity" between two sequences (the terms are used interchangeably herein) are performed as follows. The sequences are aligned for optimal comparison purposes (e.g., gaps can be introduced in one or both of a first and a second amino acid or nucleic acid sequence for optimal alignment and non-homologous sequences can be disregarded for comparison purposes). In a preferred embodiment, the length of a reference sequence aligned for comparison purposes is at least 30%, preferably at least 40%, more preferably at least 50%, even more preferably at least 60%, and even more preferably at least 70%, 80%, 90%, 100% of the length of the reference sequence. The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position (as used herein amino acid or nucleic acid "homology" is equivalent to amino acid or nucleic acid "identity"). The percent identity between the two sequences is a function of the number of identical positions shared by the sequences, taking into account the number of gaps, and the length of each gap, which need to be introduced for optimal alignment of the two sequences.

Advantageously, the BLAST algorithm (version 2.0) is employed for sequence alignment, with parameters set to default values. The BLAST algorithm is described in detail at the world wide web site of the National Center for Biotechnology Information ("NCBI") of the National Institutes of Health ("NIH") of the U.S. government ("gov"), in the "/Blast/" directory, in the "Help" file. The search parameters are defined as follows, and are advantageously set to the defined default parameters.

BLAST (Basic Local Alignment Search Tool) is the heuristic search algorithm employed by the programs blastp, blastn, blastx, tblastn, and tblastx; these programs ascribe significance to their findings using the statistical methods of Karlin and Altschul, 1990, Proc. Natl. Acad. Sci. USA 87(6): 2264-8 (see the "Help" file, as described above) with a few enhancements. The BLAST programs were tailored for sequence similarity searching, for example to identify homologues to a query sequence. The programs are not generally useful for motif-style searching. For a discussion of basic issues in similarity searching of sequence databases, see Altschul et al. (1994).

The five BLAST programs available at the National Center for Biotechnology Information web site perform the following tasks:

"blastp" compares an amino acid query sequence against a protein sequence database;

"blastn" compares a nucleotide query sequence against a nucleotide sequence database;

"blastx" compares the six-frame conceptual translation products of a nucleotide query sequence (both strands) against a protein sequence database;

"tblastn" compares a protein query sequence against a nucleotide sequence database dynamically translated in all six reading frames (both strands).

"tblastx" compares the six-frame translations of a nucleotide query sequence against the six-frame translations of a nucleotide sequence database.

BLAST uses the following search parameters:

HISTOGRAM Display a histogram of scores for each search; default is yes. (See parameter H in the BLAST Manual).

DESCRIPTIONS Restricts the number of short descriptions of matching sequences reported to the number specified; default limit is 100 descriptions. (See parameter V in the manual page). See also EXPECT and CUTOFF.

ALIGNMENTS Restricts database sequences to the number specified for which high-scoring segment pairs (HSPs) are reported; the default limit is 50. If more database sequences than this happen to satisfy the statistical significance threshold for reporting (see EXPECT and CUTOFF below), only the matches ascribed the greatest statistical significance are reported. (See parameter B in the BLAST Manual).

EXPECT The statistical significance threshold for reporting matches against database sequences; the default value is 10, such that 10 matches are expected to be found merely by chance, according to the stochastic model of Karlin and Altschul (1990). If the statistical significance ascribed to a match is greater than the EXPECT threshold, the match will not be reported. Lower EXPECT thresholds are more stringent, leading to fewer chance matches being reported. Fractional values are acceptable. (See parameter E in the BLAST Manual).

CUTOFF Cutoff score for reporting high-scoring segment pairs. The default value is calculated from the EXPECT value (see above). HSPs are reported for a database sequence only if the statistical significance ascribed to them is at least as high as would be ascribed to a lone HSP having a score equal to the CUTOFF value. Higher CUTOFF values are more stringent, leading to fewer chance matches being reported. (See parameter S in the BLAST Manual). Typically, significance thresholds can be more intuitively managed using EXPECT.

MATRIX Specify an alternate scoring matrix for BLASTP, BLASTX, TBLASTN and TBLASTX. The default matrix is BLOSUM62 (Henikoff & Henikoff, 1992, Proc. Natl. Aacad. Sci. USA 89(22):10915-9). The valid alternative choices include: PAM40, PAM120, PAM250 and IDENTITY. No alternate scoring matrices are available for BLASTN; specifying the MATRIX directive in BLASTN requests returns an error response.

STRAND Restrict a TBLASTN search to just the top or bottom strand of the database sequences; or restrict a BLASTN, BLASTX or TBLASTX search to just reading frames on the top or bottom strand of the query sequence.

FILTER Mask off segments of the query sequence that have low compositional complexity, as determined by the SEG program of Wootton & Federhen (1993) Computers and Chemistry 17:149-163, or segments consisting of short-periodicity internal repeats, as determined by the XNU program of Clayerie & States, 1993, Computers and Chemistry 17:191-201, or, for BLASTN, by the DUST program of Tatusov and Lipman (see the world wide web site of the NCBI). Filtering can eliminate statistically significant but biologically uninteresting reports from the blast output (e.g., hits against common acidic-, basic- or proline-rich regions), leaving the more biologically interesting regions of the query sequence available for specific matching against database sequences.

Low complexity sequence found by a filter program is substituted using the letter "N" in nucleotide sequence (e.g., "N" repeated 13 times) and the letter "X" in protein sequences (e.g., "X" repeated 9 times).

Filtering is only applied to the query sequence (or its translation products), not to database sequences. Default filtering is DUST for BLASTN, SEG for other programs.

It is not unusual for nothing at all to be masked by SEG, XNU, or both, when applied to sequences in SWISS-PROT, so filtering should not be expected to always yield an effect.

Furthermore, in some cases, sequences are masked in their entirety, indicating that the statistical significance of any matches reported against the unfiltered query sequence should be suspect.

NCBI-gi Causes NCBI gi identifiers to be shown in the output, in addition to the accession and/or locus name.

Most preferably, sequence comparisons are conducted using the simple BLAST search algorithm provided at the NCBI world wide web site described above, in the "/BLAST" directory.

BRIEF DESCRIPTION OF THE FIGURES

FIG. 1 shows the diversification of $V_H$/HSA at positions H50, H52, H52a, H53, H55, H56, H58, H95, H96, H97, H98 (DVT or NNK encoded respectively) which are in the antigen binding site of $V_H$ HSA. The sequence of $V_K$ is diversified at positions L50, L53. Nucleotide sequence disclosed as SEQ ID NO: 176 and amino acid sequence disclosed as SEQ ID NO: 177.

Soluble scFv from these clones of PCR are amplified in the sequence. One clone encoding a dual specific antibody K8 was chosen for further work. The figure discloses SEQ ID NOS 178-181, respectively, in order of appearance.

FIG. 3 shows an alignment of $V_H$ chains and V chains. The figure discloses SEQ ID NOS 182-195, respectively, in order of appearance.

Figure 4:
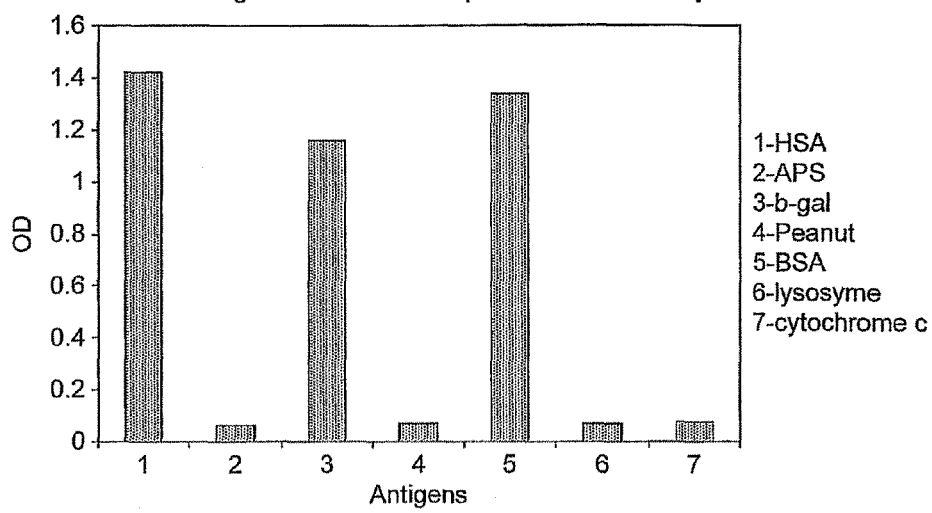

FIG. 4 shows the characterisation of the binding properties of the K8 antibody, the binding properties of the K8 antibody characterised by monoclonal phage ELISA, the dual specific K8 antibody was found to bind HSA and β-gal and displayed on the surface of the phage with absorbant signals greater than 1.0. No cross reactivity with other proteins was detected.

Figure 5:
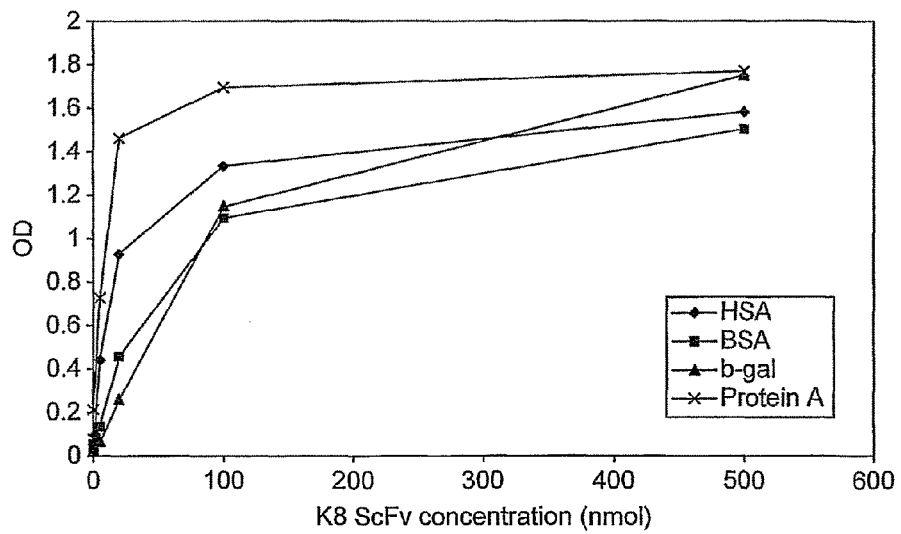

FIG. 5 shows soluble scFv ELISA performed using known concentrations of the K8 antibody fragment. A 96-well plate was coated with 100 μg of HSA, BSA and β-gal at 10 μg/ml and 100 μg/ml of Protein A at 1 μg/ml concentration. 50 μg of the serial dilutions of the K8 scFv was applied and the bound antibody fragments were detected with Protein L-HRP. ELISA results confirm the dual specific nature of the K8 antibody.

FIG. 6 shows the binding characteristics of the clone $K8V_K$/dummy $V_H$ analysed using soluble scFv ELISA. Production of the soluble scFv fragments was induced by IPTG as described by Harrison et al, Methods Enzymol. 1996; 267:83-109 and the supernatant containing scFv assayed directly. Soluble scFv ELISA is performed as described in example 1 and the bound scFvs were detected with Protein L-HRP. The ELISA results revealed that this clone was still able to bind β-gal, whereas binding BSA was abolished.

FIG. 7 shows the sequence of variable domain vectors 1 and 2. Figure discloses SEQ ID NOS 196-199, respectively, in order of appearance.

Figure 8:
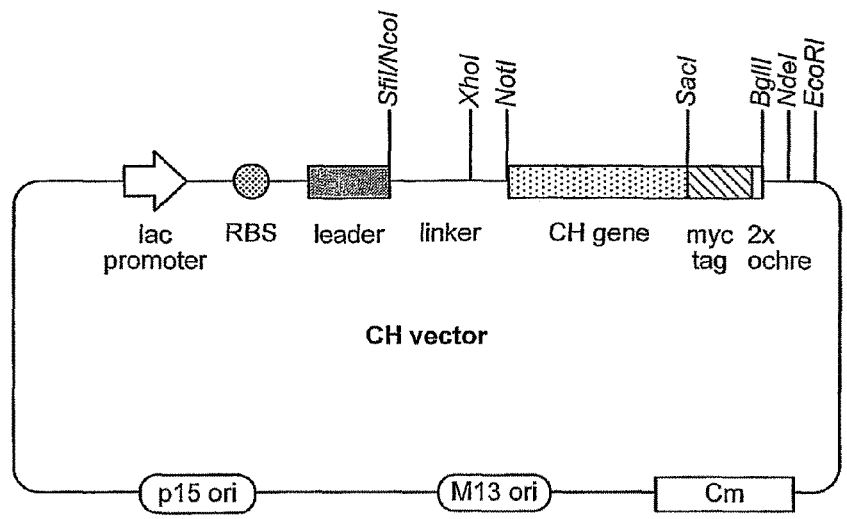

FIG. 8 is a map of the CH vector used to construct a $V_H1/V_H2$ multispecific ligand.

Figure 9:
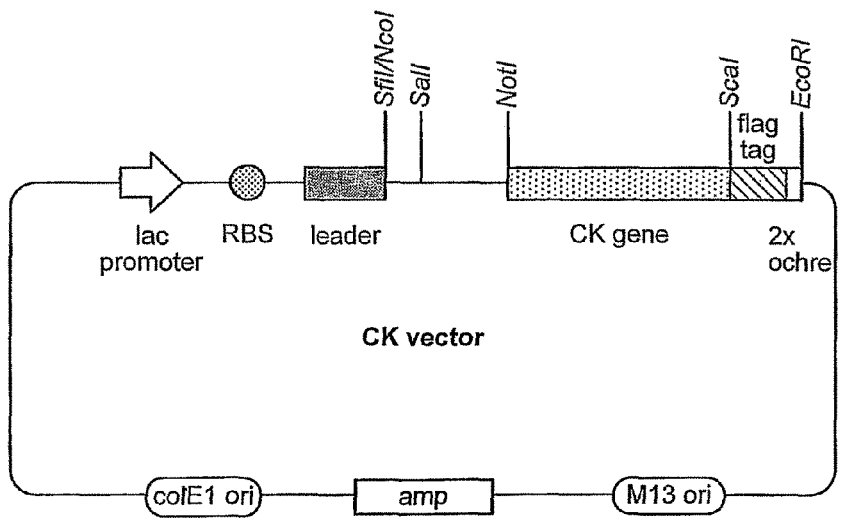

FIG. 9 is a map of the $V_K$ vector used to construct a $V_K1/V_K2$ multispecific ligand.

Figure 10:
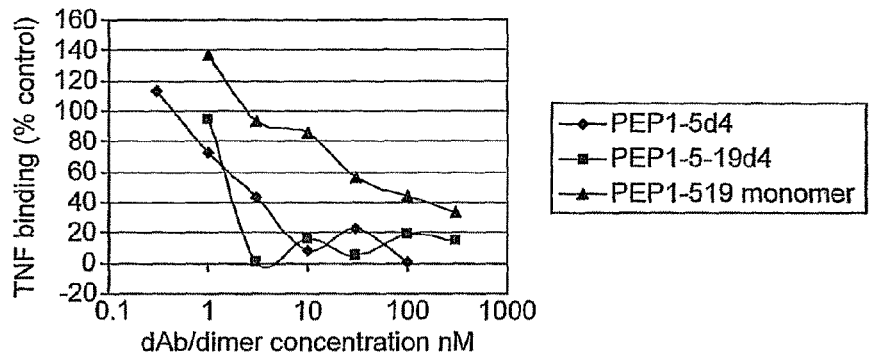

FIG. 10 TNF receptor assay comparing TAR1-5 dimer 4, TAR1-5-19 dimer 4 and TAR1-5-19 monomer.

Figure 11:
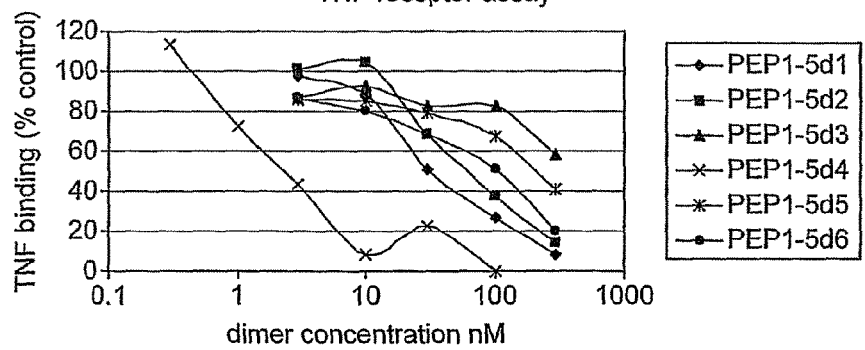

FIG. 11 TNF receptor assay comparing TAR1-5 dimers 1-6. All dimers have been FPLC purified and the results for the optimal dimeric species are shown.

Figure 12:
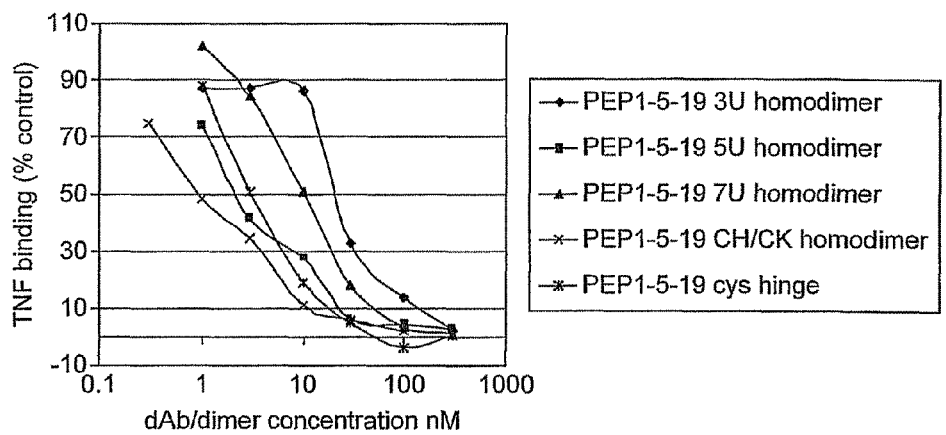

FIG. 12 TNF receptor assay of TAR1-5 19 homodimers in different formats: dAb-linker-dAb format with 3U, 5U or 7U linker, Fab format and cysteine hinge linker format.

FIG. 13 Dummy VH sequence for library 1. The sequence of the VH framework based on germ line sequence DP47-JH4b. Positions where NNK randomisation (N=A or T or C or G nucleotides; K=G or T nucleotides) has been incorporated into library 1 are indicated in bold underlined text. Nucleotide sequence disclosed as SEQ ID NO: 200 and amino acid sequence disclosed as SEQ ID NO: 182.

FIG. 14 Dummy VH sequence for library 2. The sequence of the VH framework based on germ line sequence DP47-JH4b. Positions where NNK randomisation (N=A or T or C or G nucleotides; K=G or T nucleotides) has been incorporated into library 2 are indicated in bold underlined text. Nucleotide sequence disclosed as SEQ ID NO: 201 and amino acid sequence disclosed as SEQ ID NO: 202.

FIG. 15 Dummy $V_K$ sequence for library 3. The sequence of the $V_K$ framework based on germ line sequence $DP_K9-J_K1$. Positions where NNK randomisation (N=A or T or C or G nucleotides; K=G or T nucleotides) has been incorporated into library 3 are indicated in bold underlined text. Nucleotide sequence disclosed as SEQ ID NO: 203 and amino acid sequence disclosed as SEQ ID NO: 204.

FIG. 16 Nucleotide and amino acid sequence of anti MSA dAbs MSA 16 (nucleotide sequence disclosed as SEQ ID NO: 205 and amino acid sequence disclosed as SEQ ID NO: 206) and MSA 26 (nucleotide sequence disclosed as SEQ ID NO: 207 and amino acid sequence disclosed as SEQ ID NO: 208).

Figure 17:
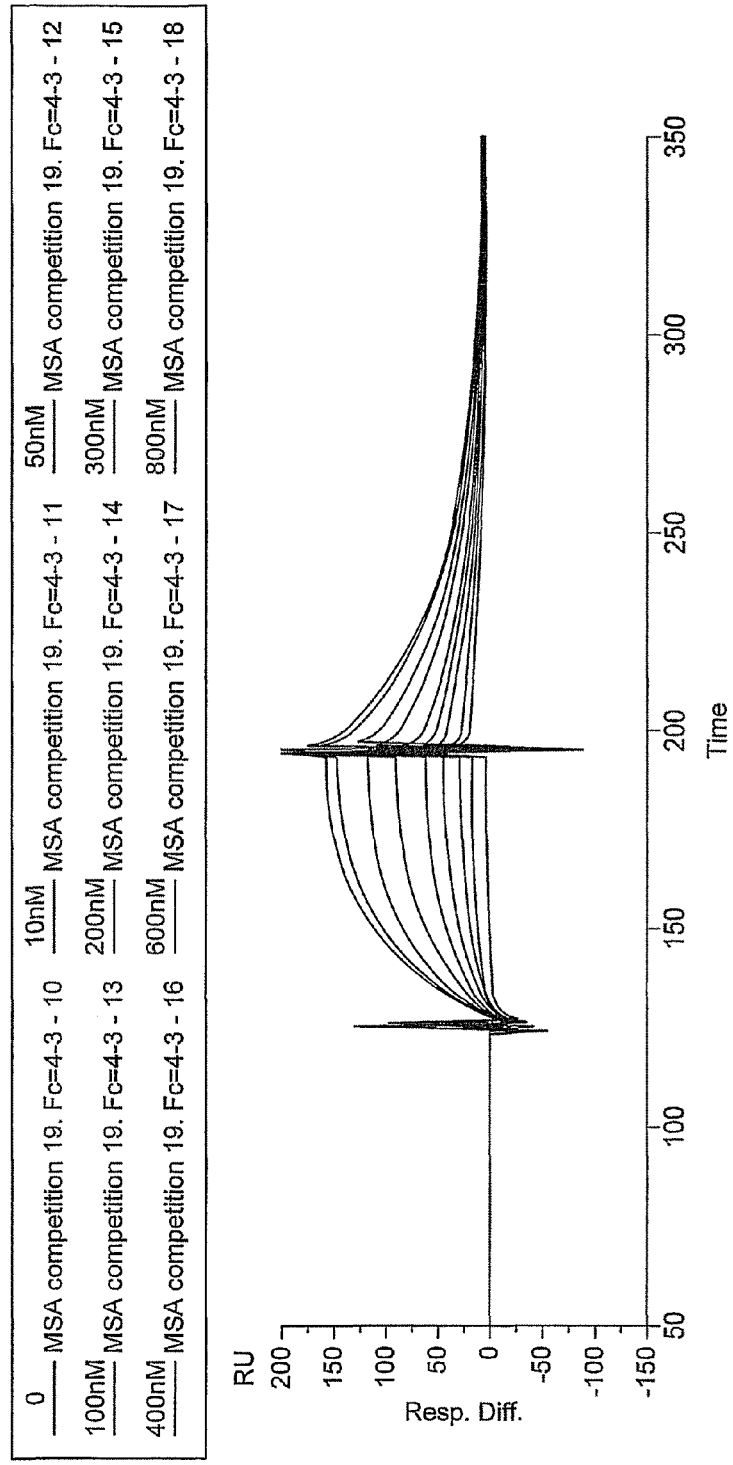

FIG. 17 Inhibition Biacore of MSA 16 and 26. Purified dAbs MSA 16 and MSA26 were analysed by inhibition Biacore to determine Kd. Briefly, the dAbs were tested to determine the concentration of dAb required to achieve 200RUs of response on a Biacore CM5 chip coated with a high density of MSA. Once the required concentrations of dAb had been determined, MSA antigen at a range of concentrations around the expected Kd was premixed with the dAb and incubated overnight. Binding to the MSA coated Biacore chip of dAb in each of the premixes was then measured at a high flow-rate of 30 μl/minute.

FIG. 18 Serum levels of MSA16 following injection. Serum half life of the dAb MSA16 was determined in mouse. MSA16 was dosed as single i.v. injections at approx 1.5 mg/kg into CD1 mice. Modelling with a 2 compartment model showed MSA16 had a t1/2α of 0.98 hr, a t1/2β of 36.5 hr and an AUC of 913 hr·mg/ml. MSA16 had a considerably lengthened half life compared with HEL4 (an anti-hen egg white lysozyme dAb) which had a t1/2a of 0.06 hr and a t1/2β of 0.34 hr.

FIG. 19 ELISA (a) and TNF receptor assay (c) showing inhibition of TNF binding with a Fab-like fragment comprising MSA26Ck and TAR1-5-19CH. The TNF receptor assay (b) was conducted in the presence of a constant concentration of heterodimer (18nM) and a dilution series of MSA and HSA. Addition of MSA with the Fab-like fragment reduces the level of inhibition. An ELISA plate coated with 1 μg/ml TNFα was probed with dual specific Vκ $C_H$ and Vκ Cκ Fab like fragment and also with a control TNFα binding dAb at a concentration calculated to give a similar signal on the ELISA. Both the dual specific and control dAb were used to probe the ELISA plate in the presence and in the absence of 2 mg/ml MSA. The signal in the dual specific well was reduced by more than 50% but the signal in the dAb well was not reduced at all (see FIG. 19a). The same dual specific protein was also put into the receptor assay with and without MSA and competition by MSA was also shown (see FIG. 19c). This demonstrates that binding of MSA to the dual specific is competitive with binding to TNFα.

Figure 20:
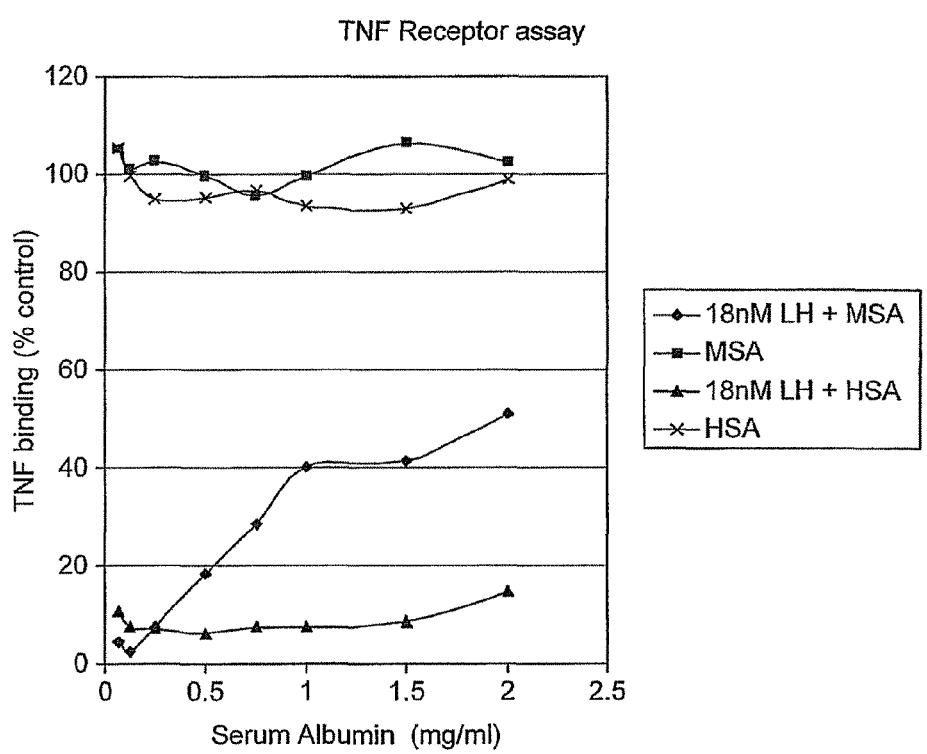

FIG. 20 TNF receptor assay showing inhibition of TNF binding with a disulphide bonded heterodimer of TAR1-5-19 dAb and MSA16 dAb. Addition of MSA with the dimer reduces the level of inhibition in a dose dependant manner. The TNF receptor assay (FIG. 19 (b)) was conducted in the presence of a constant concentration of heterodimer (18 nM) and a dilution series of MSA and HSA. The presence of HSA at a range of concentrations (up to 2 mg/ml) did not cause a reduction in the ability of the dimer to inhibit TNFα. However, the addition of MSA caused a dose dependant reduction in the ability of the dimer to inhibit TNFα (FIG. 19a). This demonstrates that MSA and TNFα compete for binding to the cys bonded TAR1-5-19, MSA16 dimer. MSA and HSA alone did not have an effect on the TNF binding level in the assay.

Figure 21:
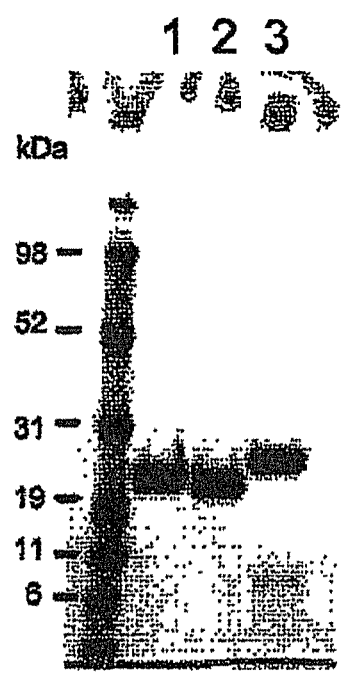

FIG. 21 Purified recombinant domains of human serum albumin (HSA), lanes 1-3 contain HSA domains I, II and III, respectively.

Figure 22:
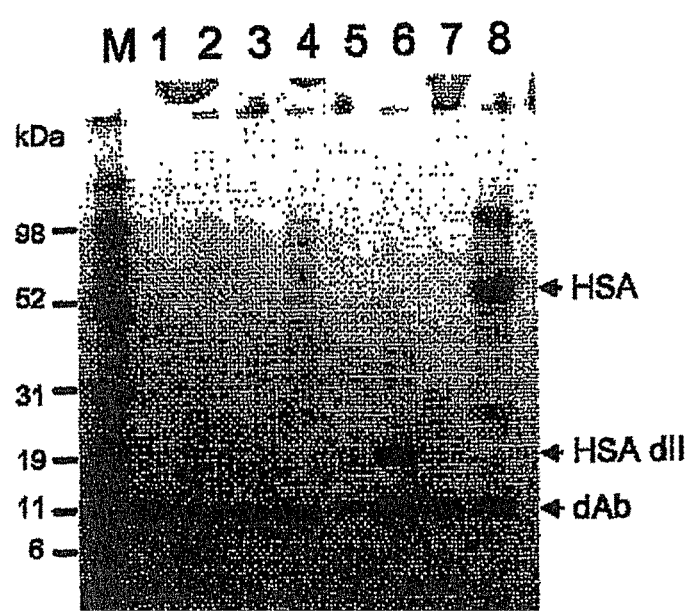

FIG. 22 Example of an immunoprecipitation showing that an HSA-binding dAb binds full length HSA (lane 8) and HSA domain II (lane 6), but does not bind HSA domains I and III (lanes 5 and 7, respectively). A non-HSA-binding dAb does not pull down either full length HSA or HSA domains I, II, or III (lanes 1-4).

Figure 23:
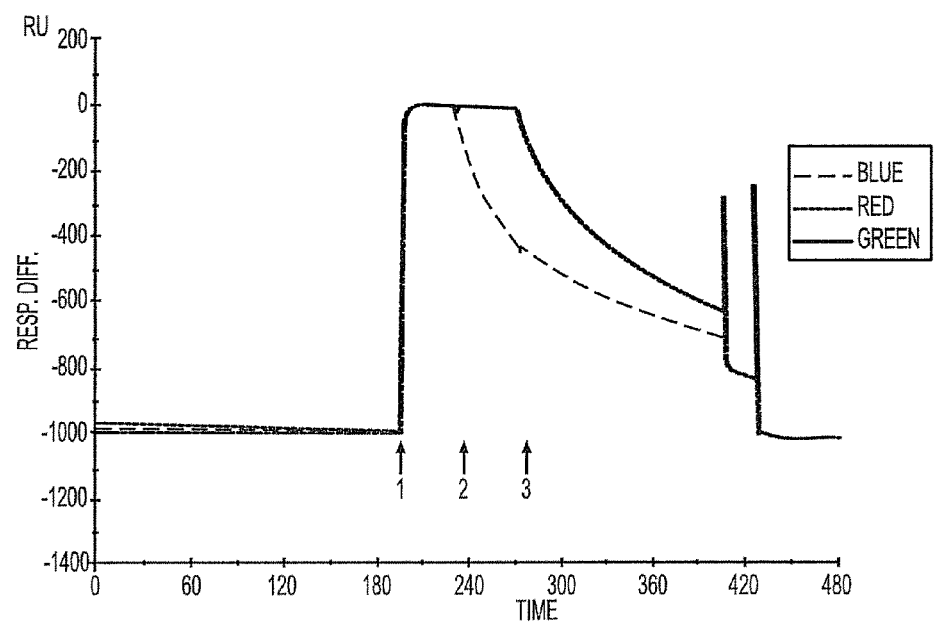
Figure 23:
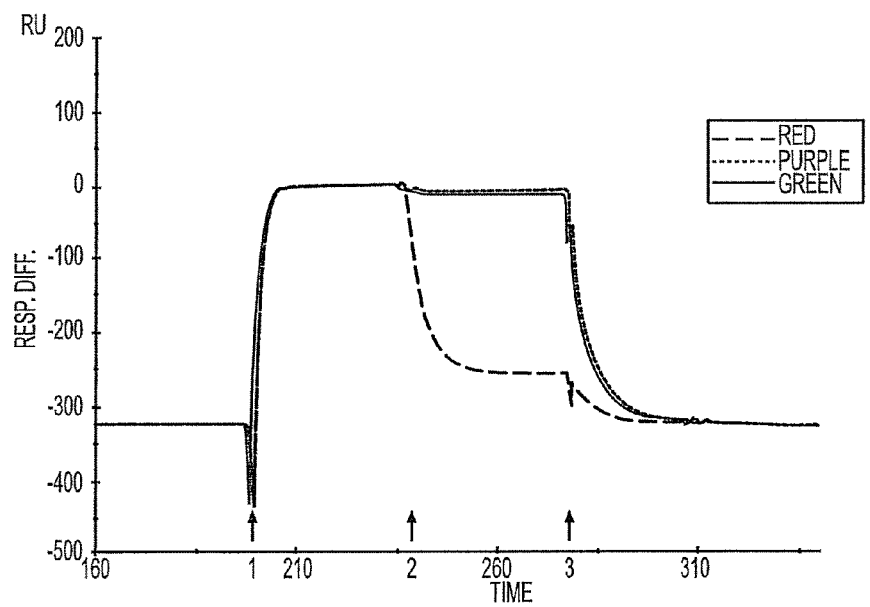

FIG. 23. Example of identification of HSA domain binding by a dAb as identified by surface plasmon resonance. The dAb under study was injected as described onto a low density coated human serum albumin CM5 sensor chip (Biacore). At point 1, the dAb under study was injected alone at 1 µM. At point 2, using the co-inject command, sample injection was switched to a mixture of 1 µM dAb plus 7 µM HSA domain 1, 2 or 3, produced in *Pichia*. At point 3, sample injection was stopped, and buffer flow continued. Results for two different dAbs are shown in 23a) and 23b). When the dAb is injected with the HSA domain that it binds, it forms a complex that can no longer bind the HSA on the chip, hence the Biacore signal drops at point 2, with an off-rate that reflects the 3-way equilibrium between dAb, soluble HSA domain, and chip bound HSA. When the domain does not bind the dAb, the signal remains unchanged at point 2, and starts to drop only at point 3, where flow is switched to buffer. In both these cases, the dAb binds HSA domain 2.

Figure 24:
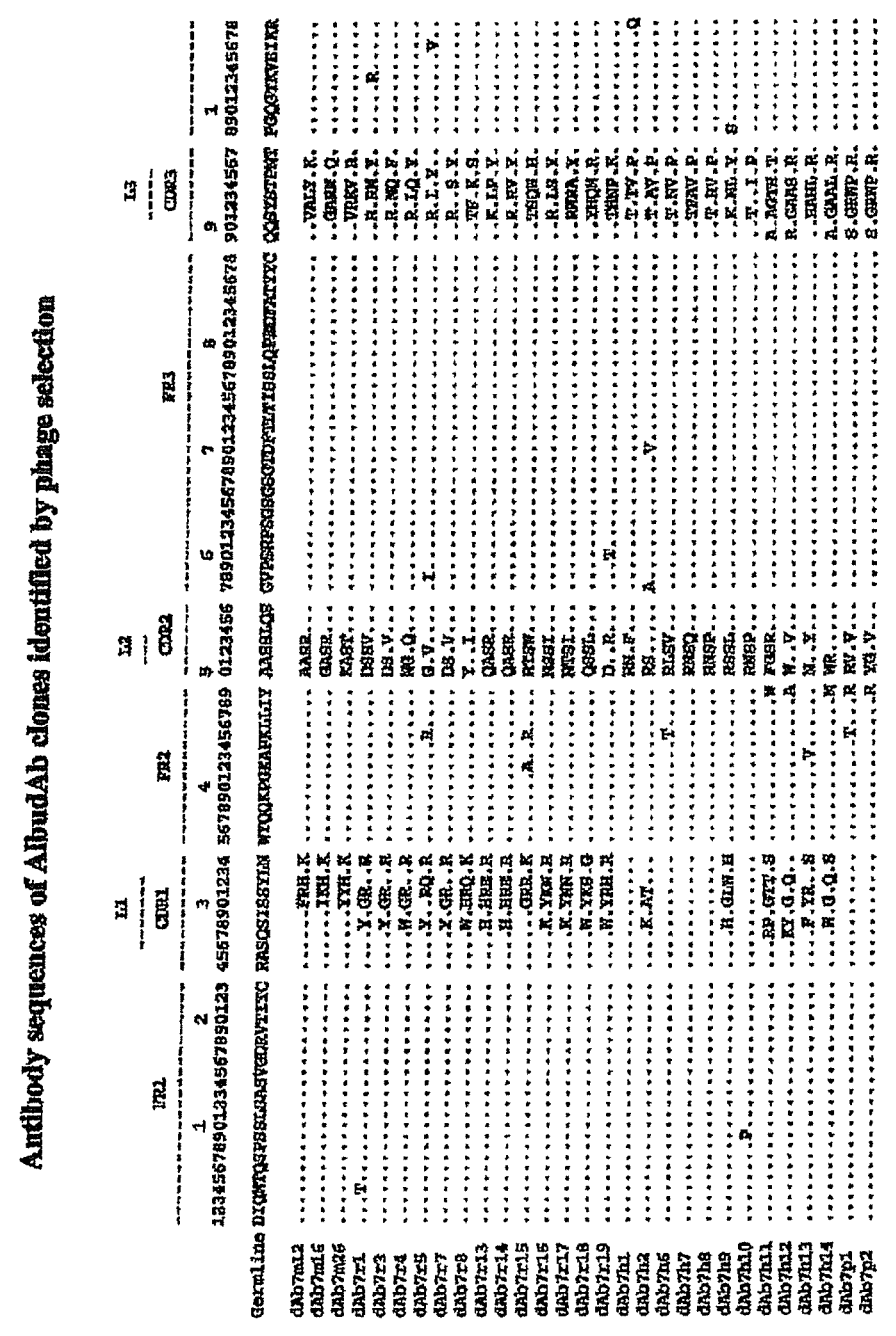
Figure 24:
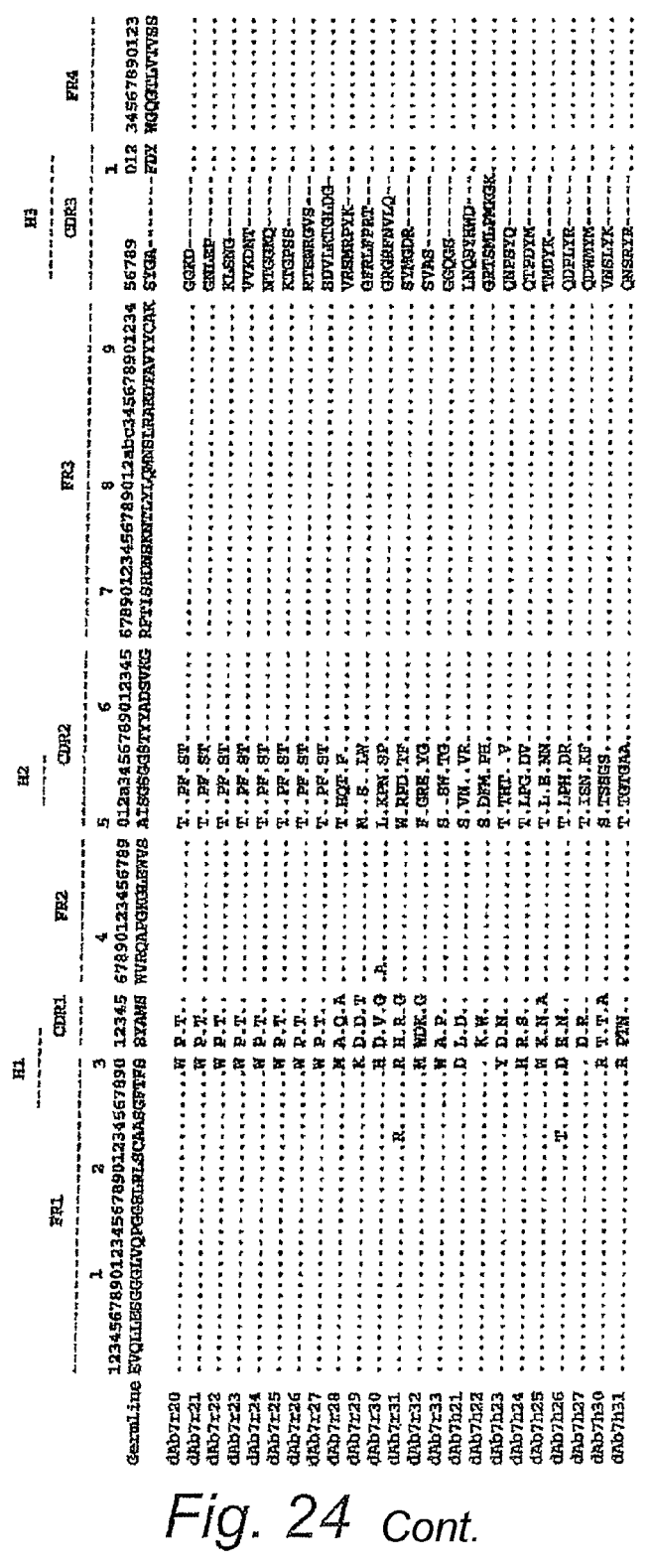

FIG. 24 Antibody sequences of AlbudAb™ (a dAb which specifically binds serum albumin) clones identified by phage selection. All clones (SEQ ID NOS 209-260, respectively, in order of appearance) have been aligned to the human germ line genes (SEQ ID NOS 192 and 182, respectively, in order of appearance). Residues that are identical to germ line have been represented by '.'. In the VH CDR3, the symbol '-' has been used to facilitate alignment but does not represent a residue. All clones were selected from libraries based on a single human framework comprising the heavy-chain germ line genes V3-23/DP47 and JH4b for the VH libraries and the K light chain genes O12/O2/DPK9 and $J_K1$ for the $V_K$ libraries with side chain diversity incorporated at positions in the antigen binding site.

FIG. 25 Alignments (SEQ ID NOS 261-263, respectively, in order of appearance) of the three domains of human serum albumin. The conservation of the cysteine residues can clearly be seen.

DETAILED DESCRIPTION OF THE INVENTION

Definitions

"Complementary" Two immunoglobulin domains are "complementary" where they belong to families of structures which form cognate pairs or groups or are derived from such families and retain this feature. For example, a $V_H$ domain and a $V_L$ domain of an antibody are complementary; two $V_H$ domains are not complementary, and two $V_L$ domains are not complementary. Complementary domains may be found in other members of the immunoglobulin superfamily, such as the $V_\alpha$ and $V_\beta$ (or γ and δ) domains of the T-cell receptor. In the context of the second configuration of the present invention, non-complementary domains do not bind a target molecule cooperatively, but act independently on different target epitopes which may be on the same or different molecules. Domains which are artificial, such as domains based on protein scaffolds which do not bind epitopes unless engineered to do so, are non-complementary. Likewise, two domains based on (for example) an immunoglobulin domain and a fibronectin domain are not complementary.

"Immunoglobulin" This refers to a family of polypeptides which retain the immunoglobulin fold characteristic of antibody molecules, which contains two β sheets and, usually, a conserved disulphide bond. Members of the immunoglobulin superfamily are involved in many aspects of cellular and non-cellular interactions in vivo, including widespread roles in the immune system (for example, antibodies, T-cell receptor molecules and the like), involvement in cell adhesion (for example the ICAM molecules) and intracellular signalling (for example, receptor molecules, such as the PDGF receptor). The present invention is applicable to all immunoglobulin superfamily molecules which possess binding domains. Preferably, the present invention relates to antibodies.

"Combining" Variable domains according to the invention are combined to form a group of domains; for example, complementary domains may be combined, such as $V_L$ domains being combined with $V_H$ domains. Non-complementary domains may also be combined. Domains may be combined in a number of ways, involving linkage of the domains by covalent or non-covalent means.

"Domain" A domain is a folded protein structure which retains its tertiary structure independently of the rest of the protein. Generally, domains are responsible for discrete functional properties of proteins, and in many cases may be added, removed or transferred to other proteins without loss of function of the remainder of the protein and/or of the domain.

As used herein, a "single variable domain" is a domain which can specifically bind an epitope, an antigen or a ligand independently, that is, without the requirement for another binding domain to co-operatively bind the epitope, antigen or ligand. Such an epitope, antigen or ligand can be naturally occurring, or can be a modification of a natural occurring epitope, antigen or ligand, or can be synthetic. The "variable" portion of the single variable domain essentially determines the binding specificity of each particular single variable domain. Thus, the term "variable" in the context of single variable domains, refers to the fact that the sequence variability is not evenly distributed through a single variable domain, but is essentially distributed between the framework or skeleton portions of the single variable domain. For example, in an antibody single variable domain, the variability is concentrated in one to three segments commonly known as complementarity determining regions (CDRs). The one or more CDRs can be distributed between antibody framework regions (FR) of a light chain or of a heavy chain to form either an antibody light chain single variable domain or an antibody heavy chain single variable domain, respectively, each of which specifically binds an epitope independently of another binding domain. Similarly structured is a T-cell receptor single variable domain, with its one to three CDRs distributed between the TCR framework domains.

Thus, the variable portions conferring the binding specificity of single variable domains may differ extensively in sequence from other single variable domains having substantially the same remaining scaffold portion, and accordingly, may have a diverse range of binding specificities. Scaffolds of single variable domains include antibody framework scaffolds, consensus antibody frameworks, and scaffolds originating and/or derived from bacterial proteins, e.g. GroEL, GroEs, SpA, SpG, and from eukaryotic proteins, e.g., CTLA-4, lipocallins, fibronectin, etc. One source of the variable portions of single variable domains include one or more CDRs, which can be grafted onto non-immunoglobulin scaffolds as well as antibody framework scaffolds to generate antibody single variable domains. Another source of variation in a single variable domain can be the diversification of chosen positions in a non-immunoglobulin framework scaffold such as fibronectin, to generate single variable domains, using molecular biology techniques, such as NNK codon diversity. Similarly, this source of variation is also applicable to an antibody single variable domain.

An antibody single variable domain can be derived from antibody sequences encoded and/or generated by an antibody producing species, and includes fragment(s) and/or derivatives of the antibody variable region, including one or more framework regions, or framework consensus sequences, and/or one or more CDRs. Accordingly, an antibody single variable domain includes fragment(s) and/or derivative(s) of an antibody light chain variable region, or of an antibody heavy chain variable region, or of an antibody VHH region. For example, antibody VHH regions include those that are endogenous to camelids: e.g., camels and llamas, and the new antigen receptor (NAR) from nurse and wobbegong sharks (Roux et al., 1998 PNAS 95(20):11804-9) and the $V_H$ region from spotted ratfish (Rast et al., 1998 Immunogenetics 47:234-245). Antibody light chain variable domains and antibody heavy chain variable domains include those endogenous to an animal species including, but preferably not limited to, human, mouse, rat, porcine, cynomolgus, hamster, horse, cow, goat, dog, cat, and avian species, e.g. human VKappa and human VH3, respectively. Antibody light chain variable regions and antibody heavy chain variable regions, also includes consensus antibody frameworks, as described infra, including those of V region families, such as the VH3 family. A T-cell receptor single variable domain is a single variable domain which is derived from a T-cell receptor chain(s), e.g., α, β, γ and δ chains, and which binds an epitope or an antigen or a ligand independently of another binding domain for that epitope, antigen or ligand, analogously to antibody single variable domains.

An antibody single variable domain also encompasses a protein domain which comprises a scaffold which is not derived from an antibody or a T-cell receptor, and which has been genetically engineered to display diversity in binding specificity relative to its pre-engineered state, by incorporating into the scaffold, one or more of a CDR1, a CDR2 and/or a CDR3, derivative or fragment thereof, or an entire antibody V domain. An antibody single variable domain can also include both non-immunoglobulin scaffold and immunoglobulin scaffolds as illustrated by the GroEL single variable domain multimers described infra. Preferably the CDR(s) is from an antibody V domain of an antibody chain, e.g., VH, VL, and VHH. The antibody chain can be one which specifically binds an antigen or epitope in concert with a second antibody chain, or the antibody chain can be one which specifically binds an antigen or epitope independently of a second antibody chain, such as VHH chain. The integration of one or more CDRs into an antibody single variable domain which comprises a non-immunoglobulin scaffold must result in the non immunoglobulin scaffold's single variable domain's ability to specifically bind an epitope or an antigen or a ligand independently of another binding domain for that epitope, antigen or ligand.

A single domain is transformed into a single variable domain by introducing diversity at the site(s) designed to become the binding site, followed by selection for desired binding characteristics using, for example, display technologies. Diversity can be introduced in specific sites of a non-immunoglobulin scaffold of interest by randomizing the amino acid sequence of specific loops of the scaffold, e.g. by introducing NNK codons. This mechanism of generating diversity followed by selection of desired binding characteristics is similar to the natural selection of high affinity, antigen-specific antibodies resulting from diversity generated in the loops which make up the antibody binding site in nature. Ideally, a single domain which is small and contains a fold similar to that of an antibody loop, is transformed into a single variable domain, variants of the single variable domain are expressed, from which single variable domains containing desired binding specificities and characteristics can be selected from libraries containing a large number of variants of the single variable domain.

Nomenclature of single variable domains: sometimes the nomenclature of an antibody single variable domain is abbreviated by leaving off the first "d" or-the letters "Dom", for example, Ab7h24 is identical to dAb7h24 which is identical to DOM7h24.

By antibody single variable domain is meant a folded polypeptide domain comprising sequences characteristic of antibody variable domains. It therefore includes complete antibody variable domains and modified variable domains, for example, in which one or more loops have been replaced by sequences which are not characteristic of antibody variable domains, or antibody variable domains which have been truncated or comprise N- or C-terminal extensions, as well as folded fragments of variable domains which retain at least in part the binding activity and specificity of the full-length domain.

"Repertoire" A collection of diverse variants, for example polypeptide variants which differ in their primary sequence. A library used in the present invention will encompass a repertoire of polypeptides comprising at least 1000 members.

"Library" The term library refers to a mixture of heterogeneous polypeptides or nucleic acids. The library is composed of members, each of which have a single polypeptide or nucleic acid sequence. To this extent, library is synonymous with repertoire. Sequence differences between library members are responsible for the diversity present in the library. The library may take the form of a simple mixture of polypeptides or nucleic acids, or may be in the form of organisms or cells, for example bacteria, viruses, animal or plant cells and the like, transformed with a library of nucleic acids. Preferably, each individual organism or cell contains only one or a limited number of library members. Advantageously, the nucleic acids are incorporated into expression vectors, in order to allow expression of the polypeptides encoded by the nucleic acids. In a preferred aspect, therefore, a library may take the form of a population of host organisms, each organism containing one or more copies of an expression vector containing a single member of the library in nucleic acid form which can be expressed to produce its corresponding polypeptide member. Thus, the population of host organisms has the potential to encode a large repertoire of genetically diverse polypeptide variants.

A "closed conformation multi-specific ligand" describes a multi-specific ligand as herein defined comprising at least two epitope binding domains as herein defined. The term 'closed conformation' (multi-specific ligand) means that the epitope binding domains of the ligand are arranged such that epitope binding by one epitope binding domain competes with epitope binding by another epitope binding domain. That is, cognate epitopes may be bound by each epitope binding domain individually but not simultaneously. The closed conformation of the ligand can be achieved using methods herein described.

"Antibody" An antibody (for example IgG, IgM, IgA, IgD or IgE) or fragment (such as a Fab, F(ab')$_2$, Fv, disulphide linked Fv, scFv, closed conformation multispecific antibody, disulphide-linked scFv, diabody) whether derived from any species naturally producing an antibody, or created by recombinant DNA technology; whether isolated from serum, B-cells, hybridomas, transfectomas, yeast or bacteria).

"Dual-specific ligand" A ligand comprising a first immunoglobulin single variable domain and a second immunoglobulin single variable domain as herein defined, wherein the variable domains are capable of binding to two different antigens or two epitopes on the same antigen which are not normally bound by a monospecific immunoglobulin. For example, the two epitopes may be on the same hapten, but are not the same epitope or sufficiently adjacent to be bound by a monospecific ligand. The dual specific ligands according to the invention are composed of variable domains which have different specificities, and do not contain mutually complementary variable domain pairs which have the same specificity. Thus, dual specific ligands, which as defined herein contain two single variable domains, are a subset of multimeric ligands, which as defined herein contain two or more single variable domains, wherein at least two of the single variable domains are capable of binding to two different antigens or to two different epitopes on the same antigen. Further, a dual specific ligand as defined herein is also distinct from a ligand comprising an antibody single variable domain, and a second antigen and/or epitope binding domain which is not a single variable domain. Further still, a dual specific ligand as defined herein is also distinct form a ligand containing a first and a second antigen/epitope binding domain, where neither antigen/epitope binding domain is a single variable domain as defined herein.

"Antigen" A molecule that is bound by a ligand according to the present invention. Typically, antigens are bound by antibody ligands and are capable of raising an antibody response in vivo. It may be a polypeptide, protein, nucleic acid or other molecule. Generally, the dual specific ligands according to the invention are selected for target specificity against a particular antigen. In the case of conventional antibodies and fragments thereof, the antibody binding site defined by the variable loops (L1, L2, L3 and H1, H2, H3) is capable of binding to the antigen.

"Epitope" A unit of structure conventionally bound by an immunoglobulin $V_H/V_L$ pair. Epitopes define the minimum binding site for an antibody, and thus represent the target of specificity of an antibody. In the case of a single domain antibody, an epitope represents the unit of structure bound by a variable domain in isolation. An epitope binding domain comprises a protein scaffold and epitope interaction sites (which are advantageously on the surface of the protein scaffold). An epitope binding domain can comprise epitope interaction sites that are nonlinear, e.g. where the epitope binding domain comprises multiple epitope interaction sites that have intervening regions between them, e.g., CDRs separated by FRs, or are present on separate polypeptide chains. Alternatively, an epitope binding domain can comprise a linear epitope interaction site composed of contiguously encoded amino acids on one polypeptide chain.

"Generic ligand" A ligand that binds to all members of a repertoire. Generally, not bound through the antigen binding site as defined above. Non-limiting examples include protein A, protein L and protein G.

"Selecting" Derived by screening, or derived by a Darwinian selection process, in which binding interactions are made between a domain and the antigen or epitope or between an antibody and an antigen or epitope. Thus a first variable domain may be selected for binding to an antigen or epitope in the presence or in the absence of a complementary variable domain.

"Universal framework" A single antibody framework sequence corresponding to the regions of an antibody conserved in sequence as defined by Kabat ("Sequences of Proteins of Immunological Interest", US Department of Health and Human Services) or corresponding to the human germ line immunoglobulin repertoire or structure as defined by Chothia and Lesk, (1987) J. Mol. Biol. 196:910-917. The invention provides for the use of a single framework, or a set of such frameworks, which has been found to permit the derivation of virtually any binding specificity though variation in the hypervariable regions alone.

As used herein "conjugate" refers to a composition comprising an antigen binding fragment of an antibody that binds serum albumin that is bonded to a drug.

As used herein, the term "small molecule" means a compound having a molecular weight of less than 1,500 daltons, preferably less than 1000 daltons.

Such conjugates include "drug conjugates," which comprise an antigen-binding fragment of an antibody that binds serum albumin to which a drug is covalently bonded, and "noncovlaent drug conjugates," which comprise an antigen-binding fragment of an antibody that binds serum albumin to which a drug is noncovalently bonded.

As used herein, "drug conjugate" refers to a composition comprising an antigen-binding fragment of an antibody that binds serum albumin to which a drug is covalently bonded. The drug can be covalently bonded to the antigen-binding fragment directly or indirectly through a suitable linker moiety. The drug can be bonded to the antigen-binding fragment at any suitable position, such as the amino-terminus, the carboxyl-terminus or through suitable amino acid side chains (e.g., the amino group of lysine).

"Half-life" The time taken for the serum concentration of the ligand to reduce by 50%, in vivo, for example due to degradation of the ligand and/or clearance or sequestration of the ligand by natural mechanisms. The ligands of the invention are stabilised in vivo and their half-life increased by binding to molecules which resist degradation and/or clearance or sequestration. Typically, such molecules are naturally occurring proteins which themselves have a long half-life in vivo. The half-life of a ligand is increased if its functional activity persists, in vivo, for a longer period than a similar ligand which is not specific for the half-life increasing molecule. Thus, a ligand specific for HSA and a target molecule is compared with the same ligand wherein the specificity for HSA is not present, that it does not bind HSA but binds another molecule. For example, it may bind a second epitope on the target molecule. Typically, the half life is increased by 10%, 20%, 30%, 40%, 50% or more. Increases in the range of 2×, 3×, 4×, 5×, 10×, 20×, 30×, 40×, 50× or more of the half life are possible. Alternatively, or in addition, increases in the range of up to 30×, 40×, 50×, 60×, 70×, 80×, 90×, 100×, 150× of the half life are possible.

The phrase "substantially the same" when used to compare the T beta half life of a ligand with the T beta half life of serum albumin in a host means that the T beta half life of the ligand in a host varies no more than 50% from the T beta half life of serum albumin itself in the same host, preferably a human host, e.g., the T beta half life of such a ligand is no more than 50% less or no more than 50% greater than the T beta half life of serum albumin in a specified host. Preferably, when referring to the phrase "substantially the same", the T beta half life of the ligand in a host varies no more than 20% to 10% from the half life of serum albumin itself, and more preferably, varies no more than 9%, 8%, 7%, 6%, 5%, 4%, 3%, 2%, or 1%, or less from the half life of serum albumin itself, or does not vary at all from the half life of serum albumin itself.

Alternatively, the phrase "not substantially the same" when used to compare the T beta half life of a ligand with the T beta half life of serum albumin in a host means that the T beta half life of the ligand in a host varies at least 50% from the T beta half life of serum albumin itself in the same host, preferably a human host, e.g., the T beta half life of the ligand is more than 50% greater than the T beta half life of serum albumin in a specified host.

"Homogeneous immunoassay" An immunoassay in which analyte is detected without need for a step of separating bound and un-bound reagents.

"Substantially identical" or "substantially homologous" A first amino acid or nucleotide sequence that contains a sufficient number of identical or equivalent (e.g., with a similar side chain, e.g., conserved amino acid substitutions) amino acid residues or nucleotides to a second amino acid or nucleotide sequence such that the first and second amino acid or nucleotide sequences have similar activities. In the case of first and second antibodies and/or single variable domains described herein, the second antibody or single variable domain has the same binding specificity as the first and has at least 50%, or at least up to 55%, 60%, 70%, 75%, 80%, 90%, 95%, 96%, 97%, 98%, 99% or 100% of the affinity of the first antibody or single variable domain.

As used herein, the terms "low stringency," "medium stringency," "high stringency," or "very high stringency conditions" describe conditions for nucleic acid hybridization and washing. Guidance for performing hybridization reactions can be found in *Current Protocols in Molecular Biology*, John Wiley & Sons, N.Y. (1989), 6.3.1-6.3.6, which is incorporated herein by reference in its entirety. Aqueous and non-aqueous methods are described in that reference and either can be used. Specific hybridization conditions referred to herein are as follows: (1) low stringency hybridization conditions in 6× sodium chloride/sodium citrate (SSC) at about 45° C., followed by two washes in 0.2×SSC, 0.1% SDS at least at 50° C. (the temperature of the washes can be increased to 55° C. for low stringency conditions); (2) medium stringency hybridization conditions in 6×SSC at about 45° C., followed by one or more washes in 0.2×SSC, 0.1% SDS at 60° C.; (3) high stringency hybridization conditions in 6×SSC at about 45° C., followed by one or more washes in 0.2×SSC, 0.1% SDS at 65° C.; and preferably (4) very high stringency hybridization conditions are 0.5M sodium phosphate, 7% SDS at 65° C., followed by one or more washes at 0.2×SSC, 1% SDS at 65° C. Very high stringency conditions (4) are the preferred conditions and the ones that should be used unless otherwise specified.

"Surface Plasmon Resonance" Competition assays can be used to determine if a specific antigen or epitope, such as human serum albumin, competes with another antigen or epitope, such as cynomolgus serum albumin, for binding to a serum albumin binding ligand described herein, such as a specific dAb. Similarly competition assays can be used to determine if a first ligand such as dAb, competes with a second ligand such as a dAb for binding to a target antigen or epitope. The term "competes" as used herein refers to substance, such as a molecule, compound, preferably a protein, which is able to interfere to any extent with the specific binding interaction between two or more molecules. The phrase "does not competitively inhibit" means that substance, such as a molecule, compound, preferably a protein, does not interfere to any measurable or significant extent with the specific binding interaction between two or more molecules. The specific binding interaction between two or more molecules preferably includes the specific binding interaction between a single variable domain and its cognate partner or target. The interfering or competing molecule can be another single variable domain or it can be a molecule that that is structurally and/or functionally similar to a cognate partner or target.

A single variable domain includes an immunoglobulin single variable domain and a non-immunoglobulin single variable domain which contains one, two, three or more CDR regions from an immunoglobulin variable domain, such as an antibody variable domain, including an antibody heavy or antibody light chain single variable domain. The single variable domain can be derived from an animal, including a human, rat, mouse, pig, monkey, camelidae, such as an antibody variable (V) region, or it can be derived from a microorganism such as *E. coli* in the case of the non-immunglobulin scaffold of GroEL and GroEs. A single variable domain can be partially or totally artificial, or can be generated using recombinant molecular biology technology.

In vitro competition assays for determining the ability of a single variable domain to compete for binding to a target to another target binding domain, such as another single variable domain, as well as for determining the Kd, are well know in the art. One preferred competition assay is a surface plasmon resonance assay, which has the advantages of being fast, sensitive and useful over a wide range of protein concentrations, and requiring small amounts of sample material. A preferred surface plasmon resonance assay competition is a competition Biacore experiment. A competition Biacore experiment can be used to determine whether, for example, cynomolgus serum albumin and human serum albumin compete for binding to a ligand such as dAb DOM7h-x. One experimental protocol for such an example is as follows.

For example, after coating a CM5 sensor chip (Biacore AB) at 25° C. with approximately 1000 resonance units (RUs) of human serum albumin (HSA), a purified dAb is injected over the antigen surface at a single concentration (e.g., 1 um) alone, and in combination with a dilution series of the cynomolgus serum albumin (CSA). The serial dilutions of HSA were mixed with a constant concentration (40 nM) of the purified dAb. A suitable dilution series of CSA would be starting at 5 uM CSA, with six two-fold dilutions down to 78 nM CSA. These solutions must be allowed to reach equilibrium before injection. Following the injection, a response reading was taken to measure the resulting binding RUs for the dAb alone and each of the several dAb/CSA mixtures, the data being used in accordance with BIA evaluation software, generate a dose-response curve for each CSA's inhibition of the AlbudAb™'s (a dAb which specifically binds serum albumin) binding to the chip on which HSA is immobilized. By comparing the bound RUs of dAb alone with the bound RUs of dAb+CSA, one will be able to see whether the CSA competes with the HSA to bind the dAb. If it does compete, then as the CSA concentration in solution is increased, the RUs of dAb bound to HSA will decrease. If there is no competition, then adding CSA will have no impact on how much dAb binds to HSA.

One of skill would know how to adapt this or other protocols in order to perform this competition assay on a variety of different ligands, including the several ligands described herein that bind serum albumin. The variety of ligands includes, but is not limited to, monomer single variable domains, including single variable domains comprising an immunoglobulin and/or a non-immunoglobulin scaffold, dAbs, dual specific ligands, and multimers of these ligands. One of skill would also know how to adapt this protocol in order to compare the binding of several different pairs of antigens and/or epitopes to a ligand using this competition assay.

These competition experiments can provide a numeric cutoff by which one can determine if an antigen or epitope competes with another antigen or epitope for binding to a specific ligand, preferably a dAb. For example, in the experiment outlined above, if 5 µM CSA in solution results in a 10%, or lower, reduction in RUs of dAb binding to HSA, then there is considered to be no competition for binding. Accordingly, a reduction in RUs of dAb binding to HSA in the presence of CSA of greater than 10% would indicate the presence of competition for binding of the dAb for binding HSA by CSA. A reduction in RUs of dAb binding to HSA of less than 10% would indicate the absence of competition by CSA for the dAb's binding HSA, with reductions of 9%, 8%, 7%, 6%, 5%, 4%, 3%, 2%, and 1% being progressively more stringent requirements for indicating the absence of competition. The greater the reduction in RUs of dAb binding to HSA, the greater the competition. Thus, increasing levels of competition can be graded according to the percent reduction in RUs binding to HSA, i.e. at least 15%, 20%, 25%, 30%, 35%, 40%, 45%, 50%, 55%, 60%, 65%, 70%, 75%, 80%, 85%, 90%, 95%, or up to 100% reduction.

A fragment as used herein refers to less than 100% of the sequence (e.g., up to 99%, 90%, 80%, 70%, 60%, 50%, 40%, 30%, 20%, 10% etc.), but comprising 5, 6, 7, 8, 9, 10, 12, 13, 14, 15, 16, 17, 18, 19, 20, 21, 22, 23, 24, 25 or more contiguous amino acids. A fragment is of sufficient length such that the serum albumin binding of interest is maintained with affinity of $1 \times 10^{-6}$ M or less. A fragment as used herein also refers to optional insertions, deletions and substitutions of one or more amino acids which do not substantially alter the ability of the altered polypeptide to bind to a single domain antibody raised against the target. The number of amino acid insertions deletions or substitutions is preferably up to 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69 or 70 amino acids.

DETAILED DESCRIPTION OF THE INVENTION

Unless defined otherwise, all technical and scientific terms used herein have the same meaning as commonly understood by one of ordinary skill in the art (e.g., in cell culture, molecular genetics, nucleic acid chemistry, hybridisation techniques and biochemistry). Standard techniques are used for molecular, genetic and biochemical methods (see generally, Sambrook et al., Molecular Cloning: A Laboratory Manual, 2d ed. (1989) Cold Spring Harbor Laboratory Press, Cold Spring Harbor, N.Y. and Ausubel et al., Short Protocols in Molecular Biology (1999) $4^{th}$ Ed, John Wiley & Sons, Inc. which are incorporated herein by reference) and chemical methods. Standards techniques for surface plasmon resonance assays include Jan Terje Andersen et al. (2006) Eur. J. Immunol. 36:304-3051 Fagerstam (1991) Tech. Protein Chem. 2:65-71, and Johnsson et al (1991) Anal. Biochem 198:268-277.

Preparation of Immunoglobulin Based Multi-Specific Ligands

Dual specific ligands according to the invention, whether open or closed in conformation according to the desired configuration of the invention, may be prepared according to previously established techniques, used in the field of antibody engineering, for the preparation of scFv, "phage" antibodies and other engineered antibody molecules. Techniques for the preparation of antibodies, and in particular bispecific antibodies, are for example described in the following reviews and the references cited therein: Winter & Milstein, (1991) Nature 349:293-299; Plueckthun (1992) Immunological Reviews 130:151-188; Wright et al., (1992) Crit. Rev. Immunol. 12:125-168; Holliger, P. & Winter, G. (1993) Curr. Op. Biotechn. 4, 446-449; Carter, et al. (1995) J. Hematother. 4, 463-470; Chester, K. A. & Hawkins, R. E. (1995) Trends Biotechn. 13, 294-300; Hoogenboom, H. R. (1997) Nature Biotechnol. 15, 125-126; Fearon, D. (1997) Nature Biotechnol. 15, 618-619; Plückthun, A. & Pack, P. (1997) Immunotechnology 3, 83-105; Carter, P. & Merchant, A. M. (1997) Curr. Opin. Biotechnol. 8, 449-454; Holliger, P. & Winter, G. (1997) Cancer Immunol. Immunother. 45, 128-130.

The invention provides for the selection of variable domains against two different antigens or epitopes, and subsequent combination of the variable domains.

The techniques employed for selection of the variable domains employ libraries and selection procedures which are known in the art. Natural libraries (Marks et al. (1991) *J. Mol. Biol.*, 222: 581; Vaughan et al. (1996) *Nature Biotech.*, 14: 309) which use rearranged V genes harvested from human B cells are well known to those skilled in the art. Synthetic libraries (Hoogenboom & Winter (1992) *J. Mol. Biol.*, 227: 381; Barbas et al. (1992) *Proc. Natl. Acad. Sci. USA*, 89: 4457; Nissim et al. (1994) *EMBO J.*, 13: 692; Griffiths et al. (1994) *EMBO J.*, 13: 3245; De Kruif et al. (1995) *J. Mol. Biol.*, 248: 97) are prepared by cloning immunoglobulin V genes, usually using PCR. Errors in the PCR process can lead to a high degree of randomisation. $V_H$ and/or $V_L$ libraries may be selected against target antigens or epitopes separately, in which case single domain binding is directly selected for, or together.

A preferred method for making a dual specific ligand according to the present invention comprises using a selection system in which a repertoire of variable domains is selected for binding to a first antigen or epitope and a repertoire of variable domains is selected for binding to a second antigen or epitope. The selected variable first and second variable domains are then combined and the dual-specific ligand selected for binding to both first and second antigen or epitope. Closed conformation ligands are selected for binding both first and second antigen or epitope in isolation but not simultaneously.

A. Library Vector Systems

A variety of selection systems are known in the art which are suitable for use in the present invention. Examples of such systems are described below.

Bacteriophage lambda expression systems may be screened directly as bacteriophage plaques or as colonies of lysogens, both as previously described (Huse et al. (1989) *Science*, 246: 1275; Caton and Koprowski (1990) *Proc. Natl. Acad. Sci. U.S.A.*, 87; Mullinax et al. (1990) *Proc. Natl. Acad. Sci. U.S.A.*, 87: 8095; Persson et al. (1991) *Proc. Natl. Acad. Sci. U.S.A.*, 88: 2432) and are of use in the invention. Whilst such expression systems can be used to screen up to $10^6$ different members of a library, they are not really suited to screening of larger numbers (greater than $10^6$ members).

Of particular use in the construction of libraries are selection display systems, which enable a nucleic acid to be linked to the polypeptide it expresses. As used herein, a selection display system is a system that permits the selection, by suitable display means, of the individual members of the library by binding the generic and/or target ligands.

Selection protocols for isolating desired members of large libraries are known in the art, as typified by phage display techniques. Such systems, in which diverse peptide sequences are displayed on the surface of filamentous bacteriophage (Scott and Smith (1990) *Science*, 249: 386), have proven useful for creating libraries of antibody fragments (and the nucleotide sequences that encoding them) for the in vitro selection and amplification of specific antibody fragments that bind a target antigen (McCafferty et al., WO 92/01047). The nucleotide sequences encoding the $V_H$ and $V_L$ regions are linked to gene fragments which encode leader signals that direct them to the periplasmic space of *E. coli* and as a result the resultant antibody fragments are displayed on the surface of the bacteriophage, typically as fusions to bacteriophage coat proteins (e.g., pIII or pVIII). Alternatively, antibody fragments are displayed externally on lambda phage capsids (phagebodies). An advantage of phage-based display systems is that, because they are biological systems, selected library members can be amplified simply by growing the phage containing the selected library member in bacterial cells. Furthermore, since the nucleotide sequence that encode the polypeptide library member is contained on a phage or phagemid vector, sequencing, expression and subsequent genetic manipulation is relatively straightforward.

Methods for the construction of bacteriophage antibody display libraries and lambda phage expression libraries are well known in the art (McCafferty et al. (1990) *Nature*, 348: 552; Kang et al. (1991) *Proc. Natl. Acad. Sci. U.S.A.*, 88: 4363; Clackson et al. (1991) *Nature*, 352: 624; Lowman et al. (1991) *Biochemistry*, 30: 10832; Burton et al. (1991) *Proc. Natl. Acad. Sci. U.S.A.*, 88: 10134; Hoogenboom et al. (1991) *Nucleic Acids Res.*, 19: 4133; Chang et al. (1991) *J. Immunol.*, 147: 3610; Breitling et al. (1991) *Gene*, 104: 147; Marks et al. (1991) supra; Barbas et al. (1992) supra; Hawkins and Winter (1992) *J. Immunol.*, 22: 867; Marks et al., 1992, *J. Biol. Chem.*, 267: 16007; Lerner et al. (1992) *Science*, 258: 1313, incorporated herein by reference).

One particularly advantageous approach has been the use of scFv phage-libraries (Huston et al., 1988, Proc. Natl. Acad. Sci. U.S.A., 85: 5879-5883; Chaudhary et al. (1990) Proc. Natl. Acad. Sci. U.S.A., 87: 1066-1070; McCafferty et al. (1990) supra; Clackson et al. (1991) *Nature*, 352: 624; Marks et al. (1991) *J. Mol. Biol.*, 222: 581; Chiswell et al. (1992) Trends Biotech., 10: 80; Marks et al. (1992) *J. Biol. Chem.*, 267). Various embodiments of scFv libraries displayed on bacteriophage coat proteins have been described. Refinements of phage display approaches are also known, for example as described in WO96/06213 and WO92/01047 (Medical Research Council et al.) and WO97/08320 (Morphosys), which are incorporated herein by reference.

Other systems for generating libraries of polypeptides involve the use of cell-free enzymatic machinery for the in vitro synthesis of the library members. In one method, RNA molecules are selected by alternate rounds of selection against a target ligand and PCR amplification (Tuerk and Gold (1990) *Science*, 249: 505; Ellington and Szostak (1990) *Nature*, 346: 818). A similar technique may be used to identify DNA sequences which bind a predetermined human transcription factor (Thiesen and Bach (1990) *Nucleic Acids Res.*, 18: 3203; Beaudry and Joyce (1992) *Science*, 257: 635; WO92/05258 and WO92/14843). In a similar way, in vitro translation can be used to synthesise polypeptides as a method for generating large libraries. These methods which generally comprise stabilised polysome complexes, are described further in WO88/08453, WO90/05785, WO90/07003, WO91/02076, WO91/05058, and WO92/02536. Alternative display systems which are not phage-based, such as those disclosed in WO95/22625 and WO95/11922 (Affymax) use the polysomes to display polypeptides for selection.

A still further category of techniques involves the selection of repertoires in artificial compartments, which allow the linkage of a gene with its gene product. For example, a selection system in which nucleic acids encoding desirable gene products may be selected in microcapsules formed by water-in-oil emulsions is described in WO99/02671, WO00/40712 and Tawfik & Griffiths (1998) *Nature Biotechnol* 16(7), 652-6. Genetic elements encoding a gene product having a desired activity are compartmentalised into microcapsules and then transcribed and/or translated to produce their respective gene products (RNA or protein) within the microcapsules. Genetic elements which produce gene product having desired activity are subsequently sorted. This approach selects gene products of interest by detecting the desired activity by a variety of means.

B. Library Construction.

Libraries intended for selection, may be constructed using techniques known in the art, for example as set forth above, or may be purchased from commercial sources. Libraries which are useful in the present invention are described, for example, in WO99/20749. Once a vector system is chosen and one or more nucleic acid sequences encoding polypeptides of interest are cloned into the library vector, one may generate diversity within the cloned molecules by undertaking mutagenesis prior to expression; alternatively, the encoded proteins may be expressed and selected, as described above, before mutagenesis and additional rounds of selection are performed. Mutagenesis of nucleic acid sequences encoding structurally optimised polypeptides is carried out by standard molecular methods. Of particular use is the polymerase chain reaction, or PCR, (Mullis and Faloona (1987) *Methods Enzymol.*, 155: 335, herein incorporated by reference). PCR, which uses multiple cycles of DNA replication catalysed by a thermostable, DNA-dependent DNA polymerase to amplify the target sequence of interest, is well known in the art. The construction of various antibody libraries has been discussed in Winter et al. (1994) Ann. Rev. Immunology 12, 433-55, and references cited therein.

PCR is performed using template DNA (at least 1 fg; more usefully, 1-1000 ng) and at least 25 µmol of oligonucleotide primers; it may be advantageous to use a larger amount of primer when the primer pool is heavily heterogeneous, as each sequence is represented by only a small fraction of the molecules of the pool, and amounts become limiting in the later amplification cycles. A typical reaction mixture includes: 2 µl of DNA, 25 µmol of oligonucleotide primer, 2.5 µl of 10×PCR buffer 1 (Perkin-Elmer, Foster City, Calif.), 0.4 µl of 1.25 µM dNTP, 0.15 µl (or 2.5 units) of Taq DNA polymerase (Perkin Elmer, Foster City, Calif.) and deionized water to a total volume of 25 µl. Mineral oil is overlaid and the PCR is performed using a programmable thermal cycler. The length and temperature of each step of a PCR cycle, as well as the number of cycles, is adjusted in accordance to the stringency requirements in effect. Annealing temperature and timing are determined both by the efficiency with which a primer is expected to anneal to a template and the degree of mismatch that is to be tolerated; obviously, when nucleic acid molecules are simultaneously amplified and mutagenised, mismatch is required, at least in the first round of synthesis. The ability to optimise the stringency of primer annealing conditions is well within the knowledge of one of moderate skill in the art. An annealing temperature of between 30° C. and 72° C. is used. Initial denaturation of the template molecules normally occurs at between 92° C. and 99° C. for 4 minutes, followed by 20-40 cycles consisting of denaturation (94-99° C. for 15 seconds to 1 minute), annealing (temperature determined as discussed above; 1-2 minutes), and extension (72° C. for 1-5 minutes, depending on the length of the amplified product). Final extension is generally for 4 minutes at 72° C., and may be followed by an indefinite (0-24 hour) step at 4° C.

C. Combining Single Variable Domains

Domains useful in the invention, once selected, may be combined by a variety of methods known in the art, including covalent and non-covalent methods.

Preferred methods include the use of polypeptide linkers, as described, for example, in connection with scFv molecules (Bird et al., (1988) Science 242:423-426). Discussion of suitable linkers is provided in Bird et al. Science 242, 423-426; Hudson et al, Journal Immunol Methods 231 (1999) 177-189; Hudson et al, Proc Nat Acad Sci USA 85, 5879-5883. Linkers are preferably flexible, allowing the two single domains to interact. One linker example is a $(Gly_4 Ser)_n$ linker (SEQ ID NO: 2), where n=1 to 8, e.g., 2, 3, 4, 5 or 7. The linkers used in diabodies, which are less flexible, may also be employed (Holliger et al., (1993) PNAS (USA) 90:6444-6448).

In one embodiment, the linker employed is not an immunoglobulin hinge region.

Variable domains may be combined using methods other than linkers. For example, the use of disulphide bridges, provided through naturally-occurring or engineered cysteine residues, may be exploited to stabilise $V_H$-$V_H$, $V_L$-$V_L$ or $V_H$-$V_L$ dimers (Reiter et al., (1994) Protein Eng. 7:697-704) or by remodelling the interface between the variable domains to improve the "fit" and thus the stability of interaction (Ridgeway et al., (1996) Protein Eng. 7:617-621; Zhu et al., (1997) Protein Science 6:781-788).

Other techniques for joining or stabilising variable domains of immunoglobulins, and in particular antibody $V_H$ domains, may be employed as appropriate.

In accordance with the present invention, dual specific ligands can be in "closed" conformations in solution. A "closed" configuration is that in which the two domains (for example $V_H$ and $V_L$) are present in associated form, such as that of an associated $V_H$-$V_L$ pair which forms an antibody binding site. For example, scFv may be in a closed conformation, depending on the arrangement of the linker used to link the $V_H$ and $V_L$ domains. If this is sufficiently flexible to allow the domains to associate, or rigidly holds them in the associated position, it is likely that the domains will adopt a closed conformation.

Similarly, $V_H$ domain pairs and $V_L$ domain pairs may exist in a closed conformation. Generally, this will be a function of close association of the domains, such as by a rigid linker, in the ligand molecule. Ligands in a closed conformation will be unable to bind both the molecule which increases the half-life of the ligand and a second target molecule. Thus, the ligand will typically only bind the second target molecule on dissociation from the molecule which increases the half-life of the ligand.

Moreover, the construction of $V_H$/$V_H$, $V_L$/$V_L$ or $V_H$/$V_L$ dimers without linkers provides for competition between the domains.

Ligands according to the invention may moreover be in an open conformation. In such a conformation, the ligands will be able to simultaneously bind both the molecule which increases the half-life of the ligand and the second target molecule. Typically, variable domains in an open configuration are (in the case of $V_H$-$V_L$ pairs) held far enough apart for the domains not to interact and form an antibody binding site and not to compete for binding to their respective epitopes. In the case of $V_H$/$V_H$ or $V_L$/$V_L$ dimers, the domains are not forced together by rigid linkers. Naturally, such domain pairings will not compete for antigen binding or form an antibody binding site.

Fab fragments and whole antibodies will exist primarily in the closed conformation, although it will be appreciated that open and closed dual specific ligands are likely to exist in a variety of equilibria under different circumstances. Binding of the ligand to a target is likely to shift the balance of the equilibrium towards the open configuration. Thus, certain ligands according to the invention can exist in two conformations in solution, one of which (the open form) can bind two antigens or epitopes independently, whilst the alternative conformation (the closed form) can only bind one antigen or epitope; antigens or epitopes thus compete for binding to the ligand in this conformation.

Although the open form of the dual specific ligand may thus exist in equilibrium with the closed form in solution, it is envisaged that the equilibrium will favour the closed form; moreover, the open form can be sequestered by target binding into a closed conformation. Preferably, therefore, certain dual specific ligands of the invention are present in an equilibrium between two (open and closed) conformations.

Dual specific ligands according to the invention may be modified in order to favour an open or closed conformation. For example, stabilisation of $V_H$-$V_L$ interactions with disulphide bonds stabilises the closed conformation. Moreover, linkers used to join the domains, including $V_H$ domain and $V_L$ domain pairs, may be constructed such that the open from is favoured; for example, the linkers may sterically hinder the association of the domains, such as by incorporation of large amino acid residues in opportune locations, or the designing of a suitable rigid structure which will keep the domains physically spaced apart.

D. Characterisation of the Dual-Specific Ligand.

The binding of the dual-specific ligand to its specific antigens or epitopes can be tested by methods which will be familiar to those skilled in the art and include ELISA. In a preferred embodiment of the invention binding is tested using monoclonal phage ELISA.

Phage ELISA may be performed according to any suitable procedure: an exemplary protocol is set forth below.

Populations of phage produced at each round of selection can be screened for binding by ELISA to the selected antigen or epitope, to identify "polyclonal" phage antibodies. Phage from single infected bacterial colonies from these populations can then be screened by ELISA to identify "monoclonal" phage antibodies. It is also desirable to screen soluble antibody fragments for binding to antigen or epitope, and this can also be undertaken by ELISA using reagents, for example, against a C- or N-terminal tag (see for example Winter et al. (1994) Ann. Rev. Immunology 12, 433-55 and references cited therein.

The diversity of the selected phage monoclonal antibodies may also be assessed by gel electrophoresis of PCR products (Marks et al. 1991, supra; Nissim et al. 1994 supra), probing (Tomlinson et al., 1992) J. Mol. Biol. 227, 776) or by sequencing of the vector DNA.

E. Structure of 'Dual-Specific Ligands'.

As described above, an antibody is herein defined as an antibody (for example IgG, IgM, IgA, IgA, IgE) or fragment (Fab, Fv, disulphide linked Fv, scFv, diabody) which comprises at least one heavy and a light chain variable domain, at least two heavy chain variable domains or at least two light chain variable domains. It may be at least partly derived from any species naturally producing an antibody, or created by recombinant DNA technology; whether isolated from serum, B-cells, hybridomas, transfectomas, yeast or bacteria).

In a preferred embodiment of the invention the dual-specific ligand comprises at least one single heavy chain variable domain of an antibody and one single light chain variable domain of an antibody, or two single heavy or light chain variable domains. For example, the ligand may comprise a $V_H$/$V_L$ pair, a pair of $V_H$ domains or a pair of $V_L$ domains.

The first and the second variable domains of such a ligand may be on the same polypeptide chain. Alternatively they may be on separate polypeptide chains. In the case that they are on the same polypeptide chain they may be linked by a linker, which is preferentially a peptide sequence, as described above.

The first and second variable domains may be covalently or non-covalently associated. In the case that they are covalently associated, the covalent bonds may be disulphide bonds.

In the case that the variable domains are selected from V-gene repertoires selected for instance using phage display technology as herein described, then these variable domains comprise a universal framework region, such that is they may be recognised by a specific generic ligand as herein defined. The use of universal frameworks, generic ligands and the like is described in WO99/20749.

Where V-gene repertoires are used variation in polypeptide sequence is preferably located within the structural loops of the variable domains. The polypeptide sequences of either variable domain may be altered by DNA shuffling or by mutation in order to enhance the interaction of each variable domain with its complementary pair. DNA shuffling is known in the art and taught, for example, by Stemmer, 1994, Nature 370: 389-391 and U.S. Pat. No. 6,297,053, both of which are incorporated herein by reference. Other methods of mutagenesis are well known to those of skill in the art.

In a preferred embodiment of the invention the 'dual-specific ligand' is a single chain Fv fragment. In an alternative embodiment of the invention, the 'dual-specific ligand' consists of a Fab format.

In a further aspect, the present invention provides nucleic acid encoding at least a 'dual-specific ligand' as herein defined.

One skilled in the art will appreciate that, depending on the aspect of the invention, both antigens or epitopes may bind simultaneously to the same antibody molecule.

Alternatively, they may compete for binding to the same antibody molecule. For example, where both epitopes are bound simultaneously, both variable domains of a dual specific ligand are able to independently bind their target epitopes. Where the domains compete, the one variable domain is capable of binding its target, but not at the same time as the other variable domain binds its cognate target; or the first variable domain is capable of binding its target, but not at the same time as the second variable domain binds its cognate target.

The variable domains may be derived from antibodies directed against target antigens or epitopes. Alternatively they may be derived from a repertoire of single antibody domains such as those expressed on the surface of filamentous bacteriophage. Selection may be performed as described below.

In general, the nucleic acid molecules and vector constructs required for the performance of the present invention may be constructed and manipulated as set forth in standard laboratory manuals, such as Sambrook et al. (1989) *Molecular Cloning: A Laboratory Manual*, Cold Spring Harbor, USA.

The manipulation of nucleic acids useful in the present invention is typically carried out in recombinant vectors.

Thus in a further aspect, the present invention provides a vector comprising nucleic acid encoding at least a 'dual-specific ligand' as herein defined.

As used herein, vector refers to a discrete element that is used to introduce heterologous DNA into cells for the expression and/or replication thereof. Methods by which to select or construct and, subsequently, use such vectors are well known to one of ordinary skill in the art. Numerous vectors are publicly available, including bacterial plasmids, bacteriophage, artificial chromosomes and episomal vectors. Such vectors may be used for simple cloning and mutagenesis; alternatively gene expression vector is employed. A vector of use according to the invention may be selected to accommodate a polypeptide coding sequence of a desired size, typically from 0.25 kilobase (kb) to 40 kb or more in length. A suitable host cell is transformed with the vector after in vitro cloning manipulations. Each vector contains various functional components, which generally include a cloning (or "polylinker") site, an origin of replication and at least one selectable marker gene. If given vector is an expression vector, it additionally possesses one or more of the following: enhancer element, promoter, transcription termination and signal sequences, each positioned in the vicinity of the cloning site, such that they are operatively linked to the gene encoding a ligand according to the invention.

Both cloning and expression vectors generally contain nucleic acid sequences that enable the vector to replicate in one or more selected host cells. Typically in cloning vectors, this sequence is one that enables the vector to replicate independently of the host chromosomal DNA and includes origins of replication or autonomously replicating sequences. Such sequences are well known for a variety of bacteria, yeast and viruses. The origin of replication from the plasmid pBR322 is suitable for most Gram-negative bacteria, the 2 micron plasmid origin is suitable for yeast, and various viral origins (e.g. SV 40, adenovirus) are useful for cloning vectors in mammalian cells. Generally, the origin of replication is not needed for mammalian expression vectors unless these are used in mammalian cells able to replicate high levels of DNA, such as COS cells.

Advantageously, a cloning or expression vector may contain a selection gene also referred to as selectable marker. This gene encodes a protein necessary for the survival or growth of transformed host cells grown in a selective culture medium. Host cells not transformed with the vector containing the selection gene will therefore not survive in the culture medium. Typical selection genes encode proteins that confer resistance to antibiotics and other toxins, e.g. ampicillin, neomycin, methotrexate or tetracycline, complement auxotrophic deficiencies, or supply critical nutrients not available in the growth media.

Since the replication of vectors encoding a ligand according to the present invention is most conveniently performed in *E. coli*, an *E. coli-selectable* marker, for example, the β-lactamase gene that confers resistance to the antibiotic ampicillin, is of use. These can be obtained from *E. coli* plasmids, such as pBR322 or a pUC plasmid such as pUC18 or pUC19.

Expression vectors usually contain a promoter that is recognized by the host organism and is operably linked to the coding sequence of interest. Such a promoter may be inducible or constitutive. The term "operably linked" refers to a juxtaposition wherein the components described are in a relationship permitting them to function in their intended manner. A control sequence "operably linked" to a coding sequence is ligated in such a way that expression of the coding sequence is achieved under conditions compatible with the control sequences.

Promoters suitable for use with prokaryotic hosts include, for example, the β-lactamase and lactose promoter systems, alkaline phosphatase, the tryptophan (trp) promoter system and hybrid promoters such as the tac promoter. Promoters for use in bacterial systems will also generally contain a Shine-Delgarno sequence operably linked to the coding sequence.

The preferred vectors are expression vectors that enables the expression of a nucleotide sequence corresponding to a polypeptide library member. Thus, selection with the first and/or second antigen or epitope can be performed by separate propagation and expression of a single clone expressing the polypeptide library member or by use of any selection display system. As described above, the preferred selection display system is bacteriophage display. Thus, phage or phagemid vectors may be used, e.g. pIT1 or pIT2. Leader sequences useful in the invention include pelB, stII, ompA, phoA, bla and pelA. One example are phagemid vectors which have an *E. coli.* origin of replication (for double stranded replication) and also a phage origin of replication (for production of single-stranded DNA). The manipulation and expression of such vectors is well known in the art (Hoogenboom and Winter (1992) supra; Nissim et al. (1994) supra). Briefly, the vector contains a β-lactamase gene to confer selectivity on the phagemid and a lac promoter upstream of a expression cassette that consists (N to C terminal) of a pelB leader sequence (which directs the expressed polypeptide to the periplasmic space), a multiple cloning site (for cloning the nucleotide version of the library member), optionally, one or more peptide tag (for detection), optionally, one or more TAG stop codon and the phage protein pIII. Thus, using various suppressor and non-suppressor strains of *E. coli* and with the addition of glucose, iso-propyl thio-β-D-galactoside (IPTG) or a helper phage, such as VCS M13, the vector is able to replicate as a plasmid with no expression, produce large quantities of the polypeptide library member only or produce phage, some of which contain at least one copy of the polypeptide-pIII fusion on their surface.

Construction of vectors encoding ligands according to the invention employs conventional ligation techniques. Isolated vectors or DNA fragments are cleaved, tailored, and religated in the form desired to generate the required vector. If desired, analysis to confirm that the correct sequences are present in the constructed vector can be performed in a known fashion. Suitable methods for constructing expression vectors, preparing in vitro transcripts, introducing DNA into host cells, and performing analyses for assessing expression and function are known to those skilled in the art. The presence of a gene sequence in a sample is detected, or its amplification and/or expression quantified by conventional methods, such as Southern or Northern analysis, Western blotting, dot blotting of DNA, RNA or protein, in situ hybridisation, immunocytochemistry or sequence analysis of nucleic acid or protein molecules. Those skilled in the art will readily envisage how these methods may be modified, if desired.

Structure of Closed Conformation Multispecific Ligands

According to one aspect of the second configuration of the invention present invention, the two or more non-complementary epitope binding domains are linked so that they are in a closed conformation as herein defined. Advantageously, they may be further attached to a skeleton which may, as an alternative, or in addition to a linker described herein, facilitate the formation and/or maintenance of the closed conformation of the epitope binding sites with respect to one another.

(I) Skeletons

Skeletons may be based on immunoglobulin molecules or may be non-immunoglobulin in origin as set forth above. Preferred immunoglobulin skeletons as herein defined includes any one or more of those selected from the following: an immunoglobulin molecule comprising at least (i) the CL (kappa or lambda subclass) domain of an antibody; or (ii) the CH1 domain of an antibody heavy chain; an immunoglobulin molecule comprising the CH1 and CH2 domains of an antibody heavy chain; an immunoglobulin molecule comprising the CH1, CH2 and CH3 domains of an antibody heavy chain; or any of the subset (ii) in conjunction with the CL (kappa or lambda subclass) domain of an antibody. A hinge region domain may also be included. Such combinations of domains may, for example, mimic natural antibodies, such as IgG or IgM, or fragments thereof, such as Fv, scFv, Fab or F(ab')$_2$ molecules. Those skilled in the art will be aware that this list is not intended to be exhaustive.

(II) Protein Scaffolds

Each epitope binding domain comprises a protein scaffold and one or more CDRs which are involved in the specific interaction of the domain with one or more epitopes. Advantageously, an epitope binding domain according to the present invention comprises three CDRs. Suitable protein scaffolds include any of those selected from the group consisting of the following: those based on immunoglobulin domains, those based on fibronectin, those based on affibodies, those based on CTLA4, those based on chaperones such as GroEL, those based on lipocallin and those based on the bacterial Fc receptors SpA, and SpD. Those skilled in the art will appreciate that this list is not intended to be exhaustive.

F: Scaffolds for Use in Constructing Dual Specific Ligands i. Selection of the Main-Chain Conformation The members of the immunoglobulin superfamily all share a similar fold for their polypeptide chain. For example, although antibodies are highly diverse in terms of their primary sequence, comparison of sequences and crystallographic structures has revealed that, contrary to expectation, five of the six antigen binding loops of antibodies (H1, H2, L1, L2, L3) adopt a limited number of main-chain conformations, or canonical structures (Chothia and Lesk (1987) *J. Mol. Biol.,* 196: 901; Chothia et al. (1989) *Nature,* 342: 877). Analysis of loop lengths and key residues has therefore enabled prediction of the main-chain conformations of H1, H2, L1, L2 and L3 found in the majority of human antibodies (Chothia et al. (1992) *J. Mol. Biol.,* 227: 799; Tomlinson et al. (1995) *EMBO J.,* 14: 4628; Williams et al. (1996) *J. Mol. Biol.,* 264: 220). Although the H3 region is much more diverse in terms of sequence, length and structure (due to the use of D segments), it also forms a limited number of main-chain conformations for short loop lengths which depend on the length and the presence of particular residues, or types of residue, at key positions in the loop and the antibody framework (Martin et al. (1996) *J. Mol. Biol.,* 263: 800; Shirai et al (1996) *FEBS Letters,* 399: 1).

The dual specific ligands of the present invention are advantageously assembled from libraries of domains, such as libraries of $V_H$ domains and/or libraries of $V_L$ domains. Moreover, the dual specific ligands of the invention may themselves be provided in the form of libraries. In one aspect of the present invention, libraries of dual specific ligands and/or domains are designed in which certain loop lengths and key residues have been chosen to ensure that the main-chain conformation of the members is known. Advantageously, these are real conformations of immunoglobulin superfamily molecules found in nature, to minimise the chances that they are non-functional, as discussed above.

Germ line V gene segments serve as one suitable basic framework for constructing antibody or T-cell receptor libraries; other sequences are also of use. Variations may occur at a low frequency, such that a small number of functional members may possess an altered main-chain conformation, which does not affect its function.

Canonical structure theory is also of use to assess the number of different main-chain conformations encoded by ligands, to predict the main-chain conformation based on ligand sequences and to chose residues for diversification which do not affect the canonical structure. It is known that, in the human $V_\kappa$ domain, the L1 loop can adopt one of four canonical structures, the L2 loop has a single canonical structure and that 90% of human $V_\kappa$ domains adopt one of four or five canonical structures for the L3 loop (Tomlinson et al. (1995) supra); thus, in the $V_\kappa$ domain alone, different canonical structures can combine to create a range of different main-chain conformations. Given that the $V_\lambda$ domain encodes a different range of canonical structures for the L1, L2 and L3 loops and that $V_\kappa$ and $V_\lambda$ domains can pair with any $V_H$ domain which can encode several canonical structures for the H1 and H2 loops, the number of canonical structure combinations observed for these five loops is very large. This implies that the generation of diversity in the main-chain conformation may be essential for the production of a wide range of binding specificities. However, by constructing an antibody library based on a single known main-chain conformation it has been found, contrary to expectation, that diversity in the main-chain conformation is not required to generate sufficient diversity to target substantially all antigens. Even more surprisingly, the single main-chain conformation need not be a consensus structure—a single naturally occurring conformation can be used as the basis for an entire library. Thus, in a preferred aspect, the dual-specific ligands of the invention possess a single known main-chain conformation.

The single main-chain conformation that is chosen is preferably commonplace among molecules of the immunoglobulin superfamily type in question. A conformation is commonplace when a significant number of naturally occurring molecules are observed to adopt it. Accordingly, in a preferred aspect of the invention, the natural occurrence of the different main-chain conformations for each binding loop of an immunoglobulin domain are considered separately, and then a naturally occurring variable domain is chosen which possesses the desired combination of main-chain conformations for the different loops. If none is available, the nearest equivalent may be chosen. It is preferable that the desired combination of main-chain conformations for the different loops is created by selecting germ line gene segments which encode the desired main-chain conformations. It is more preferable, that the selected germ line gene segments are frequently expressed in nature, and most preferable that they are the most frequently expressed of all natural germ line gene segments.

In designing dual specific ligands or libraries thereof the incidence of the different main-chain conformations for each of the six antigen binding loops may be considered separately. For H1, H2, L1, L2 and L3, a given conformation that is adopted by between 20% and 100% of the antigen binding loops of naturally occurring molecules is chosen. Typically, its observed incidence is above 35% (i.e. between 35% and 100%) and, ideally, above 50% or even above 65%. Since the vast majority of H3 loops do not have canonical structures, it is preferable to select a main-chain conformation which is commonplace among those loops which do display canonical structures. For each of the loops, the conformation which is observed most often in the natural repertoire is therefore selected. In human antibodies, the most popular canonical structures (CS) for each loop are as follows: H1-CS1 (79% of the expressed repertoire), H2-CS 3 (46%), L1-CS 2 of $V_\kappa$ (39%), L2-CS1 (100%), L3-CS 1 of $V_\kappa$ (36%) (calculation assumes a κ:λ ratio of 70:30, Hood et al. (1967) *Cold Spring Harbor Symp. Quant. Biol.*, 48: 133). For H3 loops that have canonical structures, a CDR3 length (Kabat et al. (1991) *Sequences of proteins of immunological interest*, U.S. Department of Health and Human Services) of seven residues with a salt-bridge from residue 94 to residue 101 appears to be the most common. There are at least 16 human antibody sequences in the EMBL data library with the required H3 length and key residues to form this conformation and at least two crystallographic structures in the protein data bank which can be used as a basis for antibody modelling (2 cgr and 1 tet). The most frequently expressed germ line gene segments that this combination of canonical structures are the $V_H$ segment 3-23 (DP-47), the $J_H$ segment JH4b, the $V_\kappa$ segment O2/O12 (DPK9) and the $J_\kappa$ segment $J_\kappa 1$. $V_H$ segments DP45 and DP38 are also suitable. These segments can therefore be used in combination as a basis to construct a library with the desired single main-chain conformation.

Alternatively, instead of choosing the single main-chain conformation based on the natural occurrence of the different main-chain conformations for each of the binding loops in isolation, the natural occurrence of combinations of main-chain conformations is used as the basis for choosing the single main-chain conformation. In the case of antibodies, for example, the natural occurrence of canonical structure combinations for any two, three, four, five or for all six of the antigen binding loops can be determined. Here, it is preferable that the chosen conformation is commonplace in naturally occurring antibodies and most preferable that it observed most frequently in the natural repertoire. Thus, in human antibodies, for example, when natural combinations of the five antigen binding loops, H1, H2, L1, L2 and L3, are considered, the most frequent combination of canonical structures is determined and then combined with the most popular conformation for the H3 loop, as a basis for choosing the single main-chain conformation.

ii. Diversification of the Canonical Sequence

Having selected several known main-chain conformations or, preferably a single known main-chain conformation, dual specific ligands according to the invention or libraries for use in the invention can be constructed by varying the binding site of the molecule in order to generate a repertoire with structural and/or functional diversity. This means that variants are generated such that they possess sufficient diversity in their structure and/or in their function so that they are capable of providing a range of activities.

The desired diversity is typically generated by varying the selected molecule at one or more positions. The positions to be changed can be chosen at random or are preferably selected. The variation can then be achieved either by randomization, during which the resident amino acid is replaced by any amino acid or analogue thereof, natural or synthetic, producing a very large number of variants or by replacing the resident amino acid with one or more of a defined subset of amino acids, producing a more limited number of variants.

Various methods have been reported for introducing such diversity. Efrror-prone PCR (Hawkins et al. (1992) *J. Mol. Biol.*, 226: 889), chemical mutagenesis (Deng et al. (1994) *J. Biol. Chem.*, 269: 9533) or bacterial mutator strains (Low et al. (1996) *J. Mol. Biol.*, 260: 359) can be used to introduce random mutations into the genes that encode the molecule. Methods for mutating selected positions are also well known in the art and include the use of mismatched oligonucleotides or degenerate oligonucleotides, with or without the use of PCR. For example, several synthetic antibody libraries have been created by targeting mutations to the antigen binding loops. The H3 region of a human tetanus toxoid-binding Fab has been randomised to create a range of new binding specificities (Barbas et al. (1992) *Proc. Natl. Acad. Sci. USA*, 89: 4457). Random or semi-random H3 and L3 regions have been appended to germ line V gene segments to produce large libraries with unmutated framework regions (Hoogenboom & Winter (1992) *J. Mol. Biol.*, 227: 381; Barbas et al. (1992) *Proc. Natl. Acad. Sci. USA*, 89: 4457; Nissim et al. (1994) *EMBO J.*, 13: 692; Griffiths et al. (1994) *EMBO J.*, 13: 3245; De Kruif et al. (1995) *J. Mol. Biol.*, 248: 97). Such diversification has been extended to include some or all of the other antigen binding loops (Crameri et al. (1996) *Nature Med.*, 2: 100; Riechmann et al. (1995) *Bio/Technology*, 13: 475; Morphosys, WO97/08320, supra).

Since loop randomization has the potential to create approximately more than 1015 structures for H3 alone and a similarly large number of variants for the other five loops, it is not feasible using current transformation technology or even by using cell free systems to produce a library representing all possible combinations. For example, in one of the largest libraries constructed to date, $6 \times 10^{10}$ different antibodies, which is only a fraction of the potential diversity for a library of this design, were generated (Griffiths et al. (1994) supra).

In a preferred embodiment, only those residues which are directly involved in creating or modifying the desired function of the molecule are diversified. For many molecules, the function will be to bind a target and therefore diversity should be concentrated in the target binding site, while avoiding changing residues which are crucial to the overall packing of the molecule or to maintaining the chosen main-chain conformation.

Diversification of the Canonical Sequence as it Applies to Antibody Domains

In the case of antibody dual-specific ligands, the binding site for the target is most often the antigen binding site. Thus, in a highly preferred aspect, the invention provides libraries of or for the assembly of antibody dual-specific ligands in which only those residues in the antigen binding site are varied. These residues are extremely diverse in the human antibody repertoire and are known to make contacts in high-resolution antibody/antigen complexes. For example, in L2 it is known that positions 50 and 53 are diverse in naturally occurring antibodies and are observed to make contact with the antigen. In contrast, the conventional approach would have been to diversify all the residues in the corresponding Complementarity Determining Region (CDR1) as defined by Kabat et al. (1991, supra), some seven residues compared to the two diversified in the library for use according to the invention. This represents a significant improvement in terms of the functional diversity required to create a range of antigen binding specificities. In nature, antibody diversity is the result of two processes: somatic recombination of germ line V, D and J gene segments to create a naive primary repertoire (so called germ line and junctional diversity) and somatic hypermutation of the resulting rearranged V genes. Analysis of human antibody sequences has shown that diversity in the primary repertoire is focused at the centre of the antigen binding site whereas somatic hypermutation spreads diversity to regions at the periphery of the antigen binding site that are highly conserved in the primary repertoire (see Tomlinson et al. (1996) *J. Mol. Biol.*, 256: 813). This complementarity has probably evolved as an efficient strategy for searching sequence space and, although apparently unique to antibodies, it can easily be applied to other polypeptide repertoires. The residues which are varied are a subset of those that form the binding site for the target. Different (including overlapping) subsets of residues in the target binding site are diversified at different stages during selection, if desired.

In the case of an antibody repertoire, an initial 'naive' repertoire is created where some, but not all, of the residues in the antigen binding site are diversified. As used herein in this context, the term "naive" refers to antibody molecules that have no pre-determined target. These molecules resemble those which are encoded by the immunoglobulin genes of an individual who has not undergone immune diversification, as is the case with fetal and newborn individuals, whose immune systems have not yet been challenged by a wide variety of antigenic stimuli. This repertoire is then selected against a range of antigens or epitopes. If required, further diversity can then be introduced outside the region diversified in the initial repertoire. This matured repertoire can be selected for modified function, specificity or affinity.

The invention provides two different naive repertoires of binding domains for the construction of dual specific ligands, or a naïve library of dual specific ligands, in which some or all of the residues in the antigen binding site are varied. The "primary" library mimics the natural primary repertoire, with diversity restricted to residues at the center of the antigen binding site that are diverse in the germ line V gene segments (germ line diversity) or diversified during the recombination process (junctional diversity). Those residues which are diversified include, but are preferably not limited to, H50, H52, H52a, H53, H55, H56, H58, H95, H96, H97, H98, L50, L53, L91, L92, L93, L94 and L96. In the "somatic" library, diversity is restricted to residues that are diversified during the recombination process (junctional diversity) or are highly somatically mutated). Those residues which are diversified include, but are preferably not limited to: H31, H33, H35, H95, H96, H97, H98, L30, L31, L32, L34 and L96. All the residues listed above as suitable for diversification in these libraries are known to make contacts in one or more antibody-antigen complexes. Since in both libraries, not all of the residues in the antigen binding site are varied, additional diversity is incorporated during selection by varying the remaining residues, if it is desired to do so. It shall be apparent to one skilled in the art that any subset of any of these residues (or additional residues which comprise the antigen binding site) can be used for the initial and/or subsequent diversification of the antigen binding site.

In the construction of libraries for use in the invention, diversification of chosen positions is typically achieved at the nucleic acid level, by altering the coding sequence which specifies the sequence of the polypeptide such that a number of possible amino acids (all 20 or a subset thereof) can be incorporated at that position. Using the IUPAC nomenclature, the most versatile codon is NNK, which encodes all amino acids as well as the TAG stop codon. The NNK codon is preferably used in order to introduce the required diversity. Other codons which achieve the same ends are also of use, including the NNN codon, which leads to the production of the additional stop codons TGA and TAA.

A feature of side-chain diversity in the antigen binding site of human antibodies is a pronounced bias which favours certain amino acid residues. If the amino acid composition of the ten most diverse positions in each of the $V_H$, $V_\kappa$ and $V_\lambda$ regions are summed, more than 76% of the side-chain diversity comes from only seven different residues, these being, serine (24%), tyrosine (14%), asparagine (11%), glycine (9%), alanine (7%), aspartate (6%) and threonine (6%). This bias towards hydrophilic residues and small residues which can provide main-chain flexibility probably reflects the evolution of surfaces which are predisposed to binding a wide range of antigens or epitopes and may help to explain the required promiscuity of antibodies in the primary repertoire.

Since it is preferable to mimic this distribution of amino acids, the distribution of amino acids at the positions to be varied preferably mimics that seen in the antigen binding site of antibodies. Such bias in the substitution of amino acids that permits selection of certain polypeptides (not just antibody polypeptides) against a range of target antigens is easily applied to any polypeptide repertoire. There are various methods for biasing the amino acid distribution at the position to be varied (including the use of tri-nucleotide mutagenesis, see WO97/08320), of which the preferred method, due to ease of synthesis, is the use of conventional degenerate codons. By comparing the amino acid profile encoded by all combinations of degenerate codons (with single, double, triple and quadruple degeneracy in equal ratios at each position) with the natural amino acid use it is possible to calculate the most representative codon. The codons (AGT)(AGC)T, (AGT)(AGC)C and (AGT)(AGC)(CT)—that is, DVT, DVC and DVY, respectively using IUPAC nomenclature—are those closest to the desired amino acid profile: they encode 22% serine and 11% tyrosine, asparagine, glycine, alanine, aspartate, threonine and cysteine. Preferably, therefore, libraries are constructed using either the DVT, DVC or DVY codon at each of the diversified positions.

G: Antigens Capable of Increasing Ligand Half-Life

The dual specific ligands according to the invention, in one configuration thereof, are capable of binding to one or more molecules which can increase the half-life of the ligand in vivo. Typically, such molecules are polypeptides which occur naturally in vivo and which resist degradation or removal by endogenous mechanisms which remove unwanted material from the organism. For example, the molecule which increases the half-life of the organism may be selected from the following:

Proteins from the extracellular matrix; for example collagen, laminins, integrins and fibronectin. Collagens are the major proteins of the extracellular matrix. About 15 types of collagen molecules are currently known, found in different parts of the body, e.g. type I collagen (accounting for 90% of body collagen) found in bone, skin, tendon, ligaments, cornea, internal organs or type II collagen found in cartilage, invertebral disc, notochord, vitreous humour of the eye.

Proteins found in blood, including: Plasma proteins such as fibrin, α-2 macroglobulin, serum albumin, fibrinogen A, fibrinogen B, serum amyloid protein A, heptaglobin, profilin, ubiquitin, uteroglobulin and β-2-microglobulin;

Enzymes and inhibitors such as plasminogen, lysozyme, cystatin C, alpha-1-antitrypsin and pancreatic trypsin inhibitor. Plasminogen is the inactive precursor of the trypsin-like serine protease plasmin. It is normally found circulating through the blood stream. When plasminogen becomes activated and is converted to plasmin, it unfolds a potent enzymatic domain that dissolves the fibrinogen fibers that entangle the blood cells in a blood clot. This is called fibrinolysis.

Immune system proteins, such as IgE, IgG, IgM.

Transport proteins such as retinol binding protein, α-1 microglobulin.

Defensins such as beta-defensin 1, Neutrophil defensins 1, 2 and 3.

Proteins found at the blood brain barrier or in neural tissues, such as melanocortin receptor, myelin, ascorbate transporter.

Transferrin receptor specific ligand-neuropharmaceutical agent fusion proteins (see U.S. Pat. No. 5,977,307);

brain capillary endothelial cell receptor, transferrin, transferrin receptor, insulin, insulin-like growth factor 1 (IGF 1) receptor, insulin-like growth factor 2 (IGF 2) receptor, insulin receptor.

Proteins localised to the kidney, such as polycystin, type IV collagen, organic anion transporter K1, Heymann's antigen.

Proteins localised to the liver, for example alcohol dehydrogenase, G250.

Blood coagulation factor X

α1 antitrypsin

HNF 1α

Proteins localised to the lung, such as secretory component (binds IgA).

Proteins localised to the Heart, for example HSP 27. This is associated with dilated cardiomyopathy.

Proteins localised to the skin, for example keratin.

Bone specific proteins, such as bone morphogenic proteins (BMPs), which are a subset of the transforming growth factor β superfamily that demonstrate osteogenic activity. Examples include BMP-2, -4, -5, -6, -7 (also referred to as osteogenic protein (OP-1) and -8 (OP-2).

Tumour specific proteins, including human trophoblast antigen, herceptin receptor, oestrogen receptor, cathepsins e.g. cathepsin B (found in liver and spleen).

Disease-specific proteins, such as antigens expressed only on activated T-cells: including LAG-3 (lymphocyte activation gene), osteoprotegerin ligand (OPGL) see *Nature* 402, 304-309; 1999, OX40 (a member of the TNF receptor family, expressed on activated T cells and the only costimulatory T cell molecule known to be specifically up-regulated in human T cell leukaemia virus type-I (HTLV-I)-producing cells.) See *J Immunol.* 2000 Jul. 1; 165(1):263-70; Metalloproteases (associated with arthritis/cancers), including CG6512 *Drosophila*, human paraplegin, human FtsH, human AFG3L2, murine ftsH; angiogenic growth factors, including acidic fibroblast growth factor (FGF-1), basic fibroblast growth factor (FGF-2), Vascular endothelial growth factor/vascular permeability factor (VEGF/VPF), transforming growth factor-a (TGF a), tumor necrosis factor-alpha (TNF-α), angiogenin, interleukin-3 (IL-3), interleukin-8 (IL-8), platelet-derived endothelial growth factor (PD-ECGF), placental growth factor (P1GF), midkine platelet-derived growth factor-BB (PDGF), fractalkine.

Stress proteins (heat shock proteins) HSPs are normally found intracellularly. When they are found extracellularly, it is an indicator that a cell has died and spilled out its contents. This unprogrammed cell death (necrosis) only occurs when as a result of trauma, disease or injury and therefore in vivo, extracellular HSPs trigger a response from the immune system that will fight infection and disease. A dual specific ligand which binds to extracellular HSP can be localised to a disease site.

Proteins Involved in Fc Transport

Brambell Receptor (also Known as FCRB)

This Fc receptor has two functions, both of which are potentially useful for delivery.

The functions are (1) The transport of IgG from mother to child across the placenta (2) the protection of IgG from degradation thereby prolonging its serum half life of IgG. It is thought that the receptor recycles IgG from endosome.

See Holliger et al, Nat Biotechnol 1997 July; 15(7):632-6.

Ligands according to the invention may designed to be specific for the above targets without requiring any increase in or increasing half life in vivo. For example, ligands according to the invention can be specific for targets selected from those described above which are tissue-specific, thereby enabling tissue-specific targeting of the dual specific ligand, or a dAb monomer that binds a tissue-specific therapeutically relevant target, irrespective of any increase in half-life, although this may result. Moreover, where the ligand or dAb monomer targets kidney or liver, this may redirect the ligand or dAb monomer to an alternative clearance pathway in vivo (for example, the ligand may be directed away from liver clearance to kidney clearance).

As described above, ligands described herein comprising a single variable domain as defined herein can be selected to be specific for a target and preferably may have the added attribute of increasing the half life of a target in vivo, though not required. A dual-specific ligand may be composed of an antibody heavy chain single variable domain having a binding specificity to a first epitope or antigen, and also of an antibody light chain single variable domain having a binding specificity to a second epitope or antigen, where one or both of the antigens can be serum albumin, or one or both of the epitopes is an epitope(s) of serum albumin. In one embodiment, both serum albumin epitopes are the same, in another embodiment, each serum albumin epitope is different.

In addition to these dual-specific ligands which have the attribute of increasing the half life of a target in vivo, other structural forms of ligands are described herein which have or consist of at least one single variable domain as defined herein which has the attribute of increasing the half life of a target binding ligand in vivo, e.g., by binding serum albumin. For example, the ligand can consist of, or contain, a monomer single variable domain as defined herein which binds serum albumin; or the ligand can be in a form which comprises multiple single variable domains as defined herein, where one or more of the single variable domains binds serum albumin, i.e., a multimer. Both the multimer and the monomer can further comprise other entities in addition to the one or more single variable domain(s) which binds serum albumin, e.g., in the form of a fusion protein and/or a conjugate. Such a fusion protein preferably is a single polypeptide chain and can comprise for example two or more linked single variable domains as defined herein; the linked single variable domains can be identical to each other or they can be different from each other. Such entities include e.g., one or more additional single variable domains as defined herein, which have a specificity to an antigen or epitope other than serum albumin, and/or one or more drugs, and/or one or more target binding domains which have a specificity to an antigen or epitope other than serum albumin and which are not single variable domains as defined herein. Such a multimer may have multiple valencies with respect to its single variable domain(s), e.g., univalent, divalent, trivalent, tetravalent. Such a multimer may have the form of an IgG structure or a dual specific ligand as defined herein, as well as other structures such as IgM, IgE, IgD, or IgA, and/or fragments thereof, including but not limited to fragments such as scFv fragments, Fab, Fab' etc. The ligand can be modified to contain additional moieties, such as a fusion protein, or a conjugate.

An antibody heavy chain single variable domain of a dual specific ligand or of a monomer ligand or of a multimer ligand as described herein, can specifically bind serum albumin and comprises an amino acid sequence of an antibody heavy chain single variable domain. Such an antibody heavy chain single variable domain can be selected from, but preferably is not limited to, one of the following domains: dAb7r20, dAb7r21, dAb7r22, dAb7r23, dAb7r24, dAb7r25, dAb7r26, dAb7r27, dAb7r28, dAb7r29, dAb7r30, dAb7r31, dAb7r32, dAb7r33, dAb7h21, dAb7h22, dAb7h23, Ab7h24, Ab7h25, Ab7h26, dAb7h27, dAb7h30 and dAb7h31, or a domain with an amino acid sequence that is at least 80% identical thereto, up to and including 85%, 90%, 95%, 96%, 97%, 98%, 99% identical thereto, and specifically binds serum albumin. Alternatively, the ligand comprises an antibody single variable domain, preferably an antibody heavy chain single variable domain, that competes for binding to serum albumin with one of the following domains: dAb7r20, dAb7r21, dAb7r22, dAb7r23, dAb7r24, dAb7r25, dAb7r26, dAb7r27, dAb7r28, dAb7r29, dAb7r30, dAb7r31, dAb7r32, dAb7r33, dAb7h22, dAb7h23, Ab7h24, Ab7h25, Ab7h26, dAb7h27, dAb7h30 dAb7h31, dAb7m12, dAb7m16, dAb7 m26, dAb7r1, dAb7r3, dAb7r4, dAb7r5, dAb7r7, dAb7r8, dAb7r13, dAb7r14, dAb7r15, dAb7r16, dAb7r17, dAb7r18, dAb7r19, dAb7h1, dAb7h2, dAb7h6, dAb7h7, dAb7h8, dAb7h9, dAb7h10, dAb7h11, dAb7h12, dAb7h13, dAb7h14, dAb7p1, and dAb7p2, or with a domain having an amino acid sequence that is at least 80% identical thereto, up to and including 85%, 90%, 95%, 96%, 97%, 98%, 99% identical thereto, and that specifically binds serum albumin. Alternatively, the ligand comprises, in addition to the antibody heavy chain single variable domain, an antibody light chain single variable domain which can specifically bind serum albumin and comprise an amino acid sequence of an antibody light chain single variable domain. Such an antibody light chain single variable domain can be selected from, but preferably is not limited to, one of the following domains: dAb7m12, dAb7m16, dAb7m26, dAb7r1, dAb7r3, dAb7r4, dAb7r5, dAb7r7, dAb7r8, dAb7r13, dAb7r14, dAb7r15, dAb7r16, dAb7r17, dAb7r18, dAb7r19, dAb7h1, dAb7h2, dAb7h6, dAb7h7, dAb7h8, dAb7h9, dAb7h10, dAb7h11, dAb7h12, dAb7h13, dAb7h14, dAb7p1, and dAb7p2, or a domain with an amino acid sequence that is at least 80% identical thereto, up to and including 85%, 90%, 95%, 96%, 97%, 98%, 99% identical thereto, and that specifically binds serum albumin. Alternatively, the ligand comprises an antibody single variable domain, preferably an antibody light chain single variable domain, that competes for binding to serum albumin with a domain that can be selected from, but preferably not limited to, one of the following domains: dAb7r20, dAb7r21, dAb7r22, dAb7r23, dAb7r24, dAb7r25, dAb7r26, dAb7r27, dAb7r28, dAb7r29, dAb7r30, dAb7r31, dAb7r32, dAb7r33, dAb7h21, dAb7h22, dAb7h23, Ab7h24, Ab7h25, Ab7h26, dAb7h27, dAb7h30 dAb7h31, dAb7m12, dAb7m16, dAb7m26, dAb7r1, dAb7r3, dAb7r4, dAb7r5, dAb7r7, dAb7r8, dAb7r13, dAb7r14, dAb7r15, dAb7r16, dAb7r17, dAb7r18, dAb7r19, dAb7h1, dAb7h2, dAb7h6, dAb7h7, dAb7h8, dAb7h9, dAb7h10, dAb7h11, dAb7h12, dAb7h13, dAb7h14, dAb7p1, and dAb7p2, or a domain having an amino acid sequence that is at least 80% identical thereto, up to and including 85%, 90%, 95%, 96%, 97%, 98%, 99% identical thereto, and having binding specificity for serum albumin. In one embodiment, the ligand can be an IgG immunoglobulin having any combination of one, or two of the above dual specific ligands. In one embodiment, the ligand can contain one or more monomers of the single variable domains listed above, where if the ligand contains more than one of these single variable domains, the single variable domains can be identical to each other, or not identical to each other.

In one embodiment, the ligand can be a dual specific ligand which has a first immunoglobulin single variable domain having a first antigen or epitope binding specificity and a second immunoglobulin single variable domain having a second antigen or epitope binding specificity, the first and the second immunoglobulin single variable domains being antibody heavy chain single variable domains, and where one or both of the first and second antibody heavy chain single variable domains specifically binds to serum albumin and has an amino acid sequence of an antibody heavy chain single variable domain that can be selected from, but is preferably not limited to, one of the following antibody heavy chain single variable domains: dAb7r20, dAb7r21, dAb7r22, dAb7r23, dAb7r24, dAb7r25, dAb7r26, dAb7r27, dAb7r28, dAb7r29, dAb7r30, dAb7r31, dAb7r32, dAb7r33, dAb7h21, dAb7h22, dAb7h23, Ab7h24, Ab7h25, Ab7h26, dAb7h27, dAb7h30 and dAb7h31, or an amino acid sequence that is at least 80% identical thereto, up to and including 85%, 90%, 95%, 96%, 97%, 98%, or 99% identical thereto. One embodiment of such a ligand is a dual specific ligand which has a first immunoglobulin single variable domain having a first antigen or epitope binding specificity and a second immunoglobulin single variable domain having a second antigen or epitope binding specificity, the first and the second immunoglobulin single variable domains being antibody heavy chain single variable domains, and where one or both of the first and second antibody heavy chain single variable domains specifically binds to serum albumin and competes for binding to serum albumin with a single variable domain which has an amino acid sequence of an antibody single variable domain that can be selected from, but is preferably not limited to, one of the following antibody single variable domains: dAb7r20, dAb7r21, dAb7r22, dAb7r23, dAb7r24, dAb7r25, dAb7r26, dAb7r27, dAb7r28, dAb7r29, dAb7r30, dAb7r31, dAb7r32, dAb7r33, dAb7h21, dAb7h22, dAb7h23, Ab7h24, Ab7h25, Ab7h26, dAb7h27, dAb7h30dAb7h31, dAb7m12, dAb7m16, dAb7m26, dAb7r1, dAb7r3, dAb7r4, dAb7r5, dAb7r7, dAb7r8, dAb7r13, dAb7r14, dAb7r15, dAb7r16, dAb7r17, dAb7r18, dAb7r19, dAb7h1, dAb7h2, dAb7h6, dAb7h7, dAb7h8, dAb7h9, dAb7h10, dAb7h11, dAb7h12, dAb7h13, dAb7h14, dAb7p1, and dAb7p2, or a sequence that is at least 80% identical thereto, or up to and including 85%, 90%, 95%, 96%, 97%, 98%, 99% identical thereto. In one embodiment, the ligand can be an IgG immunoglobulin having any combination of one or two of the above dual specific ligands. In one embodiment, the ligand can contain one or more monomers of the single variable domains listed above, where if the ligand contains more than one of these single variable domains, the single variable domains can be identical to each other, or not identical to each other.

In one embodiment a dual specific ligand has a first immunoglobulin single variable domain having a first antigen or epitope binding specificity and a second immunoglobulin single variable domain having a second antigen or epitope binding specificity, the first and the second immunoglobulin single variable domains being antibody light chain single variable domains, and one or both of the first and second antibody light chain single variable domains specifically binds to serum albumin and has an amino acid sequence of an antibody light chain single variable domain that can be selected from, but is preferably not limited to, one of the following antibody light chain single variable domains dAb7m12, dAb7m16, dAb7m26, dAb7r1, dAb7r3, dAb7r4, dAb7r5, dAb7r7, dAb7r8, dAb7r13, dAb7r14, dAb7r15, dAb7r16, dAb7r17, dAb7r18, dAb7r19, dAb7h1, dAb7h2, dAb7h6, dAb7h7, dAb7h8, dAb7h9, dAb7h10, dAb7h11, dAb7h12, dAb7h13, dAb7h14, dAb7p1, and dAb7p2, or a sequence that is at least 80% identical thereto, or up to and including 85%, 90%, 95%, 96%, 97%, 98%, or 99% identical thereto.

In one embodiment, the ligand can be a dual specific ligand which has a first immunoglobulin single variable domain having a first antigen or epitope binding specificity and a second immunoglobulin single variable domain having a second antigen or epitope binding specificity, the first and the second immunoglobulin single variable domains being antibody light chain single variable domains, and one or both of the first and second antibody light chain single variable domains specifically binds to serum albumin and competes for binding to serum albumin with an antibody light chain single variable domain which has an amino acid sequence of an antibody single variable domain which can be selected from, but preferably is not limited to, one of the following antibody single variable domains: dAb7r20, dAb7r21, dAb7r22, dAb7r23, dAb7r24, dAb7r25, dAb7r26, dAb7r27, dAb7r28, dAb7r29, dAb7r30, dAb7r31, dAb7r32, dAb7r33, dAb7h21, dAb7h22, dAb7h23, Ab7h24, Ab7h25, Ab7h26, dAb7h27, dAb7h30 dAb7h31, dAb7m12, dAb7m16, dAb7m26, dAb7r1, dAb7r3, dAb7r4, dAb7r5, dAb7r7, dAb7r8, dAb7r13, dAb7r14, dAb7r15, dAb7r16, dAb7r17, dAb7r18, dAb7r19, dAb7h1, dAb7h2, dAb7h6, dAb7h7, dAb7h8, dAb7h9, dAb7h10, dAb7h11, dAb7h12, dAb7h13, dAb7h14, dAb7p1 and dAb7p2, or a sequence that is at least 80% identical thereto, or up to and including 85%, 90%, 95%, 96%, 97%, 98%, or 99% identical thereto.

Described herein is a ligand which has one or more antibody heavy chain single variable domains where the one or more antibody heavy chain single variable domain specifically binds serum albumin and has an amino acid sequence of an antibody heavy chain single variable domain selected from, but preferably not limited to, that of dAb8, dAb 10, dAb36, dAb7r20, dAb7r21, dAb7r22, dAb7r23, dAb7r24, dAb7r25, dAb7r26, dAb7r27, dAb7r28, dAb7r29, dAb7r30, dAb7r31, dAb7r32, dAb7r33, dAb7h21, dAb7h22, dAb7h23, Ab7h24, Ab7h25, Ab7h26, dAb7h27, dAb7h30, dAb7h31, and a sequence that is at least 80% identical thereto, or up to and including 85%, 90%, 95%, 96%, 97%, 98%, or 99% identical thereto.

Described herein is a ligand which has one or more antibody heavy chain single variable domains, where the one or more antibody heavy chain single variable domains specifically binds serum albumin and competes for binding to serum albumin with an antibody single variable domain which has an amino acid sequence of an antibody single variable domain selected from, but preferably not limited to, that of one of the following: dAb8, dAb 10, dAb36, dAb7r20, dAb7r21, dAb7r22, dAb7r23, dAb7r24, dAb7r25, dAb7r26, dAb7r27, dAb7r28, dAb7r29, dAb7r30, dAb7r31, dAb7r32, dAb7r33, dAb7h21, dAb7h22, dAb7h23, Ab7h24, Ab7h25, Ab7h26, dAb7h27, dAb7h30, dAb7h31, dAb2, dAb4, dAb7, dAb11, dAb12, dAb13, dAb15, dAb16, dAb17, dAb18, dAb19, dAb21, dAb22, dAb23, dAb24, dAb25, dAb26, dAb27, dAb30, dAb31, dAb33, dAb34, dAb35, dAb38, dAb41, dAb46, dAb47, dAb52, dAb53, dAb54, dAb55, dAb56, dAb7m12, dAb7m16, dAb7m26, dAb7r1, dAb7r3, dAb7r4, dAb7r5, dAb7r7, dAb7r8, dAb7r13, dAb7r14, dAb7r15, dAb7r16, dAb7r17, dAb7r18, dAb7r19, dAb7h1, dAb7h2, dAb7h6, dAb7h7, dAb7h8, dAb7h9, dAb7h10, dAb7h11, dAb7h12, dAb7h13, dAb7h14, dAb7p1, and dAb7p2.

Described herein is a ligand which has an antibody heavy chain single variable domain having a binding specificity to a first antigen, or epitope thereof, and an antibody light chain single variable domain having a binding specificity to a second antigen, or epitope thereof, where one or both of the first antigen and said second antigen is serum albumin, and where the antibody heavy chain single variable domain specifically binds serum albumin and competes for binding to serum albumin with an antibody single variable domain which has an amino acid sequence of an antibody single variable domain selected from, but preferably not limited to, the group: dAb8, dAb 10, dAb36, dAb7r20, dAb7r21, dAb7r22, dAb7r23, dAb7r24, dAb7r25, dAb7r26, dAb7r27, dAb7r28, dAb7r29, dAb7r30, dAb7r31, dAb7r32, dAb7r33, dAb7h21, dAb7h22, dAb7h23, Ab7h24, Ab7h25, Ab7h26, dAb7h27, dAb7h30, dAb7h31, dAb2, dAb4, dAb7, dAb11, dAb12, dAb13, dAb15, dAb16, dAb17, dAb18, dAb19, dAb21, dAb22, dAb23, dAb24, dAb25, dAb26, dAb27, dAb30, dAb31, dAb33, dAb34, dAb35, dAb38, dAb41, dAb46, dAb47, dAb52, dAb53, dAb54, dAb55, dAb56, dAb7m12, dAb7m16, dAb7m26, dAb7r1, dAb7r3, dAb7r4, dAb7r5, dAb7r7, dAb7r8, dAb7r13, dAb7r14, dAb7r15, dAb7r16, dAb7r17, dAb7r18, dAb7r19, dAb7h1, dAb7h2, dAb7h6, dAb7h7, dAb7h8, dAb7h9, dAb7h10, dAb7h11, dAb7h12, dAb7h13, dAb7h14, dAb7p1, dAb7p2, and where the antibody light chain single variable domain specifically binds serum albumin and has an amino acid sequence of an antibody light chain single variable domain selected from, but preferably not limited to, that of the following: dAb2, dAb4, dAb7, dAb11, dAb12, dAb13, dAb15, dAb16, dAb17, dAb18, dAb19, dAb21, dAb22, dAb23, dAb24, dAb25, dAb26, dAb27, dAb30, dAb31, dAb33, dAb34, dAb35, dAb38, dAb41, dAb46, dAb47, dAb52, dAb53, dAb54, dAb55, dAb56, drdAb7m12, dAb7m16, dAb7m26, dAb7r1, dAb7r3, dAb7r4, dAb7r5, dAb7r7, dAb7r8, dAb7r13, dAb7r14, dAb7r15, dAb7r16, dAb7r17, dAb7r18, dAb7r19, dAb7h1, dAb7h2, dAb7h6, dAb7h7, dAb7h8, dAb7h9, dAb7h10, dAb7h11, dAb7h12, dAb7h13, dAb7h14, dAb7p1, and dAb7p2, and a sequence that is at least 80% identical thereto, or up to and including 85%, 90%, 95%, 96%, 97%, 98%, or 99% identical thereto.

Described herein is a ligand which has an antibody heavy chain single variable domain having a binding specificity to a first antigen or epitope thereof, and an antibody light chain single variable domain having a binding specificity to a second antigen or epitope thereof, wherein one or both of said first antigen and said second antigen is serum albumin, and wherein the antibody heavy chain single variable domain specifically binds serum albumin albumin and has an amino acid sequence of an antibody heavy chain single variable domain selected from but preferably not limited to, the group: dAb8, dAb 10, dAb36, dAb7r20, dAb7r21, dAb7r22, dAb7r23, dAb7r24, dAb7r25, dAb7r26, dAb7r27, dAb7r28, dAb7r29, dAb7r30, dAb7r31, dAb7r32, dAb7r33, dAb7h21, dAb7h22, dAb7h23, Ab7h24, Ab7h25, Ab7h26, dAb7h27, dAb7h30, dAb7h31, and a sequence that is at least 80% identical thereto, or up to and including 85%, 90%, 95%, 96%, 97%, 98%, or 99% identical thereto, and where the antibody light chain single variable domain specifically binds serum albumin and competes for binding to serum albumin with an antibody single variable domain which comprises an amino acid sequence of an antibody single variable domain selected from, but preferably not limited to the group: dAb8, dAb 10, dAb36, dAb7r20, dAb7r21, dAb7r22, dAb7r23, dAb7r24, dAb7r25, dAb7r26, dAb7r27, dAb7r28, dAb7r29, dAb7r30, dAb7r31, dAb7r32, dAb7r33, dAb7h21, dAb7h22, dAb7h23, Ab7h24, Ab7h25, Ab7h26, dAb7h27, dAb7h30, dAb7h31, dAb2, dAb4, dAb7, dAb11, dAb12, dAb13, dAb15, dAb16, dAb17, dAb18, dAb19, dAb21, dAb22, dAb23, dAb24, dAb25, dAb26, dAb27, dAb30, dAb31, dAb33, dAb34, dAb35, dAb38, dAb41, dAb46, dAb47, dAb52, dAb53, dAb54, dAb55, dAb56, dAb7m12, dAb7m16, dAb7m26, dAb7r1, dAb7r3, dAb7r4, dAb7r5, dAb7r7, dAb7r8, dAb7r13, dAb7r14, dAb7r15, dAb7r16, dAb7r17, dAb7r18, dAb7r19, dAb7h1, dAb7h2, dAb7h6, dAb7h7, dAb7h8, dAb7h9, dAb7h10, dAb7h11, dAb7h12, dAb7h13, dAb7h14, dAb7p1 and dAb7p2.

Described herein is a ligand which has one or more antibody heavy chain single variable domains having a binding specificity to a first antigen or epitope thereof, and one or more antibody light chain single variable domains having a binding specificity to a second antigen or epitope thereof, wherein one or both of the first antigen and the second antigen is serum albumin, and wherein the one or more antibody heavy chain single variable domains specifically binds serum albumin and competes for binding to serum albumin with an antibody single variable domain which has an amino acid sequence of an antibody single variable domain selected from, but preferably not limited to, the group: dAb8, dAb 10, dAb36, dAb7r20, dAb7r21, dAb7r22, dAb7r23, dAb7r24, dAb7r25, dAb7r26, dAb7r27, dAb7r28, dAb7r29, dAb7r30, dAb7r31, dAb7r32, dAb7r33, dAb7h21, dAb7h22, dAb7h23, Ab7h24, Ab7h25, Ab7h26, dAb7h27, dAb7h30, dAb7h31, dAb2, dAb4, dAb7, dAb11, dAb12, dAb13, dAb15, dAb16, dAb17, dAb18, dAb19, dAb21, dAb22, dAb23, dAb24, dAb25, dAb26, dAb27, dAb30, dAb31, dAb33, dAb34, dAb35, dAb38, dAb41, dAb46, dAb47, dAb52, dAb53, dAb54, dAb55, dAb56, dAb7m12, dAb7m16, dAb7m26, dAb7r1, dAb7r3, dAb7r4, dAb7r5, dAb7r7, dAb7r8, dAb7r13, dAb7r14, dAb7r15, dAb7r16, dAb7r17, dAb7r18, dAb7r19, dAb7h1, dAb7h2, dAb7h6, dAb7h7, dAb7h8, dAb7h9, dAb7h10, dAb7h11, dAb7h12, dAb7h13, dAb7h14, dAb7p1, dAb7p2, and where the one or more antibody light chain single variable domains specifically binds serum albumin and comprises an amino acid sequence of an antibody light chain single variable domain selected from, but preferably not limited to, the group: dAb2, dAb4, dAb7, dAb11, dAb12, dAb13, dAb15, dAb16, dAb17, dAb18, dAb19, dAb21, dAb22, dAb23, dAb24, dAb25, dAb26, dAb27, dAb30, dAb31, dAb33, dAb34, dAb35, dAb38, dAb41, dAb46, dAb47, dAb52, dAb53, dAb54, dAb55, dAb56, drdAb7m12, dAb7m16, dAb7m26, dAb7r1, dAb7r3, dAb7r4, dAb7r5, dAb7r7, dAb7r8, dAb7r13, dAb7r14, dAb7r15, dAb7r16, dAb7r17, dAb7r18, dAb7r19, dAb7h1, dAb7h2, dAb7h6, dAb7h7, dAb7h8, dAb7h9, dAb7h10, dAb7h11, dAb7h12, dAb7h13, dAb7h14, dAb7p1, and dAb7p2, and an amino acid sequence that is at least 80% identical thereto, or up to and including 85%, 90%, 95%, 96%, 97%, 98%, or 99% identical thereto.

Described herein is a ligand which has one or more antibody heavy chain single variable domains having a binding specificity to a first antigen or epitope thereof, and one or more antibody light chain single variable domains having a binding specificity to a second antigen or epitope thereof, where one or both of said first antigen and said second antigen is serum albumin, and where the one or more antibody heavy chain single variable domains specifically binds serum albumin and has an amino acid sequence of an antibody heavy chain single variable domain selected from, but preferably not limited to, the group: dAb8, dAb 10, dAb36, dAb7r20, dAb7r21, dAb7r22, dAb7r23, dAb7r24, dAb7r25, dAb7r26, dAb7r27, dAb7r28, dAb7r29, dAb7r30, dAb7r31, dAb7r32, dAb7r33, dAb7h21, dAb7h22, dAb7h23, Ab7h24, Ab7h25, Ab7h26, dAb7h27, dAb7h30, dAb7h31, and a sequence that is at least 80% identical thereto, or up to and including 85%, 90%, 95%, 96%, 97%, 98%, or 99% identical thereto, and where the one or more antibody light chain single variable domains specifically binds serum albumin and competes for binding to serum albumin with an antibody single variable domain which has an amino acid sequence of an antibody single variable domain selected from the group: dAb8, dAb 10, dAb36, dAb7r20, dAb7r21, dAb7r22, dAb7r23, dAb7r24, dAb7r25, dAb7r26, dAb7r27, dAb7r28, dAb7r29, dAb7r30, dAb7r31, dAb7r32, dAb7r33, dAb7h21, dAb7h22, dAb7h23, Ab7h24, Ab7h25, Ab7h26, dAb7h27, dAb7h30, dAb7h31, dAb2, dAb4, dAb7, dAb11, dAb12, dAb13, dAb15, dAb16, dAb17, dAb18, dAb19, dAb21, dAb22, dAb23, dAb24, dAb25, dAb26, dAb27, dAb30, dAb31, dAb33, dAb34, dAb35, dAb38, dAb41, dAb46, dAb47, dAb52, dAb53, dAb54, dAb55, dAb56, dAb7m12, dAb7m16, dAb7m26, dAb7r1, dAb7r3, dAb7r4, dAb7r5, dAb7r7, dAb7r8, dAb7r13, dAb7r14, dAb7r15, dAb7r16, dAb7r17, dAb7r18, dAb7r19, dAb7h1, dAb7h2, dAb7h6, dAb7h7, dAb7h8, dAb7h9, dAb7h10, dAb7h11, dAb7h12, dAb7h13, dAb7h14, dAb7p1 and dAb7p2.

Described herein is a ligand which has one or more antibody light chain single variable domains and where the one or more antibody light chain single variable domains specifically binds serum albumin and has an amino acid sequence of an antibody light chain single variable domain selected from, but preferably not limited to, the group: dAb2, dAb4, dAb7, dAb11, dAb12, dAb13, dAb15, dAb16, dAb17, dAb18, dAb19, dAb21, dAb22, dAb23, dAb24, dAb25, dAb26, dAb27, dAb30, dAb31, dAb33, dAb34, dAb35, dAb38, dAb41, dAb46, dAb47, dAb52, dAb53, dAb54, dAb55, dAb56, drdAb7m12, dAb7m16, dAb7 m26, dAb7r1, dAb7r3, dAb7r4, dAb7r5, dAb7r7, dAb7r8, dAb7r13, dAb7r14, dAb7r15, dAb7r16, dAb7r17, dAb7r18, dAb7r19, dAb7h1, dAb7h2, dAb7h6, dAb7h7, dAb7h8, dAb7h9, dAb7h10, dAb7h11, dAb7h12, dAb7h13, dAb7h14, dAb7p1, dAb7p2, and a sequence that is at least 80% identical thereto, or up to and including 85%, 90%, 95%, 96%, 97%, 98%, or 99% identical thereto.

Described herein is a ligand which has one or more antibody light chain single variable domains, where the one or more antibody light chain single variable domains specifically binds serum albumin and competes for binding to serum albumin with an antibody single variable domain which has an amino acid sequence of an antibody single variable domain selected from, but preferably not limited to, the group: dAb8, dAb 10, dAb36, dAb7r20, dAb7r21, dAb7r22, dAb7r23, dAb7r24, dAb7r25, dAb7r26, dAb7r27, dAb7r28, dAb7r29, dAb7r30, dAb7r31, dAb7r32, dAb7r33, dAb7h21, dAb7h22, dAb7h23, Ab7h24, Ab7h25, Ab7h26, dAb7h27, dAb7h30, dAb7h31, dAb2, dAb4, dAb7, dAb11, dAb12, dAb13, dAb15, dAb16, dAb17, dAb18, dAb19, dAb21, dAb22, dAb23, dAb24, dAb25, dAb26, dAb27, dAb30, dAb31, dAb33, dAb34, dAb35, dAb38, dAb41, dAb46, dAb47, dAb52, dAb53, dAb54, dAb55, dAb56, dAb7m12, dAb7m16, dAb7m26, dAb7r1, dAb7r3, dAb7r4, dAb7r5, dAb7r7, dAb7r8, dAb7r13, dAb7r14, dAb7r15, dAb7r16, dAb7r17, dAb7r18, dAb7r19, dAb7h1, dAb7h2, dAb7h6, dAb7h7, dAb7h8, dAb7h9, dAb7h10, dAb7h11, dAb7h12, dAb7h13, dAb7h14, dAb7p1, and dAb7p2.

Described herein is a ligand which has one or more single variable domains, where the one or more single variable domains specifically binds serum albumin and competes for binding to serum albumin with an antibody single variable domain which has an amino acid sequence of an antibody single variable domain selected from, but preferably not limited to the group: dAb8, dAb 10, dAb36, dAb7r20, dAb7r21, dAb7r22, dAb7r23, dAb7r24, dAb7r25, dAb7r26, dAb7r27, dAb7r28, dAb7r29, dAb7r30, dAb7r31, dAb7r32, dAb7r33, dAb7h21, dAb7h22, dAb7h23, Ab7h24, Ab7h25, Ab7h26, dAb7h27, dAb7h30, dAb7h31, dAb2, dAb4, dAb7, dAb11, dAb12, dAb13, dAb15, dAb16, dAb17, dAb18, dAb19, dAb21, dAb22, dAb23, dAb24, dAb25, dAb26, dAb27, dAb30, dAb31, dAb33, dAb34, dAb35, dAb38, dAb41, dAb46, dAb47, dAb52, dAb53, dAb54, dAb55, dAb56, dAb7m12, dAb7m16, dAb7 m26, dAb7r1, dAb7r3, dAb7r4, dAb7r5, dAb7r7, dAb7r8, dAb7r13, dAb7r14, dAb7r15, dAb7r16, dAb7r17, dAb7r18, dAb7r19, dAb7h1, dAb7h2, dAb7h6, dAb7h7, dAb7h8, dAb7h9, dAb7h10, dAb7h11, dAb7h12, dAb7h13, dAb7h14, dAb7p1, and dAb7p2. Preferably, the one or more single variable domains comprises a scaffold selected from, but preferably not limited to, the group consisting of CTLA-4, lipocallin, SpA, an Affibody, an avimer, GroE1 and fibronectin, and competes for binding to serum albumin with an antibody single variable domain which has an amino acid sequence of an antibody single variable domain selected from, but preferably not limited to the group: dAb8, dAb 10, dAb36, dAb7r20, dAb7r21, dAb7r22, dAb7r23, dAb7r24, dAb7r25, dAb7r26, dAb7r27, dAb7r28, dAb7r29, dAb7r30, dAb7r31, dAb7r32, dAb7r33, dAb7h21, dAb7h22, dAb7h23, Ab7h24, Ab7h25, Ab7h26, dAb7h27, dAb7h30, dAb7h31, dAb2, dAb4, dAb7, dAb11, dAb12, dAb13, dAb15, dAb16, dAb17, dAb18, dAb19, dAb21, dAb22, dAb23, dAb24, dAb25, dAb26, dAb27, dAb30, dAb31, dAb33, dAb34, dAb35, dAb38, dAb41, dAb46, dAb47, dAb52, dAb53, dAb54, dAb55, dAb56, dAb7m12, dAb7m16, dAb7m26, dAb7r1, dAb7r3, dAb7r4, dAb7r5, dAb7r7, dAb7r8, dAb7r13, dAb7r14, dAb7r15, dAb7r16, dAb7r17, dAb7r18, dAb7r19, dAb7h1, dAb7h2, dAb7h6, dAb7h7, dAb7h8, dAb7h9, dAb7h10, dAb7h11, dAb7h12, dAb7h13, dAb7h14, dAb7p1, and dAb7p2.

Described herein is a ligand which has a first immunoglobulin single variable domain having a first antigen or epitope binding specificity and a second immunoglobulin single variable domain having a second antigen or epitope binding specificity, where the first and the second immunoglobulin single variable domains are antibody heavy chain single variable domains, where the first antibody heavy chain single variable domains specifically binds to serum albumin and has an amino acid sequence of an antibody heavy chain single variable domain selected from, but preferably not limited to, the group: dAb8, dAb 10, dAb36, dAb7r20, dAb7r21, dAb7r22, dAb7r23, dAb7r24, dAb7r25, dAb7r26, dAb7r27, dAb7r28, dAb7r29, dAb7r30, dAb7r31, dAb7r32, dAb7r33, dAb7h21, dAb7h22, dAb7h23, Ab7h24, Ab7h25, Ab7h26, dAb7h27, dAb7h30, dAb7h31, and a sequence that is at least 80% identical thereto, or up to and including 85%, 90%, 95%, 96%, 97%, 98%, or 99% identical thereto, and where the second antibody heavy chain single variable domains specifically binds to serum albumin and competes for binding to serum albumin with an antibody single variable domain which has an amino acid sequence of an antibody single variable domain selected from the group: dAb8, dAb 10, dAb36, dAb7r20, dAb7r21, dAb7r22, dAb7r23, dAb7r24, dAb7r25, dAb7r26, dAb7r27, dAb7r28, dAb7r29, dAb7r30, dAb7r31, dAb7r32, dAb7r33, dAb7h21, dAb7h22, dAb7h23, Ab7h24, Ab7h25, Ab7h26, dAb7h27, dAb7h30, dAb7h31, dAb2, dAb4, dAb7, dAb11, dAb12, dAb13, dAb15, dAb16, dAb17, dAb18, dAb19, dAb21, dAb22, dAb23, dAb24, dAb25, dAb26, dAb27, dAb30, dAb31, dAb33, dAb34, dAb35, dAb38, dAb41, dAb46, dAb47, dAb52, dAb53, dAb54, dAb55, dAb56, dAb7m12, dAb7m16, dAb7 m26, dAb7r1, dAb7r3, dAb7r4, dAb7r5, dAb7r7, dAb7r8, dAb7r13, dAb7r14, dAb7r15, dAb7r16, dAb7r17, dAb7r18, dAb7r19, dAb7h1, dAb7h2, dAb7h6, dAb7h7, dAb7h8, dAb7h9, dAb7h10, dAb7h11, dAb7h12, dAb7h13, dAb7h14, dAb7p1, and dAb7p2.

Described herein is a ligand which has a first immunoglobulin single variable domain having a first antigen or epitope binding specificity and a second immunoglobulin single variable domain having a second antigen or epitope binding specificity, where the first and the second immunoglobulin single variable domains are antibody light chain single variable domains, where the first antibody light chain single variable domain specifically binds to serum albumin and has an amino acid sequence of an antibody light chain single variable domain selected from, but preferably not limited to, the group: dAb2, dAb4, dAb7, dAb11, dAb12, dAb13, dAb15, dAb16, dAb17, dAb18, dAb19, dAb21, dAb22, dAb23, dAb24, dAb25, dAb26, dAb27, dAb30, dAb31, dAb33, dAb34, dAb35, dAb38, dAb41, dAb46, dAb47, dAb52, dAb53, dAb54, dAb55, dAb56, drdAb7m12, dAb7m16, dAb7 m26, dAb7r1, dAb7r3, dAb7r4, dAb7r5, dAb7r7, dAb7r8, dAb7r13, dAb7r14, dAb7r15, dAb7r16, dAb7r17, dAb7r18, dAb7r19, dAb7h1, dAb7h2, dAb7h6, dAb7h7, dAb7h8, dAb7h9, dAb7h10, dAb7h11, dAb7h12, dAb7h13, dAb7h14, dAb7p1, dAb7p2, and a sequence that is at least 80% identical thereto, or up to and including 85%, 90%, 95%, 96%, 97%, 98%, or 99% identical thereto, and where the second antibody light chain single variable domain specifically binds to serum albumin and competes for binding to serum albumin with an antibody single variable domain which has an amino acid sequence of an antibody single variable domain selected from, but preferably not limited to, the group: dAb8, dAb 10, dAb36, dAb7r20, dAb7r21, dAb7r22, dAb7r23, dAb7r24, dAb7r25, dAb7r26, dAb7r27, dAb7r28, dAb7r29, dAb7r30, dAb7r31, dAb7r32, dAb7r33, dAb7h21, dAb7h22, dAb7h23, Ab7h24, Ab7h25, Ab7h26, dAb7h27, dAb7h30, dAb7h31, dAb2, dAb4, dAb7, dAb11, dAb12, dAb13, dAb15, dAb16, dAb17, dAb18, dAb19, dAb21, dAb22, dAb23, dAb24, dAb25, dAb26, dAb27, dAb30, dAb31, dAb33, dAb34, dAb35, dAb38, dAb41, dAb46, dAb47, dAb52, dAb53, dAb54, dAb55, dAb56, dAb7m12, dAb7m16, dAb7m26, dAb7r1, dAb7r3, dAb7r4, dAb7r5, dAb7r7, dAb7r8, dAb7r13, dAb7r14, dAb7r15, dAb7r16, dAb7r17, dAb7r18, dAb7r19, dAb7h1, dAb7h2, dAb7h6, dAb7h7, dAb7h8, dAb7h9, dAb7h10, dAb7h11, dAb7h12, dAb7h13, dAb7h14, dAb7p1, and dAb7p2.

Embodiments of ligands described supra and herein, also includes those having a structure comprising an IgG structure having any combination of one, or two of the above dual specific ligands, and/or single variable domains comprising non-immunoglobulin scaffolds. Such an immunoglobulin structure can have various combinations of antibody single variable domains, including an IgG structure that contains four antibody heavy chain single variable domains, or an IgG structure that contains four antibody light chain single variable domains, as well as an IgG structure that contains two pairs of chains, each pair containing an antibody heavy chain single variable domain and an antibody light chain single variable domain. In addition to these IgG structures, the ligands described herein can contain one or more monomers of a single variable domain, including but preferably not limited to the single variable domains listed above, where if the ligand contains more than one of these single variable domains, the single variable domains can be identical to each other, or not identical to each other.

Embodiments of ligands comprising one or more single variable domains include, but preferably are not limited to, the dAbs described herein, dual specific monomers comprising at least one single variable domain, dual specific IgG molecules containing antibody single chain monomers, and multivalent IgG molecules comprising antibody single chain monomers as described herein. These embodiments, can further comprise a binding site for a generic ligand. The generic ligand can include, but preferably is not limited to, protein A, protein L and protein G. For such dual specific ligands, including those in an IgG format, the target(s) for each second antigen or epitope binding specificity includes, but preferably is not limited to, a binding specificity for an antigen which can be characterized in a group selected from cytokines, cytokine receptors, enzymes, enzyme co-factors and DNA binding proteins, and can be selected from, but preferably is not limited to, EPO receptor, ApoE, Apo-SAA, BDNF, Cardiotrophin-1, EGF, EGF receptor, ENA-78, Eotaxin, Eotaxin-2, Exodus-2, EpoR, FGF-acidic, FGF-basic, fibroblast growth factor-10, FLT3 ligand, Fractalkine (CX3C), GDNF, G-CSF, GM-CSF, GF-β1, insulin, IFN-γ IL-1β, IL-2, IL-3, IL-4, IL-5, IL-6, IL-7, IL-8 (72 a.a.), IL-8 (77 a.a), IL-9, IL-10, IL-11, IL-12, IL-13, IL-15, IL-16, IL-17, IL-18 (IGIF), Inhibin β, Inhibin β, IP-10 keratinocyte growth factor-2 (KGF-2), KGF, Leptin, LIF, Lymphotactin, Mullerian inhibitory substance, monocyte colony inhibitory factor, monocyte attractant protein, M-CSF, MDC (67 a.a.), MDC (69 a.a.), MCP-1 (MCAF), MCP-2, MCP-3, MCP-4, MDC (67 a.a.), MDC (69 a.a), MIG, MLP-1α, MIP-3α, MIP-3β, MIP-4, myeloid progenitor inhibitor factor-1 (MPIF-1), NAP-2, Neurturin, Nerve growth factor, β-NGF, NT-3, NT-4, Oncostatin M, PDGF-AA, PDGF-AB, PDGF-BB, PF-4, RANTES, SDF1α, SDF1β TGF-β, TGF-β2, TGF-β, TNF-β, TNF receptor 1, TNF receptor II, TNIL-1, TPO, VEGF, VEGF receptor 1, VEGF receptor 2, VEGF receptor 3, GCP-2, GRO/MGSA, GRO-β, GRO-γ, HCC1, 1-309, HER 1, HER 2, HER3, HER4, CD4, human chemokine receptors CXCR4 or CCR5, non-structural protein type 3 (NS3) from the hepatitis C virus, TNF-alpha, IgE, IFN-gamma, MMP-12, CEA, *H. pylori*, TB, influenza, Hepatitis E, MMP-12, internalising receptors such as the epidermal growth factor receptor (EGFR), ErBb2 receptor on tumor cells, an internalising cellular receptor, LDL receptor, FGF2 receptor, ErbB2 receptor, transferrin receptor, PDGF receptor, VEGF receptor, PsmAr, an extracellular matrix protein, elastin, fibronectin, laminin, α1-antitrypsin, tissue factor protease inhibitor, PDK1, GSK1, Bad, caspase-9, Forkhead, an antigen of *Helicobacter pylori*, an antigen of *Mycobacterium tuberculosis*, and an antigen of influenza virus. In such a dual-specific ligand, including those dual specific ligands present in an IgG format, one or both single variable domains specifically binds an epitope or antigen with a dissociation constant (Kd) that can be selected from, but is preferably not limited to, $1\times10^{-3}$ M or less, $1\times10^{-4}$ M or less, $1\times10^{-5}$ M or less, $1\times10^{-6}$ M or less, $1\times10^{-7}$ M or less, $1\times10^{-8}$ M or less, and $1\times10^{-9}$ M or less, as determined, for example, by surface plasmon resonance. Such a dual-specific ligand, including those dual specific ligands present in an IgG format, can further contain one or more entities including, but preferably is not limited to a label, a tag and a drug. Such a dual-specific ligand, including those dual specific ligands present in an IgG format, as well as a multimeric ligand that contains one or more monomers of the single variable domains listed above, can be present in a kit, and in a composition, including a pharmaceutical composition, containing the dual specific ligand and a carrier thereof.

Similarly, for a ligand comprising one or more single variable domains as described herein, including a ligand in monomeric form and a ligand in multimeric form as defined supra, the one or more single variable domains specifically binds an epitope or antigen with a dissociation constant (Kd) that can be selected from, but is preferably not limited to, $1\times10^{-3}$ M or less, $1\times10^{-4}$ M or less, $1\times10^{-5}$ M or less, $1\times10^{-6}$ M or less, $1\times10^{-7}$ M or less, $1\times10^{-8}$ M or less, and $1\times10^{-9}$ M or less, as determined, for example, by surface plasmon resonance. Such a ligand can further contain one or more entities including, but preferably not limited to a label, a tag and a drug. Such ligand can be present in a kit, a composition, including a pharmaceutical composition, containing the ligand and a carrier thereof.

Percent identity, where recited herein can refer to the percent identity along the entire stretch of the length of the amino acid or nucleotide sequence. When specified, the percent identity of the amino acid or nucleic acid sequence refers to the percent identity to sequence(s) from one or more discrete regions of the referenced amino acid or nucleic acid sequence, for instance, along one or more antibody CDR regions, and/or along one or more antibody variable domain framework regions. For example, the sequence identity at the amino acid level across one or more CDRs of a polypeptide can have at least 80%, 85%, 90%, 91%, 92%, 93%, 94%, 95%, 96%, 97%, 98%, or 99% or higher identity to the amino acid sequence of corresponding CDRs of an antibody heavy or light chain single variable domain. Similarly, the sequence identity at the amino acid level across one or more framework regions of a polypeptide can have at least 80%, 85%, 90%, 91%, 92%, 93%, 94%, 95%, 96%, 97%, 98%, or 99% or higher identity to the amino acid sequence of a corresponding framework of an antibody heavy or light chain single variable domain. At the nucleic acid level, the nucleic acid sequence encoding one or more CDRs of a polypeptide can have at least 70%, 75%, 80%, 85%, 90%, 91%, 92%, 93%, 94%, 95%, 96%, 97%, 98%, or 99% or higher identity to the nucleic acid sequence encoding corresponding CDRs of an antibody heavy or light chain single variable domain. At the nucleic acid level, the nucleic acid sequence encoding one or more framework regions of a polypeptide can have at least 70%, 75%, 80%, 85%, 90%, 91%, 92%, 93%, 94%, 95%, 96%, 97%, 98%, or 99% or higher identity to the nucleic acid sequence encoding corresponding framework regions of an antibody heavy or light chain single variable domain, respectively. The framework regions (FW) are preferably from an antibody framework region, such as the human V3-23[DP47] JH4B heavy or the human kappa light chain DPK9/JK1. If the framework region(s) is that found in the human V3-23 [DP47]/JH4B heavy chain V region, the percent identity can be targeted to its framework regions and/or preferably to one or more of the CDR regions as illustrated in FIG. 24. If the framework is that found in the human DPK9/JK1 light chain V region, the percent identity can be compared to its referenced framework regions and/or preferably to one or more of the CDR regions as illustrated in FIG. 24.

The CDRs are preferably those of an antibody variable domain, preferably, but not limited to those of antibody single variable domains.

In some embodiments, the structural characteristic of percent identity is coupled to a functional aspect. For instance, in some embodiments, a nucleic acid sequence or amino acid sequence with less than 100% identity to a referenced nucleic acid or amino acid sequence is also required to display at least one functional aspect of the reference amino acid sequence or of the amino acid sequence encoded by the referenced nucleic acid. In other embodiments, a nucleic acid sequence or amino acid sequence with less than 100% identity to a referenced nucleic acid or amino acid sequence, respectively, is also required to display at least one functional aspect of the reference amino acid sequence or of the amino acid sequence encoded by the referenced nucleic acid, but that functional characteristic can be slightly altered, e.g., confer an increased affinity to a specified antigen relative to that of the reference.
H: Use of Multispecific Ligands According to the Second Configuration of the Invention Multispecific ligands according to the method of the second configuration of the present invention may be employed in in vivo therapeutic and prophylactic applications, in vitro and in vivo diagnostic applications, in vitro assay and reagent applications, and the like. For example antibody molecules may be used in antibody based assay techniques, such as ELISA techniques, according to methods known to those skilled in the art.

As alluded to above, the multispecific ligands according to the invention are of use in diagnostic, prophylactic and therapeutic procedures. Multispecific antibodies according to the invention are of use diagnostically in Western analysis and in situ protein detection by standard immunohistochemical procedures; for use in these applications, the ligands may be labelled in accordance with techniques known to the art. In addition, such antibody polypeptides may be used preparatively in affinity chromatography procedures, when complexed to a chromatographic support, such as a resin. All such techniques are well known to one of skill in the art.

Diagnostic uses of the closed conformation multispecific ligands according to the invention include homogenous assays for analytes which exploit the ability of closed conformation multispecific ligands to bind two targets in competition, such that two targets cannot bind simultaneously (a closed conformation), or alternatively their ability to bind two targets simultaneously (an open conformation).

A true homogenous immunoassay format has been avidly sought by manufacturers of diagnostics and research assay systems used in drug discovery and development. The main diagnostics markets include human testing in hospitals, doctor's offices and clinics, commercial reference laboratories, blood banks, and the home, non-human diagnostics (for example food testing, water testing, environmental testing, bio-defence, and veterinary testing), and finally research (including drug development; basic research and academic research).

At present all these markets utilise immunoassay systems that are built around chemiluminescent, ELISA, fluorescence or in rare cases radio-immunoassay technologies. Each of these assay formats requires a separation step (separating bound from un-bound reagents). In some cases, several separation steps are required. Adding these additional steps adds reagents and automation, takes time, and affects the ultimate outcome of the assays. In human diagnostics, the separation step may be automated, which masks the problem, but does not remove it. The robotics, additional reagents, additional incubation times, and the like add considerable cost and complexity. In drug development, such as high throughput screening, where literally millions of samples are tested at once, with very low levels of test molecule, adding additional separation steps can eliminate the ability to perform a screen. However, avoiding the separation creates too much noise in the read out. Thus, there is a need for a true homogenous format that provides sensitivities at the range obtainable from present assay formats. Advantageously, an assay possesses fully quantitative read-outs with high sensitivity and a large dynamic range. Sensitivity is an important requirement, as is reducing the amount of sample required. Both of these features are features that a homogenous system offers. This is very important in point of care testing, and in drug development where samples are precious. Heterogenous systems, as currently available in the art, require large quantities of sample and expensive reagents Applications for homogenous assays include cancer testing, where the biggest assay is that for Prostate Specific Antigen, used in screening men for prostate cancer. Other applications include fertility testing, which provides a series of tests for women attempting to conceive including beta-hcg for pregnancy. Tests for infectious diseases, including hepatitis, HIV, rubella, and other viruses and microorganisms and sexually transmitted diseases. Tests are used by blood banks, especially tests for HIV, hepatitis A, B, C, non A non B. Therapeutic drug monitoring tests include monitoring levels of prescribed drugs in patients for efficacy and to avoid toxicity, for example digoxin for arrhythmia, and phenobarbital levels in psychotic cases; theophylline for asthma. Diagnostic tests are moreover useful in abused drug testing, such as testing for cocaine, marijuana and the like. Metabolic tests are used for measuring thyroid function, anaemia and other physiological disorders and functions.

The homogenous immunoassay format is moreover useful in the manufacture of standard clinical chemistry assays. The inclusion of immunoassays and chemistry assays on the same instrument is highly advantageous in diagnostic testing. Suitable chemical assays include tests for glucose, cholesterol, potassium, and the like.

A further major application for homogenous immunoassays is drug discovery and development: high throughput screening includes testing combinatorial chemistry libraries versus targets in ultra high volume. Signal is detected, and positive groups then split into smaller groups, and eventually tested in cells and then animals. Homogenous assays may be used in all these types of test. In drug development, especially animal studies and clinical trials heavy use of immunoassays is made. Homogenous assays greatly accelerate and simplify these procedures. Other Applications include food and beverage testing: testing meat and other foods for *E. coli, salmonella*, etc; water testing, including testing at water plants for all types of contaminants including *E. coli*; and veterinary testing.

In a broad embodiment, the invention provides a binding assay comprising a detectable agent which is bound to a closed conformation multispecific ligand according to the invention, and whose detectable properties are altered by the binding of an analyte to said closed conformation multispecific ligand. Such an assay may be configured in several different ways, each exploiting the above properties of closed conformation multispecific ligands.

The assay relies on the direct or indirect displacement of an agent by the analyte, resulting in a change in the detectable properties of the agent. For example, where the agent is an enzyme which is capable of catalysing a reaction which has a detectable end-point, said enzyme can be bound by the ligand such as to obstruct its active site, thereby inactivating the enzyme. The analyte, which is also bound by the closed conformation multispecific ligand, displaces the enzyme, rendering it active through freeing of the active site. The enzyme is then able to react with a substrate, to give rise to a detectable event. In an alternative embodiment, the ligand may bind the enzyme outside of the active site, influencing the conformation of the enzyme and thus altering its activity. For example, the structure of the active site may be constrained by the binding of the ligand, or the binding of cofactors necessary for activity may be prevented.

The physical implementation of the assay may take any form known in the art. For example, the closed conformation multispecific ligand/enzyme complex may be provided on a test strip; the substrate may be provided in a different region of the test strip, and a solvent containing the analyte allowed to migrate through the ligand/enzyme complex, displacing the enzyme, and carrying it to the substrate region to produce a signal. Alternatively, the ligand/enzyme complex may be provided on a test stick or other solid phase, and dipped into an analyte/substrate solution, releasing enzyme into the solution in response to the presence of analyte.

Since each molecule of analyte potentially releases one enzyme molecule, the assay is quantitative, with the strength of the signal generated in a given time being dependent on the concentration of analyte in the solution.

Further configurations using the analyte in a closed conformation are possible. For example, the closed conformation multispecific ligand may be configured to bind an enzyme in an allosteric site, thereby activating the enzyme. In such an embodiment, the enzyme is active in the absence of analyte. Addition of the analyte displaces the enzyme and removes allosteric activation, thus inactivating the enzyme.

In the context of the above embodiments which employ enzyme activity as a measure of the analyte concentration, activation or inactivation of the enzyme refers to an increase or decrease in the activity of the enzyme, measured as the ability of the enzyme to catalyse a signal-generating reaction. For example, the enzyme may catalyse the conversion of an undetectable substrate to a detectable form thereof. For example, horseradish peroxidase is widely used in the art together with chromogenic or chemiluminescent substrates, which are available commercially. The level of increase or decrease of the activity of the enzyme may between 10% and 100%, such as 20%, 30%, 40%, 50%, 60%, 70%, 80% or 90%; in the case of an increase in activity, the increase may be more than 100%, i.e. 200%, 300%, 500% or more, or may not be measurable as a percentage if the baseline activity of the inhibited enzyme is undetectable.

In a further configuration, the closed conformation multispecific ligand may bind the substrate of an enzyme/substrate pair, rather than the enzyme. The substrate is therefore unavailable to the enzyme until released from the closed conformation multispecific ligand through binding of the analyte. The implementations for this configuration are as for the configurations which bind enzyme.

Moreover, the assay may be configured to bind a fluorescent molecule, such as a fluorescein or another fluorophore, in a conformation such that the fluorescence is quenched on binding to the ligand. In this case, binding of the analyte to the ligand will displace the fluorescent molecule, thus producing a signal. Alternatives to fluorescent molecules which are useful in the present invention include luminescent agents, such as luciferin/luciferase, and chromogenic agents, including agents commonly used in immunoassays such as HRP.

Therapeutic and prophylactic uses of multispecific ligands prepared according to the invention involve the administration of ligands according to the invention to a recipient mammal, such as a human. Multi-specificity can allow antibodies to bind to multimeric antigen with great avidity. Multispecific ligands can allow the cross-linking of two antigens, for example in recruiting cytotoxic T-cells to mediate the killing of tumour cell lines.

Substantially pure ligands or binding proteins thereof, for example dAb monomers, of at least 90 to 95% homogeneity are preferred for administration to a mammal, and 98 to 99% or more homogeneity is most preferred for pharmaceutical uses, especially when the mammal is a human. Once purified, partially or to homogeneity as desired, the ligands may be used diagnostically or therapeutically (including extracorporeally) or in developing and performing assay procedures, immunofluorescent stainings and the like (Lefkovite and Pernis, (1979 and 1981) Immunological Methods, Volumes I and II, Academic Press, NY).

The ligands or binding proteins thereof, for example dAb monomers, of the present invention will typically find use in preventing, suppressing or treating inflammatory states, allergic hypersensitivity, cancer, bacterial or viral infection, and autoimmune disorders (which include, but are preferably not limited to, Type I diabetes, asthma, multiple sclerosis, rheumatoid arthritis, systemic lupus erythematosus, Crohn's disease and myasthenia gravis).

In the instant application, the term "prevention" involves administration of the protective composition prior to the induction of the disease. "Suppression" refers to administration of the composition after an inductive event, but prior to the clinical appearance of the disease. "Treatment" involves administration of the protective composition after disease symptoms become manifest.

Animal model systems which can be used to screen the effectiveness of the antibodies or binding proteins thereof in protecting against or treating the disease are available. Methods for the testing of systemic lupus erythematosus (SLE) in susceptible mice are known in the art (Knight et al. (1978) *J. Exp. Med.*, 147: 1653; Reinersten et al. (1978) *New Eng. J. Med.*, 299: 515). Myasthenia Gravis (MG) is tested in SJL/J female mice by inducing the disease with soluble AchR protein from another species (Lindstrom et al. (1988) *Adv. Immunol.*, 42: 233). Arthritis is induced in a susceptible strain of mice by injection of Type II collagen (Stuart et al. (1984) *Ann. Rev. Immunol.*, 42: 233). A model by which adjuvant arthritis is induced in susceptible rats by injection of mycobacterial heat shock protein has been described (Van Eden et al. (1988) *Nature,* 331: 171). Thyroiditis is induced in mice by administration of thyroglobulin as described (Maron et al. (1980) *J. Exp. Med.,* 152: 1115). Insulin dependent diabetes mellitus (IDDM) occurs naturally or can be induced in certain strains of mice such as those described by Kanasawa et al. (1984) *Diabetologia,* 27: 113. EAE in mouse and rat serves as a model for MS in human. In this model, the demyelinating disease is induced by administration of myelin basic protein (see Paterson (1986) *Textbook of Immunopathology,* Mischer et al., eds., Grune and Stratton, New York, pp. 179-213; McFarlin et al. (1973) *Science,* 179: 478: and Satoh et al. (1987) *J. Immunol.,* 138: 179).

A ligand comprising a single variable domain, or composition thereof, which specifically binds vWF, e.g., human vWF, a vWF A1 domain, the A1 domain of activated vWF, or the vWF A3 domain, may further comprise a thrombolytic agent. This thrombolytic agent may be non-covalently or covalently attached to a single variable domain, in particular to an antibody single variable domain, via covalent or non-covalent means as known to one of skill in the art. Non-covalent means include via a protein interaction such as biotin/strepavidin, or via an immunoconjugate. Alternatively, the thrombolytic agent may be administered simultaneously, separately or sequentially with respect to a ligand that consists of or comprises a single variable domain that binds vWF or a vWF domain as described above, or a composition thereof. Thrombolytic agents according to the invention may include, for example, staphylokinase, tissue plasminogen activator, streptokinase, single chain streptokinase, urokinase and acyl plasminogen streptokinase complex.

Also described herein are invasive medical devices coated with a single variable domain, or a ligand comprising a single variable domain, or a composition thereof, or a single varable domain resulting from a screening method described herein. Non-limiting examples of devices include surgical tubing, occlusion devices, prosthetic devices. Application for said devices include surgical procedures which require a modulation of platelet-mediated aggregation around the site of invasion (e.g. a device coated with a single variable domain which specifically binds vWF) or a modulation of inflammation (e.g. a device coated with a single variable domain which specifically binds TNF alpha).

Generally, the present ligands will be utilised in purified form together with pharmacologically appropriate carriers. Typically, these carriers include aqueous or alcoholic/aqueous solutions, emulsions or suspensions, any including saline and/or buffered media. Parenteral vehicles include sodium chloride solution, Ringer's dextrose, dextrose and sodium chloride and lactated Ringer's. Suitable physiologically-acceptable adjuvants, if necessary to keep a polypeptide complex in suspension, may be chosen from thickeners such as carboxymethylcellulose, polyvinylpyrrolidone, gelatin and alginates. Intravenous vehicles include fluid and nutrient replenishers and electrolyte replenishers, such as those based on Ringer's dextrose. Preservatives and other additives, such as antimicrobials, antioxidants, chelating agents and inert gases, may also be present (Mack (1982) *Remington's Pharmaceutical Sciences,* 16th Edition).

The ligands of the present invention may be used as separately administered compositions or in conjunction with other agents. These can include various immunotherapeutic drugs, such as cylcosporine, methotrexate, adriamycin or cisplatinum, and immunotoxins. Pharmaceutical compositions can include "cocktails" of various cytotoxic or other agents in conjunction with the ligands of the present invention, or even combinations of ligands according to the present invention having different specificities, such as ligands selected using different target antigens or epitopes, whether or not they are pooled prior to administration.

The route of administration of pharmaceutical compositions according to the invention may be any of those commonly known to those of ordinary skill in the art. For therapy, including without limitation immunotherapy, the selected ligands thereof of the invention can be administered to any patient in accordance with standard techniques. The administration can be by any appropriate mode, including parenterally, intravenously, intramuscularly, intraperitoneally, transdermally, via the pulmonary route, or also, appropriately, by direct infusion with a catheter. The dosage and frequency of administration will depend on the age, sex and condition of the patient, concurrent administration of other drugs, counterindications and other parameters to be taken into account by the clinician.

The ligands of this invention can be lyophilised for storage and reconstituted in a suitable carrier prior to use. This technique has been shown to be effective with conventional immunoglobulins and art-known lyophilisation and reconstitution techniques can be employed. It will be appreciated by those skilled in the art that lyophilisation and reconstitution can lead to varying degrees of antibody activity loss (e.g. with conventional immunoglobulins, IgM antibodies tend to have greater activity loss than IgG antibodies) and that use levels may have to be adjusted upward to compensate.

The compositions containing the present ligands or a cocktail thereof can be administered for prophylactic and/or therapeutic treatments. In certain therapeutic applications, an adequate amount to accomplish at least partial inhibition, suppression, modulation, killing, or some other measurable parameter, of a population of selected cells is defined as a "therapeutically-effective dose". Amounts needed to achieve this dosage will depend upon the severity of the disease and the general state of the patient's own immune system, but generally range from 0.005 to 5.0 mg of ligand, e.g. antibody, receptor (e.g. a T-cell receptor) or binding protein thereof per kilogram of body weight, with doses of 0.05 to 2.0 mg/kg/dose being more commonly used. For prophylactic applications, compositions containing the present ligands or cocktails thereof may also be administered in similar or slightly lower dosages.

Treatment performed using the compositions described herein is considered "effective" if one or more symptoms is reduced (e.g., by at least 10% or at least one point on a clinical assessment scale), relative to such symptoms present before treatment, or relative to such symptoms in an individual (human or model animal) not treated with such composition. Symptoms will obviously vary depending upon the disease or disorder targeted, but can be measured by an ordinarily skilled clinician or technician. Such symptoms can be measured, for example, by monitoring the level of one or more biochemical indicators of the disease or disorder (e.g., levels of an enzyme or metabolite correlated with the disease, affected cell numbers, etc.), by monitoring physical manifestations (e.g., inflammation, tumor size, etc.), or by an accepted clinical assessment scale, for example, the Expanded Disability Status Scale (for multiple sclerosis), the Irvine Inflammatory Bowel Disease Questionnaire (32 point assessment evaluates quality of life with respect to bowel function, systemic symptoms, social function and emotional status—score ranges from 32 to 224, with higher scores indicating a better quality of life), the Quality of Life Rheumatoid Arthritis Scale, or other accepted clinical assessment scale as known in the field. A sustained (e.g., one day or more, preferably longer) reduction in disease or disorder symptoms by at least 10% or by one or more points on a given clinical scale is indicative of "effective" treatment. Similarly, prophylaxis performed using a composition as described herein is "effective" if the onset or severity of one or more symptoms is delayed, reduced or abolished relative to such symptoms in a similar individual (human or animal model) not treated with the composition.

A composition containing a ligand or cocktail thereof according to the present invention may be utilised in prophylactic and therapeutic settings to aid in the alteration, inactivation, killing or removal of a select target cell population in a mammal. In addition, the selected repertoires of polypeptides described herein may be used extracorporeally or in vitro selectively to kill, deplete or otherwise effectively remove a target cell population from a heterogeneous collection of cells. Blood from a mammal may be combined extracorporeally with the ligands, e.g. antibodies, cell-surface receptors or binding proteins thereof whereby the undesired cells are killed or otherwise removed from the blood for return to the mammal in accordance with standard techniques.

I: Use of Half-Life Enhanced Dual-Specific Ligands According to the Invention

Dual-specific ligands according to the method of the present invention, as well a ligands comprising one or more single variable domains as defined herein, may be employed in in vivo therapeutic and prophylactic applications, in vivo diagnostic applications and the like.

Therapeutic and prophylactic uses of dual-specific ligands prepared according to the invention, as well a ligands comprising one or more single variable domains as defined herein, involve the administration of ligands according to the invention to a recipient mammal, such as a human. Dual specific antibodies according to the invention as well a ligands comprising one or more single variable domains as defined herein, comprise at least one specificity for a half-life enhancing molecule; one or more further specificities may be directed against target molecules. For example, a dual-specific IgG may be specific for four epitopes, one of which is on a half-life enhancing molecule. Dual-specificity as well as tri-specificity as well as high valencies, can allow ligands comprising at least one single variable domain, to bind to multimeric antigen with great avidity. Dual-specific antibodies can allow the cross-linking of two antigens, for example in recruiting cytotoxic T-cells to mediate the killing of tumour cell lines.

Substantially pure dual-specific ligands according to the method of the present invention, as well a ligands comprising one or more single variable domains as defined herein, or binding proteins thereof, such as single variable domain monomers (i.e. dAb monomers), of at least 90 to 95% homogeneity are preferred for administration to a mammal, and 98 to 99% or more homogeneity is most preferred for pharmaceutical uses, especially when the mammal is a human. Once purified, partially or to homogeneity as desired, the ligands may be used diagnostically or therapeutically (including extracorporeally) or in developing and performing assay procedures, immunofluorescent stainings and the like (Lefkovite and Pernis, (1979 and 1981) Immunological Methods, Volumes I and II, Academic Press, NY).

Dual-specific ligands according to the method of the present invention, as well a ligands comprising one or more single variable domains as defined herein, will typically find use in preventing, suppressing or treating inflammatory states, allergic hypersensitivity, cancer, bacterial or viral infection, and autoimmune disorders (which include, but are preferably not limited to, Type I diabetes, multiple sclerosis, rheumatoid arthritis, systemic lupus erythematosus, Crohn's disease and myasthenia gravis).

In the instant application, the term "prevention" involves administration of the protective composition prior to the induction of the disease. "Suppression" refers to administration of the composition after an inductive event, but prior to the clinical appearance of the disease. "Treatment" involves administration of the protective composition after disease symptoms become manifest.

Animal model systems which can be used to screen the effectiveness of the dual specific ligands in protecting against or treating the disease are available. Methods for the testing of systemic lupus erythematosus (SLE) in susceptible mice are known in the art (Knight et al. (1978) *J. Exp. Med.*, 147: 1653; Reinersten et al. (1978) *New Eng. J. Med.*, 299: 515). Myasthenia Gravis (MG) is tested in SJL/J female mice by inducing the disease with soluble AchR protein from another species (Lindstrom et al. (1988) *Adv. Immunol.*, 42: 233). Arthritis is induced in a susceptible strain of mice by injection of Type II collagen (Stuart et al. (1984) *Ann. Rev. Immunol.*, 42: 233). A model by which adjuvant arthritis is induced in susceptible rats by injection of mycobacterial heat shock protein has been described (Van Eden et al. (1988) *Nature*, 331: 171). Thyroiditis is induced in mice by administration of thyroglobulin as described (Maron et al. (1980) *J. Exp. Med.*, 152: 1115). Insulin dependent diabetes mellitus (IDDM) occurs naturally or can be induced in certain strains of mice such as those described by Kanasawa et al. (1984) *Diabetologia*, 27: 113. EAE in mouse and rat serves as a model for MS in human. In this model, the demyelinating disease is induced by administration of myelin basic protein (see Paterson (1986) *Textbook of Immunopathology*, Mischer et al., eds., Grune and Stratton, New York, pp. 179-213; McFarlin et al. (1973) Science, 179: 478: and Satoh et al. (1987) *J. Immunol.*, 138: 179).

Dual specific ligands according to the invention and dAb monomers able to bind to extracellular targets involved in endocytosis (e.g. Clathrin) enable dual specific ligands to be endocytosed, enabling another specificity able to bind to an intracellular target to be delivered to an intracellular environment. This strategy requires a dual specific ligand with physical properties that enable it to remain functional inside the cell. Alternatively, if the final destination intracellular compartment is oxidising, a well folding ligand may not need to be disulphide free.

Generally, the present dual specific ligands will be utilised in purified form together with pharmacologically appropriate carriers. Typically, these carriers include aqueous or alcoholic/aqueous solutions, emulsions or suspensions, any including saline and/or buffered media. Parenteral vehicles include sodium chloride solution, Ringer's dextrose, dextrose and sodium chloride and lactated Ringer's. Suitable physiologically-acceptable adjuvants, if necessary to keep a polypeptide complex in suspension, may be chosen from thickeners such as carboxymethylcellulose, polyvinylpyrrolidone, gelatin and alginates.

Intravenous vehicles include fluid and nutrient replenishers and electrolyte replenishers, such as those based on Ringer's dextrose. Preservatives and other additives, such as antimicrobials, antioxidants, chelating agents and inert gases, may also be present (Mack (1982) *Remington's Pharmaceutical Sciences*, 16th Edition).

The ligands of the present invention may be used as separately administered compositions or in conjunction with other agents. These can include various immunotherapeutic drugs, such as cylcosporine, methotrexate, adriamycin or cisplatinum, and immunotoxins. Pharmaceutical compositions can include "cocktails" of various cytotoxic or other agents in conjunction with the ligands of the present invention.

The route of administration of pharmaceutical compositions according to the invention may be any of those commonly known to those of ordinary skill in the art. For therapy, including without limitation immunotherapy, the ligands of the invention can be administered to any patient in accordance with standard techniques. The administration can be by any appropriate mode, including parenterally, intravenously, intramuscularly, intraperitoneally, transdermally, via the pulmonary route, or also, appropriately, by direct infusion with a catheter. The dosage and frequency of administration will depend on the age, sex and condition of the patient, concurrent administration of other drugs, counterindications and other parameters to be taken into account by the clinician.

The ligands of the invention can be lyophilised for storage and reconstituted in a suitable carrier prior to use. This technique has been shown to be effective with conventional immunoglobulins and art-known lyophilisation and reconstitution techniques can be employed. It will be appreciated by those skilled in the art that lyophilisation and reconstitution can lead to varying degrees of antibody activity loss (e.g. with conventional immunoglobulins, IgM antibodies tend to have greater activity loss than IgG antibodies) and that use levels may have to be adjusted upward to compensate.

The compositions containing the present ligands or a cocktail thereof can be administered for prophylactic and/or therapeutic treatments. In certain therapeutic applications, an adequate amount to accomplish at least partial inhibition, suppression, modulation, killing, or some other measurable parameter, of a population of selected cells is defined as a "therapeutically-effective dose". Amounts needed to achieve this dosage will depend upon the severity of the disease and the general state of the patient's own immune system, but generally range from 0.005 to 5.0 mg of ligand per kilogram of body weight, with doses of 0.05 to 2.0 mg/kg/dose being more commonly used. For prophylactic applications, compositions containing the present ligands or cocktails thereof may also be administered in similar or slightly lower dosages.

A composition containing a ligand according to the present invention may be utilised in prophylactic and therapeutic settings to aid in the alteration, inactivation, killing or removal of a select target cell population in a mammal.

In addition, the selected repertoires of polypeptides described herein may be used extracorporeally or in vitro selectively to kill, deplete or otherwise effectively remove a target cell population from a heterogeneous collection of cells. Blood from a mammal may be combined extracorporeally with the ligands, e.g., antibodies, cell surface receptors or binding proteins thereof, whereby the undesired cells are killed or otherwise removed from the blood for return to the mammal in accordance with standard techniques.

Selection and characterization of ligands comprising a single variable domain for binding to serum albumin from a range of species A ligand can comprise one or more single variable domains, e.g., immunoglobulin single variable domains and/or non-immunoglobulin single variable domains, where at least one of the single variable domains specifically binds to serum albumin from human, as well as from non-human species. In one embodiment, the single variable domain specifically binds only serum albumin which is endogenous to a human. In another embodiment, the single variable domain specifically binds serum albumin from a non-human species. Alternatively, the single variable domain specifically binds both serum albumin which is endogenous to a human, as well as serum albumin which is endogenous to one or more non human species. As a nonlimiting example, such a single variable domain can specifically bind serum albumin endogenous to both human and cynomolgus, or serum albumin endogenous to both human and rat, or serum albumin from both human and mouse, or serum albumin from both human and pig. Alternatively, the single variable domain specifically binds to two or more serum albumin from two or more non-human species. As used herein, serum albumin can be expressed by a gene endogenous to a species, i.e. natural serum albumin, and/or by a recombinant equivalent thereof. In one embodiment, the serum albumin includes fragments, analogs and derivatives of natural and recombinant serum albumin. Such fragments of serum albumin include fragments containing domain I, domain II, and/or domain III, or combinations of one or two or more of each of domains I, II and III of serum albumin, preferably human serum albumin. Domain II of serum albumin is preferred as a target for the single variable domain as defined herein. Other preferred combinations are Domain I and Domain II; Domain I and Domain III; Domain II and Domain III; and Domain I alone; Domain II alone; and Domain III alone; and Domain I and Domain II and Domain III. In one embodiment, the serum albumin is recombinant serum albumin exogenously expressed in a non-human host, such as an animal host, or a unicellular host such as yeast or bacteria.

The species from which the serum albumin is endogenous includes any species which expresses endogenous serum albumin, including, but preferably not limited to, the species of human, mouse, murine, rat, cynomolgus, porcine, dog, cat, horse, goat, and hamster. In some instances serum albumin endogenous to camel or lama are excluded.

The single variable domain can be an immunoglobulin single variable domain, including but preferably not limited to an antibody heavy chain single variable domain, an antibody VHH heavy chain single variable domain, a human antibody heavy chain single variable domain, a human VH3 heavy chain single variable domain, an antibody light chain single variable domain, a human antibody light chain single variable domain, a human antibody kappa light chain single variable domain, and/or a human lambda light chain single variable domain.

The single variable domain which specifically binds to serum albumin can be a single variable domain comprising an immunoglobulin scaffold or a non-immunoglobulin scaffold. The serum albumin binding, single variable domain can comprise one or two or three of CDR1, CDR2 and CDR3 from an antibody variable domain, preferably from a single variable domain, where the CDR region(s) is provided on a non-immunoglobulin scaffold, such as CTLA-4, lipocallin, staphylococcal protein A (SPA), GroEL and fibronectin, transferrin (commercially available from Biorexis), an Avimer™ and an Affibody™ scaffold. Alternatively, the serum albumin binding, non-immunoglobulin single variable domain can contain neither an antibody CDR region(s) nor a complete binding domain from an antibody. Alternatively, the serum albumin binding, single variable domain(s), can be single variable domains which comprise one or two or three of any of CDR1, CDR2 and CDR3 from an antibody variable domain, preferably a single variable domain; these CDR regions can be provided on a heavy or a light chain antibody framework region. Frameworks include, for example, $V_H$ frameworks, such as VH3 (including DP47, DP38 and DP45) and VHH frameworks described supra, as well as VL frameworks, including Vkappa (such as DPK9), and Vlambda frameworks. In some embodiments, the variable domain comprises at least one human framework region having an amino acid sequence encoded by a human germ line antibody gene segment, or an amino acid sequence comprising up to 5 amino acid differences relative to the amino acid sequence encoded by a human germ line antibody gene segment. In other embodiments, the variable domain comprises four human framework regions, FW1, FW2, FW2 and FW4, having amino acid sequences encoded by a human germ line antibody gene segment, or the amino acid sequences of FW1, FW2, FW3 and FW4 collectively containing up to 10 amino acid differences relative to the amino acid sequences encoded by the human germ line antibody gene segment. In one embodiment, all three CDR regions are provided on either an immunoglobulin scaffold (e.g., heavy chain or light chain antibody scaffold) or a non-immunoglobulin scaffold as defined herein, either of which can be non-human, synthetic, semi-synthetic. Alternatively, any combination of one, two or all three of CDR1, CDR2 and/or CDR3 regions are provided on either the immunoglobulin scaffold or the non-immunoglobulin scaffold, for example, either the CDR3 region alone, or the CDR2 and CDR3 regions together, or the CDR1 and CDR2 are provided on either the immunoglobulin scaffold or the non-immunoglobulin scaffold. Suitable scaffolds and techniques for such CDR grafting will be clear to the skilled person and are well known in the art, see for example U.S. application Ser. No. 07/180,370, WO 01/27160, EP 0 605 522, EP 0 460 167, U.S. application Ser. No. 07/054,297, Nicaise et al., Protein Science (2004), 13:1882-1891; Ewert et al., Methods, 2004 October; 34(2):184-199; Kettleborough et al., Protein Eng. 1991 October; 4(7): 773-783; O'Brien and Jones, Methods Mol. Biol. 2003: 207: 81-100; and Skerra, J. Mol. Recognit. 2000:13:167-187, and Saerens et al., J. Mol. Biol. 2005 Sep. 23; 352(3):597-607, and the further references cited therein.

The ligands can comprise one or more of such single variable domains which specifically bind serum albumin, preferably comprising at least one single variable domain which specifically binds both serum albumin which is endogenous to humans and at least one additional serum albumin which is endogenous to a non-human species. In one embodiment, this single variable domain specifically binds to serum albumin which is endogenous to human with a Kd value which is within 10 fold of the Kd value with which it specifically binds (i.e. cross reacts with) to at least one serum albumin which is endogenous to a non-human species. Alternatively this single variable domain specifically binds to serum albumin which is endogenous to human with a Kd value which is within 15, 20, 25, 30, 50 or up to approximately 100 fold of the Kd value with which it specifically binds (i.e. cross reacts with) to at least one serum albumin which is endogenous to a non-human species. In some embodiments the Kd can range from 300 nM to about 5 pM. In other embodiments, the single variable domain specifically binds to serum albumin with a $K_{off}$ of at least $5\times10^{-1}$, $S^{-1}$, $5\times10^{-2}$ $S^{-1}$, $5\times10^{-3}$ $S^{-1}$, $5\times10^{-4}$ $S^{-1}$, $5\times10^{-5}$ $S^{-1}$, $5\times10^{-6}$ $S^{-1}$, $5\times10^{-7}$ $S^{-1}$, $5\times10^{-8}$ $S^{-1}$, $5\times10^{-9}$ $S^{-1}$, $5\times10^{-10}$ $S^{-1}$, or less, preferably with a $K_{off}$ ranging from $1\times10^{-6}$ $S^{-1}$ to $1\times10^{-8}$ $S^{-1}$.

In one embodiment, this single variable domain specifically binds to serum albumin which is endogenous to a first non-human species with a Kd value which is within 10 fold of the Kd value with which it specifically binds to (i.e. cross reacts to) at least one serum albumin which is endogenous to a second non-human species. Alternatively, this single variable domain specifically binds to serum albumin which is endogenous to the first non-human species with a Kd value which is within 15, 20, 25, 30, 50 or up to approximately 100 fold of the Kd value with which it specifically binds to (i.e. cross reacts to) at least one serum albumin which is endogenous to the second non-human species. In some embodiments, the Kd can range from 300 nM to about 5 pM. In other embodiments, the single variable domain specifically binds to serum albumin with a $K_{off}$ of at least $5\times10^{-1}$, $S^{-1}$, $5\times10^{-2}$ $S^{-1}$, $5\times10^{-3}$ $S^{-1}$, $5\times10^{-4}$ $S^{-1}$, $5\times10^{-5}$ $S^{-1}$, $5\times10^{-6}$ $S^{-1}$, $5\times10^{-7}$ $S^{-1}$, $5\times10^{-8}$ $S^{-1}$, $5\times10^{-9}$ $S^{-1}$, $5\times10^{-10}$ $S^{-1}$, or less, preferably with a $K_{off}$ ranging from $1\times10^{-6}$ $S^{-1}$ to $1\times10^{-8}$ $S^{-1}$.

For example, such a ligand can include an immunoglobulin single variable domain, where the immunoglobulin single variable domain specifically binds to human serum albumin and mouse serum albumin, and where the T beta half life of the ligand is substantially the same as the T beta half life of mouse serum albumin in a mouse host. In one version of such a ligand, the epitope binding domain contains a non-immunoglobulin scaffold which specifically binds to human serum albumin and mouse serum albumin, and wherein the T beta half life of the ligand is substantially the same as the T beta half life of mouse serum albumin in a mouse host. The phrase "substantially the same" means that the ligand has a T beta half life in a mouse host that is at least 50% that of mouse serum albumin in a mouse host, that is at least 55%, 60%, 65%, 70%, 75%, 80%, 85%, 90%, 92%, 94%, 95%, 96%, 97%, 98%, 99%, 100%, 101%, 102%, 105%, 110%, 125%, and up to 150% that of the T beta half life of mouse serum albumin in a mouse host. The non-immunoglobulin scaffold can optionally include fragments of an antibody single variable domain, such as one or more of the CDR regions of an antibody variable domain, including an antibody single variable domain that has a T beta half life in a human host that is at least 50%, 55%, 60%, 65%, 70%, 75%, 80%, 85%, 90%, 92%, 94%, 95%, 96%, 97%, 98%, 99%, 101%, 102%, 105%, 110%, 125%, or up to 150% that of the T beta half life of human serum albumin in a human host.

For example, one embodiment is a single variable domain, where the single variable domain specifically binds to human serum albumin and rat serum albumin, and where the T beta half life of the ligand is substantially the same as the T beta half life of rat serum albumin in a rat host. In one version of such a ligand, the single variable binding domain contains a non-immunoglobulin scaffold which specifically binds to human serum albumin and rat serum albumin, and wherein the T beta half life of the ligand is substantially the same as the T beta half life of rat serum albumin in a rat host. The phrase "substantially the same" means that the ligand has a T beta half life in a rat host that is at least 50% that of rat serum albumin in a rat host, that is up to 55%, 60%, 65%, 70%, 75%, 80%, 85%, 90%, 92%, 94%, 95%, 96%, 97%, 98%, 99%, 100%, 101%, 102%, 105%, 110%, 125%, up to 150% that of the T beta half life of rat serum albumin in a rat host. The non-immunoglobulin scaffold can optionally include fragments of an antibody single variable domain, such as one or more of the CDR regions of an antibody variable domain.

For example, a ligand can include an immunoglobulin single variable domain, where the immunoglobulin single variable domain specifically binds to human serum albumin and porcine serum albumin, and where the T beta half life of the ligand is substantially the same as the T beta half life of porcine serum albumin in a porcine host. In one version of a ligand, the epitope binding domain contains a non-immunoglobulin scaffold which specifically binds to human serum albumin and porcine serum albumin, and wherein the T beta half life of the ligand is substantially the same as the T beta half life of porcine serum albumin in a porcine host. The phrase "substantially the same" means that the ligand has a T beta half life in a porcine host that is at least 50% that of porcine serum to albumin in a porcine host, that is up to 55%, 60%, 65%, 70%, 75%, 80%, 85%, 90%, 92%, 94%, 95%, 96%, 97%, 98%, 99%, 100%, 101%, 102%, 105%, 110%, 125%, up to 150% that of the T beta half life of porcine serum albumin in a porcine host. The non-immunoglobulin scaffold can optionally include fragments of an antibody single variable domain, such as one or more of the CDR regions of an antibody variable domain, including an antibody single variable domain.

For example, a ligand can include an immunoglobulin single variable domain, where the immunoglobulin single variable domain specifically binds to human serum albumin and cynomolgus serum albumin, and where the T beta half life of the ligand is substantially the same as the T beta half life of cynomolgus serum albumin in a cynomolgus host. In one version of a ligand, the domain that binds serum albumin contains a non-immunoglobulin scaffold which specifically binds to human serum albumin and cynomolgus serum albumin, and wherein the T beta half life of the ligand is substantially the same as the T beta half life of cynomolgus serum albumin in a cynomolgus host. The phrase "substantially the same" means that the ligand has a T beta half life in a cynomolgus host that is at least 50% that of cynomolgus serum albumin in a cynomolgus host, that is up to 55%, 60%, 65%, 70%, 75%, 80%, 85%, 90%, 92%, 94%, 95%, 96%, 97%, 98%, 99%, 100%, 101%, 102%, 105%, 110%, 125%, or up to 150% that of the T beta half life of cynomolgus serum albumin in a cynomolgus host.

The non-immunoglobulin scaffold can optionally include fragments of an antibody single variable domain, such as one or more of the CDR regions of an antibody variable domain.

In one embodiment, a ligand and/or dual specific ligand contains a single variable domain which specifically binds to serum albumin that is endogenous to human, has a T beta half life in a human host that is at least 50% that of human serum albumin in a human host, up to 55%, 60%, 65%, 70%, 75%, 80%, 85%, 90%, 92%, 94%, 95%, 96%, 97%, 98%, 99%, 100%, 101%, 102%, 105%, 110%, 125% or up to 150% that of the T beta half life of human serum albumin in a human host. In a preferred embodiment, the single variable domain which specifically binds to serum albumin that is endogenous to a non-human, has a T beta half life in its respective non-human host that is at least 50% that of the non human serum albumin in its respective non-human host, up to 55%, 60%, 65%, 70%, 75%, 80%, 85%, 90%, 92%, 94%, 95%, 96%, 97%, 98%, 99%, 100%, 101%, 102%, 105%, 110%, 125%, or up to 150% that of the T beta half life of the non-human serum albumin in its respective non-human host. In a preferred embodiment, the single variable domain which specifically binds to serum albumin that is endogenous to human, and which also specifically binds specifically to serum albumin from at least one non-human species, has a T beta half life in a human host that is up to 55%, 60%, 65%, 70%, 75%, 80%, 85%, 90%, 92%, 94%, 95%, 96%, 97%, 98%, 99%, 101%, 102%, 105%, 110%, 125%, or up to 150% of human serum albumin in a human host, and a T beta half life in the non-human host that is up to 55%, 60%, 65%, 70%, 75%, 80%, 85%, 90%, 92%, 94%, 95%, 96%, 97%, 98%, 99%, 100%, 101%, 102%, 105%, 110%, 125%, or up to 150% of the non-human serum albumin in its respective non-human host. In some embodiments, the T beta half life of the single variable domain which specifically binds to serum albumin can range from as low as 2 hours up to and including 3 hours, 4 hours, 5 hours, 6 hours, 7 hours, 8 hours, 9 hours, 10 hours, 11 hours, 12 hours, 14 hours, 16 hours, 18 hours, 20 hours, 22 hours, 1 day, 2 days, 3 days, 4 days, 4 days, 6 days, 8 days, 10 days, 12 days, 14 days, 16 days, 18 days, up to as high as 21 days or more. In a human host, as well as a non-human host such as a porcine, cynomulgus, rat, murine, mouse host, the T beta half life of the single variable domain which specifically binds to serum albumin can range from as low as 2 hours up to and including 3 hours, 4 hours, 5 hours, 6 hours, 7 hours, 8 hours, 9 hours, 10 hours, 11 hours, 12 hours, 14 hours, 16 hours, 18 hours, 20 hours, 22 hours, 1 day, 2 days, 3 days, 4 days, 4 days, 6 days, 8 days, 10 days, 12 days, 14 days, 16 days, 18 days, up to as high as 21 days, or more. Other preferred T beta half lives of a ligand comprising a single variable domain which specifically binds to serum albumin include: in a monkey host from about 3 to about 5, 6, 7, or 8 days, including from as low as 2 hours, up to and including 3 hours, 4 hours, 5 hours, 6 hours, 7 hours, 8 hours, 9 hours, 10 hours, 11 hours, 12 hours, 14 hours, 16 hours, 18 hours, 20 hours, 22 hours, 1 day, 2 days, 3 days, 4 days, 4 days, 6 days, 8 days, 10 days, 12 days, 14 days, 16 days, 18 days, up to as high as 21 days. In a rat or mouse host, the T beta half life of the single variable domain which specifically binds to serum albumin can range from as low as 40 hours to as high as about 75 hours, and includes as low as 2 hours up to and including 3 hours, 4 hours, 5 hours, 6 hours, 7 hours, 8 hours, 9 hours, 10 hours, 11 hours, 12 hours, 14 hours, 16 hours, 18 hours, 20 hours, 22 hours, 1 day, 2 days, 3 days, 4 days, 4 days, 6 days, 8 days, 10 days, 12 days, 14 days, 16 days, 18 days, up to as high as 21 days.

The single variable domain which specifically binds to serum albumin includes Vkappa single variable domains, selected from, but preferably not limited to DOM7h-9 DOM7h-1, DOM7h-8, DOM7h-9, DOM7h-11, DOM7h-12, DOM7h-13 and DOM7h-14. DOM7r-3 and DOM7r-16, and/or those domains which compete for binding serum albumin, preferably human serum albumin, with the single variable domains selected from, but preferably not limited to, dAb7r20, dAb7r21, dAb7r22, dAb7r23, dAb7r24, dAb7r25, dAb7r26, dAb7r27, dAb7r28, dAb7r29, dAb7r30, dAb7r31, dAb7r32, dAb7r33, dAb7h21, dAb7h22, dAb7h23, Ab7h24, Ab7h25, Ab7h26, dAb7h27, dAb7h30 dAb7h31, dAb7m12, dAb7m16, dAb7m26, dAb7r1, dAb7r3, dAb7r4, dAb7r5, dAb7r7, dAb7r8, dAb7r13, dAb7r14, dAb7r15, dAb7r16, dAb7r17, dAb7r18, dAb7r19, dAb7h1, dAb7h2, dAb7h6, dAb7h7, dAb7h8, dAb7h9, dAb7h10, dAb7h11, dAb7h12, dAb7h13, dAb7h14, dAb7p1, and dAb7p2. The single variable domain which specifically binds to serum albumin can be an antibody heavy chain single variable domain, in particular, human $VH_3$, or VHH. An afore-mentioned single variable domain may also additionally specifically bind human serum albumin with a $K_{off}$ of at least $5\times10^{-1}$, $S^{-1}$, $5\times10^{-2}$ $S^{-1}$, $5\times10^{-3}$ $S^{-1}$, $5\times10^{-4}$ $S^{-1}$, $5\times10^{-5}$ $S^{-1}$, $5\times10^{-6}$ $S^{-1}$, $5\times10^{-7}$ $S^{-1}$, $5\times10^{-8}$ $S^{-1}$, $5\times10^{-9}$ $S^{-1}$, $5\times10^{-10}$ $S^{-1}$, or less, preferably with a $K_{off}$ ranging from $1\times10^{-6}$ $S^{-1}$ to $1\times10^{-8}$ $S^{-1}$. Single variable domains that specifically bind human serum albumin and a serum albumin that is endogenous to a non human species, can further bind a serum albumin that is endogenous to a third, fourth, fifth, sixth, seventh, eighth, ninth or tenth non human species. In one nonlimiting embodiment, the single variable domain which specifically binds to human serum albumin and rat serum albumin, further specifically binds to cynomolgus serum albumin. In another nonlimiting embodiment, the single variable domain which specifically binds to human serum albumin and mouse serum albumin, further specifically binds to cynomolgus serum albumin.

As described herein, a ligand which contains one single variable domain (monomer) or more than one single variable domains (multimer, fusion protein, conjugate, and dual specific ligand as defined herein) which specifically binds to serum albumin, can further comprise one or more entities selected from, but preferably not limited to a label, a tag, an additional single variable domain, a dAb, an antibody, and antibody fragment, a marker and a drug. One or more of these entities can be located at either the COOH terminus or at the N terminus or at both the N terminus and the COOH terminus of the ligand comprising the single variable domain, (either immunoglobulin or non-immunoglobulin single variable domain). One or more of these entities can be located at either the COOH terminus, or the N terminus, or both the N terminus and the COOH terminus of the single variable domain which specifically binds serum albumin of the ligand which contains one single variable domain (monomer) or more than one single variable domains (multimer, fusion protein, conjugate, and dual specific ligand as defined herein). Non-limiting examples of tags which can be positioned at one or both of these termini include a HA, his or a myc tag. The entities, including one or more tags, labels and drugs, can be bound to the ligand which contains one single variable domain (monomer) or more than one single variable domain (multimer, fusion protein, conjugate, and dual specific ligand as defined herein), which binds serum albumin, either directly or through linkers as described in a separate section below.

A ligand which contains one single variable domain (monomer) or more than one single variable domains (multimer, fusion protein, conjugate, and dual specific ligand as defined herein) which specifically binds to serum albumin, or which specifically binds both human serum albumin and at least one non-human serum albumin, can specifically bind to one or more of Domain I, and/or Domain II and/or domain III of human serum albumin, as described further below. In addition to containing one or more single variable domains, (for example, a serum albumin binding immunoglobulin single variable domain or a serum albumin binding non-immunoglobulin single variable domain) which specifically binds to a serum albumin, such as human serum albumin, or which specifically binds both human serum albumin and at least one non-human serum albumin, the ligand can contain one or more additional domains capable of specifically binding an antigen and/or epitope other than serum albumin, the antigen or epitope being selected from the group consisting of any animal protein, including cytokines, and/or antigens derived from microorganisms, pathogens, unicellular organisms, insects, viruses, algae and plants. These one or more additional domain(s) which bind a moiety other than serum albumin can be a non-immunoglobulin binding domain, a non-immunoglobulin single variable domain, and/or an immunoglobulin single variable domain.

In some embodiments, a dual specific ligand which contains one or more single variable domains (either an immunoglobulin single variable domain or a non-immunoglobulin single variable domain) which specifically binds to a serum albumin, such as human serum albumin, or which specifically binds both human serum albumin and at least one non-human serum albumin, can be composed of (a) the single variable domain that specifically binds serum albumin and a single variable domain that specifically binds a ligand other than serum albumin, both of the single variable domains being a heavy chain single variable domain; or (b) the single variable domain that specifically binds serum albumin and a single variable domain that specifically binds a ligand other than serum albumin, both of the single variable domains being a light chain single variable domain; or (c) the single variable domain that specifically binds serum albumin is a heavy chain single variable domain, and the single variable domain that specifically binds an antigen other than serum albumin is a light chain single variable domain; or (d) the single variable domain that specifically binds serum albumin is a light chain single variable domains, and the single variable domain that specifically binds an antigen other than serum albumin is a heavy chain single variable domain.

Also encompassed herein is an isolated nucleic acid encoding any of the ligands described herein, e.g., a ligand which contains one single variable domain (monomer) or more than one single variable domains (e.g., multimer, fusion protein, conjugate, and dual specific ligand as defined herein) which specifically binds to serum albumin, or which specifically binds both human serum albumin and at least one non-human serum albumin, or functionally active fragments thereof. Also encompassed herein is a vector and/or an expression vector thereof, a host cell comprising the vector, e.g., a plant or animal cell and/or cell line transformed with a vector, a method of expressing and/or producing one or more ligands which contains one single variable domain (monomer) or more than one single variable domains (e.g., multimer, fusion protein, conjugate, and dual specific ligand as defined herein) which specifically binds to serum albumin, or fragment(s) thereof encoded by said vectors, including in some instances culturing the host cell so that the one or more ligands or fragments thereof are expressed and optionally recovering the ligand which contains one single variable domain (monomer) or more than one single variable domains (e.g., multimer, fusion protein, conjugate, and dual specific ligand as defined herein) which specifically binds to serum albumin, from the host cell culture medium. Also encompassed are methods of contacting a ligand described herein with serum albumin, including serum albumin and/or non-human serum albumin(s), and/or one or more targets other than serum albumin, where the targets include biologically active molecules, and include animal proteins, cytokines as listed above, and include methods where the contacting is in vitro as well as administering any of the ligands described herein to an individual host animal or cell in vivo and/or ex vivo. Preferably, administering ligands described herein which comprises a single variable domain (immunoglobulin or non-immunoglobulin) directed to serum albumin and/or non-human serum albumin(s), and one or more domains directed to one or more targets other than serum albumin, will increase the half life, including the T beta half life, of the anti-target ligand. Nucleic acid molecules encoding the single domain containing ligands or fragments thereof, including functional fragments thereof, are described herein. Vectors encoding the nucleic acid molecules, including but preferably not limited to expression vectors, are described herein, as are host cells from a cell line or organism containing one or more of these expression vectors. Also described are methods of producing any the single domain containing ligands, including, but preferably not limited to any of the aforementioned nucleic acids, vectors and host cells.

Epitope Mapping of Serum Albumin

Serum albumins from mammalian species have a similar structure, containing three predominate domains with a similar folding and disulphide bonding pattern, as highlighted in FIG. 25. The protein is believed to have arisen from two tandem duplication events, and subsequent diversification of residues.

The structure of human serum albumin has been solved by X-ray crystallography, with/without a variety of bound ligands:

Atomic structure and chemistry of human serum albumin. He X M, Carter D C.

*Nature*. 1992; 358: 209-15. Erratum in: *Nature* 1993; 364: 362.

Atomic structure and chemistry of human serum albumin. He X M, Carter D C; *J Mol. Biol.* 2001; 314: 955-60.

Crystal structures of human serum albumin complexed with monounsaturated and polyunsaturated fatty acids. Petitpas I, Grune T, Bhattacharya A A, Curry S.; *J Biol. Chem.* 2001; 276: 22804-9.

Human serum albumin has been shown to be a heart shaped molecule. The individual domains, termed I, II and III, are predominantly helical, and are each composed of two subdomains, termed IA, IB, IIA, 2B, IIIA, and IIIB. They are linked by flexible, random coils.

Described herein is a ligand which contains one or more single variable domains which specifically binds to Domain II of human serum albumin. The single variable domain can be a VH antibody single variable domain. The single variable domain can be a VHH antibody single variable domain. The $V_H$ single variable domain can be a VH3 single variable domain. The VH3 single variable domain can be a human VH3 single variable domain. The ligand can alternatively, or additionally include a single variable domain which is a VKappa antibody single variable domain, including one of the following: DOM7h-1, DOM7h-8, DOM7h-9, DOM7h-11, DOM7h-12, DOM7h-13, DOM7h-14. DOM7r-3 and DOM7r-16, or a VKappa antibody single variable domain having domain having an amino acid sequence of about 80%, 85%, 90%, 91%, 92%, 93%, 94%, 95%, 96%, 97%, 98%, 99% or higher identity thereto.

The antibody single variable domain can include a set of four Kabat framework regions (FRs), which are encoded by antibody VH, preferably a VH3, framework germ line antibody gene segments. The VH3 framework is selected from the group consisting of DP47, DP38 and DP45. The antibody single variable domain can include a set of four Kabat framework regions (FRs) which are encoded by an antibody $V_L$ framework, preferably a VKappa framework, germline antibody gene segment. Preferably, the Kappa framework is DPK9.

The ligand which contains one or more single variable domains which specifically bind to Domain II of human serum albumin can further include one or more domains capable of specifically binding a moiety other than serum albumin, and can further comprise one or more entities including one or more of a label, a tag and a drug. The one or more domains capable of specifically binding a moiety other than serum albumin can be an immunoglobulin single variable domain. Also described herein is a ligand which contains one or more single variable domains which specifically binds to Domain II of human serum albumin, the domain including a non-immunoglobulin scaffold and CDR1, CDR2 and/or CDR3 regions, or where at least one of the CDR1, CDR2 and/or CDR3 regions is from a single variable domain of an antibody single variable domain that binds Domain II of human serum albumin. Non-immunoglobulin scaffolds include, but preferably are not limited to, CTLA-4, lipocallin, staphylococcal protein A (SPA), Affibody™, Avimers™, GroEL and fibronectin.

The ligand which contains one or more single variable domains which specifically binds to Domain II of human serum albumin includes those domains which specifically bind human serum albumin with a Kd of less than or equal to 300 nM. The ligand which contains one or more single variable domains which specifically binds to Domain II of human serum albumin can further comprise one or more entities including one or more of a label, a tag and a drug. The tag can include one or more of C-terminal HA or myc tags or N terminal HA or myc tags.

The ligand which contains one or more single variable domains which specifically binds to Domain II of human serum albumin, and which can further include one or more domains capable of specifically binding a moiety other than serum albumin, and which can optionally further comprise one or more entities including one or more of a label, a tag and a drug, can bind, through at least one of its single variable domains, an antigen including, but preferably not limited to a cytokine receptor, EPO receptor, ApoE, Apo-SAA, BDNF, Cardiotrophin-1, EGF, EGF receptor, ENA-78, Eotaxin, Eotaxin-2, Exodus-2, EpoR, FGF-acidic, FGF-basic, fibroblast growth factor-10, FLT3 ligand, Fractalkine (CX3C), GDNF, G-CSF, GM-CSF, GF-β1, insulin, IFN-γ, IGF-I, IGF-II, IL-1α, IL-1β, IL-2, IL-3, IL-4, IL-5, IL-6, IL-7, IL-8 (72 a.a.), IL-8 (77 a.a), IL-9, IL-10, IL-11, IL-12, IL-13, IL-15, IL-16, IL-17, IL-18 (IGIF), Inhibin α, Inhibin β, IP-10 keratinocyte growth factor-2 (KGF-2), KGF, Leptin, LiF, Lymphotactin, Mullerian inhibitory substance, monocyte colony inhibitory factor, monocyte attractant protein, M-CSF, MDC (67 a.a.), MDC (69 a.a.), MCP-1 (MCAF), MCP-2, MCP-3, MCP-4, MDC (67 a.a.), MDC (69 a.a), MIG, MLP-1α, MIP-3α, MIP-3β, MIP-4, myeloid progenitor inhibitor factor-1 (MPIF-1), NAP-2, Neurturin, Nerve growth factor, β-NGF, NT-3, NT-4, Oncostatin M, PDGF-AA, PDGF-AB, PDGF-BB, PF-4, RANTES, SDF1α, SDF1β, SCF, SCGF, stem cell factor (SCF), TARC, TGF-α, TGF-β, TGF-β2, TGF-β3, tumor necrosis factor (TNF), TNF-α, TNF-β, TNF receptor 1, TNF receptor II, TNIL-1, TPO, VEGF, VEGF receptor 1, VEGF receptor 2, VEGF receptor 3, GCP-2, GRO/MGSA, GRO-β, GRO-γ, HCC1, 1-309, HER 1, HER 2, HER3 and HER4, CD4, human chemokine receptors CXCR4 or CCR5, non-structural protein type 3 (NS3) from the hepatitis C virus, TNF-alpha, IgE, IFN-gamma, MMP-12, CEA, *H. pylori*, TB, influenza, Hepatitis E, MMP-12, internalising receptors that are over-expressed on certain cells, such as the epidermal growth factor receptor (EGFR), ErBb2 receptor on tumor cells, an internalising cellular receptor, LDL receptor, FGF2 receptor, ErbB2 receptor, transferrin receptor, PDGF receptor, VEGF receptor, PsmAr, an extracellular matrix protein, elastin, fibronectin, laminin, α1-antitrypsin, tissue factor protease inhibitor, PDK1, GSK1, Bad, caspase-9, Forkhead, an of an antigen of *Helicobacter pylori*, an antigen of *Mycobacterium tuberculosis*, and an antigen of influenza virus.

The ligand which contains one or more single variable domains which specifically binds to Domain II of human serum albumin, and which can further include one or more domains capable of specifically binding a moiety other than serum albumin, is minimally a dual specific ligand, which can have one of the following structures: (a) each said single variable domain that specifically binds to Domain II of serum albumin and said single variable domain that specifically binds a moiety other than serum albumin, is an antibody heavy chain single variable domain; or (b) each said single variable domain that specifically binds to Domain II of serum albumin and said single variable domain that specifically binds a moiety other than serum albumin, is an antibody light chain single variable domain; or (c) said single variable domain that specifically binds to Domain II of serum albumin is an antibody heavy chain single variable domain, and said single variable domain that specifically binds an antigen other than serum albumin is an antibody light chain single variable domain; or (d) said single variable domain that specifically binds to Domain II of serum albumin is an antibody light chain single variable domain, and said single variable domain that specifically binds an antigen other than serum albumin is an antibody heavy chain single variable domain. Nucleic acid molecules encoding any ligands or fragments thereof, including functional fragments thereof, described herein, vectors including but preferably not limited to expression vectors, and host cells of any type cell line or organism, containing one or more of these expression vectors is included, and/or are methods of producing any ligands, including, but preferably not limited to any the aforementioned nucleic acids, vectors and host cells.

Serum albumin has a long serum half-life compared with other serum proteins, together with a positive relationship between serum concentration and fractional catabolic rates (i.e. the higher the concentration of SA, the higher the amount degraded), a property that it shares with IgG. It has recently emerged that both IgG and serum albumin share a recycling mechanism, mediated by the neonatal Fc receptor FcRn. FcRn is a type I MHC family member, composed of a heterodimer of the membrane anchored FCRGT chain, and non-membrane-bound beta-2 microglobulin. Mouse knockout mutants of either FcRn or beta-2 microglobulin express no functional FcRn, and exhibit an increased biosynthesis rate of serum albumin (~20% increase), and an increased catabolism of serum albumin, leading to a 40% lower serum level of serum albumin, with a shorter half-life (Chaudhry et al 2005). In humans, mutations in beta-2 microglobulin have been shown give much reduced functional FcRn levels and ultimately to IgG deficiency and hypoalbuminaemia, characterised by a reduced serum half-life of HSA (Wani et al 2006, PNAS).

Though not wishing to be bound by theory, the proposed mechanism for FcRn-mediated salvage is as follows:
1. Plasma proteins are pinocytosed by cells of the endothelium lining all blood vessels, and perhaps pinocytotically active cells of the extravascular compartment. This is a non-specific step, and all proteins in circulation will be taken up. FcRn has a very low affinity for albumin (and IgGs) at serum pH, around pH 7.4.
2. Once pinocytosed, the vesicle formed acidifies to pH 5.0. Under acid conditions, FcRn has a higher affinity for albumin, and binds albumin, and also IgG. Albumin and IgG are thus bound to the FcRn receptor. FcRn binds human serum albumin at a site on Domain III, via a distinct site from that which binds IgG.
3. A sorting event occurs, by which the majority of non-receptor bound proteins are sorted into an endosome, where most proteins will be targeted for degradation. The receptor bound albumin and IgG are sorted into a vesicle targeted for the cell surface, and thus spared from degradation.
4. The cell surface targeted vesicle then either fuses with the cell surface, or briefly fuses with the cell membrane. Under these conditions, the pH of the endosome increases to approach pH 7.4, the FcRn affinity for albumin is reduced, and albumin is released back into the circulation.

We can therefore define a clear set of desirable parameters for any SA binding protein to have maximum half life. These parameters can be clearly exemplified using the serum albumin salvage receptor FcRn as a model, although will also apply to other receptors mediating a prolonged half life.

The affinity of the serum albumin binding will preferably be such that the SA binding protein does not dissociate from albumin while undergoing glomerular filtration in the kidney, thus minimising loss to the urine, and/or The binding to SA will preferably not have a detrimental effect on the binding of serum albumin to any receptors responsible for the maintenance of serum albumin levels in the circulation, as this would inhibit recycling, and hence reduce the half-life of both the serum albumin and the SA binder. Thus SA binding dAbs preferably bind a distinct epitope from that bound by FcRn on HSA domain III, and the SA/dAb complex preferably is also capable of engaging FcRn, and/or The binding to SA will preferably be maintained under the conditions under which the receptor and bound SA/SA binder complex are sorted or recycled. Endosomal pH has been shown to approach pH 5.0, therefore stable binding of the dAb to serum albumin at both pH7.4 and pH 5.0 is desirable.

As illustrated in Example 15 below, the majority of dAbs bind to the $2^{nd}$ domain of HSA and are therefore not expected to compete with binding of human serum albumin to FcRn. Two dAbs (DOM7h-27 and DOM7h-30) bind to Domain III.

An anti-SA DAb that retains sufficient affinity for SA in a pH range of 7.4 to 5.0.

In addition to affinity for SA, as well as in the absence of competition with the formation of SA:FcRn complexes, the serum-albumin-specific dAbs will preferably maintain affinity to SA within a pH range from pH 7.4 in the serum to pH 5.0 in the endosome to obtain full benefit of the FcRn-mediated salvage pathway.

In this pH range, only histidine residues and amino acid side-chains with perturbed pKa are likely to change their protonation state. If amino acid side-chains make a significant contribution to the binding energy of the complex, one could expect that a pH shift from one extreme to the other extreme in the range could result in lowering the binding affinity of the complex. Though not wishing to be bound by theory, this in turn would result in increasing the likelihood that the SA-specific dAb enters in the degradation pathway rather than being rescued through the FcRn-mediated salvage pathway.

Thus, for a SA binding AlbudAb™ (a dAb which specifically binds serum albumin), it is desirable to select one where the binding characteristics to serum albumin do not significantly change with pH (in the range of 5.0 to 7.4). A straight-forward method to ensure this would be to analyze the amino acid sequences of the anti-SA dAbs for the absence of histidine residues in the CDRs. As shown below, several selection procedures for such a property can be envisaged:

For example, a first selection round is performed with the 'naïve' dAb phage repertoire using immobilized human serum albumin in conditions where the pH of the buffer is at pH 7.4 (e.g. PBS). The recovered and amplified phage population is then submitted to a second round of selection where the incubation buffer is at pH 5.0. The alternation of buffers and pHs are optionally repeated in further rounds in order to maintain selection pressure for dAb binding to HSA at both pHs.

In a second example, all selection rounds are performed with the 'naïve' dAb phage repertoire using immobilised human serum albumin in conditions where the pH of the buffer is at pH 7.4 (e.g. PBS). However, just after washing away unbound phage with PBS (or PBS supplemented with Tween) and prior to elution of bound phage, there is added an additional wash/incubation step at pH 5.0 for a prolonged period of time (e.g. up to 4 hours). During this period, phage displaying dAbs that are unable to bind SA at pH 5.0 (but able to bind at pH 7.4) are detached from the immobilised SA. After a second series of wash steps (at pH 5.0 with(out) Tween, bound phage is recovered and analysed.

In a third example, all selection rounds are performed with the 'naïve' dAb phage repertoire using immobilized human serum albumin in conditions where the pH of the buffer is at pH 7.4 (e.g. PBS). Best dAb candidates (i.e. able to bind at pH 7.4 and pH 5.0) are then identified by screening. Typically, the genes encoding dAbs are recovered from the pooled selected phage, subcloned into an expression vector that directs the soluble dAb in the supernatant of E. coli cultures. Individual clones are picked, grown separately in the wells of microtiter plates, and induced for expression. Supernatants (or purified dAbs) are then directly loaded onto a Biacore chip to identify those dAbs displaying affinity for the immobilised serum albumin. Each supernatant is screened for binding (mainly the off-rate trace of the sensorgram) to HSA in conditions where the 'running' buffer is either at pH 7.4 or at pH 5.0. It should be noted that screening of dAb binding on the Biacore would also be used as a preferred method to identify best leads from the two above examples.

Described herein is a ligand comprising a single variable domain as defined herein, where the single variable domain specifically binds serum albumin both at a natural serum pH, and at an intracellular vesicle pH. The natural serum pH is about 7 (e.g., 7.4), and wherein said intracellular vesicle pH can range from about 4.8 to 5.2, or can be at a pH of about 5. In one embodiment, the single variable domain can specifically bind serum albumin with a pH range of about 7 to 5, or can be at a pH of 7.4. Though not wishing to be bound by theory, a further characteristic of this ligand is that the its single variable domain that specifically binds serum albumin does not substantially dissociate from serum albumin while undergoing glomerular filtration in the kidney. Though not wishing to be bound by theory, a further characteristic of this ligand is that its single variable domain that specifically binds serum albumin does not substantially interfere with the binding of FcRn to the serum albumin. This single variable domain can be an antibody single variable domain; the antibody single variable domain can be a VH3 domain and/or the antibody single variable domain can be a V kappa domain. This single variable domain can comprise a non-immunoglobulin scaffold, e.g., CTLA-4, lipocallin, SpA, Affibody™, GroEL, Avimer™ or fibronectin scaffolds, and can contain one or more of CDR1, CDR2 and/or CDR3 from an antibody single variable domain that preferably, though not necessarily, specifically binds serum albumin. The single variable domain(s) of this ligand, can specifically bind human serum albumin, and/or including serum albumin from one or more species, e.g., human, rat, monkey, procine, rabbit, hamster, mouse or goat. The intracellular compartment can be any intracellular compartment of any cell of any animal, including an endosomal compartment or intracellular vesicle or a budding vesicle. The endosomal compartment can have a pH of about 5, or 5.0. The ligands described herein can contain one or more single variable domains including immunoglobulin and/or non-immunoglobulin domains where the binding of serum albumin to the single variable domain does not substantially competitively inhibit the binding of FcRn to serum albumin. These one or more singular variable domains can preferably specifically bind serum albumin with an equilibrium dissociation constant (Kd) of less than or equal to 300 nM.

Described herein is a method for selecting for a ligand comprising a single variable domain, which contains one single variable domain (monomer), or more than one single variable domains (e.g., multimer, fusion protein, conjugate, and dual specific ligand as defined herein) which specifically binds to serum albumin, where the single variable domain specifically binds human serum albumin at a natural serum pH, and where the single variable domain does not competitively inhibit the binding of human serum albumin to FcRn, and where the single variable domain specifically binds human serum albumin at a pH of an intracellular compartment, comprising the steps of: (A) selecting for ligands comprising a single variable domain which does not bind the regions of human serum albumin that bind FcRn, (B) from the ligands selected in step (A), selecting for ligands comprising a single variable domain which binds serum albumin at said natural serum pH. (C) selecting the ligands selected in step (B) for those which bind serum albumin at the pH of said intracellular compartment. Alternatively steps (A) and (B) can be reversed as follows: (A) selecting ligands comprising a single variable domain which binds human serum albumin at said natural serum pH, (B) from the ligands selected in (A), selecting ligands comprising a single variable domain which binds human serum albumin outside the regions of HSA that bind FcRn, and (C) from the ligands selected in step (B), selecting for those which bind serum albumin at said pH of said intracellular compartment. Also described is a method for selecting for a ligand comprising a single variable domain, where the single variable domain specifically binds human serum albumin at a natural serum pH, wherein the single variable domain does not competitively inhibit the binding of human serum albumin to FcRn, and where the single variable domain specifically binds human serum albumin at a pH of an intracellular compartment, comprising the steps of: (A) selecting for ligands comprising a single variable domain which does not bind the regions of human serum albumin that bind FcRn, (B) from step (A) selecting for ligands comprising a single variable domain which binds serum albumin at said natural serum pH, and (C) genetically modifying the single variable domain of step (B) such that it binds serum albumin at said pH of said intracellular compartment. Alternatively steps (A) and (B) can be reversed as follows: (A), selecting for ligands comprising a single variable domain which binds serum albumin at said natural serum pH, (B) from the ligands selected in (A), selecting ligands comprising a single variable domain which does not bind the regions of human serum albumin that bind FcRn, and (C) genetically modifying the single variable domain of step (B) such that it binds serum albumin at said pH of said intracellular compartment.

An assay to determine if a single variable domain does not competitively inhibit the binding of human serum albumin to FcRn: A competition Biacore experiment can be used to determine if a single variable domain competitively inhibits the binding of serum albumin to a FcRn. One experimental protocol for such an example is as follows. After coating a CM5 sensor chip (Biacore AB) at 25° C. with approximately 1100 resonance units (RUs) of a purified FcRn at pH 7.4, human serum albumin (HSA), is injected over the antigen surface at a single concentration (e.g., 1 um) alone, and in combination with a dilution series of mixtures, each mixture having HSA and increasing amounts of the single variable domain in question. The resulting binding RUs are determined for the HSA alone and each of the HSA/single variable domain mixtures. By comparing the bound RUs of HSA alone with the bound RUs of HSA+single variable domain, one will be able to see whether the FcRn competes with the single variable domain to bind HSA. If it does compete, then as the single variable domain concentration in solution is increased, the RUs of HSA bound to FcRn will decrease. If there is no competition, then adding the single variable domain will have no impact on how much HSA binds to FcRn. This competition assay can optionally be repeated at pH 5.0 for a single variable domain which binds HAS at pH 5.0 in order to determine if the single variable domain competitively inhibits the binding of serum albumin to a FcRn at pH 5.0.

These ligands which have a single variable domain, which contains one single variable domain (monomer) or more than one single variable domains (e.g., multimer, fusion protein, conjugate, and dual specific ligand as defined herein) which specifically binds to serum albumin, where the single variable domain specifically binds serum albumin both at a natural serum pH, and at an intracellular vesicle pH, can further comprise at least one additional single variable domain, where each additional single variable domain specifically binds an antigen other than serum albumin at a natural serum pH, but does not bind the antigen at an intracellular vesicle pH. The natural serum pH is about 7.4, and the pH of said intracellular vesicle ranges from about 4.8 to 5.2, and in some embodiments, the pH of said intracellular vesicle is about 5.

A method based on the above ideas, includes the use of a bispecific binder with affinity for a serum albumin to prolong half-life and an affinity to a desired target antigen, as described above, to direct a bound antigen for degradation, or recycling. As described above, a serum albumin binding moiety is selected, such that binding is of high affinity at pH 5.0, such that the molecule would be sorted for non-degradation in the endosome by an FcRn mediated process. A desired target antigen binding moiety is then selected using a similar technique as described above, except that, instead of selecting for high affinity binding at pH 7.4 and pH 5 as described above, selection for high affinity binding at pH 7.4 is performed, and low or zero affinity for the target antigen at pH 5. One way to achieve this is by selecting for moieties with histidines in the contact surface. A fusion protein between the 2 molecules is then made by conventional molecular biology techniques, either by chemical derivitization and crosslinking, or by genetic fusion. The result is an increase in potency of a given AlbudAb™ (a dAb which specifically binds serum albumin) in vivo, by designing a SA binding dAb that binds SA at pH 5, while having a partner dAb that binds a ligand, which has low or zero affinity at pH 5. Though not wishing to be bound by theory, upon endosomal recycling, the target molecule will be released, and targeted to a degradative endosome and degraded, while the AlbudAb™ (a dAb which specifically binds serum albumin) is recycled to bind a fresh ligand via FcRn mediated recycling. This method offers a key advantage over PEGylated molecules or other half life extension technologies, where this pathway is not available for regeneration. Presumably in these cases, the bound ligand just sits on the PEGylated moiety and occupies it.

Described herein is a method of directing an antigen for degradation comprising administering a ligand which has at least one single variable domain, where the single variable domain specifically binds serum albumin both at a natural serum pH, and at an intracellular vesicle pH, and which further has at least one additional single variable domain, wherein the single variable domain specifically binds an antigen other than serum albumin at a natural serum pH, but does not bind said antigen at an intracellular vesicle pH, thus targeting the antigen other than serum albumin for degradation. Also described herein is, a ligand further comprising at least one additional single variable domain, wherein said single variable domain specifically binds an antigen other than serum albumin at a natural serum pH, but does not bind said antigen at an intracellular vesicle pH.

Selecting dAbs In Vitro in the Presence of Metabolites

Encompassed by the ligands described herein, is a ligand comprising a single variable domain, which contains one single variable domain (monomer) or more than one single variable domains (e.g., multimer, fusion protein, conjugate, and dual specific ligand as defined herein) which specifically binds to serum albumin, where the single variable domain specifically binds human serum albumin, and where specific binding of serum albumin by the single variable domain is not essentially blocked by binding of drugs and/or metabolites and/or small molecules to one or more sites on serum albumin. The one or more sites on human serum albumin include Sudlow site 1 and Sudlow site 2. The one or more sites can be located on any combination of one or more domains of human serum albumin selected from the group consisting of domain I, domain II and domain III.

Encompassed by the ligands described herein, is a ligand comprising a single variable domain, which contains one single variable domain (monomer) or more than one single variable domains (e.g., multimer, fusion protein, conjugate, and dual specific ligand as defined herein) which specifically binds to serum albumin, where the single variable domain specifically binds human serum albumin, and where specific binding of serum albumin by said single variable domain does not alter the binding characteristics of serum albumin for drugs and/or metabolites and/or small molecule bound to SA. In one embodiment the single variable domain of the ligand binds serum albumin in both the presence and/or absence of a drug, metabolite or other small molecule. And in another embodiment, the specific binding of serum albumin by said single variable domain does not substantially alter the binding characteristics of serum albumin for drugs and/or metabolites and/or small molecules bound to SA naturally in vivo, including, but preferably not limited to those drugs and/or metabolites and/or small molecules described in Fasano et al. (2005) 57(12):787-96. The extraordinary ligand binding properties of human serum albumin, and Bertucci, C. et al. (2002) 9(15):1463-81, Reversible and covalent binding of drugs to human serum albumin: methodological approaches and physiological relevance.

The drugs and/or metabolites and/or small molecules bound to SA may or may not overlap with the drugs and/or metabolites and/or small molecules which do not substantially inhibit or compete with serum albumin for binding to the single variable domain. The drugs and/or metabolites include, but are preferably not limited to warfarin, ibuprofen, vitamin B6, theta bilirubin, hemin, thyroxine, fatty acids, acetaldehyde, fatty acid metabolites, acyl glucuronide, metabolites of bilirubin, halothane, salicylate, benzodapenes and 1-O-gemfibrozil-B-D-glucuronide. This inhibition or competition with serum albumin for binding to the single variable domain by small molecules may occur by both direct displacement and by allosteric effects as described for small molecule binding induced changes on the binding of other small molecules, see Ascenzi et al. (2006) Mini Rev. Med. Chem. 6(4):483-9. Allosteric modulation of drug binding to human serum albumin, and Ghuman J. et al. (2005) J. Mol. Biol. 353(1):38-52 Structural basis of the drug-binding to human serum albumin. In one embodiment the small molecule, either alone, or in concert with one or more other small molecules, and/or metabolites, and/or proteins and/or drugs, binds serum albumin. In another embodiment, the small molecule either alone, or in concert with one or more other small molecules, and/or metabolites, and/or proteins and/or drugs, does not substantially inhibit or compete with serum albumin for binding to the single variable domain. In another embodiment, the small molecule, either alone or in concert with one or more other small molecules, and/or metabolites, and/or proteins and/or drugs, substantially inhibits or competes with serum albumin for binding to the single variable domain.

The single variable domain can be an antibody single variable domain. The antibody single variable domain can be a VH3 domain. The antibody single variable domain can be a V kappa domain. The single variable domain can comprise one or more non-immunoglobulin scaffolds. The non-immunoglobulin scaffold can include one or more of, but is preferably not limited to, CTLA-4, lipocallin, SpA, GroEL and fibronectin, and includes an Affibody™ and an Avimer™.

Described herein is a method of selecting a single variable domain which binds serum albumin, comprising selecting a first variable domain by its ability to bind to serum albumin in the presence of one or more metabolites and/or drugs, where the selection is performed in the presence of the one or more metabolites and/or drugs. Also described herein is a method for producing a dual specific ligand comprising a first immunoglobulin single variable domain having a first binding specificity for serum albumin in the presence of one or metabolite and/or drug, and a second immunoglobulin single variable domain having a second binding specificity, the method comprising the steps of: (a) selecting a first variable domain by its ability to bind to a first epitope in the presence of one or more metabolites and/or drugs, (b) selecting a second variable domain by its ability to bind to a second epitope, (c) combining the variable domains; and (d) selecting the ligand by its ability to bind to serum albumin in the presence of said one or more metabolites and/or ligands and said second epitopes. This method can also include a step where the first variable domain is selected for binding to said first epitope in absence of a complementary variable domain, and/or where the first variable domain is selected for binding to said first epitope in the presence of a third complementary variable domain in which said third variable domain is different from said second variable domain. These selection steps can be performed in the presence of a mixture of metabolites and/or drugs and/or proteins and/or small molecules. The selection steps can also be performed as follows: (a) selecting single variable domains which bind serum albumin in the presence of a first metabolite and/or drug and/or small molecule; and (b) from domains selected in step (a), a domain is selected in the presence of a second metabolite and/or drug and/or small molecule. Also encompassed is a method for producing a dual specific ligand having a first immunoglobulin single variable domain having a first binding specificity for serum albumin in the presence of one or metabolite and/or drug and/or small molecule, and a second immunoglobulin single variable domain having a second binding specificity, the method having the steps of: (a) selecting first variable domains by their ability to bind to serum albumin in the presence of one or more metabolites and/or drugs and/or small molecules, (b) selecting second variable domains by their ability to bind to an epitope, (c) combining the variable domains to provide ligands comprising a first and a second variable domain; and (d) from the ligands provided by step (c), and selecting a ligand by its ability to bind to serum albumin in the presence of the one or more metabolites and/or drugs and its ability to bind to said epitopes, thereby producing a dual specific ligand. In one embodiment, the first variable domain is selected for binding to serum albumin in absence of a complementary variable domain. In another embodiment, the first variable domain is selected for binding to the first epitope in the presence of a complementary variable domain in which the complementary variable domain is different from the second variable domain.

Described herein is a ligand comprising a single variable domain, where the single variable domain specifically binds serum albumin in vitro both at pH 7 and at an intracellular compartment pH, and where the single variable domain is a non-naturally occurring single variable domain. Also described herein is a ligand comprising an antibody single variable domain, where the antibody single variable domain specifically binds serum albumin in vitro both at pH 7 and at an intracellular compartment pH. In one embodiment the intracellular compartment pH ranges from 4.8 to 5.2. In another embodiment, the binding of serum albumin to the antibody single variable domain does not substantially inhibit the binding of FcRn to the serum albumin, as determined by an in vitro Surface Plasmon Resonance competition assay. In another embodiment, the antibody single variable domain is an antibody heavy chain single variable domain. The antibody heavy chain single variable domain can be a VH3 single variable domain, and the VH3 single variable domain can be a human VH3 single variable domain, in additional embodiments. In another embodiment, the antibody single variable domain is an antibody light chain single variable domain. The antibody light chain single variable domain is a Vkappa single variable domain in one embodiment, and in another embodiment is a Vlambda single variable domain.

In another embodiment, the antibody single variable domain comprises one or more of antibody CDR regions selected from the group consisting of: CDR1, CDR2 and CDR3. In another embodiment, the antibody single variable domain comprises a scaffold selected from the group consisting of: CTLA-4, lipocallin, staphylococcal protein A (SpA), GroEL, GroES, transferrin and fibronectin. The binding of serum albumin to the single variable domain does not substantially compete with the binding of FcRn to serum albumin in one embodiment, and in another embodiment the antibody single variable domain specifically binds serum albumin with an equilibrium dissociation constant (Kd) of less than or equal to 300 nM.

In another embodiment, the antibody single variable domain further comprises at least one additional antibody single variable domain, where the additional antibody single variable domain specifically binds an antigen other than serum albumin at pH 7, but does not bind the antigen at the intracellular compartment pH. Also described herein is a method of directing an antigen for degradation in an individual comprising administering a ligand comprising a single variable domain, such as an antibody single variable domain, which specifically binds serum albumin in vitro both at pH 7 and at an intracellular compartment pH, to the individual, the ligand further comprising at least one additional antibody single variable domain comprising a single variable domain, e.g., an antibody single variable domain, where the antigen other than serum albumin is the antigen which is targeted for degradation.

In one embodiment of the ligands of the invention, the specific binding of human serum albumin by the antibody single variable domain is not blocked by binding of a pre-determined drug and/or a metabolite and/or a small molecule to one or more sites on the human serum albumin. In these embodiments, the additional antibody single variable domain can be an antibody heavy chain single variable domain or an antibody light chain single variable domain which comprises one or more antibody CDRs selected from the group consisting of: CDR1, CDR2 and/or CDR3. The single variable domains can comprises a scaffold selected from the group consisting of: CTLA-4, lipocallin, staphylococcal protein A (SpA), GroEL, GroES, transferrin and fibronectin.

Another embodiment of a ligand described herein, is a ligand which comprises a single variable domain, where the single variable domain is a non-naturally occurring single variable domain, where the single variable domain specifically binds human serum albumin in vitro both at pH 7 and at an intracellular compartment pH, where the specific binding of human serum albumin by the single variable domain is not blocked by binding of a pre-determined drug and/or a metabolite and/or a small molecule to one or more sites on the human serum albumin, where the one or more sites on human serum albumin include Sudlow site 1 and Sudlow site 2 or the one or more sites are located on one or more domains of human serum albumin selected from the group consisting of: domain I, domain II and domain III.

Linkers

Connecting an AlbudAb™ (a dAb which specifically binds serum albumin) (anti-serum albumin domain antibody or single variable domain) to another biologically active moiety can be obtained by recombinant engineering techniques. Basically, the genes encoding both proteins of interest are fused in frame. Several formats can be considered where the anti-serum albumin domain antibody is either at the N-terminal end of the fusion (i.e. AlbudAb™-Y where Y is a biologically active polypeptide), at the C-terminal end of the fusion (i.e. Z-AlbudAb™ where Z is a biologically active peptide). In some instances, one may consider fusing more than one biologically active polypeptide to an AlbudAb™ (a dAb which specifically binds serum albumin), resulting in a number of possibilities regarding the fusion design. For example, the fusion could be as follows: Z-Y-AlbudAb™, Z-AlbudAb™-Y or AlbudAb™-Z-Y.

In all these fusion molecules, two polypeptides are covalently linked together via at least one peptide bond. In its most simplistic approach, the AlbudAb™ (a dAb which specifically binds serum albumin) and the biologically polypeptide(s) are directly linked. Thus, the junction between the AlbudAb™ (a dAb which specifically binds serum albumin) and the polypeptide would be as follows:

a) For an AlbudAb™ (a dAb which specifically binds serum albumin) at the C-terminal end,
Where the AlbudAb™ is a VK:—
xxxDIQ
xxxNIQ
xxxAIQ
xxxAIR
xxxVIW
xxxDIV
xxxDVV
xxxEIV
xxxETT
Where the AlbudAb™ (a dAb which specifically binds serum albumin) is a Vλ:—
xxxQSV
xxxQSA
xxxSYE
xxxSSE
xxxSYV
xxxLPV
xxxQPV
xxxQLV
xxxQAV
xxxNFM
xxxQTV
xxxQAG
Where the AlbudAb™ (a dAb which specifically binds serum albumin) is a VH (e.g., human VH):—
xxxQVQ
xxxQMQ
xxxEVQ
xxxQIT
xxxQVT
xxxQLQ
Where the AlbudAb™ (a dAb which specifically binds serum albumin) is a VHH (e.g., Camelid heavy chain variable domain):—
xxxEVQ
xxxQVQ
xxxDVQ
xxxQVK
xxxAVQ
b) For an AlbudAb™ (a dAb which specifically binds serum albumin) at the N-terminal end,
Where the AlbudAb™ (a dAb which specifically binds serum albumin) is a VK:—
KVEIKxxx (SEQ ID NO: 3)
KLEIKxxx (SEQ ID NO: 4)
KVDIKxxx (SEQ ID NO: 5)
RLEIKxxx (SEQ ID NO: 6)
EIKRxxx (SEQ ID NO: 7)
Where the AlbudAb™ (a dAb which specifically binds serum albumin) is a Vλ:—
KVDVLxxx (SEQ ID NO: 8)
KLDVLxxx (SEQ ID NO: 9)
QLDVLxxx (SEQ ID NO: 10)
Where the AlbudAb™ (a dAb which specifically binds serum albumin) is a VH (e.g., human VH):—
VTVSSxxx (SEQ ID NO: 11)
Where the AlbudAb™ (a dAb which specifically binds serum albumin) is a VHH (e.g., Camelid heavy chain variable domain):—
VTVSSxxx (SEQ ID NO: 11)
'xxx' represents the first or last three amino acids of the (first) biologically active polypeptide fused to the AlbudAb™ (a dAb which specifically binds serum albumin).

However, there may be instances where the production of a recombinant fusion protein that recovers the functional activities of both polypeptides may be facilitated by connecting the encoding genes with a bridging DNA segment encoding a peptide linker that is spliced between the polypeptides connected in tandem. Optimal peptide linker length is usually devised empirically: it can be as short as one amino acid or extend up to 50 amino acids. Linkers of different designs have been proposed and are well know in the art. The following examples are meant to provide a broad—but not comprehensive—list of possible linker approaches:

1. Flexible Linkers:

Flexible linkers are designed to adopt no stable secondary structure when connecting two polypeptide moieties, thus allowing a range of conformations in the fusion protein. These linkers are preferably hydrophilic in nature to prevent these from interacting with one or both fused polypeptides. Usually small polar residues such as glycine and serine are prevalent in those linkers in order to increase the flexible and hydrophilic characteristics of the peptide backbone, respectively. The length of these linkers is variable and best determined either empirically or with the aid of 3D computing approaches. In general, a preferred linker length will be the smallest compatible with good expression, good solubility and full recovery of the native functions and structures of interest. Because of their flexible characteristics, flexible linkers may constitute good substrates for endogenous proteases. In general, unless it is a desirable feature flexible linkers are devoid of amino acids such as charged amino acids or large hydrophobic/aromatic which are readily recognized by endogenous proteases with broad substrate specificity. In addition cysteine residues are preferably avoided since free cysteines can react together to form cysteines, thereby resulting in (i) bridging two fusion proteins via the linkers, and/or (ii) compromised expression/folding of the fusion protein if one or more of the bioactive polypeptides comprises one or more cysteine residue ('cysteine scrambling').

Examples of flexible linkers are: (i) glycine-rich linkers based on the repetition of a $(GGGGS)_y$ motif (SEQ ID NO: 12) where y is at least 1, though y can be 2, 3, 4, 5, 6, 7, 8 and 9, or more (see PCT International Publications No: EP 0 753 551, U.S. Pat. No. 5,258,498, EP 0 623 679), (ii) serine-rich linkers based on the repetition of a $(SSSSG)_y$ motif (SEQ ID NO: 13) where y is at least 1, though y can be 2, 3, 4, 5, 6, 7, 8 and 9, or more (see PCT International Publications No: EP 0 573 551, U.S. Pat. No. 5,525,491).

1. Constrained Linkers:

Constrained linkers are designed to adopt a stable secondary structure when connecting two polypeptide moieties, thus restricting the range of conformations in the fusion protein. Such linkers usually adopt a helical structure spanning several turns. Again the length of these linkers is variable and best determined either empirically or with the aid of computing approaches. The main reason for choosing constrained linkers is to maintain the longest distance between each polypeptide of the fusion. This is particularly relevant when both polypeptides have a tendency to form hetero-aggregates. By virtue of their structure, constrained linkers can also be more resistant to proteolytic degradation, thereby offering an advantage when injected in vivo.

Examples of constrained linkers are cited in PCT International Publications No: WO 00/24884 (e.g. SSSASASSA (SEQ ID NO: 14), GSPGSPG (SEQ ID NO: 15), or ATTTGSSPGPT (SEQ ID NO: 16)), U.S. Pat. No. 6,132,992 (e.g. helical peptide linkers).

3. 'Natural' Linkers:

Natural linkers are polypeptide sequences (of variable lengths) that—by opposition—are not synthetic, i.e. the polypeptide sequences composing the linkers are found in nature. Natural linkers can be either flexible or constrained and can be very diverse in amino acid sequence and composition. Their degree of resistance to proteolysis depends on which proteins they originate from and which biological environment these proteins are facing in nature (extracellular, intracellular, prokaryotic, eukaryotic, etc). One class of linkers is particularly relevant for the development of biological therapeutics in man: linkers based on peptides found in human proteins. Indeed such linkers are by nature non—or very weakly—immunogenic and therefore potentially safer for human therapy.

Examples of natural linkers are: (i) KESGSVSSEQLAQ-FRSLD (SEQ ID NO: 17) (see Bird et al. (1988) Science, 242, 423-426), (ii) sequences corresponding to the hinge domain of immunoglobulins devoid of light chains (see Hamers-Casterman et al. (1993) Nature, 363, 446-448 and PCT International Publication No: WO 096/34103). Examples of linkers for use with anti-albumin domain antibodies (e.g., human, humanized, camelized human or Camelid VHH domain antibodies) are EPKIPQPQPKPQPQPQPQPQPKPQPKPEP-ECTCPKCP (SEQ ID NO: 18) and GTNEVCKCPKCP (SEQ ID NO: 19). Other linkers derived from human and camelid hinges are disclosed in EP0656946, incorporated herein by reference. The hinge derived linkers can have variable lengths, for example from 0 to about 50 amino acids, including 1, 2, 3, 4, 5, 6, 7, 8, 9, 10 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48 or 49 amino acids.

As used herein, "drug" refers to any compound (e.g., small organic molecule, nucleic acid, polypeptide) that can be administered to an individual to produce a beneficial, therapeutic or diagnostic effect through binding to and/or altering the function of a biological target molecule in the individual. The target molecule can be an endogenous target molecule encoded by the individual's genome (e.g. an enzyme, receptor, growth factor, cytokine encoded by the individual's genome) or an exogenous target molecule encoded by the genome of a pathogen (e.g. an enzyme encoded by the genome of a virus, bacterium, fungus, nematode or other pathogen).

The drug composition can be a conjugate wherein the drug is covalently or noncovalently bonded to the polypeptide binding moiety. The drug can be; covalently or noncovalently bonded to the polypeptide binding moiety directly or indirectly (e.g., through a suitable linker and/or noncovalent binding of complementary binding partners (e.g., biotin and avidin)). When complementary binding partners are employed, one of the binding partners can be covalently bonded to the drug directly or through a suitable linker moiety, and the complementary binding partner can be covalently bonded to the polypeptide binding moiety directly or through a suitable linker moiety. When the drug is a polypeptide or peptide, the drug composition can be a fusion protein, wherein the polypeptide or peptide, drug and the polypeptide binding moiety are discrete parts (moieties) of a continuous polypeptide chain. As described herein, the polypeptide binding moieties and polypeptide drug moieties can be directly bonded to each other through a peptide bond, or linked through a suitable amino acid, or peptide or polypeptide linker.

Decreased Immunogenicity

Described herein is a method of reducing the immunogenicity of a pharmaceutical agent, comprising modifying said agent so that the agent further contains a single variable domain region, where the single variable domain specifically binds serum albumin in vivo and/or ex vivo, and where the agent can include a drug, a metabolite, a ligand, an antigen and a protein. The serum albumin can be human serum albumin. The single variable domain can be an immunoglobulin single variable domain. The immunoglobulin single variable domain can be a VH antibody single variable domain. The $V_H$ single variable domain can be a VH3 single variable domain. The VH3 single variable domain can be a human VH3 single variable domain. The single variable domain can be a Vkappa or a Vlambda antibody single variable domain. The antibody single variable domain can comprise a set of four Kabat framework regions (FRs which are encoded by VH3 framework germ line antibody gene segments. The VH3 framework is selected from the group consisting of DP47, DP38 and DP45. The antibody single variable domain can contain a set of four Kabat framework regions (FRs), which are encoded by VKappa framework germ line antibody gene segments. A nonlimiting example of a Kappa framework is DPK9. The single variable domain can contain an immunoglobulin or non-immunoglobulin scaffold which contains CDR1, CDR2 and/or CDR3 regions, wherein at least one of the CDR1, CDR2 and CDR3 regions is from an antibody variable domain which specifically binds serum albumin. The non-immunoglobulin scaffold can include, but is preferably not limited to, CTLA-4, lipocallin, SpA, Affibody™, GroEL, Avimers™ and fibronectin. The serum albumin can be human serum albumin. The immunoglobulin single variable domain and/or the non-immunoglobulin single variable domain can specifically bind to human serum albumin with a Kd of less than 300 nM. The immunoglobulin single variable domain and/or the non-immunoglobulin single variable domain can specifically bind to both human serum albumin and one or more non-human serum albumins, with Kd values within 10 fold of each other. The immunoglobulin single variable domain and/or non-immunoglobulin single variable domain can specifically bind to both human serum albumin and one or more non-human serum albumins, and wherein the T beta half life of the ligand is substantially the same as the T beta half life of human serum albumin in a human host. Further, the immunoglobulin single variable domain and/or non-immunoglobulin single variable domain can specifically bind to Domain II of human serum albumin. The immunoglobulin single variable domain and/or the non-immunoglobulin single variable domain can further specifically bind serum albumin both at a natural serum pH, and at an intracellular vesicle pH. The specific binding of serum albumin by said immunoglobulin single variable domain and/or the non-immunoglobulin single variable domain is preferably not substantially blocked by binding of drugs and/or metabolites to one or more sites on serum albumin. In one embodiment, the specific binding of serum albumin by the single variable domain does not alter the binding characteristics of serum albumin for drugs and/or metabolites and/or small molecules bound to SA. In one embodiment the method of modifying the agent results in the formation of an modified agent having a formula comprising: a-(X)n1-b-(Y)n2-c-(Z)n3-d or a-(Z)n3-b-(Y)n2-c-(X)n-d, wherein X is a polypeptide drug that has binding specificity for a first target; Y is a single variable domain, e.g. an antibody single variable domain that specifically binds serum albumin in vivo and/or ex vivo; Z is a polypeptide drug that has binding specificity for a second target; a, b, c and d are independently a polypeptide comprising one to about amino acid residues or absent; n1 is one to about 10; n2 is one to about 10; and n3 is zero to about 10. In a further embodiment, when n1 and n2 are both one and n3 is zero, X does not comprise an antibody chain or a fragment of an antibody chain.

Described herein is a method of reducing the immunogenicity of a pharmaceutical agent, comprising modifying the agent so that the agent further comprises a single variable domain, where the single variable domain specifically binds serum albumin, where the single variable domain is a non-naturally occurring single variable domain, and where the agent is selected from the group consisting of: a drug, a metabolite, a ligand, an antigen and a protein. Also described herein is a method of reducing the immunogenicity of a pharmaceutical agent, comprising modifying the agent so that the agent further comprises an antibody single variable domain, where the antibody single variable domain specifically binds serum albumin, and where the agent is selected from the group consisting of: a drug, a metabolite, a ligand, an antigen and a protein. In one embodiment, the antibody single variable domain is an antibody heavy chain single variable domain, e.g., antibody VH3 single variable domain, or a human antibody VH3 single variable domain. In another embodiment, the antibody single variable domain is an antibody light chain single variable domain, e.g., an antibody Vkappa or an antibody Vlambda single variable domain. In one embodiment, the antibody single variable domain comprises CDR1, CDR2 and CDR3 regions, where at least one of the CDR1, CDR2 and CDR3 regions is from an antibody variable domain which specifically binds serum albumin, and optionally further comprises a scaffold selected from the group consisting of: CTLA-4, lipocallin, staphylococcal protein A (SpA), GroEL, GroES, transferrin and fibronectin. In another embodiment of these methods, the single variable domain, e.g., the antibody single variable domain specifically binds to human serum albumin with a kd of less than 300 nM, and in another embodiment of these methods, the single variable domain, e.g., the antibody single variable domain, specifically binds to human serum albumin and one or more non-human serum albumins, with Kd values within 10 fold of each other. In another embodiment of these methods, the single variable domain, e.g., the antibody single variable domain, specifically binds to human serum albumin and a non-human serum albumin, and the T beta half life of the ligand is substantially the same as the T beta half life of human serum albumin in a human host. In another embodiment of these methods, the single variable domain, e.g., the antibody single variable domain, specifically binds to Domain II of human serum albumin. In another embodiment of these methods, the single variable domain, e.g., the antibody single variable domain, specifically binds serum albumin both at a pH 7, and at an intracellular compartment pH.

The invention is further described, for the purposes of illustration only, in the following examples. As used herein, for the purposes of dAb nomenclature, human TNFα is referred to as TAR1 and human TNFα receptor 1 (p55 receptor) is referred to as TAR2.

Example 1

Selection of a Dual Specific scFv Antibody (K8) Directed Against Human Serum Albumin (HSA) and β-Galactosidase (β-Gal)

This example explains a method for making a dual specific antibody directed against β-gal and HSA in which a repertoire of $V_\kappa$ variable domains linked to a germ line (dummy) $V_H$ domain is selected for binding to β-gal and a repertoire of $V_H$ variable domains linked to a-germ line (dummy) $V_\kappa$ domain is selected for binding to HSA. The selected variable $V_H$ HSA and $V_\kappa$ β-gal domains are then combined and the antibodies selected for binding to β-gal and HSA. HSA is a half-life increasing protein found in human blood.

Four human phage antibody libraries were used in this experiment.

| Library 1 | Germ line $V_\kappa$/DVT $V_H$ | $8.46 \times 10^7$ |
| Library 2 | Germ line $V_\kappa$/NNK $V_H$ | $9.64 \times 10^7$ |
| Library 3 | Germ line $V_H$/DVT $V_\kappa$ | $1.47 \times 10^8$ |
| Library 4 | Germ line $V_H$/NNK $V_\kappa$ | $1.45 \times 10^8$ |

All libraries are based on a single human framework for $V_H$ (V3-23/DP47 and $J_H$4b) and $V_\kappa$ (O12/O2/DPK9 and $J_\kappa$1) with side chain diversity incorporated in complementarity determining regions (CDR2 and CDR3).

Library 1 and Library 2 contain a dummy $V_\kappa$ sequence, whereas the sequence of $V_H$ is diversified at positions H50, H52, H52a, H53, H55, H56, H58, H95, H96, H97 and H98 (DVT or NNK encoded, respectively) (FIG. 1). Library 3 and Library 4 contain a dummy $V_H$ sequence, whereas the sequence of $V_\kappa$ is diversified at positions L50, L53, L91, L92, L93, L94 and L96 (DVT or NNK encoded, respectively) (FIG. 1). The libraries are in phagemid pIT2/ScFv format (FIG. 2) and have been preselected for binding to generic ligands, Protein A and Protein L, so that the majority of clones in the unselected libraries are functional. The sizes of the libraries shown above correspond to the sizes after preselection. Library 1 and Library 2 were mixed prior to selections on antigen to yield a single $V_H$/dummy $V_\kappa$ library and Library 3 and Library 4 were mixed to form a single $V_\kappa$/dummy $V_H$ library.

Three rounds of selections were performed on β-gal using $V_\kappa$/dummy $V_H$ library and three rounds of selections were performed on HSA using $V_H$/dummy $V_\kappa$ library. In the case of β-gal the phage titres went up from $1.1 \times 10^6$ in the first round to $2.0 \times 10^8$ in the third round. In the case of HSA the phage titres went up from $2 \times 10^4$ in the first round to $1.4 \times 10^9$ in the third round. The selections were performed as described by Griffith et al., (1993), except that KM13 helper phage (which contains a pIII protein with a protease cleavage site between the D2 and D3 domains) was used and phage were eluted with 1 mg/ml trypsin in PBS. The addition of trypsin cleaves the pIII proteins derived from the helper phage (but not those from the phagemid) and elutes bound scFv-phage fusions by cleavage in the c-myc tag (FIG. 2), thereby providing a further enrichment for phages expressing functional scFvs and a corresponding reduction in background (Kristensen & Winter, Folding & Design 3: 321-328, Jul. 9, 1998). Selections were performed using immunotubes coated with either HSA or β-gal at 100 μg/ml concentration.

To check for binding, 24 colonies from the third round of each selection were screened by monoclonal phage ELISA. Phage particles were produced as described by Harrison et al., Methods Enzymol. 1996; 267:83-109. 96-well ELISA plates were coated with 100 μl of HSA or β-gal at 10 μg/ml concentration in PBS overnight at 4° C. A standard ELISA protocol was followed (Hoogenboom et al., 1991) using detection of bound phage with anti-M13-HRP conjugate. A selection of clones gave ELISA signals of greater than 1.0 with 50 μl supernatant.

Next, DNA preps were made from $V_H$/dummy $V_K$ library selected on HSA and from $V_K$/dummy $V_H$ library selected on β-gal using the QIAprep Spin Miniprep kit (Qiagen). To access most of the diversity, DNA preps were made from each of the three rounds of selections and then pulled together for each of the antigens. DNA preps were then digested with SalI/NotI overnight at 37° C. Following gel purification of the fragments, $V_K$ chains from the $V_K$/dummy $V_H$ library selected on β-gal were ligated in place of a dummy $V_K$ chain of the $V_H$/dummy $V_K$ library selected on HSA creating a library of $3.3 \times 10^9$ clones.

This library was then either selected on HSA (first round) and β-gal (second round), HSA/β-gal selection, or on β-gal (first round) and HSA (second round), β-gal/HSA selection. Selections were performed as described above. In each case after the second round 48 clones were tested for binding to HSA and β-gal by the monoclonal phage ELISA (as described above) and by ELISA of the soluble scFv fragments. Soluble antibody fragments were produced as described by Harrison et al., (1996), and standard ELISA protocol was followed Hoogenboom et al. (1991) Nucleic Acids Res., 19: 4133, except that 2% Tween/PBS was used as a blocking buffer and bound scFvs were detected with Protein L-HRP. Three clones (E4, E5 and E8) from the HSA/β-gal selection and two clones (K8 and K10) from the β-gal/HSA selection were able to bind both antigens. scFvs from these clones were PCR amplified and sequenced as described by Ignatovich et al., (1999) J Mol Biol 1999 Nov. 26; 294(2): 457-65, using the primers LMB3 and pHENseq. Sequence analysis revealed that all clones were identical. Therefore, only one clone encoding a dual specific antibody (K8) was chosen for further work (FIG. 3).

Example 2

Characterisation of the Binding Properties of the K8 Antibody

Firstly, the binding properties of the K8 antibody were characterised by the monoclonal phage ELISA. A 96-well plate was coated with 100 μl of HSA and β-gal alongside with alkaline phosphatase (APS), bovine serum albumin (BSA), peanut agglutinin, lysozyme and cytochrome c (to check for cross-reactivity) at 10 μg/ml concentration in PBS overnight at 4° C. The phagemid from K8 clone was rescued with KM13 as described by Harrison et al., (1996) and the supernatant (50 μl) containing phage assayed directly. A standard ELISA protocol was followed (Hoogenboom et al., 1991) using detection of bound phage with anti-M13-HRP conjugate. The dual specific K8 antibody was found to bind to HSA and 1-gal when displayed on the surface of the phage with absorbance signals greater than 1.0 (FIG. 4). Strong binding to BSA was also observed (FIG. 4). Since HSA and BSA are 76% homologous on the amino acid level, it is not surprising that K8 antibody recognised both of these structurally related proteins. No cross-reactivity with other proteins was detected (FIG. 4).

Secondly, the binding properties of the K8 antibody were tested in a soluble scFv ELISA. Production of the soluble scFv fragment was induced by IPTG as described by Harrison et al., (1996). To determine the expression levels of $K_8$ scFv, the soluble antibody fragments were purified from the supernatant of 50 ml inductions using Protein A-Sepharose columns as described by Harlow and Lane, Antibodies: a Laboratory Manual, (1988) Cold Spring Harbor. $OD_{280}$ was then measured and the protein concentration calculated as described by Sambrook et al., (1989). K8 scFv was produced in supernatant at 19 mg/l.

A soluble scFv ELISA was then performed using known concentrations of the K8 antibody fragment. A 96-well plate was coated with 100 μl of HSA, BSA and β-gal at 10 μg/ml and 100 μl of Protein A at 1 μg/ml concentration. 50 μl of the serial dilutions of the K8 scFv was applied and the bound antibody fragments were detected with Protein L-HRP. ELISA results confirmed the dual specific nature of the K8 antibody (FIG. 5).

Figure 2:
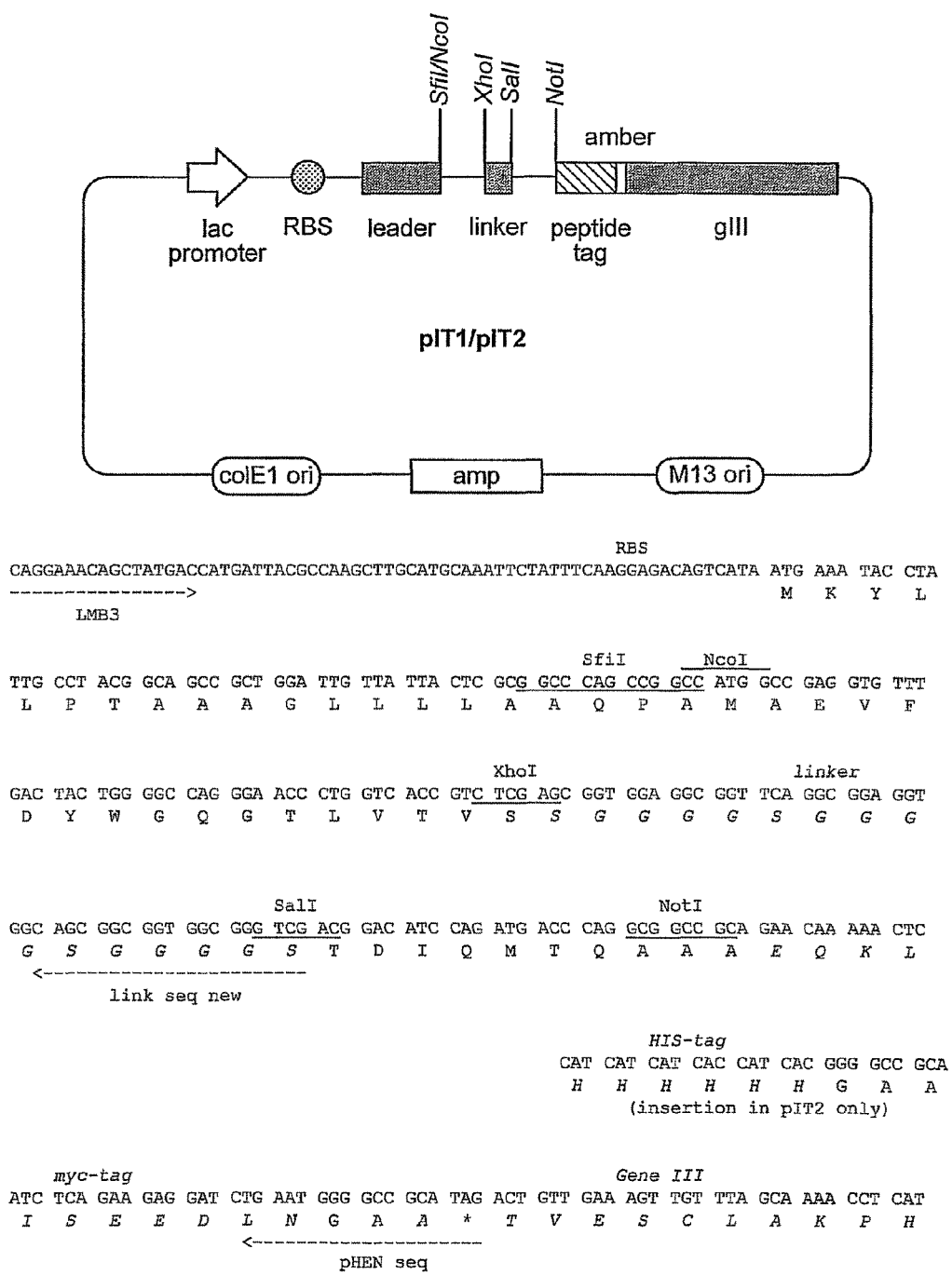
FIG. 2 shows
  Library 1: Germ line $V_K$/DVT $V_H$,
  Library 2: Germ line $V_K$/NNK $V_H$,
  Library 3: Germ line $V_H$/DVT $V_K$
  Library 4: Germ line $V_H$/NNK $V_K$ In phage display/ScFv format. These libraries were preselected for binding to generic ligands protein A and protein L so that the majority of the clones and selected libraries are functional. Libraries were selected on HSA (first round) and β-gal (second round) or HSA β-gal selection or on β-gal (first round) and HSA (second round) β-gal HSA selection.

To confirm that binding to β-gal is determined by the $V_K$ domain and binding to HSA/BSA by the $V_H$ domain of the K8 scFv antibody, the $V_K$ domain was cut out from K8 scFv DNA by SalI/NotI digestion and ligated into a SalI/NotI digested pIT2 vector containing dummy $V_H$ chain (FIGS. 1 and 2). Binding characteristics of the resulting clone K8$V_K$/dummy $V_H$ were analysed by soluble scFv ELISA. Production of the soluble scFv fragments was induced by IPTG as described by Harrison et al., (1996) and the supernatant (50μ) containing scFvs assayed directly. Soluble scFv ELISA was performed as described in Example 1 and the bound scFvs were detected with Protein L-HRP. The ELISA results revealed that this clone was still able to bind β-gal, whereas binding to BSA was abolished (FIG. 6).

Example 3

Selection of Single $V_H$ Domain Antibodies Antigens A and B and Single $V_K$ Domain Antibodies Directed Against Antigens C and D This example describes a method for making single $V_H$ domain antibodies directed against antigens A and B and single $V_K$ domain antibodies directed against antigens C and D by selecting repertoires of virgin single antibody variable domains for binding to these antigens in the absence of the complementary variable domains.

Selections and characterisation of the binding clones is performed as described previously (see Example 5, PCT/GB 02/003014). Four clones are chosen for further work:

VH1—Anti A $V_H$

VH2—Anti B $V_H$

VK1—Anti C $V_K$

VK2—Anti D $V_K$

The procedures described above in Examples 1-3 may be used, in a similar manner as that described, to produce dimer molecules comprising combinations of $V_H$ domains (i.e., $V_H$-$V_H$ ligands) and combinations of $V_L$ domains ($V_L$-$V_L$ ligands).

Example 4

Creation and Characterisation of the Dual Specific ScFv Antibodies (VH1/VH2 Directed Against Antigens A and B and VK1/VK2 Directed Against Antigens C and D)

This example demonstrates that dual specific ScFv antibodies (VH1/VH2 directed against antigens A and B and VK1/VK2 directed against antigens C and D) could be created by combining $V_\kappa$ and $V_H$ single domains selected against respective antigens in a ScFv vector.

To create dual specific antibody VH1/VH2, VH1 single domain is excised from variable domain vector 1 (FIG. 7) by NcoI/XhoI digestion and ligated into NcoI/XhoI digested variable domain vector 2 (FIG. 7) to create VH1/variable domain vector 2. VH2 single domain is PCR amplified from variable domain vector 1 using primers to introduce SalI restriction site to the 5' end and NotI restriction site to the 3' end. The PCR product is then digested with SalI/NotI and ligated into SalI/NotI digested VH1/variable domain vector 2 to create VH1/VH2/variable domain vector 2.

VK1/VK2/variable domain vector 2 is created in a similar way. The dual specific nature of the produced VH1/VH2 ScFv and VK1/VK2 ScFv is tested in a soluble ScFv ELISA as described previously (see Example 6, PCT/GB 02/003014). Competition ELISA is performed as described previously (see Example 8, PCT/GB 02/003014).

Possible outcomes:
VH1/VH2 ScFv is able to bind antigens A and B simultaneously
VK1/VK2 ScFv is able to bind antigens C and D simultaneously
VH1/VH2 ScFv binding is competitive (when bound to antigen A, VH1/VH2 ScFv cannot bind to antigen B)
VK1/VK2 ScFv binding is competitive (when bound to antigen C, VK1/VK2 ScFv cannot bind to antigen D)

Example 5

Construction of Dual Specific VH1/VH2 Fab and VK1/VK2 Fab and Analysis of Their Binding Properties To create VH1/VH2 Fab, VH1 single domain is ligated into NcoI/XhoI digested CH vector (FIG. 8) to create VH1/CH and VH2 single domain is ligated into SalI/NotI digested CK vector (FIG. 9) to create VH2/CK. Plasmid DNA from VH1/CH and VH2/CK is used to co-transform competent *E. coli* cells as described previously (see Example 8, PCT/GB02/003014).

The clone containing VH1/CH and VH2/CK plasmids is then induced by IPTG to produce soluble VH1/VH2 Fab as described previously (see Example 8, PCT/GB 02/003014).

VK1/VK2 Fab is produced in a similar way.

Binding properties of the produced Fabs are tested by competition ELISA as described previously (see Example 8, PCT/GB 02/003014).

Possible outcomes:
VH1/VH2 Fab is able to bind antigens A and B simultaneously
VK1/VK2 Fab is able to bind antigens C and D simultaneously
VH1/VH2 Fab binding is competitive (when bound to antigen A, VH1/V1H$_2$Fab cannot bind to antigen B)
VK1/VK2 Fab binding is competitive (when bound to antigen C, VK1/VK2 Fab cannot bind to antigen D)

Example 6

Chelating dAb Dimers

Summary

VH and VK homo-dimers are created in a dAb-linker-dAb format using flexible polypeptide linkers. Vectors were created in the dAb linker-dAb format containing glycine-serine linkers of different lengths 3U:$(Gly_4Ser)_3$ (SEQ ID NO: 20), 5U:$(Gly_4Ser)_5$ (SEQ ID NO: 21), 7U:$(Gly_4Ser)_7$ (SEQ ID NO: 22) Dimer libraries were created using guiding dAbs upstream of the linker: TAR1-5 (VK), TAR1-27(VK), TAR2-5(VH) or TAR2-6(VK) and a library of corresponding second dAbs after the linker. Using this method, novel dimeric dAbs were selected. The effect of dimerisation on antigen binding was determined by ELISA and Biacore studies and in cell neutralisation and receptor binding assays. Dimerisation of both TAR1-5 and TAR1-27 resulted in significant improvement in binding affinity and neutralisation levels.

1.0 Methods
1.1 Library Generation
1.1.1 Vectors pEDA3U, pEDA5U and pEDA7U vectors were designed to introduce different linker lengths compatible with the dAb-linker-dAb format. For pEDA3U, sense and anti-sense 73-base pair oligo linkers were annealed using a slow annealing program (95° C.-5 mins, 80° C.-10 mins, 70° C.-15 mins, 56° C.-15 mins, 42° C. until use) in buffer containing 0.1MNaCl, 10 mM Tris-HCl pH7.4 and cloned using the Xho1 and Not1 restriction sites. The linkers encompassed 3 $(Gly_4Ser)$ units (SEQ ID NO: 20) and a stuffer region housed between Sal1 and Not1 cloning sites (scheme 1). In order to reduce the possibility of monomeric dAbs being selected for by phage display, the stuffer region was designed to include 3 stop codons, a Sac1 restriction site and a frame shift mutation to put the region out of frame when no second dAb was present. For pEDA5U and 7U due to the length of the linkers required, overlapping oligo-linkers were designed for each vector, annealed and elongated using Klenow. The fragment was then purified and digested using the appropriate enzymes before cloning using the Xho1 and Not1 restriction sites.

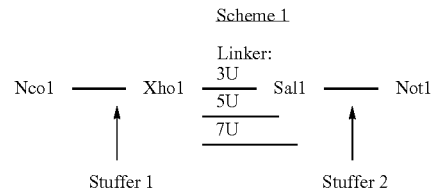

Scheme 1

1.1.2 Library Preparation

The N-terminal V gene corresponding to the guiding dAb was cloned upstream of the linker using Nco1 and Xho1 restriction sites. VH genes have existing compatible sites, however cloning VK genes required the introduction of suitable restriction sites. This was achieved by using modifying PCR primers (VK-DLIBF: 5' cggccatggcgtcaacggacat (SEQ ID NO: 23); VKXho1R: 5' atgtgcgctcgagcgtttgattt 3 (SEQ ID NO: 24)) in 30 cycles of PCR amplification using a 2:1 mixture of SuperTaq (HTBiotechnology Ltd) and pfu turbo (Stratagene). This maintained the Nco1 site at the 5' end while destroying the adjacent Sal1 site and introduced the Xho1 site at the 3' end. 5 guiding dAbs were cloned into each of the 3 dimer vectors: TAR1-5 (VK), TAR1-27(VK), TAR2-5(VH), TAR2-6(VK) and TAR2-7(VK). All constructs were verified by sequence analysis.

Having cloned the guiding dAbs upstream of the linker in each of the vectors (pEDA3U, 5U and 7U): TAR1-5 (VK), TAR1-27(VK), TAR2-5(VH) or TAR2-6(VK) a library of corresponding second dAbs were cloned after the linker. To achieve this, the complimentary dAb libraries were PCR amplified from phage recovered from round 1 selections of either a VK library against Human TNFα (at approximately $1 \times 10^6$ diversity after round 1) when TAR1-5 or TAR1-27 are the guiding dAbs, or a $V_H$ or $V_\kappa$ library against human p55 TNF receptor (both at approximately $1 \times 10^5$ diversity after round 1) when TAR2-5 or TAR2-6 respectively are the guiding dAbs. For $V_\kappa$ libraries PCR amplification was conducted using primers in 30 cycles of PCR amplification using a 2:1 mixture of SuperTaq and pfu turbo. VH libraries were PCR amplified using primers in order to introduce a SalI restriction site at the 5' end of the gene. The dAb library PCRs were digested with the appropriate restriction enzymes, ligated into the corresponding vectors down stream of the linker, using SalI/NotI restriction sites and electroporated into freshly prepared competent TG1 cells.

The titres achieved for each library are as follows:
TAR1-5: pEDA3U=$4 \times 10^8$, pEDA5U=$8 \times 10^7$, pEDA7U=$1 \times 10^8$
TAR1-27: pEDA3U=$6.2 \times 10^8$, pEDA5U=$1 \times 10^8$, pEDA7U=$1 \times 10^9$
TAR2h-5: pEDA3U=$4 \times 10^7$, pEDA5U=$2 \times 10^8$, pEDA7U=$8 \times 10^7$
TAR2h-6: pEDA3U=$7.4 \times 10^8$, pEDA5U=$1.2 \times 10^8$, pEDA7U=$2.2 \times 10^8$ 1.2 Selections 1.2.1 TNFα

Selections were conducted using human TNFα passively coated on immunotubes. Briefly, Immunotubes are coated overnight with 1-4 mls of the required antigen. The immunotubes were then washed 3 times with PBS and blocked with 2% milk powder in PBS for 1-2 hrs and washed a further 3 times with PBS. The phage solution is diluted in 2% milk powder in PBS and incubated at room temperature for 2 hrs. The tubes are then washed with PBS and the phage eluted with 1 mg/ml trypsin-PBS. Three selection strategies were investigated for the TAR1-5 dimer libraries. The first round selections were carried out in immunotubes using human TNFα coated at 1 μg/ml or 20 μg/ml with 20 washes in PBS 0.1% Tween. TG1 cells are infected with the eluted phage and the titres are determined (e.g., Marks et al J Mol. Biol. 1991 Dec. 5; 222(3):581-97, Richmann et al Biochemistry. 1993 Aug. 31; 32(34):8848-55).

The titres recovered were:
pEDA3U=$2.8 \times 10^7$ (1 μg/ml TNF) $1.5 \times 10^8$ (20 μg/ml TNF),
pEDA5U=$1.8 \times 10^7$ (1 g/ml TNF), $1.6 \times 10^8$ (20 μg/ml TNF)
pEDA7U=$8 \times 10^6$ (1 g/ml TNF), $7 \times 10^7$ (20 μg/ml TNF).

The second round selections were carried out using 3 different methods.
1. In immunotubes, 20 washes with overnight incubation followed by a further 10 washes.
2. In immunotubes, 20 washes followed by 1 hr incubation at RT in wash buffer with (1 μg/ml TNFα) and 10 further washes.
3. Selection on streptavidin beads using 33 pmoles biotinylated human TNFα (Henderikx et al., 2002, *Selection of antibodies against biotinylated antigens*. Antibody Phage Display: Methods and protocols, Ed. O'Brien and Atkin, Humana Press). Single clones from round 2 selections were picked into 96 well plates and crude supernatant preps were made in 2 ml 96 well plate format.

|  | Round 1 Human TNFα immunotube coating concentration | Round 2 selection method 1 | Round 2 selection method 2 | Round 2 selection method 3 |
| --- | --- | --- | --- | --- |
| pEDA3U | 1 μg/ml | $1 \times 10^9$ | $1.8 \times 10^9$ | $2.4 \times 10^{10}$ |
| pEDA3U | 20 μg/ml | $6 \times 10^9$ | $1.8 \times 10^{10}$ | $8.5 \times 10^{10}$ |
| pEDA5U | 1 μg/ml | $9 \times 10^8$ | $1.4 \times 10^9$ | $2.8 \times 10^{10}$ |
| pEDA5U | 20 μg/ml | $9.5 \times 10^9$ | $8.5 \times 10^9$ | $2.8 \times 10^{10}$ |
| pEDA7U | 1 μg/ml | $7.8 \times 10^8$ | $1.6 \times 10^8$ | $4 \times 10^{10}$ |
| pEDA7U | 20 μg/ml | $1 \times 10^{10}$ | $8 \times 10^9$ | $1.5 \times 10^{10}$ |

For TAR1-27, selections were carried out as described previously with the following modifications. The first round selections were carried out in immunotubes using human TNFα coated at 1 μg/ml or 20 μg/ml with 20 washes in PBS 0.1% Tween. The second round selections were carried out in immunotubes using 20 washes with overnight incubation followed by a further 20 washes. Single clones from round 2 selections were picked into 96 well plates and crude supernatant preps were made in 2 ml 96 well plate format.

TAR1-27 titres are as follows:

|  | Human TNFα immunotube coating conc | Round 1 | Round 2 |
| --- | --- | --- | --- |
| pEDA3U | 1 μg/ml | $4 \times 10^9$ | $6 \times 10^9$ |
| pEDA3U | 20 μg/ml | $5 \times 10^9$ | $4.4 \times 10^{10}$ |
| pEDA5U | 1 μg/ml | $1.5 \times 10^9$ | $1.9 \times 10^{10}$ |
| pEDA5U | 20 μg/ml | $3.4 \times 10^9$ | $3.5 \times 10^{10}$ |
| pEDA7U | 1 μg/ml | $2.6 \times 10^9$ | $5 \times 10^9$ |
| pEDA7U | 20 μg/ml | $7 \times 10^9$ | $1.4 \times 10^{10}$ |

1.2.2 TNF Receptor 1 (p55 Receptor; TAR2)

Selections were conducted as described previously for the TAR2h-5 libraries only. Three rounds of selections were carried out in immunotubes using either 1 μg/ml human p55 TNF receptor or 10 μg/ml human p55 TNF receptor with 20 washes in PBS 0.1% Tween with overnight incubation followed by a further 20 washes. Single clones from round 2 and 3 selections were picked into 96 well plates and crude supernatant preps were made in 2 ml, 96 well plate format.

TAR2h-5 Titres are as Follows:

|  | Round 1 human p55 TNF receptor immunotube coating concentration | Round 1 | Round 2 | Round 3 |
| --- | --- | --- | --- | --- |
| pEDA3U | 1 μg/ml | $2.4 \times 10^6$ | $1.2 \times 10^7$ | $1.9 \times 10^9$ |
| pEDA3U | 10 μg/ml | $3.1 \times 10^7$ | $7 \times 10^7$ | $1 \times 10^9$ |
| pEDA5U | 1 μg/ml | $2.5 \times 10^6$ | $1.1 \times 10^7$ | $5.7 \times 10^8$ |
| pEDA5U | 10 μg/ml | $3.7 \times 10^7$ | $2.3 \times 10^8$ | $2.9 \times 10^9$ |
| pEDA7U | 1 μg/ml | $1.3 \times 10^6$ | $1.3 \times 10^7$ | $1.4 \times 10^9$ |
| pEDA7U | 10 μg/ml | $1.6 \times 10^7$ | $1.9 \times 10^7$ | $3 \times 10^{10}$ |

1.3 Screening

Single clones from round 2 or 3 selections were picked from each of the 3U, 5U and 7U libraries from the different selections methods, where appropriate. Clones were grown in 2×TY with 100 μg/ml ampicillin and 1% glucose overnight at 37° C. A 1/100 dilution of this culture was inoculated into 2 mls of 2×TY with 100 µg/ml ampicillin and 0.1% glucose in 2 ml, 96 well plate format and grown at 37° C. shaking until OD600 was approximately 0.9. The culture was then induced with 1 mM IPTG overnight at 30° C. The supernatants were clarified by centrifugation at 4000 rpm for 15 mins in a sorval plate centrifuge. The supernatant preps the used for initial screening.

1.3.1 Elisa

Binding activity of dimeric recombinant proteins was compared to monomer by Protein A/L ELISA or by antigen ELISA. Briefly, a 96 well plate is coated with antigen or Protein A/L overnight at 4° C. The plate washed with 0.05% Tween-PBS, blocked for 2 hrs with 2% Tween-PBS. The sample is added to the plate incubated for 1 hr at room temperature. The plate is washed and incubated with the secondary reagent for 1 hr at room temperature. The plate is washed and developed with TMB substrate. Protein A/L-HRP or India-HRP was used as a secondary reagent. For antigen ELISAs, the antigen concentrations used were 1 µg/ml in PBS for Human TNFα and human THF receptor 1. Due to the presence of the guiding dAb in most cases dimers gave a positive ELISA signal, therefore off rate determination was examined by Biacore.

1.3.2 Biacore

Biacore analysis was conducted for TAR1-5 and TAR2h-5 clones. For screening, Human TNFα was coupled to a CM5 chip at high density (approximately 10000 RUs). 50 µl of Human TNFα(50 µg/ml) was coupled to the chip at 5 µl/min in acetate buffer—pH5.5. Regeneration of the chip following analysis using the standard methods is not possible due to the instability of Human TNFα, therefore after each sample was analysed, the chip was washed for 10 mins with buffer.

For TAR1-5, clones supernatants from the round 2 selection were screened by Biacore. 48 clones were screened from each of the 3U, 5U and 7U libraries obtained using the following selection methods:

R1: 1 µg/ml human TNFα immunotube, R2 1 µg/ml human TNFα immunotube, overnight wash.

R1: 20 µg/ml human TNFα immunotube, R220 µg/ml human TNFα immunotube, overnight wash.

R1: 1 µg/ml human TNFα immunotube, R2 33 pmoles biotinylated human TNFα on beads.

R1: 20 µg/ml human TNFα immunotube, R2 33 pmoles biotinylated human TNFα beads.

For screening, human p55 TNF receptor was coupled to a CM5 chip at high density (approximately 4000 RUs). 100 µl of human p55 TNF receptor (10 µg/ml) was coupled to the chip at 5 µl/min in acetate buffer—pH5.5. Standard regeneration conditions were examined (glycine pH2 or pH3) but in each case antigen was removed from the surface of the chip therefore as with TNFα, therefore after each sample was analysed, the chip was washed for 10 mins with buffer.

For TAR2-5, clones supernatants from the round 2 selection were screened.

48 clones were screened from each of the 3U, 5U and 7U libraries, using the following selection methods:

R1: 1 µg/ml human p55 TNF receptor immunotube, R2 1 µg/ml human p55 TNF receptor immunotube, overnight wash.

R1: 10 µg/ml human p55 TNF receptor immunotube, R210 µg/ml human p55 TNF receptor immunotube, overnight wash.

1.3.3 Receptor and Cell Assays

The ability of the dimers to neutralize in the receptor assay was conducted as follows:

Receptor Binding

Anti-TNF dAbs were tested for the ability to inhibit the binding of TNF to recombinant TNF receptor 1 (p55). Briefly, Maxisorp plates were incubated overnight with 30 mg/ml anti-human Fc mouse monoclonal antibody (Zymed, San Francisco, USA). The wells were washed with phosphate buffered saline (PBS) containing 0.05% Tween-20 and then blocked with 1% BSA in PBS before being incubated with 100 ng/ml TNF receptor 1 Fc fusion protein (R&D Systems, Minneapolis, USA). Anti-TNF dAb was mixed with TNF which was added to the washed wells at a final concentration of 10 ng/ml. TNF binding was detected with 0.2 mg/ml biotinylated anti-TNF antibody (HyCult biotechnology, Uben, Netherlands) followed by 1 in 500 dilution of horse radish peroxidase labelled streptavidin (Amersham Biosciences, UK) and then incubation with TMB substrate (KPL, Gaithersburg, USA). The reaction was stopped by the addition of HCl and the absorbance was read at 450 nm. Anti-TNF dAb activity lead to a decrease in TNF binding and therefore a decrease in absorbance compared with the TNF only control.

L929 Cytotoxicity Assay

Anti-TNF dAbs were also tested for the ability to neutralise the cytotoxic activity of TNF on mouse L929 fibroblasts (Evans, T. (2000) Molecular Biotechnology 15, 243-248). Briefly, L929 cells plated in microtiter plates were incubated overnight with anti-TNF dAb, 100 pg/ml TNF and 1 mg/ml actinomycin D (Sigma, Poole, UK). Cell viability was measured by reading absorbance at 490 nm following an incubation with [3-(4,5-dimethylthiazol-2-yl)-5-(3-carboxymethoxyphenyl)-2-(4-sulfophenyl)-2H-tetrazolium (Promega, Madison, USA). Anti-TNF dAb activity lead to a decrease in TNF cytotoxicity and therefore an increase in absorbance compared with the TNF only control.

In the initial screen, supernatants prepared for Biacore analysis, described above, were also used in the receptor assay. Further analysis of selected dimers was also conducted in the receptor and cell assays using purified proteins.

HeLa IL-8 Assay

Anti-TNFR1 or anti-TNF alpha dAbs were tested for the ability to neutralize the induction of IL-8 secretion by TNF in HeLa cells (method adapted from that of Akeson, L. et al (1996) Journal of Biological Chemistry 271, 30517-30523, describing the induction of IL-8 by IL-1 in HUVEC; here we look at induction by human TNF alpha and we use HeLa cells instead of the HUVEC cell line). Briefly, HeLa cells plated in microtitre plates were incubated overnight with dAb and 300 pg/ml TNF. Post incubation the supernatant was aspirated off the cells and IL-8 concentration measured via a sandwich ELISA (R&D Systems). Anti-TNFR1 dAb activity lead to a decrease in IL-8 secretion into the supernatant compared with the TNF only control.

The L929 assay is used throughout the following experiments; however, the use of the HeLa IL-8 assay is preferred to measure anti-TNF receptor 1 (p55) ligands; the presence of mouse p55 in the L929 assay poses certain limitations in its use.

1.4 Sequence Analysis

Dimers that proved to have interesting properties in the Biacore and the receptor assay screens were sequenced. Sequences are detailed in the sequence listing.

1.5 Formatting 1.5.1 TAR1-5-19 Dimers

The TAR1-5 dimers that were shown to have good neutralisation properties were re-formatted and analysed in the cell and receptor assays. The TAR1-5 guiding dAb was substituted with the affinity matured clone TAR1-5-19. To achieve this TAR1-5 was cloned out of the individual dimer pair and substituted with TAR1-5-19 that had been amplified by PCR. In addition, TAR1-5-19 homodimers were also constructed in the 3U, 5U and 7U vectors. The N terminal copy of the gene was amplified by PCR and cloned as described above and the C-terminal gene fragment was cloned using existing SalI and NotI restriction sites.

1.5.2 Mutagenesis

The amber stop codon present in dAb2, one of the C-terminal dAbs in the TAR1-5 dimer pairs was mutated to a glutamine by site-directed mutagenesis.

1.5.3 Fabs

The dimers containing TAR1-5 or TAR1-5-19 were reformatted into Fab expression vectors. dAbs were cloned into expression vectors containing either the CK or CH genes using SfiI and NotI restriction sites and verified by sequence analysis. The CK vector is derived from a pUC based ampicillin resistant vector and the CH vector is derived from a pACYC chloramphenicol resistant vector. For Fab expression the dAb-CH and dAb-CK constructs were co-transformed into HB2151 cells and grown in 2×TY containing 0.1% glucose, 100 µg/ml ampicillin and 10 µg/ml chloramphenicol.

1.5.3 Hinge Dimerisation

Dimerisation of dAbs via cysteine bond formation was examined. A short sequence of amino acids EPKSGDKTH-TCPPCP (SEQ ID NO: 25) a modified form of the human IgGC1 hinge was engineered at the C terminal region on the dAb. An oligo linker encoding for this sequence was synthesised and annealed, as described previously. The linker was cloned into the pEDA vector containing TAR1-5-19 using Xho1 and Not1 restriction sites. Dimerisation occurs in situ in the periplasm.

1.6 Expression and Purification 1.6.1 Expression

Supernatants were prepared in the 2 ml, 96-well plate format for the initial screening as described previously. Following the initial screening process selected dimers were analysed further. Dimer constructs were expressed in TOP10F' or HB2151 cells as supernatants. Briefly, an individual colony from a freshly streaked plate was grown overnight at 37° C. in 2×TY with 100 µg/ml ampicillin and 1% glucose. A 1/100 dilution of this culture was inoculated into 2×TY with 100 µg/ml ampicillin and 0.1% glucose and grown at 37° C. shaking until OD600 was approximately 0.9. The culture was then induced with 1 mM IPTG overnight at 30° C. The cells were removed by centrifugation and the supernatant purified with protein A or L agarose.

Fab and cysteine hinge dimers were expressed as periplasmic proteins in HB2152 cells. A 1/100 dilution of an overnight culture was inoculated into 2×TY with 0.1% glucose and the appropriate antibiotics and grown at 30° C. shaking until OD600 was approximately 0.9. The culture was then induced with 1 mM IPTG for 3-4 hours at 25° C. The cells were harvested by centrifugation and the pellet resuspended in periplasmic preparation buffer (30 mM Tris-HCl pH8.0, 1 mM EDTA, 20% sucrose). Following centrifugation the supernatant was retained and the pellet resuspended in 5 mM MgSO$_4$. The supernatant was harvested again by centrifugation, pooled and purified.

1.6.2 Protein A/L Purification

Optimisation of the purification of dimer proteins from Protein L agarose (Affitech, Norway) or Protein A agarose (Sigma, UK) was examined. Protein was eluted by batch or by column elution using a peristaltic pump. Three buffers were examined 0.1M Phosphate-citrate buffer pH2.6, 0.2M *Glycine* pH2.5 and 0.1M *Glycine* pH2.5. The optimal condition was determined to be under peristaltic pump conditions using 0.1M *Glycine* pH2.5 over 10 column volumes. Purification from protein A was conducted peristaltic pump conditions using 0.1M *Glycine* pH2.5.

1.6.3 FPLC Purification

Further purification was carried out by FPLC analysis on the AKTA Explorer 100 system (Amersham Biosciences Ltd). TAR1-5 and TAR1-5-19 dimers were fractionated by cation exchange chromatography (1 ml Resource S—Amersham Biosciences Ltd) eluted with a 0-1M NaCl gradient in 50 mM acetate buffer pH4. Hinge dimers were purified by ion exchange (1 ml Resource Q Amersham Biosciences Ltd) eluted with a 0-1M NaCl gradient in 25 mMTris HCl pH 8.0. Fabs were purified by size exclusion chromatography using a superose 12 (Amersham Biosciences Ltd) column run at a flow rate of 0.5 ml/min in PBS with 0.05% tween. Following purification samples were concentrated using vivaspin 5K cut off concentrators (Vivascience Ltd).

2.0 Results 2.1 TAR1-5 Dimers

6×96 clones were picked from the round 2 selection encompassing all the libraries and selection conditions. Supernatant preps were made and assayed by antigen and Protein L ELISA, Biacore and in the receptor assays. In ELISAs, positive binding clones were identified from each selection method and were distributed between 3U, 5U and 7U libraries. However, as the guiding dAb is always present, it was not possible to discriminate between high and low affinity binders by this method therefore Biacore analysis was conducted.

Biacore analysis was conducted using the 2 ml supernatants. Biacore analysis revealed that the dimer Koff rates were vastly improved compared to monomeric TAR1-5. Monomer Koff rate was in the range of $10^{-1}$M compared with dimer Koff rates which were in the range of $10^{-3}$-$10^{-4}$M. Sixteen clones that appeared to have very slow off rates were selected, these came from the 3U, 5U and 7U libraries and were sequenced. In addition, the supernatants were analysed for the ability to neutralise human TNFα in the receptor assay.

6 lead clones (d1-d6 below) that neutralised in these assays and have been sequenced. The results shows that out of the 6 clones obtained, there are only 3 different second dAbs (dAb1, dAb2 and dAb3); however where the second dAb is found more than once they are linked with different length linkers.

TAR1-5d1: 3U linker $2^{nd}$ dAb=dAb1-1 µg/ml Ag immunotube overnight wash

TAR1-5d2: 3U linker $2^{nd}$ dAb=dAb2-1 µg/ml Ag immunotube overnight wash

TAR1-5d3: 5U linker $2^{nd}$ dAb=dAb2-1 µg/ml Ag immunotube overnight wash

TAR1-5d4: 5U linker $2^{nd}$ dAb=dAb3-20 µg/ml Ag immunotube overnight wash

TAR1-5d5: 5U linker $2^{nd}$ dAb=dAb1-20 µg/ml Ag immunotube overnight wash

TAR1-5d6:7 U linker $2^{nd}$ dAb=dAb1-R1:1 µg/ml Ag immunotube overnight wash, R2:beads The six lead clones were examined further. Protein was produced from the periplasm and supernatant, purified with protein L agarose and examined in the cell and receptor assays. The levels of neutralisation were variable (Table 1). The optimal conditions for protein preparation were determined. Protein produced from HB2151 cells as supernatants gave the highest yield (approximately 10 mgs/L of culture). The supernatants were incubated with protein L agarose for 2 hrs at room temperature or overnight at 4° C. The beads were washed with PBS/NaCl and packed onto an FPLC column using a peristaltic pump. The beads were washed with 10 column volumes of PBS/NaCl and eluted with 0.1M glycine pH2.5. In general, dimeric protein is eluted after the monomer.

TAR1-5d1-6 dimers were purified by FPLC. Three species were obtained, by FPLC purification and were identified by SDS PAGE. One species corresponds to monomer and the other two species corresponds to dimers of different sizes. The larger of the two species is possibly due to the presence of C terminal tags. These proteins were examined in the receptor assay. The data presented in the Table 1 represents the optimum results obtained from the two dimeric species (FIG. 11).

The three second dAbs from the dimer pairs (i.e., dAb1, dAb2 and dAb3) were cloned as monomers and examined by ELISA and in the cell and receptor assay. All three dAbs bind specifically to TNF by antigen ELISA and do not cross react with plastic or BSA. As monomers, none of the dAbs neutralise in the cell or receptor assays.

2.1.2 TAR1-5-19 Dimers

TAR1-5-19 was substituted for TAR1-5 in the six lead clones. Analysis of all TAR1-5-19 dimers in the cell and receptor assays was conducted using total protein (protein L purified only) unless otherwise stated (Table 2). TAR1-5-19d4 and TAR1-5-19d3 have the best $ND_{50}$ (~5 nM) in the cell assay, this is consistent with the receptor assay results and is an improvement over TAR1-5-19 monomer ($ND_{50}$~30 nM). Although purified TAR1-5 dimers give variable results in the receptor and cell assays, TAR1-5-19 dimers were more consistent. Variability was shown when using different elution buffers during the protein purification. Elution using 0.1 M Phosphate-citrate buffer pH2.6 or 0.2 M *Glycine* pH2.5, although removing all protein from the protein L agarose in most cases rendered it less functional.

TAR1-5-19d4 was expressed in the fermenter and purified on cation exchange FPLC to yield a completely pure dimer. As with TAR1-5d4 three species were obtained, by FPLC purification corresponding to monomer and two dimer species. This dimer was amino acid sequenced. TAR1-5-19 monomer and TAR1-5-19d4 were then examined in the receptor assay and the resulting IC50 for monomer was 30 nM and for dimer was 8 nM. The results of the receptor assay comparing TAR1-5-19 monomer, TAR1-5-19d4 and TAR1-5d4 is shown in FIG. 10.

TAR1-5-19 homodimers were made in the 3U, 5U and 7U vectors, expressed and purified on Protein L. The proteins were examined in the cell and receptor assays and the resulting $IC_{50}$s (for receptor assay) and $ND_{50}$s (for cell assay) were determined (Table 3, FIG. 12).

2.2 Fabs

TAR1-5 and TAR1-5-19 dimers were also cloned into Fab format, expressed and purified on protein L agarose. Fabs were assessed in the receptor assays (Table 4). The results showed that for both TAR1-5-19 and TAR1-5 dimers the neutralisation levels were similar to the original $Gly_4Ser$ linker (SEQ ID NO: 1) dimers from which they were derived. A TAR1-5-19 Fab where TAR1-5-19 was displayed on both CH and CK was expressed, protein L purified and assessed in the receptor assay. The resulting IC50 was approximately 1 nM.

2.3 TAR1-27 dimers

3×96 clones were picked from the round 2 selection encompassing all the libraries and selection conditions. 2 ml supernatant preps were made for analysis in ELISA and bioassays. Antigen ELISA gave 71 positive clones. The receptor assay of crude supernatants yielded 42 clones with inhibitory properties (TNF binding 0-60%). In the majority of cases inhibitory properties correlated with a strong ELISA signal. 42 clones were sequenced, 39 of these have unique second dAb sequences. The 12 dimers that gave the best inhibitory properties were analysed further.

The 12 neutralising clones were expressed as 200 ml supernatant preps and purified on protein L. These were assessed by protein L and antigen ELISA, Biacore and in the receptor assay. Strong positive ELISA signals were obtained in all cases. Biacore analysis revealed all clones to have fast on and off rates. The off rates were improved compared to monomeric TAR1-27, however the off rate of TAR1-27 dimers was faster (Koff is approximately in the range of $10^{-1}$ and $10^{-2}$M) than the TAR1-5 dimers examined previously (Koff is approximately in the range of $10^{-3}$-$10^{-4}$M). The stability of the purified dimers was questioned and therefore in order to improve stability, the addition on 5% glycerol, 0.5% Triton X100 or 0.5% NP40 (Sigma) was included in the purification of 2 TAR1-27 dimers (d2 and d16). Addition of NP40 or Triton X100™ improved the yield of purified product approximately 2 fold. Both dimers were assessed in the receptor assay. TAR1-27d2 gave IC50 of ~30 nM under all purification conditions. TAR1-27d16 showed no neutralisation effect when purified without the use of stabilising agents but gave an IC50 of ~50 nM when purified under stabilising conditions. No further analysis was conducted.

2.4 TAR2-5 Dimers

3×96 clones were picked from the second round selections encompassing all the libraries and selection conditions. 2 ml supernatant preps were made for analysis. Protein A and antigen ELISAs were conducted for each plate. 30 interesting clones were identified as having good off-rates by Biacore (Koff ranges between $10^{-2}$-$10^{-3}$M). The clones were sequenced and 13 unique dimers were identified by sequence analysis.

TABLE 1

TAR1-5 dimers

| Dimer | Cell type | Purification | Protein Fraction | Elution conditions | Receptor/Cell assay |
|---|---|---|---|---|---|
| TAR1-5d1 | HB2151 | Protein L + FPLC | small dimeric species | 0.1M glycine pH 2.5 | RA ~30 nM |
| TAR1-5d2 | HB2151 | Protein L + FPLC | small dimeric species | 0.1M glycine pH 2.5 | RA ~50 nM |
| TAR1-5d3 | HB2151 | Protein L + FPLC | large dimeric species | 0.1M glycine pH 2.5 | RA ~300 nM |
| TAR1-5d4 | HB2151 | Protein L + FPLC | small dimeric species | 0.1M glycine pH 2.5 | RA ~3 nM |
| TAR1-5d5 | HB2151 | Protein L + FPLC | large dimeric species | 0.1M glycine pH 2.5 | RA ~200 nM |

TABLE 1-continued

TAR1-5 dimers

| Dimer | Cell type | Purification | Protein Fraction | Elution conditions | Receptor/Cell assay |
|---|---|---|---|---|---|
| TAR1-5d6 | HB2151 | Protein L + FPLC | Large dimeric species | 0.1M glycine pH 2.5 | RA ~100 nM |

*note dimer 2 and dimer 3 have the same second dAb (called dAb2), however have different linker lengths (d2 = (Gly$_4$Ser)$_3$ (SEQ ID NO: 20), d3 = (Gly$_4$Ser)$_3$ (SEQ ID NO: 20)). dAb1 is the partner dAb to dimers 1, 5 and 6. dAb3 is the partner dAb to dimer4. None of the partner dAbs neutralise alone. FPLC purification is by cation exchange unless otherwise stated. The optimal dimeric species for each dimer obtained by FPLC was determined in these assays.

TABLE 2

TAR1-5-19 dimers

| Dimer | Cell type | Purification | Protein Fraction | Elution conditions | Receptor/Cell assay |
|---|---|---|---|---|---|
| TAR1-5-19 d1 | TOP10F' | Protein L | Total protein | 0.1M glycine pH 2.0 | RA ~15 nM |
| TAR1-5-19 d2 (no stop codon) | TOP10F' | Protein L | Total protein | 0.1M glycine pH 2.0 + 0.05% NP40 | RA ~2 nM |
| TAR1-5-19d3 (no stop codon) | TOP10F' | Protein L | Total protein | 0.1M glycine pH 2.5 + 0.05% NP40 | RA ~8 nM |
| TAR1-5-19d4 | TOP10F' | Protein L + FPLC | FPLC purified fraction | 0.1M glycine pH 2.0 | RA ~2-5 nM CA~12 nM |
| TAR1-5-19d5 | TOP10F' | Protein L | Total protein | 0.1M glycine pH 2.0 + NP40 | RA ~8 nM CA~10 nM |
| TAR1-5-19 d6 | TOP10F' | Protein L | Total protein | 0.1M glycine pH 2.0 | RA ~10 nM |

TABLE 3

TAR1-5-19 homodimers

| Dimer | Cell type | Purification | Protein Fraction | Elution conditions | Receptor/Cell assay |
|---|---|---|---|---|---|
| TAR1-5-19 3U homodimer | HB2151 | Protein L | Total protein | 0.1M glycine pH 2.5 | RA ~20 nM CA ~30 nM |
| TAR1-5-19 5U homodimer | HB2151 | Protein L | Total protein | 0.1M glycine pH 2.5 | RA ~2 nM CA ~3 nM |
| TAR1-5-19 7U homodimer | HB2151 | Protein L | Total protein | 0.1M glycine pH 2.5 | RA ~10 nM CA ~15 nM |
| TAR1-5-19 cys hinge | HB2151 | Protein L + FPLC | FPLC purified dimer fraction | 0.1M glycine pH 2.5 | RA ~2 nM |
| TAR1-5-19CH/TAR1-5-19 CK | HB2151 | Protein | Total protein | 0.1M glycine pH 2.5 | RA ~1 nM |

TABLE 4

TAR1-5/TAR1-5-19 Fabs

| Dimer | Cell type | Purification | Protein Fraction | Elution conditions | Receptor/Cell assay |
|---|---|---|---|---|---|
| TAR1-5CH/ dAb1 CK | HB2151 | Protein L | Total protein | 0.1M citrate pH 2.6 | RA ~90 nM |
| TAR1-5CH/ dAb2 CK | HB2151 | Protein L | Total protein | 0.1M glycine pH 2.5 | RA ~30 nM CA ~60 nM |
| dAb3CH/ TAR1-5CK | HB2151 | Protein L | Total protein | 0.1M citrate pH 2.6 | RA ~100 nM |
| TAR1-5-19CH/ dAb1 CK | HB2151 | Protein L | Total protein | 0.1M glycine pH 2.0 | RA ~6 nM |
| dAb1 CH/ TAR1-5-19CK | HB2151 | Protein L | 0.1M glycine pH 2.0 | Myc/flag | RA ~6 nM |
| TAR1-5-19CH/ dAb2 CK | HB2151 | Protein L | Total protein | 0.1M glycine pH 2.0 | RA ~8 nM CA ~12 nM |

TABLE 4-continued

TAR1-5/TAR1-5-19 Fabs

| Dimer | Cell type | Purification | Protein Fraction | Elution conditions | Receptor/Cell assay |
|---|---|---|---|---|---|
| TAR1-5-19CH/ dAb3CK | HB2151 | Protein L | Total protein | 0.1M glycine pH 2.0 | RA ~3 nM |

Example 7 dAb Dimerisation by Terminal Cysteine Linkage

Summary

For dAb dimerisation, a free cysteine has been engineered at the C-terminus of the protein. When expressed the protein forms a dimer which can be purified by a two step purification method.
PCR Construction of TAR1-5-19CYS Dimer
See example 8 describing the dAb trimer. The trimer protocol gives rise to a mixture of monomer, dimer and trimer.
Expression and Purification of TAR1-5-19CYS Dimer
The dimer was purified from the supernatant of the culture by capture on Protein L agarose as outlined in the example 8.
Separation of TAR1-5-19CYS Monomer from the TAR1-5-19CYS Dimer
Prior to cation exchange separation, the mixed monomer/dimer sample was buffer exchanged into 50 mM sodium acetate buffer pH 4.0 using a PD-10 column (Amersham Pharmacia), following the manufacturer's guidelines. The sample was then applied to a 1 mL Resource S cation exchange column (Amersham Pharmacia), which had been pre-equilibrated with 50 mM sodium acetate pH 4.0. The monomer and dimer were separated using the following salt gradient in 50 mM sodium acetate pH 4.0:
150 to 200 mM sodium chloride over 15 column volumes
200 to 450 mM sodium chloride over 10 column volumes
450 to 1000 mM sodium chloride over 15 column volumes
Fractions containing dimer only were identified using SDS-PAGE and then pooled and the pH increased to 8 by the addition of ⅕ volume of 1M Tris pH 8.0.
In vitro Functional Binding Assay: TNF Receptor Assay and Cell Assay
The affinity of the dimer for human TNFα was determined using the TNF receptor and cell assay. IC50 in the receptor assay was approximately 0.3-0.8 nM; ND50 in the cell assay was approximately 3-8 nM.

Other Possible TAR1-5-19CYS Dimer Formats
PEG Dimers and Custom Synthetic Maleimide Dimers
Nektar (Shearwater) offer a range of bi-maleimide PEGs [mPEG2-(MAL)2 or mPEG-(MAL)2] which would allow the monomer to be formatted as a dimer, with a small linker separating the dAbs and both being linked to a PEG ranging in size from 5 to 40 Kda. It has been shown that the 5 Kda mPEG-(MAL)$_2$ (i.e., [TAR1-5-19]-Cys-maleimide-PEG×2, wherein the maleimides are linked together in the dimer) has an affinity in the TNF receptor assay of ~1-3 nM. Also the dimer can also be produced using TMEA (Tris[2-maleimidoethyl]amine) (Pierce Biotechnology) or other bi-functional linkers.
It is also possible to produce the disulphide dimer using a chemical coupling procedure using 2,2'-dithiodipyridine (Sigma Aldrich) and the reduced monomer.
Addition of a Polypeptide Linker or Hinge to the C-Terminus of the dAb.
A small linker, either (Gly$_4$Ser)$_n$ (SEQ ID NO: 26) where n=1 to 10, e.g., 1, 2, 3, 4, 5, 6 or 7, an immunoglobulin (e.g., IgG hinge region or random peptide sequence (e.g., selected from a library of random peptide sequences) can be engineered between the dAb and the terminal cysteine residue. This can then be used to make dimers as outlined above.

Example 8 dAb Trimerisation

Summary

For dAb trimerisation, a free cysteine is required at the C-terminus of the protein. The cysteine residue, once reduced to give the free thiol, can then be used to specifically couple the protein to a trimeric maleimide molecule, for example TMEA (Tris[2-maleimidoethyl]amine).
PCR Construction of TAR1-5-19CYS
The following oligonucleotides were used to specifically PCR TAR1-5-19 with a SalI and BamHI sites for cloning and also to introduce a C-terminal cysteine residue:

```
        SalI
      ~~~~~~~~
      Trp Ser Ala Ser Thr Asp* Ile Gln Met Thr Gln Ser Pro Ser Ser Leu Ser Ala Ser Val
   1 TGG AGC GCG TCG ACG GAC ATC CAG ATG ACC CAG TCT CCA TCC TCT CTG TCT GCA TCT GTA
     ACC TCG CGC AGC TGC CTG TAG GTC TAC TGG GTC AGA GGT AGG AGA GAC AGA CGT AGA CAT

Gly Asp Arg Val Thr Ile Thr Cys Arg Ala Ser Gln Ser Ile Asp Ser Tyr Leu His Trp
  61 GGA GAC CGT GTC ACC ATC ACT TGC CGG GCA AGT CAG AGC ATT GAT AGT TAT TTA CAT TGG
     CCT CTG GCA CAG TGG TAG TGA ACG GCC CGT TCA GTC TCG TAA CTA TCA ATA AAT GTA ACC

Tyr Gln Gln Lys Pro Gly Lys Ala Pro Lys Leu Leu Ile Tyr Ser Ala Ser Glu Leu Gln
 121 TAC CAG CAG AAA CCA GGG AAA GCC CCT AAG CTC CTG ATC TAT AGT GCA TCC GAG TTG CAA
     ATG GTC GTC TTT GGT CCC TTT CGG GGA TTC GAG GAC TAG ATA TCA CGT AGG CTC AAC GTT

Ser Gly Val Pro Ser Arg Phe Ser Gly Ser Gly Ser Gly Thr Asp Phe Thr Leu Thr Ile
 181 AGT GGG GTC CCA TCA CGT TTC AGT GGC AGT GGA TCT GGG ACA GAT TTC ACT CTC ACC ATC
     TCA CCC CAG GGT AGT GCA AAG TCA CCG TCA CCT AGA CCC TGT CTA AAG TGA GAG TGG TAG
```

-continued

```
    Ser Ser Leu Gln Pro Glu Asp Phe Ala Thr Tyr Tyr Cys Gln Gln Val Val Trp Arg Pro
241 AGC AGT CTG CAA CCT GAA GAT TTT GCT ACG TAC TAC TGT CAA CAG GTT GTG TGG CGT CCT
    TCG TCA GAC GTT GGA CTT CTA AAA CGA TGC ATG ATG ACA GTT GTC CAA CAC ACC GCA GGA

BamHI
                                                                        ~~~~~~~~
    Phe Thr Phe Gly Gln Gly Thr Lys Val Glu Ile Lys Arg Cys * * Gly Ser Gly
301 TTT ACG TTC GGC CAA GGG ACC AAG GTG GAA ATC AAA CGG TGC TAA TAA GGA TCC GGC
    AAA TGC AAG CCG GTT CCC TGG TTC CAC CTT TAG TTT GCC ACG ATT ATT CCT AGG CCG
```

(* start of TAR1-5-19CYS sequence. Nucleodide sequence disclosed as
SEQ ID NO: 27 and the amino acid sequence disclosed as SEQ ID NO: 28.)

Forward primer
5'-TGGAGCGCGTCGACGGACATCCAGATGACCCAGTCTCCA-3' (SEQ ID NO: 29)

Reverse primer
5'-TTAGCAGCCGGATCCTTATTAGCACCGTTTGATTTCCAC-3' (SEQ ID NO: 30)

The PCR reaction (50 µL volume) was set up as follows: 200 µM dNTPs, 0.4 µM of each primer, 5 µL of 10× PfuTurbo buffer (Stratagene), 100 ng of template plasmid (encoding TAR1-5-19), 1 µL of PfuTurbo enzyme (Stratagene) and the volume adjusted to 50 µL using sterile water. The following PCR conditions were used: initial denaturing step 94° C. for 2 mins, then 25 cycles of 94° C. for 30 secs, 64° C. for 30 sec and 72° C. for 30 sec. A final extension step was also included of 72° C. for 5 mins. The PCR product was purified and digested with SalI and BamHI and ligated into the vector which had also been cut with the same restriction enzymes. Correct clones were verified by DNA sequencing.

Expression and Purification of TAR1-5-19CYS

TAR1-5-19CYS vector was transformed into BL21 (DE3) pLysS chemically competent cells (Novagen) following the manufacturer's protocol. Cells carrying the dAb plasmid were selected for using 100 µg/mL carbenicillin and 37 µg/mL chloramphenicol. Cultures were set up in 2 L baffled flasks containing 500 mL of terrific broth (Sigma-Aldrich), 100 µg/mL carbenicillin and 37 µg/mL chloramphenicol. The cultures were grown at 30° C. at 200 rpm to an O.D.600 of 1-1.5 and then induced with 1 mM IPTG (isopropyl-beta-D-thiogalactopyranoside, from Melford Laboratories). The expression of the dAb was allowed to continue for 12-16 hrs at 30° C. It was found that most of the dAb was present in the culture media. Therefore, the cells were separated from the media by centrifugation (8,000×g for 30 mins), and the supernatant used to purify the dAb. Per liter of supernatant, 30 mL of Protein L agarose (Affitech) was added and the dAb allowed to batch bind with stirring for 2 hours. The resin was then allowed to settle under gravity for a further hour before the supernatant was siphoned off. The agarose was then packed into a XK 50 column (Amersham Pharmacia) and was washed with 10 column volumes of PBS. The bound dAb was eluted with 100 mM glycine pH 2.0 and protein containing fractions were then neutralized by the addition of ⅕ volume of 1 M Tris pH 8.0. Per liter of culture supernatant 20 mg of pure protein was isolated, which contained a 50:50 ratio of monomer to dimer.

Trimerisation of TAR1-5-19CYS 2.5 ml of 100 µM TAR1-5-19CYS was reduce with 5 mM dithiothreitol and left at room temperature for 20 minutes. The sample was then buffer exchanged using a PD-10 column (Amersham Pharmacia). The column had been pre-equilibrated with 5 mM EDTA, 50 mM sodium phosphate pH 6.5, and the sample applied and eluted following the manufactures guidelines. The sample was placed on ice until required. TMEA (Tris[2-maleimidoethyl]amine) was purchased from Pierce Biotechnology. A 20 mM stock solution of TMEA was made in 100% DMSO (dimethyl sulphoxide). It was found that a concentration of TMEA greater than 3:1 (molar ratio of dAb:TMEA) caused the rapid precipitation and cross-linking of the protein. Also the rate of precipitation and cross-linking was greater as the pH increased. Therefore using 100 µM reduced TAR1-5-19CYS, 25 HM TMEA was added to trimerise the protein and the reaction allowed to proceed at room temperature for two hours. It was found that the addition of additives such as glycerol or ethylene glycol to 20% (v/v), significantly reduced the precipitation of the trimer as the coupling reaction proceeded. After coupling, SDS-PAGE analysis showed the presence of monomer, dimer and trimer in solution.

Purification of the Trimeric TAR1-5-19CYS

40 µL of 40% glacial acetic acid was added per mL of the TMEA-TAR1-5-19cys reaction to reduce the pH to ~4. The sample was then applied to a 1 mL Resource S cation exchange column (Amersham Pharmacia), which had been pre-equilibrated with 50 mM sodium acetate pH 4.0. The dimer and trimer were partially separated using a salt gradient of 340 to 450 mM Sodium chloride, 50 mM sodium acetate pH 4.0 over 30 column volumes. Fractions containing trimer only were identified using SDS-PAGE and then pooled and the pH increased to 8 by the addition of ⅕ volume of 1M Tris pH 8.0. To prevent precipitation of the trimer during concentration steps (using 5K cut off Viva spin concentrators; Vivascience), 10% glycerol was added to the sample.

In vitro Functional Binding Assay: TNF Receptor Assay and Cell Assay

The affinity of the trimer for human TNFα was determined using the TNF receptor and cell assay. IC50 in the receptor assay was 0.3 nM; ND50 in the cell assay was in the range of 3 to 10 nM (e.g., 3 nM).

Other Possible TAR1-5-19CYS Trimer Formats

TAR1-5-19CYS may also be formatted into a trimer using the following reagents:

PEG Trimers and Custom Synthetic Maleimide Trimers

Nektar (Shearwater) offer a range of multi arm PEGs, which can be chemically modified at the terminal end of the PEG. Therefore using a PEG trimer with a maleimide functional group at the end of each arm would allow the trimerisation of the dAb in a manner similar to that outlined above using TMEA. The PEG may also have the advantage in increasing the solubility of the trimer thus preventing the problem of aggregation. Thus, one could produce a dAb trimer in which each dAb has a C-terminal cysteine that is linked to a maleimide functional group, the maleimide functional groups being linked to a PEG trimer.

Addition of a Polypeptide Linker or Hinge to the C-Terminus of the dAb

A small linker, either (Gly$_4$Ser)$_n$ (SEQ ID NO: 26) where n=1 to 10, e.g., 1, 2, 3, 4, 5, 6 or 7, an immunoglobulin (e.g., IgG hinge region or random peptide sequence (e.g., selected from a library of random peptide sequences) could be engineered between the dAb and the terminal cysteine residue. When used to make multimers (e.g., dimers or trimers), this again would introduce a greater degree of flexibility and distance between the individual monomers, which may improve the binding characteristics to the target, e.g., a multisubunit target such as human TNFα.

Example 9

Selection of a Collection of Single Domain Antibodies (dAbs) Directed Against Human Serum Albumin (HSA) and Mouse Serum Albumin (MSA)

This example explains a method for making a single domain antibody (dAb) directed against serum albumin. Selection of dAbs against both mouse serum albumin (MSA) and human serum albumin (HSA) is described. Three human phage display antibody libraries were used in this experiment, each based on a single human framework for V$_H$ (see FIG. 13: sequence of dummy V$_H$ based on V3-23/DP47 and JH4b) or V$_κ$ (see FIG. 15: sequence of dummy V$_κ$ based on o12/o2/DPK9 and Jk1) with side chain diversity encoded by NNK codons incorporated in complementarity determining regions (CDR1, CDR2 and CDR3).

Library 1 (V$_H$):
Diversity at positions: H30, H31, H33, H35, H50, H52, H52a, H53, H55, H56, H58, H95, H97, H98.
Library size: 6.2×10$^9$
Library 2 (V$_H$):
Diversity at positions: H30, H31, H33, H35, H50, H52, H52a, H53, H55, H56, H58, H95, H97, H98, H99, H100, H100a, H100b.
Library size: 4.3×10$^9$
Library 3 (Vκ):
Diversity at positions: L30, L31, L32, L34, L50, L53, L91, L92, L93, L94, L96
Library size: 2×10$^9$ The V$_H$ and Vκ libraries have been preselected for binding to generic ligands protein A and protein L respectively so that the majority of clones in the unselected libraries are functional. The sizes of the libraries shown above correspond to the sizes after preselection.

Two rounds of selection were performed on serum albumin using each of the libraries separately. For each selection, antigen was coated on immunotube (nunc) in 4 ml of PBS at a concentration of 100 μg/ml. In the first round of selection, each of the three libraries was panned separately against HSA (Sigma) and MSA (Sigma). In the second round of selection, phage from each of the six first round selections was panned against (i) the same antigen again (e.g. 1$^{st}$ round MSA, 2$^{nd}$ round MSA) and (ii) against the reciprocal antigen (e.g. 1$^{st}$ round MSA, 2$^{nd}$ round HSA) resulting in a total of twelve 2$^{nd}$ round selections. In each case, after the second round of selection 48 clones were tested for binding to HSA and MSA. Soluble dAb fragments were produced as described for scFv fragments by Harrison et al, Methods Enzymol. 1996; 267: 83-109 and standard ELISA protocol was followed (Hoogenboom et al. (1991) Nucleic Acids Res., 19: 4133) except that 2% tween PBS was used as a blocking buffer and bound dAbs were detected with either protein L-HRP (Sigma) (for the Vκs) and protein A-HRP (Amersham Pharmacia Biotech) (for the V$_H$s).

dAbs that gave a signal above background indicating binding to MSA, HSA or both were tested in ELISA insoluble form for binding to plastic alone but all were specific for serum albumin. Clones were then sequenced (see Table 5) revealing that 21 unique dAb sequences had been identified. The minimum similarity (at the amino acid level) between the Vκ dAb clones selected was 86.25% ((69/80)×100; the result when all the diversified residues are different, e.g. clones 24 and 34). The minimum similarity between the V$_H$ dAb clones selected was 94% ((127/136)×100).

Next, the serum albumin binding dAbs were tested for their ability to capture biotinylated antigen from solution. ELISA protocol (as above) was followed except that ELISA plate was coated with 1 μg/ml protein L (for the Vκ clones) and 1 μg/ml protein A (for the V$_H$ clones). Soluble dAb was captured from solution as in the protocol and detection was with biotinylated MSA or HSA and streptavidin HRP. The biotinylated MSA and HSA had been prepared according to the manufacturer's instructions, with the aim of achieving an average of 2 biotins per serum albumin molecule. Twenty four clones were identified that captured biotinylated MSA from solution in the ELISA, Table 5. Two of these (clones 2 and 38 below) also captured biotinylated HSA. Next, the dAbs were tested for their ability to bind MSA coated on a CM5 Biacore chip. Eight clones were found that bound MSA on the Biacore.

TABLE 5

| dAb (all capture biotinylated MSA) | H or κ | CDR1 | CDR2 | CDR3 | Binds MSA in Biacore | Captures biotinylated HSA |
|---|---|---|---|---|---|---|
| V$_κ$ library 3 template (dummy) | κ | XXXLX | XASXLQS (SEQ ID NO: 49) | QQXXXXPXT (SEQ ID NO: 66) | | |
| 2, 4, 7, 41, | κ | SSYLN (SEQ ID NO: 31) | RASPLQS (SEQ ID NO: 50) | QQTYSVPPT (SEQ ID NO: 67) | ✓ | all 4 bind |
| 38, 54 46, 47, 52, | κ | SSYLN (SEQ ID NO: 31) | RASPLQS (SEQ ID NO: 50) | QQTYRIPPT (SEQ ID NO: 68) | ✓ | both bind |
| 56 | κ | FKSLK (SEQ ID NO: 32) | NASYLQS (SEQ ID NO: 51) | QQVYWPVT (SEQ ID NO: 69) | | |
| 13, 15 | κ | YYHLK (SEQ ID NO: 33) | KASTLQS (SEQ ID NO: 52) | QQVRKVPRT (SEQ ID NO: 70) | | |

TABLE 5-continued

| dAb (all capture biotinylated MSA) | H or κ CDR1 | CDR2 | CDR3 | Binds MSA in Biacore | Captures biotinylated HSA |
|---|---|---|---|---|---|
| 30, 35 | κ RRYLK (SEQ ID NO: 34) | QASVLQS (SEQ ID NO: 53) | QQGLYPPIT (SEQ ID NO: 71) | | |
| 19, | κ YNWLK (SEQ ID NO: 35) | RASSLQS (SEQ ID NO: 54) | QQNVVIPRT (SEQ ID NO: 72) | | |
| 22, | κ LWHLR (SEQ ID NO: 36) | HASLLQS (SEQ ID NO: 55) | QQSAVYPKT (SEQ ID NO: 73) | | |
| 23, | κ FRYLA (SEQ ID NO: 37) | HASHLQS (SEQ ID NO: 56) | QQRLLYPKT (SEQ ID NO: 74) | | |
| 24, | κ FYHLA (SEQ ID NO: 38) | PASKLQS (SEQ ID NO: 57) | QQRARWPRT (SEQ ID NO: 75) | | |
| 31, | κ IWHLN (SEQ ID NO: 39) | RASRLQS (SEQ ID NO: 58) | QQVARVPRT (SEQ ID NO: 76) | | |
| 33, | κ YRYLR (SEQ ID NO: 40) | KASSLQS (SEQ ID NO: 59) | QQYVGYPRT (SEQ ID NO: 77) | | |
| 34, | κ LKYLK (SEQ ID NO: 41) | NASHLQS (SEQ ID NO: 60) | QQTTYYPIT (SEQ ID NO: 78) | | |
| 53, | κ LRYLR (SEQ ID NO: 42) | KASWLQS (SEQ ID NO: 61) | QQVLYYPQT (SEQ ID NO: 79) | | |
| 11, | κ LRSLK (SEQ ID NO: 43) | AASRLQS (SEQ ID NO: 62) | QQVVYWPAT (SEQ ID NO: 80) | ✓ | |
| 12, | κ FRHLK (SEQ ID NO: 44) | AASRLQS (SEQ ID NO: 62) | QQVALYPKT (SEQ ID NO: 81) | ✓ | |
| 17, | κ RKYLR (SEQ ID NO: 45) | TASSLQS (SEQ ID NO: 63) | QQNLFWPRT (SEQ ID NO: 82) | ✓ | |
| 18, | κ RRYLN (SEQ ID NO: 46) | AASSLQS (SEQ ID NO: 64) | QQMLFYPKT (SEQ ID NO: 83) | ✓ | |
| 16, 21 | κ IKHLK (SEQ ID NO: 47) | GASRLQS (SEQ ID NO: 65) | QQGARWPQT (SEQ ID NO: 84) | ✓ | |
| 25, 26 | κ YYHLK (SEQ ID NO: 33) | KASTLQS (SEQ ID NO: 52) | QQVRKVPRT (SEQ ID NO: 70) | ✓ | |
| 27, | κ YKHLK (SEQ ID NO: 48) | NASHLQS (SEQ ID NO: 60) | QQVGRYPKT (SEQ ID NO: 85) | ✓ | |
| 55, | κ FKSLK (SEQ ID NO: 32) | NASYLQS (SEQ ID NO: 51) | QQVVYWPVT (SEQ ID NO: 69) | ✓ | |
| V$_H$ library 1 (and 2) template (dummy) | H XXYXXX | XIXXXGXXTXYADSVKG (SEQ ID NO: 88) | XXXX(XXXX)FDY | | |
| 8, 10 | H WVYQMD (SEQ ID NO: 86) | SISAFGAKTLYADSVKG (SEQ ID NO: 89) | LSGKFDY (SEQ ID NO: 91) | | |
| 36, | H WSYQMT (SEQ ID NO: 87) | SISSFGSSTLYADSVKG (SEQ ID NO: 90) | GRDHNYSLFDY (SEQ ID NO: 92) | | |

In all cases the frameworks were identical to the frameworks in the corresponding dummy sequence, with diversity in the CDRs as indicated in Table 5.

Of the eight clones that bound MSA on the Biacore, two clones that are highly expressed in E. coli (clones MSA16 and MSA26) were chosen for further study (see Example 10). Full nucleotide and amino acid sequences for MSA16 and 26 are given in FIG. 16.

Example 10

Determination of Affinity and Serum Half-Life in Mouse of MSA Binding dAbs MSA16 and MSA26

As described in US20060251644, one common method for determining binding affinity is by assessing the association and dissociation rate constants using a Biacore™ surface plasmon resonance system (Biacore, Inc.). A biosensor chip is activated for covalent coupling of the target according to the manufacturer's (Biacore) instructions. The target is then diluted and injected over the chip to obtain a signal in response units (RU) of immobilized material. Since the signal in RU is proportional to the mass of immobilized material, this represents a range of immobilized target densities on the matrix. Dissociation data are fit to a one-site model to obtain $k_{off}$+/−s.d. (standard deviation of measurements). Pseudo-first order rate constant (Kd's) are calculated for each association curve, and plotted as a function of protein concentration to obtain $k_{on}$+/−s.e. (standard error of fit). Equilibrium dissociation constants for binding, Kd's, are calculated from SPR measurements as $k_{off}/k_{on}$.

dAbs MSA16 and MSA26 were expressed in the periplasm of E. coli and purified using batch absorption to protein L-agarose affinity resin (Affitech, Norway) followed by elution with glycine at pH 2.2. The purified dAbs were then analysed by inhibition Biacore to determine Kd. Briefly, purified MSA16 and MSA26 were tested to determine the concentration of dAb required to achieve 200RUs of response on a Biacore CM5 chip coated with a high density of MSA. Once the required concentrations of dAb had been determined, MSA antigen at a range of concentrations around the expected Kd was premixed with the dAb and incubated overnight. Binding to the MSA coated Biacore chip of dAb in each of the premixes was then measured at a high flow-rate of 30 µl/minute. The affinities are determined using surface plasmon resonance (SPR) and the Biacore (Karlsson et al., 1991). The Biacore system (Uppsala, Sweden) is a preferred method for determining binding affinity. The Biacore system uses surface plasmon resonance (SPR, Welford K. 1991, Opt. Quant. Elect. 23:1; Morton and Myszka, 1998, Methods in Enzymology 295: 268) to monitor biomolecular interactions in real time. Biacore analysis conveniently generates association rate constants, dissociation rate constants, equilibrium dissociation constants, and affinity constants. The resulting curves were used to create Klotz plots, (Klotz, I. M. (1982) Science 217:1247-1249 and Klotz, I. M. (1983) J. Trends in Pharmacol. Sci. 4:253-255) which gave an estimated Kd of 200 nM for MSA16 and 70 nM for MSA 26 (FIGS. 17 A & B).

Next, clones MSA16 and MSA26 were cloned into an expression vector with the HA tag (nucleic acid sequence: TATCCTTATGATGTTCCTGATTATGCA (SEQ ID NO: 93) and amino acid sequence: YPYDVPDYA (SEQ ID NO: 94)) and 2-10 mg quantities were expressed in E. coli and purified from the supernatant with protein L-agarose affinity resin (Affitech, Norway) and eluted with glycine at pH2.2. Serum half life of the dAbs was determined in mouse. MSA26 and MSA16 were dosed as single i.v. injections at approx 1.5 mg/kg into CD1 mice. Analysis of serum levels was by goat anti-HA (Abcam, UK) capture and protein L-HRP (invitrogen) detection ELISA which was blocked with 4% Marvel. Washing was with 0.05% tween PBS. Standard curves of known concentrations of dAb were set up in the presence of 1× mouse serum to ensure comparability with the test samples. Modelling with a 2 compartment model showed MSA-26 had a t1/2α of 0.16 hr, a t1/2β of 14.5 hr and an area under the curve (AUC) of 465 hr·mg/ml (data not shown) and MSA-16 had a t1/2α of 0.98 hr, a t1/2β of 36.5 hr and an AUC of 913 hr·mg/ml (FIG. 18). Both anti-MSA clones had considerably lengthened half life compared with HEL4 (an anti-hen egg white lysozyme dAb) which had a t1/2α of 0.06 hr, and a t1/2β of 0.34 hr.

Example 11

Creation of $V_H$-$V_H$ and Vκ-Vκ Dual Specific Fab Like Fragments

This example describes a method for making $V_H$-$V_H$ and Vκ-Vκ dual specifics as Fab like fragments. Before constructing each of the Fab like fragments described, dAbs that bind to targets of choice were first selected from dAb libraries similar to those described in example 9. A $V_H$ dAb, HEL4, that binds to hen egg lysozyme (Sigma) was isolated and a second $V_H$ dAb (TAR2h-5) that binds to TNFα receptor (R and D systems) was also isolated. The sequences of these are given in the sequence listing. A $V_κ$ dAb that binds TNFα (TAR1-5-19) was isolated by selection and affinity maturation and the sequence is also set forth in the sequence listing. A second Vκ dAb (MSA 26) described in example 9 whose sequence is in FIG. 17B was also used in these experiments.

DNA from expression vectors containing the four dAbs described above was digested with enzymes SalI and NotI to excise the DNA coding for the dAb. A band of the expected size (300-400 bp) was purified by running the digest on an agarose gel and excising the band, followed by gel purification using the Qiagen gel purification kit (Qiagen, UK). The DNA coding for the dAbs was then inserted into either the CH or CK vectors (FIGS. 8 and 9) as indicated in Table 6.

TABLE 6

| dAb | Target antigen | dAb $V_H$ or dAb $V_κ$ | Inserted into vector | tag (C terminal) | Antibiotic resistance |
|---|---|---|---|---|---|
| HEL4 | Hen egg lysozyme | $V_H$ | $C_H$ | myc | Chloramphenicol |
| TAR2-5 | TNF receptor | $V_H$ | $C_κ$ | flag | Ampicillin |
| TAR1-5-19 | TNF α | $V_κ$ | $C_H$ | myc | Chloramphenicol |
| MSA 26 | Mouse serum albumin | $V_κ$ | $C_κ$ | flag | Ampicillin |

The $V_H C_H$ and $V_H$ Cκ constructs were cotransformed into HB2151 cells. Separately, the Vκ $C_H$ and Vκ Cκ constructs were cotransformed into HB2151 cells. Cultures of each of the cotransformed cell lines were grown overnight (in 2×Ty containing 5% glucose, 10 μg/ml chloramphenicol and 100 μg/ml ampicillin to maintain antibiotic selection for both $C_H$ and Cκ plasmids). The overnight cultures were used to inoculate fresh media (2×Ty, 10 μg/ml chloramphenicol and 100 μg/ml ampicillin) and grown to OD 0.7-0.9 before induction by the addition of IPTG to express their $C_H$ and Cκ constructs. Expressed Fab like fragment was then purified from the periplasm by protein A purification (for the cotransformed $V_H C_H$ and $V_H$ Cκ) and MSA affinity resin purification (for the cotransformed Vκ $C_H$ and Vκ Cκ).

$V_H$-$V_H$ Dual Specific

Expression of the $V_H C_H$ and $V_H$ Cκ dual specific was tested by running the protein on a gel. The gel was blotted and a band the expected size for the Fab fragment could be detected on the Western blot via both the myc tag and the flag tag, indicating that both the $V_H C_H$ and $V_H$ Cκ parts of the Fab like fragment were present. Next, in order to determine whether the two halves of the dual specific were present in the same Fab-like fragment, an ELISA plate was coated overnight at 4° C. with 100 μl per well of hen egg lysozyme (HEL) at 3 mg/ml in sodium bicarbonate buffer. The plate was then blocked (as described in example 1) with 2% tween PBS followed by incubation with the $V_H C_H$/$V_H$ Cκ dual specific Fab like fragment. Detection of binding of the dual specific to the HEL was via the non cognate chain using 9e10 (a monoclonal antibody that binds the myc tag, Roche) and anti mouse IgG-HRP (Amersham Pharmacia Biotech). The signal for the $V_H C_H$/$V_H$ Cκ dual specific Fab like fragment was 0.154 compared to a background signal of 0.069 for the $V_H$ Cκ chain expressed alone. This demonstrates that the Fab like fragment has binding specificity for target antigen.

$V_κ$-$V_κ$ Dual Specific

After purifying the cotransformed Vκ $C_H$ and Vκ $C_κ$ dual specific Fab like fragment on an MSA affinity resin, the resulting protein was used to probe an ELISA plate coated with 1 μg/ml TNFα and an ELISA plate coated with 10 μg/ml MSA. As predicted, there was signal above background when detected with protein L-HRP on both ELISA plates (data not shown). This indicated that the fraction of protein able to bind to MSA (and therefore purified on the MSA affinity column) was also able to bind TNFα in a subsequent ELISA, confirming the dual specificity of the antibody fragment. This fraction of protein was then used for two subsequent experiments. Firstly, an ELISA plate coated with 1 μg/ml TNFα was probed with dual specific Vκ $C_H$ and Vκ Cκ Fab like fragment and also with a control TNFα binding dAb at a concentration calculated to give a similar signal on the ELISA. Both the dual specific and control dAb were used to probe the ELISA plate in the presence and in the absence of 2 mg/ml MSA. The signal in the dual specific well was reduced by more than 50% but the signal in the dAb well was not reduced at all (see FIG. 19a). The same protein was also put into the receptor assay with and without MSA and competition by MSA was also shown (see FIG. 19c). This demonstrates that binding of MSA to the dual specific is competitive with binding to TNFα.

Example 12

Creation of a Vκ-Vκ Dual Specific cys Bonded Dual Specific with Specificity for Mouse Serum Albumin and TNFα

This example describes a method for making a dual specific antibody fragment specific for both mouse serum albumin and TNFα by chemical coupling via a disulphide bond. Both MSA16 (from example 1) and TAR1-5-19 dAbs were recloned into a pET based vector with a C terminal cysteine and no tags. The two dAbs were expressed at 4-10 mg levels and purified from the supernatant using protein L-agarose affinity resin (Affitiech, Norway). The cysteine tagged dAbs were then reduced with dithiothreitol. The TAR1-5-19 dAb was then coupled with dithiodipyridine to block reformation of disulphide bonds resulting in the formation of PEP 1-5-19 homodimers. The two different dAbs were then mixed at pH 6.5 to promote disulphide bond formation and the generation of TAR1-5-19, MSA16 cys bonded heterodimers. This method for producing conjugates of two unlike proteins was originally described by King et al. (King T P, Li Y Kochoumian L Biochemistry. 1978 vol 17:1499-506 Preparation of protein conjugates via intermolecular disulfide bond formation.) Heterodimers were separated from monomeric species by cation exchange. Separation was confirmed by the presence of a band of the expected size on a SDS gel. The resulting heterodimeric species was tested in the TNF receptor assay and found to have an IC50 for neutralising TNF of approximately 18 nM. Next, the receptor assay was repeated with a constant concentration of heterodimer (18 nM) and a dilution series of MSA and HSA. The presence of HSA at a range of concentrations (up to 2 mg/ml) did not cause a reduction in the ability of the dimer to inhibit TNFα. However, the addition of MSA caused a dose dependant reduction in the ability of the dimer to inhibit TNFα (FIG. 20). This demonstrates that MSA and TNFα compete for binding to the cys bonded TAR1-5-19, MSA16 dimer.

Data Summary

A summary of data obtained in the experiments set forth in the preceding examples is set forth in Annex 4.

Example 13

Selection and characterisation of dAbs for binding to serum albumin from a range of species.

dAbs against human serum albumin, mouse serum albumin and porcine serum albumin were selected as previously described for the anti-MSA dAbs except for the following modifications to the protocol: The phage libraries of synthetic $V_H$ domains were the libraries 4G and 6G, which are based on a human $V_H$3 comprising the DP47 germ line gene and the $J_H$4 segment for the $V_H$ and a human Vκ1 comprising the DPK9 germ line gene and the Jκ1 segment for the Vκ. The libraries comprise 1×10$^{10}$ individual clones. A subset of the $V_H$ and Vκ libraries had been preselected for binding to generic ligands protein A and protein L respectively so that the majority of clones in the unselected libraries were functional. The sizes of the libraries shown above correspond to the sizes after preselection.

Two or three rounds of selection were performed on mouse, porcine and human serum albumin using subsets of the $V_H$ and Vκ libraries separately. For each selection, antigen was either (i) coated on immunotube (nunc) in 4 ml of PBS at a concentration of 100 μg/ml, or (ii) bitotinylated and then used for soluble selection followed by capture on streptavidin beads or neutravidin beads. In each case, after the second or third round of selection, DNA from the selection was cloned into an expression vector for production of soluble dAb, and individual colonies were picked. Soluble dAb fragments were produced as described for scFv fragments by Harrison et al (Methods Enzymol. 1996; 267:83-109) and for each selection, 96 soluble clones were tested for binding to a range of serum albumins.

Screening of clones for binding to serum albumins from a range of species was done using a Biacore surface plasmon resonance instrument (Biacore AB). A CM-5 Biacore chip was coated with serum albumin from different species at high density on each of flow cells 2 to 4. dAbs which exhibited binding to one or more serum albumins of interest were sequenced and expressed at a 50 ml scale, purified on protein L and then screened at a known concentration for binding to a panel of serum albumins on a CM-5 Biacore chip coated with a low density of serum albumin on flow cells 2 to 4. Several dAbs which bind serum albumin from a range of different species were found, with the preferred candidates being listed, along with their binding profiles, in Table 7.

TABLE 7

| | HSA (affinity if measured) | RSA (affinity if measured) | MSA (affinity if measured) | Cyno (affinity if measured) |
|---|---|---|---|---|
| DOM7h-9 | Binds 200 nM | binds | binds | binds |
| DOM7h-10 | binds | ND | ND | ND |
| DOM7h-11 | binds | binds | binds | binds |
| DOM7h-12 | binds | ND | binds | binds |
| DOM7h-13 | binds | binds | binds | |
| DOM7h-14 | Binds 38 nM | binds | Binds 27 nM | Binds 123 nM |

In this experiment, we have therefore isolated dAbs that bind HSA and albumin from one or more of a range of non-human species. For example, we found dAbs that bind (i) human and mouse, (ii) human and cynomolgus, (iii) human and rat and (iv) human, mouse, rat and cyno albumin.

Example 14

Determination of the serum half-life in rat and cynomolgus monkey of serum albumin binding dAb/HA epitope tag or dAb/myc epitope tag fusion proteins and determination of serum half life.

Anti-cynomolgus serum albumin dAbs were expressed with C-terminal HA or myc tags in the periplasm of *E. coli* and purified using batch absorption to protein L-agarose affinity resin (Affitech, Norway) for Vk dAbs and batch absorption to protein A affinity resin for VH dAbs, followed by elution with glycine at pH 2.0. In order to determine serum half life, groups of 3 cynomolgus macaques were given a single i.v. injection at 2.5 mg/Kg of DOM7h-9, DOM7h-11 or DOM7h-14. Blood samples were obtained by serial bleeds from a femoral vein or artery over a 21 day period and serum prepared from each sample. Serum samples were analysed by sandwich ELISA using goat anti-HA (Abcam, Cambridge UK) or goat anti myc (Abcam, Cambridge UK) coated on an ELISA plate, followed by detection with protein L-HRP. Standard curves of known concentrations of dAb were set up in the presence of cynomolgus serum at the same concentration as for the experimental samples to ensure comparability with the test samples. Fitting a double exponential Modelling with a 2 compartment model (using kaleidograph software (Synergy software, PA, USA)) was used to calculate t1/2β, see Table 8.

Anti-rat serum albumin dAbs were expressed with C-terminal HA or myc tags in the periplasm of *E. coli* and purified using batch absorption to protein L-agarose affinity resin (Affitech, Norway) followed by elution with glycine at pH 2.0. dAbs were then labelled with $^3H$ using the following method: One vial per protein was prepared: 300 μL of NSP was dispensed into the vial and the solvent removed under a gentle stream of nitrogen at ≤30° C. The residue was then re-suspended in DMSO (100 μL). An aliquot of protein solution (2.5 mL) was added to the DMSO solution and the mixture incubated for 60 minutes at room temperature. Exactly 2.5 ml of the solution was then be loaded onto a pre-equilibrated PD10 column (pre-equilibrated with 25 mL Phosphate buffered saline, PBS) and the eluate discarded. Phosphate buffered saline (PBS, 3.5 mL) will be added and the eluate collected. This provided a labelled protein solution at approximately 2 mg/mL. The specific activity of the material was determined and conditional on efficient labelling, the solution was used immediately or stored at −20° C. until required.

In order to determine serum half life, groups of 4 rats were given a single i.v. injection at 2.5 mg/Kg of DOM7h-9, DOM7h-11, DOM7h-13 or DOM7h-14. Blood samples were obtained from a tail vein over a 7 day period and plasma prepared. Levels of $^3H$ were determined by liquid scintillation counting and concentration of labelled protein in each sample calculated according to the known specific activity of the protein administered at the start of the experiment. Fitting a double exponential Modelling with a 2 compartment model (using kaleidograph software (Synergy software, PA, USA)) was used to calculate t1/2β, see Table 8.

TABLE 8

| Agent | Scaffold | t½β (cyno) | t½β (rat) |
|---|---|---|---|
| DOM7h-9 | $V_K$ | 3.8 days | 66 hours |
| DOM7h-11 | $V_K$ | 5.2 days | 61 hours |
| DOM7h-13 | $V_K$ | not tested | 73 hours |
| DOM7h-14 | $V_K$ | 6.8 days | 56 hours |
| DOM7r-3 | $V_K$ | | 53 hours |
| DOM7r-16 | $V_K$ | | 43 hours |
| DOM7h-9 | $V_K$ | 3.8 days | 66 hours |
| DOM7h-11 | $V_K$ | 5.2 days | 61 hours |
| DOM7h-13 | $V_K$ | not tested | 73 hours |
| DOM7h-14 | $V_K$ | 6.8 days | 56 hours |
| DOM7r-3 | $V_K$ | | 53 hours |
| DOM7r-16 | $V_K$ | | 43 hours |

The half life of albumin in rat and cynomolgus monkey is 53 hours (determined experimentally) and 7-8 days (estimated) respectively. It can be seen from Table 8 that the half life of dAbs DOM7r-3, DOM7h-9, DOM7h-11, DOM7h-13 and DOM7h-14 in rat approach or are substantially the same as the half life of albumin in rat. Also, it can be seen that that the half life of dAbs DOM7h-11 and DOM7h-14 in cynomolgus approach or are substantially the same as the half life of albumin in cynomolgus. dAb DOM7h-14 has a half life in both rat and cynomolgus that is substantially the same as the half life of albumin in both species.

Example 15

Epitope Mapping

The three domains of human serum albumin have previously been expressed in *Pichia pastoris* (Dockal Carter and Ruker (1999) *J. Biol. Chem.* 2000 Feb. 4; 275(5):3042-50. We expressed the same domains using the *Pichia pastoris* pPIC-ZaA vector and where required purified them to homogeneity on Mimetic Blue SA matrix (supplier: Prometic Biosciences) FIG. 21. The identification of the serum albumin domain bound by dAbs was assessed by one of two methods, immunoprecipitation of domain antibodies and by competition Biacore. Results are shown below in FIG. 22 and FIG. 23.

For immunoprecipitation assay, 1 ml of *Pichia pastoris* supernatant expressing either HSA domain I, II or III was adjusted to pH7.4, and mixed with 1 μg dAb, and 10 μl of Protein A or Protein L agarose (for $V_H$ or $V_K$ dAbs respectively). The mixture was mixed by inversion for 1 hour to allow complex formation, then the agarose bound complex was recovered by centrifugation at 13,000×g for 10 minutes, the supernatant decanted, and the pelleted material washed once with PBS, and recovered by centrifugation. The beads were then resuspended in SDS-PAGE loading buffer containing dithiothreitol (DTT), heated to 70° C. for 10 minutes, then run on a 4-12% NuPAGE SDS-PAGE gels (supplier: Invitrogen), and stained with SimplyBlue safestain.

For competition Biacore assay, purified dAbs were made up to 1 μM in HBS-EP at pH7.4, or 1 μM in 50 mM citrate phosphate buffer, 150 mM NaCl, pH5.0, and where required, with 7 μM purified HSA domain. Biacore runs were carried out at a flow rate of 30 μl min over a CM5 chip surface coated with 500-1000 RU of human serum albumin, and a blank reference cell used to do baseline subtraction.

Table 9 provides a list of dAbs specific for human serum albumin and the domain(s) of human serum albumin to which they map (as determined by immunoprecipitation and/or Biacore):

TABLE 9

| Clone | H/K | Mapped HSA domain |
|---|---|---|
| DOM7h-1 | K | Domain II |
| DOM7h-2 | K | Nd |
| DOM7h-6 | K | Nd |
| DOM7h-7 | K | Nd |
| DOM7h-8 | K | Domain II |
| DOM7h-9 | K | Domain II |
| DOM7h-10 | K | Nd |
| DOM7h-11 | K | Domain II |
| DOM7h-12 | K | Domain II |
| DOM7h-13 | K | Domain II |
| DOM7h-14 | K | Domain II |
| DOM7h-21 | H | Nd |
| DOM7h-22 | H | Domain I + III |
| DOM7h-23 | H | Nd |
| DOM7h-24 | H | Nd |
| DOM7h-25 | H | Nd |
| DOM7h-26 | H | Nd |
| DOM7h-27 | H | Domain III |
| DOM7h-30 | H | Domain III |
| DOM7h-31 | H | Nd |

Nd: not determined

In conclusion, the majority of dAbs bind to the $2^{nd}$ domain of HSA and are therefore not expected to compete with binding of human serum albumin to FcRn. Two dAbs (DOM7h-27 and DOM7h-30) bind to Domain III.

| dAb | HSA domain bound | RU HSA binding at 1 μM pH 7.4 | RU HSA binding 1 μM pH 5.0 | His in CDR |
|---|---|---|---|---|
| OM7h-1 | II | 600c | 150 | no |
| OM7h-3 | NI | 0 | 0 | |
| OM7h-4 | NI | 0 | 0 | |
| OM7h-8 | II | 1000 | 250 | no |
| OM7h-9 | II | 150 | 0 | CDR1 |
| OM7h-11 | II | 250 | 0 | CDR3 |
| OM7h-12 | IIa | 55 | 0 | no |
| OM7h-13 | II | 300 | 40 | 2 in CDR3 |
| OM7h-14 | II | 20 | 0 | no |
| OM7h-22 | I + IIIb | 100c | 0 | CDR2 |

-continued

| dAb | HSA domain bound | RU HSA binding at 1 μM pH 7.4 | RU HSA binding 1 μM pH 5.0 | His in CDR |
|---|---|---|---|---|
| OM7h-27 | III | 50 | 0 | no |
| OM7h-30 | III | 320 | 35 | no |

Summary of results of epitope mapping of HSA binding AlbudAb™s (dAbs which specifically binds serum albumin) and Biacore data at pH7.4 and 5.0.

Example 16

Selecting dAbs In Vitro in the Presence of Metabolites

Albumin molecules accumulate the effects of exposure to other compounds in serum during their lifetime of around 19 days. These effects include the binding of numerous molecules that have affinity for albumin which include but are preferably not limited to cysteine and glutathione carried as mixed disulphides, vitamin $B_6$, δ-bilurubin, hemin, thyroxine, long and medium, chain fatty acids and glucose carried on ε-amino groups. Also, metabolites such as acetaldehyde (a product of ethanol metabolism in the liver), fatty acid metabolites, acyl glucuronide and metabolites of bilirubin. In addition, many drugs such as warfarin, halothane, salicylate, benzodiazepines and others (reviewed in Fasano et al 2005, FUBMB Life)) and also 1-O-gemfibrozil-β-D-glucuronide bind to serum albumin.

Compounds found bound to serum albumin tend to bind at certain sites on the albumin molecule, thereby potentially blocking these sites for the binding of other molecules such as AlbudAbs™ (a dAb which specifically binds serum albumin). The binding sites for many ligands has been identified, the main and most well characterised binding sites are termed "Sudlow site 1" and "Sudlow site 2". According to this nomenclature, Site 1 is located in sub-domain IIA, and binds warfarin and other drugs which generally are bulky, heterocyclic anionic molecules. Site 2 is located in sub domain IIIA, and binds aromatic carboxylic acids with an extended conformation, with the negative charge towards one end, such as the stereotypical site 2 ligand, ibuprofen. Secondary binding sites for both Warfarin and ibuprofen have been identified on domains II and I respectively. Other binding sites and subsites of these also exist, meaning that in the circulation, serum albumin exists with a complex mixture of bound ligands, with affinities that vary from $1\times10^{-2}$M to $1\times10^{-8}$M. Oleic acid for example binds to up 7 sites on SA (*J Mol. Biol.* 2001; 314: 955-60).

Human serum albumin has been in crystallized complex with fatty acids (Petitpas I, Grune T, Bhattacharya A A, Curry S, *Nat. Struct Biol.* (1998) 5: 827-35). The binding sites for these molecules are situated in hydrophobic clefts around the SA surface, with an asymmetric distribution, despite the near three-fold symmetry of the HSA molecule.

Later, the use of various recombinant fragments of serum albumin has aided more precise assignment of the contribution of the domains to formation of the binding sites (for example: *Protein Sci* (2000) 9:1455-65; *J Biol. Chem.* (1999) 274:29303-10). Displacement of bound ligands from SA plays an important role in drug interactions, for example the half life of warfarin is reduced as it is displaced from SA by ethanol (*J Biol. Chem.* (2000) 275:38731-8). Other drugs affinity for SA is modified by the presence of other drugs in other binding sites. For example, diazepam binding to site 2 increases the affinity of site 1 for tenoxicam, as a result of conformational changes on binding. This significantly affects the pharmacokinetic properties (Fundam Clin Pharmacol. (1989) 3:267-79).

Thus, for a SA binding AlbudAb™ (a dAb which specifically binds serum albumin), it is desirable to select one that does not alter the binding characteristics of serum albumin for drugs bound to SA. Additionally, where drug binding has been shown to alter the conformation of SA, it is desirable to have an AlbudAb™ (a dAb which specifically binds serum albumin) that binds SA in both in the presence or absence of the drug. These approaches mean that it will be possible to identify an AlbudAb™ (a dAb which specifically binds serum albumin) such that there are not significant positive or negative drug interactions with key pharmaceuticals. Therefore, this example describes a phage selection to identify dAbs that bind serum albumin in the presence of compounds and metabolites likely to be present bound to albumin in vivo. Phage selections are performed in the presence of one or several of the metabolites or compounds known to interact with serum albumin in vivo. These selections identify AlbudAb™s (a dAb which specifically binds serum albumin) that will bind to serum albumin in a manner that is unlikely to be hindered by the presence of metabolites or other compounds.

The phage libraries described in Example 1 are used as described in Example 1 for selection against albumin from one or more of a range of species including human, cynomolgus monkey, rat and mouse. The albumin used as an antigen is different from that described in Example 1 in that it will be preincubated overnight with ametabolite or compound at a 10-100 fold higher concentration than the albumin itself. This can either be with a single compound or metabolite, or with more than one compound or metabolite. In particular, it can be in the presence of compounds occupying albumin site I or site II or both. This concentration of metabolite is also present in the buffer used to coat the immunotubes with antigen and in the buffers used during key steps of the selection. Steps where metabolites are present include the MPBS blocking buffer used to block the antigen coated immunotubes or the biotinylated antigen (for solution selections) and also the buffer in which the phage library is blocked. In this way, when the blocked phage are added to the immunotube or biotinylated antigen, the concentration of metabolite is maintained. Therefore, throughout the phases of the selection in which the phage that bind to albumin are selected, metabolites that may block certain sites on the albumin molecule in vivo are also present, competing with the phage for binding and biasing the selection in favour of those dAbs that bind sites on albumin different from those blocked by metabolites.

In another set of selections, alternating rounds of selection against serum albumin in the presence and absence of bound compounds or metabolites are performed. This ensures that dAbs able to bind serum albumin in both the presence and absence of bound compounds are selected. In both selection schemes, it is possible that dAbs that are capable of displacing drug bound to serum albumin will be selected, and this is screened for by measuring the ability of the AlbudAb™ (a dAb which specifically binds serum albumin) to displace SA bound drug. Such assays are well established for small molecule drugs, and easily adapted for this purpose. A variety of methods well known in the art may be used to determine the ability of an AlbudAb™ (a dAb which specifically binds serum albumin) to displace SA bound drugs. These range from equilibrium dialysis, chromatographic methods on immobilised ligands or serum albumin, through NMR analysis. The following example describes the use of the simplest equilibrium dialysis method. The other more technically complex methods will give essentially the same information.

A solution of serum albumin is made at a defined concentration in a physiological buffer, for example, 20 mM sodium phosphate buffer, 150 mM NaCl, pH7.4. The drug is made up in a similar buffer, and has been synthesised such that it retains its original pharmacological properties, but is radiolabelled, for example with tritium or $^{14}$C. The serum albumin binding antibody fragment is made up at a defined concentration in a similar buffer.

The serum albumin solution is placed in a series of tubes, and increasing amount of AlbudAb™ (a dAb which specifically binds serum albumin) is added, such that the concentration of serum albumin in each tube is fixed (for example at 1% w/v, approx 150 µM), while the (a dAb which specifically binds serum albumin)™ concentration ranges from 0 to 150 µM over the tube series. This comprises one experimental set.

A dialysis tube or container containing a fixed concentration of the radiolabelled ligand for each set is added to the tube. A concentration range from 0.2 to 10 mM may be suitable, depending on the ligand used, its affinity and solubility.

The cut-off size of the membrane used for dialysis should be such that the serum albumin and AlbudAb™ (a dAb which specifically binds serum albumin) do not diffuse through, but the radiolabelled ligand can diffuse freely. A cut off size of 3.5 Kda is sufficient for this purpose.

The mixture is stirred at a fixed temperature, for example 37° C., for a fixed period of time, to allow equilibrium of the radiolabelled drug between both compartments, for example, 5 hours. After this time, equilibrium should be attained which is influenced by the ability of the AlbudAb™ (a dAb which specifically binds serum albumin) binding the serum albumin to inhibit drug binding.

Both compartments are samples, and the radioactivity counted, using a scintillation counter. The concentration of albumin bound ligand can be determined by the difference in counts between the two compartments. The stoichiometric binding constant K' can be calculated from the equilibrium concentration of bound ligand, b, free ligand, c, and albumin, p, in accordance with the equation $K'=b/c(p-b)$. This assumes the binding of 1 molecule of ligand to one molecule of serum albumin.

Binding data can then be measured using a Scatchard plot in accordance with the equation $r/c=nk-rk$, where r is the fraction of albumin to which ligand is bound (i.e. b/p, and n is the number of binding sites per albumin molecule, and k is the site association constant. Values of n and k can be determined from plots of r/c against r.

Where the binding of an AlbudAb™ (a dAb which specifically binds serum albumin) blocks radiolabelled ligand binding, this will affect both the stoichiometric binding constant of the ligand, and also the apparent number of binding sites for the ligand. It may be predicted that as the AlbudAb™ (a dAb which specifically binds serum albumin) will bind at one defined site on the surface of serum albumin, and some ligands have more than one binding site on serum albumin, that not all binding sites will be blocked. In the situation where The AlbudAb™ (a dAb which specifically binds serum albumin) specifically binds to drug complexed serum albumin and displaces it, and the drug has a low therapeutic index and is serum bound, then a cut-off affinity for distinguishing between an AlbudAb™ (a dAb which specifically binds serum albumin) able to displace serum albumin bound to the drug from an AlbudAb™ (a dAb which specifically binds serum albumin) not able to displace serum albumin to drug, would range from 10 nM to 100 nM. This method is exemplified in the following paper: Livesey and Lund Biochem J. 204(1): 265-272 Binding of branched-chain 2-oxo acids to bovine serum albumin.

Example 17

Generation of Dual-Specific Ligand Comprising a Serum Albumin-Binding CTLA-4 Non-Immunoglobulin Scaffold Via CDR Grafting The CDR domains of dAb7h14 are used to construct a cytotoxic T-lymphocyte associated antigen 4 (CTLA-4) non-immunoglobulin scaffold polypeptide that binds human serum albumin in the following manner. The CDR1 (RASQWIGSQLS; SEQ ID NO.: 95), CDR2 (WRSSLQS; SEQ ID NO.: 96), and CDR3 (AQGAALPRT; SEQ ID NO.: 97) sequences of dAb7h14 are grafted into a soluble truncated mutant of CTLA-4 comprising the CTLA-4 V-like domain (as described in WO 99/45110; optionally, an engineered form of CTLA-4, e.g., in which A2 and A3 domains are deleted) in replacement of native CTLA-4 amino acid residues corresponding to CDR1 (SPGKATE; SEQ ID NO.: 98) within the S1-S2 loop (the BC loop), CDR2 (YMMGNELTF; SEQ ID NO.: 99), and CDR3 (LMYPPPYYL; SEQ ID NO.: 100) within the S5-S6 loop, respectively (for details of the CTLA-4 scaffold composition and/or structure refer to WO 00/60070; WO 99/45110; Metzler et al. *Nat. Struct. Biol.* 4: 527-53; and Nuttall et al. *Proteins Struct. Funct. Genet.* 36:217-27, all incorporated herein by reference in their entirety). Expression of this CLTA-4-derived polypeptide in a pGC-, pPOW-based, or other art-recognized expression system is performed, with the anticipated production of predominantly monomeric soluble protein. Protein solubility of this CTLA-4-derived polypeptide is examined, and is anticipated to be superior to native extracellular CTLA-4 polypeptide. ELISA analysis is used to examine whether purified monomeric polypeptide specifically binds human serum albumin compared to non-specific antigens and compared to extracellular CTLA-4-derived polypeptides grafted with non-specific polypeptides (e.g., somatostatin substituted within the CDR1 loop structure). Real-time binding analysis by Biacore is performed to assess whether human serum albumin specifically binds to immobilized CTLA-4-derived polypeptide comprising the anti-human serum albumin CDR domains of dAb7h14. (One of skill in the art will recognize that binding affinity can be assessed using any appropriate method, including, e.g., precipitation of labeled human serum albumin, competitive Biacore assay, etc.) Optionally, expression of the CTLA-4 anti-human serum albumin polypeptide is enhanced via adjustment of the coding sequence using splice overlap PCR to incorporate codons preferential for *E. coli* expression. If no or low human serum albumin affinity (e.g., Kd values in the pM range or higher) is detected, at least one of a number of strategies is employed to improve the human serum albumin binding properties of the CDR-grafted CTLA-4 polypeptide, including any of the following methods that contribute to binding affinity.

Human serum albumin binding of CDR-grafted CTLA-4 polypeptide(s) presenting dAb7h14 CDRs is optimized via mutagenesis, optionally in combination with parallel and/or iterative selection methods as described below and/or as otherwise known in the art. CTLA-4 scaffold polypeptide domains surrounding grafted dAb7h14 CDR polypeptide sequences are subjected to randomized and/or NNK mutagenesis, performed as described infra. Such mutagenesis is performed within the CTLA-4 polypeptide sequence upon non-CDR amino acid residues, for the purpose of creating new or improved human serum albumin-binding polypeptides. Optionally, dAb7h14 CDR polypeptide domains presented within the CDR-grafted CTLA-4 polypeptide are subjected to mutagenesis via, e.g., random mutagenesis, NNK mutagenesis, look-through mutagenesis and/or other art-recognized method. PCR is optionally used to perform such methods of mutagenesis, resulting in the generation of sequence diversity across targeted sequences within the CDR-grafted CTLA-4 polypeptides. Such approaches are similar to those described infra for dAb library generation. In addition to random and/or look-through methods of mutagenesis, directed mutagenesis of targeted amino acid residues is employed where structural information establishes specific amino acid residues to be critical to binding of human serum albumin.

CTLA-4 polypeptides comprising grafted dAb7h14 CDR sequences engineered as described above are subjected to parallel and/or iterative selection methods to identify those CTLA-4 polypeptides that are optimized for human serum albumin binding. For example, following production of a library of dAb7h14 CDR-grafted CTLA-4 polypeptide sequences, this library of such polypeptides is displayed on phage and subjected to multiple rounds of selection requiring serum albumin binding and/or proliferation, as is described infra for selection of serum albumin-binding dAbs from libraries of dAbs. Optionally, selection is performed against serum albumin immobilized on immunotubes or against biotinlyated serum albumin in solution. Optionally, binding affinity is determined using surface plasmon resonance (SPR) and the Biacore (Karlsson et al., 1991), using a Biacore system (Uppsala, Sweden), with fully optimized CTLA-4-derived polypeptides ideally achieving human serum albumin binding affinity Kd values in the nM range or better.

Following identification of CTLA-4-derived polypeptides that bind human serum albumin, such polypeptides are then used to generate dual-specific ligand compositions by any of the methods described infra.

Example 18

Generation of Dual-Specific Ligand Comprising a Serum Albumin-Binding CTLA-4 Non-Immunoglobulin Scaffold Via Selection of Serum Albumin Binding Moieties A soluble truncated mutant of CTLA-4 comprising the native CTLA-4 V-like domain (as described in WO 99/45110; optionally, an engineered form of CTLA-4, e.g., in which A2 and A3 domains are deleted) and which has been engineered to contain regions(s) of variability, are displayed in a library and subjected to selection and, optionally, affinity maturation techniques in order to produce human serum albumin-binding CTLA-4 non-immunoglobulin scaffold molecules for use in the ligands of the invention.

Expression of this CLTA-4-derived polypeptide in a pGC-, pPOW-based, or other art-recognized expression system is performed. Protein solubility of this CTLA-4-derived polypeptide is examined, and mutagenesis is performed to enhance solubility of CTLA-4-derived polypeptide(s) relative to that of a native extracellular CTLA-4 polypeptide. ELISA analysis is used to examine whether purified monomeric polypeptide optionally specifically binds human serum albumin compared to non-specific single variable domains comprising a CTLA-4 derived scaffold, and compared to extracellular CTLA-4-derived polypeptides grafted with non-specific polypeptides (e.g., CTLA-4 polypeptide with somatostatin substituted within the CDR1 loop structure). Real-time binding analysis by Biacore is performed to assess whether human serum albumin specifically binds to immobilized CTLA-4-derived polypeptide. Optionally, expression of the CTLA-4 anti-human serum albumin polypeptide is enhanced via adjustment of the coding sequence using splice overlap PCR to incorporate codons preferential for *E. coli* expression. Following detection of no or low binding affinity (e.g., Kd values in the µM range or higher) of a CTLA-4 polypeptide for human serum albumin, at least one of a number of strategies is employed to impart human serum albumin binding properties to the CTLA-4 polypeptide, including one or more of the following methods that contribute to binding affinity.

Human serum albumin binding of CTLA-4 scaffold polypeptide(s) is achieved and optimized via mutagenic methods, optionally in combination with parallel and/or iterative selection methods as described below and/or as otherwise known in the art. CTLA-4 polypeptide domains are subjected to randomized and/or NNK mutagenesis, performed as described infra. Such mutagenesis is performed upon the entirety of the CTLA-4 polypeptide or upon specific sequences within the CTLA-4 polypeptide, optionally targeting CDR-corresponding amino acids (e.g., CDR1 and/or CDR3 sequences are randomized, and resulting polypeptides are subjected to selection, e.g., as described in Example 6 of WO 99/45110). Optionally, specific amino acid residues determined or predicted to be structurally important to CDR-like loop presentation are targeted for mutagenesis. Mutagenesis, especially randomized mutagenesis, is performed in order to evolve new or improved human serum albumin-binding polypeptides. PCR is optionally used to perform such methods of mutagenesis, resulting in the generation of sequence diversity across targeted sequences within the CTLA-4 polypeptides. (Such approaches are similar to those described infra for dAb library generation.) In addition to random methods of mutagenesis, directed mutagenesis of targeted amino acid residues is employed where structural information establishes specific amino acid residues of CTLA-4 polypeptides to be critical to binding of human serum albumin.

CTLA-4 polypeptides engineered as described above are subjected to parallel and/or iterative selection methods to identify those CTLA-4 polypeptides that are optimized for human serum albumin binding. For example, following production of a library of mutagenized CTLA-4 polypeptide sequences, said library of polypeptides is displayed on phage and subjected to multiple rounds of selection requiring serum albumin binding and/or proliferation, as is described infra for selection of serum albumin-binding dAbs from libraries of dAbs. Optionally, selection is performed against serum albumin immobilized on immunotubes or against biotinlyated serum albumin in solution. Optionally, binding affinity is determined using surface plasmon resonance (SPR) and the Biacore (Karlsson et al., 1991), using a Biacore system (Uppsala, Sweden), with fully optimized CTLA-4-derived polypeptides ideally achieving human serum albumin binding affinity Kd values in the nM range or better.

Following identification of CTLA-4 polypeptides that bind human serum albumin, such polypeptides are then used to generate dual-specific ligand compositions by any of the methods described infra.

CTLA-4 V-Like Domains

CTLA-4 is an example of a non-immunoglobulin ligand that binds to a specific binding partner and also comprises V-like domains. These V-like domains are distinguished from those of antibodies or T-cell receptors because they have no propensity to join together into Fv-type molecules. Such a non-immunoglobulin ligand provides an alternative framework for the development of novel binding moieties with high affinities for target molecules. Single domain V-like binding molecules derived from CTLA-4 which are soluble are therefore desirable.

Cytotoxic T-lymphocyte associated antigen 4 (CTLA-4) is involved in T-cell regulation during the immune response. CTLA-4 is a 44 Kda homodimer expressed primarily and transiently on the surface of activated T-cells, where it interacts with CD80 and CD86 surface antigens on antigen presenting cells to effect regulation of the immune response (Waterhouse et al. 1996 *Immunol Rev* 153: 183-207, van der Merwe et al. 1997 *J Exp Med* 185: 393-403). Each CTLA-4 monomeric subunit consists of an N-terminal extracellular domain, transmembrane region and C-terminal intracellular domain. The extracellular domain comprises an N-terminal V-like domain (VLD; of approximately 14 Kda predicted molecular weight by homology to the immunoglobulin superfamily) and a stalk of about 10 residues connecting the VLD to the transmembrane region. The VLD comprises surface loops corresponding to CDR-1, CDR-2 and CDR-3 of an antibody V-domain (Metzler et al. 1997 *Nat Struct Biol* 4: 527-531). Recent structural and mutational studies on CTLA-4 indicate that binding to CD80 and CD86 occurs via the VLD surface formed from A'GFCC' V-like beta-strands and also from the highly conserved MYPPPY sequence (SEQ ID NO: 101) in the CDR3-like surface loop (Peach et al. 1994 *J Exp Med* 180: 2049-2058; Morton et al. 1996 *J. Immunol.* 156: 1047-1054; Metzler et al. 1997 *Nat Struct Biol* 4: 527-531). Dimerisation between CTLA-4 monomers occurs through a disulphide bond between cysteine residues (CYS120) in the two stalks, which results in tethering of the two extracellular domains, but without any apparent direct association between V-like domains (Metzler et al. 1997 *Nat Struct Biol* 4: 527-531).

Replacement of CDR loop structures within the VLDs has previously been shown to result in the production of monomeric, correctly folded molecules with altered binding specificities and improved solubility. Accordingly, in certain embodiments, a binding moiety comprising at least one monomeric V-like domain (VLD) derived from CTLA-4 is generated, wherein the at least one monomeric V-like domain is characterized in that at least one CDR loop structure or part thereof is modified or replaced such that the solubility of the modified VLD is improved when compared with the unmodified VLD.

In certain embodiments, at least one CDR loop structure or part thereof is modified or replaced such that (i) the size of the CDR loop structure is increased when compared with corresponding CDR loop structure in the unmodified VLD; and/or (ii) the modification or replacement results in the formation of a disulphide bond within or between one or more of the CDR loop structures.

In certain embodiments, the present invention provides a binding moiety comprising at least one monomeric V-like domain (VLD) derived from CTLA-4, the at least one monomeric V-like domain being characterized in that at least one CDR loop structure or part thereof is modified or replaced such that (i) the size of the CDR loop structure is altered when compared with corresponding CDR loop structure in the unmodified VLD; and/or (ii) the modification or replacement results in the formation of a disulphide bond within or between one or more of the CDR loop structures.

In certain embodiments, the size of the CDR loop structure is increased by at least two, more preferably at least three, more preferably at least six and more preferably at least nine amino acid residues. In further embodiments, the modified binding moiety of the invention also exhibits an altered binding affinity or specificity when compared with the unmodified binding moiety. Preferably, the effect of replacing or modifying the CDR loop structure is to reduce or abolish the affinity of the VLD to one or more natural ligands of the unmodified VLD. Preferably, the effect of replacing or modifying the CDR loop structure is also to change the binding specificity of the VLD (e.g., to produce a composition that binds human serum albumin). Thus, it is preferred that the modified VLD binds to a specific binding partner (e.g., human serum albumin) that is different to that of the unmodified VLD.

The phrase "VLD" is intended to refer to a domain which has similar structural features to the variable heavy (VH) or variable light (VL) antibody. These similar structural features include CDR loop structures.

As used herein, the term "CDR loop structures" refers to surface polypeptide loop structures or regions like the complementarity determining regions in antibody V-domains.

It will be appreciated that the CTLA-4-derived binding moieties of the present invention may be coupled together, either chemically or genetically, to form multivalent or multifunctional reagents. For example, the addition of C-terminal tails, such as in the native CTLA-4 with Cys'20, will result in a dimer. The binding moieties of the present invention may also be coupled to other molecules for various formulations, including those comprising dual specific ligands. For example, the CTLA-4 VLDs may comprise a C-terminal polypeptide tail or may be coupled to streptavidin or biotin. The CTLA-4 VLDs may also be coupled to radioisotopes, dye markers or other imaging reagents for in vivo detection and/or localization of cancers, blood clots, etc. The CTLA-4 VLDs may also be immobilized by coupling onto insoluble devices and platforms for diagnostic and biosensor applications.

In certain embodiments of the present invention, the extracellular CTLA-4 V-like domain is used. One or more surface loops of the CTLA-4 V-like domain and preferably the CDR1, CDR2 or CDR3 loop structures are replaced with a polypeptide which has a binding affinity for serum albumin (e.g., CDR domains of dAb7h14 and sequences derived therefrom, as exemplified infra). It will be appreciated that these CTLA-4 VLDs may be polyspecific, having affinities directed by both their natural surfaces and modified polypeptide loops.

One or more of the CDR loop structures of the CTLA-4 VLD can be replaced with one or more CDR loop structures derived from an antibody. The antibody may be derived from any species. In a preferred embodiment, the antibody is derived from a human, rat, mouse, camel, llama or shark. The CDR1 and CDR3 loop structures may adopt non-canonical conformations which are extremely heterologous in length. The V-like domain may also possess a disulphide linkage interconnecting the CDR1 and CDR3 loop structures (as found in some camel VHH antibodies) or the CDR2 and CDR3 loop structures (as found in some llama VHH antibodies).

For in vivo applications it is preferable that VLDs are homologous to the subject of treatment or diagnosis and that any possible xenoantigens are removed. Accordingly, it is preferred that VLD molecules for use in clinical applications are substantially homologous to naturally occurring human immunoglobulin superfamily members.

Serum albumin binding of CTLA-4 polypeptides (e.g., VLDs derived from CTLA-4) can be optimized via selection of a binding moiety with an affinity for serum albumin, e.g., comprising screening a library of polynucleotides for expression of a binding moiety with an affinity for serum albumin, wherein the polynucleotides have been subjected to mutagenesis which results in a modification or replacement in at least one CDR loop structure in at least one VLD and wherein the solubility of the isolated modified VLD is improved when compared with the isolated unmodified VLD.

It will be appreciated by those skilled in the art that within the context of such affinity screening method, any method of random or targeted mutagenesis may be used to introduce modifications into the V-like domains. In a preferred embodiment, the mutagenesis is targeted mutagenesis. Optionally, the targeted mutagenesis involves replacement of at least one sequence within at least one CDR loop structure using, e.g., splice overlap or other PCR technology.

It will also be appreciated by those skilled in the art that the polynucleotide library may contain sequences which encode VLDs comprising CDR loop structures which are substantially identical to CDR loop structures found in naturally occurring immunoglobulins and/or sequences which encode VLDs comprising non-naturally occurring CDR loop structures. Optionally, the screening process involves displaying the modified V-like domains as gene III protein fusions on the surface of bacteriophage particles.

The library may comprise bacteriophage vectors such as pHFA, fd-tet-dog or pFAB.5c containing the polynucleotides encoding the V-like domains. The screening process can also involve displaying the modified V-like domains in a ribosomal display selection system.

The preferred CTLA-4-derived serum albumin binding molecules of the present invention provide the following advantages (i) use of a native human protein obviates the need for subsequent humanization of the recombinant molecule, a step often required to protect against immune system response if used in human treatment; (ii) the domain is naturally monomeric as described above (incorporation of residue Cys120 in a C-terminal tail results in production of a dimeric molecule); and (iii) structural modifications have resulted in improved *E. coli* expression levels.

Initial determination of native CTLA-4 structure allowed modeling and prediction of the regions corresponding to antibody CDR1, 2 and 3 regions. It was hypothesized that such areas would be susceptible to mutation or substitution without substantial effect upon the molecular framework and hence would allow expression of a correctly folded molecule. The published structure of CTLA-4 (Metzler et al. 1997 *Nat Struct Biol* 4: 527-531) showed these predictions to be accurate, despite the unexpected separation of CDR1 from the ligand-binding site, and the extensive bending of CDR3 to form a planar surface contiguous with the ligand binding face.

V-like domains provide a basic framework for constructing soluble, single domain molecules, where the binding specificity of the molecule may be engineered by modification of the CDR loop structures. The basic framework residues of the V-like domain may be modified in accordance with structural features present in camelid antibodies. The camel heavy chain immunoglobulins differ from "conventional" antibody structures by consisting of VHH chains, (Hamers-Casterman et al. 1993 *Nature* 363: 446-448). Cammelid antibodies consist of two heavy chains, each comprising a VHH domain. Several unique features allow these antibodies to overcome the dual problems of solubility and inability to present a sufficiently large antigen binding surface.

First, several non-conventional substitutions (predominantly hydrophobic to polar in nature) at exposed framework residues reduce the hydrophobic surface, while maintaining the internal beta-sheet framework structure (Desmyter et al.

1996 *Nat Struct Biol* 3:803-811). Further, within the three CDR loops several structural features compensate for the loss of antigen binding-surface usually provided by the VL domain. While the CDR2 loop does not differ extensively from other $V_H$ domains, the CDR1 and CDR3 loops adopt non-canonical conformations which are extremely heterologous in length. For example, the H1 loop may contain anywhere between 2-8 residues compared to the usual five in Ig molecules. However, it is the CDR3 loop which exhibits greatest variation: in 17 camel antibody sequences reported, the length of this region varies between 7 and 21 residues (Muyldermans et al. 1994 *Protein Eng* 7: 1129-1135). Thirdly, many camelid VHH domains possess a disulphide linkage interconnecting CDR1 and CDR3 in the case of camels and interconnecting CDR1 and CDR2 in the case of llamas (Vu et al. 1997 *Molec. Immunol.* 34: 1121-113). The function of this structural feature appears to be maintenance of loop stability and providing a more contoured, as distinct from planar, loop conformation which both allows binding to pockets within the antigen and gives an increased surface area. However, not all camelid antibodies possess this disulphide bond, indicating that it is not an absolute structural requirement.

The present invention also relates to a method for generating and selecting single VLD molecules with novel binding affinities for target molecules (e.g., human serum albumin). This method involves the application of well known molecular evolution techniques to CTLA-4-derived polypeptides. The method may involve the production of phage or ribosomal display libraries for screening large numbers of mutated CTLA-4-derived polypeptides.

Filamentous fd-bacteriophage genomes are engineered such that the phage display, on their surface, proteins such as the Ig-like proteins (scFv, Fabs) which are encoded by the DNA that is contained within the phage (Smith, 1985 *Science* 228: 1315-1317; Huse et al. 1989 *Science* 246: 1275-81; McCafferty et al., 1990 *Nature* 348: 552-4; Hoogenboom et al., 1991 *Nucleic Acids Res.* 19: 4133-4137). Protein molecules can be displayed on the surface of Fd bacteriophage, covalently coupled to phage coat proteins encoded by gene III, or less commonly gene VIII. Insertion of antibody genes into the gene III coat protein gives expression of 3-5 recombinant protein molecules per phage, situated at the ends. In contrast, insertion of antibody genes into gene VIII has the potential to display about 2000 copies of the recombinant protein per phage particle, however this is a multivalent system which could mask the affinity of a single displayed protein. Fd phagemid vectors are also used, since they can be easily switched from the display of functional Ig-like fragments on the surface of fd-bacteriophage to secreting soluble Ig-like fragments in *E. coli*. Phage-displayed recombinant protein fusions with the N-terminus of the gene III coat protein are made possible by an amber codon strategically positioned between the two protein genes. In amber suppressor strains of *E. coli*, the resulting Ig domain-gene III fusions become anchored in the phage coat.

A selection process based on protein affinity can be applied to any high-affinity binding reagents such as antibodies, antigens, receptors and ligands (see, e.g., Winter and Milstein, 1991 *Nature* 349: 293-299, the entire contents of which are incorporated herein by reference). Thus, the selection of the highest affinity binding protein displayed on bacteriophage is coupled to the recovery of the gene encoding that protein. Ig- or non-Ig scaffold-displaying phage can be affinity selected by binding to cognate binding partners covalently coupled to beads or adsorbed to plastic surfaces in a manner similar to ELISA or solid phase radioimmunoassays. While almost any plastic surface will adsorb protein antigens, some commercial products are especially formulated for this purpose, such as Nunc Immunotubes.

Ribosomal display libraries involve polypeptides synthesized de novo in cell-free translation systems and displayed on the surface of ribosomes for selection purposes (Hanes and Pluckthun, 1997 *Proc. Natl. Acad. Sci. USA*. 94: 4937-4942; He and Taussig, 1997 *Nucl. Acids Res.* 25: 5132-5134). The "cell-free translation system" comprises ribosomes, soluble enzymes required for protein synthesis (usually from the same cell as the ribosomes), transfer RNAs, adenosine triphosphate, guanosine triphosphate, a ribonucleoside triphosphate regenerating system (such as phosphoenol pyruvate and pyruvate kinase), and the salts and buffer required to synthesize a protein encoded by an exogenous mRNA. The translation of polypeptides can be made to occur under conditions which maintain intact polysomes, i.e. where ribosomes, mRNA molecule and translated polypeptides are associated in a single complex. This effectively leads to "ribosome display" of the translated polypeptide. For selection, the translated polypeptides, in association with the corresponding ribosome complex, are mixed with a target (e.g., serum albumin) molecule which is bound to a matrix (e.g., Dynabeads). The ribosomes displaying the translated polypeptides will bind the target molecule and these complexes can be selected and the mRNA re-amplified using RT-PCR.

Although there are several alternative approaches to modify binding molecules, the general approach for all displayed proteins conforms to a pattern in which individual binding reagents are selected from display libraries by affinity to their cognate ligand and/or receptor. The genes encoding these reagents are modified by any one or combination of a number of in vivo and in vitro mutation strategies and constructed as a new gene pool for display and selection of the highest affinity binding molecules.

Assessment of Binding Affinities

In certain embodiments, the dual-specific ligands of the present invention, including component molecules thereof (e.g., non-immunoglobulin molecules that bind human serum albumin) are assessed for binding affinity to target protein (e.g., human serum albumin). Binding of target protein epitopes can be measured by conventional antigen binding assays, such as ELISA, by fluorescence based techniques, including FRET, or by techniques such as surface plasmon resonance which measure the mass of molecules. Specific binding of an antigen-binding protein to an antigen or epitope can be determined by a suitable assay, including, for example, Scatchard analysis and/or competitive binding assays, such as radioimmunoassays (RIA), enzyme immunoassays such as ELISA and sandwich competition assays, and the different variants thereof.

Binding affinity is preferably determined using surface plasmon resonance (SPR) and the Biacore (Karlsson et al., 1991), using a Biacore system (Uppsala, Sweden). The Biacore system uses surface plasmon resonance (SPR, Welford K. 1991, *Opt. Quant. Elect.* 23: 1; Morton and Myszka, 1998, *Methods in Enzymology* 295: 268) to monitor biomolecular interactions in real time, and uses surface plasmon resonance which can detect changes in the resonance angle of light at the surface of a thin gold film on a glass support as a result of changes in the refrative index of the surface up to 300 nm away. Biacore analysis conveniently generates association rate constants, dissociation rate constants, equilibrium dissociation constants, and affinity constants. Binding affinity is obtained by assessing the association and dissociation rate constants using a Biacore surface plasmon resonance system (Biacore, Inc.). A biosensor chip is activated for covalent coupling of the target according to the manufacturer's (Biacore) instructions. The target is then diluted and injected over the chip to obtain a signal in response units (RU) of immobilized material. Since the signal in RU is proportional to the mass of immobilized material, this represents a range of immobilized target densities on the matrix. Dissociation data are fit to a one-site model to obtain $k_{off}$+/−s.d. (standard deviation of measurements). Pseudo-first order rate constant (Kd's) are calculated for each association curve, and plotted as a function of protein concentration to obtain $k_{on}$+/−s.e. (standard error of fit). Equilibrium dissociation constants for binding, Kd's, are calculated from SPR measurements as $k_{off}/k_{on}$.

As described by Phizicky and Field in *Microb. Rev.* (1995) 59: 114-115, a suitable antigen, such as HSA, is immobilized on a dextran polymer, and a solution containing a ligand for HSA, such as a single variable domain, flows through a cell, contacting the immobilized HSA. The single variable domain retained by immobilized HSA alters the resonance angle of impinging light, resulting in a change in refractive index brought about by increased amounts of protein, i.e. the single variable domain, near the dextran polymer. Since all proteins have the same refractive index and since there is a linear correlation between resonance angle shift and protein concentration near the surface, changes in the protein concentration at the surface due to protein/protein binding can be measured, see Phizicky and Field, supra. To determine a binding constant, the increase in resonance units is measured as a function of time by passing a solution of single variable domain protein past the immobilized ligand (HSA) until the RU values stabilize, then the decrease in RU is measured as a function of time with buffer lacking the single variable domain. This procedure is repeated at several different concentrations of single variable domain protein. Detailed theoretical background and procedures are described by R. Karlsson, et. al. (991) *J. Immunol Methods,* 145, 229.

The instrument software produces an equilibrium dissociation constant (Kd) as described above. An equilibrium dissociation constant determined through the use of Surface plasmon resonance (SPR) is described in U.S. Pat. No. 5,573,957, as being based on a table of $dR_A/dt$ and $R_A$ values, where R in this example is the HSA/single variable domain complex as measured by the Biacore in resonance units and where dR/dt is the rate of formation of HSA/single variable domain complexes, i.e. the derivative of the binding curve; plotting the graph $dR_A/dt$ vs. $R_A$ for several different concentrations of single variable domain, and subsequently plotting the slopes of these lines vs. the concentration of single variable domain, the slope of this second graph being the association rate constant ($M^{-1}$, $s^{-1}$). The Dissociation Rate Constant or the rate at which the HSA and the single variable domain release from each other can be determined utilizing the dissociation curve generated on the Biacore. By plotting and determining the slope of the log of the drop in response vs. time curve, the dissociation rate constant can be measured. The Equilibrium dissociation constant Kd=Dissociation Rate Constant/association rate constant.

A ligand according to any aspect of the present invention, includes a ligand having or consisting of at least one single variable domain, in the form of a monomer single variable domain or in the form of multiple single variable domains, i.e. a multimer. The ligand can be modified to contain additional moieties, such as a fusion protein, or a conjugate. Such a multimeric ligand, e.g., in the form of a dual-specific ligand, and/or such a ligand comprising or consisting of a single variable domain, i.e. a dAb monomer useful in constructing such a multimeric ligand, may advantageously dissociate from their cognate target(s) with a Kd of 300 nM or less, 300 nM to 5 pM (i.e., $3\times10^{-7}$ to $5\times10^{-12}$M), preferably 50 nM to 20 pM, or 5 nM to 200 pM or 1 nM to 100 pM, $1\times10^{-7}$ M or less, $1\times10^{-8}$ M or less, $1\times10^{-9}$ M or less, $1\times10^{-10}$ M or less, $1\times10^{-11}$ M or less; and/or a $K_{off}$ rate constant ranging from $5\times10^{-1}$ to $1\times10^{-7}$ $S^{-1}$, preferably $1\times10^{-6}$ to $1\times10^{-8}$ $S^{-1}$, preferably $1\times10^{-2}$ to $1\times10^{-6}$ $S^{-1}$, or $5\times10^{-3}$ to $1\times10^{-5}$ $S^{-1}$, or $5\times10^{-1}$ $S^{-1}$ or less, or $1\times10^{-2}$ $S^{-1}$ or less, or $1\times10^{-3}$ $S^{-1}$ or less, or $1\times10^{-4}$ $S^{-1}$ or less, or $1\times10^{-5}$ $S^{-1}$ or less, or $1\times10^{-6}$ $S^{-1}$ or less as determined, for example, by surface plasmon resonance. The Kd rate constant is defined as $K_{off}/K_{on}$. Preferably, a single variable domain will specifically bind a target antigen or epitope with an affinity of less than 500 nM, preferably less than 200 nM, and more preferably less than 10 nM, such as less than 500 pM Lipocalins Example 19

Generation of Dual-Specific Ligand Comprising a Serum Albumin-Binding Lipocalin Non-Immunoglobulin Scaffold Via Selection of Serum Albumin Binding Moieties The bilin-binding protein (BBP), a lipocalin derived from *Pieris brassicae* can be reshaped by combinatorial protein design such that it recognizes human serum albumin. To this end, native BBP is subjected to library selection and, optionally, affinity maturation in order to produce human serum albumin-binding BBP molecules for use in dual-specific ligands of the invention.

The capability of a native BBP to bind human serum albumin is initially ascertained via Biacore assay, as described infra for CTLA-4-derived polypeptides. (One of skill in the art will recognize that binding affinity can be assessed using any appropriate method, including, e.g., precipitation of labeled human serum albumin, competitive Biacore assay, etc.) Following detection of no or low binding affinity (e.g., Kd values in the μM range or higher) of BBP for human serum albumin, at least one of a number of strategies are employed to impart human serum albumin binding properties to BBP, including one or more of the following methods that contribute to binding affinity.

Human serum albumin binding of BBP and BBP-derived polypeptide(s) is achieved and optimized via mutagenic methods, optionally in combination with parallel and/or iterative selection methods as described below and/or as otherwise known in the art. BBP polypeptide domains are subjected to randomized and/or NNK mutagenesis, performed as described infra. Such mutagenesis is performed upon the entirety of the BBP (or BBP-derived) polypeptide and/or is performed upon specific sequences within the BBP polypeptide, including 16 amino acid residues identified to reside at the center of the native BBP binding site, which is formed by four loops on top of an eight-stranded beta-barrel (Beste et al. 1999 *Proc. Natl. Acad. Sci. USA* 96: 1898-903). Optionally, such mutagenesis procedures are randomized in order to evolve new or improved human serum albumin-binding polypeptides; and multiple rounds of mutagenesis may be performed during the process of creating a BBP that optimally binds to human serum albumin. PCR is optionally used to perform such methods of mutagenesis, resulting in the generation of sequence diversity across targeted sequences within the BBP (or BBP-derived) polypeptides. (Such approaches are similar to those described infra for dAb library generation.) In addition to random methods of mutagenesis, directed mutagenesis of targeted amino acid residues is employed where structural information establishes specific amino acid residues of BBP (or BBP-derived) polypeptides to be critical to binding of human serum albumin.

BBP (or BBP-derived) polypeptides engineered as described above are subjected to parallel and/or iterative selection methods to identify those BBP polypeptides that are optimized for human serum albumin binding. For example, following production of a library of mutagenized BBP polypeptide sequences, said library of polypeptides is displayed on phage and subjected to multiple rounds of selection requiring serum albumin binding and/or proliferation, as is described infra for selection of serum albumin-binding dAbs from libraries of dAbs. Optionally, selection is performed against serum albumin immobilized on immunotubes or against biotinlyated serum albumin in solution. Optionally, binding affinity is determined using surface plasmon resonance (SPR) and the Biacore (Karlsson et al., 1991), using a Biacore system (Uppsala, Sweden), with fully optimized BBP-derived polypeptides ideally achieving human serum albumin binding affinity Kd values in the nM range or better.

Following identification of BBP polypeptides that bind human serum albumin, such polypeptides are then used to generate dual-specific ligand compositions by any of the methods described infra.

Lipocalin Scaffold Proteins

The lipocalins (Pervaiz and Brew, FASEB J. 1 (1987), 209-214) are a family of small, often monomeric secretory proteins that have been isolated from various organisms, and whose physiological role lies in the storage or in the transport of different ligands as well as in more complex biological functions (Flower, Biochem. J. 318 (1996), 1-14). The lipocalins exhibit relatively little mutual sequence similarity and their belonging to the same protein structural family was first elucidated by X-ray structure analysis (Sawyer et al., Nature 327 (1987), 659).

The first lipocalin of known spatial structure was the retinol-binding protein, Rbp, which effects the transport of water-insoluble vitamin A in blood serum (Newcomer et al., EMBO J. 3 (1984), 1451-1454). Shortly thereafter, the tertiary structure of the bilin-binding protein, Bbp, from the butterfly Pieris brassicae was determined (Huber et al., J. Mol. Biol. 195 (1987), 423-434). The essential structural features of this class of proteins is illustrated in the spatial structure of this lipocalin. The central element in the folding architecture of the lipocalins is a cylindrical β-pleated sheet structure, a so-called β-barrel, which is made up of eight nearly circularly arranged antiparallel β-strands.

This super secondary structural element can also be viewed as a "sandwich"-arrangement of two four-stranded β-sheet structures. Additional structural elements are an extended segment at the amino-terminus of the polypeptide chain and an α-helix close to the carboxy-terminus, which itself is followed by an extended segment. These additional features are, however, not necessarily revealed in all lipocalins. For example, a significant part of the N-terminal segment is missing in the epididymal retinoic acid-binding protein (Newcomer, Structure (1993) 1: 7-18). Additional peculiar structural elements are also known, such as, for example, membrane anchors (Bishop and Weiner, Trends Biochem. Sci. (1996) 21: 127) which are only present in certain lipocalins.

The β-barrel is closed on one end by dense amino acid packing as well as by loop segments. On the other end, the β-barrel forms a binding pocket in which the respective ligand of the lipocalin is complexed. The eight neighboring antiparallel β-strands there are connected in a respective pairwise fashion by hairpin bends in the polypeptide chain which, together with the adjacent amino acids which are still partially located in the region of the cylindrical β-pleated sheet structure, each form a loop element. The binding pocket for the ligands is formed by these in total four peptide loops. In the case of Bbp, biliverdin IXγ is complexed in this binding pocket. Another typical ligand for lipocalins is vitamin A in the case of Rbp as well as β-lactoglobulin (Papiz et al., Nature 324 (1986), 383-385).

As described, for example, in U.S. Publication No. 20060058510, members of the lipocalin family of polypeptides can be used to produce a class of molecules termed "anticalins" designed to recognize novel ligands via mutation of amino acids which are located in the region of the four peptide loops at the end of the cylindrical β-pleated sheet structure, and which are characterized in that they bind given ligands (e.g., human serum albumin) with a determinable affinity.

Ligand-binding sites of the lipocalins are constructed more simply than those of immunoglobulins. Lipocalin polypeptides comprise only one ring of 8 antiparallel β-strands: the β-barrel. This cyclic β-pleated sheet structure is conserved in the protein fold of the lipocalins. The binding site is formed in the entry region of the β-barrel by the four peptide loops, each of which connects two neighboring β-strands with one another. These peptide loops can vary significantly in their structure between the individual members of the lipocalin family.

To use a lipocalin polypeptide as a non-immunoglobulin scaffold, one or more of the four peptide loops forming the ligand-binding site of a lipocalin is subjected to mutagenesis, followed by choosing, i.e. selecting those protein variants (muteins), that exhibit the desired binding activity for a given ligand. The lipocalin muteins obtained in this way have been termed "anticalins".

The four peptide loops of the lipocalins which, during production of anticalins, are modified in their sequence by mutagenesis, are characterized by those segments in the linear polypeptide sequence of BBP comprising amino acid positions 28 to 45, 58 to 69, 86 to 99 and 114 to 129 of Bbp. Each of these sequence segments begins before the C-terminus of one of the conserved β-strands at the open side of the β-barrel, includes the actual peptide hairpin, and ends after the N-terminus of the likewise conserved β-strand which follows in the sequence.

Sequence alignments or structural superpositions allow the sequence positions given for Bbp to be assigned to other lipocalins. For example, sequence alignments corresponding to the published alignment of Peitsch and Boguski (New Biologist 2 (1990), 197-206) reveal that the four peptide loops of ApoD include the amino acid positions 28 to 44, 59 to 70, 85 to 98 and 113 to 127. It is also possible to identify the corresponding peptide loops in new lipocalins which are suitable for mutagenesis in the same way.

In some cases, relatively weak sequence homology of the lipocalins may prove to be problematic in the determination of the conserved β-strands. It is therefore crucial that the polypeptide sequence be capable of forming the cyclic β-pleated sheet structure made of 8 antiparallel β-strands. This can be determined by employing methods of structural analysis such as protein crystallography or multidimensional nuclear magnetic resonance spectroscopy.

In non-Bbp lipocalins, such as, for example, ApoD or Rbp, sequence segments suitable for mutagenesis can easily be longer or shorter than that of Bbp based on the individually varying structure of the peptide loops. It can even be advantageous to additionally modify the length of sequence segments by deletion or insertion of one or more amino acids. In certain embodiments, those amino acid positions corresponding to sequence positions 34 to 37, 58, 60, 69, 88, 90, 93, 95, 97, 114, 116, 125, and 127 of Bbp are mutated. Correspondingly, in the case of ApoD, the sequence positions 34 to 37, 59, 61, 70, 87, 89, 92, 94, 96, 113, 115, 123 and 125 are preferred for mutagenesis. However, for the production of anticalins, not all of the sequence positions listed above have to be subjected to mutagenesis.

Other lipocalins are also suitable as an underlying structure for the production of anticalins. Preferably, the lipocalins Rbp, Bbp or ApoD, which presently have already been exhaustively studied biochemically, are used. The use of lipocalins of human origin is especially preferred for the production of anticalins. This especially applies when an application of the resulting anticalin(s) is intended for humans since, for example, in diagnostic or therapeutic applications in vivo, a minimal immunogenic effect is to be expected as compared to lipocalins from other organisms. However, other lipocalins as well as lipocalins which, possibly, have yet to be discovered can prove to be especially advantageous for the production of anticalins. Artificial proteins with a folding element which is structurally equivalent to the β-barrel of the lipocalins can also be used.

Preferably the anticalin molecules of the invention should be able to bind the desired ligand (e.g., human serum albumin) with a determinable affinity, i.e., with an affinity constant of at least $10^5$ $M^{-1}$. Affinities lower than this are generally no longer exactly measurable with common methods and are therefore of secondary importance for practical applications. Especially preferred are anticalins which bind the desired ligand with an affinity of at least $10^6$ $M^{-1}$, corresponding to a dissociation constant for the complex of 1 µM. The binding affinity of an anticalin to the desired ligand can be measured by the person skilled in the art by a multitude of methods, for example by fluorescence titration, by competition ELISA or by the technique of surface plasmon resonance.

The lipocalin cDNA, which can be produced and cloned by the person skilled in the art by known methods, can serve as a starting point for mutagenesis of the peptide loop, as it was for example described for Bbp (Schmidt and Skerra, *Eur. J. Biochem.* 219 (1994), 855-863). Alternatively, genomic DNA can also be employed for gene synthesis or a combination of these methods can be performed. For the mutagenesis of the amino acids in the four peptide loops, the person skilled in the art has at his disposal the various known methods for site-directed mutagenesis or for mutagenesis by means of the polymerase chain reaction. The mutagenesis method can, for example, be characterized in that mixtures of synthetic oligodeoxynucleotides, which bear a degenerate base composition at the desired positions, can be used for introduction of the mutations. The implementation of nucleotide building blocks with reduced base pair specificity, as for example inosine, is also an option for the introduction of mutations into the chosen sequence segment or amino acid positions. The procedure for mutagenesis of ligand-binding sites is simplified as compared to antibodies, since for the lipocalins only four instead of six sequence segments—corresponding to the four above cited peptide loops—have to be manipulated for this purpose.

In the methods of site-directed random mutagenesis implementing synthetic oligodeoxynucleotides, the relevant amino acid positions in the lipocalin structure which are to be mutated can be determined in advance. The ideal selection of the amino acid positions to be mutated can depend on the one hand on the lipocalin used, and on the other hand on the desired ligand (e.g., human serum albumin). It can be useful to maintain the total number of mutated amino acid positions within a single experiment low enough such that the collection of variants obtained by mutagenesis, i.e. the so-called library, can in its totality or, at least in a representative selection therefrom, be realized as completely as possible in its combinatorial complexity, not only at the level of the coding nucleic acids, but also at the level of the gene products.

It is possible to choose the amino acid positions to be mutated in a meaningful way especially when structural information exists pertaining to the lipocalin itself which is to be used, as is the case with BBP and Rbp or at least pertaining to a lipocalin with a similar structure, as for example in the case of ApoD. The set of amino acid positions chosen can further depend on the characteristics of the desired ligand. It can also prove advantageous to exclude single amino acid positions in the region of the ligand-binding pocket from mutagenesis if these, for example, prove to be essential for the folding efficiency or the folding stability of the protein. Specific oligonucleotide-based methods of lipocalin mutagenesis are described, for example, in U.S. Publication No. 20060058510, the entire contents of which are incorporated herein by reference.

After expressing the coding nucleic acid sequences subjected to mutagenesis, clones carrying the genetic information for anticalins which bind a given ligand (e.g., human serum albumin) can be selected from the differing clones of the library obtained. Known expression strategies and selection strategies can be implemented for the selection of these clones. Methods of this sort have been described in the context of the production or the engineering of recombinant antibody fragments, such as the "phage display" technique or "colony screening" methods (Skerra et al., *Anal. Biochem.* 196 (1991), 151-155).

Descriptions of "phage display" techniques are found, for example, in Hoess, *Curr. Opin. Struct. Biol.* 3 (1993), 572-579; Wells and Lowman, *Curr. Opin. Struct. Biol.* 2 (1992), 597-604; and Kay et al., Phage Display of Peptides and Proteins—A Laboratory Manual (1996), Academic Press. Briefly, in an exemplary embodiment, phasmids are produced which effect the expression of the mutated lipocalin structural gene as a fusion protein with a signal sequence at the N-terminus, preferably the OmpA-signal sequence, and with the coat protein pIII of the phage M13 (Model and Russel, in "The Bacteriophages", Vol. 2 (1988), Plenum Press, New York, 375-456) or fragments of this coat protein, which are incorporated into the phage coat, at the C-terminus. The C-terminal fragment ApIII of the phage coat protein, which contains only amino acids 217 to 406 of the natural coat protein pIII, is preferably used to produce the fusion proteins. Especially preferred is a C-terminal fragment from pIII in which the cysteine residue at position 201 is missing or is replaced by another amino acid. Further description of phage display methods, selection methods, etc., that can be applied to lipocalins in production of "anticalins" possessing specific binding properties is detailed in, for example, U.S. Publication No. 20060058510, the entire contents of which are incorporated herein by reference.

Anticalins can be identified and produced, for example, using the above-described methods, to possess high affinity for a given ligand (e.g., human serum albumin). Ligand binding constants of more than $10^6$ $M^{-1}$ can be achieved for anticalins, even in cases where a novel ligand bears no structural relationship whatsoever to biliverdin IXγ, the original ligand of Bbp (refer to U.S. Publication No. 20060058510). Such affinities for novel ligands attainable with the anticalins are comparable with the affinities which are known for antibodies from the secondary immune response. Furthermore, there additionally exists the possibility to subject the anticalins produced to a further, optionally partial random mutagenesis in order to select variants of even higher affinity from the new library thus obtained. Corresponding procedures have already been described for the case of recombinant antibody fragments for the purpose of an "affinity maturation" (Low et al., *J. Mol. Biol.* 260 (1996), 359-368; Barbas and Burton, *Trends Biotechnol.* 14 (1996), 230-234) and can also be applied to anticalins in a corresponding manner by the person skilled in the art.

Staphylococcal Protein A (SPA)/Affibody

Example 20

Generation of Dual-Specific Ligand Comprising a Serum Albumin-Binding Affibody (Staphylococcal Protein a (SPA)) Non-Immunoglobulin Scaffold Via Selection of Serum Albumin Binding Moieties The Z domain of staphylococcal protein A (SPA) is subjected to library selection and, optionally, affinity maturation techniques in order to produce human serum albumin-binding SPA-derived non-immunoglobulin scaffold molecules (termed "affibodies") for use in dual-specific ligands of the invention.

Real-time binding analysis by Biacore is performed to assess whether human serum albumin specifically binds to immobilized SPA polypeptide. (One of skill in the art will recognize that binding affinity can be assessed using any appropriate method, including, e.g., precipitation of labeled human serum albumin, competitive Biacore assay, etc.) Following detection of no or low binding affinity (e.g., Kd values in the μM range or higher) of an unaltered SPA polypeptide for human serum albumin, at least one of a number of strategies are employed to impart human serum albumin binding properties to the SPA polypeptide, including one or more of the following methods designed to impart and/or enhance binding affinity of the molecule for target antigen.

Human serum albumin binding of SPA scaffold polypeptide(s) is achieved and optimized via mutagenic methods, optionally in combination with parallel and/or iterative selection methods as described below and/or as otherwise known in the art. SPA scaffold polypeptide domains are subjected to randomized and/or NNK mutagenesis, performed as described infra. Such mutagenesis is performed upon the entirety of the Z domain of the SPA polypeptide or upon specific sequences within the SPA polypeptide, e.g., upon 13 solvent-accessible surface residues of domain Z as identified in Nord et al. (1997 *Nat. Biotechnol.* 15: 772-77), and is optionally randomized in order to evolve new or improved human serum albumin-binding polypeptides. PCR is optionally used to perform such methods of mutagenesis, resulting in the generation of sequence diversity across targeted sequences within the SPA polypeptides. (Such approaches are similar to those described infra for dAb library generation.) In addition to random methods of mutagenesis, directed mutagenesis of targeted amino acid residues is employed where structural information establishes specific amino acid residues of SPA polypeptides to be critical to binding of human serum albumin. In certain embodiments, repertoires of mutant Z domain genes are assembled and inserted into a phagemid vector adapted for monovalent phage display. Libraries comprising, e.g., millions of transformants, are constructed using, e.g., NN(G/T) or alternative (C/A/G)NN degeneracy for mutagenesis.

SPA polypeptides engineered as described above are subjected to parallel and/or iterative selection methods to identify those SPA polypeptides that are optimized for human serum albumin binding. For example, following production of a library of mutagenized SPA polypeptide sequences, said library of polypeptides is displayed on phage and subjected to multiple rounds of selection requiring serum albumin binding and/or proliferation, as is described infra for selection of serum albumin-binding dAbs from libraries of dAbs. Biopanning against the human serum albumin target protein is performed to achieve significant enrichment for serum albumin binding SPA molecules. Selected clones are subsequently expressed in *E. coli* and analyzed by SDS-PAGE, circular dichroism spectroscopy, and binding studies to human serum albumin by biospecific interaction analysis. The SPA molecules (affibodies) that bind to human serum albumin are anticipated to have a secondary structure similar to the native Z domain and have micromolar dissociation constants (Kd) for their respective targets in the range of μM or better (e.g., nM or pM).

Optionally, selection is performed against serum albumin immobilized on immunotubes or against biotinlyated serum albumin in solution. Optionally, binding affinity is determined using surface plasmon resonance (SPR) and the Biacore (Karlsson et al., 1991), using a Biacore system (Uppsala, Sweden), with fully optimized SPA-derived polypeptides ideally achieving human serum albumin binding affinity Kd values in the nM range or better.

Following identification of SPA polypeptides that bind human serum albumin, such polypeptides are then used to generate dual-specific ligand compositions by any of the methods described infra.

Staphylococcal Protein A (SPA) Affibody Polypeptides

Solvent-exposed surfaces of bacterial receptors can be targeted for random mutagenesis followed by phenotypic selection for purpose of imparting, e.g., binding affinity for serum albumin to such receptor molecules. Such proteins can be unusually stable, which makes them suitable for various applications (Alexander et al. (1992) Biochemistry 31: 3597-3603). In particular, for bacterial receptors containing helix bundle structures, the conformation can be expected to be tolerant to changes in the side chains of residues not involved in helix packing interfaces. Examples of such molecules are the relatively small (58 residues) IgG-binding domain B of staphylococcal protein A (SPA) and the synthetic analogue of domain B, designated domain Z (Nilsson et al. (1987) Protein Engineering 1: 107-113).

The SPA-derived domain Z is the primary domain of SPA utilized as a scaffold for purpose of constructing domain variants with novel binding properties (refer to, e.g., WO 00/63243 and WO 95/19374, incorporated herein by reference in their entireties). The SPA Z domain is a 58 amino acid residue cysteine-free three-helix bundle domain that is used as a scaffold for construction of combinatorial phagemid libraries from which variants are selected that target desired molecules (e.g., human serum albumin) using phage display technology (Nilsson et al. 1987 Protein Eng. 1: 107-113; Nord et al. 1997 Nat. Biotechnol. 15: 772-777; Nord et al. 2000 J. Biotechnol. 80: 45-54; Hansson et al. 1999 Immunotechnology 4: 237-252; Eklund et al., 2002 Proteins 48: 454-462; Ronnmark et al. 2002 Eur. J. Biochem. 269: 2647-2655). Such target-binding variants, termed "affibody" molecules, are selected as binders to target proteins by phage display of combinatorial libraries in which typically 13 side-chains on the surface of helices 1 and 2 (Q9, Q10, N11, F13, Y14, L17, H18, E24, E25, R27, N28, Q32 and K35) in the Z domain have been randomized (Lendel et al. 2006 J. Mol. Biol. 359:

1293-304). The simple, robust structure of such affibody molecules, together with their low molecular weight (7 Kda), make them suitable for a wide variety of applications. Documented efficacy has been shown in bioprocess- and laboratory-scale bioseparations (Nord et al. 2000 J. Biotechnol. 80: 45-54; Nord et al. 2001 Eur. J. Biochem. 268: 4269-4277; Gräslund et al. 2002 J. Biotechnol. 99: 41-50), and promising results have been obtained when evaluating affibody ligands as detection reagents (Karlström and Nygren 2001 Anal. Biochem. 295: 22-30; Rönnmark et al. 2002 J. Immunol. Methods 261: 199-211), to engineer adenoviral tropism (Henning et al. 2002 Hum. Gene Ther. 13: 1427-1439) and to inhibit receptor interactions (Sandstrom et al. 2003 Protein Eng. 16: 691-697). Thus, engineered affibody ligands that, e.g., bind to human serum albumin are desirable components of certain dual-specific ligand compositions of the present invention.

Libraries of polypeptides derived from the Z domain of staphylococcal protein A may be generated by any method of mutagenesis as known in the art and/or as described infra. Following creation of such polypeptide libraries variants capable of binding desired target molecules (e.g., human serum albumin) can be efficiently selected and identified using, for example, in vitro selection technologies such as phage display (Dunn 1996; Smith and Patrenko 1997; Hoogenboom et al. 1998), ribosomal display (Hanes and Pluckthun 1997; He and Taussig 1997) peptides on plasmids (Schatz 1993) or bacterial display (Georgiou et al. 1997). For such selections, a correlation between library size (complexity) and the likelihood of isolating binders of higher affinities ($K_D = 10^{-8}$ M or lower) has been theoretically considered (Perelson and Oster 1979) and experimentally demonstrated (Griffiths et al. 1994; Vaughan et al. 1996; Aujame et al. 1997).

Affibodies have several advantages over traditional antibodies, e.g. (i) a lower cost of manufacture; (ii) smaller size; (iii) increased stability and robustness; and (iv) the ability of being produced recombinantly in a bacterial host, or by chemical synthesis, which obviates the risk for viral contamination.

An affibody is a polypeptide which is a derivative of a staphylococcal protein A (SPA) domain, said SPA domain being the B or Z domain, wherein a number of the amino acid residues have been substituted by other amino acid residues, said substitution being made without substantial loss of the basic structure and stability of the said SPA domain, and said substitution resulting in interaction capacity of the said polypeptide with at least one domain of a target antigen (e.g., human serum albumin). The number of substituted amino acid residues could be from 1 to about 30, or from 1 to about 13. Other possible ranges are from 4 to about 30; from 4 to about 13; from 5 to about 20, or from 5 to about 13 amino acid residues. It will be understood by the skilled person, e.g., from Nord et al. 1997 *Nat. Biotechnol.* 15: 772-777, that preferentially amino residues located on the surface of the Z-domain can be substituted, while the core of the bundle should be kept constant to conserve the structural properties of the molecule.

A process for the manufacture of an affibody is set forth, e.g., in WO 00/63243, and for purposes of the present invention could involve, e.g., the following steps: (i) displaying, by e.g. phage display (for a review, see, e.g., Kay, K. et al. (eds.) Phage Display of Peptides and Proteins: A Laboratory Manual, Academic Press, San Diego, ISBN 0-12-4023 80-0), ribosomal display (for a review, see e.g. Hanes, J. et al. (1998) *Proc. Natl. Acad. Sci. USA* 95: 14130-14135) or cell display (for a review, see e.g. Daugherty, P. S. et al. (1998) *Protein Eng.* 11: 825-832), polypeptide variants from a protein library embodying a repertoire of polypeptide variants derived from SPA domain B or Z; (ii) selecting clones expressing polypeptides that bind to human serum albumin; and (iii) producing polypeptides by recombinant expression of the selected clones or by chemical synthesis.

Avimer

Example 21

Generation of Dual-Specific Ligand Comprising a Serum Albumin-Binding Avimer Via CDR Grafting The CDR domains of dAb7h14 are used to construct an avimer polypeptide that binds human serum albumin in the following manner. The CDR1 (RASQWIGSQLS; SEQ ID NO.: 95), CDR2 (WRSSLQS; SEQ ID NO.: 96), and CDR3 (AQGAALPRT; SEQ ID NO.: 97) sequences of dAb7h14 are grafted into a C2 monomer (described in US Patent Publication No. 2005/0221384, incorporated herein by reference in its entirety) at residues 17-28, 49-53 and 78-85, respectively, which constitute the loop regions 1, 2 and 3, respectively of the C2 monomer. Real-time binding analysis by Biacore is performed to assess whether human serum albumin specifically binds to immobilized C2-derived monomer polypeptide comprising the anti-human serum albumin CDR domains of dAb7h14. (One of skill in the art will recognize that binding affinity can be assessed using any appropriate method, including, e.g., precipitation of labeled human serum albumin, competitive Biacore assay, etc.) If no or low human serum albumin affinity (e.g., Kd values in the µM range or higher) is detected, at least one of a number of strategies are employed to improve the human serum albumin binding properties of the CDR-grafted C2 monomer (and/or of avimer dimers, trimers and other higher-order iteration compositions), including any of the following methods that contribute to binding affinity.

The length(s) of dAb7h14 CDR-grafted regions of the initial C2 monomer polypeptide (and/or of iteratively-produced avimer dimer, trimer, etc. polypeptides) corresponding to solvent-exposed loop regions within the native C2 monomer (and/or within other native monomers used in the avimer compositions) are adjusted through the use of linker polypeptides. For example, the nine amino acid residue CDR3 peptide sequence of dAb7h14 can be extended to 13 amino acid residues in length using amino acid linkers of, e.g., zero to four residues in length located on either and/or both the N- or C-terminal flanks of the dAb7h14 CDR3 polypeptide sequence, thereby achieving a total grafted peptide sequence length of 13 amino acids within the CDR3-grafted domain corresponding to loop 3 of the C2 monomer polypeptide. Such use of linker polypeptide(s) is optionally combined with mutagenesis of the linker sequences, CDR sequences and/or non-CDR C2 monomer polypeptide sequences (e.g., using mutagenic optimization procedures as described below), in order to improve the human serum albumin binding capability of CDR-grafted C2 monomer polypeptide(s) (e.g., via optimization of both CDR and C2 monomer polypeptide sequences within the CDR-grafted C2 monomer polypeptides). The polypeptide linkers employed for such purpose either possess a predetermined sequence, or, optionally, are selected from a population of randomized polypeptide linker sequences via assessment of the human serum albumin binding capabilities of linker-containing CDR-grafted C2 monomer polypeptides. Optimization methods are performed in parallel and/or iteratively. Both parallel and iterative optimization (e.g., affinity maturation) processes employ selection methods as described below and/or as known in the art as useful for optimization of polypeptide binding properties.

Human serum albumin binding of CDR-grafted C2 monomer polypeptide(s) (and/or of avimer dimer, trimer, etc. iteratively-produced higher-order compositions, or individual additional monomers contributing to same) presenting dAb7h14 CDRs is optimized via mutagenesis, optionally in combination with parallel and/or iterative selection methods as described below and/or as otherwise known in the art. For the exemplary C2 monomer scaffold polypeptide, domains surrounding grafted dAb7h14 CDR polypeptide sequences are subjected to randomized and/or NNK mutagenesis, performed as described infra. Such mutagenesis is optionally performed within the C2 monomer polypeptide sequence upon selected amino acid residues as set forth, e.g., in US Patent Publication No. 2005/0221384, or is optionally performed upon all non-CDR amino acid residues, and is optionally randomized in order to evolve new or improved human serum albumin-binding polypeptides. Optionally, dAb7h14 CDR polypeptide domains presented within the CDR-grafted C2 monomer polypeptide are subjected to mutagenesis via, e.g., random mutagenesis, NNK mutagenesis, look-through mutagenesis and/or other art-recognized method. PCR is optionally used to perform such methods of mutagenesis, resulting in the generation of sequence diversity across targeted sequences within the CDR-grafted C2 monomer polypeptides. Such approaches are similar to those described infra for dAb library generation. In addition to random and/or look-through methods of mutagenesis, directed mutagenesis of targeted amino acid residues is employed where structural information establishes specific amino acid residues to be critical to binding of human serum albumin.

C2 monomer polypeptides (and/or iteratively produced avimer compositions comprising individual monomers) comprising grafted dAb7h14 CDR sequences engineered as described above are subjected to parallel and/or iterative selection methods to identify those C2 monomer polypeptides (and avimer compositions) that are optimized for human serum albumin binding. For example, following production of a library of dAb7h14 CDR-grafted C2 monomer polypeptide sequences, this library of such polypeptides is displayed on phage and subjected to multiple rounds of selection requiring serum albumin binding and/or proliferation, as is described infra for selection of serum albumin-binding dAbs from libraries of dAbs. Optionally, selection is performed against serum albumin immobilized on immunotubes or against biotinlyated serum albumin in solution. Optionally, binding affinity is determined using surface plasmon resonance (SPR) and the Biacore (Karlsson et al., 1991), using a Biacore system (Uppsala, Sweden), with fully optimized avimers comprising C2-derived monomers ideally achieving human serum albumin binding affinity Kd values in the nM range or better.

Upon identification of C2 monomer-derived polypeptides that bind human serum albumin, human serum binding properties of such initial monomers may be further enhanced via combination of such monomers with other monomers, followed by further mutagenesis and/or selection, thereby forming an avimer composition possessing specific affinity for human serum albumin. Following identification of an avimer composition possessing affinity for human serum albumin, such avimer polypeptides are then used to generate dual-specific ligand compositions by any of the methods described infra.

Example 22

Generation of Dual-Specific Ligand Comprising a Serum Albumin-Binding Avimer Non-Immunoglobulin Scaffold Via Selection of Serum Albumin Binding Moieties The native C2 monomer polypeptide as set forth in is subjected to library selection and, optionally, affinity maturation techniques, then combined with an additional monomer (e.g., a fibronectin monomer, for which human serum albumin affinity optionally can be optimized in parallel) and optionally iteratively subjected to library selection and, optionally, affinity maturation techniques in order to produce a human serum albumin-binding avimer non-immunoglobulin scaffold molecule for use in dual-specific ligands of the invention.

Real-time binding analysis by Biacore is performed to assess whether human serum albumin specifically binds to an immobilized C2 monomer polypeptide (and/or an iteratively-produced avimer molecule). Following detection of no or low binding affinity (e.g., Kd values in the µM range or higher) of a C2 monomer polypeptide for human serum albumin, at least one of a number of strategies are employed to impart human serum albumin binding properties to the C2 monomer polypeptide, including one or more of the following methods that contribute to binding affinity.

Human serum albumin binding of C2 monomer polypeptide(s) (and/or iteratively produced avimer dimer, trimer, etc. molecules) is achieved and optimized via mutagenic methods, optionally in combination with parallel and/or iterative selection methods as described below and/or as otherwise known in the art. C2 monomer polypeptide domains are subjected to randomized and/or NNK mutagenesis, performed as described infra. Such mutagenesis is performed upon the entirety of the C2 monomer polypeptide or upon specific sequences within the C2 monomer polypeptide upon selected amino acid residues as set forth, e.g., in US Patent Publication No. 2005/0221384, and is optionally randomized in order to evolve new or improved human serum albumin-binding polypeptides. PCR is optionally used to perform such methods of mutagenesis, resulting in the generation of sequence diversity across targeted sequences within the C2 monomer polypeptides and/or avimer molecules. (Such approaches are similar to those described infra for dAb library generation.) In addition to random methods of mutagenesis, directed mutagenesis of targeted amino acid residues is employed where structural information establishes specific amino acid residues of C2 monomer and/or avimer molecules to be critical to binding of human serum albumin.

C2 monomer polypeptides engineered as described above are subjected to parallel and/or iterative selection methods to identify those C2 monomer polypeptides and/or avimer molecules that are optimized for human serum albumin binding. For example, following production of a library of mutagenized C2 monomer polypeptide sequences, said library of polypeptides is displayed on phage and subjected to multiple rounds of selection requiring serum albumin binding and/or proliferation, as is described infra for selection of serum albumin-binding dAbs from libraries of dAbs. Optionally, the rounds of selection may include iterations within which additional monomer subunits are added to form a new avimer molecule. Optionally, selection is performed against serum albumin immobilized on immunotubes or against biotinlyated serum albumin in solution. Optionally, binding affinity is determined using surface plasmon resonance (SPR) and the Biacore (Karlsson et al., 1991), using a Biacore system (Uppsala, Sweden), with fully optimized avimers comprising C2-derived monomer polypeptides ideally achieving human serum albumin binding affinity Kd values in the nM range or better.

Upon identification of C2 monomer-derived polypeptides that bind human serum albumin, human serum binding properties of such initial monomers may be further enhanced via combination of such monomers with other monomers, followed by further mutagenesis and/or selection, thereby forming an avimer composition possessing specific affinity for human serum albumin. Following identification of an avimer composition possessing affinity for human serum albumin, such avimer polypeptides are then used to generate dual-specific ligand compositions by any of the methods described infra.

Production and Use of Avimer Polypeptides

Avimers are evolved from a large family of human extracellular receptor domains by in vitro exon shuffling and phage display, generating multidomain proteins with binding and/or inhibitory properties. Linking multiple independent binding domains (selected, e.g., in iterative fashion for binding to a target protein, e.g., human serum albumin) creates avidity and results in improved affinity and specificity compared with conventional single-epitope binding proteins. Other potential advantages include simple and efficient production of multi-target-specific molecules in *E. coli*, improved thermostability and resistance to proteases. Avimers can be produced that possess sub-nM affinities against a target protein. For example, an avimer that inhibits interleukin 6 with 0.8 µM $IC_{50}$ in cell-based assays has been produced and characterized as biologically active (Silverman et al. 2005 Nature Biotechnology 23: 1556-1561; also see, for example, U.S. Patent Application Publ. Nos. 2005/0221384, 2005/0164301, 2005/0053973 and 2005/0089932, 2005/0048512, and 2004/0175756, each of which is hereby incorporated by reference herein in its entirety).

Avimer synthesis involves phage display libraries derived from the human repertoire of A domains. Synthetic recombination is used to create a highly diverse pool of monomers, as described in Silverman et al. (2005 Nature Biotechnology 23: 1556-1561). Following generation of a pool of monomers, the pool is screened against target protein (e.g., human serum albumin). Initial candidates are identified, and an additional monomer is added and the resulting dimer library is screened against the target protein to identify candidate target-binding dimers. The method is then iterated to obtain a trimer with very high binding affinity for the target protein, and, optionally, may be iterated further to identify higher order candidate complexes. Candidate complexes that are identified to bind with high affinity and specificity to target proteins are termed avimers (for "avidity multimer").

Monomer domains of avimers can be polypeptide chains of any size. For example, monomer domains can have about 25 to about 500, about 30 to about 200, about 30 to about 100, about 90 to about 200, about 30 to about 250, about 30 to about 60, about 9 to about 150, about 100 to about 150, about 25 to about 50, or about 30 to about 150 amino acids. Similarly, a monomer domain of an avimer can comprise, e.g., from about 30 to about 200 amino acids; from about 25 to about 180 amino acids; from about 40 to about 150 amino acids; from about 50 to about 130 amino acids; or from about 75 to about 125 amino acids. Monomer domains and immuno-domains can typically maintain stable conformation in solution. Sometimes, monomer domains of avimers and immuno-domains can fold independently into a stable conformation. The stable conformation can be stabilized by metal ions. The stable conformation can optionally contain disulfide bonds (e.g., at least one, two, or three or more disulfide bonds). The disulfide bonds can optionally be formed between two cysteine residues.

Publications describing monomer domains and mosaic proteins and references cited within include the following: Hegyi, H and Bork, P. 1997 *J. Protein Chem.*, 16: 545-551; Baron et al. 1991 *Trends Biochem. Sci.* 16: 13-17; Ponting et al. 2000 *Adv. Protein Chem.* 54: 185-244; Doolittle 1995 *Annu. Rev. Biochem* 64: 287-314; Doolitte and Bork 1993 *Scientific American* 269: 50-6; and Bork 1991 *FEBS letters* 286: 47-54. Monomer domains used in avimers can also include those domains found in Pfam database and the SMART database. See Schultz et al. 2000 *Nucleic Acid Res.* 28: 231-34.

Monomer domains that are particularly suitable for use in avimer compositions are (1) β-sandwich domains; (2) β-barrel domains; or (3) cysteine-rich domains comprising disulfide bonds. Cysteine-rich domains employed in avimers typically do not form an α-helix, a β-sheet, or a β-barrel structure. Typically, the disulfide bonds promote folding of the domain into a three-dimensional structure. Usually, cysteine-rich domains have at least two disulfide bands, more typically at least three disulfide bonds.

Monomer domains of avimers can have any number of characteristics. For example, the domains can have low or no immunogenicity in an animal (e.g., a human). Domains can have a small size, for example, the domains may be small enough to penetrate skin or other tissues. Domains can possess a range of in vivo half-lives or stabilities.

Illustrative monomer domains suitable for use in avimer compositions include, e.g., an EGF-like domain, a Kringle-domain, a fibronectin type I domain, a fibronectin type II domain, a fibronectin type III domain, a PAN domain, a Gla domain, a SRCR domain, a Kunitz/Bovine pancreatic trypsin Inhibitor domain, a Kazal-type serine protease inhibitor domain, a Trefoil (P-type) domain, a von Willebrand factor type C domain, an Anaphylatoxin-like domain, a CUB domain, a thyroglobulin type I repeat, LDL-receptor class A domain, a Sushi domain, a Link domain, a Thrombospondin type I domain, a thyroglobulin monomer domain, an Immunoglobulin-like domain, a C-type lectin domain, a MAM domain, a von Willebrand factor type A domain, a Somatomedin B domain, a WAP-type four disulfide core domain, a F5/8 type C domain, a Hemopexin domain, an SH2 domain, an SH3 domain, a Laminin-type EGF-like domain, a C2 domain, and other such domains known to those of ordinary skill in the art, as well as derivatives and/or variants thereof. US Patent Publication No. 20050221384 presents schematic diagrams of various exemplary forms of monomer domains found in molecules in the LDL-receptor family.

Suitable monomer domains (e.g., domains with the ability to fold independently or with some limited assistance) can be selected from the families of protein domains that contain β-sandwich or β-barrel three dimensional structures as defined by such computational sequence analysis tools as Simple Modular Architecture Research Tool (SMART; see Shultz et al. 2000 *Nucleic Acids Research* 28: 231-234) or CATH (see Pearl et al. 2000 *Nucleic Acids Research* 28: 277-282). Exemplary monomer domains of avimers also include domains of fibronectin type III domain, an anticalin domain and a Ig-like domain from CTLA-4. Some aspects of these domains are described in WO 01/64942 by Lipovsek et al., WO99/16873 by Beste et al., and WO 00/60070 by Desmet et al., the contents of which are incorporated in their entirety herein by reference.

Monomer domains of avimers are optionally cysteine rich. Suitable cysteine rich monomer domains include, e.g., the LDL receptor class A domain ("A-domain") or the EGF-like domain. The monomer domains can also have a cluster of negatively charged residues. Optionally, the monomer domains contain a repeated sequence, such as YWTD (SEQ ID NO: 102) as found in the Propeller domain. Another exemplary monomer domain suitable for use in avimers is the C2 domain. Exemplary A domain and C2 domain sequences and consensus sequences useful in avimer production, including exemplary selections of amino acid residues (e.g., surface-exposed loop residues) most desirable for mutagenic targeting, are presented in US Patent Publication No. 2005/0221384.

Polynucleotides (also referred to as nucleic acids) encoding the monomer domains are typically employed to make monomer domains via expression. Nucleic acids that encode monomer domains can be derived from a variety of different sources. Libraries of monomer domains can be prepared by expressing a plurality of different nucleic acids encoding naturally occurring monomer domains, altered monomer domains (i.e., monomer domain variants), or a combinations thereof.

Monomer domains that bind to a selected or desired ligand (e.g., human serum albumin) or mixture of ligands are identified, optionally as an initial step in avimer production. In some embodiments, monomer domains and/or immuno-domains are identified or selected for a desired property (e.g., binding affinity for human serum albumin) and then the monomer domains and/or immuno-domains are formed into multimers. For those embodiments, any method resulting in selection of domains with a desired property (e.g., human serum albumin binding) can be used. For example, the methods can comprise providing a plurality of different nucleic acids, each nucleic acid encoding a monomer domain; translating the plurality of different nucleic acids, thereby providing a plurality of different monomer domains; screening the plurality of different monomer domains for binding of the desired ligand or a mixture of ligands; and, identifying members of the plurality of different monomer domains that bind the desired ligand or mixture of ligands.

Monomer domains for avimer production can be naturally-occurring or altered (non-natural variants). The term "naturally occurring" is used herein to indicate that an object can be found in nature. For example, natural monomer domains can include human monomer domains or optionally, domains derived from different species or sources, e.g., mammals, primates, rodents, fish, birds, reptiles, plants, etc. The natural occurring monomer domains can be obtained by a number of methods, e.g., by PCR amplification of genomic DNA or cDNA. The term "native", as used herein, is used in reference to a nucleic acid and/or polypeptide that has not been altered via mutagenesis or otherwise via performance of any of the methods described infra.

Monomer domains of avimers can be naturally-occurring domains or non-naturally occurring variants. Libraries of monomer domains employed in synthesis of avimers may contain naturally-occurring monomer domain, non-naturally occurring monomer domain variants, or a combination thereof.

A variety of reporting display vectors or systems can be used to express nucleic acids encoding monomer domains and avimers, and to test for a desired activity (e.g., human serum albumin binding). For example, a phage display system is a system in which monomer domains are expressed as fusion proteins on the phage surface (Pharmacia, Milwaukee Wis.). Phage display can involve the presentation of a polypeptide sequence encoding monomer domains and/or immuno-domains on the surface of a filamentous bacteriophage, typically as a fusion with a bacteriophage coat protein. Exemplary methods of affinity enrichment and phage display are set forth, for example, in PCT patent publication Nos. 91/17271, 91/18980, and 91/19818 and 93/08278, incorporated herein by reference in their entireties.

Examples of other display systems include ribosome displays, a nucleotide-linked display (see, e.g., U.S. Pat. Nos. 6,281,344; 6,194,550, 6,207,446, 6,214,553, and 6,258,558), cell surface displays and the like. The cell surface displays include a variety of cells, e.g., E. coli, yeast and/or mammalian cells. When a cell is used as a display, the nucleic acids, e.g., obtained by PCR amplification followed by digestion, are introduced into the cell and translated. Optionally, polypeptides encoding monomer domains or avimers can be introduced, e.g., by injection, into the cell.

As described infra and in the art, avimers are multimeric compositions. In exemplary embodiments, multimers comprise at least two monomer domains and/or immuno-domains. For example, multimers of the invention can comprise from 2 to about 10 monomer domains and/or immuno-domains, from 2 and about 8 monomer domains and/or immuno-domains, from about 3 and about 10 monomer domains and/or immuno-domains, about 7 monomer domains and/or immuno-domains, about 6 monomer domains and/or immuno-domains, about 5 monomer domains and/or immuno-domains, or about 4 monomer domains and/or immuno-domains. In some embodiments, the multimer comprises at least 3 monomer domains and/or immuno-domains. Typically, the monomer domains have been pre-selected for binding to the target molecule of interest (e.g., human serum albumin).

Within an avimer, each monomer domain may specifically bind to one target molecule (e.g., human serum albumin). Optionally, each monomer binds to a different position (analogous to an epitope) on a target molecule. Multiple monomer domains and/or immuno-domains that bind to the same target molecule can result in an avidity effect resulting in improved avidity of the multimer avimer for the target molecule compared to each individual monomer. Optionally, the multimer can possess an avidity of at least about 1.5, 2, 3, 4, 5, 10, 20, 50 or 100 times the avidity of a monomer domain alone for target protein (e.g., human serum albumin).

Selected monomer domains can be joined by a linker to form a multimer (avimer). For example, a linker is positioned between each separate discrete monomer domain in a multimer. Typically, immuno-domains are also linked to each other or to monomer domains via a linker moiety. Linker moieties that can be readily employed to link immuno-domain variants together are the same as those described for multimers of monomer domain variants. Exemplary linker moieties suitable for joining immuno-domain variants to other domains into multimers are described herein.

Joining of selected monomer domains via a linker to form an avimer can be accomplished using a variety of techniques known in the art. For example, combinatorial assembly of polynucleotides encoding selected monomer domains can be achieved by DNA ligation, or optionally, by PCR-based, self-priming overlap reactions. The linker can be attached to a monomer before the monomer is identified for its ability to bind to a target multimer or after the monomer has been selected for the ability to bind to a target multimer.

As mentioned above, the polypeptide(s) comprising avimers can be altered. Descriptions of a variety of diversity generating procedures for generating modified or altered nucleic acid sequences encoding these polypeptides are described above and below in the following publications and the references cited therein: Soong, N. et al., Molecular breeding of viruses, (2000) Nat Genet 25(4):436-439; Stemmer, et al., Molecular breeding of viruses for targeting and other clinical properties, (1999) Tumor Targeting 4:1-4; Ness et al., DNA Shuffling of subgenomic sequences of subtilisin, (1999) Nature Biotechnology 17:893-896; Chang et al., Evolution of a cytokine using DNA family shuffling, (1999) Nature Biotechnology 17:793-797; Minshull and Stemmer, Protein evolution by molecular breeding, (1999) Current Opinion in Chemical Biology 3:284-290; Christians et al., Directed evolution of thymidine kinase for AZT phosphorylation using DNA family shuffling, (1999) Nature Biotechnology 17:259-264; Crameri et al., DNA shuffling of a family of genes from diverse species accelerates directed evolution, (1998) Nature 391:288-291; Crameri et al., Molecular evolution of an arsenate detoxification pathway by DNA shuffling, (1997) Nature Biotechnology 15:436-438; Zhang et al., Directed evolution of an effective fucosidase from a galactosidase by DNA shuffling and screening (1997) Proc. Natl. Acad. Sci. USA 94:4504-4509; Patten et al., Applications of DNA Shuffling to Pharmaceuticals and Vaccines, (1997) Current Opinion in Biotechnology 8:724-733; Crameri et al., Construction and evolution of antibody-phage libraries by DNA shuffling, (1996) Nature Medicine 2:100-103; Crameri et al., Improved green fluorescent protein by molecular evolution using DNA shuffling, (1996) Nature Biotechnology 14:315-319; Gates et al., Affinity selective isolation of ligands from peptide libraries through display on a lac repressor 'headpiece dimer', (1996) Journal of Molecular Biology 255:373-386; Stemmer, Sexual PCR and Assembly PCR, (1996) In: The Encyclopedia of Molecular Biology. VCH Publishers, New York. pp. 447-457; Crameri and Stemmer, Combinatorial multiple cassette mutagenesis creates all the permutations of mutant and wildtype cassettes, (1995) BioTechniques 18:194-195; Stemmer et al., Single-step assembly of a gene and entire plasmid form large numbers of oligodeoxy-ribonucleotides, (1995) Gene, 164:49-53; Stemmer, The Evolution of Molecular Computation, (1995) Science 270:1510; Stemmer. Searching Sequence Space, (1995) Bio/Technology 13:549-553; Stemmer, Rapid evolution of a protein in vitro by DNA shuffling, (1994) Nature 370:389-391; and Stemmer, DNA shuffling by random fragmentation and reassembly: In vitro recombination for molecular evolution, (1994) Proc. Natl. Acad. Sci. USA 91:10747-10751.

Mutational methods of generating diversity include, for example, site-directed mutagenesis (Ling et al., Approaches to DNA mutagenesis: an overview, (1997) Anal Biochem. 254(2): 157-178; Dale et al., Oligonucleotide-directed random mutagenesis using the phosphorothioate method, (1996) Methods Mol. Biol. 57:369-374; Smith, In vitro mutagenesis, (1985) Ann. Rev. Genet. 19:423-462; Botstein & Shortle, Strategies and applications of in vitro mutagenesis, (1985) Science 229:1193-1201; Carter, Site-directed mutagenesis, (1986) Biochem. J. 237:1-7; and Kunkel, The efficiency of oligonucleotide directed mutagenesis, (1987) in Nucleic Acids & Molecular Biology (Eckstein, F. and Lilley, D. M. J. eds., Springer Verlag, Berlin)); mutagenesis using uracil containing templates (Kunkel, Rapid and efficient site-specific mutagenesis without phenotypic selection, (1985) Proc. Natl. Acad. Sci. USA 82:488-492; Kunkel et al., Rapid and efficient site-specific mutagenesis without phenotypic selection, (1987) Methods in Enzymol. 154, 367-382; and Bass et al., Mutant Trp repressors with new DNA-binding specificities, (1988) Science 242:240-245); oligonucleotide-directed mutagenesis ((1983) Methods in Enzymol. 100: 468-500; (1987) Methods in Enzymol. 154: 329-350; Zoller & Smith, Oligonucleotide-directed mutagenesis using M13-derived vectors: an efficient and general procedure for the production of point mutations in any DNA fragment, (1982) Nucleic Acids Res. 10:6487-6500; Zoller & Smith, Oligonucleotide-directed mutagenesis of DNA fragments cloned into M13 vectors, (1983) Methods in Enzymol. 100:468-500; and Zoller & Smith, Oligonucleotide-directed mutagenesis: a simple method using two oligonucleotide primers and a single-stranded DNA template, (1987) Methods in Enzymol. 154: 329-350); phosphorothioate-modified DNA mutagenesis (Taylor et al., The use of phosphorothioate-modified DNA in restriction enzyme reactions to prepare nicked DNA, (1985) Nucl. Acids Res. 13: 8749-8764; Taylor et al., The rapid generation of oligonucleotide-directed mutations at high frequency using phosphorothioate-modified DNA, (1985) Nucl. Acids Res. 13: 8765-8787; Nakamaye & Eckstein, Inhibition of restriction endonuclease Nci I cleavage by phosphorothioate groups and its application to oligonucleotide-directed mutagenesis, (1986) Nucl. Acids Res. 14: 9679-9698; Sayers et al., Y-T Exonucleases in phosphorothioate-based oligo-nucleotide-directed mutagenesis, (1988) Nucl. Acids Res. 16:791-802; and Sayers et al., Strand specific cleavage of phosphorothioate-containing DNA by reaction with restriction endonucleases in the presence of ethidium bromide, (1988) Nucl. Acids Res. 16: 803-814); mutagenesis using gapped duplex DNA (Kramer et al., The gapped duplex DNA approach to oligonucleotide-directed mutation construction, (1984) Nucl. Acids Res. 12: 9441-9456; Kramer & Fritz Oligonucleotide-directed construction of mutations via gapped duplex DNA, (1987) Methods in Enzymol. 154:350-367; Kramer et al., Improved enzymatic in vitro reactions in the gapped duplex DNA approach to oligonucleotide-directed construction of mutations, (1988) Nucl. Acids Res. 16: 7207; and Fritz et al., Oligonucleotide-directed construction of mutations: a gapped duplex DNA procedure without enzymatic reactions in vitro, (1988) Nucl. Acids Res. 16: 6987-6999).

Additional suitable methods include point mismatch repair (Kramer et al., Point Mismatch Repair, (1984) Cell 38:879-887), mutagenesis using repair-deficient host strains (Carter et al., Improved oligonucleotide site-directed mutagenesis using M13 vectors, (1985) Nucl. Acids Res. 13: 4431-4443; and Carter, Improved oligonucleotide-directed mutagenesis using M13 vectors, (1987) Methods in Enzymol. 154: 382-403), deletion mutagenesis (Eghtedarzadeh & Henikoff, Use of oligonucleotides to generate large deletions, (1986) Nucl. Acids Res. 14: 5115), restriction-selection and restriction-purification (Wells et al., Importance of hydrogen-bond formation in stabilizing the transition state of subtilisin, (1986) Phil. Trans. R. Soc. Lond. A 317: 415-423), mutagenesis by total gene synthesis (Nambiar et al., Total synthesis and cloning of a gene coding for the ribonuclease S protein, (1984) Science 223: 1299-1301; Sakamar and Khorana, Total synthesis and expression of a gene for the a-subunit of bovine rod outer segment guanine nucleotide-binding protein (transducin), (1988) Nucl. Acids Res. 14: 6361-6372; Wells et al., Cassette mutagenesis: an efficient method for generation of multiple mutations at defined sites, (1985) Gene 34:315-323; and Grundstrom et al., Oligonucleotide-directed mutagenesis by microscale 'shot-gun' gene synthesis, (1985) Nucl. Acids Res. 13: 3305-3316), double-strand break repair (Mandecki, Oligonucleotide-directed double-strand break repair in plasmids of *Escherichia coli*: a method for site-specific mutagenesis, (1986) Proc. Natl. Acad. Sci. USA, 83:7177-7181; and Arnold, Protein engineering for unusual environments, (1993) Current Opinion in Biotechnology 4:450-455). Additional details on many of the above methods can be found in Methods in Enzymology Volume 154, which also describes useful controls for trouble-shooting problems with various mutagenesis methods.

Additional details regarding various diversity generating methods can be found in the following U.S. patents, PCT publications and applications, and EPO publications: U.S. Pat. No. 5,605,793 to Stemmer (Feb. 25, 1997), "Methods for In Vitro Recombination;" U.S. Pat. No. 5,811,238 to Stemmer et al. (Sep. 22, 1998) "Methods for Generating Polynucleotides having Desired Characteristics by Iterative Selection and Recombination;" U.S. Pat. No. 5,830,721 to Stemmer et al. (Nov. 3, 1998), "DNA Mutagenesis by Random Fragmentation and Reassembly;" U.S. Pat. No. 5,834,252 to Stemmer, et al. (Nov. 10, 1998) "End-Complementary Polymerase Reaction;" U.S. Pat. No. 5,837,458 to Minshull, et al. (Nov. 17, 1998), "Methods and Compositions for Cellular and Metabolic Engineering;" WO 95/22625, Stemmer and Crameri, "Mutagenesis by Random Fragmentation and Reassembly;" WO 96/33207 by Stemmer and Lipschutz "End Complementary Polymerase Chain Reaction;" WO 97/20078 by Stemmer and Crameri "Methods for Generating Polynucleotides having Desired Characteristics by Iterative Selection and Recombination;" WO 97/35966 by Minshull and Stemmer, "Methods and Compositions for Cellular and Metabolic Engineering;" WO 99/41402 by Punnonen et al. "Targeting of Genetic Vaccine Vectors;" WO 99/41383 by Punnonen et al. "Antigen Library Immunization;" WO 99/41369 by Punnonen et al. "Genetic Vaccine Vector Engineering;" WO 99/41368 by Punnonen et al. "Optimization of Immunomodulatory Properties of Genetic Vaccines;" EP 752008 by Stemmer and Crameri, "DNA Mutagenesis by Random Fragmentation and Reassembly;" EP 0932670 by Stemmer "Evolving Cellular DNA Uptake by Recursive Sequence Recombination;" WO 99/23107 by Stemmer et al., "Modification of Virus Tropism and Host Range by Viral Genome Shuffling;" WO 99/21979 by Apt et al., "Human Papillomavirus Vectors;" WO 98/31837 by del Cardayre et al. "Evolution of Whole Cells and Organisms by Recursive Sequence Recombination;" WO 98/27230 by Patten and Stemmer, "Methods and Compositions for Polypeptide Engineering;" WO 98/27230 by Stemmer et al., "Methods for Optimization of Gene Therapy by Recursive Sequence Shuffling and Selection," WO 00/00632, "Methods for Generating Highly Diverse Libraries," WO 00/09679, "Methods for Obtaining in Vitro Recombined Polynucleotide Sequence Banks and Resulting Sequences," WO 98/42832 by Arnold et al., "Recombination of Polynucleotide Sequences Using Random or Defined Primers," WO 99/29902 by Arnold et al., "Method for Creating Polynucleotide and Polypeptide Sequences," WO 98/41653 by Vind, "An in Vitro Method for Construction of a DNA Library," WO 98/41622 by Borchert et al., "Method for Constructing a Library Using DNA Shuffling," and WO 98/42727 by Pati and Zarling, "Sequence Alterations using Homologous Recombination;" WO 00/18906 by Patten et al., "Shuffling of Codon-Altered Genes;" WO 00/04190 by del Cardayre et al. "Evolution of Whole Cells and Organisms by Recursive Recombination;" WO 00/42561 by Crameri et al., "Oligonucleotide Mediated Nucleic Acid Recombination;" WO 00/42559 by Selifonov and Stemmer "Methods of Populating Data Structures for Use in Evolutionary Simulations;" WO 00/42560 by Selifonov et al., "Methods for Making Character Strings, Polynucleotides & Polypeptides Having Desired Characteristics;" WO 01/23401 by Welch et al., "Use of Codon-Varied Oligonucleotide Synthesis for Synthetic Shuffling;" and PCT/US01/06775 "Single-Stranded Nucleic Acid Template-Mediated Recombination and Nucleic Acid Fragment Isolation" by Affholter.

The polypeptides (e.g., avimers) used in the present invention are optionally expressed in cells. Multimer domains can be synthesized as a single protein using expression systems well known in the art. In addition to the many texts noted above, general texts which describe molecular biological techniques useful herein, including the use of vectors, promoters and many other topics relevant to expressing nucleic acids such as monomer domains, selected monomer domains, multimers and/or selected multimers, include Berger and Kimmel, Guide to Molecular Cloning Techniques, Methods in Enzymology volume 152 Academic Press, Inc., San Diego, Calif. (Berger); Sambrook et al., Molecular Cloning—A Laboratory Manual (2nd Ed.), Vol. 1-3, Cold Spring Harbor Laboratory, Cold Spring Harbor, N.Y., 1989 ("Sambrook") and Current Protocols in Molecular Biology, F. M. Ausubel et al., eds., Current Protocols, a joint venture between Greene Publishing Associates, Inc. and John Wiley & Sons, Inc., (supplemented through 1999) ("Ausubel")). Examples of techniques sufficient to direct persons of skill through in vitro amplification methods, useful in identifying isolating and cloning monomer domains and multimers coding nucleic acids, including the polymerase chain reaction (PCR) the ligase chain reaction (LCR), Q-replicase amplification and other RNA polymerase mediated techniques (e.g., NASBA), are found in Berger, Sambrook, and Ausubel, as well as Mullis et al., (1987) U.S. Pat. No. 4,683,202; PCR Protocols A Guide to Methods and Applications (Innis et al. eds) Academic Press Inc. San Diego, Calif. (1990) (Innis); Arnheim & Levinson (Oct. 1, 1990) C&EN 36-47; The Journal Of NIH Research (1991) 3, 81-94; (Kwoh et al. (1989) Proc. Natl. Acad. Sci. USA 86, 1173; Guatelli et al. (1990) Proc. Natl. Acad. Sci. USA 87, 1874; Lomell et al. (1989) J. Clin. Chem 35, 1826; Landegren et al., (1988) Science 241, 1077-1080; Van Brunt (1990) Biotechnology 8, 291-294; Wu and Wallace, (1989) Gene 4, 560; Barringer et al. (1990) Gene 89, 117, and Sooknanan and Malek (1995) Biotechnology 13: 563-564. Improved methods of cloning in vitro amplified nucleic acids are described in Wallace et al., U.S. Pat. No. 5,426,039. Improved methods of amplifying large nucleic acids by PCR are summarized in Cheng et al. (1994) Nature 369: 684-685 and the references therein, in which PCR amplicons of up to 40 kb are generated. One of skill will appreciate that essentially any RNA can be converted into a double stranded DNA suitable for restriction digestion, PCR expansion and sequencing using reverse transcriptase and a polymerase.

Vectors encoding, e.g., monomer domains and/or avimers may be introduced into host cells, produced and/or selected by recombinant techniques. Host cells are genetically engineered (i.e., transduced, transformed or transfected) with such vectors, which can be, for example, a cloning vector or an expression vector. The vector can be, for example, in the form of a plasmid, a viral particle, a phage, etc. The engineered host cells can be cultured in conventional nutrient media modified as appropriate for activating promoters, selecting transformants, or amplifying the monomer domain, selected monomer domain, multimer and/or selected multimer gene(s) of interest. The culture conditions, such as temperature, pH and the like, are those previously used with the host cell selected for expression, and will be apparent to those skilled in the art and in the references cited herein, including, e.g., Freshney (1994) Culture of Animal Cells, a Manual of Basic Technique, third edition, Wiley-Liss, New York and the references cited therein.

The polypeptides of the invention can also be produced in non-animal cells such as plants, yeast, fungi, bacteria and the like. Indeed, as noted throughout, phage display is an especially relevant technique for producing such polypeptides. In addition to Sambrook, Berger and Ausubel, details regarding cell culture can be found in Payne et al. (1992) Plant Cell and Tissue Culture in Liquid Systems John Wiley & Sons, Inc. New York, N.Y.; Gamborg and Phillips (eds) (1995) Plant Cell, Tissue and Organ Culture; Fundamental Methods Springer Lab Manual, Springer-Verlag (Berlin Heidelberg New York) and Atlas and Parks (eds) The Handbook of Microbiological Media (1993) CRC Press, Boca Raton, Fla.

Avimers can also possess alterations of monomer domains, immuno-domains and/or multimers that improve pharmacological properties, reduce immunogenicity, or facilitate the transport of the multimer and/or monomer domain into a cell or tissue (e.g., through the blood-brain barrier, or through the skin). These types of alterations include a variety of modifications (e.g., the addition of sugar-groups or glycosylation), the addition of PEG, the addition of protein domains that bind a certain protein (e.g., HSA or other serum protein), the addition of proteins fragments or sequences that signal movement or transport into, out of and through a cell. Additional components can also be added to a multimer and/or monomer domain to manipulate the properties of the multimer and/or monomer domain. A variety of components can also be added including, e.g., a domain that binds a known receptor (e.g., a Fc-region protein domain that binds a Fc receptor), a toxin(s) or part of a toxin, a prodomain that can be optionally cleaved off to activate the multimer or monomer domain, a reporter molecule (e.g., green fluorescent protein), a component that bind a reporter molecule (such as a radionuclide for radiotherapy, biotin or avidin) or a combination of modifications.

As used herein, "directed evolution" refers to a process by which polynucleotide variants are generated, expressed, and screened for an activity (e.g., a polypeptide with binding activity for a human serum albumin target protein) in a recursive process. One or more candidates in the screen are selected and the process is then repeated using polynucleotides that encode the selected candidates to generate new variants. Directed evolution involves at least two rounds of variation generation and can include 3, 4, 5, 10, or more rounds of variation generation and selection. Variation can be generated by any method known to those of skill in the art, including, e.g., by error-prone PCR, gene shuffling, chemical mutagenesis and the like.

The term "shuffling" is used herein to indicate recombination between non-identical sequences. In some embodiments, shuffling can include crossover via homologous recombination or via non-homologous recombination, such as via cre/lox and/or flp/frt systems. Shuffling can be carried out by employing a variety of different formats, including for example, in vitro and in vivo shuffling formats, in silico shuffling formats, shuffling formats that utilize either double-stranded or single-stranded templates, primer based shuffling formats, nucleic acid fragmentation-based shuffling formats, and oligonucleotide-mediated shuffling formats, all of which are based on recombination events between non-identical sequences and are described in more detail or referenced herein below, as well as other similar recombination-based formats.

The term "random" as used herein refers to a polynucleotide sequence or an amino acid sequence composed of two or more amino acids and constructed by a stochastic or random process. The random polynucleotide sequence or amino acid sequence can include framework or scaffolding motifs, which can comprise invariant sequences.

GroEL and GroES

Example 24

Generation of Dual-Specific Ligand Comprising a Serum Albumin-Binding cpn10 (GroES) Non-Immunoglobulin Scaffold via CDR Grafting The CDR3 domain of dAb7h14 is used to construct a cpn10 (GroES) non-immunoglobulin scaffold polypeptide that binds human serum albumin in the following manner. The CDR3 (AQGAALPRT; SEQ ID NO.: 97) sequence of dAb7h14 is grafted into the cpn10 polypeptide in replacement of native cpn10 amino acid residues at positions 19-27 (mobile loop residues). Real-time binding analysis by Biacore is performed to assess whether human serum albumin specifically binds to immobilized cpn10-derived polypeptide comprising the anti-human serum albumin CDR3 domain of dAb7h14. (One of skill in the art will recognize that binding affinity can be assessed using any appropriate method, including, e.g., precipitation of labeled human serum albumin, competitive Biacore assay, etc.) If no or low human serum albumin affinity (e.g., Kd values in the pM range or higher) is detected, at least one of a number of strategies are employed to improve the human serum albumin binding properties of the CDR3-grafted cpn10 polypeptide, including any of the following methods that contribute to binding affinity.

The length of the dAb7h14 CDR3-grafted region of the cpn10 polypeptide corresponding to the mobile loop region within the native cpn10 polypeptide is adjusted through deletion of amino acid residues and/or the use of linker polypeptides. For example, the nine amino acid residue CDR3 peptide sequence of dAb7h14 is extended to 16 amino acid residues in length using amino acid linkers of, e.g., zero to seven residues in length located on either and/or both the N- or C-terminal flanks of the dAb7h14 CDR3 polypeptide sequence, thereby achieving a total grafted peptide sequence length of 16 amino acids within the CDR3-grafted domain corresponding to the mobile loop in the native cpn10 sequence. Such use of linker polypeptide(s) is optionally combined with mutagenesis of the linker sequences, CDR3 sequence(s) and/or non-CDR cpn10 sequences (e.g., using mutagenic optimization procedures as described below), in order to improve the human serum albumin binding capability of CDR3-grafted cpn10 polypeptides (e.g., via optimization of both CDR and fibronectin sequences within the CDR3-grafted cpn10 polypeptides). The polypeptide linkers employed for such purpose either possess a predetermined sequence, or, optionally, are selected from a population of randomized polypeptide linker sequences via assessment of the human serum albumin binding capabilities of linker-containing CDR3-grafted cpn10 polypeptides. Optimization methods are performed in parallel and/or iteratively. Both parallel and iterative optimization (e.g., affinity maturation) processes employ selection methods as described below and/or as known in the art as useful for optimization of polypeptide binding properties.

Human serum albumin binding of CDR-grafted cpn10 polypeptide(s) presenting dAb7h14 CDR3 is optimized via mutagenesis, optionally in combination with parallel and/or iterative selection methods as described below and/or as otherwise known in the art. Cpn10 scaffold polypeptide domains surrounding grafted dAb7h14 CDR3 polypeptide sequence are subjected to randomized and/or NNK mutagenesis, performed as described infra. Such mutagenesis is performed within the cpn10 polypeptide sequence upon non-grafted amino acid residues, and is optionally randomized in order to evolve new or improved human serum albumin-binding polypeptides. Optionally, the dAb7h14 CDR3 polypeptide domain presented within the CDR3-grafted cpn10 polypeptide is subjected to mutagenesis via, e.g., random mutagenesis, NNK mutagenesis, look-through mutagenesis and/or other art-recognized method. PCR is optionally used to perform such methods of mutagenesis, resulting in the generation of sequence diversity across targeted sequences within the CDR3-grafted cpn10 polypeptides. Such approaches are similar to those described infra for dAb library generation. In addition to random and/or look-through methods of mutagenesis, directed mutagenesis of targeted amino acid residues is employed where structural information establishes specific amino acid residues to be critical to binding of human serum albumin.

Cpn10 polypeptides comprising grafted dAb7h14 CDR3 sequence engineered as described above are subjected to parallel and/or iterative selection methods to identify those cpn10 polypeptides that are optimized for human serum albumin binding. For example, following production of a library of dAb7h14 CDR3-grafted cpn10 polypeptide sequences, this library of such polypeptides is displayed on phage and subjected to multiple rounds of selection requiring serum albumin binding and/or proliferation, as is described infra for selection of serum albumin-binding dAbs from libraries of dAbs. Optionally, selection is performed against serum albumin immobilized on immunotubes or against biotinlyated serum albumin in solution. Optionally, binding affinity is determined using surface plasmon resonance (SPR) and the Biacore (Karlsson et al., 1991), using a Biacore system (Uppsala, Sweden), with fully optimized monomeric and/or oligomeric cpn10-derived polypeptides ideally achieving human serum albumin binding affinity Kd values in the nM range or better.

Upon identification of monomeric cpn10-derived polypeptides that bind human serum albumin, human serum binding properties of such initial monomers may be further enhanced via combination of such monomers with other monomers, followed by further mutagenesis and/or selection, thereby forming an oligomeric cpn10/GroES composition possessing specific affinity for human serum albumin. Following identification of an oligomeric cpn10/GroES composition possessing affinity for human serum albumin, such polypeptides are then used to generate dual-specific ligand compositions by any of the methods described infra.

Example 25

Generation of Dual-Specific Ligand Comprising a Serum Albumin-Binding cpn10 Non-Immunoglobulin Scaffold Via Selection of Serum Albumin Binding Moieties The native cpn10 polypeptide is subjected to library selection and, optionally, affinity maturation techniques in order to produce human serum albumin-binding cpn10 non-immunoglobulin scaffold molecules for use in dual-specific ligands of the invention.

The capability of a native cpn10 polypeptide to bind human serum albumin is initially ascertained via Biacore assay as described above. Following detection of no or low binding affinity (e.g., Kd values in the μM range or higher) of a cpn10 polypeptide for human serum albumin, at least one of a number of strategies are employed to impart human serum albumin binding properties to the cpn10 polypeptide, including one or more of the following methods that contribute to binding affinity.

Human serum albumin binding of cpn10 scaffold polypeptide(s) is achieved and optimized via mutagenic methods, optionally in combination with parallel and/or iterative selection methods as described below and/or as otherwise known in the art. Cpn10 scaffold polypeptide domains are subjected to randomized and/or NNK mutagenesis, performed as described infra. Such mutagenesis is performed upon the entirety of the cpn10 polypeptide or upon specific sequences within the cpn10 polypeptide, including mobile loop amino acid residues at positions 19-27, and is optionally randomized in order to evolve new or improved human serum albumin-binding polypeptides. PCR is optionally used to perform such methods of mutagenesis, resulting in the generation of sequence diversity across targeted sequences within the cpn10 polypeptides. (Such approaches are similar to those described infra for dAb library generation.) In addition to random methods of mutagenesis, directed mutagenesis of targeted amino acid residues is employed where structural information establishes specific amino acid residues of cpn10 polypeptides to be critical to binding of human serum albumin.

Cpn10 polypeptides engineered as described above are subjected to parallel and/or iterative selection methods to identify those cpn10 polypeptides that are optimized for human serum albumin binding. For example, following production of a library of mutagenized cpn10 polypeptide sequences, said library of polypeptides is displayed on phage and subjected to multiple rounds of selection requiring serum albumin binding and/or proliferation, as is described infra for selection of serum albumin-binding dAbs from libraries of dAbs. Optionally, selection is performed against serum albumin immobilized on immunotubes or against biotinlyated serum albumin in solution. Optionally, binding affinity is determined using surface plasmon resonance (SPR) and the Biacore (Karlsson et al., 1991), using a Biacore system (Uppsala, Sweden), with fully optimized monomeric and/or oligomeric cpn10-derived polypeptides ideally achieving human serum albumin binding affinity Kd values in the nM range or better.

Upon identification of monomeric cpn10-derived polypeptides that bind human serum albumin, human serum binding properties of such initial monomers may be further enhanced via combination of such monomers with other monomers, followed by further mutagenesis and/or selection, thereby forming an oligomeric cpn10/GroES composition possessing specific affinity for human serum albumin. Following identification of an oligomeric cpn10/GroES composition possessing affinity for human serum albumin, such polypeptides are then used to generate dual-specific ligand compositions by any of the methods described infra.

GroEL Polypeptides

GroEL is a key molecular chaperone in *E. coli* that consists of 14 subunits each of some 57.5 Kd molecular mass arranged in two seven membered rings (Braig et al. 1994 *Proc. Natl. Acad. Sci.* 90: 3978-3982). There is a large cavity in the GroEL ring system, and it is widely believed that the cavity is required for successful protein folding activity. For optimal activity, a co-chaperone, GroES, is required which consists of a seven membered ring of 10 Kd subunits (Hunt et al. 1996 *Nature* 379: 37-45). Each GroES subunit uses a mobile loop with a conserved hydrophobic tripeptide for interaction with GroEL (Landry et al. 1993 *Nature* 364: 255-258). The mobile loops are generally less than 16 amino acids in length and undergo a transition from disordered loops to β-hairpins concomitant with binding the apical domains of GroEL (Shewmaker et al. 2001 *J. Biol. Chem.* 276: 31257-31264). The activity of the GroEL/GroES complex requires ATP. GroEL and GroES are widespread throughout all organisms, and often referred to as chaperonin (cpn) molecules, cpn60 and cpn10, respectively.

GroEL is an allosteric protein. Allosteric proteins are a special class of oligomeric proteins, which alternate between two or more different three-dimensional structures during binding of ligands and substrates. Allosteric proteins are often involved in control processes in biology or where mechanical and physico-chemical energies are interconverted. The role of ATP is to trigger this allosteric change, causing GroEL to convert from a state that binds denatured proteins tightly to one that binds denatured proteins weakly. The co-chaperone, GroES, aids in this process by favoring the weak-binding state. It may also act as a cap, sealing off the cavity of GroEL. Further, its binding to GroEL is likely directly to compete with the binding of denatured substrates. The net result is that the binding of GroES and ATP to GroEL which has a substrate bound in its denatured form is to release the denatured substrate either into the cavity or into solution where it can refold.

GroEL and GroES are polypeptide scaffolds that can be used to multimerize monomeric polypeptides or protein domains, to produce multimeric proteins having any desired characteristic. As also described infra for, e.g., avimer compositions, it is often desirable to multimerize polypeptide monomers.

Many proteins require the assistance of molecular chaperones in order to be folded in vivo or to be refolded in vitro in high yields. Molecular chaperones are proteins, which are often large and require an energy source such as ATP to function. A key molecular chaperone in *E. coli* is GroEL, which consists of 14 subunits each of some 57.5 Kda molecular mass arranged in two seven membered rings. There is a large cavity in the GroEL ring system, and it is widely believed that the cavity is required for successful protein folding activity. For optimal activity, a co-chaperone, GroES, is required which consists of a seven membered ring of 10 Kda subunits. The activity of the GroEL/GroES complex requires energy source ATP.

Minichaperones have been described in detail elsewhere (see International patent application WO99/05163, the disclosure of which in incorporated herein by reference). Minichaperone polypeptides possess chaperoning activity when in monomeric form and do not require energy in the form of ATP. Defined fragments of the apical domain of GroEL of approximately 143-186 amino acid residues in length have molecular chaperone activity towards proteins either in solution under monomeric conditions or when monodispersed and attached to a support.

The GroEL and/or GroES scaffolds allow for the oligomerisation of polypeptides to form functional protein oligomers which have activities which surpass those of recombinant monomeric polypeptides. Cpn10 is a widespread component of the cpn60/cpn10 chaperonin system. Examples of cpn10 include bacterial GroES and bacteriophage T4 Gp31, and are also listed below. Further members of the cpn10 family will be known to those skilled in the art.

Protein scaffold subunits assemble to form a protein scaffold. Such a scaffold may have any shape and may comprise any number of subunits. For certain GroEL and GroES embodiments, the scaffold comprises between 2 and 20 subunits, between 5 and 15 subunits, or about 10 subunits. The naturally-occurring scaffold structure of cpn10 family members comprises seven subunits, in the shape of a seven-membered ring or annulus. In certain embodiments, therefore, the scaffold is a seven-membered ring.

A heterologous amino acid sequence, which may be, e.g., a CDR3 domain derived from an antibody or antigen binding fragment thereof possessing affinity for a target protein (e.g., human serum albumin) or, optionally, which may be a single residue such as cysteine which allows for the linkage of further groups or molecules to the scaffold, can be inserted into the sequence of the oligomerisable protein scaffold subunit such that both the N- and C-termini of the polypeptide monomer are formed by the sequence of the oligomerisable protein scaffold subunit. Thus, the heterologous polypeptide is included with the sequence of the scaffold subunit, for example by replacing one or more amino acids thereof.

It is known that cpn10 subunits possess a "mobile loop" within their structure. The mobile loop is positioned between amino acids 15 and 34, preferably between amino acids 16 to 33, of the sequence of *E. coli* GroES, and equivalent positions on other members of the cpn10 family. The mobile loop of T4 Gp31 is located between residues 22 to 45, preferably 23 to 44. Optionally, the heterologous polypeptide can be inserted by replacing all or part of the mobile loop of a cpn10 family polypeptide. Where the protein scaffold subunit is a cpn10 family polypeptide, the heterologous sequence may moreover be incorporated at the N- or C-terminus thereof, or in positions which are equivalent to the roof b hairpin of cpn10 family peptides. This position is located between positions 54 and 67, preferably 55 to 66, and preferably 59 and 61 of bacteriophage T4 Gp31, or between positions 43 to 63, preferably 44 to 62, advantageously 50 to 53 of *E. coli* GroES.

Optionally, a polypeptide may be inserted at the N- or C-terminus of a scaffold subunit in association with circular permutation of the subunit itself. Circular permutation is described in Graf and Schachman, *PNAS(USA)* 1996, 93: 11591. Essentially, the polypeptide is circularized by fusion of the existing N- and C-termini, and cleavage of the polypeptide chain elsewhere to create novel N- and C-termini. In a preferred embodiment of the invention, the heterologous polypeptide may be included at the N- and/or C-terminus formed after circular permutation. The site of formation of the novel termini may be selected according to the features desired, and may include the mobile loop and/or the roof β hairpin.

Advantageously, heterologous sequences, which may be the same or different, may be inserted at more than one of the positions and/or at different positions than the above-identified positions within the protein scaffold subunit. Thus, each subunit may comprise two or more heterologous polypeptides, which are displayed on the scaffold when this is assembled. Heterologous polypeptides may be displayed on a scaffold subunit in free or constrained form, depending on the degree of freedom provided by the site of insertion into the scaffold sequence. For example, varying the length of the sequences flanking the mobile or β hairpin loops in the scaffold will modulate the degree of constraint of any heterologous polypeptide inserted therein.

GroEL and/or GroES compositions also may comprise a polypeptide oligomer comprising two or more monomers. The oligomer may be configured as a heterooligomer, comprising two or more different amino acid sequences inserted into the scaffold, or as a homooligomer, in which the sequences inserted into the scaffold are the same.

The monomers which constitute the oligomer may be covalently crosslinked to each other. Crosslinking may be performed by recombinant approaches, such that the monomers are expressed ab initio as an oligomer; alternatively, crosslinking may be performed at Cys residues in the scaffold. For example, unique Cys residues inserted between positions 50 and 53 of the GroES scaffold, or equivalent positions on other members of the cpn10 family, may be used to cross-link scaffold subunits.

The nature of the heterologous polypeptide inserted into the scaffold subunit may be selected at will. In certain embodiments, scaffold proteins are synthesized which display antibodies or fragments thereof such as scFv, natural or camelised V$_H$ domains and VH CDR3 fragments.

In an exemplary embodiment, a polypeptide monomer capable of oligomerisation can be prepared as described above and/or as set forth in WO 00/69907, incorporated herein by reference in its entirety. The method of such preparation can comprise insertion of a nucleic acid sequence encoding a heterologous polypeptide into a nucleic acid sequence encoding a subunit of an oligomerisable protein scaffold, incorporating the resulting nucleic acid into an expression vector, and expressing the nucleic acid to produce the polypeptide monomers. Optionally, a polypeptide oligomer may then be produced via a process that comprises allowing the polypeptide monomers produced as above to associate into an oligomer. In certain embodiments, the monomers are cross-linked to form the oligomer.

In certain embodiments, a scaffold polypeptide is based on members of the cpn10/Hsp10 family, such as GroES or an analogue thereof. A highly preferred analogue is the T4 polypeptide Gp31. GroES analogues, including Gp31, possess a mobile loop (Hunt, J. F., et al., (1997) Cell 90, 361-371; Landry, S. J., et al., (1996) Proc. Natl. Acad. Sci. U.S.A. 93, 11622-11627) which may be inserted into, or replaced, in order to fuse the heterologous polypeptide to the scaffold.

Cpn10 homologues are widespread throughout animals, plants and bacteria. For example, a search of GenBank indicates that cpn10 homologues are known in the following species: *Actinobacillus actinomycetemcomitans; Actinobacillus pleuropneumoniae; Aeromonas salmonicida; Agrobacterium tumefaciens; Allochromatium vinosum; Amoeba proteus symbiotic bacterium; Aqui/ex aeolicus; Arabidopsis thaliana; Bacillus sp; Bacillus stearothermophilus; Bacillus subtilis; Bartonella henselae; Bordetella pertussis; Borrelia burgdorferi; Brucella abortus; Buchnera aphidicola; Burkholderia cepacia; Burkholderia vietnamiensis; Campylobacter jejuni, Caulobacter crescentus; Chlamydia muridarum; Chlamydia trachomatis; Chlamydophila pneumoniae; Clostridium acetobutylicum; Clostridium perfringens; Clostridium thermocellum*; coliphage *T-Cowdria ruminantium; Cyanelle Cyanophora paradoxa; Ehrlichia canis; Ehrlichia chaffeensis; Ehrlichia equi; Ehrlichia phagocytophila, Ehrlichia risticii; Ehrlichia sennetsu, Ehrlichia* sp 'HGE agent; *Enterobacter aerogenes; Enterobacter agglomerans; Enterobacter amnigenus; Enterobacter asburiae; Enterobacter gergoviae; Enterobacter intermedius, Erwinia aphidicola, Erwinia carotovora; Erwinia herbicola; Escherichia coli; Francisella tularensis, Glycine max; Haemophilus ducreyi, Haemophilus influenzae* Rd; *Helicobacter pylori; Holospora obtusa; Homo sapiens; Klebsiella ornithinolytica; Klebsiella oxytoca, Klebsiella planticola; Klebsiella pneumoniae; Lactobacillus helvetictis; Lactobacillus zeae; Lactococcus lactis, Lawsonia intracellularis, Leptospira interrogans; Methylovorus* sp strain SS; *Mycobacterium avium; Mycobacterium avium* subsp *avium; Mycobacterium avium* subsp *paratuberculosis; Mycobacterium leprae; Mycobacterium tuberculosis; Mycoplasma genitalium; Mycoplasma pneumoniae; Myzus persicae primary endosymbiont; Neisseria gonorrhoeae; Oscillatoria* sp NKBG,-*Pantoea ananas; Pasteurella multocida; Porphyromonas gingivalis; Pseudomonas aeruginosa; Pseudomonas aeruginosa; Pseudomonas putida; Rattus norvegicus; Rattus norvegicus, Rhizobium leguminosarum; Rhodobacter capsulatus; Rhodobacter sphaeroides; Rhodothermus marinus; Rickettsia prowazekii; Rickettsia rickettsii; Saccharomyces cerevisiae; Serratia ficaria; Serratia marcescens; Serratia rubidaea, Sinorhizobium meliloti; Sitophilus oryzae principal endosymbiont; Stenotrophomonas maltophilia; Streptococcus pneumoniae, Streptomyces albus; Streptomyces coelicolor; Streptomyces coelicolor, Streptomyces lividans; Synechococcus* sp; *Synechococcus vulcanus, Synechocystis* sp; *Thermoanaerobacter brockii; Thermotoga maritima; Thermus aquaticus; Treponema pallidum; Wolbachia* sp; *Zymomonas mobilis.*

An advantage of cpn10 family subunits is that they possess a mobile loop, responsible for the protein folding activity of the natural chaperonin, which may be removed without affecting the scaffold. Cpn10 with a deleted mobile loop possesses no biological activity, making it an advantageously inert scaffold, thus minimizing any potentially deleterious effects.

Insertion of an appropriate biologically active polypeptide can confer a biological activity (e.g., human serum albumin binding) on the novel polypeptide thus generated. Indeed, the biological activity of the inserted polypeptide may be improved by incorporation of the biologically active polypeptide into the scaffold, especially, e.g., when mutagenesis and affinity-based screening methods as described herein are used to optimize target protein binding of a scaffold-presented polypeptide.

Alternative sites for peptide insertion are possible. An advantageous option is in the position equivalent to the roof β hairpin in GroES. This involves replacement of Glu- in Gp31 by the desired peptide. The amino acid sequence is Pro (59)-Glu(60)-Gly(61). This is conveniently converted to a SmaI site at the DNA level (CCC:GGG) encoding Pro-Gly, leaving a blunt-ended restriction site for peptide insertion as a DNA fragment. Similarly, an insertion may be made at between positions 50 and 53 of the GroES sequence, and at equivalent positions in other cpn10 family members. Alternatively, inverse PCR may be used, to display the peptide on the opposite side of the scaffold.

Members of the cpn60/Hsp60 family of chaperonin molecules may also be used as scaffolds. For example, the tetradecameric bacterial chaperonin GroEL may be used. In certain embodiments, heterologous polypeptides would be inserted between positions 191 and 376, in particular between positions 197 and 333 (represented by SacII engineered and unique Cla I sites) to maintain intact the hinge region between the equatorial and the apical domains in order to impart mobility to the inserted polypeptide. The choice of scaffold may depend upon the intended application of the oligomer (or dual-specific ligand comprising and/or derived from such an oligomer): for example, if the oligomer is intended for vaccination purposes, the use of an immunogenic scaffold, such as that derived from *Mycobacterium tuberculosis*, is highly advantageous and confers an adjuvant effect.

Mutants of cpn60 molecules can also be used. For example, the single ring mutant of GroEL (GroELSRI) contains four point mutations which effect the major attachment between the two rings of GroEL (R452E, E461A, S463A and V464A) and is functionally inactive in vitro because it is released to bind GroES. GroELSR2 has an additional mutation at Glu191-Gly, which restores activity by reducing the affinity for GroES. Both of these mutants form ring structures and would be suitable for use as scaffolds.

Certain naturally-occurring scaffold molecules are bacteriophage products: for this reason, naturally occurring antibodies to such scaffolds are rare. This enhances the use of scaffold fusions as vaccine agents. T4 Gp31 with a deleted loop has no biological activity (except as a dominant-negative or intracellular vaccine against T4 bacteriophage) thus minimizing deleterious effects on the host. However, insertion of appropriate sequences encoding polypeptides can confer biological activity on the novel proteins. Indeed, the biological activity may be improved by insertion into the scaffold protein.

The affinity of antibodies or antibody fragments for antigens (e.g., human serum albumins) may be increased by oligomerisation according to the present invention. Antibody fragments may be fragments such as Fv, Fab and F(ab')$_2$ fragments or any derivatives thereof, such as a single chain Fv fragments. The antibodies or antibody fragments may be non-recombinant, recombinant or humanized. The antibody may be of any immunoglobulin isotype, e.g., IgG, IgM, and so forth.

In certain embodiments, the antibody fragments may be camelised VH domains. It is known that the main intermolecular interactions between antibodies and their cognate antigens are mediated through VH CDR3.

Use of GroEL and/or GroES (cpn10) scaffold molecules as described infra and as known in the art provides for the oligomerisation Of VH domains, or VH CDR3 domains, to produce a high-affinity oligomer. Two or more domains may be included in such an oligomer; in an oligomer based on a cpn10 scaffold, up to 7 domains may be included, forming a hetpameric oligomeric molecule (heptabody) that binds to a target protein (e.g., human serum albumin).

For purpose of imparting and/or optimizing the affinity of certain scaffold polypeptides/oligomers for a target protein (e.g., human serum albumin), variation may be introduced into heterologous polypeptides inserted into scaffold polypeptides, such that the specificity and/or affinity of such polypeptides/oligomers for their ligands/substrates can be examined and/or mapped. Variants may be produced of the same loop, or a set of standard different loops may be devised, in order to assess rapidly the affinity of a novel polypeptide for target protein (e.g., human serum albumin). Variants may be produced by randomization of sequences according to known techniques, such as PCR. They may be subjected to selection by a screening protocol, such as phage display, before incorporation into protein scaffolds.

An "oligomerisable scaffold", as referred to herein, is a polypeptide which is capable of oligomerising or being oligomerised to form a scaffold and to which a heterologous polypeptide may be fused, preferably covalently, without abolishing the oligomerisation capabilities. Thus, it provides a "scaffold" using which polypeptides may be arranged into multimers in accordance with the present invention. Optionally, parts of the wildtype polypeptide from which the scaffold is derived may be removed, for example by replacement with the heterologous polypeptide which is to be presented on the scaffold.

Monomers are polypeptides which possess the potential to oligomerise or to be oligomerised. Oligomerisation can be brought about by the incorporation, in the polypeptide, of an oligomerisable scaffold subunit which will oligomerise with further scaffold subunits if combined therewith. Optionally, oligomerisation can be brought about via use of art-recognized linkers for purpose of joining together monomers.

As used herein, "oligomer" is synonymous with "polymer" or "multimer" and is used to indicate that the object in question is not monomeric. Thus, oligomeric polypeptides comprise at least two monomeric units joined together covalently or non-covalently. The number of monomeric units employed will depend on the intended use of the oligomer, and may be between 2 and 20 or more. Optionally, it is between 5 and 10, and preferably about 7.

Phage Display

Phage display technology has proved to be enormously useful in biological research. It enables ligands to be selected from large libraries of molecules. Scaffold technology can harness the power of phage display in a uniquely advantageous manner. Cpn10 molecules can be displayed as monomers on fd bacteriophages, similar to single-chain Fv molecule display. Libraries of insertions (in place of the highly mobile loop, e.g., using CDR3 polypeptides derived from human serum albumin-binding antibodies) are constructed by standard methods, and the resulting libraries screened for molecules of interest. Such selection is affinity-based. After identification of molecules that possess affinity for target protein (e.g., human serum albumin), potentially via one or more iterations of mutagenesis, expression (the GroEL proteins, ~57.5 Kda GroEL and ~10 Kda GroES, can be expressed and purified as previously described (Chatellier et al. 1998 Proc. Natl. Acad. Sci. USA 95: 9861-9866; Corrales and Fersht 1996 1: 265-273), or by any art-recognized method) and affinity screening, such molecules can be oligomerised, thereby taking advantage of the avidity of such molecules. Optionally, certain selected monomers will be able to crosslink or oligomerise their binding partners.

Fibronectin

Example 26

Generation of Dual-Specific Ligand Comprising a Serum Albumin-Binding Fibronectin Non-Immunoglobulin Scaffold Via CDR Grafting The CDR domains of dAb7h14 are used to construct a fibronectin non-immunoglobulin scaffold polypeptide that binds human serum albumin in the following manner. The CDR1 (RASQWIGSQLS; SEQ ID NO.: 95), CDR2 (WRSSLQS; SEQ ID NO.: 96), and CDR3 (AQGAALPRT; SEQ ID NO.: 97) sequences of dAb7h14 are grafted into $^{10}$Fn3 in replacement of native $^{10}$Fn3 amino acid residues at positions 21-31 (the BC loop), 51-56 (the DE loop), and 76-88 (the FG loop), respectively. Real-time binding analysis by Biacore is performed to assess whether human serum albumin specifically binds to immobilized fibronectin-derived polypeptide comprising the anti-human serum albumin CDR domains of dAb7h14. (One of skill in the art will recognize that binding affinity can be assessed using any appropriate method, including, e.g., precipitation of labeled human serum albumin, competitive Biacore assay, etc.) If no or low human serum albumin affinity (e.g., Kd values in the pM range or higher) is detected, at least one of a number of strategies are employed to improve the human serum albumin binding properties of the CDR-grafted fibronectin polypeptide, including any of the following methods that contribute to binding affinity.

The length(s) of dAb7h14 CDR-grafted regions of the fibronectin polypeptide corresponding to solvent-exposed loop regions within the native fibronectin polypeptide are adjusted through the use of linker polypeptides. For example, the nine amino acid residue CDR3 peptide sequence of dAb7h14 is extended to 13 amino acid residues in length using amino acid linkers of, e.g., zero to four residues in length located on either and/or both the N- or C-terminal flanks of the dAb7h14 CDR3 polypeptide sequence, thereby achieving a total grafted peptide sequence length of 13 amino acids within the CDR3-grafted domain corresponding to the FG loop in the native fibronectin sequence. Such use of linker polypeptide(s) is optionally combined with mutagenesis of the linker sequences, CDR sequences and/or non-CDR fibronectin sequences (e.g., using mutagenic optimization procedures as described below), in order to improve the human serum albumin binding capability of CDR-grafted fibronectin polypeptides (e.g., via optimization of both CDR and fibronectin sequences within the CDR-grafted fibronectin polypeptides). The polypeptide linkers employed for such purpose either possess a predetermined sequence, or, optionally, are selected from a population of randomized polypeptide linker sequences via assessment of the human serum albumin binding capabilities of linker-containing CDR-grafted fibronectin polypeptides. Optimization methods are performed in parallel and/or iteratively. Both parallel and iterative optimization (e.g., affinity maturation) processes employ selection methods as described below and/or as known in the art as useful for optimization of polypeptide binding properties.

Human serum albumin binding of CDR-grafted fibronectin polypeptide(s) presenting dAb7h14 CDRs is optimized via mutagenesis, optionally in combination with parallel and/or iterative selection methods as described below and/or as otherwise known in the art. $^{10}$Fn3 scaffold polypeptide domains surrounding grafted dAb7h14 CDR polypeptide sequences are subjected to randomized and/or NNK mutagenesis, performed as described infra. Such mutagenesis is performed within the $^{10}$Fn3 polypeptide sequence upon amino acids 1-9, 44-50, 61-54, 82-94 (edges of beta sheets); 19, 21, 30-46 (even), 79-65 (odd) (solvent-accessible faces of both beta sheets); and 14-16 and 3645 (non-CDR-like solvent-accessible loops and beta turns), and is optionally randomized in order to evolve new or improved human serum albumin-binding polypeptides. Optionally, dAb7h14 CDR polypeptide domains presented within the CDR-grafted fibronectin polypeptide are subjected to mutagenesis via, e.g., random mutagenesis, NNK mutagenesis, look-through mutagenesis and/or other art-recognized method. PCR is optionally used to perform such methods of mutagenesis, resulting in the generation of sequence diversity across targeted sequences within the CDR-grafted fibronectin polypeptides. Such approaches are similar to those described infra for dAb library generation. In addition to random and/or look-through methods of mutagenesis, directed mutagenesis of targeted amino acid residues is employed where structural information establishes specific amino acid residues to be critical to binding of human serum albumin.

Fibronectin polypeptides comprising grafted dAb7h14 CDR sequences engineered as described above are subjected to parallel and/or iterative selection methods to identify those fibronectin polypeptides that are optimized for human serum albumin binding. For example, following production of a library of dAb7h14 CDR-grafted fibronectin polypeptide sequences, this library of such polypeptides is displayed on phage and subjected to multiple rounds of selection requiring serum albumin binding and/or proliferation, as is described infra for selection of serum albumin-binding dAbs from libraries of dAbs. Optionally, selection is performed against serum albumin immobilized on immunotubes or against biotinlyated serum albumin in solution. Optionally, binding affinity is determined using surface plasmon resonance (SPR) and the Biacore (Karlsson et al., 1991), using a Biacore system (Uppsala, Sweden), with fully optimized fibronectin-derived polypeptides ideally achieving human serum albumin binding affinity Kd values in the nM range or better. Following identification of fibronectin-derived polypeptides that bind human serum albumin, such polypeptides are then used to generate dual-specific ligand compositions by any of the methods described infra.

Example 27

Generation of Dual-Specific Ligand Comprising a Serum Albumin-Binding Fibronectin Non-Immunoglobulin Scaffold Via Selection of Serum Albumin Binding Moieties The native fibronectin protein—specifically the $^{10}$Fn3 polypeptide of fibronectin—is subjected to library selection and, optionally, affinity maturation techniques in order to produce human serum albumin-binding fibronectin non-immunoglobulin scaffold molecules for use in dual-specific ligands of the invention.

Real-time binding analysis by Biacore is performed to assess whether human serum albumin specifically binds to immobilized native fibronectin and/or fibronectin-derived polypeptide. Following detection of no or low binding affinity (e.g., Kd values in the □M range or higher) of a fibronectin polypeptide for human serum albumin, at least one of a number of strategies are employed to impart human serum albumin binding properties to the fibronectin polypeptide, including one or more of the following methods that contribute to binding affinity.

Human serum albumin binding of fibronectin scaffold polypeptide(s) is achieved and optimized via mutagenic methods, optionally in combination with parallel and/or iterative selection methods as described below and/or as otherwise known in the art. $^{10}$Fn3 scaffold polypeptide domains are subjected to randomized and/or NNK mutagenesis, performed as described infra. Such mutagenesis is performed upon the entirety of the $^{10}$Fn3 polypeptide or upon specific sequences within the $^{10}$Fn3 polypeptide, including amino acids 1-9, 44-50, 61-54, 82-94 (edges of beta sheets); 19, 21, 30-46 (even), 79-65 (odd) (solvent-accessible faces of both beta sheets); 21-31, 51-56, 76-88 (CDR-like solvent-accessible loops); and 14-16 and 36-45 (other solvent-accessible loops and beta turns), and is optionally randomized in order to evolve new or improved human serum albumin-binding polypeptides. PCR is optionally used to perform such methods of mutagenesis, resulting in the generation of sequence diversity across targeted sequences within the fibronectin polypeptides. (Such approaches are similar to those described infra for dAb library generation.) In addition to random methods of mutagenesis, directed mutagenesis of targeted amino acid residues is employed where structural information establishes specific amino acid residues of fibronectin polypeptides to be critical to binding of human serum albumin.

Fibronectin polypeptides engineered as described above are subjected to parallel and/or iterative selection methods to identify those fibronectin polypeptides that are optimized for human serum albumin binding. For example, following production of a library of mutagenized fibronectin polypeptide sequences, said library of polypeptides is displayed on phage and subjected to multiple rounds of selection requiring serum albumin binding and/or proliferation, as is described infra for selection of serum albumin-binding dAbs from libraries of dAbs. Optionally, selection is performed against serum albumin immobilized on immunotubes or against biotinlyated serum albumin in solution. Optionally, binding affinity is determined using surface plasmon resonance (SPR) and the Biacore (Karlsson et al., 1991), using a Biacore system (Uppsala, Sweden), with fully optimized fibronectin-derived polypeptides ideally achieving human serum albumin binding affinity Kd values in the nM range or better.

Following identification of fibronectin polypeptides that bind human serum albumin, such polypeptides are then used to generate dual-specific ligand compositions by any of the methods described infra.

Fibronectin Non-Immunoglobulin Scaffolds

In certain embodiments of the invention, a non-immunoglobulin scaffold comprising fibronectin, or a functional moiety and/or fragment thereof, is engineered to bind serum albumin. A non-immunoglobulin scaffold structure derived from the fibronectin type III module (Fn3) is used. The fibronectin type III module is a common domain found in mammalian blood and structural proteins, that occurs more than 400 times in the protein sequence database and is estimated to occur in 2% of all proteins sequenced to date. Proteins that include an Fn3 module sequence include fibronectins, tenascin, intracellular cytoskeletal proteins, and prokaryotic enzymes (Bork and Doolittle, *Proc. Natl. Acad. Sci.* USA 89:8990, 1992; Bork et al., *Nature Biotech.* 15:553, 1997; Meinke et al., *J. Bacteriol.* 175:1910, 1993; Watanabe et al., *J. Biol. Chem.* 265:15659, 1990). A particular non-immunoglobulin scaffold of fibronectin is the tenth module of human Fn3 ($^{10}$Fn3), which comprises 94 amino acid residues. The overall fold of this domain is closely related to that of the smallest functional antibody fragment, the variable region of the heavy chain, which comprises the entire antigen recognition unit in camel and llama IgG. The major differences between camel and llama domains and the $^{10}$Fn3 domain are that (i) $^{10}$Fn3 has fewer beta strands (seven vs. nine) and (ii) the two beta sheets packed against each other are connected by a disulfide bridge in the camel and llama domains, but not in $^{10}$Fn3.

The three loops of $^{10}$Fn3 corresponding to the antigen-binding loops of the IgG heavy chain run between amino acid residues 21-31 (BC), 51-56 (DE), and 76-88 (FG) (refer to FIG. 3 of U.S. Pat. No. 7,115,396, the complete contents of which are incorporated herein by reference). The lengths of the BC and DE loops, 11 and 6 residues, respectively, fall within the narrow range of the corresponding antigen-recognition loops found in antibody heavy chains, that is, 7-10 and 4-8 residues, respectively.

Accordingly, a CDR grafting strategy can be readily employed to introduce heavy chain CDR sequences into these domains. Additionally and/or alternatively, these two loops can be subjected to introduction of genetic variability by any art-recognized method (e.g., site-directed, look-through or other mutagenesis method, randomization, etc.) and, optionally, the resulting polypeptide may be subjected to selection for high antigen affinity. (Alternatively, introduction of genetic variability and/or selection procedures can be used to identify compositions with lowered binding affinity and/or optimized properties such as stability, toxicity, etc.) Through use of such methods, the BC and DE loops of fibronectin can be engineered to make contacts with antigens equivalent to the contacts of the corresponding CDR1 and CDR2 domains in antibodies.

Unlike the BC and DE loops, the FG loop of $^{10}$Fn3 is 12 residues long, whereas the corresponding loop in antibody heavy chains ranges from 4-28 residues. Accordingly, to optimize antigen binding, the FG loop of $^{10}$Fn3 can be varied in length (e.g., via use of randomization and/or use of polypeptide linker sequences (which also can be randomized)) as well as in sequence to cover the CDR3 length range of 4-28 residues to obtain the greatest possible flexibility and affinity in antigen binding. Indeed, for both those methods in which CDRs are directly grafted into a fibronectin scaffold and those in which a native fibronectin scaffold is selected and/or optimized for binding of serum albumin (or other target antigen), the lengths as well as the sequences of the CDR-like loops of the antibody mimics may be randomized during in vitro or in vivo affinity maturation (as described in more detail below).

The tenth human fibronectin type III domain, $^{10}$Fn3, refolds rapidly even at low temperature; its backbone conformation has been recovered within 1 second at 5° C. Thermodynamic stability of $^{10}$Fn3 is high ($\Delta G_u$=24 kJ/mol=5.7 kcal/mol), correlating with its high melting temperature of 110° C.

One of the physiological roles of $^{10}$Fn3 is as a subunit of fibronectin, a glycoprotein that exists in a soluble form in body fluids and in an insoluble form in the extracellular matrix (Dickinson et al., *J. Mol. Biol.* 236:1079, 1994). A fibronectin monomer of 220-250 Kd contains 12 type I modules, two type II modules, and 17 fibronectin type III modules (Potts and Campbell, *Curr. Opin. Cell Biol.* 6:648, 1994). Different type III modules are involved in the binding of fibronectin to integrins, heparin, and chondroitin sulfate. $^{10}$Fn3 was found to mediate cell adhesion through an integrin-binding Arg-Gly-Asp (RGD) motif on one of its exposed loops. Similar RGD motifs have been shown to be involved in integrin binding by other proteins, such as fibrinogen, von Wellebrand factor, and vitronectin (Hynes et al., Cell 69:11, 1992). No other matrix- or cell-binding roles have been described for $^{10}$Fn3.

The observation that $^{10}$Fn3 has only slightly more adhesive activity than a short peptide containing RGD is consistent with the conclusion that the cell-binding activity of $^{10}$Fn3 is localized in the RGD peptide rather than distributed throughout the $^{10}$Fn3 structure (Baron et al., *Biochemistry* 31:2068, 1992). The fact that $^{10}$Fn3 without the RGD motif is unlikely to bind to other plasma proteins or extracellular matrix makes $^{10}$Fn3 a useful scaffold to replace antibodies. In addition, the presence of $^{10}$Fn3 in natural fibrinogen in the bloodstream indicates that $^{10}$Fn3 itself is unlikely to be immunogenic in the organism of origin.

In addition, it was shown that the $^{10}$Fn3 framework possesses exposed loop sequences tolerant of randomization, facilitating the generation of diverse pools of antibody mimics. This determination was made by examining the flexibility of the $^{10}$Fn3 sequence. In particular, the human $^{10}$Fn3 sequence was aligned with the sequences of fibronectins from other sources as well as sequences of related proteins, and the results of this alignment were mapped onto the three-dimensional structure of the human $^{10}$Fn3 domain. This alignment revealed that the majority of conserved residues were found in the core of the beta sheet sandwich, whereas the highly variable residues were located along the edges of the beta sheets, including the N- and C-termini, on the solvent-accessible faces of both beta sheets, and on three solvent-accessible loops that served as the hypervariable loops for affinity maturation of the antibody mimics. In view of these results, the randomization of these three loops was determined to be unlikely to have an adverse effect on the overall fold or stability of the $^{10}$Fn3 framework itself.

For the human $^{10}$Fn3 sequence, this analysis indicated that, at a minimum, amino acids 1-9, 44-50, 61-54, 82-94 (edges of beta sheets); 19, 21, 30-46 (even), 79-65 (odd) (solvent-accessible faces of both beta sheets); 21-31, 51-56, 76-88 (CDR-like solvent-accessible loops); and 14-16 and 36-45 (other solvent-accessible loops and beta turns) could be randomized to evolve new or improved compound-binding proteins. In addition, as discussed above, alterations in the lengths of one or more solvent exposed loops could also be included in such directed evolution methods.

Alternatively, changes in the A-sheet sequences could also be used to evolve new proteins. These mutations change the scaffold and thereby indirectly alter loop structure(s). If this approach is taken, mutations should not saturate the sequence, but rather few mutations should be introduced. Preferably, no more than between 3-20 changes should be introduced to the β-sheet sequences by this approach.

Sequence variation can be introduced by any technique including, for example, mutagenesis by Taq polymerase (Tindall and Kunkel, *Biochemistry* 27:6008 (1988)), fragment recombination, or a combination thereof. Similarly, an increase of the structural diversity of libraries, for example, by varying the length as well as the sequence of the CDR-presenting and/or CDR-like loops, or by structural redesign based on the advantageous framework mutations found in selected pools, can be used to introduce further improvements in non-immunoglobulin scaffolds.

Fusion Proteins Comprising Fibronectin Scaffold Polypeptides

The fibronectin scaffold polypeptides described herein may be fused to other protein domains. For example, fibronectin scaffold polypeptides identified to bind human serum albumin can be fused with heavy chain single variable domains, or antigen binding fragments thereof, in order to generate a dual-specific ligand of the invention comprising a fibronectin-based serum albumin binding moiety. Fibronectin scaffold polypeptides additionally may be integrated with the human immune response by fusing the constant region of an IgG ($F_c$) with a fibronectin scaffold polypeptide, such as an $^{10}$Fn3 module, preferably through the C-terminus of $^{10}$Fn3. The $F_c$ in such a $^{10}$Fn3-$F_c$ fusion molecule activates the complement component of the immune response and can serve to increase the therapeutic value of the engineered fibronectin polypeptide. Similarly, a fusion between a fibronectin scaffold polypeptide, such as $^{10}$Fn3, and a complement protein, such as C1q, may be used to target cells, and a fusion between a fibronectin scaffold polypeptide, such as $^{10}$Fn3, and a toxin may be used to specifically destroy cells that carry a particular antigen. Any of these fusions may be generated by standard techniques, for example, by expression of the fusion protein from a recombinant fusion gene constructed using publicly available gene sequences and/or as otherwise described infra.

Scaffold Multimers

In addition to monomers, any of the fibronectin scaffold constructs described herein may be generated as dimers or multimers of scaffolds as a means to increase the valency and thus the avidity of antigen (e.g., serum albumin) binding. Such multimers may be generated through covalent binding. For example, individual 10Fn3 modules may be bound by imitating the natural 8Fn3-9Fn3-10Fn3 C-to-N-terminus binding or by imitating antibody dimers that are held together through their constant regions. A 10Fn3-Fc construct may be exploited to design dimers of the general scheme of 10Fn3-Fc::Fc-10Fn3. The bonds engineered into the Fc::Fc interface may be covalent or non-covalent. In addition, dimerizing or multimerizing partners other than Fc, such as other non-immunoglobulin scaffold moieties and/or immunoglobulin-based antigen-binding moieties, can be used in hybrids, such as 10Fn3 hybrids, to create such higher order structures. Other examples of multimers include single variable domains described herein.

In particular examples, covalently bonded multimers may be generated by constructing fusion genes that encode the multimer or, alternatively, by engineering codons for cysteine residues into monomer sequences and allowing disulfide bond formation to occur between the expression products. Non-covalently bonded multimers may also be generated by a variety of techniques. These include the introduction, into monomer sequences, of codons corresponding to positively and/or negatively charged residues and allowing interactions between these residues in the expression products (and therefore between the monomers) to occur. This approach may be simplified by taking advantage of charged residues naturally present in a monomer subunit, for example, the negatively charged residues of fibronectin. Another means for generating non-covalently bonded compositions comprising fibronectin scaffold polypeptides is to introduce, into the monomer gene (for example, at the amino- or carboxy-termini), the coding sequences for proteins or protein domains known to interact. Such proteins or protein domains include coil-coil motifs, leucine zipper motifs, and any of the numerous protein subunits (or fragments thereof) known to direct formation of dimers or higher order multimers.

Fibronectin-Like Molecules

Although $^{10}$Fn3 represents a preferred scaffold for the generation of antibody mimics, other molecules may be substituted for $^{10}$Fn3 in the molecules described herein. These include, without limitation, human fibronectin modules $^{1}$Fn3-$^{9}$Fn3 and $^{11}$Fn3-$^{17}$Fn3 as well as related Fn3 modules from non-human animals and prokaryotes. In addition, Fn3 modules from other proteins with sequence homology to $^{10}$Fn3, such as tenascins and undulins, may also be used. Other exemplary scaffolds having immunoglobulin-like folds (but with sequences that are unrelated to the $V_H$ domain) include N-cadherin, ICAM-2, titin, GCSF receptor, cytokine receptor, glycosidase inhibitor, E-cadherin, and antibiotic chromoprotein. Further domains with related structures may be derived from myelin membrane adhesion molecule P0, CD8, CD4, CD2, class I MHC, T-cell antigen receptor, CD1, C2 and I-set domains of VCAM-1,1-set immunoglobulin domain of myosin-binding protein C, 1-set immunoglobulin domain of myosin-binding protein H, I-set immunoglobulin domain of telokin, telikin, NCAM, twitchin, neuroglian, growth hormone receptor, erythropoietin receptor, prolactin receptor, GC-SF receptor, interferon-gamma receptor, β-galactosidase/glucuronidase, β-glucuronidase, and transglutaminase. Alternatively, any other protein that includes one or more immunoglobulin-like folds may be utilized. Such proteins may be identified, for example, using the program SCOP (Murzin et al., *J. Mol. Biol.* 247:536 (1995); Lo Conte et al., *Nucleic Acids Res.* 25:257 (2000).

Generally, any molecule that exhibits a structural relatedness to the $V_H$ domain (as identified, for example, using the SCOP computer program above) can be utilized as a non-immunoglobulin scaffold. Such molecules may, like fibronectin, include three loops at the N-terminal pole of the molecule and three loops at the C-terminal pole, each of which may be randomized to create diverse libraries; alternatively, larger domains may be utilized, having larger numbers of loops, as long as a number of such surface randomizable loops are positioned closely enough in space that they can participate in antigen binding. Examples of polypeptides possessing more than three loops positioned close to each other include T-cell antigen receptor and superoxide dismutase, which each have four loops that can be randomized; and an Fn3 dimer, tissue factor domains, and cytokine receptor domains, each of which have three sets of two similar domains where three randomizable loops are part of the two domains (bringing the total number of loops to six).

In yet another alternative, any protein having variable loops positioned close enough in space may be utilized for candidate binding protein production. For example, large proteins having spatially related, solvent accessible loops may be used, even if unrelated structurally to an immunoglobulin-like fold. Exemplary proteins include, without limitation, cytochrome F, green fluorescent protein, GroEL, and thaumatin. The loops displayed by these proteins may be randomized and superior binders selected from a randomized library as described herein, e.g. Example 1. Because of their size, molecules may be obtained that exhibit an antigen binding surface considerably larger than that found in an antibody-antigen interaction. Other useful scaffolds of this type may also be identified using the program SCOP (Murzin et al., *J. Mol. Biol.* 247: 536 (1995)) to browse among candidate proteins having numerous loops, particularly loops positioned among parallel beta sheets or a number of alpha-helices.

Modules from different organisms and parent proteins may be most appropriate for different applications. For example, in designing a fibronectin scaffold polypeptide of the invention, it may be most desirable to generate that protein from a fibronectin or fibronectin-like molecule native to the organism for which a therapeutic is intended. In contrast, the organism of origin is less important or even irrelevant for fibronectin scaffolds that are to be used for in vitro applications, such as diagnostics, or as research reagents.

For any of these molecules, libraries may be generated and used to select binding proteins by any of the methods described herein.

Directed Evolution of Scaffold-Based Binding Proteins

The non-immunoglobulin scaffolds described herein may be used in any technique for evolving new or improved binding proteins. In one particular example, the target of binding (e.g., serum albumin) is immobilized on a solid support, such as a column resin or microtiter plate well, and the target contacted with a library of candidate non-immunoglobulin scaffold-based binding proteins. Such a library may consist of fibronectin scaffold clones, such as $^{10}$Fn3 clones constructed from the native (wild type) $^{10}$Fn3 scaffold through randomization of the sequence and/or the length of the $^{10}$Fn3 CDR-like loops. If desired, this library may be an RNA-protein fusion library generated, for example, by the techniques described in Szostak et al., U.S. Ser. No. 09/007,005 and Ser. No. 09/247,190; Szostak et al., WO98/31700; and Roberts & Szostak, Proc. Natl. Acad. Sci. USA (1997) vol. 94, p. 12297-12302. Alternatively, it may be a DNA-protein library (for example, as described in Lobse, DNA-Protein Fusions and Uses Thereof, U.S. Ser. No. 60/110,549, U.S. Ser. No. 09/459,190, and WO 00/32823). The fusion library is incubated with the immobilized target, the support is washed to remove non-specific binders, and the tightest binders are eluted under very stringent conditions and subjected to PCR to recover the sequence information or to create a new library of binders which may be used to repeat the selection process, with or without further mutagenesis of the sequence. A number of rounds of selection may be performed until binders of sufficient affinity for the antigen (e.g., serum albumin) are obtained.

In one particular example, the $^{10}$Fn3 scaffold may be used as the selection target. For example, if a protein is required that binds a specific peptide sequence (e.g., serum albumin) presented in a ten residue loop, a single $^{10}$Fn3 clone is constructed in which one of its loops has been set to the length of ten and to the desired sequence. The new clone is expressed in vivo and purified, and then immobilized on a solid support. An RNA-protein fusion library based on an appropriate scaffold is then allowed to interact with the support, which is then washed, and desired molecules eluted and re-selected as described above.

Similarly, the scaffolds described herein, for example, the $^{10}$Fn3 scaffold, may be used to find natural proteins that interact with the peptide sequence displayed by the scaffold, for example, in an $^{10}$Fn3 loop. The scaffold protein, such as the $^{10}$Fn3 protein, is immobilized as described above, and an RNA-protein fusion library is screened for binders to the displayed loop. The binders are enriched through multiple rounds of selection and identified by DNA sequencing.

In addition, in the above approaches, although RNA-protein libraries represent exemplary libraries for directed evolution, any type of scaffold-based library may be used in the selection methods of the invention.

Use of Fibronectin Scaffold Polypeptides

The fibronectin scaffold polypeptides described herein may be evolved to bind serum albumin or any antigen of interest. Such fibronectin scaffold proteins have thermodynamic properties superior to those of natural antibodies and can be evolved rapidly in vitro. Accordingly, these fibronectin scaffold polypeptides may be employed to produce binding domains for use in the research, therapeutic, and diagnostic fields.

Mutagenic Affinity Maturation

The selections described herein may also be combined with mutagenesis after all or a subset of the selection steps to further increase library diversity. Methods of affinity maturation may employ, e.g., error-prone PCR (Cadwell and Joyce, *PCR Methods Appl* 2:28 (1992)) or alternative forms of random mutagenesis, NNK mutagenesis as described infra, look-through mutagenesis (wherein CDR-grafted fibronectin scaffold polypeptides are engineered to optimize antigen binding through use of naturally-occurring CDR diversity—refer, e.g., to WO 06/023144, incorporated herein by reference), and/or other art-recognized mutagenic approach for creating polypeptide diversity, that is combined with one or more rounds of selection for antigen-binding affinity.

Any of the scaffold proteins described infra may be combined with one another for use, e.g., in the dual-specific ligand compositions of the present invention. For example, CDRs may be grafted on to a CTLA-4 scaffold and used together with antibody VH or VL domains to form a multivalent ligand. Likewise, fibronectin, lipocalin, affibodies, and other scaffolds may be combined.

All publications mentioned in the present specification, and references cited in said publications, are herein incorporated by reference. Various modifications and variations of the described methods and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in molecular biology or related fields are intended to be within the scope of the following claims.

ANNEX 1

Polypeptides which Enhance Half-Life In Vivo

Alpha-1 Glycoprotein (Orosomucoid) (AAG)
Alpha-1 Antichyromotrypsin (ACT)
Alpha-1 Antitrypsin (AAT)
Alpha-1 Microglobulin (Protein HC) (AIM)
Alpha-2 Macroglobulin (A2M)
Antithrombin III (AT III)
Apolipoprotein A-1 (Apo A-1)
Apoliprotein B (Apo B)
Beta-2-microglobulin (B2M)

Ceruloplasmin (Cp)
Complement Component (C3)
Complement Component (C4)
C1 Esterase Inhibitor (C1 INH)
C-Reactive Protein (CRP)
Cystatin C (Cys C)
Ferritin (FER)
Fibrinogen (FIB)
Fibronectin (FN)
Haptoglobin (Hp)
Hemopexin (HPX)
Immunoglobulin A (IgA)
Immunoglobulin D (IgD)
Immunoglobulin E (IgE)
Immunoglobulin G (IgG)
Immunoglobulin M (IgM)
Immunoglobulin Light Chains (kapa/lambda)
Lipoprotein(a) [Lp(a)]
Mannose-bindign protein (MBP)
Myoglobin (Myo)
Plasminogen (PSM)
Prealbumin (Transthyretin) (PAL)
Retinol-binding protein (RBP)
Rheomatoid Factor (RF)
Serum Amyloid A (SAA)
Soluble Tranferrin Receptor (sTfR)
Transferrin (Tf)

Annex 2

| Pairing | Therapeutic relevant references. |
| --- | --- |
| TNF ALPHA/TGF-β | TGF-b and TNF when injected into the ankle joint of collagen induced arthritis model significantly enhanced joint inflammation. In non-collagen challenged mice there was no effect. |
| TNF ALPHA/IL-1 | TNF and IL-1 synergize in the pathology of uveitis. TNF and IL-1 synergize in the pathology of malaria (hypoglycaemia, NO). TNF and IL-1 synergize in the induction of polymorphonuclear (PMN) cells migration in inflammation. IL-1 and TNF synergize to induce PMN infiltration into the peritoneum. IL-1 and TNF synergize to induce the secretion of IL-1 by endothelial cells. Important in inflammation. IL-1 or TNF alone induced some cellular infiltration into knee synovium. IL-1 induced PMNs, TNF - monocytes. Together they induced a more severe infiltration due to increased PMNs. Circulating myocardial depressant substance (present in sepsis) is low levels of IL-1 and TNF acting synergistically. |
| TNF ALPHA/IL-2 | Most relating to synergisitic activation of killer T-cells. |
| TNF ALPHA/IL-3 | Synergy of interleukin 3 and tumor necrosis factor alpha in stimulating clonal growth of acute myelogenous leukemia blasts is the result of induction of secondary hematopoietic cytokines by tumor necrosis factor alpha. Cancer Res. 1992 Apr 15; 52(8): 2197-201. |
| TNF ALPHA/IL-4 | IL-4 and TNF synergize to induce VCAM expression on endothelial cells. Implied to have a role in asthma. Same for synovium - implicated in RA. TNF and IL-4 synergize to induce IL-6 expression in keratinocytes. Sustained elevated levels of VCAM-1 in cultured fibroblast-like synoviocytes can be achieved by TNF-alpha in combination with either IL-4 or IL-13 through increased mRNA stability. Am J Pathol. 1999 Apr; 154(4): 1149-58 |
| TNF ALPHA/IL-5 | Relationship between the tumor necrosis factor system and the serum interleukin-4, interleukin-5, interleukin-8, eosinophil cationic protein, and immunoglobulin E levels in the bronchial hyperreactivity of adults and their children. Allergy Asthma Proc. 2003 Mar-Apr; 24(2): 111-8. |
| TNF ALPHA/IL-6 | TNF and IL-6 are potent growth factors for OH-2, a novel human myeloma cell line. Eur J Haematol. 1994 Jul; 53(1): 31-7. |
| TNF ALPHA/IL-8 | TNF and IL-8 synergized with PMNs to activate platelets. Implicated in Acute Respiratory Distress Syndrome. See IL-5/TNF (asthma). Synergism between interleukin-8 and tumor necrosis factor-alpha for neutrophil-mediated platelet activation. Eur Cytokine Netw. 1994 Sep-Oct; 5(5): 455-60. (adult respiratory distress syndrome (ARDS)) |
| TNF ALPHA/IL-9 | |
| TNF ALPHA/IL-10 | IL-10 induces and synergizes with TNF in the induction of HIV expression in chronically infected T-cells. |
| TNF ALPHA/IL-11 | Cytokines synergistically induce osteoclast differentiation: support by immortalized or normal calvarial cells. Am J Physiol Cell Physiol. 2002 Sep; 283(3): C679-87. (Bone loss) |
| TNF ALPHA/IL-12 | |
| TNF ALPHA/IL-13 | Sustained elevated levels of VCAM-1 in cultured fibroblast-like synoviocytes can be achieved by TNF-alpha in combination with either IL-4 or IL-13 through increased mRNA stability. Am J Pathol. 1999 Apr; 154(4): 1149-58. Interleukin-13 and tumour necrosis factor-alpha synergistically induce eotaxin production in human nasal fibroblasts. Clin Exp Allergy. 2000 Mar; 30(3): 348-55. Interleukin-13 and tumour necrosis factor-alpha synergistically induce eotaxin production in human nasal fibroblasts. Clin Exp Allergy. 2000 Mar; 30(3): 348-55 (allergic inflammation) Implications of serum TNF-beta and IL-13 in the treatment response of childhood nephrotic syndrome. Cytokine. 2003 Feb 7; 21(3): 155-9. |
| TNF ALPHA/IL-14 | Effects of inhaled tumour necrosis factor alpha in subjects with mild asthma. Thorax. 2002 Sep; 57(9): 774-8. |

-continued

Annex 2

| Pairing | Therapeutic relevant references. |
| --- | --- |
| TNF ALPHA/IL-15 | Effects of inhaled tumour necrosis factor alpha in subjects with mild asthma. Thorax. 2002 Sep; 57(9): 774-8. |
| TNF ALPHA/IL-16 | Tumor necrosis factor-alpha-induced synthesis of interleukin-16 in airway epithelial cells: priming for serotonin stimulation. Am J Respir Cell Mol Biol. 2003 Mar; 28(3): 354-62. (airway inflammation) <br> Correlation of circulating interleukin 16 with proinflammatory cytokines in patients with rheumatoid arthritis. Rheumatology (Oxford). 2001 Apr; 40(4): 474-5. No abstract available. <br> Interleukin 16 is up-regulated in Crohn's disease and participates in TNBS colitis in mice. Gastroenterology. 2000 Oct; 119(4): 972-82. |
| TNF ALPHA/IL-17 | Inhibition of interleukin-17 prevents the development of arthritis in vaccinated mice challenged with Borrelia burgdorferi. Infect Immun. 2003 Jun; 71(6): 3437-42. <br> Interleukin 17 synergises with tumour necrosis factor alpha to induce cartilage destruction in vitro. Ann Rheum Dis. 2002 Oct; 61(10): 870-6. <br> A role of GM-CSF in the accumulation of neutrophils in the airways caused by IL-17 and TNF-alpha. Eur Respir J. 2003 Mar; 21(3): 387-93. (Airway inflammation) <br> Abstract Interleukin-1, tumor necrosis factor alpha, and interleukin-17 synergistically up-regulate nitric oxide and prostaglandin E2 production in explants of human osteoarthritic knee menisci. Arthritis Rheum. 2001 Sep; 44(9): 2078-83. |
| TNF ALPHA/IL-18 | Association of interleukin-18 expression with enhanced levels of both interleukin-1beta and tumor necrosis factor alpha in knee synovial tissue of patients with rheumatoid arthritis. Arthritis Rheum. 2003 Feb; 48(2): 339-47. <br> Abstract Elevated levels of interleukin-18 and tumor necrosis factor-alpha in serum of patients with type 2 diabetes mellitus: relationship with diabetic nephropathy. Metabolism. 2003 May; 52(5): 605-8. |
| TNF ALPHA/IL-19 | Abstract IL-19 induces production of IL-6 and TNF-alpha and results in cell apoptosis through TNF-alpha. J Immunol. 2002 Oct 15; 169(8): 4288-97. |
| TNF ALPHA/IL-20 | Abstract Cytokines: IL-20-a new effector in skin inflammation. Curr Biol. 2001 Jul 10; 11(13): R531-4 |
| TNF ALPHA/Complement | Inflammation and coagulation: implications for the septic patient. Clin Infect Dis. 2003 May 15; 36(10): 1259-65. Epub 2003 May 08. Review. |
| TNF ALPHA/IFN-γ | MHC induction in the brain. <br> Synergize in anti-viral response/IFN-β induction. <br> Neutrophil activation/respiratory burst. <br> Endothelial cell activation <br> Toxicities noted when patients treated with TNF/IFN-γ as anti-viral therapy <br> Fractalkine expression by human astrocytes. <br> Many papers on inflammatory responses - i.e. LPS, also macrophage activation. <br> Anti-TNF and anti-IFN-γ synergize to protect mice from lethal endotoxemia. |
| TGF-β/IL-1 | Prostaglndin synthesis by osteoblasts <br> IL-6 production by intestinal epithelial cells (inflammation model) <br> Stimulates IL-11 and IL-6 in lung fibroblasts (inflammation model) <br> IL-6 and IL-8 production in the retina |
| TGF-β/IL-6 | Chondrocarcoma proliferation |
| IL-1/IL-2 | B-cell activation <br> LAK cell activation <br> T-cell activation <br> IL-1 synergy with IL-2 in the generation of lymphokine activated killer cells is mediated by TNF-alpha and beta (lymphotoxin). Cytokine. 1992 Nov; 4(6): 479-87. |
| IL-1/IL-3 | |
| IL-1/IL-4 | B-cell activation <br> IL-4 induces IL-1 expression in endothelial cell activation. |
| IL-1/IL-5 | |
| IL-1/IL-6 | B cell activation <br> T cell activation (can replace accessory cells) <br> IL-1 induces IL-6 expression <br> C3 and serum amyloid expression (acute phase response) <br> HIV expression <br> Cartilage collagen breakdown. |
| IL-1/IL-7 | IL-7 is requisite for IL-1-induced thymocyte proliferation. Involvement of IL-7 in the synergistic effects of granulocyte-macrophage colony-stimulating factor or tumor necrosis factor with IL-1. J Immunol. 1992 Jan 1; 148(1): 99-105. |
| IL-1/IL-8 | |
| IL-1/IL-10 | |
| IL-1/IL-11 | Cytokines synergistically induce osteoclast differentiation: support by immortalized or normal calvarial cells. Am J Physiol Cell Physiol. 2002 Sep; 283(3): C679-87. (Bone loss) |
| IL-1/IL-16 | Correlation of circulating interleukin 16 with proinflammatory cytokines in patients with rheumatoid arthritis. Rheumatology (Oxford). 2001 Apr; 40(4): 474-5. No abstract available. |

-continued

Annex 2

| Pairing | Therapeutic relevant references. |
|---|---|
| IL-1/IL-17 | Inhibition of interleukin-17 prevents the development of arthritis in vaccinated mice challenged with Borrelia burgdorferi. Infect Immun. 2003 Jun; 71(6): 3437-42.<br>Contribution of interleukin 17 to human cartilage degradation and synovial inflammation in osteoarthritis. Osteoarthritis Cartilage. 2002 Oct; 10(10): 799-807. Abstract Interleukin-1, tumor necrosis factor alpha, and interleukin-17 synergistically up-regulate nitric oxide and prostaglandin E2 production in explants of human osteoarthritic knee menisci. Arthritis Rheum. 2001 Sep; 44(9): 2078-83. |
| IL-1/IL-18 | Association of interleukin-18 expression with enhanced levels of both interleukin-1beta and tumor necrosis factor alpha in knee synovial tissue of patients with rheumatoid arthritis. Arthritis Rheum. 2003 Feb; 48(2): 339-47. |
| IL-1/IFN-g | |
| IL-2/IL-3 | T-cell proliferation<br>B cell proliferation |
| IL-2/IL-4 | B-cell proliferation<br>T-cell proliferation<br>(selectively inducing activation of CD8 and NK lymphocytes)IL-2R beta agonist P1-30 acts in synergy with IL-2, IL-4, IL-9, and IL-15: biological and molecular effects. J Immunol. 2000 Oct 15; 165(8): 4312-8. |
| IL-2/IL-5 | B-cell proliferation/Ig secretion<br>IL-5 induces IL-2 receptors on B-cells |
| IL-2/IL-6 | Development of cytotoxic T-cells |
| IL-2/IL-7 | |
| IL-2/IL-9 | See IL-2/IL-4 (NK-cells) |
| IL-2/IL-10 | B-cell activation |
| IL-2/IL-12 | IL-12 synergizes with IL-2 to induce lymphokine-activated cytotoxicity and perform and granzyme gene expression in fresh human NK cells. Cell Immunol. 1995 Oct 1; 165(1): 33-43. (T-cell activation) |
| IL-2/IL-15 | See IL-2/IL-4 (NK cells)<br>(T cell activation and proliferation) IL-15 and IL-2: a matter of life and death for T cells in vivo. Nat Med. 2001 Jan; 7(1): 114-8. |
| IL-2/IL-16 | Synergistic activation of CD4+ T cells by IL-16 and IL-2. J Immunol. 1998 Mar 1; 160(5): 2115-20. |
| IL-2/IL-17 | Evidence for the early involvement of interleukin 17 in human and experimental renal allograft rejection. J Pathol. 2002 Jul; 197(3): 322-32. |
| IL-2/IL-18 | Interleukin 18 (IL-18) in synergy with IL-2 induces lethal lung injury in mice: a potential role for cytokines, chemokines, and natural killer cells in the pathogenesis of interstitial pneumonia. Blood. 2002 Feb 15; 99(4): 1289-98. |
| IL-2/TGF-β | Control of CD4 effector fate: transforming growth factor beta 1 and interleukin 2 synergize to prevent apoptosis and promote effector expansion. J Exp Med. 1995 Sep 1; 182(3): 699-709. |
| IL-2/IFN-γ | Ig secretion by B-cells<br>IL-2 induces IFN-γ expression by T-cells |
| IL-2/IFN-α/β | None |
| IL-3/IL-4 | Synergize in mast cell growth<br>Synergistic effects of IL-4 and either GM-CSF or IL-3 on the induction of CD23 expression by human monocytes: regulatory effects of IFN-alpha and IFN-gamma. Cytokine. 1994 Jul; 6(4): 407-13. |
| IL-3/IL-5 | |
| IL-3/IL-6 | |
| IL-3/IFN-γ | IL-4 and IFN-gamma synergistically increase total polymeric IgA receptor levels in human intestinal epithelial cells. Role of protein tyrosine kinases. J Immunol. 1996 Jun 15; 156(12): 4807-14. |
| IL-3/GM-CSF | Differential regulation of human eosinophil IL-3, IL-5, and GM-CSF receptor alpha-chain expression by cytokines: IL-3, IL-5, and GM-CSF down-regulate IL-5 receptor alpha expression with loss of IL-5 responsiveness, but up-regulate IL-3 receptor alpha expression. J Immunol. 2003 Jun 1; 170(11): 5359-66. (allergic inflammation) |
| IL-4/IL-2 | IL-4 synergistically enhances both IL-2- and IL-12-induced IFN-{gamma} expression in murine NK cells. Blood. 2003 Mar 13 [Epub ahead of print] |
| IL-4/IL-5 | Enhanced mast cell histamine etc. secretion in response to IgE<br>A Th2-like cytokine response is involved in bullous pemphigoid. the role of IL-4 and IL-5 in the pathogenesis of the disease. Int J Immunopathol Pharmacol. 1999 May-Aug; 12(2): 55-61. |
| IL-4/IL-6 | |
| IL-4/IL-10 | |
| IL-4/IL-11 | Synergistic interactions between interleukin-11 and interleukin-4 in support of proliferation of primitive hematopoietic progenitors of mice. Blood. 1991 Sep 15; 78(6): 1448-51. |
| IL-4/IL-12 | Synergistic effects of IL-4 and IL-18 on IL-12-dependent IFN-gamma production by dendritic cells. J Immunol. 2000 Jan 1; 164(1): 64-71. (increase Th1/Th2 differentiation)<br>IL-4 synergistically enhances both IL-2- and IL-12-induced IFN-{gamma} expression in murine NK cells. Blood. 2003 Mar 13 [Epub ahead of print] |

-continued

Annex 2

| Pairing | Therapeutic relevant references. |
| --- | --- |
| IL-4/IL-13 | Abstract Interleukin-4 and interleukin-13 signaling connections maps. Science. 2003 Jun 6; 300(5625): 1527-8. (allergy, asthma) Inhibition of the IL-4/IL-13 receptor system prevents allergic sensitization without affecting established allergy in a mouse model for allergic asthma. J Allergy Clin Immunol. 2003 Jun; 111(6): 1361-1369. |
| IL-4/IL-16 | (asthma) Interleukin (IL)-4/IL-9 and exogenous IL-16 induce IL-16 production by BEAS-2B cells, a bronchial epithelial cell line. Cell Immunol. 2001 Feb 1; 207(2): 75-80 |
| IL-4/IL-17 | Interleukin (IL)-4 and IL-17 synergistically stimulate IL-6 secretion in human colonic myofibroblasts. Int J Mol Med. 2002 Nov; 10(5): 631-4. (Gut inflammation) |
| IL-4/IL-24 | IL-24 is expressed by rat and human macrophages. Immunobiology. 2002 Jul; 205(3): 321-34. |
| IL-4/IL-25 | Abstract New IL-17 family members promote Th1 or Th2 responses in the lung: in vivo function of the novel cytokine IL-25. J Immunol. 2002 Jul 1; 169(1): 443-53. (allergic inflammation) Abstract Mast cells produce interleukin-25 upon Fcepsilon RI-mediated activation. Blood. 2003 May 1; 101(9): 3594-6. Epub 2003 Jan 02. (allergic inflammation) |
| IL-4/IFN-γ | Abstract Interleukin 4 induces interleukin 6 production by endothelial cells: synergy with interferon-gamma. Eur J Immunol. 1991 Jan; 21(1): 97-101. |
| IL-4/SCF | Regulation of human intestinal mast cells by stem cell factor and IL-4. Immunol Rev. 2001 Feb; 179: 57-60. Review. |
| IL-5/IL-3 | Differential regulation of human eosinophil IL-3, IL-5, and GM-CSF receptor alpha-chain expression by cytokines: IL-3, IL-5, and GM-CSF down-regulate IL-5 receptor alpha expression with loss of IL-5 responsiveness, but up-regulate IL-3 receptor alpha expression. J Immunol. 2003 Jun 1; 170(11): 5359-66. (Allergic inflammation see abstract) |
| IL-5/IL-6 | |
| IL-5/IL-13 | Inhibition of allergic airways inflammation and airway hyperresponsiveness in mice by dexamethasone: role of eosinophils, IL-5, eotaxin, and IL-13. J Allergy Clin Immunol. 2003 May; 111(5): 1049-61. |
| IL-5/IL-17 | Interleukin-17 orchestrates the granulocyte influx into airways after allergen inhalation in a mouse model of allergic asthma. Am J Respir Cell Mol Biol. 2003 Jan; 28(1): 42-50. |
| IL-5/IL-25 | Abstract New IL-17 family members promote Th1 or Th2 responses in the lung: in vivo function of the novel cytokine IL-25. J Immunol. 2002 Jul 1; 169(1): 443-53. (allergic inflammation) Abstract Mast cells produce interleukin-25 upon Fcepsilon RI-mediated activation. Blood. 2003 May 1; 101(9): 3594-6. Epub 2003 Jan 02. (allergic inflammation) |
| IL-5/IFN-γ | |
| IL-5/GM-CSF | Differential regulation of human eosinophil IL-3, IL-5, and GM-CSF receptor alpha-chain expression by cytokines: IL-3, IL-5, and GM-CSF down-regulate IL-5 receptor alpha expression with loss of IL-5 responsiveness, but up-regulate IL-3 receptor alpha expression. J Immunol. 2003 Jun 1; 170(11): 5359-66. (Allergic inflammation) |
| IL-6/IL-10 | |
| IL-6/IL-11 | |
| IL-6/IL-16 | Interleukin-16 stimulates the expression and production of pro-inflammatory cytokines by human monocytes. Immunology. 2000 May; 100(1): 63-9. |
| IL-6/IL-17 | Stimulation of airway mucin gene expression by interleukin (IL)-17 through IL-6 paracrine/autocrine loop. J Biol Chem. 2003 May 9; 278(19): 17036-43. Epub 2003 Mar 06. (airway inflammation, asthma) |
| IL-6/IL-19 | Abstract IL-19 induces production of IL-6 and TNF-alpha and results in cell apoptosis through TNF-alpha. J Immunol. 2002 Oct 15; 169(8): 4288-97. |
| IL-6/IFN-g | |
| IL-7/IL-2 | Interleukin 7 worsens graft-versus-host disease. Blood. 2002 Oct 1; 100(7): 2642-9. |
| IL-7/IL-12 | Synergistic effects of IL-7 and IL-12 on human T cell activation. J Immunol. 1995 May 15; 154(10): 5093-102. |
| IL-7/IL-15 | Interleukin-7 and interleukin-15 regulate the expression of the bcl-2 and c-myb genes in cutaneous T-cell lymphoma cells. Blood. 2001 Nov 1; 98(9): 2778-83. (growth factor) |
| IL-8/IL-11 | Abnormal production of interleukin (IL)-11 and IL-8 in polycythaemia vera. Cytokine. 2002 Nov 21; 20(4): 178-83. |
| IL-8/IL-17 | The Role of IL-17 in Joint Destruction. Drug News Perspect. 2002 Jan; 15(1): 17-23. (arthritis) Abstract Interleukin-17 stimulates the expression of interleukin-8, growth-related oncogene-alpha, and granulocyte-colony-stimulating factor by human airway epithelial cells. Am J Respir Cell Mol Biol. 2002 Jun; 26(6): 748-53. (airway inflammation) |

Annex 2

| Pairing | Therapeutic relevant references. |
|---|---|
| IL-8/GSF | Interleukin-8: an autocrine/paracrine growth factor for human hematopoietic progenitors acting in synergy with colony stimulating factor-1 to promote monocyte-macrophage growth and differentiation. Exp Hematol. 1999 Jan; 27(1): 28-36. |
| IL-8/VGEF | Intracavitary VEGF, bFGF, IL-8, IL-12 levels in primary and recurrent malignant glioma. J Neurooncol. 2003 May; 62(3): 297-303. |
| IL-9/IL-4 | Anti-interleukin-9 antibody treatment inhibits airway inflammation and hyperreactivity in mouse asthma model. Am J Respir Crit Care Med. 2002 Aug 1; 166(3): 409-16. |
| IL-9/IL-5 | Pulmonary overexpression of IL-9 induces Th2 cytokine expression, leading to immune pathology. J Clin Invest. 2002 Jan; 109(1): 29-39. Th2 cytokines and asthma. Interleukin-9 as a therapeutic target for asthma. Respir Res. 2001; 2(2): 80-4. Epub 2001 Feb 15. Review. Abstract Interleukin-9 enhances interleukin-5 receptor expression, differentiation, and survival of human eosinophils. Blood. 2000 Sep 15; 96(6): 2163-71 (asthma) |
| IL-9/IL-13 | Anti-interleukin-9 antibody treatment inhibits airway inflammation and hyperreactivity in mouse asthma model. Am J Respir Crit Care Med. 2002 Aug 1; 166(3): 409-16. Direct effects of interleukin-13 on epithelial cells cause airway hyperreactivity and mucus overproduction in asthma. Nat Med. 2002 Aug; 8(8): 885-9. |
| IL-9/IL-16 | See IL-4/IL-16 |
| IL-10/IL-2 | The interplay of interleukin-10 (IL-10) and interleukin-2 (IL-2) in humoral immune responses: IL-10 synergizes with IL-2 to enhance responses of human B lymphocytes in a mechanism which is different from upregulation of CD25 expression. Cell Immunol. 1994 Sep; 157(2): 478-88. |
| IL-10/IL-12 | |
| IL-10/TGF-β | IL-10 and TGF-beta cooperate in the regulatory T cell response to mucosal allergens in normal immunity and specific immunotherapy. Eur J Immunol. 2003 May; 33(5): 1205-14. |
| IL-10/IFN-γ | |
| IL-11/IL-6 | Interleukin-6 and interleukin-11 support human osteoclast formation by a RANKL-independent mechanism. Bone. 2003 Jan; 32(1): 1-7. (bone resorption in inflammation) |
| IL-11/IL-17 | Polarized in vivo expression of IL-11 and IL-17 between acute and chronic skin lesions. J Allergy Clin Immunol. 2003 Apr; 111(4): 875-81. (allergic dermatitis) IL-17 promotes bone erosion in murine collagen-induced arthritis through loss of the receptor activator of NF-kappa B ligand/osteoprotegerin balance. J Immunol. 2003 Mar 1; 170(5): 2655-62. |
| IL-11/TGF-β | Polarized in vivo expression of IL-11 and IL-17 between acute and chronic skin lesions. J Allergy Clin Immunol. 2003 Apr; 111(4): 875-81. (allergic dermatitis) |
| IL-12/IL-13 | Relationship of Interleukin-12 and Interleukin-13 imbalance with class-specific rheumatoid factors and anticardiolipin antibodies in systemic lupus erythematosus. Clin Rheumatol. 2003 May; 22(2): 107-11. |
| IL-12/IL-17 | Upregulation of interleukin-12 and -17 in active inflammatory bowel disease. Scand J Gastroenterol. 2003 Feb; 38(2): 180-5. |
| IL-12/IL-18 | Synergistic proliferation and activation of natural killer cells by interleukin 12 and interleukin 18. Cytokine. 1999 Nov; 11(11): 822-30. Inflammatory Liver Steatosis Caused by IL-12 and IL-18. J Interferon Cytokine Res. 2003 Mar; 23(3): 155-62. |
| IL-12/IL-23 | nterleukin-23 rather than interleukin-12 is the critical cytokine for autoimmune inflammation of the brain. Nature. 2003 Feb 13; 421(6924): 744-8. Abstract A unique role for IL-23 in promoting cellular immunity. J Leukoc Biol. 2003 Jan; 73(1): 49-56. Review. |
| IL-12/IL-27 | Abstract IL-27, a heterodimeric cytokine composed of EBI3 and p28 protein, induces proliferation of naive CD4(+) T cells. Immunity. 2002 Jun; 16(6): 779-90. |
| IL-12/IFN-γ | IL-12 induces IFN-γ expression by B and T-cells as part of immune stimulation. |
| IL-13/IL-5 | See IL-5/IL-13 |
| IL-13/IL-25 | Abstract New IL-17 family members promote Th1 or Th2 responses in the lung: in vivo function of the novel cytokine IL-25. J Immunol. 2002 Jul 1; 169(1): 443-53. (allergic inflammation) Abstract Mast cells produce interleukin-25 upon Fcepsilon RI-mediated activation. Blood. 2003 May 1; 101(9): 3594-6. Epub 2003 Jan 02. (allergic inflammation) |
| IL-15/IL-13 | Differential expression of interleukins (IL)-13 and IL-15 in ectopic and eutopic endometrium of women with endometriosis and normal fertile women. Am J Reprod Immunol. 2003 Feb; 49(2): 75-83. |
| IL-15/IL-16 | IL-15 and IL-16 overexpression in cutaneous T-cell lymphomas: stage-dependent increase in mycosis fungoides progression. Exp Dermatol. 2000 Aug; 9(4): 248-51. |

Annex 2

| Pairing | Therapeutic relevant references. |
|---|---|
| IL-15/IL-17 | Abstract IL-17, produced by lymphocytes and neutrophils, is necessary for lipopolysaccharide-induced airway neutrophilia: IL-15 as a possible trigger. J Immunol. 2003 Feb 15; 170(4): 2106-12. (airway inflammation) |
| IL-15/IL-21 | IL-21 in Synergy with IL-15 or IL-18 Enhances IFN-gamma Production in Human NK and T Cells. J Immunol. 2003 Jun 1; 170(11): 5464-9. |
| IL-17/IL-23 | Interleukin-23 promotes a distinct CD4 T cell activation state characterized by the production of interleukin-17. J Biol Chem. 2003 Jan 17; 278(3): 1910-4. Epub 2002 Nov 03 |
| IL-17/TGF-β | Polarized in vivo expression of IL-11 and IL-17 between acute and chronic skin lesions. J Allergy Clin Immunol. 2003 Apr; 111(4): 875-81. (allergic dermatitis) |
| IL-18/IL-12 | Synergistic proliferation and activation of natural killer cells by interleukin 12 and interleukin 18. Cytokine. 1999 Nov; 11(11): 822-30. Abstract Inhibition of in vitro immunoglobulin production by IL-12 in murine chronic graft-vs.-host disease: synergism with IL-18. Eur J Immunol. 1998 Jun; 28(6): 2017-24. |
| IL-18/IL-21 | IL-21 in Synergy with IL-15 or IL-18 Enhances IFN-gamma Production in Human NK and T Cells. J Immunol. 2003 Jun 1; 170(11): 5464-9. |
| IL-18/TGF-β | Interleukin 18 and transforming growth factor beta1 in the serum of patients with Graves' ophthalmopathy treated with corticosteroids. Int Immunopharmacol. 2003 Apr; 3(4): 549-52. |
| IL-18/IFN-γ | |
| Anti-TNF ALPHA/anti-CD4 | Synergistic therapeutic effect in DBA/1 arthritic mice. |

Annex 3: Oncology combinations

| Target | Disease | Pair with |
|---|---|---|
| CD89* | Use as cytotoxic cell recruiter | all |
| CD19 | B cell lymphomas | HLA-DR |
| | | CD5 |
| HLA-DR | B cell lymphomas | CD89 |
| | | CD19 |
| | | CD5 |
| CD38 | Multiple myeloma | CD138 |
| | | CD56 |
| | | HLA-DR |
| CD138 | Multiple myeloma | CD38 |
| | | CD56 |
| | | HLA-DR |
| CD138 | Lung cancer | CD56 |
| | | CEA |
| CD33 | Acute myelod lymphoma | CD34 |
| | | HLA-DR |
| CD56 | Lung cancer | CD138 |
| | | CEA |
| CEA | Pan carcinoma | MET receptor |
| VEGF | Pan carcinoma | MET receptor |
| VEGF receptor | Pan carcinoma | MET receptor |
| IL-13 | Asthma/pulmonary inflammation | IL-4 |
| | | IL-5 |
| | | Eotaxin(s) |
| | | MDC |
| | | TARC |
| | | TNFα |
| | | IL-9 |
| | | EGFR |
| | | CD40L |
| | | IL-25 |
| | | MCP-1 |
| | | TGFβ |
| IL-4 | Asthma | IL-13 |
| | | IL-5 |
| | | Eotaxin(s) |
| | | MDC |
| | | TARC |
| | | TNFα |
| | | IL-9 |
| | | EGFR |
| | | CD40L |
| | | IL-25 |
| | | MCP-1 |
| | | TGFβ |
| Eotaxin | Asthma | IL-5 |
| | | Eotaxin-2 |
| | | Eotaxin-3 |
| EGFR | cancer | HER2/neu |
| | | HER3 |
| | | HER4 |
| HER2 | cancer | HER3 |
| | | HER4 |
| TNFR1 | RA/Crohn's disease | IL-1R |
| | | IL-6R |
| | | IL-18R |
| TNFα | RA/Crohn's disease | IL-1α/β |
| | | IL-6 |
| | | IL-18 |
| | | ICAM-1 |
| | | IL-15 |
| | | IL-17 |
| IL-1R | RA/Crohn's disease | IL-6R |
| | | IL-18R |
| IL-18R | RA/Crohn's disease | IL-6R |

Annex 4
Data Summary

| TARGET | dAb | Equilibrium dissocation constant (Kd = Koff/Kon) | Koff | IC50 for ligand assay | ND50 for cell based neutralisn assay |
|---|---|---|---|---|---|
| TAR1 | TAR1 monomers | 300 nM to 5 pM (ie, $3 \times 10^{-7}$ to $5 \times 10^{-12}$), preferably 50 nM to 20 pM | $5 \times 10^{-1}$ to $1 \times 10^{-7}$ | 500 nM to 100 pM | 500 nM to 50 pM |
| | TAR1 dimers | As TAR1 monomer | As TAR1 monomer | As TAR1 monomer | As TAR1 monomer |
| | TAR1 trimers TAR1-5 TAR1-27 | As TAR1 monomer | As TAR1 monomer | As TAR1 monomer | As TAR1 monomer |
| | TAR1-5-19 monomer | 30 nM | | | |
| | TAR1-5-19 homodimer | | | With (Gly$_4$Ser)$_3$ linker (SEQ ID NO: 20) = 20 nm | =30 nM |
| | | | | With (Gly$_4$Ser)$_5$ linker (SEQ ID NO: 21) = 2 nm | =3 nM |
| | | | | With (Gly$_4$Ser)$_7$ linker (SEQ ID NO: 22) = 10 nm | =15 nM |
| | | | | In Fab format = 1 nM | |
| | TAR1-5-19 heterodimers | | | With (Gly$_4$Ser)$_n$ linker (SEQ ID NO: 1) TAR1-5-19 d2 = 2 nM TAR1-5-19 d3 = 8 nM TAR1-5-19 d4 = 2-5 nM TAR1-5-19 d5 = 8 nM In Fab format TAR1-5-19CH d1CK = 6 nM TAR1-5-19CK d1CH = 6 nM TAR1-5-19CH d2CK = 8 nM TAR1-5-19CH d3CK = 3 nM | =12 nM =10 nM =12 nM |
| | TAR1-5 heterodimers | | | With (Gly$_4$Ser)$_n$ linker (SEQ ID NO: 1) TAR1-5d1 = 30 nM TAR1-5d2 = 50 nM TAR1-5d3 = 300 nM TAR1-5d4 = 3 nM TAR1-5d5 = 200 nM TAR1-5d6 = 100 nM In Fab format TAR1-5CH d2CK = 30 nM TAR1-5CK d3CH = 100 nM | =60 nM |
| | TAR1-5-19 homotrimer | | | 0.3 nM | 3-10 nM (eg, 3 nM) |
| TAR2 | TAR2 monomers TAR2-10 TAR2-5 | As TAR1 monomer | As TAR1 monomer | 500 nM to 100 pM | 500 nM to 50 pM |
| Serum Albumin | Anti-SA monomers | 1 nM to 500 μM, preferably 100 nM to 10 μM In Dual Specific format, target affinity is 1 to 100,000 × affinity of SA dAb affinity, eg 100 pM (target) and 10 μM SA affinity. | | 1 nM to 500 μM, preferably 100 nM to 10 μM In Dual Specific format, target affinity is 1 to 100,000 × affinity of SA dAb affinity, eg 100 pM (target) and 10 μM SA affinity. | |
| | MSA-16 | 200 nM | | | |
| | MSA-26 | 70 nM | | | |

The invention claimed is:

1. An isolated ligand comprising an antibody single variable domain that has a binding site with binding specificity for Domain II of serum albumin, wherein said antibody single variable domain with binding specificity for Domain II of serum albumin comprises SEQ ID NO: 95 (CDR1), SEQ ID NO: 96 (CDR2) and SEQ ID NO: 97 (CDR3) of the amino acid sequence of SEQ ID NO: 235 (dAb7h14).

2. The isolated ligand of claim 1, wherein said ligand comprises a monomer of said antibody single variable domain.

3. The isolated ligand of claim 2, wherein said antibody single variable domain is conjugated to a drug.

4. The isolated ligand of claim 1, wherein said antibody single variable domain comprises a set of four Kabat antibody framework regions (FRs), wherein said four FRs consist of the amino acids encoded by human germ line antibody framework gene segments.

5. The isolated ligand of claim 1, wherein said antibody single variable domain specifically binds Domain II or serum albumin with a dissociation constant (Kd) selected from the group consisting of: $1\times10^{-3}$ M or less, $1\times10^{-4}$ M or less, $1\times10^{-5}$ M or less, $1\times10^{-6}$ M or less, $1\times10^{-7}$ M or less, $1\times10^{-8}$ M or less, and $1\times10^{-9}$ M or less, as determined by surface plasmon resonance.

6. The isolated ligand of any one of the claims 1 and 3, wherein said ligand further comprises at least one entity selected from the group consisting of: a label, a tag and a drug.

7. A composition comprising the isolated ligand of any one of the claims 1 and 2, and a carrier thereof.

* * * * *

SEQUENCE LISTING

<160> NUMBER OF SEQ ID NOS: 295

<210> SEQ ID NO 1
<211> LENGTH: 5
<212> TYPE: PRT
<213> ORGANISM: Artificial Sequence
<220> FEATURE:
<223> OTHER INFORMATION: Synthetic peptide

<400> SEQUENCE: 1

Gly Gly Gly Gly Ser

```
                1               5

<210> SEQ ID NO 2
<211> LENGTH: 40
<212> TYPE: PRT
<213> ORGANISM: Artificial Sequence
<220> FEATURE:
<223> OTHER INFORMATION: Synthetic peptide

<400> SEQUENCE: 2

Gly Gly Gly Gly Ser Gly Gly Gly Ser Gly Gly Gly Ser Gly
1               5                  10                  15

Gly Gly Gly Ser Gly Gly Gly Ser Gly Gly Gly Ser Gly Gly
                20                  25                  30

Gly Gly Ser Gly Gly Gly Gly Ser
        35                  40

<210> SEQ ID NO 3
<211> LENGTH: 8
<212> TYPE: PRT
<213> ORGANISM: Artificial Sequence
<220> FEATURE:
<223> OTHER INFORMATION: Synthetic peptide
<220> FEATURE:
<221> NAME/KEY: VARIANT
<222> LOCATION: 6, 7, 8
<223> OTHER INFORMATION: Xaa = Any Amino Acid

<400> SEQUENCE: 3

Lys Val Glu Ile Lys Xaa Xaa Xaa
1               5

<210> SEQ ID NO 4
<211> LENGTH: 8
<212> TYPE: PRT
<213> ORGANISM: Artificial Sequence
<220> FEATURE:
<223> OTHER INFORMATION: Synthetic peptide
<220> FEATURE:
<221> NAME/KEY: VARIANT
<222> LOCATION: 6, 7, 8
<223> OTHER INFORMATION: Xaa = Any Amino Acid

<400> SEQUENCE: 4

Lys Leu Glu Ile Lys Xaa Xaa Xaa
1               5

<210> SEQ ID NO 5
<211> LENGTH: 8
<212> TYPE: PRT
<213> ORGANISM: Artificial Sequence
<220> FEATURE:
<223> OTHER INFORMATION: Synthetic peptide
<220> FEATURE:
<221> NAME/KEY: VARIANT
<222> LOCATION: 6, 7, 8
<223> OTHER INFORMATION: Xaa = Any Amino Acid

<400> SEQUENCE: 5

Lys Val Asp Ile Lys Xaa Xaa Xaa
1               5

<210> SEQ ID NO 6
<211> LENGTH: 8
<212> TYPE: PRT
<213> ORGANISM: Artificial Sequence
<220> FEATURE:
<223> OTHER INFORMATION: Synthetic peptide
```

```
<220> FEATURE:
<221> NAME/KEY: VARIANT
<222> LOCATION: 6, 7, 8
<223> OTHER INFORMATION: Xaa = Any Amino Acid

<400> SEQUENCE: 6

Arg Leu Glu Ile Lys Xaa Xaa Xaa
1               5

<210> SEQ ID NO 7
<211> LENGTH: 7
<212> TYPE: PRT
<213> ORGANISM: Artificial Sequence
<220> FEATURE:
<223> OTHER INFORMATION: Synthetic peptide
<220> FEATURE:
<221> NAME/KEY: VARIANT
<222> LOCATION: 5, 6, 7
<223> OTHER INFORMATION: Xaa = Any Amino Acid

<400> SEQUENCE: 7

Glu Ile Lys Arg Xaa Xaa Xaa
1               5

<210> SEQ ID NO 8
<211> LENGTH: 8
<212> TYPE: PRT
<213> ORGANISM: Artificial Sequence
<220> FEATURE:
<223> OTHER INFORMATION: Synthetic peptide
<220> FEATURE:
<221> NAME/KEY: VARIANT
<222> LOCATION: 6, 7, 8
<223> OTHER INFORMATION: Xaa = Any Amino Acid

<400> SEQUENCE: 8

Lys Val Asp Val Leu Xaa Xaa Xaa
1               5

<210> SEQ ID NO 9
<211> LENGTH: 8
<212> TYPE: PRT
<213> ORGANISM: Artificial Sequence
<220> FEATURE:
<223> OTHER INFORMATION: Synthetic peptide
<220> FEATURE:
<221> NAME/KEY: VARIANT
<222> LOCATION: 6, 7, 8
<223> OTHER INFORMATION: Xaa = Any Amino Acid

<400> SEQUENCE: 9

Lys Leu Asp Val Leu Xaa Xaa Xaa
1               5

<210> SEQ ID NO 10
<211> LENGTH: 8
<212> TYPE: PRT
<213> ORGANISM: Artificial Sequence
<220> FEATURE:
<223> OTHER INFORMATION: Synthetic peptide
<220> FEATURE:
<221> NAME/KEY: VARIANT
<222> LOCATION: 6, 7, 8
<223> OTHER INFORMATION: Xaa = Any Amino Acid

<400> SEQUENCE: 10

Gln Leu Asp Val Leu Xaa Xaa Xaa
1               5
```

```
<210> SEQ ID NO 11
<211> LENGTH: 8
<212> TYPE: PRT
<213> ORGANISM: Artificial Sequence
<220> FEATURE:
<223> OTHER INFORMATION: Synthetic peptide
<220> FEATURE:
<221> NAME/KEY: VARIANT
<222> LOCATION: 6, 7, 8
<223> OTHER INFORMATION: Xaa = Any Amino Acid

<400> SEQUENCE: 11

Val Thr Val Ser Ser Xaa Xaa Xaa
 1               5

<210> SEQ ID NO 12
<211> LENGTH: 45
<212> TYPE: PRT
<213> ORGANISM: Artificial Sequence
<220> FEATURE:
<223> OTHER INFORMATION: Synthetic peptide

<400> SEQUENCE: 12

Gly Gly Gly Gly Ser Gly Gly Gly Gly Ser Gly Gly Gly Gly Ser Gly
 1               5                  10                  15

Gly Gly Gly Ser Gly Gly Gly Gly Ser Gly Gly Gly Gly Ser Gly Gly
                20                  25                  30

Gly Gly Ser Gly Gly Gly Gly Ser Gly Gly Gly Gly Ser
            35                  40                  45

<210> SEQ ID NO 13
<211> LENGTH: 45
<212> TYPE: PRT
<213> ORGANISM: Artificial Sequence
<220> FEATURE:
<223> OTHER INFORMATION: Synthetic peptide

<400> SEQUENCE: 13

Ser Ser Ser Ser Gly Ser Ser Ser Gly Ser Ser Ser Gly Ser Gly Ser
 1               5                  10                  15

Ser Ser Ser Gly Ser Ser Ser Ser Gly Ser Ser Ser Ser Gly Ser Ser
                20                  25                  30

Ser Ser Gly Ser Ser Ser Ser Gly Ser Ser Ser Ser Gly
            35                  40                  45

<210> SEQ ID NO 14
<211> LENGTH: 9
<212> TYPE: PRT
<213> ORGANISM: Artificial Sequence
<220> FEATURE:
<223> OTHER INFORMATION: Synthetic peptide

<400> SEQUENCE: 14

Ser Ser Ser Ala Ser Ala Ser Ser Ala
 1               5

<210> SEQ ID NO 15
<211> LENGTH: 7
<212> TYPE: PRT
<213> ORGANISM: Artificial Sequence
<220> FEATURE:
<223> OTHER INFORMATION: Synthetic peptide

<400> SEQUENCE: 15

Gly Ser Pro Gly Ser Pro Gly
 1               5
```

```
<210> SEQ ID NO 16
<211> LENGTH: 11
<212> TYPE: PRT
<213> ORGANISM: Artificial Sequence
<220> FEATURE:
<223> OTHER INFORMATION: Synthetic peptide

<400> SEQUENCE: 16

Ala Thr Thr Thr Gly Ser Ser Pro Gly Pro Thr
 1               5                  10

<210> SEQ ID NO 17
<211> LENGTH: 2
<212> TYPE: PRT
<213> ORGANISM: unknown
<220> FEATURE:
<223> OTHER INFORMATION: Natural peptide linker

<400> SEQUENCE: 17

Leu Asp
 1

<210> SEQ ID NO 18
<211> LENGTH: 35
<212> TYPE: PRT
<213> ORGANISM: Camelus dromedarius

<400> SEQUENCE: 18

Glu Pro Lys Ile Pro Gln Pro Gln Pro Lys Pro Gln Pro Gln Pro Gln
 1               5                  10                  15

Pro Gln Pro Lys Pro Gln Pro Lys Pro Glu Pro Glu Cys Thr Cys Pro
            20                  25                  30

Lys Cys Pro
         35

<210> SEQ ID NO 19
<211> LENGTH: 12
<212> TYPE: PRT
<213> ORGANISM: Camelus dromedarius

<400> SEQUENCE: 19

Gly Thr Asn Glu Val Cys Lys Cys Pro Lys Cys Pro
 1               5                  10

<210> SEQ ID NO 20
<211> LENGTH: 15
<212> TYPE: PRT
<213> ORGANISM: Artificial Sequence
<220> FEATURE:
<223> OTHER INFORMATION: Synthetic peptide

<400> SEQUENCE: 20

Gly Gly Gly Gly Ser Gly Gly Gly Gly Ser Gly Gly Gly Gly Ser
 1               5                  10                  15

<210> SEQ ID NO 21
<211> LENGTH: 25
<212> TYPE: PRT
<213> ORGANISM: Artificial Sequence
<220> FEATURE:
<223> OTHER INFORMATION: Synthetic peptide

<400> SEQUENCE: 21

Gly Gly Gly Gly Ser Gly Gly Gly Gly Ser Gly Gly Gly Gly Ser Gly
```

```
1               5                   10                  15
Gly Gly Gly Ser Gly Gly Gly Ser
            20                  25

<210> SEQ ID NO 22
<211> LENGTH: 35
<212> TYPE: PRT
<213> ORGANISM: Artificial Sequence
<220> FEATURE:
<223> OTHER INFORMATION: Synthetic peptide

<400> SEQUENCE: 22

Gly Gly Gly Gly Ser Gly Gly Gly Gly Ser Gly Gly Gly Gly Ser Gly
1               5                   10                  15

Gly Gly Gly Ser Gly Gly Gly Gly Ser Gly Gly Gly Gly Ser Gly Gly
            20                  25                  30

Gly Gly Ser
        35

<210> SEQ ID NO 23
<211> LENGTH: 22
<212> TYPE: DNA
<213> ORGANISM: Artificial Sequence
<220> FEATURE:
<223> OTHER INFORMATION: Synthetic primer

<400> SEQUENCE: 23
cggccatggc gtcaacggac at                                            22

<210> SEQ ID NO 24
<211> LENGTH: 23
<212> TYPE: DNA
<213> ORGANISM: Artificial Sequence
<220> FEATURE:
<223> OTHER INFORMATION: Synthetic primer

<400> SEQUENCE: 24
atgtgcgctc gagcgtttga ttt                                           23

<210> SEQ ID NO 25
<211> LENGTH: 15
<212> TYPE: PRT
<213> ORGANISM: Artificial Sequence
<220> FEATURE:
<223> OTHER INFORMATION: Synthetic peptide

<400> SEQUENCE: 25

Glu Pro Lys Ser Gly Asp Lys Thr His Thr Cys Pro Pro Cys Pro
1               5                   10                  15

<210> SEQ ID NO 26
<211> LENGTH: 50
<212> TYPE: PRT
<213> ORGANISM: Artificial Sequence
<220> FEATURE:
<223> OTHER INFORMATION: Synthetic peptide

<400> SEQUENCE: 26

Gly Gly Gly Gly Ser Gly Gly Gly Gly Ser Gly Gly Gly Gly Ser Gly
1               5                   10                  15

Gly Gly Gly Ser Gly Gly Gly Gly Ser Gly Gly Gly Gly Ser Gly Gly
            20                  25                  30

Gly Gly Ser Gly Gly Gly Gly Ser Gly Gly Gly Gly Ser Gly Gly Gly
        35                  40                  45
```

<210> SEQ ID NO 27
<211> LENGTH: 357
<212> TYPE: DNA
<213> ORGANISM: Artificial Sequence
<220> FEATURE:
<223> OTHER INFORMATION: Synthetic polynucleotide

<400> SEQUENCE: 27
tggagcgcgt cgacggacat ccagatgacc cagtctccat cctctctgtc tgcatctgta    60
ggagaccgtg tcaccatcac ttgccgggca agtcagagca ttgatagtta tttacattgg   120
taccagcaga aaccagggaa agcccctaag ctcctgatct atagtgcatc cgagttgcaa   180
agtggggtcc catcacgttt cagtggcagt ggatctggga cagatttcac tctcaccatc   240
agcagtctgc aacctgaaga ttttgctacg tactactgtc aacaggttgt gtggcgtcct   300
tttacgttcg gccaagggac caaggtggaa atcaaacggt gctaataagg atccggc     357

<210> SEQ ID NO 28
<211> LENGTH: 114
<212> TYPE: PRT
<213> ORGANISM: Artificial Sequence
<220> FEATURE:
<223> OTHER INFORMATION: Synthetic polypeptide

<400> SEQUENCE: 28

Trp Ser Ala Ser Thr Asp Ile Gln Met Thr Gln Ser Pro Ser Ser Leu
 1               5                  10                  15

Ser Ala Ser Val Gly Asp Arg Val Thr Ile Thr Cys Arg Ala Ser Gln
            20                  25                  30

Ser Ile Asp Ser Tyr Leu His Trp Tyr Gln Gln Lys Pro Gly Lys Ala
        35                  40                  45

Pro Lys Leu Leu Ile Tyr Ser Ala Ser Glu Leu Gln Ser Gly Val Pro
    50                  55                  60

Ser Arg Phe Ser Gly Ser Gly Ser Gly Thr Asp Phe Thr Leu Thr Ile
65                  70                  75                  80

Ser Ser Leu Gln Pro Glu Asp Phe Ala Thr Tyr Tyr Cys Gln Gln Val
                85                  90                  95

Val Trp Arg Pro Phe Thr Phe Gly Gln Gly Thr Lys Val Glu Ile Lys
            100                 105                 110

Arg Cys

<210> SEQ ID NO 29
<211> LENGTH: 39
<212> TYPE: DNA
<213> ORGANISM: Artificial Sequence
<220> FEATURE:
<223> OTHER INFORMATION: Synthetic primer

<400> SEQUENCE: 29
tggagcgcgt cgacggacat ccagatgacc cagtctcca                            39

<210> SEQ ID NO 30
<211> LENGTH: 39
<212> TYPE: DNA
<213> ORGANISM: Artificial Sequence
<220> FEATURE:
<223> OTHER INFORMATION: Synthetic primer

<400> SEQUENCE: 30
ttagcagccg gatccttatt agcaccgttt gatttccac         39

<210> SEQ ID NO 31
<211> LENGTH: 5
<212> TYPE: PRT
<213> ORGANISM: Artificial Sequence
<220> FEATURE:
<223> OTHER INFORMATION: Synthetic peptide

<400> SEQUENCE: 31

Ser Ser Tyr Leu Asn
1               5

<210> SEQ ID NO 32
<211> LENGTH: 5
<212> TYPE: PRT
<213> ORGANISM: Artificial Sequence
<220> FEATURE:
<223> OTHER INFORMATION: Synthetic peptide

<400> SEQUENCE: 32

Phe Lys Ser Leu Lys
1               5

<210> SEQ ID NO 33
<211> LENGTH: 5
<212> TYPE: PRT
<213> ORGANISM: Artificial Sequence
<220> FEATURE:
<223> OTHER INFORMATION: Synthetic peptide

<400> SEQUENCE: 33

Tyr Tyr His Leu Lys
1               5

<210> SEQ ID NO 34
<211> LENGTH: 5
<212> TYPE: PRT
<213> ORGANISM: Artificial Sequence
<220> FEATURE:
<223> OTHER INFORMATION: Synthetic peptide

<400> SEQUENCE: 34

Arg Arg Tyr Leu Lys
1               5

<210> SEQ ID NO 35
<211> LENGTH: 5
<212> TYPE: PRT
<213> ORGANISM: Artificial Sequence
<220> FEATURE:
<223> OTHER INFORMATION: Synthetic peptide

<400> SEQUENCE: 35

Tyr Asn Trp Leu Lys
1               5

<210> SEQ ID NO 36
<211> LENGTH: 5
<212> TYPE: PRT
<213> ORGANISM: Artificial Sequence
<220> FEATURE:
<223> OTHER INFORMATION: Synthetic peptide

<400> SEQUENCE: 36

Leu Trp His Leu Arg
1               5

<210> SEQ ID NO 37
<211> LENGTH: 5
<212> TYPE: PRT
<213> ORGANISM: Artificial Sequence
<220> FEATURE:
<223> OTHER INFORMATION: Synthetic peptide

<400> SEQUENCE: 37

Phe Arg Tyr Leu Ala
1               5

<210> SEQ ID NO 38
<211> LENGTH: 5
<212> TYPE: PRT
<213> ORGANISM: Artificial Sequence
<220> FEATURE:
<223> OTHER INFORMATION: Synthetic peptide

<400> SEQUENCE: 38

Phe Tyr His Leu Ala
1               5

<210> SEQ ID NO 39
<211> LENGTH: 5
<212> TYPE: PRT
<213> ORGANISM: Artificial Sequence
<220> FEATURE:
<223> OTHER INFORMATION: Synthetic peptide

<400> SEQUENCE: 39

Ile Trp His Leu Asn
1               5

<210> SEQ ID NO 40
<211> LENGTH: 5
<212> TYPE: PRT
<213> ORGANISM: Artificial Sequence
<220> FEATURE:
<223> OTHER INFORMATION: Synthetic peptide

<400> SEQUENCE: 40

Tyr Arg Tyr Leu Arg
1               5

<210> SEQ ID NO 41
<211> LENGTH: 5
<212> TYPE: PRT
<213> ORGANISM: Artificial Sequence
<220> FEATURE:
<223> OTHER INFORMATION: Synthetic peptide

<400> SEQUENCE: 41

Leu Lys Tyr Leu Lys
1               5

<210> SEQ ID NO 42
<211> LENGTH: 5
<212> TYPE: PRT
<213> ORGANISM: Artificial Sequence
<220> FEATURE:
<223> OTHER INFORMATION: Synthetic peptide

<400> SEQUENCE: 42

Leu Arg Tyr Leu Arg

```
                1               5

<210> SEQ ID NO 43
<211> LENGTH: 5
<212> TYPE: PRT
<213> ORGANISM: Artificial Sequence
<220> FEATURE:
<223> OTHER INFORMATION: Synthetic peptide

<400> SEQUENCE: 43

Leu Arg Ser Leu Lys
1               5

<210> SEQ ID NO 44
<211> LENGTH: 5
<212> TYPE: PRT
<213> ORGANISM: Artificial Sequence
<220> FEATURE:
<223> OTHER INFORMATION: Synthetic peptide

<400> SEQUENCE: 44

Phe Arg His Leu Lys
1               5

<210> SEQ ID NO 45
<211> LENGTH: 5
<212> TYPE: PRT
<213> ORGANISM: Artificial Sequence
<220> FEATURE:
<223> OTHER INFORMATION: Synthetic peptide

<400> SEQUENCE: 45

Arg Lys Tyr Leu Arg
1               5

<210> SEQ ID NO 46
<211> LENGTH: 5
<212> TYPE: PRT
<213> ORGANISM: Artificial Sequence
<220> FEATURE:
<223> OTHER INFORMATION: Synthetic peptide

<400> SEQUENCE: 46

Arg Arg Tyr Leu Asn
1               5

<210> SEQ ID NO 47
<211> LENGTH: 5
<212> TYPE: PRT
<213> ORGANISM: Artificial Sequence
<220> FEATURE:
<223> OTHER INFORMATION: Synthetic peptide

<400> SEQUENCE: 47

Ile Lys His Leu Lys
1               5

<210> SEQ ID NO 48
<211> LENGTH: 5
<212> TYPE: PRT
<213> ORGANISM: Artificial Sequence
<220> FEATURE:
<223> OTHER INFORMATION: Synthetic peptide

<400> SEQUENCE: 48

Tyr Lys His Leu Lys
1               5
```

```
<210> SEQ ID NO 49
<211> LENGTH: 7
<212> TYPE: PRT
<213> ORGANISM: Artificial Sequence
<220> FEATURE:
<223> OTHER INFORMATION: Synthetic peptide
<220> FEATURE:
<221> NAME/KEY: VARIANT
<222> LOCATION: 1, 4
<223> OTHER INFORMATION: Xaa = Any Amino Acid

<400> SEQUENCE: 49

Xaa Ala Ser Xaa Leu Gln Ser
 1               5

<210> SEQ ID NO 50
<211> LENGTH: 7
<212> TYPE: PRT
<213> ORGANISM: Artificial Sequence
<220> FEATURE:
<223> OTHER INFORMATION: Synthetic peptide

<400> SEQUENCE: 50

Arg Ala Ser Pro Leu Gln Ser
 1               5

<210> SEQ ID NO 51
<211> LENGTH: 7
<212> TYPE: PRT
<213> ORGANISM: Artificial Sequence
<220> FEATURE:
<223> OTHER INFORMATION: Synthetic peptide

<400> SEQUENCE: 51

Asn Ala Ser Tyr Leu Gln Ser
 1               5

<210> SEQ ID NO 52
<211> LENGTH: 7
<212> TYPE: PRT
<213> ORGANISM: Artificial Sequence
<220> FEATURE:
<223> OTHER INFORMATION: Synthetic peptide

<400> SEQUENCE: 52

Lys Ala Ser Thr Leu Gln Ser
 1               5

<210> SEQ ID NO 53
<211> LENGTH: 7
<212> TYPE: PRT
<213> ORGANISM: Artificial Sequence
<220> FEATURE:
<223> OTHER INFORMATION: Synthetic peptide

<400> SEQUENCE: 53

Gln Ala Ser Val Leu Gln Ser
 1               5

<210> SEQ ID NO 54
<211> LENGTH: 7
<212> TYPE: PRT
<213> ORGANISM: Artificial Sequence
<220> FEATURE:
<223> OTHER INFORMATION: Synthetic peptide

<400> SEQUENCE: 54
```

Arg Ala Ser Ser Leu Gln Ser
1               5

<210> SEQ ID NO 55
<211> LENGTH: 7
<212> TYPE: PRT
<213> ORGANISM: Artificial Sequence
<220> FEATURE:
<223> OTHER INFORMATION: Synthetic peptide

<400> SEQUENCE: 55

His Ala Ser Leu Leu Gln Ser
1               5

<210> SEQ ID NO 56
<211> LENGTH: 7
<212> TYPE: PRT
<213> ORGANISM: Artificial Sequence
<220> FEATURE:
<223> OTHER INFORMATION: Synthetic peptide

<400> SEQUENCE: 56

His Ala Ser His Leu Gln Ser
1               5

<210> SEQ ID NO 57
<211> LENGTH: 7
<212> TYPE: PRT
<213> ORGANISM: Artificial Sequence
<220> FEATURE:
<223> OTHER INFORMATION: Synthetic peptide

<400> SEQUENCE: 57

Pro Ala Ser Lys Leu Gln Ser
1               5

<210> SEQ ID NO 58
<211> LENGTH: 7
<212> TYPE: PRT
<213> ORGANISM: Artificial Sequence
<220> FEATURE:
<223> OTHER INFORMATION: Synthetic peptide

<400> SEQUENCE: 58

Arg Ala Ser Arg Leu Gln Ser
1               5

<210> SEQ ID NO 59
<211> LENGTH: 7
<212> TYPE: PRT
<213> ORGANISM: Artificial Sequence
<220> FEATURE:
<223> OTHER INFORMATION: Synthetic peptide

<400> SEQUENCE: 59

Lys Ala Ser Ser Leu Gln Ser
1               5

<210> SEQ ID NO 60
<211> LENGTH: 7
<212> TYPE: PRT
<213> ORGANISM: Artificial Sequence
<220> FEATURE:
<223> OTHER INFORMATION: Synthetic peptide

<400> SEQUENCE: 60

Asn Ala Ser His Leu Gln Ser
1               5

<210> SEQ ID NO 61
<211> LENGTH: 7
<212> TYPE: PRT
<213> ORGANISM: Artificial Sequence
<220> FEATURE:
<223> OTHER INFORMATION: Synthetic peptide

<400> SEQUENCE: 61

Lys Ala Ser Trp Leu Gln Ser
1               5

<210> SEQ ID NO 62
<211> LENGTH: 7
<212> TYPE: PRT
<213> ORGANISM: Artificial Sequence
<220> FEATURE:
<223> OTHER INFORMATION: Synthetic peptide

<400> SEQUENCE: 62

Ala Ala Ser Arg Leu Gln Ser
1               5

<210> SEQ ID NO 63
<211> LENGTH: 7
<212> TYPE: PRT
<213> ORGANISM: Artificial Sequence
<220> FEATURE:
<223> OTHER INFORMATION: Synthetic peptide

<400> SEQUENCE: 63

Thr Ala Ser Ser Leu Gln Ser
1               5

<210> SEQ ID NO 64
<211> LENGTH: 7
<212> TYPE: PRT
<213> ORGANISM: Artificial Sequence
<220> FEATURE:
<223> OTHER INFORMATION: Synthetic peptide

<400> SEQUENCE: 64

Ala Ala Ser Ser Leu Gln Ser
1               5

<210> SEQ ID NO 65
<211> LENGTH: 7
<212> TYPE: PRT
<213> ORGANISM: Artificial Sequence
<220> FEATURE:
<223> OTHER INFORMATION: Synthetic peptide

<400> SEQUENCE: 65

Gly Ala Ser Arg Leu Gln Ser
1               5

<210> SEQ ID NO 66
<211> LENGTH: 9
<212> TYPE: PRT
<213> ORGANISM: Artificial Sequence
<220> FEATURE:
<223> OTHER INFORMATION: Synthetic peptide
<220> FEATURE:
<221> NAME/KEY: VARIANT
<222> LOCATION: 3, 4, 5, 6, 8
<223> OTHER INFORMATION: Xaa = Any Amino Acid

```
<400> SEQUENCE: 66

Gln Gln Xaa Xaa Xaa Xaa Pro Xaa Thr
 1               5

<210> SEQ ID NO 67
<211> LENGTH: 9
<212> TYPE: PRT
<213> ORGANISM: Artificial Sequence
<220> FEATURE:
<223> OTHER INFORMATION: Synthetic peptide

<400> SEQUENCE: 67

Gln Gln Thr Tyr Ser Val Pro Pro Thr
 1               5

<210> SEQ ID NO 68
<211> LENGTH: 9
<212> TYPE: PRT
<213> ORGANISM: Artificial Sequence
<220> FEATURE:
<223> OTHER INFORMATION: Synthetic peptide

<400> SEQUENCE: 68

Gln Gln Thr Tyr Arg Ile Pro Pro Thr
 1               5

<210> SEQ ID NO 69
<211> LENGTH: 9
<212> TYPE: PRT
<213> ORGANISM: Artificial Sequence
<220> FEATURE:
<223> OTHER INFORMATION: Synthetic peptide

<400> SEQUENCE: 69

Gln Gln Val Val Tyr Trp Pro Val Thr
 1               5

<210> SEQ ID NO 70
<211> LENGTH: 9
<212> TYPE: PRT
<213> ORGANISM: Artificial Sequence
<220> FEATURE:
<223> OTHER INFORMATION: Synthetic peptide

<400> SEQUENCE: 70

Gln Gln Val Arg Lys Val Pro Arg Thr
 1               5

<210> SEQ ID NO 71
<211> LENGTH: 9
<212> TYPE: PRT
<213> ORGANISM: Artificial Sequence
<220> FEATURE:
<223> OTHER INFORMATION: Synthetic peptide

<400> SEQUENCE: 71

Gln Gln Gly Leu Tyr Pro Pro Ile Thr
 1               5

<210> SEQ ID NO 72
<211> LENGTH: 9
<212> TYPE: PRT
<213> ORGANISM: Artificial Sequence
<220> FEATURE:
<223> OTHER INFORMATION: Synthetic peptide
```

<400> SEQUENCE: 72

Gln Gln Asn Val Val Ile Pro Arg Thr
1               5

<210> SEQ ID NO 73
<211> LENGTH: 9
<212> TYPE: PRT
<213> ORGANISM: Artificial Sequence
<220> FEATURE:
<223> OTHER INFORMATION: Synthetic peptide

<400> SEQUENCE: 73

Gln Gln Ser Ala Val Tyr Pro Lys Thr
1               5

<210> SEQ ID NO 74
<211> LENGTH: 9
<212> TYPE: PRT
<213> ORGANISM: Artificial Sequence
<220> FEATURE:
<223> OTHER INFORMATION: Synthetic peptide

<400> SEQUENCE: 74

Gln Gln Arg Leu Leu Tyr Pro Lys Thr
1               5

<210> SEQ ID NO 75
<211> LENGTH: 9
<212> TYPE: PRT
<213> ORGANISM: Artificial Sequence
<220> FEATURE:
<223> OTHER INFORMATION: Synthetic peptide

<400> SEQUENCE: 75

Gln Gln Arg Ala Arg Trp Pro Arg Thr
1               5

<210> SEQ ID NO 76
<211> LENGTH: 9
<212> TYPE: PRT
<213> ORGANISM: Artificial Sequence
<220> FEATURE:
<223> OTHER INFORMATION: Synthetic peptide

<400> SEQUENCE: 76

Gln Gln Val Ala Arg Val Pro Arg Thr
1               5

<210> SEQ ID NO 77
<211> LENGTH: 9
<212> TYPE: PRT
<213> ORGANISM: Artificial Sequence
<220> FEATURE:
<223> OTHER INFORMATION: Synthetic peptide

<400> SEQUENCE: 77

Gln Gln Tyr Val Gly Tyr Pro Arg Thr
1               5

<210> SEQ ID NO 78
<211> LENGTH: 9
<212> TYPE: PRT
<213> ORGANISM: Artificial Sequence
<220> FEATURE:
<223> OTHER INFORMATION: Synthetic peptide

<400> SEQUENCE: 78

Gln Gln Thr Thr Tyr Tyr Pro Ile Thr
1               5

<210> SEQ ID NO 79
<211> LENGTH: 9
<212> TYPE: PRT
<213> ORGANISM: Artificial Sequence
<220> FEATURE:
<223> OTHER INFORMATION: Synthetic peptide

<400> SEQUENCE: 79

Gln Gln Val Leu Tyr Tyr Pro Gln Thr
1               5

<210> SEQ ID NO 80
<211> LENGTH: 9
<212> TYPE: PRT
<213> ORGANISM: Artificial Sequence
<220> FEATURE:
<223> OTHER INFORMATION: Synthetic peptide

<400> SEQUENCE: 80

Gln Gln Val Val Tyr Trp Pro Ala Thr
1               5

<210> SEQ ID NO 81
<211> LENGTH: 9
<212> TYPE: PRT
<213> ORGANISM: Artificial Sequence
<220> FEATURE:
<223> OTHER INFORMATION: Synthetic peptide

<400> SEQUENCE: 81

Gln Gln Val Ala Leu Tyr Pro Lys Thr
1               5

<210> SEQ ID NO 82
<211> LENGTH: 9
<212> TYPE: PRT
<213> ORGANISM: Artificial Sequence
<220> FEATURE:
<223> OTHER INFORMATION: Synthetic peptide

<400> SEQUENCE: 82

Gln Gln Asn Leu Phe Trp Pro Arg Thr
1               5

<210> SEQ ID NO 83
<211> LENGTH: 9
<212> TYPE: PRT
<213> ORGANISM: Artificial Sequence
<220> FEATURE:
<223> OTHER INFORMATION: Synthetic peptide

<400> SEQUENCE: 83

Gln Gln Met Leu Phe Tyr Pro Lys Thr
1               5

<210> SEQ ID NO 84
<211> LENGTH: 9
<212> TYPE: PRT
<213> ORGANISM: Artificial Sequence
<220> FEATURE:
<223> OTHER INFORMATION: Synthetic peptide

<400> SEQUENCE: 84

Gln Gln Gly Ala Arg Trp Pro Gln Thr
1               5

<210> SEQ ID NO 85
<211> LENGTH: 9
<212> TYPE: PRT
<213> ORGANISM: Artificial Sequence
<220> FEATURE:
<223> OTHER INFORMATION: Synthetic peptide

<400> SEQUENCE: 85

Gln Gln Val Gly Arg Tyr Pro Lys Thr
1               5

<210> SEQ ID NO 86
<211> LENGTH: 6
<212> TYPE: PRT
<213> ORGANISM: Artificial Sequence
<220> FEATURE:
<223> OTHER INFORMATION: Synthetic peptide

<400> SEQUENCE: 86

Trp Val Tyr Gln Met Asp
1               5

<210> SEQ ID NO 87
<211> LENGTH: 6
<212> TYPE: PRT
<213> ORGANISM: Artificial Sequence
<220> FEATURE:
<223> OTHER INFORMATION: Synthetic peptide

<400> SEQUENCE: 87

Trp Ser Tyr Gln Met Thr
1               5

<210> SEQ ID NO 88
<211> LENGTH: 17
<212> TYPE: PRT
<213> ORGANISM: Artificial Sequence
<220> FEATURE:
<223> OTHER INFORMATION: Synthetic peptide
<220> FEATURE:
<221> NAME/KEY: VARIANT
<222> LOCATION: 1, 3, 4, 5, 7, 8, 10
<223> OTHER INFORMATION: Xaa = Any Amino Acid

<400> SEQUENCE: 88

Xaa Ile Xaa Xaa Xaa Gly Xaa Xaa Thr Xaa Tyr Ala Asp Ser Val Lys
1               5                   10                  15

Gly

<210> SEQ ID NO 89
<211> LENGTH: 17
<212> TYPE: PRT
<213> ORGANISM: Artificial Sequence
<220> FEATURE:
<223> OTHER INFORMATION: Synthetic peptide

<400> SEQUENCE: 89

Ser Ile Ser Ala Phe Gly Ala Lys Thr Leu Tyr Ala Asp Ser Val Lys
1               5                   10                  15

Gly

<210> SEQ ID NO 90
<211> LENGTH: 17

```
<212> TYPE: PRT
<213> ORGANISM: Artificial Sequence
<220> FEATURE:
<223> OTHER INFORMATION: Synthetic peptide

<400> SEQUENCE: 90

Ser Ile Ser Ser Phe Gly Ser Ser Thr Leu Tyr Ala Asp Ser Val Lys
1               5                   10                  15

Gly

<210> SEQ ID NO 91
<211> LENGTH: 7
<212> TYPE: PRT
<213> ORGANISM: Artificial Sequence
<220> FEATURE:
<223> OTHER INFORMATION: Synthetic peptide

<400> SEQUENCE: 91

Leu Ser Gly Lys Phe Asp Tyr
1               5

<210> SEQ ID NO 92
<211> LENGTH: 11
<212> TYPE: PRT
<213> ORGANISM: Artificial Sequence
<220> FEATURE:
<223> OTHER INFORMATION: Synthetic peptide

<400> SEQUENCE: 92

Gly Arg Asp His Asn Tyr Ser Leu Phe Asp Tyr
1               5                   10

<210> SEQ ID NO 93
<211> LENGTH: 27
<212> TYPE: DNA
<213> ORGANISM: Artificial Sequence
<220> FEATURE:
<223> OTHER INFORMATION: Synthetic oligonucleotide

<400> SEQUENCE: 93
tatccttatg atgttcctga ttatgca                                         27

<210> SEQ ID NO 94
<211> LENGTH: 9
<212> TYPE: PRT
<213> ORGANISM: Artificial Sequence
<220> FEATURE:
<223> OTHER INFORMATION: Synthetic peptide

<400> SEQUENCE: 94

Tyr Pro Tyr Asp Val Pro Asp Tyr Ala
1               5

<210> SEQ ID NO 95
<211> LENGTH: 11
<212> TYPE: PRT
<213> ORGANISM: Artificial Sequence
<220> FEATURE:
<223> OTHER INFORMATION: Synthetic peptide

<400> SEQUENCE: 95

Arg Ala Ser Gln Trp Ile Gly Ser Gln Leu Ser
1               5                   10

<210> SEQ ID NO 96
<211> LENGTH: 7
```

```
<212> TYPE: PRT
<213> ORGANISM: Artificial Sequence
<220> FEATURE:
<223> OTHER INFORMATION: Synthetic peptide

<400> SEQUENCE: 96

Trp Arg Ser Ser Leu Gln Ser
1               5

<210> SEQ ID NO 97
<211> LENGTH: 9
<212> TYPE: PRT
<213> ORGANISM: Artificial Sequence
<220> FEATURE:
<223> OTHER INFORMATION: Synthetic peptide

<400> SEQUENCE: 97

Ala Gln Gly Ala Ala Leu Pro Arg Thr
1               5

<210> SEQ ID NO 98
<211> LENGTH: 7
<212> TYPE: PRT
<213> ORGANISM: Homo sapiens

<400> SEQUENCE: 98

Ser Pro Gly Lys Ala Thr Glu
1               5

<210> SEQ ID NO 99
<211> LENGTH: 9
<212> TYPE: PRT
<213> ORGANISM: Homo sapiens

<400> SEQUENCE: 99

Tyr Met Met Gly Asn Glu Leu Thr Phe
1               5

<210> SEQ ID NO 100
<211> LENGTH: 9
<212> TYPE: PRT
<213> ORGANISM: Homo sapiens

<400> SEQUENCE: 100

Leu Met Tyr Pro Pro Tyr Tyr Leu
1               5

<210> SEQ ID NO 101
<211> LENGTH: 6
<212> TYPE: PRT
<213> ORGANISM: Homo sapiens

<400> SEQUENCE: 101

Met Tyr Pro Pro Pro Tyr
1               5

<210> SEQ ID NO 102
<211> LENGTH: 4
<212> TYPE: PRT
<213> ORGANISM: unknown
<220> FEATURE:
<223> OTHER INFORMATION: Peptide

<400> SEQUENCE: 102

Tyr Trp Thr Asp
1
```

<210> SEQ ID NO 103
<211> LENGTH: 360
<212> TYPE: DNA
<213> ORGANISM: Homo sapiens

<400> SEQUENCE: 103
gaggtgcagc tgttggagtc tgggggaggc ttggtacagc ctgggggtc cctgcgtctc      60 tcctgtgcag cctccggatt taggattagc gatgaggata tgggctgggt ccgccaggct     120
ccagggaagg gtctagagtg ggtatcaagc atttatggcc tagcggtag cacatactac     180 gcagactccg tgaagggccg gttcaccatc tcccgtgaca attccaagaa cacgctgtat     240
ctgcaaatga acagcctgcg tgccgaggac accgcggtat attattgcgc gagtgctttg     300
gagccgcttt cggagcccct gggctttgg ggtcaggaa ccctggtcac cgtctcgagc      360

<210> SEQ ID NO 104
<211> LENGTH: 120
<212> TYPE: PRT
<213> ORGANISM: Homo sapiens

<400> SEQUENCE: 104

Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Arg Ile Ser Asp Glu
            20                  25                  30

Asp Met Gly Trp Val Arg Gln Ala Pro Gly Lys Gly Leu Glu Trp Val
        35                  40                  45

Ser Ser Ile Tyr Gly Pro Ser Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Ser Ala Leu Glu Pro Leu Ser Glu Pro Leu Gly Phe Trp Gly Gln
            100                 105                 110

Gly Thr Leu Val Thr Val Ser Ser
        115                 120

<210> SEQ ID NO 105
<211> LENGTH: 348
<212> TYPE: DNA
<213> ORGANISM: Homo sapiens

<400> SEQUENCE: 105
gaggtgcagc tgttggagtc tgggggaggc ttggtacagc ctgggggtc cctgcgtctc      60 tcctgtgcag cctccggatt cacctttgat ctttataata tgttttgggt ccgccaggct    120
ccagggaagg gtctagagtg ggtctcattt attagtcaga ctggtaggct acatggtac     180 gcagactccg tgaagggccg gttcaccatc tcccgcgaca attccaagaa cacgctgtat    240
ctgcaaatga acagcctgcg tgccgaggac accgcggtat attactgtgc gaaacgctg    300 gaggattttg actactgggg ccagggaacc ctggtcaccg tctcgagc                 348

<210> SEQ ID NO 106
<211> LENGTH: 116
<212> TYPE: PRT
<213> ORGANISM: Homo sapiens
<220> FEATURE:

<223> OTHER INFORMATION: Peptide

<400> SEQUENCE: 106

| Glu | Val | Gln | Leu | Leu | Glu | Ser | Gly | Gly | Gly | Leu | Val | Gln | Pro | Gly | Gly |
|---|---|---|---|---|---|---|---|---|---|---|---|---|---|---|---|
| 1 | | | | 5 | | | | | 10 | | | | | 15 | |

| Ser | Leu | Arg | Leu | Ser | Cys | Ala | Ala | Ser | Gly | Phe | Thr | Phe | Asp | Leu | Tyr |
|---|---|---|---|---|---|---|---|---|---|---|---|---|---|---|---|
| | | | 20 | | | | | 25 | | | | | 30 | | |

| Asn | Met | Phe | Trp | Val | Arg | Gln | Ala | Pro | Gly | Lys | Gly | Leu | Glu | Trp | Val |
|---|---|---|---|---|---|---|---|---|---|---|---|---|---|---|---|
| | | 35 | | | | | 40 | | | | | 45 | | | |

| Ser | Phe | Ile | Ser | Gln | Thr | Gly | Arg | Leu | Thr | Trp | Tyr | Ala | Asp | Ser | Val |
|---|---|---|---|---|---|---|---|---|---|---|---|---|---|---|---|
| | 50 | | | | | 55 | | | | | 60 | | | | |

| Lys | Gly | Arg | Phe | Thr | Ile | Ser | Arg | Asp | Asn | Ser | Lys | Asn | Thr | Leu | Tyr |
|---|---|---|---|---|---|---|---|---|---|---|---|---|---|---|---|
| 65 | | | | | 70 | | | | | 75 | | | | | 80 |

| Leu | Gln | Met | Asn | Ser | Leu | Arg | Ala | Glu | Asp | Thr | Ala | Val | Tyr | Tyr | Cys |
|---|---|---|---|---|---|---|---|---|---|---|---|---|---|---|---|
| | | | | 85 | | | | | 90 | | | | | 95 | |

| Ala | Lys | Thr | Leu | Glu | Asp | Phe | Asp | Tyr | Trp | Gly | Gln | Gly | Thr | Leu | Val |
|---|---|---|---|---|---|---|---|---|---|---|---|---|---|---|---|
| | | | 100 | | | | | 105 | | | | | 110 | | |

| Thr | Val | Ser | Ser |
|---|---|---|---|
| | | | 115 |

<210> SEQ ID NO 107
<211> LENGTH: 324
<212> TYPE: DNA
<213> ORGANISM: Homo sapiens

<400> SEQUENCE: 107

```
gacatccaga tgacccagtc tccatcctcc ctgtctgcat ctgtaggaga ccgtgtcacc      60
atcacttgcc gggcaagtca gagcgttaag gagtttttat ggtggtacca gcagaaacca     120
gggaaagccc ctaagctcct gatctatatg catccaatt tgcaaagtgg ggtcccatca      180
cgtttcagtg gcagtggatc tgggacagat ttcactctca ccatcagcag tctgcaacct     240
gaagattttg ctacgtacta ctgtcaacag aagtttaagc tgcctcgtac gttcggccaa     300
gggaccaagg tggaaatcaa acgg                                             324
```

<210> SEQ ID NO 108
<211> LENGTH: 108
<212> TYPE: PRT
<213> ORGANISM: Homo sapiens

<400> SEQUENCE: 108

| Asp | Ile | Gln | Met | Thr | Gln | Ser | Pro | Ser | Ser | Leu | Ser | Ala | Ser | Val | Gly |
|---|---|---|---|---|---|---|---|---|---|---|---|---|---|---|---|
| 1 | | | | 5 | | | | | 10 | | | | | 15 | |

| Asp | Arg | Val | Thr | Ile | Thr | Cys | Arg | Ala | Ser | Gln | Ser | Val | Lys | Glu | Phe |
|---|---|---|---|---|---|---|---|---|---|---|---|---|---|---|---|
| | | | 20 | | | | | 25 | | | | | 30 | | |

| Leu | Trp | Trp | Tyr | Gln | Gln | Lys | Pro | Gly | Lys | Ala | Pro | Lys | Leu | Leu | Ile |
|---|---|---|---|---|---|---|---|---|---|---|---|---|---|---|---|
| | | 35 | | | | | 40 | | | | | 45 | | | |

| Tyr | Met | Ala | Ser | Asn | Leu | Gln | Ser | Gly | Val | Pro | Ser | Arg | Phe | Ser | Gly |
|---|---|---|---|---|---|---|---|---|---|---|---|---|---|---|---|
| | 50 | | | | | 55 | | | | | 60 | | | | |

| Ser | Gly | Ser | Gly | Thr | Asp | Phe | Thr | Leu | Thr | Ile | Ser | Ser | Leu | Gln | Pro |
|---|---|---|---|---|---|---|---|---|---|---|---|---|---|---|---|
| 65 | | | | | 70 | | | | | 75 | | | | | 80 |

| Glu | Asp | Phe | Ala | Thr | Tyr | Tyr | Cys | Gln | Gln | Lys | Phe | Lys | Leu | Pro | Arg |
|---|---|---|---|---|---|---|---|---|---|---|---|---|---|---|---|
| | | | | 85 | | | | | 90 | | | | | 95 | |

| Thr | Phe | Gly | Gln | Gly | Thr | Lys | Val | Glu | Ile | Lys | Arg |
|---|---|---|---|---|---|---|---|---|---|---|---|
| | | | 100 | | | | | 105 | | | |

<210> SEQ ID NO 109

-continued

<211> LENGTH: 362
<212> TYPE: DNA
<213> ORGANISM: Homo sapiens

<400> SEQUENCE: 109

```
gaggtgcagc tgttggagtc tgggggaggc ttggtacagc ctgggggtc  cctgcgtctc    60
tcctgtgcag cctccggatt cacctttgag tggtattgga tgggttgggt ccgccaggct   120
ccagggaagg gtctagagtg ggtctcagct attagtggta gtggtggtag cacatactac   180
gcagactccg tgaagggccg gttcaccatc tcccgcgaca attccaagaa cacgctgtat   240
ctgcaaatga acagcctgcg tgccgaggac accgcggtat attactgtgc gaaagttaag   300
ttgggggggg ggcctaattt tgactactgg ggccaggaa  ccctggtcac cgtctcgagc   360
gc                                                                  362
```

<210> SEQ ID NO 110
<211> LENGTH: 120
<212> TYPE: PRT
<213> ORGANISM: Homo sapiens

<400> SEQUENCE: 110

Glu Val Gln Leu Leu Glu Ser Gly Gly Gly Leu Val Gln Pro Gly Gly
1               5                   10                  15
Ser Leu Arg Leu Ser Cys Ala Ala Ser Gly Phe Thr Phe Glu Trp Tyr
            20                  25                  30
Trp Met Gly Trp Val Arg Gln Ala Pro Gly Lys Gly Leu Glu Trp Val
        35                  40                  45
Ser Ala Ile Ser Gly Ser Gly Gly Ser Thr Tyr Tyr Ala Asp Ser Val
    50                  55                  60
Lys Gly Arg Phe Thr Ile Ser Arg Asp Asn Ser Lys Asn Thr Leu Tyr
65                  70                  75                  80
Leu Gln Met Asn Ser Leu Arg Ala Glu Asp Thr Ala Val Tyr Tyr Cys
                85                  90                  95
Ala Lys Val Lys Leu Gly Gly Gly Pro Asn Phe Asp Tyr Trp Gly Gln
            100                 105                 110
Gly Thr Leu Val Thr Val Ser Ser
        115                 120

<210> SEQ ID NO 111
<211> LENGTH: 360
<212> TYPE: DNA
<213> ORGANISM: Homo sapiens

<400> SEQUENCE: 111

```
gaggtgcagc tgttggagtc tgggggaggc ttggtacagc ctgggggtc  cctgcgtctc    60
tcctgtgcag cctccggatt cacctttgag tggtattgga tgggttgggt ccgccaggct   120
ccagggaagg gtctagagtg ggtctcagct attagtggta gtggtggtag cacatactac   180
gcagactccg tgaagggccg gttcaccatc tcccgcgaca attccaagaa cacgctgtat   240
ctgcaaatga acagcctgcg tgccgaggac accgcggtat attactgtgc gaaagttaag   300
ttgggggggg ggcctaattt tgactactgg ggccaggaa  ccctggtcac cgtctcgagc   360
```

<210> SEQ ID NO 112
<211> LENGTH: 324
<212> TYPE: DNA
<213> ORGANISM: Homo sapiens

<400> SEQUENCE: 112

```
gacatccaga tgacccagtc tccatcctct ctgtctgcat ctgtaggaga ccgtgtcacc    60
atcacttgcc gggcaagtca gagcattgat agttatttac attggtacca gcagaaacca   120
gggaaagccc ctaagctcct gatctatagt gcatccgagt tgcaaagtgg ggtcccatca   180
cgtttcagtg gcagtggatc tgggacagat ttcactctca ccatcagcag tctgcaacct   240
gaagattttg ctacgtacta ctgtcaacag gttgtgtggc gtcctttac gttcggccaa    300 gggaccaagg tggaaatcaa acgc                                          324
```

<210> SEQ ID NO 113
<211> LENGTH: 108
<212> TYPE: PRT
<213> ORGANISM: Homo sapiens

<400> SEQUENCE: 113

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Asp Ser Tyr
            20                  25                  30

Leu His Trp Tyr Gln Gln Lys Pro Gly Lys Ala Pro Lys Leu Leu Ile
        35                  40                  45

Tyr Ser Ala Ser Glu Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Val Val Trp Arg Pro Phe
                85                  90                  95

Thr Phe Gly Gln Gly Thr Lys Val Glu Ile Lys Arg
            100                 105

<210> SEQ ID NO 114
<211> LENGTH: 324
<212> TYPE: DNA
<213> ORGANISM: Homo sapiens

<400> SEQUENCE: 114

```
gacatccaga tgacccagtc tccatcctcc ctgtctgcat ctgtaggaga ccgtgtcacc    60
atcacttgcc gggcaagtca gagcattttt atgaatttat tgtggtacca gcagaaacca   120
gggaaagccc ctaagctcct gatctataat gcatccgtgt tgcaaagtgg ggtcccatca   180
cgtttcagtg gcagtggatc tgggacagat ttcactctca ccatcagcag tctgcaacct   240
gaagattttg ctacgtacta ctgtcaacag gttgtgtggc gtcctttac gttcggccaa    300 gggaccaagg tggaaatcaa acgg                                          324
```

<210> SEQ ID NO 115
<211> LENGTH: 108
<212> TYPE: PRT
<213> ORGANISM: Homo sapiens

<400> SEQUENCE: 115

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Phe Met Asn
            20                  25                  30

Leu Leu Trp Tyr Gln Gln Lys Pro Gly Lys Ala Pro Lys Leu Leu Ile
        35                  40                  45

```
Tyr Asn Ala Ser Val Leu Gln Ser Gly Val Pro Ser Arg Phe Ser Gly
 50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Val Val Trp Arg Pro Phe
                 85                  90                  95

Thr Phe Gly Gln Gly Thr Lys Val Glu Ile Lys Arg
            100                 105
```

<210> SEQ ID NO 116
<211> LENGTH: 324
<212> TYPE: DNA
<213> ORGANISM: Homo sapiens

<400> SEQUENCE: 116

```
gacatccaga tgacccagtc tccatcctcc ctgtctgcat ctgtaggaga ccgtgtcacc     60
atcacttgcc gggcaagtca gagcatttat gatgcgttag agtggtacca gcagaaacca   120
gggaaagccc ctaagctcct gatctatact gcatcccggt tgcaaagtgg ggtcccatca   180
cgtttcagtg gcagtggatc tgggacagat ttcactctca ccatcagcag tctgcaacct   240
gaagattttg ctacgtacta ctgtcaacag gttatgcagc gtcctgttac gttcggccaa   300
gggaccaagg tggaaatcaa acgg                                          324
```

<210> SEQ ID NO 117
<211> LENGTH: 108
<212> TYPE: PRT
<213> ORGANISM: Homo sapiens

<400> SEQUENCE: 117

```
Asp Ile Gln Met Thr Gln Ser Pro Ser Ser Leu Ser Ala Ser Val Gly
  1               5                  10                  15

Asp Arg Val Thr Ile Thr Cys Arg Ala Ser Gln Ser Ile Tyr Asp Ala
                 20                  25                  30

Leu Glu Trp Tyr Gln Gln Lys Pro Gly Lys Ala Pro Lys Leu Leu Ile
             35                  40                  45

Tyr Thr Ala Ser Arg Leu Gln Ser Gly Val Pro Ser Arg Phe Ser Gly
 50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Val Met Gln Arg Pro Val
                 85                  90                  95

Thr Phe Gly Gln Gly Thr Lys Val Glu Ile Lys Arg
            100                 105
```

<210> SEQ ID NO 118
<211> LENGTH: 324
<212> TYPE: DNA
<213> ORGANISM: Homo sapiens

<400> SEQUENCE: 118

```
gacatccaga tgacccagtc tccatcctcc ctgtctgcat ctgtaggaga ccgtgtcacc     60
atcacttgcc gggcaagtca gagcatttat gatgctttac agtggtacca gcagaaacca   120
gggaaagccc ctaagctcct gatctatact gcatcccggt tgcaaagtgg ggtcccatca   180
cgtttcagtg gcagtggatc tgggacagat ttcactctca ccatcagcag tctgcaacct   240
gaagattttg ctacgtacca ctgtcaacag gttatgcagc gtcctgttac gttcggccaa   300
```

```
gggaccaagg tggaaatcaa acgg                                              324
```

<210> SEQ ID NO 119
<211> LENGTH: 108
<212> TYPE: PRT
<213> ORGANISM: Homo sapiens

<400> SEQUENCE: 119

Asp Ile Gln Met Thr Gln Ser Pro Ser Ser Leu Ser Ala Ser Val Gly
 1               5                   10                  15

Asp Arg Val Thr Ile Thr Cys Arg Ala Ser Gln Ser Ile Tyr Asp Ala
                20                  25                  30

Leu Gln Trp Tyr Gln Gln Lys Pro Gly Lys Ala Pro Lys Leu Leu Ile
            35                  40                  45

Tyr Thr Ala Ser Arg Leu Gln Ser Gly Val Pro Ser Arg Phe Ser Gly
 50                  55                  60

Ser Gly Ser Gly Thr Asp Phe Thr Leu Thr Ile Ser Ser Leu Gln Pro
65                  70                  75                  80

Glu Asp Phe Ala Thr Tyr His Cys Gln Gln Val Met Gln Arg Pro Val
                85                  90                  95

Thr Phe Gly Gln Gly Thr Lys Val Glu Ile Lys Arg
            100                 105

<210> SEQ ID NO 120
<211> LENGTH: 324
<212> TYPE: DNA
<213> ORGANISM: Homo sapiens

<400> SEQUENCE: 120

```
gacatccaga tgacccagtc tccatcctcc ctgtctgcat ctgtaggaga ccgtgtcacc     60
atcacttgcc gggcaagtca gagcgttaag gagttttat ggtggtacca gcagaaacca    120
gggaaagccc ctaagctcct gatctatatg catccaatt tgcaaagtgg ggtcccatca    180
cgtttcagtg gcagtggatc tgggacagat ttcactctca ccatcagcag tctgcaacct    240
gaagattttg ctacgtacta ctgtcaacag aagtttaagc tgcctcgtac gttcggccaa    300
gggaccaagg tggaaatcaa acgg                                          324
```

<210> SEQ ID NO 121
<211> LENGTH: 108
<212> TYPE: PRT
<213> ORGANISM: Homo sapiens

<400> SEQUENCE: 121

Asp Ile Gln Met Thr Gln Ser Pro Ser Ser Leu Ser Ala Ser Val Gly
 1               5                   10                  15

Asp Arg Val Thr Ile Thr Cys Arg Ala Ser Gln Ser Val Lys Glu Phe
                20                  25                  30

Leu Trp Trp Tyr Gln Gln Lys Pro Gly Lys Ala Pro Lys Leu Leu Ile
            35                  40                  45

Tyr Met Ala Ser Asn Leu Gln Ser Gly Val Pro Ser Arg Phe Ser Gly
 50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Lys Phe Lys Leu Pro Arg
                85                  90                  95

Thr Phe Gly Gln Gly Thr Lys Val Glu Ile Lys Arg
            100                 105

<210> SEQ ID NO 122
<211> LENGTH: 324
<212> TYPE: DNA
<213> ORGANISM: Homo sapiens

<400> SEQUENCE: 122
gacatccaga tgacccagtc tccatcctcc ctgtctgcat ctgtaggaga ccgtgtcacc     60
atcacttgcc gggcaagtca gagcatttgg acgaagttac attggtacca gcagaaacca    120
gggaaagccc ctaagctcct gatctatatg catccagtt tgcaaagtgg ggtcccatca     180
cgtttcagtg gcagtggatc tgggacagat ttcactctca ccatcagcag tctgcaacct    240
gaagattttg ctacgtacta ctgtcaacag tggtttagta atcctagtac gttcggccaa    300
gggaccaagg tggaaatcaa acgc                                           324

<210> SEQ ID NO 123
<211> LENGTH: 108
<212> TYPE: PRT
<213> ORGANISM: Homo sapiens

<400> SEQUENCE: 123

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Trp Thr Lys
            20                  25                  30

Leu His Trp Tyr Gln Gln Lys Pro Gly Lys Ala Pro Lys Leu Leu Ile
        35                  40                  45

Tyr Met Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Trp Phe Ser Asn Pro Ser
                85                  90                  95

Thr Phe Gly Gln Gly Thr Lys Val Glu Ile Lys Arg
            100                 105

<210> SEQ ID NO 124
<211> LENGTH: 324
<212> TYPE: DNA
<213> ORGANISM: Homo sapiens

<400> SEQUENCE: 124
gacatccaga tgacccagtc tccatcctcc ctgtctgcat ctgtaggaga ccgtgtcacc     60
atcacttgcc gggcaagtca gagcatttag ccgattttat gttggtacca gcagaaacca    120
gggaaagccc ctaagctcct gatctatgct gcatccagtt tgcaaagtgg ggtcccatca    180
cgtttcagtg gcagtggatc tgggacagat ttcactctca ccatcagcag tctgcaacct    240
gaagattttg ctacgtacta ctgtcaacag attcagcata ttcctgtgac gttcggccaa    300
gggaccaagg tggaaatcaa acgg                                           324

<210> SEQ ID NO 125
<211> LENGTH: 108
<212> TYPE: PRT
<213> ORGANISM: Homo sapiens

<400> SEQUENCE: 125

Asp Ile Gln Met Thr Gln Ser Pro Ser Ser Leu Ser Ala Ser Val Gly

```
          1               5                   10                  15
Asp Arg Val Thr Ile Thr Cys Arg Ala Ser Gln Ser Ile Gln Pro Ile
                    20                  25                  30

Leu Cys Trp Tyr Gln Gln Lys Pro Gly Lys Ala Pro Lys Leu Leu Ile
                35                  40                  45

Tyr Ala Ala Ser Ser Leu Gln Ser Gly Val Pro Ser Arg Phe Ser Gly
            50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ile Gln His Ile Pro Val
                    85                  90                  95

Thr Phe Gly Gln Gly Thr Lys Val Glu Ile Lys Arg
                100                 105
```

<210> SEQ ID NO 126
<211> LENGTH: 324
<212> TYPE: DNA
<213> ORGANISM: Homo sapiens

<400> SEQUENCE: 126

```
gacatccaga tgacccagtc tccatcctcc ctgtctgcat ctgtaggaga ccgtgtcacc    60
atcacttgcc gggcaagtca gagcattggg taggatttac attggtacca gcagaaacca   120
gggaaagccc ctaagctcct gatctatacg gcatccctt tgcaaagtgg ggtcccatca    180
cgtttcagtg gcagtggatc tgggacagat ttcactctca ccatcagcag tctgcaacct   240
gaagattttg ctacgtacta ctgtcaacag cagagtgctt ttcctaatac gctcggccaa   300
gggaccaagg tggaaatcaa acgg                                          324
```

<210> SEQ ID NO 127
<211> LENGTH: 108
<212> TYPE: PRT
<213> ORGANISM: Homo sapiens

<400> SEQUENCE: 127

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Gly Gln Asp
                    20                  25                  30

Leu His Trp Tyr Gln Gln Lys Pro Gly Lys Ala Pro Lys Leu Leu Ile
                35                  40                  45

Tyr Thr Ala Ser Leu Leu Gln Ser Gly Val Pro Ser Arg Phe Ser Gly
            50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Gln Ser Ala Phe Pro Asn
                    85                  90                  95

Thr Leu Gly Gln Gly Thr Lys Val Glu Ile Lys Arg
                100                 105
```

<210> SEQ ID NO 128
<211> LENGTH: 324
<212> TYPE: DNA
<213> ORGANISM: Homo sapiens

<400> SEQUENCE: 128

```
gacatccaga tgacccagtc tccatcctcc ctgtctgcat ccgtaggaga ccgtgtcacc    60
```

```
atcacttgcc gggcaagtca gagcataacg aagaattttac tttggtacca gcagaaacca    120
gggaaagccc ctaagctcct gatctattag gcatcctctt tgcaaagtgg ggtcccatca    180
cgtttcagtg gcagtggatc tgggacagat ttcactctca ccatcagcag tctgcaacct    240
gaagattttg ctacgtacta ctgtcaacag cttcgtcata agcctccgac gttcggccaa    300
gggaccaagg tggaaatcaa acgg                                            324
```

<210> SEQ ID NO 129
<211> LENGTH: 108
<212> TYPE: PRT
<213> ORGANISM: Homo sapiens

<400> SEQUENCE: 129

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Thr Lys Asn
            20                  25                  30

Leu Leu Trp Tyr Gln Gln Lys Pro Gly Lys Ala Pro Lys Leu Leu Ile
        35                  40                  45

Tyr Gln Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Leu Arg His Lys Pro Pro
                85                  90                  95

Thr Phe Gly Gln Gly Thr Lys Val Glu Ile Lys Arg
            100                 105
```

<210> SEQ ID NO 130
<211> LENGTH: 324
<212> TYPE: DNA
<213> ORGANISM: Homo sapiens

<400> SEQUENCE: 130

```
gacatccaga tgacccagtc tccatcctcc ctgtctgcat ctgtaggaga ccgtgtcacc     60
atcacttgcc gggcaagtca gagcatttag aagtctgacc gtgtcaccat cacttgccgg    120
gcaagtcaga gcatttagaa gtcttatcat gcatccgatt tgcaaagtgg ggtcccatca    180
cgtttcagtg gcagtggatc tgggacagat ttcactctca ccatcagcag tctgcaacct    240
gaagattttg ctacgtacta ctgtcaacag atggttaata gtcctgttac gttcggccaa    300
gggaccaagg tggaaatcaa acgg                                            324
```

<210> SEQ ID NO 131
<211> LENGTH: 108
<212> TYPE: PRT
<213> ORGANISM: Homo sapiens

<400> SEQUENCE: 131

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Gln Lys Ser
            20                  25                  30

Leu Arg Trp Tyr Gln Gln Lys Pro Gly Lys Ala Pro Lys Leu Leu Ile
        35                  40                  45

Tyr His Ala Ser Asp Leu Gln Ser Gly Val Pro Ser Arg Phe Ser Gly
    50                  55                  60
```

```
Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Met Val Asn Ser Pro Val
                 85                  90                  95

Thr Phe Gly Gln Gly Thr Lys Val Glu Ile Lys Arg
            100                 105
```

<210> SEQ ID NO 132
<211> LENGTH: 324
<212> TYPE: DNA
<213> ORGANISM: Homo sapiens

<400> SEQUENCE: 132

```
gacatccaga tgacccagtc tccatcctcc ctgtctgcat ctgtaggaga ccgtgtcacc    60
atcacttgcc gggcaagtca gagcatttag acggcgttac attggtacca gcagaaacca   120
gggaaagccc ctaagctcct gatctattct gcatccagtt tgcaaagtgg ggtcccatca   180
cgtttcagtg gcagtggatc tgggacagat ttcactctca ccatcagcag tctgcaacct   240
gaagattttg ctacgtacta ctgtcaacag tcgagttttt tgccttttac gttcggccaa   300
gggaccaagg tggaaatcaa acgg                                          324
```

<210> SEQ ID NO 133
<211> LENGTH: 108
<212> TYPE: PRT
<213> ORGANISM: Homo sapiens

<400> SEQUENCE: 133

```
Asp Ile Gln Met Thr Gln Ser Pro Ser Ser Leu Ser Ala Ser Val Gly
  1               5                  10                  15

Asp Arg Val Thr Ile Thr Cys Arg Ala Ser Gln Ser Ile Gln Thr Ala
                 20                  25                  30

Leu His Trp Tyr Gln Gln Lys Pro Gly Lys Ala Pro Lys Leu Leu Ile
             35                  40                  45

Tyr Ser Ala Ser Ser Leu Gln Ser Gly Val Pro Ser Arg Phe Ser Gly
 50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Ser Ser Phe Leu Pro Phe
                 85                  90                  95

Thr Phe Gly Gln Gly Thr Lys Val Glu Ile Lys Arg
            100                 105
```

<210> SEQ ID NO 134
<211> LENGTH: 324
<212> TYPE: DNA
<213> ORGANISM: Homo sapiens

<400> SEQUENCE: 134

```
gacatccaga tgacccagtc tccatcctcc ctgtctgcat ctgtaggaga ccgtgtcacc    60
atcacttgcc gggcaagtca gagcattggg ccgaatttag agtggtacca gcagaaacca   120
gggaaagccc ctaagctcct gatctatgct gcatccagtt tgcaaagtgg ggtcccatca   180
cgtttcagtg gcagtggatc tgggacagat ttcactctca ccatcagcag tctgcaacct   240
gaagattttg ctacgtacta ctgtcaacag cagatggggc gtcctcggac gttcggccaa   300
gggaccaagg tggaaatcaa acgg                                          324
```

<210> SEQ ID NO 135
<211> LENGTH: 108
<212> TYPE: PRT
<213> ORGANISM: Homo sapiens

<400> SEQUENCE: 135

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Gly Pro Asn
            20                  25                  30

Leu Glu Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Met Gly Arg Pro Arg
                85                  90                  95

Thr Phe Gly Gln Gly Thr Lys Val Glu Ile Lys Arg
            100                 105

<210> SEQ ID NO 136
<211> LENGTH: 324
<212> TYPE: DNA
<213> ORGANISM: Homo sapiens

<400> SEQUENCE: 136
gacatccaga tgacccagtc tccatcctcc ctgtctgcat ctgtaggaga ccgtgtcacc      60
atcacttgcc gggcaagtca gagcattaag cattagttag cttggtacca gcagaaacca    120
gggaaagccc ctaagctcct gatctataag gcatccgtgt tgcaaagtgg ggtcccatca    180
cgtttcagtg gcagtggatc tgggacagat ttcactctca ccatcagcag tctgcaacct    240
gaagattttg ctacgtacta ctgtcaacag cttaggcgtc gtcctactac gttcggccaa    300
gggaccaagg tggaaatcaa acgg                                           324

<210> SEQ ID NO 137
<211> LENGTH: 108
<212> TYPE: PRT
<213> ORGANISM: Homo sapiens

<400> SEQUENCE: 137

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Lys His Gln
            20                  25                  30

Leu Ala Trp Tyr Gln Gln Lys Pro Gly Lys Ala Pro Lys Leu Leu Ile
        35                  40                  45

Tyr Lys Ala Ser Val Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Leu Arg Arg Arg Pro Thr
                85                  90                  95

Thr Phe Gly Gln Gly Thr Lys Val Glu Ile Lys Arg
            100                 105

<210> SEQ ID NO 138

<211> LENGTH: 324
<212> TYPE: DNA
<213> ORGANISM: Homo sapiens

<400> SEQUENCE: 138

```
gacatccaga tgacccagtc tccatcctcc ctgtctgcat ctgtaggaga ccgtgtcacc      60
atcacttgcc gggcaagtca gagcgttaag gcttagttaa cttggtacca gcagaaacca     120
gggaaagccc ctaagctcct gatctataag gcatccactt tgcaaagtgg ggtcccatca     180
cgtttcagtg gcagtggatc tgggacagat ttcactctca ccatcagcag tctgcaacct     240
gaagattttg ctacgtacta ctgtcaacag catagttcta ggccttatac gttcggccaa     300
gggaccaagg tggaaatcaa acgg                                            324
```

<210> SEQ ID NO 139
<211> LENGTH: 108
<212> TYPE: PRT
<213> ORGANISM: Homo sapiens

<400> SEQUENCE: 139

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Val Lys Ala Gln
            20                  25                  30

Leu Thr Trp Tyr Gln Lys Pro Gly Lys Ala Pro Lys Leu Leu Ile
        35                  40                  45

Tyr Lys Ala Ser Thr Leu Gln Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln His Ser Ser Arg Pro Tyr
                85                  90                  95

Thr Phe Gly Gln Gly Thr Lys Val Glu Ile Lys Arg
            100                 105
```

<210> SEQ ID NO 140
<211> LENGTH: 324
<212> TYPE: DNA
<213> ORGANISM: Homo sapiens

<400> SEQUENCE: 140

```
gacatccaga tgacccagtc tccatcctcc ctgtctgcat ctgtaggaga ccgtgtcacc      60
atcacttgcc gggcaagtca gagcattgag aatcggttag gttggtacca gcagaaacca     120
gggaaagccc ctaagctcct gatctattag gcgtccttgt tgcaaagtgg ggtcccatca     180
cgtttcagtg gcagtggatc tgggacagat ttcactctca ccatcagcag tctgcaacct     240
gaagattttg ctacgtacta ctgtcaacag gattcgtatt ttcctcgtac gttcggccaa     300
gggaccaagg tggaaatcaa acgg                                            324
```

<210> SEQ ID NO 141
<211> LENGTH: 108
<212> TYPE: PRT
<213> ORGANISM: Homo sapiens

<400> SEQUENCE: 141

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Glu Asn Arg
```

```
                20                  25                  30
Leu Gly Trp Tyr Gln Gln Lys Pro Gly Lys Ala Pro Lys Leu Leu Ile
            35                  40                  45

Tyr Gln Ala Ser Leu Leu Gln Ser Gly Val Pro Ser Arg Phe Ser Gly
        50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Asp Ser Tyr Phe Pro Arg
                85                  90                  95

Thr Phe Gly Gln Gly Thr Lys Val Glu Ile Lys Arg
            100                 105

<210> SEQ ID NO 142
<211> LENGTH: 324
<212> TYPE: DNA
<213> ORGANISM: Homo sapiens

<400> SEQUENCE: 142
gacatccaga tgacccagtc tccatcctcc ctgtctgcat ctgtaggaga ccgtgtcacc    60
atcacttgcc gggcaagtca gagcattatg gataagttaa agtggtacca gcagaaacca   120
gggaaagccc ctaagctcct gatctattag gcatccattt tgcaaagtgg ggtcccatca   180
cgtttcagtg gcagtggatc tgggacagat tcactctcac catcagcagt ctgcaacct   240 gaagattttg ctacgtacta ctgtcaacag gatagtgggg gtcctaatac gttcggccaa   300
gggaccaagg tggaaatcaa acgg                                          324

<210> SEQ ID NO 143
<211> LENGTH: 108
<212> TYPE: PRT
<213> ORGANISM: Homo sapiens

<400> SEQUENCE: 143

Asp Ile Gln Met Thr Gln Ser Pro Ser Ser Leu Ser Ala Ser Val Gly
 1               5                  10                  15

Asp Arg Val Thr Ile Thr Cys Arg Ala Ser Gln Ser Ile Met Asp Lys
            20                  25                  30

Leu Lys Trp Tyr Gln Gln Lys Pro Gly Lys Ala Pro Lys Leu Leu Ile
            35                  40                  45

Tyr Gln Ala Ser Ile Leu Gln Ser Gly Val Pro Ser Arg Phe Ser Gly
        50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Asp Ser Gly Gly Pro Asn
                85                  90                  95

Thr Phe Gly Gln Gly Thr Lys Val Glu Ile Lys Arg
            100                 105

<210> SEQ ID NO 144
<211> LENGTH: 324
<212> TYPE: DNA
<213> ORGANISM: Homo sapiens

<400> SEQUENCE: 144
gacatccaga tgacccagtc tccatcctcc ctgtctgcat ctgtaggaga ccgtgtcacc    60
atcacttgcc gggcaagtca gagcattggg aggaatttag agtggtacca gcagaaacca   120
gggaaagccc ctaagctcct gatctatgat gcatcccatt tgcaaagtgg ggtcccatca   180
```
cgtttcagtg gcagtggatc tgggacagat ttcactctca ccatcagcag tctgcaacct    240
gaagattttg ctacgtacta ctgtcaacag tcgcgttggc ttcctcgtac gttcggccaa    300
gggaccaagg tggaaatcaa acgg    324

<210> SEQ ID NO 145
<211> LENGTH: 108
<212> TYPE: PRT
<213> ORGANISM: Homo sapiens

<400> SEQUENCE: 145

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Gly Arg Asn
            20                  25                  30

Leu Glu Trp Tyr Gln Gln Lys Pro Gly Lys Ala Pro Lys Leu Leu Ile
        35                  40                  45

Tyr Asp Ala Ser His Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Arg Trp Leu Pro Arg
                85                  90                  95

Thr Phe Gly Gln Gly Thr Lys Val Glu Ile Lys Arg
            100                 105

<210> SEQ ID NO 146
<211> LENGTH: 324
<212> TYPE: DNA
<213> ORGANISM: Homo sapiens

<400> SEQUENCE: 146
gacatccaga tgacccagtc tccatcctcc ctgtctgcat ctgtaggaga ccgtgtcacc    60
atcacttgcc gggcaagtca gagcattagg aagatgttag tttggtacca gcagaaacca    120
gggaaagccc ctaagctcct gatctatcgg gcatcctatt tgcaaagtgg ggtcccatca    180
cgtttcagtg gcagtggatc tgggacagat ttcactctca ccatcagcag tctgcaacct    240
gaagattttg ctacgtacta ctgtcaacag gcttttcggc ggcctaggac gttcggccaa    300
gggaccaagg tggaaatcaa acgg    324

<210> SEQ ID NO 147
<211> LENGTH: 108
<212> TYPE: PRT
<213> ORGANISM: Homo sapiens

<400> SEQUENCE: 147

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Arg Lys Met
            20                  25                  30

Leu Val Trp Tyr Gln Gln Lys Pro Gly Lys Ala Pro Lys Leu Leu Ile
        35                  40                  45

Tyr Arg Ala Ser Tyr Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ala Phe Arg Arg Pro Arg
            85                  90                  95

Thr Phe Gly Gln Gly Thr Lys Val Glu Ile Lys Arg
            100                 105

<210> SEQ ID NO 148
<211> LENGTH: 345
<212> TYPE: DNA
<213> ORGANISM: Homo sapiens

<400> SEQUENCE: 148
gaggtgcagc tgttggagtc tgggggaggc ttggtacagc ctggggggtc cctgcgtctc     60
tcctgtgcag cctccggatt cacctttgat ctttataata tgttttgggt ccgccaggct    120
ccagggaagg gtctagagtg ggtctcattt attagtcaga ctggtaggct tacatggtac    180
gcagactccg tgaagggccg gttcaccatc tcccgcgaca attccaagaa cacgctgtat    240
ctgcaaatga acagcctgcg tgccgaggac accgcggtat attactgtgc gaaaacgctg    300
gaggattttg actactgggg ccagggaacc ctggtcaccg tctcg                   345

<210> SEQ ID NO 149
<211> LENGTH: 115
<212> TYPE: PRT
<213> ORGANISM: Homo sapiens

<400> SEQUENCE: 149

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Asp Leu Tyr
            20                  25                  30

Asn Met Phe Trp Val Arg Gln Ala Pro Gly Lys Gly Leu Glu Trp Val
        35                  40                  45

Ser Phe Ile Ser Gln Thr Gly Arg Leu Thr Trp Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
            85                  90                  95

Ala Lys Thr Leu Glu Asp Phe Asp Tyr Trp Gly Gln Gly Thr Leu Val
            100                 105                 110

Thr Val Ser
        115

<210> SEQ ID NO 150
<211> LENGTH: 357
<212> TYPE: DNA
<213> ORGANISM: Homo sapiens

<400> SEQUENCE: 150
gaggtgcagc tgttggagtc tgggggaggc ttggtacagc ctggggggtc cctgcgtctc     60
tcctgtgcag cctccggatt caccttccg gtttatatga tgggttgggt ccgccaggct    120
ccagggaagg gtctagagtg ggtctcatcg attgatgctc ttggtgggcg gacaggttac    180
gcagactccg tgaagggccg gttcaccatc tcccgcgaca attccaagaa cacgctgtat    240
ctgcaaatga acagcctgcg tgccgaggac accgcggtat attactgtgc gaaaactatg    300
tcgaataaga cgcatacgtt tgactactgg ggccagggaa ccctggtcac cgtctcg      357

<210> SEQ ID NO 151
<211> LENGTH: 119
<212> TYPE: PRT
<213> ORGANISM: Homo sapiens

<400> SEQUENCE: 151

Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Pro Val Tyr
            20                  25                  30

Met Met Gly Trp Val Arg Gln Ala Pro Gly Lys Gly Leu Glu Trp Val
        35                  40                  45

Ser Ser Ile Asp Ala Leu Gly Gly Arg Thr Gly Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Thr Met Ser Asn Lys Thr His Thr Phe Asp Tyr Trp Gly Gln
            100                 105                 110

Gly Thr Leu Val Thr Val Ser
        115

<210> SEQ ID NO 152
<211> LENGTH: 345
<212> TYPE: DNA
<213> ORGANISM: Homo sapiens

<400> SEQUENCE: 152
gaggtgcagc tgttggagtc tgggggaggc ttggtacagc ctgggggtc cctgcgtctc        60 tcctgtgcag cctccggatt cacctttgtg gcttataata tgacttgggt ccgccaggct       120
ccagggaagg gtctagagtg gtctcaagt attaatactt ttggtaatta gacaaggtac        180
gcagactccg tgaagggccg gttcaccatc tcccgcgaca attccaagaa cacgctgtat       240
ctgcaaatga acagcctgcg tgccgaggac accgcggtat attactgtgc gaaaggtagt       300
aggccttttg actactgggg ccagggaacc ctggtcaccg tctcg                      345

<210> SEQ ID NO 153
<211> LENGTH: 115
<212> TYPE: PRT
<213> ORGANISM: Homo sapiens

<400> SEQUENCE: 153

Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Val Ala Tyr
            20                  25                  30

Asn Met Thr Trp Val Arg Gln Ala Pro Gly Lys Gly Leu Glu Trp Val
        35                  40                  45

Ser Ser Ile Asn Thr Phe Gly Asn Gln Thr Arg Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Gly Ser Arg Pro Phe Asp Tyr Trp Gly Gln Gly Thr Leu Val
            100                 105                 110

-continued

Thr Val Ser
    115

<210> SEQ ID NO 154
<211> LENGTH: 357
<212> TYPE: DNA
<213> ORGANISM: Homo sapiens

<400> SEQUENCE: 154
gaggtgcagc tgttggagtc tgggggaggc ttggtacagc ctggggggtc cctgcgtctc    60
tcctgtgcag cctccggatt cacctttag  gggtatcgta tgggttgggt ccgccaggct   120
ccagggaagg gtctagagtg ggtctcatgg attacgcgta ctggtgggac gacacagtac   180
gcagactccg tgaagggccg gttcaccatc tcccgcgaca attccaagaa cacgctgtat   240
ctgcaaatga acagcctgcg tgccgaggac accgcggtat attactgtgc gaaaccggcg   300
aagcttgttg gggttgggtt tgactactgg ggccagggaa ccctggtcac cgtctcg     357

<210> SEQ ID NO 155
<211> LENGTH: 119
<212> TYPE: PRT
<213> ORGANISM: Homo sapiens

<400> SEQUENCE: 155

Glu Val Gln Leu Leu Glu Ser Gly Gly Gly Leu Val Gln Pro Gly Gly
 1               5                  10                  15
Ser Leu Arg Leu Ser Cys Ala Ala Ser Gly Phe Thr Phe Gln Gly Tyr
            20                  25                  30
Arg Met Gly Trp Val Arg Gln Ala Pro Gly Lys Gly Leu Glu Trp Val
        35                  40                  45
Ser Trp Ile Thr Arg Thr Gly Thr Thr Gln Tyr Ala Asp Ser Val
    50                  55                  60
Lys Gly Arg Phe Thr Ile Ser Arg Asp Asn Ser Lys Asn Thr Leu Tyr
65                  70                  75                  80
Leu Gln Met Asn Ser Leu Arg Ala Glu Asp Thr Ala Val Tyr Tyr Cys
                85                  90                  95
Ala Lys Pro Ala Lys Leu Val Gly Val Gly Phe Asp Tyr Trp Gly Gln
            100                 105                 110
Gly Thr Leu Val Thr Val Ser
        115

<210> SEQ ID NO 156
<211> LENGTH: 357
<212> TYPE: DNA
<213> ORGANISM: Homo sapiens

<400> SEQUENCE: 156
gaggtgcagc tgttggagtc tgggggaggc ttggtacagc ctggggggtc cctgcgtctc    60
tcctgtgcag cctccggatt cacctttcgg aagtattaga tggggtgggt ccgccaggct   120
ccagggaagg gtctagagtg ggtctcacag attggtgcga aggtcagtc  tacagattac   180
gcagactccg tgaagggccg gttcaccatc tcccgcgaca attccaagaa cacgctgtat   240
ctgcaaatga acagcctgcg tgccgaggac accgcggtat attactgtgc gaaaaagaag   300
aggggggaga attatttttt tgactactgg ggccagggaa ccctggtcac cgtctcg     357

<210> SEQ ID NO 157
<211> LENGTH: 119

```
<212> TYPE: PRT
<213> ORGANISM: Homo sapiens

<400> SEQUENCE: 157

Glu Val Gln Leu Leu Glu Ser Gly Gly Gly Leu Val Gln Pro Gly Gly
 1               5                  10                  15
Ser Leu Arg Leu Ser Cys Ala Ala Ser Gly Phe Thr Phe Arg Lys Tyr
            20                  25                  30
Gln Met Gly Trp Val Arg Gln Ala Pro Gly Lys Gly Leu Glu Trp Val
        35                  40                  45
Ser Gln Ile Gly Ala Lys Gly Gln Ser Thr Asp Tyr Ala Asp Ser Val
    50                  55                  60
Lys Gly Arg Phe Thr Ile Ser Arg Asp Asn Ser Lys Asn Thr Leu Tyr
65                  70                  75                  80
Leu Gln Met Asn Ser Leu Arg Ala Glu Asp Thr Ala Val Tyr Tyr Cys
                85                  90                  95
Ala Lys Lys Lys Arg Gly Glu Asn Tyr Phe Phe Asp Tyr Trp Gly Gln
            100                 105                 110
Gly Thr Leu Val Thr Val Ser
        115

<210> SEQ ID NO 158
<211> LENGTH: 357
<212> TYPE: DNA
<213> ORGANISM: Homo sapiens

<400> SEQUENCE: 158
gaggtgcagc tgttggagtc tgggggaggc ttggtacagc ctggggggtc cctgcgtctc      60
tcctgtgcag cctccggatt cacctttcgg cggtatagta tgtcgtgggt ccgccaggct     120
ccagggaagg gtctagagtg gtctcagata atttctcgtt ctggtcggta tacacattac     180
gcagactccg tgaagggccg gttcaccatc tcccgcgaca attccaagaa cacgctgtat     240
ctgcaaatga acagcctgcg tgccgaggac accgcggtat attactgtgc gaaacgtatt     300
gattcttctc agaatgggtt tgactactgg ggccagggaa ccctggtcac cgtctcg       357

<210> SEQ ID NO 159
<211> LENGTH: 119
<212> TYPE: PRT
<213> ORGANISM: Homo sapiens

<400> SEQUENCE: 159

Glu Val Gln Leu Leu Glu Ser Gly Gly Gly Leu Val Gln Pro Gly Gly
 1               5                  10                  15
Ser Leu Arg Leu Ser Cys Ala Ala Ser Gly Phe Thr Phe Arg Arg Tyr
            20                  25                  30
Ser Met Ser Trp Val Arg Gln Ala Pro Gly Lys Gly Leu Glu Trp Val
        35                  40                  45
Ser Asp Ile Ser Arg Ser Gly Tyr Thr His Tyr Ala Asp Ser Val
    50                  55                  60
Lys Gly Arg Phe Thr Ile Ser Arg Asp Asn Ser Lys Asn Thr Leu Tyr
65                  70                  75                  80
Leu Gln Met Asn Ser Leu Arg Ala Glu Asp Thr Ala Val Tyr Tyr Cys
                85                  90                  95
Ala Lys Arg Ile Asp Ser Ser Gln Asn Gly Phe Asp Tyr Trp Gly Gln
            100                 105                 110
Gly Thr Leu Val Thr Val Ser
```

<210> SEQ ID NO 160
<211> LENGTH: 345
<212> TYPE: DNA
<213> ORGANISM: Homo sapiens

<400> SEQUENCE: 160
gaggtgcagc tgttggagtc tgggggaggc ttggtacagc ctgggggtc cctgcgtctc      60 tcctgtgcag cctccggatt cacctttag gggtataaga tgttttgggt ccgccaggct     120
ccagggaagg gtctagagtg gtctcagct attagtggta gtggtggtag cacatactac     180
gcagactccg tgaagggccg gttcaccatc tcccgcgaca attccaagaa cacgctgtat     240
ctgcaaatga acagcctgcg tgccgaggac accgcggtat attactgtgc gaaacagaag     300
gagaattttg actactgggg ccagggaacc ctggtcaccg tctcg                    345

<210> SEQ ID NO 161
<211> LENGTH: 115
<212> TYPE: PRT
<213> ORGANISM: Homo sapiens

<400> SEQUENCE: 161

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Gln Gly Tyr
            20                  25                  30

Lys Met Phe Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Gln Lys Glu Asn Phe Asp Tyr Trp Gly Gln Gly Thr Leu Val
            100                 105                 110

Thr Val Ser
        115

<210> SEQ ID NO 162
<211> LENGTH: 357
<212> TYPE: DNA
<213> ORGANISM: Homo sapiens

<400> SEQUENCE: 162
gaggtgcagc tgttggagtc tgggggaggc ttggtacagc ctgggggtc cctgcgtctc      60 tcctgtgcag cctccggatt cacctttggg gattatgcta tgtggtgggt ccgccaggct     120
ccagggaagg gtctagagtg gtctcagtg attagttcga atggtgggag tacattttac     180
gcagactccg tgaagggccg gttcaccatc tcccgcgaca attccaagaa cacgctgtat     240
ctgcaaatga acagcctgcg tgccgaggac accgcggtat attactgtgc gaaacgtgtt     300
cgtaagagga ctcctgagtt tgactactgg ggccagggaa ccctggtcac cgtctcg       357

<210> SEQ ID NO 163
<211> LENGTH: 119
<212> TYPE: PRT
<213> ORGANISM: Homo sapiens

<400> SEQUENCE: 163

| Glu | Val | Gln | Leu | Leu | Glu | Ser | Gly | Gly | Gly | Leu | Val | Gln | Pro | Gly | Gly |
|---|---|---|---|---|---|---|---|---|---|---|---|---|---|---|---|
| 1 | | | | 5 | | | | | 10 | | | | | 15 | |

| Ser | Leu | Arg | Leu | Ser | Cys | Ala | Ala | Ser | Gly | Phe | Thr | Phe | Gly | Asp | Tyr |
| | | | 20 | | | | | 25 | | | | | 30 | | |

| Ala | Met | Trp | Val | Arg | Gln | Ala | Pro | Gly | Lys | Gly | Leu | Glu | Trp | Val |
| | | 35 | | | | | 40 | | | | | 45 | | |

| Ser | Val | Ile | Ser | Ser | Asn | Gly | Ser | Thr | Phe | Tyr | Ala | Asp | Ser | Val |
| | 50 | | | | | 55 | | | | | 60 | | | |

| Lys | Gly | Arg | Phe | Thr | Ile | Ser | Arg | Asp | Asn | Ser | Lys | Asn | Thr | Leu | Tyr |
| 65 | | | | | 70 | | | | | 75 | | | | | 80 |

| Leu | Gln | Met | Asn | Ser | Leu | Arg | Ala | Glu | Asp | Thr | Ala | Val | Tyr | Tyr | Cys |
| | | | | 85 | | | | | 90 | | | | | 95 | |

| Ala | Lys | Arg | Val | Arg | Lys | Arg | Thr | Pro | Glu | Phe | Asp | Tyr | Trp | Gly | Gln |
| | | | 100 | | | | | 105 | | | | | 110 | | |

| Gly | Thr | Leu | Val | Thr | Val | Ser |
| | | | | | | |
| | | 115 | | | | |

<210> SEQ ID NO 164
<211> LENGTH: 357
<212> TYPE: DNA
<213> ORGANISM: Homo sapiens

<400> SEQUENCE: 164

```
gaggtgcagc tgttggagtc tgggggaggc ttggtacagc ctgggggtc cctgcgtctc       60
tcctgtgcag cctccggatt cacctttagg aggtataaga tgggttgggt ccgccaggct     120
ccagggaagg gtctagagtg ggtctcagcg attgggagga atggtacgaa gacaaattac     180
gcagactccg tgaagggccg gttcaccatc tcccgcgaca attccaagaa cacgctgtat     240
ctgcaaatga acagcctgcg tgccgaggac accgcggtat attactgtgc gaaaatttat     300
acggggaagc ctgctgcgtt tgactactgg ggccaggaa ccctggtcac cgtctcg        357
```

<210> SEQ ID NO 165
<211> LENGTH: 119
<212> TYPE: PRT
<213> ORGANISM: Homo sapiens

<400> SEQUENCE: 165

| Glu | Val | Gln | Leu | Leu | Glu | Ser | Gly | Gly | Gly | Leu | Val | Gln | Pro | Gly | Gly |
|---|---|---|---|---|---|---|---|---|---|---|---|---|---|---|---|
| 1 | | | | 5 | | | | | 10 | | | | | 15 | |

| Ser | Leu | Arg | Leu | Ser | Cys | Ala | Ala | Ser | Gly | Phe | Thr | Phe | Arg | Arg | Tyr |
| | | | 20 | | | | | 25 | | | | | 30 | | |

| Lys | Met | Gly | Trp | Val | Arg | Gln | Ala | Pro | Gly | Lys | Gly | Leu | Glu | Trp | Val |
| | | 35 | | | | | 40 | | | | | 45 | | | |

| Ser | Ala | Ile | Gly | Arg | Asn | Gly | Thr | Lys | Thr | Asn | Tyr | Ala | Asp | Ser | Val |
| | 50 | | | | | 55 | | | | | 60 | | | | |

| Lys | Gly | Arg | Phe | Thr | Ile | Ser | Arg | Asp | Asn | Ser | Lys | Asn | Thr | Leu | Tyr |
| 65 | | | | | 70 | | | | | 75 | | | | | 80 |

| Leu | Gln | Met | Asn | Ser | Leu | Arg | Ala | Glu | Asp | Thr | Ala | Val | Tyr | Tyr | Cys |
| | | | | 85 | | | | | 90 | | | | | 95 | |

| Ala | Lys | Ile | Tyr | Thr | Gly | Lys | Pro | Ala | Ala | Phe | Asp | Tyr | Trp | Gly | Gln |
| | | | 100 | | | | | 105 | | | | | 110 | | |

| Gly | Thr | Leu | Val | Thr | Val | Ser |
| | | | | | | |
| | | 115 | | | | |

<210> SEQ ID NO 166
<211> LENGTH: 357
<212> TYPE: DNA
<213> ORGANISM: Homo sapiens

<400> SEQUENCE: 166

```
gaggtgcagc tgttggagtc tgggggaggc ttggtacagc ctggggggtc cctgcgtctc    60
tcctgtgcag cctccggatt cacctttaag aagtattaga tgtcttgggt ccgccaggct   120
ccagggaagg gtctagagtg ggtctcagct attagtggta gtggtggtag cacatactac   180
gcagactccg tgaagggccg gttcaccatc tcccgcgaca attccaagaa cacgctgtat   240
ctgcaaatga acagcctgcg tgccgaggac accgcggtat attactgtgc gaaaatgctg   300
aggactaaga ataaggtgtt tgactactgg ggccagggaa ccctggtcac cgtctcg      357
```

<210> SEQ ID NO 167
<211> LENGTH: 119
<212> TYPE: PRT
<213> ORGANISM: Homo sapiens

<400> SEQUENCE: 167

```
Glu Val Gln Leu Leu Glu Ser Gly Gly Gly Leu Val Gln Pro Gly Gly
  1               5                  10                  15

Ser Leu Arg Leu Ser Cys Ala Ala Ser Gly Phe Thr Phe Lys Lys Tyr
             20                  25                  30

Gln Met Ser Trp Val Arg Gln Ala Pro Gly Lys Gly Leu Glu Trp Val
         35                  40                  45

Ser Ala Ile Ser Gly Ser Gly Gly Ser Thr Tyr Tyr Ala Asp Ser Val
     50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Lys Met Leu Arg Thr Lys Asn Lys Val Phe Asp Tyr Trp Gly Gln
            100                 105                 110

Gly Thr Leu Val Thr Val Ser
        115
```

<210> SEQ ID NO 168
<211> LENGTH: 357
<212> TYPE: DNA
<213> ORGANISM: Homo sapiens

<400> SEQUENCE: 168

```
gaggtgcagc tgttggagtc tgggggaggc ttggtacagc ctggggggtc cctgcgtctc    60
tcctgtgcag cctccggatt cacctttagg aggtataaga tgggttgggt ccgccaggct   120
ccagggaagg gtctagagtg ggtctcagcg attgggagga atggtacgaa gacaaattac   180
gcagactccg tgaagggccg gttcaccatc tcccgcgaca attccaagaa cacgctgtat   240
ctgcaaatga acagcctgcg tgccgaggac accgcggtat attactgtgc gaaaatttat   300
acggggaagc tgctgcgtt tgactactgg ggccagggaa ccctggtcac cgtctcg       357
```

<210> SEQ ID NO 169
<211> LENGTH: 119
<212> TYPE: PRT
<213> ORGANISM: Homo sapiens

<400> SEQUENCE: 169

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Arg Arg Tyr
            20                  25                  30

Lys Met Gly Trp Val Arg Gln Ala Pro Gly Lys Gly Leu Glu Trp Val
        35                  40                  45

Ser Ala Ile Gly Arg Asn Gly Thr Lys Thr Asn Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Ile Tyr Thr Gly Lys Pro Ala Ala Phe Asp Tyr Trp Gly Gln
            100                 105                 110

Gly Thr Leu Val Thr Val Ser
            115

<210> SEQ ID NO 170
<211> LENGTH: 357
<212> TYPE: DNA
<213> ORGANISM: Homo sapiens

<400> SEQUENCE: 170
gaggtgcagc tgttggagtc tgggggaggc ttggtacagc ctggggggtc cctgcgtctc    60
tcctgtgcag cctccggatt cacctttag agttatcgga tgggttgggt ccgccaggct    120
ccagggaagg gtctagagtg ggtctcaagt atttcgtcga ggggtaggca tacatcttac    180
gcagactccg tgaagggccg gttcaccatc tcccgcgaca attccaagaa cacgctgtat    240
ctgcaaatga acagcctgcg tgccgaggac accgcgtat attactgtgc gaaaagggtt    300
ccgggtcggg ggcgttcttt tgactactgg ggccagggaa ccctggtcac cgtctcg     357

<210> SEQ ID NO 171
<211> LENGTH: 119
<212> TYPE: PRT
<213> ORGANISM: Homo sapiens

<400> SEQUENCE: 171

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Gln Ser Tyr
            20                  25                  30

Arg Met Gly Trp Val Arg Gln Ala Pro Gly Lys Gly Leu Glu Trp Val
        35                  40                  45

Ser Ser Ile Ser Ser Arg Gly Arg His Thr Ser Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Arg Val Pro Gly Arg Gly Arg Ser Phe Asp Tyr Trp Gly Gln
            100                 105                 110

Gly Thr Leu Val Thr Val Ser
            115

<210> SEQ ID NO 172

<211> LENGTH: 357
<212> TYPE: DNA
<213> ORGANISM: Homo sapiens

<400> SEQUENCE: 172

```
gaggtgcagc tgttggagtc tgggggaggc ttggtacagc ctgggggtc cctgcgtctc      60
tcctgtgcag cctccggatt ccctttcgt cggtatcgga tgaggtgggt ccgccaggct     120
ccagggaagg gtctagagtg gtctcaggt atttctccgg gtggtaagca tacaacgtac     180
gcagactccg tgaagggccg gttcaccatc tcccgcgaca attccaagaa cacgctgtat    240
ctgcaaatga acagcctgcg tgccgaggac accgcggtat attactgtgc gaaaggtgag    300
gggggggcga gttctgcgtt tgactactgg ggccaggaa ccctggtcac cgtctcg        357
```

<210> SEQ ID NO 173
<211> LENGTH: 119
<212> TYPE: PRT
<213> ORGANISM: Homo sapiens

<400> SEQUENCE: 173

```
Glu Val Gln Leu Leu Glu Ser Gly Gly Gly Leu Val Gln Pro Gly Gly
  1               5                  10                  15

Ser Leu Arg Leu Ser Cys Ala Ala Ser Gly Phe Pro Phe Arg Arg Tyr
             20                  25                  30

Arg Met Arg Trp Val Arg Gln Ala Pro Gly Lys Gly Leu Glu Trp Val
         35                  40                  45

Ser Gly Ile Ser Pro Gly Gly Lys His Thr Thr Tyr Ala Asp Ser Val
     50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Lys Gly Glu Gly Gly Ala Ser Ser Ala Phe Asp Tyr Trp Gly Gln
            100                 105                 110

Gly Thr Leu Val Thr Val Ser
        115
```

<210> SEQ ID NO 174
<211> LENGTH: 357
<212> TYPE: DNA
<213> ORGANISM: Homo sapiens

<400> SEQUENCE: 174

```
gaggtgcagc tgttggagtc tgggggaggc ttggtacagc ctgggggtc cctgcgtctc      60
tcctgtgcag cctccggatt cacctttag cggtatggga tggtttgggt ccgccaggct    120
ccagggaagg gtctagagtg gtctcagct attagtggta gtggtggtag cacatactac    180
gcagactccg tgaagggccg gttcaccatc tcccgcgaca attccaagaa cacgctgtat    240
ctgcaaatga acagcctgcg tgccgaggac accgcggtat attactgtgc gaaacggcat    300
agttctgagg ctaggcagtt tgactactgg ggccagggaa ccctggtcac cgtctcg       357
```

<210> SEQ ID NO 175
<211> LENGTH: 119
<212> TYPE: PRT
<213> ORGANISM: Homo sapiens

<400> SEQUENCE: 175

```
Glu Val Gln Leu Leu Glu Ser Gly Gly Gly Leu Val Gln Pro Gly Gly
```

```
            1               5                   10                  15
Ser Leu Arg Leu Ser Cys Ala Ala Ser Gly Phe Thr Phe Gln Arg Tyr
            20                  25                  30

Gly Met Val Trp Val Arg Gln Ala Pro Gly Lys Gly Leu Glu Trp Val
            35                  40                  45

Ser Ala Ile Ser Gly Ser Gly Gly Ser Thr Tyr Tyr Ala Asp Ser Val
            50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
            85                  90                  95

Ala Lys Arg His Ser Ser Glu Ala Arg Gln Phe Asp Tyr Trp Gly Gln
            100                 105                 110

Gly Thr Leu Val Thr Val Ser
            115

<210> SEQ ID NO 176
<211> LENGTH: 720
<212> TYPE: DNA
<213> ORGANISM: Homo sapiens

<400> SEQUENCE: 176
gaggtgcagc tgttggagtc tgggggaggc ttggtacagc ctggggggtc cctgcgtctc      60
tcctgtgcag cctccggatt cacctttagc agctatgcca tgagctgggt ccgccaggct     120
ccagggaagg gtctagagtg gtctcagct attagtggta gtggtggtag cacatactac     180
gcagactccg tgaagggccg gttcaccatc tcccgtgaca attccaagaa cacgctgtat     240
ctgcaaatga acagcctgcg tgccgaggac accgcggtat attactgtgc gaaaagttat     300
ggtgcttttg actactgggg ccagggaacc ctggtcaccg tctcgagcgg tggaggcggt     360
tcaggcggag gtggcagcgg cggtggcggg tcgacggaca tccagatgac ccagtctcca     420
tcctccctgt ctgcatctgt aggagaccgt gtcaccatca cttgccgggc aagtcagagc     480
attagcagct atttaaattg gtaccagcag aaaccaggga agcccctaa gctcctgatc      540 tatgctgcat ccagttggca aagtggggtc ccatcacgtt tcagtggcag tggatctggg     600
acagatttca ctctcaccat cagcagtctg caacctgaag attttgctac gtactactgt     660
caacagagtt acagtacccc taatacgttc ggccaaggga ccaaggtgga aatcaaacgg     720

<210> SEQ ID NO 177
<211> LENGTH: 240
<212> TYPE: PRT
<213> ORGANISM: Homo sapiens

<400> SEQUENCE: 177

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
            35                  40                  45

Ser Ala Ile Ser Gly Ser Gly Gly Ser Thr Tyr Tyr Ala Asp Ser Val
            50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
```

```
            85                  90                  95
Ala Lys Ser Tyr Gly Ala Phe Asp Tyr Trp Gly Gln Gly Thr Leu Val
            100                 105                 110

Thr Val Ser Ser Gly Gly Gly Gly Ser Gly Gly Gly Gly Ser Gly Gly
            115                 120                 125

Gly Gly Ser Thr Asp Ile Gln Met Thr Gln Ser Pro Ser Ser Leu Ser
        130                 135                 140

Ala Ser Val Gly Asp Arg Val Thr Ile Thr Cys Arg Ala Ser Gln Ser
145                 150                 155                 160

Ile Ser Ser Tyr Leu Asn Trp Tyr Gln Gln Lys Pro Gly Lys Ala Pro
                165                 170                 175

Lys Leu Leu Ile Tyr Ala Ala Ser Ser Trp Gln Ser Gly Val Pro Ser
            180                 185                 190

Arg Phe Ser Gly Ser Gly Ser Gly Thr Asp Phe Thr Leu Thr Ile Ser
        195                 200                 205

Ser Leu Gln Pro Glu Asp Phe Ala Thr Tyr Tyr Cys Gln Gln Ser Tyr
    210                 215                 220

Ser Thr Pro Asn Thr Phe Gly Gln Gly Thr Lys Val Glu Ile Lys Arg
225                 230                 235                 240

<210> SEQ ID NO 178
<211> LENGTH: 269
<212> TYPE: DNA
<213> ORGANISM: Homo sapiens

<400> SEQUENCE: 178
caggaaacag ctatgaccat gattacgcca agcttgcatg caaattctat ttcaaggaga     60
cagtcataat gaaataccta ttgcctacgg cagccgctgg attgttatta ctcgcggccc    120
agccggccat ggccgaggtg tttgactact ggggccaggg aaccctggtc accgtctcga    180
gcggtggagg cggttcaggc ggaggtggca gcggcggtgg cgggtcgacg gacatccaga    240
tgacccaggc ggccgcagaa caaaaactc                                     269

<210> SEQ ID NO 179
<211> LENGTH: 67
<212> TYPE: PRT
<213> ORGANISM: Homo sapiens

<400> SEQUENCE: 179

Met Lys Tyr Leu Leu Pro Thr Ala Ala Ala Gly Leu Leu Leu Leu Ala
1               5                   10                  15

Ala Gln Pro Ala Met Ala Glu Val Phe Asp Tyr Trp Gly Gln Gly Thr
            20                  25                  30

Leu Val Thr Val Ser Ser Gly Gly Gly Gly Ser Gly Gly Gly Gly Ser
        35                  40                  45

Gly Gly Gly Gly Ser Thr Asp Ile Gln Met Thr Gln Ala Ala Ala Glu
    50                  55                  60

Gln Lys Leu
65

<210> SEQ ID NO 180
<211> LENGTH: 90
<212> TYPE: DNA
<213> ORGANISM: Homo sapiens

<400> SEQUENCE: 180
catcatcatc accatcacgg ggccgcaatc tcagaagagg atctgaatgg ggccgcatag     60
```

```
actgttgaaa gttgtttagc aaaacctcat                                                90
```

<210> SEQ ID NO 181
<211> LENGTH: 30
<212> TYPE: PRT
<213> ORGANISM: Homo sapiens

<400> SEQUENCE: 181

His His His His His His Gly Ala Ala Ile Ser Glu Glu Asp Leu Asn
1               5                   10                  15

Gly Ala Ala Gln Thr Val Glu Ser Cys Leu Ala Lys Pro His
            20                  25                  30

<210> SEQ ID NO 182
<211> LENGTH: 116
<212> TYPE: PRT
<213> ORGANISM: Homo sapiens

<400> SEQUENCE: 182

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Ser Tyr Gly Ala Phe Asp Tyr Trp Gly Gln Gly Thr Leu Val
            100                 105                 110

Thr Val Ser Ser
        115

<210> SEQ ID NO 183
<211> LENGTH: 116
<212> TYPE: PRT
<213> ORGANISM: Homo sapiens

<400> SEQUENCE: 183

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser His Ile Ser Pro Tyr Gly Ala Asn Thr Arg Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Gly Leu Arg Ala Phe Asp Tyr Trp Gly Gln Gly Thr Leu Val
            100                 105                 110

Thr Val Ser Ser

-continued

```
<210> SEQ ID NO 184
<211> LENGTH: 116
<212> TYPE: PRT
<213> ORGANISM: Homo sapiens

<400> SEQUENCE: 184

Glu Val Gln Leu Leu Glu Ser Gly Gly Gly Leu Val Gln Pro Gly Gly
  1               5                  10                  15

Ser Leu Arg Leu Ser Cys Ala Ala Ser Gly Phe Thr Phe Ser Ser Tyr
             20                  25                  30

Ala Met Ser Trp Val Arg Gln Ala Pro Gly Lys Gly Leu Glu Trp Val
         35                  40                  45

Ser Asp Ile Gly Ala Thr Gly Ser Lys Thr Gly Tyr Ala Asp Pro Val
     50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Lys Lys Val Leu Thr Phe Asp Tyr Trp Gly Gln Gly Thr Leu Val
            100                 105                 110

Thr Val Ser Ser
        115

<210> SEQ ID NO 185
<211> LENGTH: 116
<212> TYPE: PRT
<213> ORGANISM: Homo sapiens

<400> SEQUENCE: 185

Glu Val Gln Leu Leu Glu Ser Gly Gly Gly Leu Val Gln Pro Gly Gly
  1               5                  10                  15

Ser Leu Arg Leu Ser Cys Ala Ala Ser Gly Phe Thr Phe Ser Ser Tyr
             20                  25                  30

Ala Met Ser Trp Val Arg Gln Ala Pro Gly Lys Gly Leu Glu Trp Val
         35                  40                  45

Ser Arg Ile Asn Gly Pro Gly Gln Ala Thr Gly Tyr Ala Asp Ser Val
     50                  55                  60

Lys Gly Arg Phe Thr Ile Ser Arg Asp Asn Ser Lys Asn Thr Leu Tyr
 65                  70                  75                  80

Leu Gln Ile Asn Ser Leu Arg Ala Glu Asp Thr Ala Val Tyr Tyr Cys
                 85                  90                  95

Ala Lys His Gly Ala Pro Phe Asp Tyr Trp Gly Gln Gly Thr Leu Val
            100                 105                 110

Thr Val Ser Ser
        115

<210> SEQ ID NO 186
<211> LENGTH: 116
<212> TYPE: PRT
<213> ORGANISM: Homo sapiens

<400> SEQUENCE: 186

Glu Val Gln Leu Leu Glu Ser Gly Gly Gly Leu Val Gln Pro Gly Gly
  1               5                  10                  15

Ser Leu Arg Leu Ser Cys Ala Ala Ser Gly Phe Thr Phe Ser Ser Tyr
             20                  25                  30
```

```
Ala Met Asn Trp Val Arg Gln Ala Pro Gly Lys Gly Leu Glu Trp Val
            35                  40                  45

Ser Ser Ile Pro Ala Ser Gly Leu His Thr Arg Tyr Ala Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Lys Pro Gly Leu Gly Phe Asp Tyr Trp Gly Gln Gly Thr Leu Val
            100                 105                 110

Thr Val Ser Ser
        115

<210> SEQ ID NO 187
<211> LENGTH: 116
<212> TYPE: PRT
<213> ORGANISM: Homo sapiens

<400> SEQUENCE: 187

Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Ser Ser Tyr
             20                  25                  30

Ala Met Ser Trp Val Arg Gln Ala Pro Gly Lys Gly Leu Glu Trp Val
            35                  40                  45

Ser Asp Ile Glu Arg Thr Gly Tyr Gln Thr Arg Tyr Ala Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Lys Lys Val Leu Val Phe Asp Tyr Trp Gly Gln Gly Thr Leu Val
            100                 105                 110

Thr Val Ser Ser
        115

<210> SEQ ID NO 188
<211> LENGTH: 116
<212> TYPE: PRT
<213> ORGANISM: Homo sapiens

<400> SEQUENCE: 188

Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Ser Ser Tyr
             20                  25                  30

Ala Met Ser Trp Val Arg Gln Ala Pro Gly Lys Gly Leu Glu Trp Val
            35                  40                  45

Ser Glu Ile Ser Ala Asn Gly Ser Lys Thr Gln Tyr Ala Asp Ser Val
 50                  55                  60

Lys Gly Arg Leu Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Lys Lys Val Leu Gln Phe Asp Tyr Trp Gly Gln Gly Thr Leu Val
            100                 105                 110
```

-continued

Thr Val Ser Ser
        115

<210> SEQ ID NO 189
<211> LENGTH: 116
<212> TYPE: PRT
<213> ORGANISM: Homo sapiens

<400> SEQUENCE: 189

Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Thr Ile Pro Ala Asn Gly Gln Val Thr Arg Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Ser Leu Leu Gln Phe Asp Tyr Trp Gly Gln Gly Thr Leu Val
            100                 105                 110

Thr Val Ser Ser
        115

<210> SEQ ID NO 190
<211> LENGTH: 116
<212> TYPE: PRT
<213> ORGANISM: Homo sapiens

<400> SEQUENCE: 190

Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Asp Ile Ala Ala Thr Gly Ser Ala Thr Ser Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Lys Ile Leu Lys Phe Asp Tyr Trp Gly Gln Gly Thr Leu Val
            100                 105                 110

Thr Val Ser Ser
        115

<210> SEQ ID NO 191
<211> LENGTH: 116
<212> TYPE: PRT
<213> ORGANISM: Homo sapiens

<400> SEQUENCE: 191

Glu Val Gln Leu Leu Glu Ser Gly Gly Gly Leu Val Gln Pro Gly Gly
 1               5                  10                  15

Ser Leu Arg Leu Ser Cys Ala Ala Ser Gly Ser Thr Phe Ser Ser Tyr
            20                  25                  30

Ala Met Ser Trp Val Arg Gln Ala Pro Gly Lys Gly Leu Glu Trp Val
        35                  40                  45

Ser Thr Ile Ser Ser Val Gly Gln Ser Thr Arg Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asn Leu Met Ser Phe Asp Tyr Trp Gly Gln Gly Thr Leu Val
            100                 105                 110

Thr Val Ser Ser
        115

<210> SEQ ID NO 192
<211> LENGTH: 108
<212> TYPE: PRT
<213> ORGANISM: Homo sapiens

<400> SEQUENCE: 192

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Asn
                85                  90                  95

Thr Phe Gly Gln Gly Thr Lys Val Glu Ile Lys Arg
            100                 105

<210> SEQ ID NO 193
<211> LENGTH: 108
<212> TYPE: PRT
<213> ORGANISM: Homo sapiens

<400> SEQUENCE: 193

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Arg Ala Ser His Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Pro Trp Arg Ser Pro Gly
                85                  90                  95

Thr Phe Gly Gln Gly Thr Lys Val Glu Ile Lys Arg
            100                 105

<210> SEQ ID NO 194
<211> LENGTH: 108
<212> TYPE: PRT
<213> ORGANISM: Homo sapiens

<400> SEQUENCE: 194

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Val Ser Ser Tyr
            20                  25                  30

Leu Asn Trp Tyr Gln Gln Lys Pro Gly Lys Ala Pro Lys Leu Leu Ile
        35                  40                  45

Tyr Leu Ala Ser Arg Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Asn Trp Trp Leu Pro Pro
                85                  90                  95

Thr Phe Gly Gln Gly Thr Lys Val Glu Ile Lys Arg
            100                 105

<210> SEQ ID NO 195
<211> LENGTH: 108
<212> TYPE: PRT
<213> ORGANISM: Homo sapiens

<400> SEQUENCE: 195

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Gln Ala Ser Leu Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Arg Val Tyr Asp Pro Leu
                85                  90                  95

Thr Phe Gly Gln Gly Thr Lys Val Glu Ile Lys Arg
            100                 105

<210> SEQ ID NO 196
<211> LENGTH: 269
<212> TYPE: DNA
<213> ORGANISM: Homo sapiens

<400> SEQUENCE: 196
caggaaacag ctatgaccat gattacgcca agcttgcatg caaattctat ttcaaggaga    60
cagtcataat gaaataccta ttgcctacgg cagccgctgg attgttatta ctcgcggccc   120
agccggccat ggccgaggtg tttgactact ggggccaggg aaccctggtc accgtctcga   180
gcggtggagg cggttcaggc ggaggtggca gcggcggtgg cgggtcgacg gacatccaga   240
tgacccaggc ggccgcagaa caaaaactc                                    269

<210> SEQ ID NO 197
<211> LENGTH: 67

<212> TYPE: PRT
<213> ORGANISM: Homo sapiens

<400> SEQUENCE: 197

Met Lys Tyr Leu Leu Pro Thr Ala Ala Ala Gly Leu Leu Leu Leu Ala
1               5                   10                  15

Ala Gln Pro Ala Met Ala Glu Val Phe Asp Tyr Trp Gly Gln Gly Thr
            20                  25                  30

Leu Val Thr Val Ser Ser Gly Gly Gly Gly Ser Gly Gly Gly Gly Ser
        35                  40                  45

Gly Gly Gly Gly Ser Thr Asp Ile Gln Met Thr Gln Ala Ala Ala Glu
    50                  55                  60

Gln Lys Leu
65

<210> SEQ ID NO 198
<211> LENGTH: 90
<212> TYPE: DNA
<213> ORGANISM: Homo sapiens

<400> SEQUENCE: 198
catcatcatc accatcacgg ggccgcaatc tcagaagagg atctgaatgg ggccgcatag   60
actgttgaaa gttgtttagc aaaacctcat                                   90

<210> SEQ ID NO 199
<211> LENGTH: 30
<212> TYPE: PRT
<213> ORGANISM: Homo sapiens

<400> SEQUENCE: 199

His His His His His His Gly Ala Ala Ile Ser Glu Glu Asp Leu Asn
1               5                   10                  15

Gly Ala Ala Gln Thr Val Glu Ser Cys Leu Ala Lys Pro His
            20                  25                  30

<210> SEQ ID NO 200
<211> LENGTH: 348
<212> TYPE: DNA
<213> ORGANISM: Homo sapiens

<400> SEQUENCE: 200
gaggtgcagc tgttggagtc tgggggaggc ttggtacagc ctggggggtc cctgcgtctc   60
tcctgtgcag cctccggatt cacctttagc agctatgcca tgagctgggt ccgccaggct  120
ccagggaagg gtctagagtg ggtctcagct attagtggta gtggtggtag cacatactac  180
gcagactccg tgaagggccg gttcaccatc tcccgtgaca attccaagaa cacgctgtat  240
ctgcaaatga acagcctgcg tgccgaggac accgcggtat attactgtgc gaaaagttat  300
ggtgcttttg actactgggg ccagggaacc ctggtcaccg tctcgagc               348

<210> SEQ ID NO 201
<211> LENGTH: 360
<212> TYPE: DNA
<213> ORGANISM: Homo sapiens
<220> FEATURE:
<221> NAME/KEY: misc_feature
<222> LOCATION: 307, 308, 310, 311, 313, 314, 316, 317
<223> OTHER INFORMATION: n = A,T,C or G

<400> SEQUENCE: 201
gaggtgcagc tgttggagtc tgggggaggc ttggtacagc ctggggggtc cctgcgtctc   60

```
tcctgtgcag cctccggatt cacctttagc agctatgcca tgagctgggt ccgccaggct    120
ccagggaagg gtctagagtg ggtctcagct attagtggta gtggtggtag cacatactac    180
gcagactccg tgaagggccg gttcaccatc tcccgtgaca attccaagaa cacgctgtat    240
ctgcaaatga acagcctgcg tgccgaggac accgcggtat attactgtgc gaaagtttat    300
ggtgctnnkn nknnknnktt tgactactgg ggccagggaa ccctggtcac cgtctcgagc    360
```

<210> SEQ ID NO 202
<211> LENGTH: 120
<212> TYPE: PRT
<213> ORGANISM: Homo sapiens
<220> FEATURE:
<221> NAME/KEY: VARIANT
<222> LOCATION: 103, 104, 105, 106
<223> OTHER INFORMATION: Xaa = Any Amino Acid

<400> SEQUENCE: 202

```
Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Ser Tyr Gly Ala Xaa Xaa Xaa Xaa Phe Asp Tyr Trp Gly Gln
            100                 105                 110

Gly Thr Leu Val Thr Val Ser Ser
        115                 120
```

<210> SEQ ID NO 203
<211> LENGTH: 324
<212> TYPE: DNA
<213> ORGANISM: Homo sapiens

<400> SEQUENCE: 203

```
gacatccaga tgacccagtc tccatcctcc ctgtctgcat ctgtaggaga ccgtgtcacc     60
atcacttgcc gggcaagtca gagcattagc agctatttaa attggtacca gcagaaacca    120
gggaaagccc ctaagctcct gatctatgct gcatccagtt tgcaaagtgg ggtcccatca    180
cgtttcagtg gcagtggatc tgggacagat ttcactctca ccatcagcag tctgcaacct    240
gaagattttg ctacgtacta ctgtcaacag agttacagta cccctaatac gttcggccaa    300
gggaccaagg tggaaatcaa acgg                                           324
```

<210> SEQ ID NO 204
<211> LENGTH: 108
<212> TYPE: PRT
<213> ORGANISM: Homo sapiens

<400> SEQUENCE: 204

```
Asp Ile Gln Met Thr Gln Ser Pro Ser Ser Leu Ser Ala Ser Val Gly
 1               5                  10                  15

Asp Arg Val Thr Ile Thr Cys Arg Ala Ser Gln Ser Ile Ser Ser Tyr
```

```
                20                  25                  30
Leu Asn Trp Tyr Gln Gln Lys Pro Gly Lys Ala Pro Lys Leu Leu Ile
            35                  40                  45

Tyr Ala Ala Ser Ser Leu Gln Ser Gly Val Pro Ser Arg Phe Ser Gly
         50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Ser Tyr Ser Thr Pro Asn
                 85                  90                  95

Thr Phe Gly Gln Gly Thr Lys Val Glu Ile Lys Arg
            100                 105
```

<210> SEQ ID NO 205
<211> LENGTH: 324
<212> TYPE: DNA
<213> ORGANISM: Homo sapiens

<400> SEQUENCE: 205

| | | |
|---|---|---|
| gacatccaga tgacccagtc tccatcctcc ctgtctgcat ctgtaggaga ccgtgtcacc | 60 |
| atcacttgcc gggcaagtca gagcattatt aagcatttaa agtggtacca gcagaaacca | 120 |
| gggaaagccc ctaagctcct gatctatggt gcatcccggt tgcaaagtgg ggtcccatca | 180 |
| cgtttcagtg gcagtggatc tgggacagat ttcactctca ccatcagcag tctgcaacct | 240 |
| gaagattttg ctacgtacta ctgtcaacag ggggctcggt ggcctcagac gttcggccaa | 300 |
| gggaccaagg tggaaatcaa acgg | 324 |

<210> SEQ ID NO 206
<211> LENGTH: 108
<212> TYPE: PRT
<213> ORGANISM: Homo sapiens

<400> SEQUENCE: 206

```
Asp Ile Gln Met Thr Gln Ser Pro Ser Ser Leu Ser Ala Ser Val Gly
 1               5                  10                  15

Asp Arg Val Thr Ile Thr Cys Arg Ala Ser Gln Ser Ile Ile Lys His
             20                  25                  30

Leu Lys Trp Tyr Gln Gln Lys Pro Gly Lys Ala Pro Lys Leu Leu Ile
         35                  40                  45

Tyr Gly Ala Ser Arg Leu Gln Ser Gly Val Pro Ser Arg Phe Ser Gly
     50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Gly Ala Arg Trp Pro Gln
                 85                  90                  95

Thr Phe Gly Gln Gly Thr Lys Val Glu Ile Lys Arg
            100                 105
```

<210> SEQ ID NO 207
<211> LENGTH: 324
<212> TYPE: DNA
<213> ORGANISM: Homo sapiens

<400> SEQUENCE: 207

| | | |
|---|---|---|
| gacatccaga tgacccagtc tccatcctcc ctgtctgcat ctgtaggaga ccgtgtcacc | 60 |
| atcacttgcc gggcaagtca gagcatttat tatcatttaa agtggtacca gcagaaacca | 120 |
| gggaaagccc ctaagctcct gatctataag gcatccacgt tgcaaagtgg ggtcccatca | 180 | cgtttcagtg gcagtggatc tgggacagat ttcactctca ccatcagcag tctgcaacct    240 gaagattttg ctacgtacta ctgtcaacag gttcggaagg tgcctcggac gttcggccaa    300 gggaccaagg tggaaatcaa acgg    324

<210> SEQ ID NO 208
<211> LENGTH: 108
<212> TYPE: PRT
<213> ORGANISM: Homo sapiens

<400> SEQUENCE: 208

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Tyr Tyr His
            20                  25                  30

Leu Lys Trp Tyr Gln Gln Lys Pro Gly Lys Ala Pro Lys Leu Leu Ile
        35                  40                  45

Tyr Lys Ala Ser Thr Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Val Arg Lys Val Pro Arg
                85                  90                  95

Thr Phe Gly Gln Gly Thr Lys Val Glu Ile Lys Arg
            100                 105

<210> SEQ ID NO 209
<211> LENGTH: 108
<212> TYPE: PRT
<213> ORGANISM: Artificial Sequence
<220> FEATURE:
<223> OTHER INFORMATION: Synthetic polypeptide

<400> SEQUENCE: 209

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Phe Arg His
            20                  25                  30

Leu Lys Trp Tyr Gln Gln Lys Pro Gly Lys Ala Pro Lys Leu Leu Ile
        35                  40                  45

Tyr Ala Ala Ser Arg Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Val Ala Leu Tyr Pro Lys
                85                  90                  95

Thr Phe Gly Gln Gly Thr Lys Val Glu Ile Lys Arg
            100                 105

<210> SEQ ID NO 210
<211> LENGTH: 108
<212> TYPE: PRT
<213> ORGANISM: Artificial Sequence
<220> FEATURE:
<223> OTHER INFORMATION: Synthetic polypeptide

<400> SEQUENCE: 210

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ile Lys His
            20                  25                  30

Leu Lys Trp Tyr Gln Gln Lys Pro Gly Lys Ala Pro Lys Leu Leu Ile
        35                  40                  45

Tyr Gly Ala Ser Arg Leu Gln Ser Gly Val Pro Ser Arg Phe Ser Gly
 50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Gly Ala Arg Trp Pro Gln
                85                  90                  95

Thr Phe Gly Gln Gly Thr Lys Val Glu Ile Lys Arg
            100                 105

<210> SEQ ID NO 211
<211> LENGTH: 108
<212> TYPE: PRT
<213> ORGANISM: Artificial Sequence
<220> FEATURE:
<223> OTHER INFORMATION: Synthetic polypeptide

<400> SEQUENCE: 211

Asp Ile Gln Met Thr Gln Ser Pro Ser Ser Leu Ser Ala Ser Val Gly
 1               5                  10                  15

Asp Arg Val Thr Ile Thr Cys Arg Ala Ser Gln Ser Ile Tyr Tyr His
            20                  25                  30

Leu Lys Trp Tyr Gln Gln Lys Pro Gly Lys Ala Pro Lys Leu Leu Ile
        35                  40                  45

Tyr Lys Ala Ser Thr Leu Gln Ser Gly Val Pro Ser Arg Phe Ser Gly
 50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Val Arg Lys Val Pro Arg
                85                  90                  95

Thr Phe Gly Gln Gly Thr Lys Val Glu Ile Lys Arg
            100                 105

<210> SEQ ID NO 212
<211> LENGTH: 108
<212> TYPE: PRT
<213> ORGANISM: Artificial Sequence
<220> FEATURE:
<223> OTHER INFORMATION: Synthetic polypeptide

<400> SEQUENCE: 212

Asp Ile Gln Thr Thr Gln Ser Pro Ser Ser Leu Ser Ala Ser Val Gly
 1               5                  10                  15

Asp Arg Val Thr Ile Thr Cys Arg Ala Ser Gln Tyr Ile Gly Arg Tyr
            20                  25                  30

Leu Arg Trp Tyr Gln Gln Lys Pro Gly Lys Ala Pro Lys Leu Leu Ile
        35                  40                  45

Tyr Asp Ser Ser Val Leu Gln Ser Gly Val Pro Ser Arg Phe Ser Gly
 50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Arg Tyr Arg Met Pro Tyr
                85                  90                  95

Thr Phe Gly Gln Gly Thr Arg Val Glu Ile Lys Arg

<210> SEQ ID NO 213
<211> LENGTH: 108
<212> TYPE: PRT
<213> ORGANISM: Artificial Sequence
<220> FEATURE:
<223> OTHER INFORMATION: Synthetic polypeptide

<400> SEQUENCE: 213

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Tyr Ile Gly Arg Tyr
            20                  25                  30

Leu Arg Trp Tyr Gln Gln Lys Pro Gly Lys Ala Pro Lys Leu Leu Ile
        35                  40                  45

Tyr Asp Ser Ser Val Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Arg Tyr Met Gln Pro Phe
                85                  90                  95

Thr Phe Gly Gln Gly Thr Lys Val Glu Ile Lys Arg
            100                 105

<210> SEQ ID NO 214
<211> LENGTH: 108
<212> TYPE: PRT
<213> ORGANISM: Artificial Sequence
<220> FEATURE:
<223> OTHER INFORMATION: Synthetic polypeptide

<400> SEQUENCE: 214

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Trp Ile Gly Arg Tyr
            20                  25                  30

Leu Arg Trp Tyr Gln Gln Lys Pro Gly Lys Ala Pro Lys Leu Leu Ile
        35                  40                  45

Tyr Asn Gly Ser Gln Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Arg Tyr Leu Gln Pro Tyr
                85                  90                  95

Thr Phe Gly Gln Gly Thr Lys Val Glu Ile Lys Arg
            100                 105

<210> SEQ ID NO 215
<211> LENGTH: 108
<212> TYPE: PRT
<213> ORGANISM: Artificial Sequence
<220> FEATURE:
<223> OTHER INFORMATION: Synthetic polypeptide

<400> SEQUENCE: 215

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Tyr Ile Ser Arg Gln
            20                  25                  30

Leu Arg Trp Tyr Gln Gln Lys Pro Gly Lys Ala Pro Arg Leu Leu Ile
            35                  40                  45

Tyr Gly Ala Val Ser Leu Gln Ser Gly Ile Pro Ser Arg Phe Ser Gly
        50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Arg Tyr Ile Thr Tyr Asn
                85                  90                  95

Thr Phe Gly Gln Gly Thr Lys Val Glu Val Lys Arg
            100                 105

<210> SEQ ID NO 216
<211> LENGTH: 108
<212> TYPE: PRT
<213> ORGANISM: Artificial Sequence
<220> FEATURE:
<223> OTHER INFORMATION: Synthetic polypeptide

<400> SEQUENCE: 216

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Tyr Ile Gly Arg Tyr
            20                  25                  30

Leu Arg Trp Tyr Gln Gln Lys Pro Gly Lys Ala Pro Lys Leu Leu Ile
            35                  40                  45

Tyr Asp Ser Ser Val Leu Gln Ser Gly Val Pro Ser Arg Phe Ser Gly
        50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Arg Tyr Ser Ser Pro Tyr
                85                  90                  95

Thr Phe Gly Gln Gly Thr Lys Val Glu Ile Lys Arg
            100                 105

<210> SEQ ID NO 217
<211> LENGTH: 108
<212> TYPE: PRT
<213> ORGANISM: Artificial Sequence
<220> FEATURE:
<223> OTHER INFORMATION: Synthetic polypeptide

<400> SEQUENCE: 217

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Trp Ile His Arg Gln
            20                  25                  30

Leu Lys Trp Tyr Gln Gln Lys Pro Gly Lys Ala Pro Lys Leu Leu Ile
            35                  40                  45

Tyr Tyr Ala Ser Ile Leu Gln Ser Gly Val Pro Ser Arg Phe Ser Gly
        50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Thr Phe Ser Lys Pro Ser
                85                  90                  95

Thr Phe Gly Gln Gly Thr Lys Val Glu Ile Lys Arg
            100                 105

```
<210> SEQ ID NO 218
<211> LENGTH: 108
<212> TYPE: PRT
<213> ORGANISM: Artificial Sequence
<220> FEATURE:
<223> OTHER INFORMATION: Synthetic polypeptide

<400> SEQUENCE: 218
```

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln His Ile His Arg Glu
            20                  25                  30

Leu Arg Trp Tyr Gln Gln Lys Pro Gly Lys Ala Pro Lys Leu Leu Ile
        35                  40                  45

Tyr Gln Ala Ser Arg Leu Gln Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Lys Tyr Leu Pro Pro Tyr
                85                  90                  95

Thr Phe Gly Gln Gly Thr Lys Val Glu Ile Lys Arg
            100                 105

```
<210> SEQ ID NO 219
<211> LENGTH: 108
<212> TYPE: PRT
<213> ORGANISM: Artificial Sequence
<220> FEATURE:
<223> OTHER INFORMATION: Synthetic polypeptide

<400> SEQUENCE: 219
```

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln His Ile His Arg Glu
            20                  25                  30

Leu Arg Trp Tyr Gln Gln Lys Pro Gly Lys Ala Pro Lys Leu Leu Ile
        35                  40                  45

Tyr Gln Ala Ser Arg Leu Gln Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Arg Tyr Arg Val Pro Tyr
                85                  90                  95

Thr Phe Gly Gln Gly Thr Lys Val Glu Ile Lys Arg
            100                 105

```
<210> SEQ ID NO 220
<211> LENGTH: 108
<212> TYPE: PRT
<213> ORGANISM: Artificial Sequence
<220> FEATURE:
<223> OTHER INFORMATION: Synthetic polypeptide

<400> SEQUENCE: 220
```

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Gly Arg Arg
            20                  25                  30

Leu Lys Trp Tyr Gln Gln Lys Pro Gly Ala Ala Pro Arg Leu Leu Ile
        35                  40                  45

```
Tyr Arg Thr Ser Trp Leu Gln Ser Gly Val Pro Ser Arg Phe Ser Gly
        50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Thr Ser Gln Trp Pro His
                85                  90                  95

Thr Phe Gly Gln Gly Thr Lys Val Glu Ile Lys Arg
            100                 105
```

<210> SEQ ID NO 221
<211> LENGTH: 108
<212> TYPE: PRT
<213> ORGANISM: Artificial Sequence
<220> FEATURE:
<223> OTHER INFORMATION: Synthetic polypeptide

<400> SEQUENCE: 221

```
Asp Ile Gln Met Thr Gln Ser Pro Ser Ser Leu Ser Ala Ser Val Gly
 1               5                  10                  15

Asp Arg Val Thr Ile Thr Cys Arg Ala Ser Gln Lys Ile Tyr Lys Asn
            20                  25                  30

Leu Arg Trp Tyr Gln Gln Lys Pro Gly Lys Ala Pro Lys Leu Leu Ile
        35                  40                  45

Tyr Asn Ser Ser Ile Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Arg Tyr Leu Ser Pro Tyr
                85                  90                  95

Thr Phe Gly Gln Gly Thr Lys Val Glu Ile Lys Arg
            100                 105
```

<210> SEQ ID NO 222
<211> LENGTH: 108
<212> TYPE: PRT
<213> ORGANISM: Artificial Sequence
<220> FEATURE:
<223> OTHER INFORMATION: Synthetic polypeptide

<400> SEQUENCE: 222

```
Asp Ile Gln Met Thr Gln Ser Pro Ser Ser Leu Ser Ala Ser Val Gly
 1               5                  10                  15

Asp Arg Val Thr Ile Thr Cys Arg Ala Ser Gln Lys Ile Tyr Asn Asn
            20                  25                  30

Leu Arg Trp Tyr Gln Gln Lys Pro Gly Lys Ala Pro Lys Leu Leu Ile
        35                  40                  45

Tyr Asn Thr Ser Ile Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Arg Trp Arg Ala Pro Tyr
                85                  90                  95

Thr Phe Gly Gln Gly Thr Lys Val Glu Ile Lys Arg
            100                 105
```

<210> SEQ ID NO 223
<211> LENGTH: 108
<212> TYPE: PRT

```
<213> ORGANISM: Artificial Sequence
<220> FEATURE:
<223> OTHER INFORMATION: Synthetic polypeptide

<400> SEQUENCE: 223

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Trp Ile Tyr Lys Ser
            20                  25                  30

Leu Gly Trp Tyr Gln Gln Lys Pro Gly Lys Ala Pro Lys Leu Leu Ile
        35                  40                  45

Tyr Gln Ser Ser Leu Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr His Gln Met Pro Arg
                85                  90                  95

Thr Phe Gly Gln Gly Thr Lys Val Glu Ile Lys Arg
            100                 105

<210> SEQ ID NO 224
<211> LENGTH: 108
<212> TYPE: PRT
<213> ORGANISM: Artificial Sequence
<220> FEATURE:
<223> OTHER INFORMATION: Synthetic polypeptide

<400> SEQUENCE: 224

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Trp Ile Tyr Arg His
            20                  25                  30

Leu Arg Trp Tyr Gln Gln Lys Pro Gly Lys Ala Pro Lys Leu Leu Ile
        35                  40                  45

Tyr Asp Ala Ser Arg Leu Gln Ser Gly Val Pro Thr Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Thr His Asn Pro Pro Lys
                85                  90                  95

Thr Phe Gly Gln Gly Thr Lys Val Glu Ile Lys Arg
            100                 105

<210> SEQ ID NO 225
<211> LENGTH: 108
<212> TYPE: PRT
<213> ORGANISM: Artificial Sequence
<220> FEATURE:
<223> OTHER INFORMATION: Synthetic polypeptide

<400> SEQUENCE: 225

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Arg Asn Ser Phe Leu Gln Ser Gly Val Pro Thr Arg Phe Ser Gly
    50                  55                  60
```

```
Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Thr Tyr Thr Val Pro Pro
                 85                  90                  95

Thr Phe Gly Gln Gly Thr Lys Val Glu Ile Lys Gln
            100                 105
```

<210> SEQ ID NO 226
<211> LENGTH: 108
<212> TYPE: PRT
<213> ORGANISM: Artificial Sequence
<220> FEATURE:
<223> OTHER INFORMATION: Synthetic polypeptide

<400> SEQUENCE: 226

```
Asp Ile Gln Met Thr Gln Ser Pro Ser Ser Leu Ser Ala Ser Val Gly
  1               5                  10                  15

Asp Arg Val Thr Ile Thr Cys Arg Ala Ser Gln Lys Ile Ala Thr Tyr
                 20                  25                  30

Leu Asn Trp Tyr Gln Gln Lys Pro Gly Lys Ala Pro Lys Leu Leu Ile
             35                  40                  45

Tyr Arg Ser Ser Ser Leu Gln Ser Ala Val Pro Thr Arg Phe Ser Gly
     50                  55                  60

Ser Gly Ser Gly Thr Val Phe Thr Leu Thr Ile Ser Ser Leu Gln Pro
 65                  70                  75                  80

Glu Asp Phe Ala Thr Tyr Tyr Cys Gln Gln Thr Tyr Ala Val Pro Pro
                 85                  90                  95

Thr Phe Gly Gln Gly Thr Lys Val Glu Ile Lys Arg
            100                 105
```

<210> SEQ ID NO 227
<211> LENGTH: 108
<212> TYPE: PRT
<213> ORGANISM: Artificial Sequence
<220> FEATURE:
<223> OTHER INFORMATION: Synthetic polypeptide

<400> SEQUENCE: 227

```
Asp Ile Gln Met Thr Gln Ser Pro Ser Ser Leu Ser Ala Ser Val Gly
  1               5                  10                  15

Asp Arg Val Thr Ile Thr Cys Arg Ala Ser Gln Ser Ile Ser Ser Tyr
                 20                  25                  30

Leu Asn Trp Tyr Gln Gln Lys Pro Gly Lys Ala Pro Thr Leu Leu Ile
             35                  40                  45

Tyr Arg Leu Ser Val Leu Gln Ser Gly Val Pro Thr Arg Phe Ser Gly
     50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Thr Tyr Asn Val Pro Pro
                 85                  90                  95

Thr Phe Gly Gln Gly Thr Lys Val Glu Ile Lys Arg
            100                 105
```

<210> SEQ ID NO 228
<211> LENGTH: 108
<212> TYPE: PRT
<213> ORGANISM: Artificial Sequence
<220> FEATURE:
<223> OTHER INFORMATION: Synthetic polypeptide

<400> SEQUENCE: 228

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Arg Asn Ser Gln Leu Gln Ser Gly Val Pro Thr Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Thr Phe Ala Val Pro Pro
                85                  90                  95

Thr Phe Gly Gln Gly Thr Lys Val Glu Ile Lys Arg
            100                 105

<210> SEQ ID NO 229
<211> LENGTH: 108
<212> TYPE: PRT
<213> ORGANISM: Artificial Sequence
<220> FEATURE:
<223> OTHER INFORMATION: Synthetic polypeptide

<400> SEQUENCE: 229

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Arg Asn Ser Pro Leu Gln Ser Gly Val Pro Thr Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Thr Tyr Arg Val Pro Pro
                85                  90                  95

Thr Phe Gly Gln Gly Thr Lys Val Glu Ile Lys Arg
            100                 105

<210> SEQ ID NO 230
<211> LENGTH: 109
<212> TYPE: PRT
<213> ORGANISM: Artificial Sequence
<220> FEATURE:
<223> OTHER INFORMATION: Synthetic polypeptide

<400> SEQUENCE: 230

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln His Ile Gly Leu Trp
            20                  25                  30

Leu His Asn Trp Tyr Gln Gln Lys Pro Gly Lys Ala Pro Lys Leu Leu
        35                  40                  45

Ile Tyr Arg Ser Ser Leu Leu Gln Ser Gly Val Pro Ser Arg Phe Ser
    50                  55                  60

Gly Ser Gly Ser Gly Thr Asp Phe Thr Leu Thr Ile Ser Ser Leu Gln
65                  70                  75                  80

-continued

```
Pro Glu Asp Phe Ala Thr Tyr Tyr Cys Gln Gln Lys Tyr Asn Leu Pro
                85                  90                  95

Tyr Thr Ser Gly Gln Gly Thr Lys Val Glu Ile Lys Arg
            100                 105
```

<210> SEQ ID NO 231
<211> LENGTH: 108
<212> TYPE: PRT
<213> ORGANISM: Artificial Sequence
<220> FEATURE:
<223> OTHER INFORMATION: Synthetic polypeptide

<400> SEQUENCE: 231

```
Asp Ile Gln Met Thr Gln Ser Pro Ser Leu Ser Ala Ser Val Gly
 1               5                  10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Arg Asn Ser Pro Leu Gln Ser Gly Val Pro Thr Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Thr Tyr Ser Ile Pro Pro
                85                  90                  95

Thr Phe Gly Gln Gly Thr Lys Val Glu Ile Lys Arg
            100                 105
```

<210> SEQ ID NO 232
<211> LENGTH: 108
<212> TYPE: PRT
<213> ORGANISM: Artificial Sequence
<220> FEATURE:
<223> OTHER INFORMATION: Synthetic polypeptide

<400> SEQUENCE: 232

```
Asp Ile Gln Met Thr Gln Ser Pro Ser Ser Leu Ser Ala Ser Val Gly
 1               5                  10                  15

Asp Arg Val Thr Ile Thr Cys Arg Ala Ser Arg Pro Ile Gly Thr Thr
            20                  25                  30

Leu Ser Trp Tyr Gln Gln Lys Pro Gly Lys Ala Pro Thr Leu Leu Ile
        35                  40                  45

Trp Phe Gly Ser Arg Leu Gln Ser Gly Val Pro Thr Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Ala Gln Ala Gly Thr His Pro Thr
                85                  90                  95

Thr Phe Gly Gln Gly Thr Lys Val Glu Ile Lys Arg
            100                 105
```

<210> SEQ ID NO 233
<211> LENGTH: 108
<212> TYPE: PRT
<213> ORGANISM: Artificial Sequence
<220> FEATURE:
<223> OTHER INFORMATION: Synthetic polypeptide

<400> SEQUENCE: 233

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Lys Tyr Ile Gly Ser Gln
            20                  25                  30

Leu Asn Trp Tyr Gln Gln Lys Pro Gly Lys Ala Pro Thr Leu Leu Ile
        35                  40                  45

Ala Trp Ala Ser Val Leu Gln Ser Gly Val Pro Thr Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Arg Gln Gly Ala Ala Ser Pro Arg
                85                  90                  95

Thr Phe Gly Gln Gly Thr Lys Val Glu Ile Lys Arg
            100                 105
```

<210> SEQ ID NO 234
<211> LENGTH: 108
<212> TYPE: PRT
<213> ORGANISM: Artificial Sequence
<220> FEATURE:
<223> OTHER INFORMATION: Synthetic polypeptide

<400> SEQUENCE: 234

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Phe Ile Tyr Arg Tyr
            20                  25                  30

Leu Ser Trp Tyr Gln Gln Lys Pro Gly Lys Val Pro Thr Leu Leu Ile
        35                  40                  45

Tyr Asn Ala Ser Tyr Leu Gln Ser Gly Val Pro Thr Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln His Ala His Leu Pro Arg
                85                  90                  95

Thr Phe Gly Gln Gly Thr Lys Val Glu Ile Lys Arg
            100                 105
```

<210> SEQ ID NO 235
<211> LENGTH: 108
<212> TYPE: PRT
<213> ORGANISM: Artificial Sequence
<220> FEATURE:
<223> OTHER INFORMATION: Synthetic polypeptide

<400> SEQUENCE: 235

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Trp Ile Gly Ser Gln
            20                  25                  30

Leu Ser Trp Tyr Gln Gln Lys Pro Gly Lys Ala Pro Lys Leu Leu Ile
        35                  40                  45

Met Trp Arg Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Ala Gln Gly Ala Ala Leu Pro Arg
                85                  90                  95
```

```
Thr Phe Gly Gln Gly Thr Lys Val Glu Ile Lys Arg
            100                 105
```

<210> SEQ ID NO 236
<211> LENGTH: 108
<212> TYPE: PRT
<213> ORGANISM: Artificial Sequence
<220> FEATURE:
<223> OTHER INFORMATION: Synthetic polypeptide

<400> SEQUENCE: 236

```
Asp Ile Gln Met Thr Gln Ser Pro Ser Ser Leu Ser Ala Ser Val Gly
 1               5                  10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Thr Leu Leu Ile
        35                  40                  45

Arg Arg Val Ser Val Leu Gln Ser Gly Val Pro Thr Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Ser Gln Gly Arg Trp Pro Pro Arg
                85                  90                  95

Thr Phe Gly Gln Gly Thr Lys Val Glu Ile Lys Arg
            100                 105
```

<210> SEQ ID NO 237
<211> LENGTH: 108
<212> TYPE: PRT
<213> ORGANISM: Artificial Sequence
<220> FEATURE:
<223> OTHER INFORMATION: Synthetic polypeptide

<400> SEQUENCE: 237

```
Asp Ile Gln Met Thr Gln Ser Pro Ser Ser Leu Ser Ala Ser Val Gly
 1               5                  10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Tyr Gly Ser Val Leu Gln Ser Gly Val Pro Thr Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Ser Gln Gly Arg Trp Pro Pro Arg
                85                  90                  95

Thr Phe Gly Gln Gly Thr Lys Val Glu Ile Lys Arg
            100                 105
```

<210> SEQ ID NO 238
<211> LENGTH: 116
<212> TYPE: PRT
<213> ORGANISM: Artificial Sequence
<220> FEATURE:
<223> OTHER INFORMATION: Synthetic polypeptide

<400> SEQUENCE: 238

```
Glu Val Gln Leu Leu Glu Ser Gly Gly Gly Leu Val Gln Pro Gly Gly
 1               5                  10                  15
```

```
Ser Leu Arg Leu Ser Cys Ala Ala Ser Gly Phe Thr Phe Trp Pro Tyr
            20                  25                  30

Thr Met Ser Trp Val Arg Gln Ala Pro Gly Lys Gly Leu Glu Trp Val
        35                  40                  45

Ser Thr Ile Ser Pro Phe Gly Ser Thr Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Gly Gly Lys Asp Phe Asp Tyr Trp Gly Gln Gly Thr Leu Val
            100                 105                 110

Thr Val Ser Ser
        115
```

<210> SEQ ID NO 239
<211> LENGTH: 117
<212> TYPE: PRT
<213> ORGANISM: Artificial Sequence
<220> FEATURE:
<223> OTHER INFORMATION: Synthetic polypeptide

<400> SEQUENCE: 239

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Trp Pro Tyr
            20                  25                  30

Thr Met Ser Trp Val Arg Gln Ala Pro Gly Lys Gly Leu Glu Trp Val
        35                  40                  45

Ser Thr Ile Ser Pro Phe Gly Ser Thr Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Gly Asn Leu Glu Pro Phe Asp Tyr Trp Gly Gln Gly Thr Leu
            100                 105                 110

Val Thr Val Ser Ser
        115
```

<210> SEQ ID NO 240
<211> LENGTH: 117
<212> TYPE: PRT
<213> ORGANISM: Artificial Sequence
<220> FEATURE:
<223> OTHER INFORMATION: Synthetic polypeptide

<400> SEQUENCE: 240

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Trp Pro Tyr
            20                  25                  30

Thr Met Ser Trp Val Arg Gln Ala Pro Gly Lys Gly Leu Glu Trp Val
        35                  40                  45

Ser Thr Ile Ser Pro Phe Gly Ser Thr Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80
```

```
Leu Gln Met Asn Ser Leu Arg Ala Glu Asp Thr Ala Val Tyr Tyr Cys
                85                  90                  95

Ala Lys Lys Leu Ser Asn Gly Phe Asp Tyr Trp Gly Gln Gly Thr Leu
            100                 105                 110

Val Thr Val Ser Ser
        115
```

<210> SEQ ID NO 241
<211> LENGTH: 118
<212> TYPE: PRT
<213> ORGANISM: Artificial Sequence
<220> FEATURE:
<223> OTHER INFORMATION: Synthetic polypeptide

<400> SEQUENCE: 241

```
Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Trp Pro Tyr
            20                  25                  30

Thr Met Ser Trp Val Arg Gln Ala Pro Gly Lys Gly Leu Glu Trp Val
        35                  40                  45

Ser Thr Ile Ser Pro Phe Gly Ser Thr Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Val Val Lys Asp Asn Thr Phe Asp Tyr Trp Gly Gln Gly Thr
            100                 105                 110

Leu Val Thr Val Ser Ser
        115
```

<210> SEQ ID NO 242
<211> LENGTH: 118
<212> TYPE: PRT
<213> ORGANISM: Artificial Sequence
<220> FEATURE:
<223> OTHER INFORMATION: Synthetic polypeptide

<400> SEQUENCE: 242

```
Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Trp Pro Tyr
            20                  25                  30

Thr Met Ser Trp Val Arg Gln Ala Pro Gly Lys Gly Leu Glu Trp Val
        35                  40                  45

Ser Thr Ile Ser Pro Phe Gly Ser Thr Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asn Thr Gly Gly Lys Gln Phe Asp Tyr Trp Gly Gln Gly Thr
            100                 105                 110

Leu Val Thr Val Ser Ser
        115
```

<210> SEQ ID NO 243
<211> LENGTH: 118
<212> TYPE: PRT
<213> ORGANISM: Artificial Sequence
<220> FEATURE:
<223> OTHER INFORMATION: Synthetic polypeptide

<400> SEQUENCE: 243

```
Glu Val Gln Leu Leu Glu Ser Gly Gly Gly Leu Val Gln Pro Gly Gly
  1               5                  10                  15

Ser Leu Arg Leu Ser Cys Ala Ala Ser Gly Phe Thr Phe Trp Pro Tyr
             20                  25                  30

Thr Met Ser Trp Val Arg Gln Ala Pro Gly Lys Gly Leu Glu Trp Val
         35                  40                  45

Ser Thr Ile Ser Pro Phe Gly Ser Thr Thr Tyr Tyr Ala Asp Ser Val
     50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Lys Lys Thr Gly Pro Ser Ser Phe Asp Tyr Trp Gly Gln Gly Thr
            100                 105                 110

Leu Val Thr Val Ser Ser
            115
```

<210> SEQ ID NO 244
<211> LENGTH: 120
<212> TYPE: PRT
<213> ORGANISM: Artificial Sequence
<220> FEATURE:
<223> OTHER INFORMATION: Synthetic polypeptide

<400> SEQUENCE: 244

```
Glu Val Gln Leu Leu Glu Ser Gly Gly Gly Leu Val Gln Pro Gly Gly
  1               5                  10                  15

Ser Leu Arg Leu Ser Cys Ala Ala Ser Gly Phe Thr Phe Trp Pro Tyr
             20                  25                  30

Thr Met Ser Trp Val Arg Gln Ala Pro Gly Lys Gly Leu Glu Trp Val
         35                  40                  45

Ser Thr Ile Ser Pro Phe Gly Ser Thr Thr Tyr Tyr Ala Asp Ser Val
     50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Lys Arg Thr Glu Asn Arg Gly Val Ser Phe Asp Tyr Trp Gly Gln
            100                 105                 110

Gly Thr Leu Val Thr Val Ser Ser
            115                 120
```

<210> SEQ ID NO 245
<211> LENGTH: 122
<212> TYPE: PRT
<213> ORGANISM: Artificial Sequence
<220> FEATURE:
<223> OTHER INFORMATION: Synthetic polypeptide

<400> SEQUENCE: 245

```
Glu Val Gln Leu Leu Glu Ser Gly Gly Gly Leu Val Gln Pro Gly Gly
  1               5                  10                  15
```

-continued

Ser Leu Arg Leu Ser Cys Ala Ala Ser Gly Phe Thr Phe Trp Pro Tyr
        20                  25                  30

Thr Met Ser Trp Val Arg Gln Ala Pro Gly Lys Gly Leu Glu Trp Val
        35                  40                  45

Ser Thr Ile Ser Pro Phe Gly Ser Thr Thr Tyr Ala Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                85                  90                  95

Ala Lys Ser Asp Val Leu Lys Thr Gly Leu Asp Gly Phe Asp Tyr Trp
                100                 105                 110

Gly Gln Gly Thr Leu Val Thr Val Ser Ser
            115                 120

<210> SEQ ID NO 246
<211> LENGTH: 119
<212> TYPE: PRT
<213> ORGANISM: Artificial Sequence
<220> FEATURE:
<223> OTHER INFORMATION: Synthetic polypeptide

<400> SEQUENCE: 246

Glu Val Gln Leu Leu Glu Ser Gly Gly Gly Leu Val Gln Pro Gly Gly
 1               5                   10                  15

Ser Leu Arg Leu Ser Cys Ala Ala Ser Gly Phe Thr Phe Met Ala Tyr
            20                  25                  30

Gln Met Ala Trp Val Arg Gln Ala Pro Gly Lys Gly Leu Glu Trp Val
        35                  40                  45

Ser Thr Ile His Gln Thr Gly Phe Thr Tyr Tyr Ala Asp Ser Val Lys
 50                  55                  60

Gly Arg Phe Thr Ile Ser Arg Asp Asn Ser Lys Asn Thr Leu Tyr Leu
 65                  70                  75                  80

Gln Met Asn Ser Leu Arg Ala Glu Asp Thr Ala Val Tyr Tyr Cys Ala
                85                  90                  95

Lys Val Arg Ser Met Arg Pro Tyr Lys Phe Asp Tyr Trp Gly Gln Gly
                100                 105                 110

Thr Leu Val Thr Val Ser Ser
            115

<210> SEQ ID NO 247
<211> LENGTH: 120
<212> TYPE: PRT
<213> ORGANISM: Artificial Sequence
<220> FEATURE:
<223> OTHER INFORMATION: Synthetic polypeptide

<400> SEQUENCE: 247

Glu Val Gln Leu Leu Glu Ser Gly Gly Gly Leu Val Gln Pro Gly Gly
 1               5                   10                  15

Ser Leu Arg Leu Ser Cys Ala Ala Ser Gly Phe Thr Phe Lys Asp Tyr
            20                  25                  30

Asp Met Thr Trp Val Arg Gln Ala Pro Gly Lys Gly Leu Glu Trp Val
        35                  40                  45

Ser Met Ile Ser Ser Ser Gly Leu Trp Thr Tyr Tyr Ala Asp Ser Val
 50                  55                  60

Lys Gly Arg Phe Thr Ile Ser Arg Asp Asn Ser Lys Asn Thr Leu Tyr

```
               65                  70                  75                  80
Leu Gln Met Asn Ser Leu Arg Ala Glu Asp Thr Ala Val Tyr Tyr Cys
                    85                  90                  95

Ala Lys Gly Phe Arg Leu Phe Pro Arg Thr Phe Asp Tyr Trp Gly Gln
                100                 105                 110

Gly Thr Leu Val Thr Val Ser Ser
                115                 120

<210> SEQ ID NO 248
<211> LENGTH: 121
<212> TYPE: PRT
<213> ORGANISM: Artificial Sequence
<220> FEATURE:
<223> OTHER INFORMATION: Synthetic polypeptide

<400> SEQUENCE: 248

Glu Val Gln Leu Leu Glu Ser Gly Gly Gly Leu Val Gln Pro Gly Gly
  1               5                  10                  15

Ser Leu Arg Leu Ser Cys Ala Ala Ser Gly Phe Thr Phe His Asp Tyr
                 20                  25                  30

Val Met Gly Trp Ala Arg Gln Ala Pro Gly Lys Gly Leu Glu Trp Val
             35                  40                  45

Ser Leu Ile Lys Pro Asn Gly Ser Pro Thr Tyr Tyr Ala Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Lys Gly Arg Gly Arg Phe Asn Val Leu Gln Phe Asp Tyr Trp Gly
                100                 105                 110

Gln Gly Thr Leu Val Thr Val Ser Ser
                115                 120

<210> SEQ ID NO 249
<211> LENGTH: 118
<212> TYPE: PRT
<213> ORGANISM: Artificial Sequence
<220> FEATURE:
<223> OTHER INFORMATION: Synthetic polypeptide

<400> SEQUENCE: 249

Glu Val Gln Leu Leu Glu Ser Gly Gly Gly Leu Val Gln Pro Gly Gly
  1               5                  10                  15

Ser Leu Arg Leu Ser Cys Arg Ala Ser Gly Phe Thr Phe Arg His Tyr
                 20                  25                  30

Arg Met Gly Trp Val Arg Gln Ala Pro Gly Lys Gly Leu Glu Trp Val
             35                  40                  45

Ser Trp Ile Arg Pro Asp Gly Thr Phe Thr Tyr Tyr Ala Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Lys Ser Tyr Met Gly Asp Arg Phe Asp Tyr Trp Gly Gln Gly Thr
                100                 105                 110

Leu Val Thr Val Ser Ser
                115
```

<210> SEQ ID NO 250
<211> LENGTH: 116
<212> TYPE: PRT
<213> ORGANISM: Artificial Sequence
<220> FEATURE:
<223> OTHER INFORMATION: Synthetic polypeptide

<400> SEQUENCE: 250

```
Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Met Trp Asp
             20                  25                  30

Lys Met Gly Trp Val Arg Gln Ala Pro Gly Lys Gly Leu Glu Trp Val
         35                  40                  45

Ser Phe Ile Gly Arg Glu Gly Tyr Gly Thr Tyr Tyr Ala Asp Ser Val
     50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Lys Ser Val Ala Ser Phe Asp Tyr Trp Gly Gln Gly Thr Leu Val
            100                 105                 110

Thr Val Ser Ser
        115
```

<210> SEQ ID NO 251
<211> LENGTH: 117
<212> TYPE: PRT
<213> ORGANISM: Artificial Sequence
<220> FEATURE:
<223> OTHER INFORMATION: Synthetic polypeptide

<400> SEQUENCE: 251

```
Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Trp Ala Tyr
             20                  25                  30

Pro Met Ser Trp Val Arg Gln Ala Pro Gly Lys Gly Leu Glu Trp Val
         35                  40                  45

Ser Ser Ile Ser Ser Trp Gly Thr Gly Thr Tyr Tyr Ala Asp Ser Val
     50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Lys Gly Gly Gln Ser Phe Asp Tyr Trp Gly Gln Gly Thr Leu
            100                 105                 110

Val Thr Val Ser Ser
        115
```

<210> SEQ ID NO 252
<211> LENGTH: 120
<212> TYPE: PRT
<213> ORGANISM: Artificial Sequence
<220> FEATURE:
<223> OTHER INFORMATION: Synthetic polypeptide

<400> SEQUENCE: 252

```
Glu Val Gln Leu Leu Glu Ser Gly Gly Gly Leu Val Gln Pro Gly Gly
```

```
                1               5                  10                 15
Ser Leu Arg Leu Ser Cys Ala Ala Ser Gly Phe Thr Phe Asp Leu Tyr
                20                      25                 30

Asp Met Ser Trp Val Arg Gln Ala Pro Gly Lys Gly Leu Glu Trp Val
            35                      40                 45

Ser Ser Ile Val Asn Ser Gly Val Arg Thr Tyr Tyr Ala Asp Ser Val
 50                     55                      60

Lys Gly Arg Phe Thr Ile Ser Arg Asp Asn Ser Lys Asn Thr Leu Tyr
 65                     70                  75                      80

Leu Gln Met Asn Ser Leu Arg Ala Glu Asp Thr Ala Val Tyr Tyr Cys
                 85                      90                      95

Ala Lys Leu Asn Gln Ser Tyr His Trp Asp Phe Asp Tyr Trp Gly Gln
                100                     105                110

Gly Thr Leu Val Thr Val Ser Ser
                115                 120
```

<210> SEQ ID NO 253
<211> LENGTH: 123
<212> TYPE: PRT
<213> ORGANISM: Artificial Sequence
<220> FEATURE:
<223> OTHER INFORMATION: Synthetic polypeptide

<400> SEQUENCE: 253

```
Glu Val Gln Leu Leu Glu Ser Gly Gly Gly Leu Val Gln Pro Gly Gly
 1               5                  10                 15

Ser Leu Arg Leu Ser Cys Ala Ala Ser Gly Phe Thr Phe Ser Lys Tyr
                20                      25                 30

Trp Met Ser Trp Val Arg Gln Ala Pro Gly Lys Gly Leu Glu Trp Val
            35                      40                 45

Ser Ser Ile Asp Phe Met Gly Pro His Thr Tyr Tyr Ala Asp Ser Val
 50                     55                      60

Lys Gly Arg Phe Thr Ile Ser Arg Asp Asn Ser Lys Asn Thr Leu Tyr
 65                     70                  75                      80

Leu Gln Met Asn Ser Leu Arg Ala Glu Asp Thr Ala Val Tyr Tyr Cys
                 85                      90                      95

Ala Lys Gly Arg Thr Ser Met Leu Pro Met Lys Gly Lys Phe Asp Tyr
                100                     105                110

Trp Gly Gln Gly Thr Leu Val Thr Val Ser Ser
                115                 120
```

<210> SEQ ID NO 254
<211> LENGTH: 119
<212> TYPE: PRT
<213> ORGANISM: Artificial Sequence
<220> FEATURE:
<223> OTHER INFORMATION: Synthetic polypeptide

<400> SEQUENCE: 254

```
Glu Val Gln Leu Leu Glu Ser Gly Gly Gly Leu Val Gln Pro Gly Gly
 1               5                  10                 15

Ser Leu Arg Leu Ser Cys Ala Ala Ser Gly Phe Thr Phe Tyr Asp Tyr
                20                      25                 30

Asn Met Ser Trp Val Arg Gln Ala Pro Gly Lys Gly Leu Glu Trp Val
            35                      40                 45

Ser Thr Ile Thr His Thr Gly Val Ser Thr Tyr Tyr Ala Asp Ser
 50                     55                      60
```

```
Val Lys Gly Arg Phe Thr Ile Ser Arg Asp Asn Ser Lys Asn Thr Leu
 65                  70                  75                  80

Tyr Leu Gln Met Asn Ser Leu Arg Ala Glu Asp Thr Ala Val Tyr Tyr
                 85                  90                  95

Cys Ala Lys Gln Asn Pro Ser Tyr Gln Phe Asp Tyr Trp Gly Gln Gly
            100                 105                 110

Thr Leu Val Thr Val Ser Ser
        115
```

<210> SEQ ID NO 255
<211> LENGTH: 118
<212> TYPE: PRT
<213> ORGANISM: Artificial Sequence
<220> FEATURE:
<223> OTHER INFORMATION: Synthetic polypeptide

<400> SEQUENCE: 255

```
Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe His Arg Tyr
            20                  25                  30

Ser Met Ser Trp Val Arg Gln Ala Pro Gly Lys Gly Leu Glu Trp Val
        35                  40                  45

Ser Thr Ile Leu Pro Gly Gly Asp Val Thr Tyr Tyr Ala Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Lys Gln Thr Pro Asp Tyr Met Phe Asp Tyr Trp Gly Gln Gly Thr
            100                 105                 110

Leu Val Thr Val Ser Ser
        115
```

<210> SEQ ID NO 256
<211> LENGTH: 117
<212> TYPE: PRT
<213> ORGANISM: Artificial Sequence
<220> FEATURE:
<223> OTHER INFORMATION: Synthetic polypeptide

<400> SEQUENCE: 256

```
Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Trp Lys Tyr
            20                  25                  30

Asn Met Ala Trp Val Arg Gln Ala Pro Gly Lys Gly Leu Glu Trp Val
        35                  40                  45

Ser Thr Ile Leu Gly Glu Gly Asn Asn Thr Tyr Tyr Ala Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Lys Thr Met Asp Tyr Lys Phe Asp Tyr Trp Gly Gln Gly Thr Leu
            100                 105                 110

Val Thr Val Ser Ser
        115
```

<210> SEQ ID NO 257
<211> LENGTH: 118
<212> TYPE: PRT
<213> ORGANISM: Artificial Sequence
<220> FEATURE:
<223> OTHER INFORMATION: Synthetic polypeptide

<400> SEQUENCE: 257

```
Glu Val Gln Leu Leu Glu Ser Gly Gly Gly Leu Val Gln Pro Gly Gly
  1               5                  10                  15

Ser Leu Arg Leu Ser Cys Thr Ala Ser Gly Phe Thr Phe Asp Glu Tyr
             20                  25                  30

Asn Met Ser Trp Val Arg Gln Ala Pro Gly Lys Gly Leu Glu Trp Val
         35                  40                  45

Ser Thr Ile Leu Pro His Gly Asp Arg Thr Tyr Tyr Ala Asp Ser Val
     50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Lys Gln Asp Pro Leu Tyr Arg Phe Asp Tyr Trp Gly Gln Gly Thr
            100                 105                 110

Leu Val Thr Val Ser Ser
            115
```

<210> SEQ ID NO 258
<211> LENGTH: 118
<212> TYPE: PRT
<213> ORGANISM: Artificial Sequence
<220> FEATURE:
<223> OTHER INFORMATION: Synthetic polypeptide

<400> SEQUENCE: 258

```
Glu Val Gln Leu Leu Glu Ser Gly Gly Gly Leu Val Gln Pro Gly Gly
  1               5                  10                  15

Ser Leu Arg Leu Ser Cys Ala Ala Ser Gly Phe Thr Phe Ser Asp Tyr
             20                  25                  30

Arg Met Ser Trp Val Arg Gln Ala Pro Gly Lys Gly Leu Glu Trp Val
         35                  40                  45

Ser Thr Ile Ile Ser Asn Gly Lys Phe Thr Tyr Tyr Ala Asp Ser Val
     50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Lys Gln Asp Trp Met Tyr Met Phe Asp Tyr Trp Gly Gln Gly Thr
            100                 105                 110

Leu Val Thr Val Ser Ser
            115
```

<210> SEQ ID NO 259
<211> LENGTH: 118
<212> TYPE: PRT
<213> ORGANISM: Artificial Sequence
<220> FEATURE:
<223> OTHER INFORMATION: Synthetic polypeptide

<400> SEQUENCE: 259

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Arg Thr Tyr
            20                  25                  30

Thr Met Ala Trp Val Arg Gln Ala Pro Gly Lys Gly Leu Glu Trp Val
        35                  40                  45

Ser Ser Ile Thr Ser Ser Gly Ser Ser Thr Tyr Tyr Ala Asp Ser Val
50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
            85                  90                  95

Ala Lys Val Asn Ser Leu Tyr Lys Phe Asp Tyr Trp Gly Gln Gly Thr
            100                 105                 110

Leu Val Thr Val Ser Ser
            115

<210> SEQ ID NO 260
<211> LENGTH: 118
<212> TYPE: PRT
<213> ORGANISM: Artificial Sequence
<220> FEATURE:
<223> OTHER INFORMATION: Synthetic polypeptide

<400> SEQUENCE: 260

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Arg Pro Thr
            20                  25                  30

Asn Met Ser Trp Val Arg Gln Ala Pro Gly Lys Gly Leu Glu Trp Val
        35                  40                  45

Ser Thr Ile Thr Gly Thr Gly Ala Ala Thr Tyr Tyr Ala Asp Ser Val
50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
            85                  90                  95

Ala Lys Gln Asn Ser Arg Tyr Arg Phe Asp Tyr Trp Gly Gln Gly Thr
            100                 105                 110

Leu Val Thr Val Ser Ser
            115

<210> SEQ ID NO 261
<211> LENGTH: 197
<212> TYPE: PRT
<213> ORGANISM: Homo sapiens

<400> SEQUENCE: 261

Asp Ala His Lys Ser Glu Val Ala His Arg Phe Lys Asp Leu Gly Glu
1               5                   10                  15

Glu Asn Phe Lys Ala Leu Val Leu Ile Ala Phe Ala Gln Tyr Leu Gln
            20                  25                  30

Gln Cys Pro Phe Glu Asp His Val Lys Leu Val Asn Glu Val Thr Glu
            35                  40                  45

Phe Ala Lys Thr Cys Val Ala Asp Glu Ser Ala Glu Asn Cys Asp Lys
50                  55                  60

Ser Leu His Thr Leu Phe Gly Asp Lys Leu Cys Thr Val Ala Thr Leu

```
                65                  70                  75                  80
Arg Glu Thr Tyr Gly Glu Met Ala Asp Cys Cys Ala Lys Gln Glu Pro
                        85                  90                  95

Glu Arg Asn Glu Cys Phe Leu Gln His Lys Asp Asp Asn Pro Asn Leu
            100                 105                 110

Pro Arg Leu Val Arg Pro Glu Val Asp Val Met Cys Thr Ala Phe His
        115                 120                 125

Asp Asn Glu Glu Thr Phe Leu Lys Lys Leu Tyr Leu Glu Ile Ala Arg
    130                 135                 140

Arg His Pro Tyr Phe Tyr Ala Pro Glu Leu Leu Phe Phe Ala Lys Arg
145                 150                 155                 160

Tyr Lys Ala Ala Phe Thr Glu Cys Cys Gln Ala Ala Asp Lys Ala Ala
                165                 170                 175

Cys Leu Leu Pro Lys Leu Asp Glu Leu Arg Asp Glu Gly Lys Ala Ser
                180                 185                 190

Ser Ala Lys Gln Arg
            195

<210> SEQ ID NO 262
<211> LENGTH: 196
<212> TYPE: PRT
<213> ORGANISM: Homo sapiens

<400> SEQUENCE: 262

Gly Lys Ala Ser Ser Ala Lys Gln Arg Leu Lys Cys Ala Ser Leu Gln
1               5                   10                  15

Lys Phe Gly Glu Arg Ala Phe Lys Ala Trp Ala Val Ala Arg Leu Ser
            20                  25                  30

Gln Arg Phe Pro Lys Ala Glu Phe Ala Glu Val Ser Lys Leu Val Thr
        35                  40                  45

Asp Leu Thr Lys Val His Thr Glu Cys Cys His Gly Asp Leu Leu Glu
    50                  55                  60

Cys Ala Asp Asp Arg Ala Asp Leu Ala Lys Tyr Ile Cys Glu Asn Gln
65                  70                  75                  80

Asp Ser Ile Ser Ser Lys Leu Lys Glu Cys Cys Glu Lys Pro Leu Leu
                85                  90                  95

Glu Lys Ser His Cys Ile Ala Glu Val Glu Asn Asp Glu Met Pro Ala
            100                 105                 110

Asp Leu Pro Ser Leu Ala Ala Asp Phe Val Glu Ser Lys Asp Val Cys
        115                 120                 125

Lys Asn Tyr Ala Glu Ala Lys Asp Val Phe Leu Gly Met Phe Leu Tyr
    130                 135                 140

Glu Tyr Ala Arg Arg His Pro Asp Tyr Ser Val Val Leu Leu Leu Arg
145                 150                 155                 160

Leu Ala Lys Thr Tyr Glu Thr Thr Leu Glu Lys Cys Cys Ala Ala Ala
                165                 170                 175

Asp Pro His Glu Cys Tyr Ala Lys Val Phe Asp Glu Phe Lys Pro Leu
                180                 185                 190

Val Glu Glu Pro
            195

<210> SEQ ID NO 263
<211> LENGTH: 204
<212> TYPE: PRT
<213> ORGANISM: Homo sapiens
```

<400> SEQUENCE: 263

Val Glu Glu Pro Gln Asn Leu Ile Lys Gln Asn Cys Glu Leu Phe Glu
1               5                   10                  15
Gln Leu Gly Glu Tyr Lys Phe Gln Asn Ala Leu Leu Val Arg Tyr Thr
            20                  25                  30
Lys Lys Val Pro Gln Val Ser Thr Pro Thr Leu Val Glu Val Ser Arg
        35                  40                  45
Asn Leu Gly Lys Val Gly Ser Lys Cys Cys Lys His Pro Glu Ala Lys
    50                  55                  60
Arg Met Pro Cys Ala Glu Asp Tyr Leu Ser Val Val Leu Asn Gln Leu
65                  70                  75                  80
Cys Val Leu His Glu Lys Thr Pro Val Ser Asp Arg Val Thr Lys Cys
                85                  90                  95
Cys Thr Glu Ser Leu Val Asn Arg Arg Pro Cys Phe Ser Ala Leu Glu
            100                 105                 110
Val Asp Glu Thr Tyr Val Pro Lys Glu Phe Asn Ala Glu Thr Phe Thr
        115                 120                 125
Phe His Ala Asp Ile Cys Thr Leu Ser Glu Lys Glu Arg Gln Ile Lys
    130                 135                 140
Lys Gln Thr Ala Leu Val Glu Leu Val Lys His Lys Pro Lys Ala Thr
145                 150                 155                 160
Lys Glu Gln Leu Lys Ala Val Met Asp Asp Phe Ala Ala Phe Val Glu
                165                 170                 175
Lys Cys Cys Lys Ala Asp Asp Lys Glu Thr Cys Phe Ala Glu Glu Gly
            180                 185                 190
Lys Lys Leu Val Ala Ala Ser Gln Ala Ala Leu Gly
        195                 200

<210> SEQ ID NO 264
<211> LENGTH: 324
<212> TYPE: DNA
<213> ORGANISM: Homo sapiens

<400> SEQUENCE: 264
ctgtaggtct actgggtcag aggtaggaga gacagacgta gacatcctct ggcacagtgg      60
tagtgaacgg cccgttcagt ctcgtaacta tcaataaatg taaccatggt cgtctttggt     120
ccctttcggg gattcgagga ctagatatca cgtaggctca acgtttcacc ccagggtagt     180
gcaaagtcac cgtcacctag accctgtcta aagtgagagt ggtagtcgtc agacgttgga     240
cttctaaaac gatgcatgat gacagttgtc caacacaccg caggaaaatg caagccggtt     300
ccctggttcc acctttagtt tgcg                                            324

<210> SEQ ID NO 265
<211> LENGTH: 324
<212> TYPE: DNA
<213> ORGANISM: Homo sapiens

<400> SEQUENCE: 265
ctgtaggtct actgggtcag aggtaggagg gacagacgta gacatcctct ggcacagtgg      60
tagtgaacgg cccgttcagt ctcgtaaaaa tacttaaata acaccatggt cgtctttggt     120
ccctttcggg gattcgagga ctagatatta cgtaggcaca acgtttcacc ccagggtagt     180
gcaaagtcac cgtcacctag accctgtcta aagtgagagt ggtagtcgtc agacgttgga     240
cttctaaaac gatgcatgat gacagttgtc caacacaccg caggaaaatg caagccggtt     300

```
cctggttcc acctttagtt tgcc                                              324

<210> SEQ ID NO 266
<211> LENGTH: 324
<212> TYPE: DNA
<213> ORGANISM: Homo sapiens

<400> SEQUENCE: 266
ctgtaggtct actgggtcag aggtaggagg gacagacgta gacatcctct ggcacagtgg      60
tagtgaacgg cccgttcagt ctcgtaaata ctacgcaatc tcaccatggt cgtctttggt    120
cccttcgggg gattcgagga ctagatatga cgtagggcca acgtttcacc ccagggtagt    180
gcaaagtcac cgtcacctag accctgtcta aagtgagagt ggtagtcgtc agacgttgga    240
cttctaaaac gatgcatgat gacagttgtc caatacgtcg caggacaatg caagccggtt    300
ccctggttcc acctttagtt tgcc                                              324

<210> SEQ ID NO 267
<211> LENGTH: 324
<212> TYPE: DNA
<213> ORGANISM: Homo sapiens

<400> SEQUENCE: 267
ctgtaggtct actgggtcag aggtaggagg gacagacgta gacatcctct ggcacagtgg      60
tagtgaacgg cccgttcagt ctcgtaaata ctacgaaatg tcaccatggt cgtctttggt    120
cccttcgggg gattcgagga ctagatatga cgtagggcca acgtttcacc ccagggtagt    180
gcaaagtcac cgtcacctag accctgtcta aagtgagagt ggtagtcgtc agacgttgga    240
cttctaaaac gatgcatggt gacagttgtc caatacgtcg caggacaatg caagccggtt    300
ccctggttcc acctttagtt tgcc                                              324

<210> SEQ ID NO 268
<211> LENGTH: 324
<212> TYPE: DNA
<213> ORGANISM: Homo sapiens

<400> SEQUENCE: 268
ctgtaggtct actgggtcag aggtaggagg gacagacgta gacatcctct ggcacagtgg      60
tagtgaacgg cccgttcagt ctcgcaattc ctcaaaaata ccaccatggt cgtctttggt    120
cccttcgggg gattcgagga ctagatatac cgtaggttaa acgtttcacc ccagggtagt    180
gcaaagtcac cgtcacctag accctgtcta aagtgagagt ggtagtcgtc agacgttgga    240
cttctaaaac gatgcatgat gacagttgtc ttcaaattcg acggagcatg caagccggtt    300
ccctggttcc acctttagtt tgcc                                              324

<210> SEQ ID NO 269
<211> LENGTH: 324
<212> TYPE: DNA
<213> ORGANISM: Homo sapiens

<400> SEQUENCE: 269
ctgtaggtct actgggtcag aggtaggagg gacagacgta gacatcctct ggcacagtgg      60
tagtgaacgg cccgttcagt ctcgtaaacc tgcttcaatg taaccatggt cgtctttggt    120
cccttcgggg gattcgagga ctagatatac cgtaggtcaa acgtttcacc ccagggtagt    180
gcaaagtcac cgtcacctag accctgtcta aagtgagagt ggtagtcgtc agacgttgga    240
cttctaaaac gatgcatgat gacagttgtc accaaatcat taggatcatg caagccggtt    300
```

```
cctggttcc acctttagtt tgcg                                              324

<210> SEQ ID NO 270
<211> LENGTH: 324
<212> TYPE: DNA
<213> ORGANISM: Homo sapines

<400> SEQUENCE: 270
ctgtaggtct actgggtcag aggtaggagg gacagacgta gacatcctct ggcacagtgg      60
tagtgaacgg cccgttcagt ctcgtaaatc ggctaaaata caaccatggt cgtctttggt     120 cccttttcggg gattcgagga ctagatacga cgtaggtcaa acgtttcacc ccagggtagt    180
gcaaagtcac cgtcacctag accctgtcta aagtgagagt ggtagtcgtc agacgttgga    240
cttctaaaac gatgcatgat gacagttgtc taagtcgtat aaggacactg caagccggtt    300 cctggttcc acctttagtt tgcc                                              324

<210> SEQ ID NO 271
<211> LENGTH: 324
<212> TYPE: DNA
<213> ORGANISM: Homo sapiens

<400> SEQUENCE: 271
ctgtaggtct actgggtcag aggtaggagg gacagacgta gacatcctct ggcacagtgg      60
tagtgaacgg cccgttcagt ctcgtaaccc atcctaaatg taaccatggt cgtctttggt    120 cccttttcggg gattcgagga ctagatatgc cgtagggaaa acgtttcacc ccagggtagt    180
gcaaagtcac cgtcacctag accctgtcta aagtgagagt ggtagtcgtc agacgttgga    240
cttctaaaac gatgcatgat gacagttgtc gtctcacgaa aaggattatg cgagccggtt    300 cctggttcc acctttagtt tgcc                                              324

<210> SEQ ID NO 272
<211> LENGTH: 324
<212> TYPE: DNA
<213> ORGANISM: Homo sapiens

<400> SEQUENCE: 272
ctgtaggtct actgggtcag aggtaggagg gacagacgta ggcatcctct ggcacagtgg      60
tagtgaacgg cccgttcagt ctcgtattgc ttcttaaatg aaaccatggt cgtctttggt    120 cccttttcggg gattcgagga ctagataatc cgtaggagaa acgtttcacc ccagggtagt    180
gcaaagtcac cgtcacctag accctgtcta aagtgagagt ggtagtcgtc agacgttgga    240
cttctaaaac gatgcatgat gacagttgtc gaagcagtat tcggaggctg caagccggtt    300 cctggttcc acctttagtt tgcc                                              324

<210> SEQ ID NO 273
<211> LENGTH: 324
<212> TYPE: DNA
<213> ORGANISM: Homo sapiens

<400> SEQUENCE: 273
ctgtaggtct actgggtcag aggtaggagg gacagacgta gacatcctct ggcacagtgg      60
tagtgaacgg cccgttcagt ctcgtaaatc ttcagaaatt ccaccatggt cgtctttggt    120 cccttttcggg gattcgagga ctagatagta cgtaggctaa acgtttcacc ccagggtagt    180
gcaaagtcac cgtcacctag accctgtcta aagtgagagt ggtagtcgtc agacgttgga    240
```

```
cttctaaaac gatgcatgat gacagttgtc taccaattat caggacaatg caagccggtt    300
ccctggttcc acctttagtt tgcc                                           324

<210> SEQ ID NO 274
<211> LENGTH: 324
<212> TYPE: DNA
<213> ORGANISM: Homo sapiens

<400> SEQUENCE: 274
ctgtaggtct actgggtcag aggtaggagg gacagacgta gacatcctct ggcacagtgg     60
tagtgaacgg cccgttcagt ctcgtaaatc tgccgcaatg taaccatggt cgtctttggt    120 cccttttcggg gattcgagga ctagataaga cgtaggtcaa acgtttcacc ccagggtagt   180
gcaaagtcac cgtcacctag accctgtcta aagtgagagt ggtagtcgtc agacgttgga    240
cttctaaaac gatgcatgat gacagttgtc agctcaaaaa acggaaaatg caagccggtt    300
ccctggttcc acctttagtt tgcc                                           324

<210> SEQ ID NO 275
<211> LENGTH: 324
<212> TYPE: DNA
<213> ORGANISM: Homo sapiens

<400> SEQUENCE: 275
ctgtaggtct actgggtcag aggtaggagg gacagacgta gacatcctct ggcacagtgg     60
tagtgaacgg cccgttcagt ctcgtaaccc ggcttaaatc tcaccatggt cgtctttggt    120 cccttttcggg gattcgagga ctagatacga cgtaggtcaa acgtttcacc ccagggtagt   180
gcaaagtcac cgtcacctag accctgtcta aagtgagagt ggtagtcgtc agacgttgga    240
cttctaaaac gatgcatgat gacagttgtc gtctaccccg caggagcctg caagccggtt    300
ccctggttcc acctttagtt tgcc                                           324

<210> SEQ ID NO 276
<211> LENGTH: 324
<212> TYPE: DNA
<213> ORGANISM: Homo sapiens

<400> SEQUENCE: 276
ctgtaggtct actgggtcag aggtaggagg gacagacgta gacatcctct ggcacagtgg     60
tagtgaacgg cccgttcagt ctcgtaattc gtaatcaatc gaaccatggt cgtctttggt    120 cccttttcggg gattcgagga ctagatattc cgtaggcaca acgtttcacc ccagggtagt   180
gcaaagtcac cgtcacctag accctgtcta aagtgagagt ggtagtcgtc agacgttgga    240
cttctaaaac gatgcatgat gacagttgtc gaatccgcag caggatgatg caagccggtt    300
ccctggttcc acctttagtt tgcc                                           324

<210> SEQ ID NO 277
<211> LENGTH: 324
<212> TYPE: DNA
<213> ORGANISM: Homo sapiens

<400> SEQUENCE: 277
ctgtaggtct actgggtcag aggtaggagg gacagacgta gacatcctct ggcacagtgg     60
tagtgaacgg cccgttcagt ctcgcaattc cgaatcaatt gaaccatggt cgtctttggt    120 cccttttcggg gattcgagga ctagatattc cgtaggtgaa acgtttcacc ccagggtagt   180
gcaaagtcac cgtcacctag accctgtcta aagtgagagt ggtagtcgtc agacgttgga    240
```

```
cttctaaaac gatgcatgat gacagttgtc gtatcaagat ccggaatatg caagccggtt      300
ccctggttcc acctttagtt tgcc                                              324
```

<210> SEQ ID NO 278
<211> LENGTH: 324
<212> TYPE: DNA
<213> ORGANISM: Homo sapiens

<400> SEQUENCE: 278

```
ctgtaggtct actgggtcag aggtaggagg gacagacgta gacatcctct ggcacagtgg      60
tagtgaacgg cccgttcagt ctcgtaactc ttagccaatc caaccatggt cgtctttggt     120
ccctttcggg gattcgagga ctagataatc cgcaggaaca acgtttcacc ccagggtagt     180
gcaaagtcac cgtcacctag accctgtcta aagtgagagt ggtagtcgtc agacgttgga     240
cttctaaaac gatgcatgat gacagttgtc ctaagcataa aaggagcatg caagccggtt      300
ccctggttcc acctttagtt tgcc                                              324
```

<210> SEQ ID NO 279
<211> LENGTH: 324
<212> TYPE: DNA
<213> ORGANISM: Homo sapiens

<400> SEQUENCE: 279

```
ctgtaggtct actgggtcag aggtaggagg gacagacgta gacatcctct ggcacagtgg      60
tagtgaacgg cccgttcagt ctcgtaatac ctattcaatt tcaccatggt cgtctttggt     120
ccctttcggg gattcgagga ctagataatc cgtaggtaaa acgtttcacc ccagggtagt     180
gcaaagtcac cgtcacctag accctgtcta aagtgagagt ggtagtcgtc agacgttgga     240
cttctaaaac gatgcatgat gacagttgtc ctatcacccc caggattatg caagccggtt      300
ccctggttcc acctttagtt tgcc                                              324
```

<210> SEQ ID NO 280
<211> LENGTH: 324
<212> TYPE: DNA
<213> ORGANISM: Homo sapiens

<400> SEQUENCE: 280

```
ctgtaggtct actgggtcag aggtaggagg gacagacgta gacatcctct ggcacagtgg      60
tagtgaacgg cccgttcagt ctcgtaaccc tccttaaatc tcaccatggt cgtctttggt     120
ccctttcggg gattcgagga ctagatacta cgtagggtaa acgtttcacc ccagggtagt     180
gcaaagtcac cgtcacctag accctgtcta aagtgagagt ggtagtcgtc agacgttgga     240
cttctaaaac gatgcatgat gacagttgtc agcgcaaccg aaggagcatg caagccggtt      300
ccctggttcc acctttagtt tgcc                                              324
```

<210> SEQ ID NO 281
<211> LENGTH: 324
<212> TYPE: DNA
<213> ORGANISM: Homo sapiens

<400> SEQUENCE: 281

```
ctgtaggtct actgggtcag aggtaggagg gacagacgta gacatcctct ggcacagtgg      60
tagtgaacgg cccgttcagt ctcgtaatcc ttctacaatc aaaccatggt cgtctttggt     120
ccctttcggg gattcgagga ctagatagcc cgtaggataa acgtttcacc ccagggtagt     180
```

```
gcaaagtcac cgtcacctag accctgtcta aagtgagagt ggtagtcgtc agacgttgga    240
cttctaaaac gatgcatgat gacagttgtc cgaaaagccg ccggatcctg caagccggtt    300
ccctggttcc acctttagtt tgcc                                           324
```

<210> SEQ ID NO 282
<211> LENGTH: 345
<212> TYPE: DNA
<213> ORGANISM: Homo sapiens

<400> SEQUENCE: 282

```
ctccacgtcg acaacctcag accccctccg aaccatgtcg acccccag ggacgcagag      60 aggacacgtc ggaggcctaa gtggaaacta gaaatattat acaaaaccca ggcggtccga   120
ggtcccttcc cagatctcac ccagagtaaa taatcagtct gaccatccga atgtaccatg   180
cgtctgaggc acttcccggc caagtggtag agggcgctgt taaggttctt gtgcgacata   240
gacgtttact tgtcggacgc acggctcctg tggcgccata taatgacacg cttttgcgac   300
ctcctaaaac tgatgacccc ggtcccttgg gaccagtggc agagc                    345
```

<210> SEQ ID NO 283
<211> LENGTH: 357
<212> TYPE: DNA
<213> ORGANISM: Homo sapiens

<400> SEQUENCE: 283

```
ctccacgtcg acaacctcag accccctccg aaccatgtcg acccccag ggacgcagag      60 aggacacgtc ggaggcctaa gtggaaaggc caaatatact acccaaccca ggcggtccga   120
ggtcccttcc cagatctcac ccagagtagc taactacgag aaccaccgc ctgtccaatg   180 cgtctgaggc acttcccggc caagtggtag agggcgctgt taaggttctt gtgcgacata   240
gacgtttact tgtcggacgc acggctcctg tggcgccata taatgacacg cttttgatac   300
agcttattct gcgtatgcaa actgatgacc ccggtcccttgggaccagtg gcagagc        357
```

<210> SEQ ID NO 284
<211> LENGTH: 345
<212> TYPE: DNA
<213> ORGANISM: Homo sapiens

<400> SEQUENCE: 284

```
ctccacgtcg acaacctcag accccctccg aaccatgtcg acccccag ggacgcagag      60 aggacacgtc ggaggcctaa gtggaaacac cgaatattat actgaaccca ggcggtccga   120
ggtcccttcc cagatctcac ccagagttca taattatgaa aaccattaat ctgttccatg   180
cgtctgaggc acttcccggc caagtggtag agggcgctgt taaggttctt gtgcgacata   240
gacgtttact tgtcggacgc acggctcctg tggcgccata taatgacacg ctttccatca   300
tccggaaaac tgatgacccc ggtcccttgg gaccagtggc agagc                    345
```

<210> SEQ ID NO 285
<211> LENGTH: 357
<212> TYPE: DNA
<213> ORGANISM: Homo sapiens

<400> SEQUENCE: 285

```
ctccacgtcg acaacctcag accccctccg aaccatgtcg acccccag ggacgcagag      60 aggacacgtc ggaggcctaa gtggaaaatc cccatagcat acccaaccca ggcggtccga   120
ggtcccttcc cagatctcac ccagagtacc taatgcgcat gaccacccctg ctgtgtcatg  180
```
cgtctgaggc acttcccggc caagtggtag agggcgctgt taaggttctt gtgcgacata    240
gacgtttact tgtcggacgc acggctcctg tggcgccata taatgacacg ctttggccgc    300
ttcgaacaac cccaacccaa actgatgacc ccggtccctt gggaccagtg gcagagc       357

<210> SEQ ID NO 286
<211> LENGTH: 357
<212> TYPE: DNA
<213> ORGANISM: Homo sapiens

<400> SEQUENCE: 286
ctccacgtcg acaacctcag accccctccg aaccatgtcg acccccccag ggacgcagag    60
aggacacgtc ggaggcctaa gtggaaagcc ttcataatct accccaccca ggcggtccga    120
ggtcccttcc cagatctcac ccagagtgtc taaccacgct tcccagtcag atgtctaatg    180
cgtctgaggc acttcccggc caagtggtag agggcgctgt taaggttctt gtgcgacata    240
gacgtttact tgtcggacgc acggctcctg tggcgccata taatgacacg ctttttcttc    300
tcccccctct taataaaaaa actgatgacc ccggtccctt gggaccagtg gcagagc       357

<210> SEQ ID NO 287
<211> LENGTH: 357
<212> TYPE: DNA
<213> ORGANISM: Homo sapiens

<400> SEQUENCE: 287
ctccacgtcg acaacctcag accccctccg aaccatgtcg acccccccag ggacgcagag    60
aggacacgtc ggaggcctaa gtggaaagcc gccatatcat acagcaccca ggcggtccga    120
ggtcccttcc cagatctcac ccagagtcta taaagagcaa gaccagccat atgtgtaatg    180
cgtctgaggc acttcccggc caagtggtag agggcgctgt taaggttctt gtgcgacata    240
gacgtttact tgtcggacgc acggctcctg tggcgccata taatgacacg ctttgcataa    300
ctaagaagag tcttacccaa actgatgacc ccggtccctt gggaccagtg gcagagc       357

<210> SEQ ID NO 288
<211> LENGTH: 345
<212> TYPE: DNA
<213> ORGANISM: Homo sapiens

<400> SEQUENCE: 288
ctccacgtcg acaacctcag accccctccg aaccatgtcg acccccccag ggacgcagag    60
aggacacgtc ggaggcctaa gtggaaaatc cccatattct acaaaaccca ggcggtccga    120
ggtcccttcc cagatctcac ccagagtcga taatcaccat caccaccatc gtgtatgatg    180
cgtctgaggc acttcccggc caagtggtag agggcgctgt taaggttctt gtgcgacata    240
gacgtttact tgtcggacgc acggctcctg tggcgccata taatgacacg ctttgtcttc    300
ctcttaaaac tgatgacccc ggtcccttgg gaccagtggc agagc                    345

<210> SEQ ID NO 289
<211> LENGTH: 357
<212> TYPE: DNA
<213> ORGANISM: Homo sapiens

<400> SEQUENCE: 289
ctccacgtcg acaacctcag accccctccg aaccatgtcg acccccccag ggacgcagag    60
aggacacgtc ggaggcctaa gtggaaaccc ctaatacgat acaccaccca ggcggtccga    120

```
ggtcccttcc cagatctcac ccagagtcac taatcaagct taccaccctc atgtaaaatg    180
cgtctgaggc acttcccggc caagtggtag agggcgctgt taaggttctt gtgcgacata    240
gacgtttact tgtcggacgc acggctcctg tggcgccata taatgacacg ctttgcacaa    300
gcattctcct gaggactcaa actgatgacc ccggtccctt gggaccagtg gcagagc       357
```

<210> SEQ ID NO 290
<211> LENGTH: 357
<212> TYPE: DNA
<213> ORGANISM: Homo sapiens

<400> SEQUENCE: 290

```
ctccacgtcg acaacctcag accccctccg aaccatgtcg acccccag ggacgcagag     60 aggacacgtc ggaggcctaa gtggaaatcc tccatattct acccaaccca ggcggtccga    120
ggtcccttcc cagatctcac ccagagtcgc taaccctcct taccatgctt ctgtttaatg    180
cgtctgaggc acttcccggc caagtggtag agggcgctgt taaggttctt gtgcgacata    240
gacgtttact tgtcggacgc acggctcctg tggcgccata taatgacacg cttttaaata    300
tgccccttcg acgacgcaa actgatgacc ccggtccctt gggaccagtg gcagagc        357
```

<210> SEQ ID NO 291
<211> LENGTH: 357
<212> TYPE: DNA
<213> ORGANISM: Homo sapiens

<400> SEQUENCE: 291

```
ctccacgtcg acaacctcag accccctccg aaccatgtcg acccccag ggacgcagag     60 aggacacgtc ggaggcctaa gtggaaattc ttcataatct acagaaccca ggcggtccga    120
ggtcccttcc cagatctcac ccagagtcga taatcaccat caccaccatc gtgtatgatg    180
cgtctgaggc acttcccggc caagtggtag agggcgctgt taaggttctt gtgcgacata    240
gacgtttact tgtcggacgc acggctcctg tggcgccata taatgacacg cttttacgac    300
tcctgattct tattccacaa actgatgacc ccggtccctt gggaccagtg gcagagc       357
```

<210> SEQ ID NO 292
<211> LENGTH: 357
<212> TYPE: DNA
<213> ORGANISM: Homo sapiens

<400> SEQUENCE: 292

```
ctccacgtcg acaacctcag accccctccg aaccatgtcg acccccag ggacgcagag     60 aggacacgtc ggaggcctaa gtggaaatcc tccatattct acccaaccca ggcggtccga    120
ggtcccttcc cagatctcac ccagagtcgc taaccctcct taccatgctt ctgtttaatg    180
cgtctgaggc acttcccggc caagtggtag agggcgctgt taaggttctt gtgcgacata    240
gacgtttact tgtcggacgc acggctcctg tggcgccata taatgacacg cttttaaata    300
tgccccttcg acgacgcaa actgatgacc ccggtccctt gggaccagtg gcagagc        357
```

<210> SEQ ID NO 293
<211> LENGTH: 357
<212> TYPE: DNA
<213> ORGANISM: Homo sapiens

<400> SEQUENCE: 293

```
ctccacgtcg acaacctcag accccctccg aaccatgtcg acccccag ggacgcagag     60 aggacacgtc ggaggcctaa gtggaaaatc tcaatagcct acccaaccca ggcggtccga    120
```

```
ggtcccttcc cagatctcac ccagagttca taaagcagct ccccatccgt atgtagaatg      180
cgtctgaggc acttcccggc caagtggtag agggcgctgt taaggttctt gtgcgacata      240
gacgtttact tgtcggacgc acggctcctg tggcgccata taatgacacg ctttccccaa      300
ggcccagccc ccgcaagaaa actgatgacc ccggtccctt gggaccagtg gcagagc        357

<210> SEQ ID NO 294
<211> LENGTH: 357
<212> TYPE: DNA
<213> ORGANISM: Homo sapiens

<400> SEQUENCE: 294
ctccacgtcg acaacctcag accccctccg aaccatgtcg gaccccccag ggacgcagag       60
aggacacgtc ggaggcctaa ggggaaagca gccatagcct actccaccca ggcggtccga      120
ggtcccttcc cagatctcac ccagagtcca taaagaggcc caccattcgt atgttgcatg      180
cgtctgaggc acttcccggc caagtggtag agggcgctgt taaggttctt gtgcgacata      240
gacgtttact tgtcggacgc acggctcctg tggcgccata taatgacacg ctttccactc      300 ccccccgct caagacgcaa actgatgacc ccggtccctt gggaccagtg gcagagc         357

<210> SEQ ID NO 295
<211> LENGTH: 357
<212> TYPE: DNA
<213> ORGANISM: Homo sapiens

<400> SEQUENCE: 295
ctccacgtcg acaacctcag accccctccg aaccatgtcg gaccccccag ggacgcagag       60
aggacacgtc ggaggcctaa gtggaaaatc gccatacccct accaaaccca ggcggtccga     120
ggtcccttcc cagatctcac ccagagtcga taatcaccat caccaccatc gtgtatgatg     180
cgtctgaggc acttcccggc caagtggtag agggcgctgt taaggttctt gtgcgacata     240
gacgtttact tgtcggacgc acggctcctg tggcgccata taatgacacg ctttgccgta    300
tcaagactcc gatccgtcaa actgatgacc ccggtccctt gggaccagtg gcagagc       357
```